(12) United States Patent
Myers et al.

(10) Patent No.: US 11,673,910 B2
(45) Date of Patent: *Jun. 13, 2023

(54) MACROLIDES WITH MODIFIED DESOSAMINE SUGARS AND USES THEREOF

(71) Applicants: Zikani Therapeutics, Inc., Watertown, MA (US); President and Fellows of Harvard College, Cambridge, MA (US)

(72) Inventors: Andrew G. Myers, Boston, MA (US); Ziyang Zhang, San Francisco, CA (US); Takehiro Fukuzaki, Tokyo (JP); Udara Anulal Premachandra Ilandari Dewage, Waukegan, IL (US); Senkara Rao Allu, Arlington, MA (US); Roger B. Clark, Lexington, MA (US); Jonathan F. Lawrence, Somerville, MA (US); Wesley Francis Austin, Cambridge, MA (US); Xiben Li, Lexington, MA (US); Wenying Wang, Boston, MA (US); Sushmita D. Lahiri, Lexington, MA (US); Yoshitaka Ichikawa, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/609,120

(22) PCT Filed: Apr. 27, 2018

(86) PCT No.: PCT/US2018/030002
§ 371 (c)(1),
(2) Date: Oct. 28, 2019

(87) PCT Pub. No.: WO2018/201076
PCT Pub. Date: Nov. 1, 2018

(65) Prior Publication Data
US 2022/0306673 A1    Sep. 29, 2022

Related U.S. Application Data

(60) Provisional application No. 62/522,581, filed on Jun. 20, 2017, provisional application No. 62/491,890, filed on Apr. 28, 2017.

(51) Int. Cl.
*C07H 17/08* (2006.01)
*C07H 15/18* (2006.01)

(52) U.S. Cl.
CPC ............. *C07H 17/08* (2013.01); *C07H 15/18* (2013.01)

(58) Field of Classification Search
None
See application file for complete search history.

(56) References Cited

U.S. PATENT DOCUMENTS

| 6,046,171 A | 4/2000 | Yat et al. |
| 6,645,941 B1 | 11/2003 | Guoquiang et al. |
| 6,764,998 B1 | 7/2004 | Guoquiang et al. |
| 2009/0264380 A1 | 10/2009 | Kim et al. |

FOREIGN PATENT DOCUMENTS

| WO | 1999021864 | 5/1999 |
| WO | 2004011477 | 2/2004 |
| WO | 2005067564 | 7/2005 |
| WO | 2005072204 | 8/2005 |
| WO | 2006119313 | 11/2006 |
| WO | 2008014221 | 1/2008 |
| WO | 2014165792 A2 | 10/2014 |
| WO | 2016057798 A1 | 4/2016 |
| WO | 2016154533 A1 | 9/2016 |
| WO | 2016154591 | 9/2016 |
| WO | 2016154591 A1 | 9/2016 |

OTHER PUBLICATIONS

International Search Report for PCT/US2018/030002, dated Jan. 21, 2019.
Liang C H et al: "Synthesis and biological activity of new 5-O-sugar modified ketolide and 2-fluoro-ketolide antibiotics", Bioorganiz & Medicinal Chemistry Letters, Pergamon, Amsterdam, NL, vol. 15, No. 5 Mar. 1, 2005 (Mar. 1, 2005), pp. 1307-1310, XP.
Romero A et al: "An efficient entry to new sugar modified ketotide antibiotics", Tetrahedron Letters, Elsevier, Amsterdam, NL, vol. 46, No. 9, Feb. 28, 2005 (Feb. 28, 2005), pp. 1483-1487, XP027862363.
Ma Z et al: "Regioselective Systhesis of Bifunctional Macrolides for Probing Ribosomal Binding", Organic Letters, American Chemical Society, US, vol. 4. No. 6, Jan. 1, 2002 (Jan. 1, 2002), pp. 987-990.
Wu Y-J et al: "Recent Developments on Ketolides and Macrolides", Current Medicinal Chemistry: The New International Journal for Timely In-Depth Reviews in Medicinal Chemi, Bentham, NL, vol. 8, No. 15, Dec. 1, 2001, pp. 1727-1758.
Wang G et al: "Synthesis of Novel 6, 11-0-Bridged Bicyclic Ketolides via a Palladium-Catalyzed Bis-allyation", Organic Letters, American Chemical Society, US, vol. 6, No. 24, Aug. 20, 2004, pp. 4455-4458, XP-002384142.

(Continued)

*Primary Examiner* — Layla D Berry
(74) *Attorney, Agent, or Firm* — Honigman LLP; Heidi M. Berven

(57) ABSTRACT

Provided are macrolide compounds for the treatment of infectious diseases. The macrolides disclosed herein include 14-membered ketolides and 14-15-membered azaketolides, and may comprise modified sugars which are desosamine analogues. The disclosed macrolides may have a bicyclic structure. Also provided are pharmaceutical compositions and methods of treating infectious diseases, and in particular, disease which results from Gram negative bacteria using the disclosed macrolides. This disclosure additionally provides methods of preparing the macrolides by a strategy that enables late-stage modification of the 6'-position of the sugar moiety, thereby allowing facile access to previously difficult-to-make macrolide compounds.

3 Claims, 2 Drawing Sheets

(56) References Cited

OTHER PUBLICATIONS

Spencer Knapp et al: "Synthesis of the Ezomycin Nucleoside Disaccharide", Organic Letters, American Chemical Society, US, vol. 2, No. 10, May 1, 2000, pp. 1391-1393.

Phan et al: "Synthesis of 2-Fluoro-6-O-propargyl-11,12-carbamate Ketolides." Organic Letters, American Chemical Society, US, vol. 2, No. 19, Jun. 19, 2000, pp. 2951-2954.

L.-J. Jiang et al: "Pharmacokinetics of EDP-420 after Multiple Oral Doses in Healthy Adult Volunteers and in a Bioequivalence Study", Antimicrobial Agents and Chemotherapy, vol. 53, No. 8, Aug. 1, 2009 (Aug. 1, 2009), pp. 3218-3225, XP055524554, US ISSN: 0066-4804, DOI: 10.1128/AAC.00022-09, figure 1.

David Crich et al: "Direct Stereocontrolled Synthesis of 3-Amino-3-deoxy[beta]-Manoopyranosides: Importance of the Nitrogen Protecting Group on Stereoselectivity", Journal of Organic Chemistry, vol. 72, No. 14, Jul. 1, 2007 (Jul. 1, 2007), pp. 5183-5192, XP055521174, ISSN: 0022-3263, DOI: 10.1021/jo070473 conversion of a compound 23->24.

Wang A-Peng et al: "An efficient method to synthesize novel 5-0-(6'-modified)-mycaminose 14-membered ketolides", Tetrahedron, vol. 72, No. 2, Nov. 19, 2015 (Nov. 19, 2015), pp. 235-297, XP029364736, ISSN: 0040-4020, DOI: 10.1016/J.TET.2015.11.029 the whole document.

MACROLIDES WITH MODIFIED DESOSAMINE SUGARS AND USES THEREOF

RELATED APPLICATIONS

This application is a United States National Phase filing of PCT/US2018/030002, filed Apr. 27, 2018, which claims the benefit of priority to U.S. Provisional Application No. 62/522,581, filed Jun. 20, 2017, and to U.S. Provisional Application No. 62/491,890, filed Apr. 28, 2017, the entire contents of which are incorporated herein by reference.

BACKGROUND

Emerging resistance to existing antibiotics is rapidly developing as a crisis of global proportions, especially for infections originating from drug resistant Gram-negative bacteria. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. This year, >99,000 people will die in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 122:160-166. The current crisis is exacerbated by the fact that most major pharmaceutical companies have essentially abandoned research in the development of new antibiotics. See, e.g., Projan, *Curr. Opin. Microbiol.* (2003) 6:427-430. The current rate of introduction of new antibiotics does not adequately address growing resistance, and with the ease of international travel and increasing population densities, the need for innovation in the field has never been higher.

The macrolides are one of the few major clinically important classes of antibiotics for which the only practical access has been through semi-synthesis, or chemical manipulation of structurally complex fermentation products, in routes as long as 16 steps. See, e.g., Paterson, *Tetrahedron* (1985) 41:3569-3624; Omura, Ed., *Macrolide Antibiotics: Chemistry, Biology, andPractice, Second Edition*; Academic Press, 2002. The macrolide class of antibiotics has proven safe and effective in the battle against pathogenic bacteria since the discovery of erythromycin over 60 years ago. See, e.g., Wu et al., *Curr. Med. Chem.* (2001) 8:1727-1758. Erythromycin displays a spectrum of antibacterial activity against Gram-positive bacteria similar to that of penicillin but has a lesser propensity to induce allergic interactions, and has been routinely prescribed for upper and lower respiratory tract infections and urogenital infections. See, e.g., Washington et al., *Mayo. Clin. Proc.* (1985) 60:189-203; Washington et al., *Mayo. Clin. Proc.* (1985) 60:271-278. However, erythromycin is known to undergo acid-promoted internal ketalization (cyclization of the C6 and C12 hydroxyl groups onto the C9 ketone) in the gut, which leads to adverse gastrointestinal events. See, e.g., Kurath et al., *Experientia* (1971) 27:362. Second-generation macrolide antibiotics clarithromycin and azithromycin addressed issues of acid instability and were prepared semi-synthetically in 4-6 steps from erythromycin, which is readily available through large-scale fermentation. See, e.g., Ma et al., *Curr. Med. Chem.* (2011) 18:1993-2015; Wu et al., *Curr. Pharm. Des.* (2000) 6:181-223; Ma et al., *Mini-Rev. Med. Chem.* (2010) 10:272-286; Asaka et al., *Curr. Top. Med. Chem.* (Sharjah, UnitedArab Emirates) (2003) 3:961-989; Morimoto et al., *J. Antibiot.* (1990) 43:286-294; Morimoto et al., *J. Antibiot.* (1984) 37:187-189; Watanabe et al., *J. Antibiot.* (1993) 46: 1163-1167; Watanabe et al., *J. Antibiot.* (1993) 46:647-660; Bright et al., *J. Antibiot.* (1988) 41: 1029-1047; Djokic et al., *J. Antibiot.* (1987) 40:1006-1015; Mutak et al., *J. Antibiot.* (2007) 60: 85-122; and Retsema et al., *Antimicrob. Agents Chemother.* (1987) 31:1939-1947. Azithromycin has been shown to exhibit markedly improved efficacy against Gram-negative organisms, and has a longer half-life and higher tissue distribution than the other macrolide antibiotics, thought to correlate with its 15-membered ring containing a tertiary amine. See, e.g., Ferwerda et al., *J. Antimicrob. Chemother.* (2001) 47:441-446; Girard et al., *Antimicrob. Agents Chemother.* (1987) 31:1948-1954. The natural product tylosin, a 16-membered macrolide used in veterinary medicine, has been shown by X-ray crystallography to occupy the same binding pocket as erythromycin and azithromycin, suggesting that there is a high tolerance for variability in ring size and composition of the macrocycle.

The three primary causes of resistance to macrolides in bacterial organisms are ribosome methylation encoded by erm genes, mutations in ribosomal RNA or peptides, and cell efflux mediated by mef and msr genes. See, e.g., Leclercq et al., *Antimicrob. Agents Chemother.* (1991) 35:1273-1276; Leclercq et al., *Antimicrob. Agents Chemother.* (1991) 35:1267-1272; Weisblum, *Antimicrob. Agents Chemother.* (1995) 39:577-585; Vester et al., *Antimicrob. Agents Chemother.* (2001) 45:1-12; Prunier et al., *Antimicrob. Agents Chemother.* (2002) 46:3054-3056; Li et al., *J. Antimicrob. Chemother.* (2011) 66:1983-1986; Sutcliffe et al., *Antimicrob. Agents Chemother.* (1996) 40:1817-1824; Wondrack et al., *Antimicrob. Agents Chemother.* (1996) 40: 992-998. Ketolides such as telithromycin and solithromycin defeat the efflux mechanism of resistance by replacement of the C3 cladinose sugar with a carbonyl group (hence the name "ketolides"), and are thought to exhibit greatly increased binding by virtue of favorable interactions between the novel aryl-alkyl sidechain and the ribosome. See, e.g., Ma et al., *Curr. Med. Chem.* (2011) 18:1993-2015; Ma et al., *Mini-Rev. Med. Chem.* (2010) 10:272-286. Despite greatly improved ribosomal binding, ketolides such as telithromycin and solithromycin have not addressed several of the newest forms of macrolide resistance that have evolved in nosocomial settings, especially ribosome methylation and RNA point mutations.

Accordingly, the discovery and development of new antibiotics effective against drug-resistant bacteria, especially Gram-negative bacteria, represents a currently unmet medical need.

SUMMARY

Macrolides are an important class of antibiotics, and have proven to be safe and effective in the treatment of infectious diseases for decades. A critical component of erythromycin, and many other macrolide antibiotics (e.g., azithromycin, carbomycin, cethromycin, clarithromycin, roxithromycin, solithromycin, telithromycin, tylosin), is the desosamine or mycaminose sugar at the C5 position of the macrolide. For example, in erythromycin (shown below with the typical carbon numbering for a 14-membered macrolide), the C5 sugar is D-desosamine.

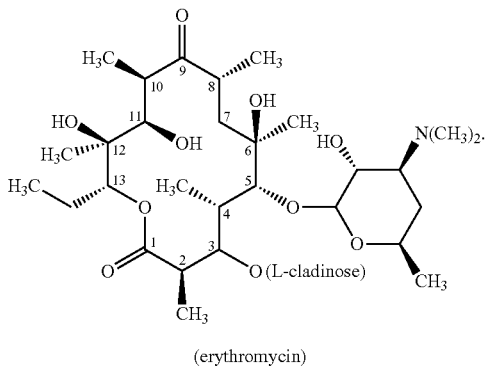 [SMILES: CC[C@H]1OC(=O)[C@H](C)C(O)[C@H](C)[C@@H](OC2O[C@H](C)C[C@H](N(C)C)[C@H]2O)[C@](C)(O)C[C@@H](C)C(=O)[C@H](C)[C@@H](O)[C@]1(C)O]

(erythromycin)

X-ray crystallographic studies reveal that the C5 sugar makes extensive contacts with the 23S subunit of bacterial ribosomal RNA, and thus it is thought that it plays a key role in antibiotic activity of macrolides. See, e.g., Tu et al., *Cell* (2005) 121:257-270; Mankin et al., *Current Opinion in Microbiology* (2008) 11:414-421. Variation of the sugar at the C5 position of the macrolide (e.g., desosamine and mycaminose analogs) affords macrolide antibiotics with desired and/or improved pharmaceutical properties (e.g., efficacy against resistant strains, improved pharmacokinetics, and reduced side-effects). As described herein, the C6 position of the sugar (e.g., desosamine) can be modified to afford novel macrolide antibiotics that have unexpectedly potent activity against a variety of Gram negative bacteria, including several drug-resistant strains.

In one aspect, the compounds described herein comprise macrolides with a modified sugar (e.g., desosamine) at the C5 position of the macrolide. In certain embodiments, the sugar at the C5 position of the macrolide is modified at the C6 position of the sugar. Such compounds are provided as macrolides of Formula (I):

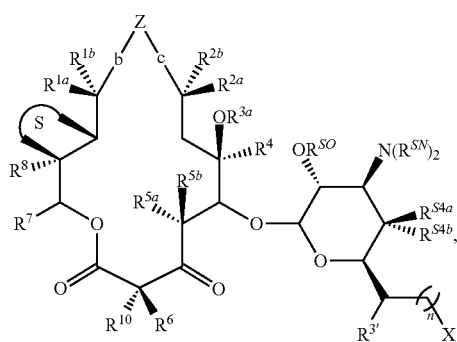
(I)

or a pharmaceutically acceptable salt thereof, wherein:
ring S is

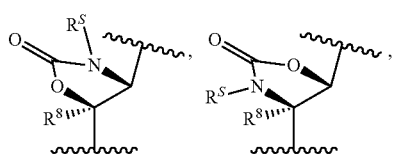

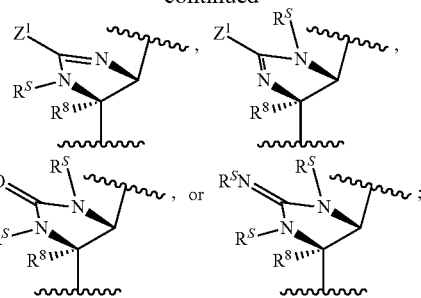

$Z^1$ is $N(R^S)_2$ or $C(R^S)_3$ and each $R^S$ is independently H, $C_1$-$C_6$ alkyl, or $C_2$-$C_6$ alkenyl;

Z is —C(=O)— or —$NR^{Z2}$—;

$R^{Z2}$ is hydrogen, optionally substituted alkyl, acyl, or a nitrogen protecting group;

when Z is —$NR^{Z2}$—, one of b and c is $CH_2$ or —C(=O)—, and the other is a bond, or both b and c are a bond;

when Z is —C(=O)—, b and c are both a bond;

n is 0 or 1;

X is optionally substituted $C_{1\text{-}6}$ alkyl, —$OR^A$, or —$NR^B$—$(CR^xR^x)_t$-A-$(R^y)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)$CH_2NR^{x1}R^{y1}$;

each $R^x$ is independently hydrogen or $C_{1\text{-}3}$ alkyl;

A is arylene, heteroarylene, heterocyclylene, cycloalkylene, alkylene, alkenylene, alkynylene, or a bond;

each $R^y$ is independently, hydrogen, $C_{1\text{-}6}$ alkyl, $C_{1\text{-}6}$ alkoxy, halogen, hydroxyl, cyano, dialkylamino, haloalkyl, C(O)OC$_{1\text{-}3}$ alkyl, C(O)OH, C(O)CH$_2$NR$^{x1}$R$^{y1}$, C(O)NR$^{x1}$R$^{y1}$, C(O)C$_{1\text{-}6}$ alkyl, $C_{1\text{-}6}$ alkylsulfonyl, heteroaryl, or heteroaryloxy;

or when A is a bond, and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{3'}$ is H, $C_{1\text{-}3}$ alkyl, OH, or oxo;

each of $R^{S4a}$ and $R^{S4b}$ is independently hydrogen, halogen, optionally substituted $C_{1\text{-}6}$ alkyl, or —$OR^{SO}$;

each $R^{SN}$ is independently hydrogen, optionally substituted $C_{1\text{-}6}$ alkyl, or a nitrogen protecting group, or two $R^{SN}$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_{1\text{-}6}$ alkyl, or —$OR^{SO}$;

each $R^{SO}$ is independently hydrogen, optionally substituted $C_{1\text{-}6}$ alkyl, a carbohydrate, or an oxygen protecting group;

each of $R^{1a}$ and $R^{1b}$ is independently hydrogen, halogen, or optionally substituted alkyl;

each of $R^{2a}$ and $R^{2b}$ is independently hydrogen, halogen, or optionally substituted alkyl;

$R^{3'}$ is hydrogen, optionally substituted alkyl, optionally substituted alkenyl, optionally substituted alkynyl, or an oxygen protecting group;

or $R^{3a}$ and $R^6$ are joined to form an optionally substituted heterocyclyl ring; or $R^{3a}$ and $R^{10}$ are joined to form an optionally substituted heterocyclyl ring, or $R^{3a}$ and $R^S$ are joined to form an optionally substituted heterocyclyl ring;

$R^4$ is hydrogen, halogen, or optionally substituted alkyl;

each of $R^{5a}$ and $R^{5b}$ is independently hydrogen, halogen, or optionally substituted alkyl;

$R^6$ is hydrogen, halogen, or optionally substituted alkyl;

$R^{10}$ is hydrogen, halogen, or optionally substituted alkyl;

$R^7$ is hydrogen, halogen, optionally substituted alkyl, $C_2$-$C_6$-alkenyl, $C_2$-$C_6$-alkynyl, or $C_1$-$C_6$-alkoxy; and $R^8$ is hydrogen, halogen, or optionally substituted $C_{1-6}$ alkyl.

In certain embodiments, the present disclosure provides compounds of Formulae (I-a), (I-b), (I-c), (I-d), (I-e-i), (I-f-i), (I-g-i), (I-h-i), (I-i-i), (I-e-ii), (I-f-ii), (I-g-i), (I-h-ii), (I-i-ii), (I-j-ii), (I-k), (I-l), (I-m), (II), (II-a), (II-b), (II-c), (II-d), (II-e), and (II-f), and pharmaceutically acceptable salts thereof, as described herein.

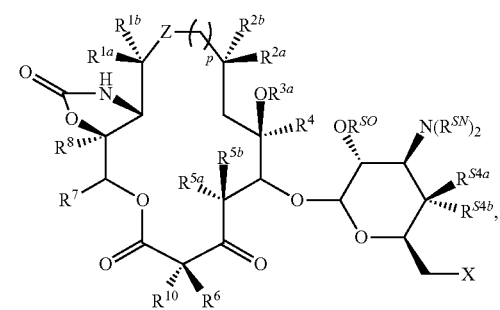

(I-a)

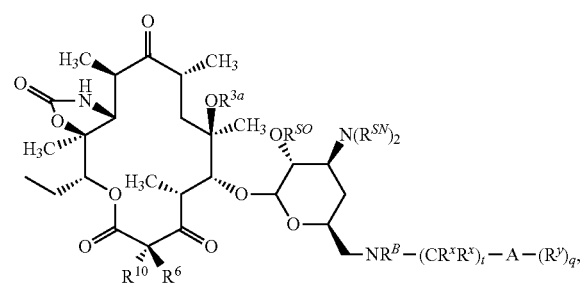

(I-b)

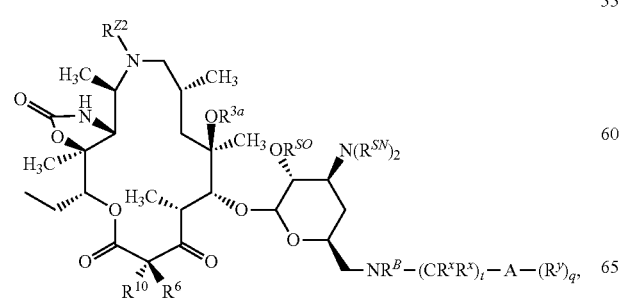

(I-c)

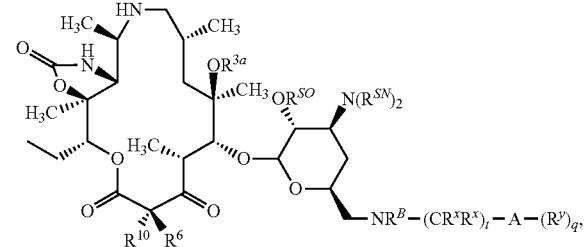

(I-d)

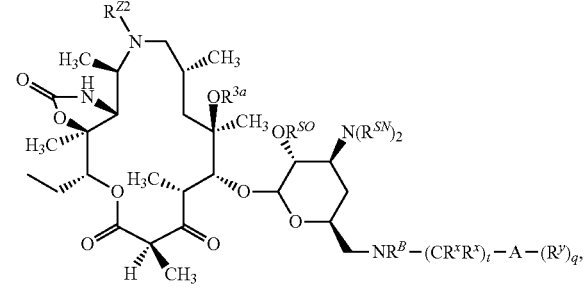

(I-e-i)

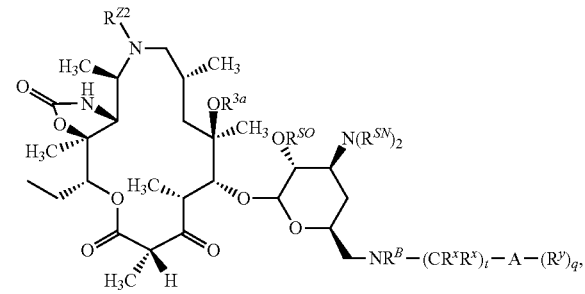

(I-e-ii)

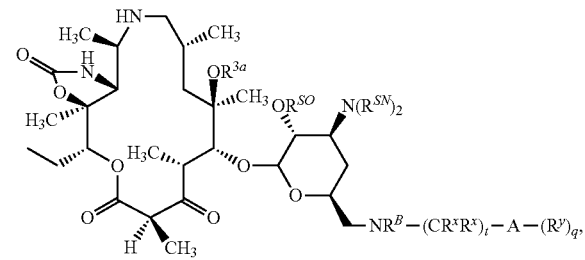

(I-f-i)

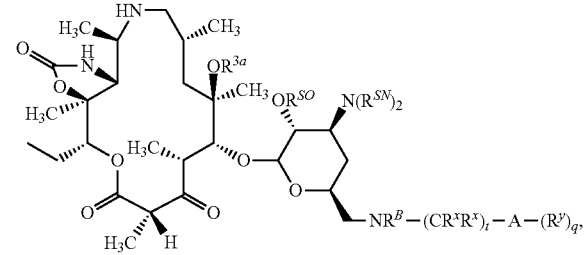

(I-f-ii)

-continued
(I-g-i)
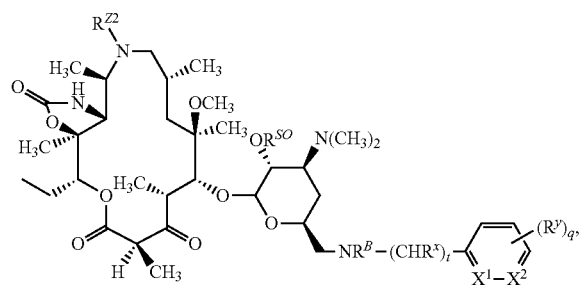
(I-g-ii)
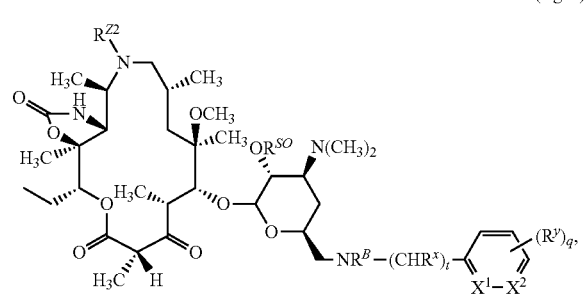
(I-h-i)
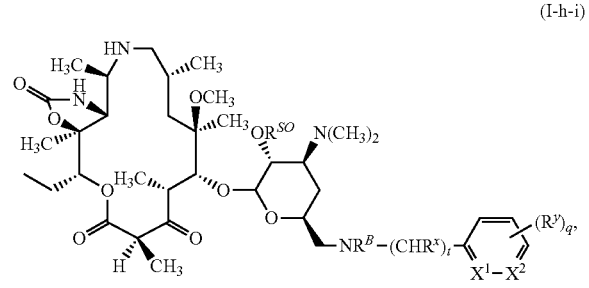
(I-h-ii)
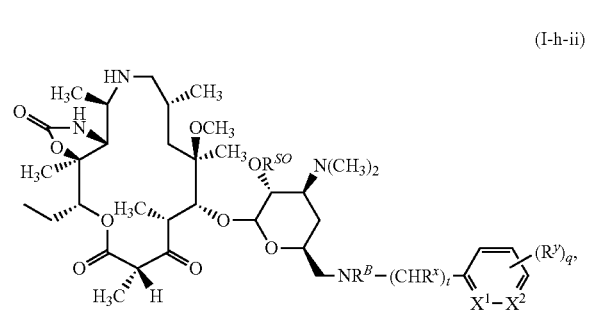
(I-i-i)
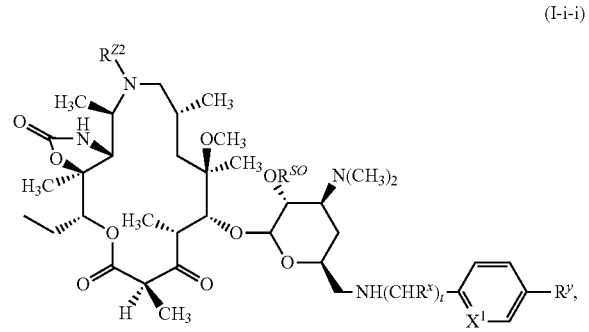
(I-i-ii)
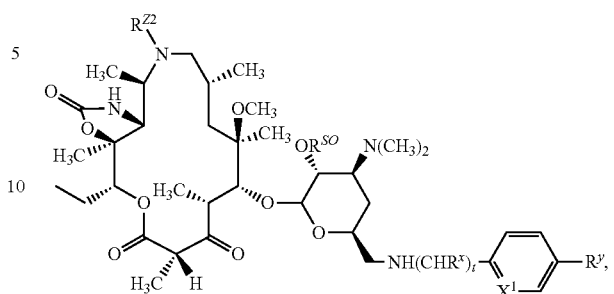
(I-j-i)
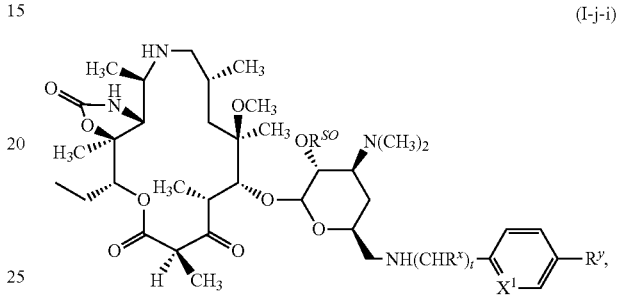
(I-j-ii)
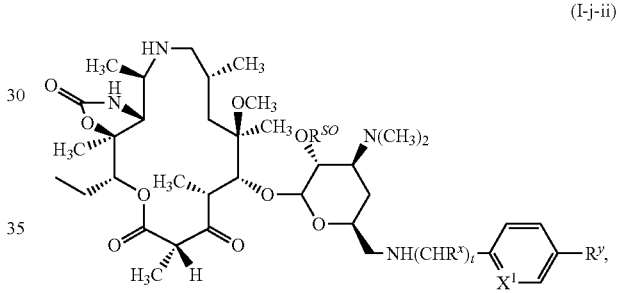
(I-k)
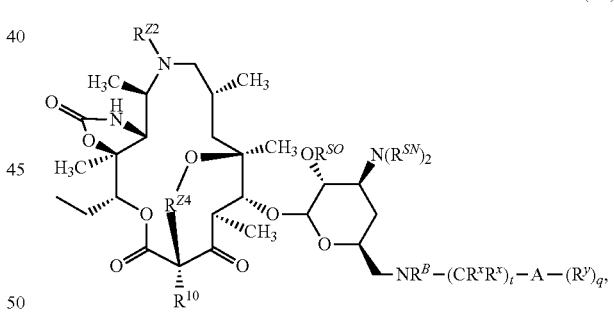
(I-l)
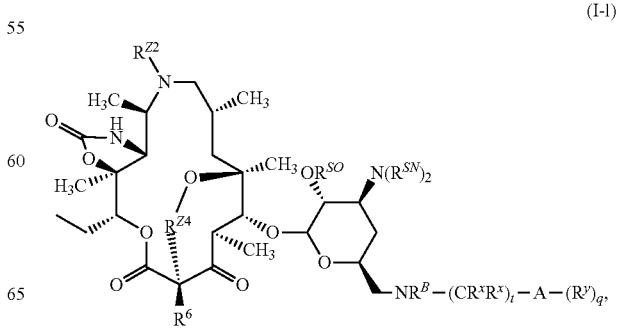

-continued

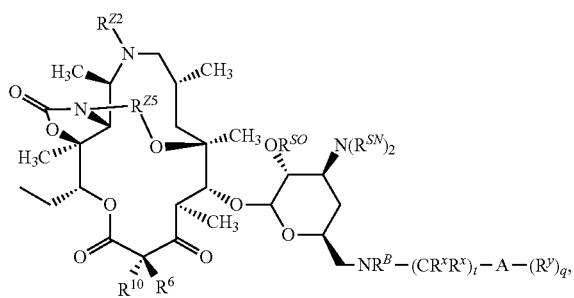
(I-m)

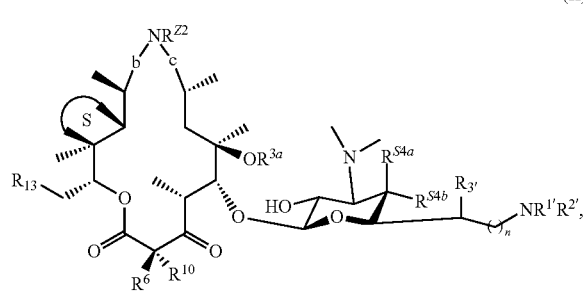
(II)

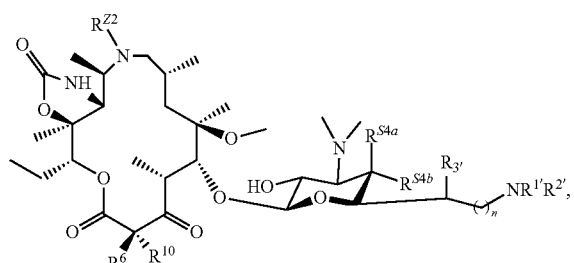
(II-a)

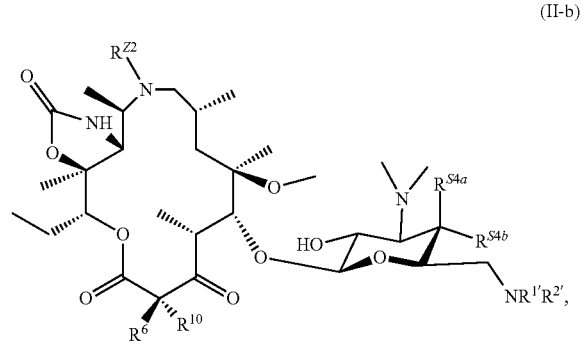
(II-b)

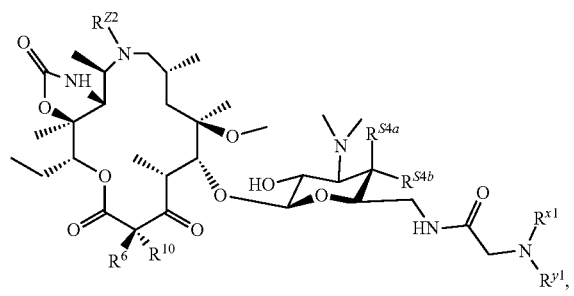
(II-c)

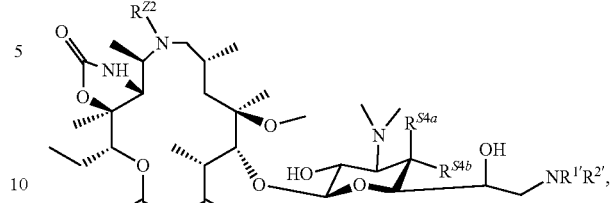
(II-d)

(II-e)

(II-f)

In another aspect, disclosed are compounds of Formula (III):

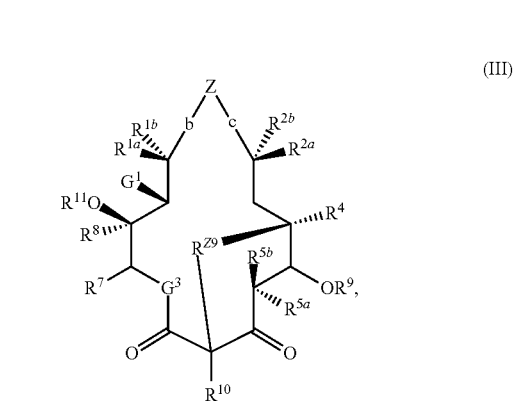
(III)

and pharmaceutically acceptable salts thereof, wherein:

Z is —C(=O)— or —NR$^{Z2}$—;

when Z is —NR$^{Z2}$—, one of b and c is CH$_2$ or —C(=O)—, and the other is a bond, or both b and c are a bond;

when Z is —C(=O)—, b and c are both a bond;

each instance of R$^{1a}$, R$^{1b}$, R$^{2a}$, and R$^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or wherein $R^{1a}$ and $R^{1b}$ or $R^{2a}$ and $R^{2b}$ can be taken together to form a carbonyl or

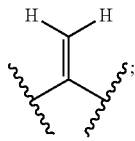 [SMILES: *C(*)=C]

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, guanidino, a nitrogen protecting group, —C(=O)$R^{Z8}$, —C(=O)N($R^{Z8}$)$_2$, or —C(=O)O$R^{Z8}$, or a group of formula:

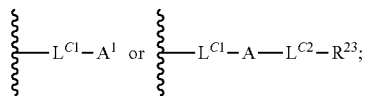

$R^{Z9}$ is optionally substituted heteroalkylene, optionally substituted heteroalkenylene, optionally substituted heteroalkynylene, optionally substituted alkylene, optionally substituted alkenylene, or optionally substituted alkynylene;

$R^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

$R^{5a}$ and $R^{5b}$ are each independently hydrogen, halogen, silyl, optionally substituted alkyl, optionally substituted carbocyclyl, or optionally substituted heterocyclyl;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)$R^{Z8}$, —C(=O)N($R^{Z8}$)$_2$, an oxygen protecting group, or a carbohydrate;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaryl, optionally substituted heteroaralkyl, —OR$^{Z8}$, —SR$^{Z8}$, —N(R$^{Z8}$)$_2$, or acyl;

$G^3$ is —O—, —S—, or —N(R$^{G1}$)—, wherein $R^{G1}$ is hydrogen, optionally substituted alkyl, or a nitrogen protecting group;

$G^1$ is —OR$^{12}$ or —NR$^{13}$R$^{14}$;

provided when $G^1$ is —OR$^{12}$, then $R^{11}$ and $R^{12}$ are joined as a group of formula —C(=O) to provide a cyclic carbonate, or $R^{11}$ and $R^{12}$ are not joined, and $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

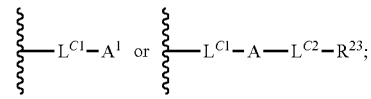

or provided when $G^1$ is —NR$^{13}$R$^{14}$, then $R^{11}$ and $R^{13}$ are joined as a group of formula —C(=O)— to provide a cyclic carbamate, or $R^{11}$ and $R^{13}$ are not joined, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, $R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)R$^{Z8}$, or —C(=O)OR$^{Z8}$, or a group of formula:

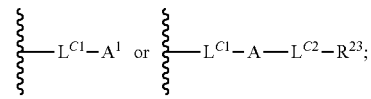

or $R^{13}$ and $R^{14}$ are joined to form an optionally substituted heterocyclyl or optionally substituted heteroaryl;

each instance of $L^{C1}$ and $L^{C2}$ is independently a bond, optionally substituted alkylene, optionally substituted alkenylene, optionally substituted alkynylene, optionally substituted heteroalkylene, optionally substituted heteroalkenylene, optionally substituted heteroalkynylene, or combinations thereof;

each instance of $A^1$ is independently a leaving group (LG), —SH, —OH, —NH$_2$, —NH—, NH$_2$, —N$_3$, —O—NH$_2$, —C(=O)R$^{X1}$,

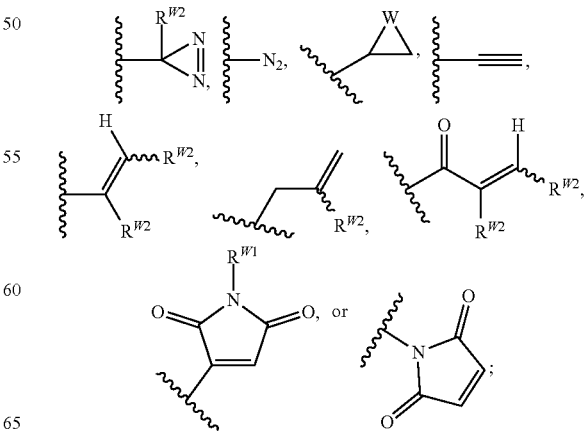

A is optionally substituted carbocyclyl, optionally substituted heterocyclyl, optionally substituted aryl, optionally substituted heteroaryl, —NH—, —NH—NH—, —NH—O—, —O—NH—, —S—, —O—,

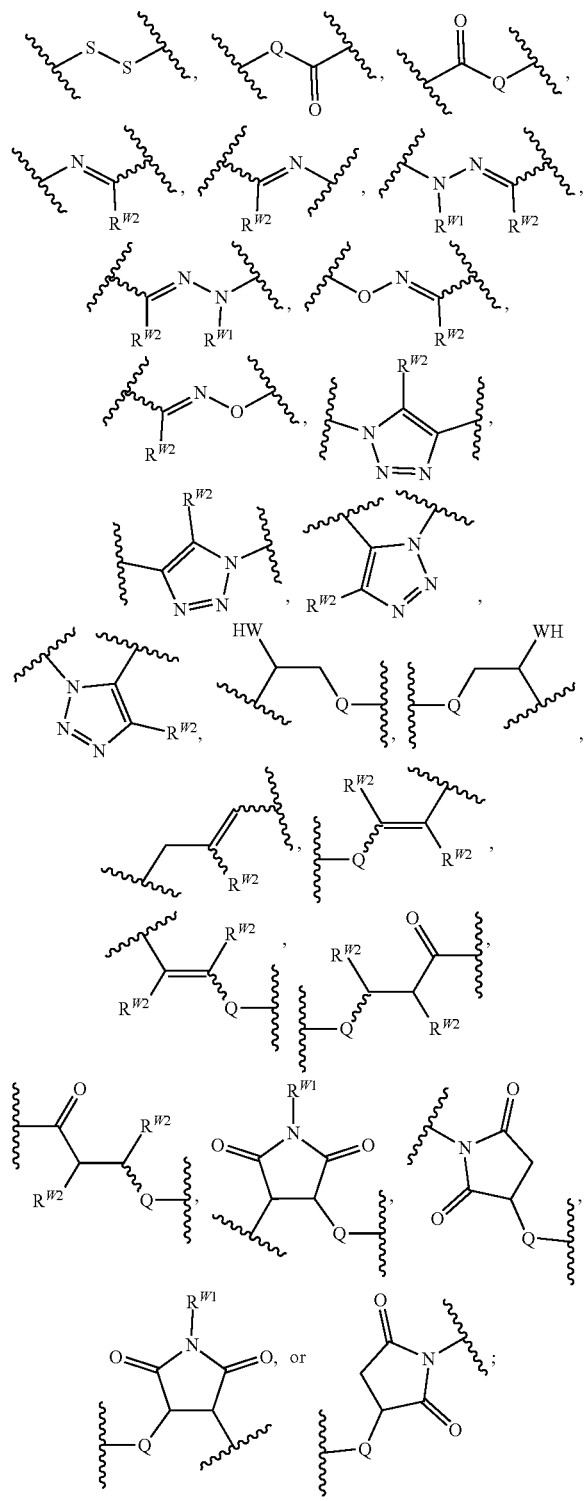

Q is —NH—, —NH—NH—, —O—NH—, —NH—O—, —S—, or —O—;
W is O, S, or NR$^{W1}$;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

R$^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two R$^{W2}$ groups are joined to form an optionally substituted cyclic moiety;

R$^{X1}$ is hydrogen, halogen, or —OR$^{X2}$, wherein R$^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

R$^{23}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of R$^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{Z8}$ groups are joined to form an optionally substituted heterocyclyl or optionally substituted heteroaryl ring.

In another aspect, disclosed are compounds of Formula (IV):

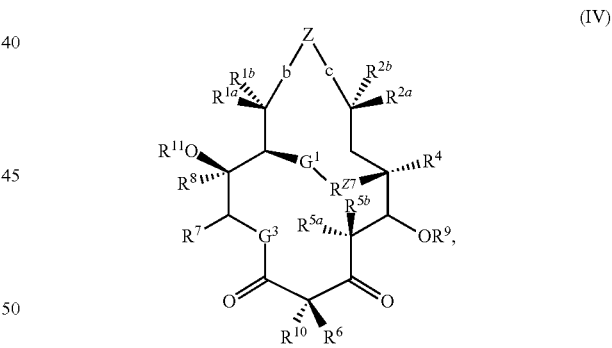

and pharmaceutically acceptable salts thereof, wherein:
Z is —C(=O)— or —NR$^{Z2}$—;
when Z is —NR$^{Z2}$—, one of b and c is CH$_2$ or —C(=O)—, and the other is a bond, or both b and c are a bond;
when Z is —C(=O)—, b and c are both a bond;
each instance of R$^{1a}$, R$^{1b}$, R$^{2a}$, and R$^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or wherein R$^{1a}$ and R$^{1b}$ or R$^{2a}$ and R$^{2b}$ can be taken together to form a carbonyl or

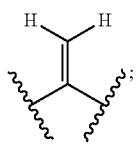 [SMILES: *C(*)=C]

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, guanidino, a nitrogen protecting group, —C(=O)$R^{Z8}$, —C(=O)N($R^{Z8}$)$_2$, or —C(=O)O$R^{Z8}$, or a group of formula:

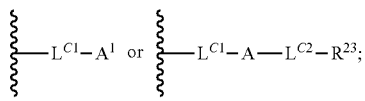

$R^{27}$ is optionally substituted heteroalkylene, optionally substituted heteroalkenylene, optionally substituted heteroalkynylene, optionally substituted alkylene, optionally substituted alkenylene, or optionally substituted alkynylene;

$R^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

$R^{5a}$ and $R^{5b}$ are each independently hydrogen, halogen, silyl, optionally substituted alkyl, optionally substituted carbocyclyl, or optionally substituted heterocyclyl;

$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, —O$R^{Z8}$, —S$R^{Z8}$, —N($R^{Z8}$)$_2$, or acyl;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)$R^{Z8}$, —C(=O)N($R^{Z8}$)$_2$, an oxygen protecting group, or a carbohydrate;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaryl, optionally substituted heteroaralkyl, —O$R^{Z8}$, —S$R^{Z8}$, —N($R^{Z8}$)$_2$, or acyl;

$G^3$ is —O—, —S—, or —N($R^{G1}$)—, wherein $R^{G1}$ is hydrogen, optionally substituted alkyl, or a nitrogen protecting group;

$G^1$ is —O— or —N$R^{13}$—;

$R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)$R^{Z8}$, or —C(=O)O$R^{Z8}$, or a group of formula:

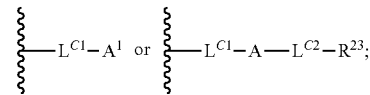

or $R^{11}$ and $R^{13}$ are joined as a group of formula —C(=O)— to provide a cyclic carbamate;

each instance of $L^{C1}$ and $L^{C2}$ is independently a bond, optionally substituted alkylene, optionally substituted alkenylene, optionally substituted alkynylene, optionally substituted heteroalkylene, optionally substituted heteroalkenylene, optionally substituted heteroalkynylene, or combinations thereof;

each instance of $A^1$ is independently a leaving group (LG), —SH, —OH, —NH$_2$, —NH—, NH$_2$, —N$_3$, —O—NH$_2$, —C(=O)$R^{X1}$,

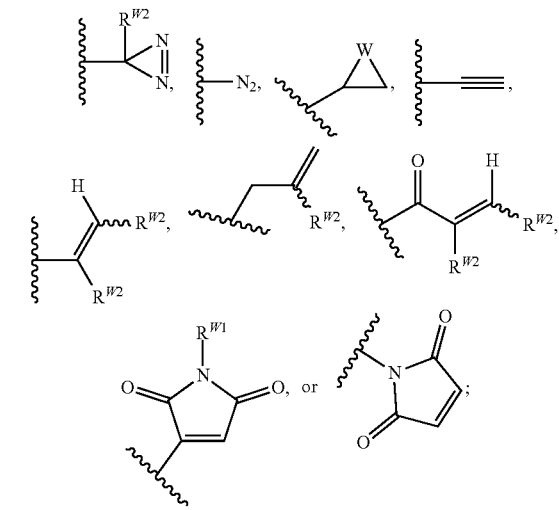

A is optionally substituted carbocyclyl, optionally substituted heterocyclyl, optionally substituted aryl, optionally substituted heteroaryl, —NH—, —NH—NH—, —NH—O—, —O—NH—, —S—, —O—,

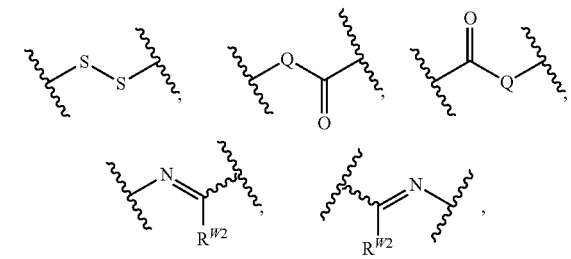

-continued

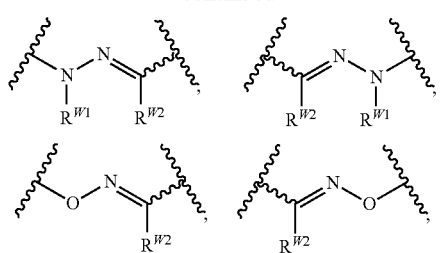

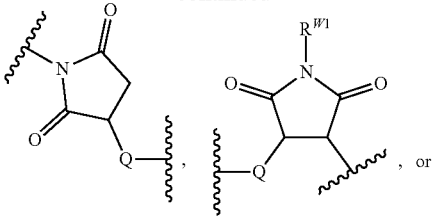

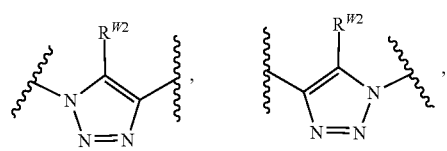

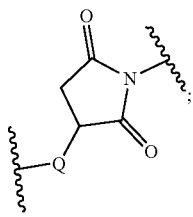, or

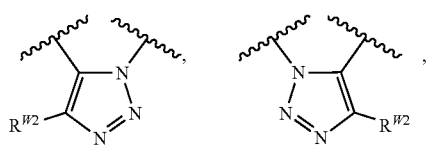

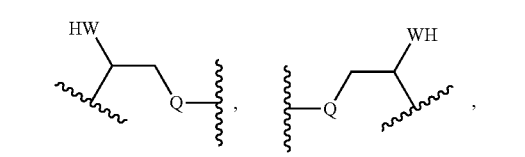

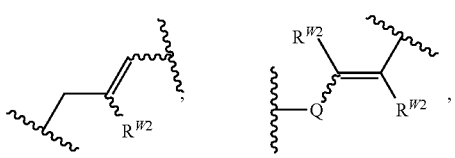

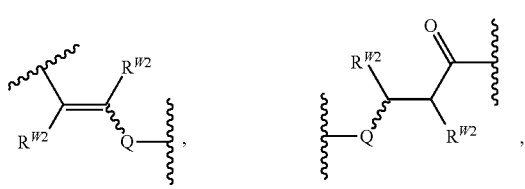

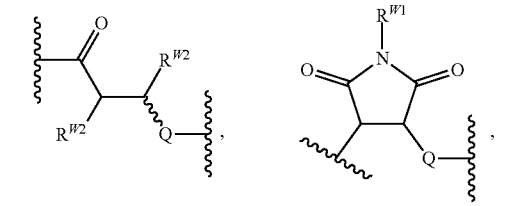

Q is —NH—, —NH—NH—, —O—NH—, —NH—O—, —S—, or —O—;

W is O, S, or $NR^{W1}$;

$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

$R^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two $R^{W2}$ groups are joined to form an optionally substituted cyclic moiety;

$R^{X1}$ is hydrogen, halogen, or —$OR^{X2}$, wherein $R^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

$R^{Z3}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocyclyl or optionally substituted heteroaryl ring.

The disclosed macrolides have anti-microbial activity and may be used to treat and/or prevent infectious diseases. Pharmaceutical compositions of the compounds, and methods of treatment using the compounds or compositions thereof are provided herein. Infectious diseases which may be treated with a compound of the invention include, but are not limited to, bacterial infections caused by *Staphylococcus*, *Acinetobacter*, *Klebsiella*, *Escherichia*, and *Pseudomonas* species.

Methods of preparing macrolides with modified C5 sugars are also provided herein. The general synthetic methodology involves construction and employment of a modified sugar component with a novel protecting group arrangement. After macrocyclization, the orthogonality of the protecting groups allows selective functionalization of the 6'-position of the sugar moiety at a late-stage intermediate. The present disclosure also provides intermediates in the preparation of the macrolides described herein. The details of certain embodiments of the invention are set forth in the Detailed Description of Certain Embodiments, as described below. Other features, objects, and advantages of the invention will be apparent from the Definitions, Drawings, Examples, and Claims.

DETAILED DESCRIPTION OF CERTAIN EMBODIMENTS

Figure 1:
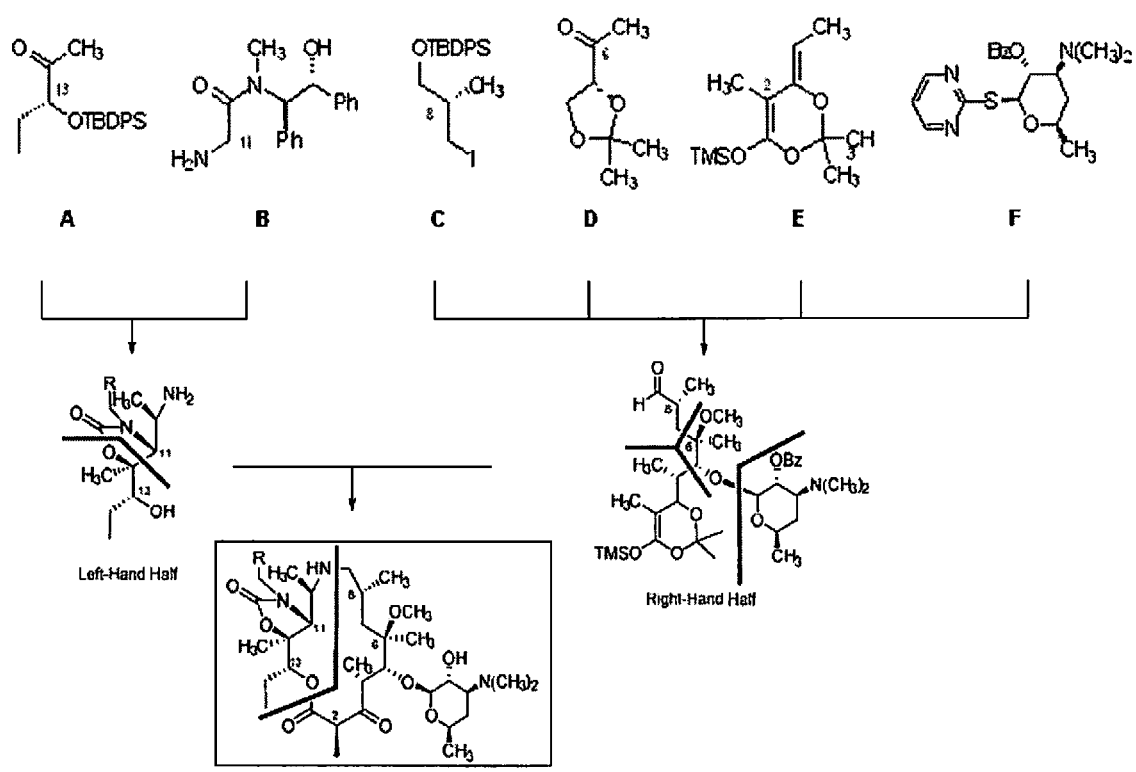
FIG. 1 is a retrosynthetic scheme showing the modular synthesis of exemplary 15-membered azaketolides.

The macrolides disclosed herein include 14-membered ketolides and 14-15-membered azaketolides. The disclosed macrolides may have a bicyclic structure. The disclosed macrolides may include 6'-modified desosamines. The 6'-modified structure of the disclosed compounds provide an unexpected and potent activity against Gram negative bacteria. Also disclosed are methods for the preparation of the disclosed macrolides, enabling the preparation of novel macrolides.

Unless otherwise stated, any formulae described herein are also meant to include salts, solvates, hydrates, polymorphs, co-crystals, tautomers, stereoisomers, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of $^{19}$F with $^{18}$F, or the replacement of a $^{12}$C by a $^{13}$C or $^{14}$C are within the scope of the disclosure. In certain embodiments, the provided compound is a deuterated form of any of the formulae described herein.

In one aspect, the invention provides macrolides with modified sugars at the C5 position of the macrolide (e.g., desosamine analogues), wherein the sugar is modified at the C6 position of the sugar. In certain embodiments, the invention provides compounds of Formula (I):

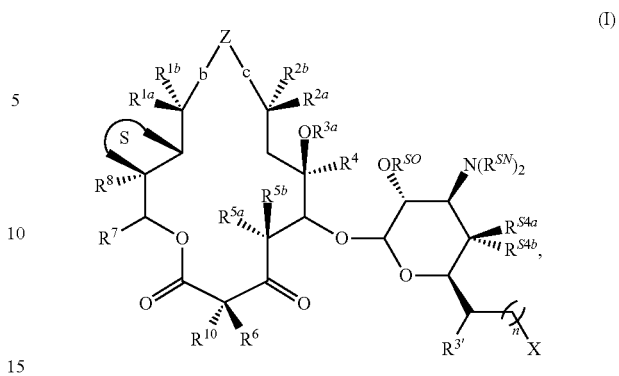

and pharmaceutically acceptable salts thereof, wherein: ring S is

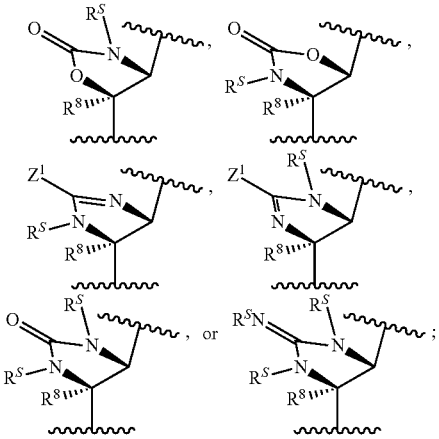

$Z^1$ is $N(R^S)_2$ or $C(R^S)_3$ and each $R^S$ is independently H, $C_1$-$C_6$ alkyl, or $C_2$-$C_6$ alkenyl;

Z is —C(=O)— or —NR$^{Z2}$—;

$R^{Z2}$ is hydrogen, optionally substituted alkyl, acyl, or a nitrogen protecting group;

when Z is —NR$^{Z2}$—, one of b and c is CH$_2$ or —C(=O)—, and the other is a bond, or both b and c are a bond;

when Z is —C(=O)—, b and c are both a bond;

n is 0 or 1;

X is optionally substituted $C_{1-6}$ alkyl, —OR$^A$, or —NR$^B$—(CR$^x$R$^x$)$_t$-A-(R$^y$)$_q$;

t is 0, 1, or 2;

q is 1, 2, or 3;

$R^A$ is hydrogen, optionally substituted alkyl, optionally substituted heteroalkyl, optionally substituted alkenyl, or —C(=O)—R$^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-6}$ alkyl sulfonyl, heteroaryl, or heteroaryloxy;

or when A is a bond, and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{3'}$ is H, $C_{1-3}$ alkyl, OH, or oxo;

each of $R^{S4a}$ and $R^{S4b}$ is independently hydrogen, halogen, optionally substituted $C_{1-6}$ alkyl, or —$OR^{SO}$;

each $R^{SN}$ is independently hydrogen, optionally substituted $C_{1-6}$ alkyl, or a nitrogen protecting group, or two $R^{SN}$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_{1-6}$ alkyl, or —$OR^{SO}$;

each $R^{SO}$ is independently hydrogen, optionally substituted $C_{1-6}$ alkyl, a carbohydrate, or an oxygen protecting group;

each of $R^{1a}$ and $R^{1b}$ is independently hydrogen, halogen, or optionally substituted alkyl;

each of $R^{2a}$ and $R^{2b}$ is independently hydrogen, halogen, or optionally substituted alkyl;

$R^{3a}$ is hydrogen, optionally substituted alkyl, optionally substituted alkenyl, optionally substituted alkynyl, or an oxygen protecting group;

or $R^{3a}$ and $R^6$ are joined to form an optionally substituted heterocyclyl ring; or $R^{3a}$ and $R^{10}$ are joined to form an optionally substituted heterocyclyl ring, or $R^{3a}$ and $R^S$ are joined to form an optionally substituted heterocyclyl ring;

$R^4$ is hydrogen, halogen, or optionally substituted alkyl;

each of $R^{5a}$ and $R^{5b}$ is independently hydrogen, halogen, or optionally substituted alkyl;

$R^6$ is hydrogen, halogen, or optionally substituted alkyl;

$R^{10}$ is hydrogen, halogen, or optionally substituted alkyl;

$R^7$ is hydrogen, halogen, or optionally substituted alkyl, $C_2$-$C_6$-alkenyl, $C_2$-$C_6$-alkynyl, or $C_1$-$C_6$-alkoxy; and $R^8$ is hydrogen, halogen, or optionally substituted $C_{1-6}$ alkyl.

Group Z

As generally defined herein, Z may be —C(=O)— or —$NR^{Z2}$—. Attached to group Z is a methylene (i.e., —$CH_2$—) group, which may be represented by variable b or variable c. In certain embodiments, when Z is —C(=O)—, b and c are both a bond to give a 14-membered ketolide. In certain embodiments, Z is —$NR^{Z2}$—, and b and c are both a bond to give a 14-membered azaketolide. In certain embodiments, Z is —$NR^{Z2}$—; b is $CH_2$; and c is a bond to give a 15-membered azaketolide. In certain embodiments, Z is —$NR^{Z2}$—; c is $CH_2$; and b is a bond to give a 15-membered azaketolide. In certain embodiments, Z is $NR^{Z2}$—; c is C=O; and b is a bond to give a 15-membered azaketolide. In certain embodiments, Z is $NR^{Z2}$—; b is C=O; and c is a bond to give a 15-membered azaketolide. In certain embodiments, Z is —NH—, and b and c are both a bond. In certain embodiments, Z is —NH—; b is $CH_2$; and c is a bond. In certain embodiments, Z is —NH—; c is $CH_2$; and b is a bond.

In certain embodiments, $R^{Z2}$ is hydrogen, optionally substituted alkyl, acyl, or a nitrogen protecting group. In certain embodiments, $R^{Z2}$ is hydrogen.

In certain embodiments, $R^{Z2}$ is acyl. In certain embodiments, $R^{Z2}$ is an aldehyde (—CHO). In certain embodiments $R^{Z2}$ is a nitrogen protecting group.

In certain embodiments, $R^{Z2}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$ alkyl. In certain embodiments, $R^{Z2}$ is —$CH_3$. In certain embodiments, $R^{Z2}$ is alkyl substituted with one or more halogen atoms, e.g., optionally substituted haloalkyl; e.g., —$CF_3$, —$CF_2CF_3$, or —$CF_2H$. In certain embodiments, $R^{Z2}$ is —$CH_2CHO$.

Group X

As generally defined herein, X is optionally substituted $C_{1-6}$ alkyl, —$OR^A$ or —$NR^B$—$(CR^xR^x)_r$-A-$(R^y)_q$. In certain embodiments, X is —$OR^A$. In certain embodiments, X is —$NR^B$—$(CR^xR^x)_r$-A-$(R^y)_q$. In certain embodiments, X is optionally substituted $C_{1-6}$ alkyl.

In certain embodiments, X is optionally substituted $C_{1-6}$ alkyl, and X is: Me,

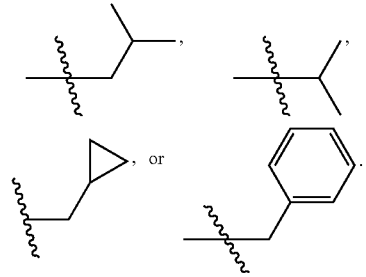

As generally defined herein, $R^A$ is hydrogen, optionally substituted alkyl, optionally substituted heteroalkyl, optionally substituted alkenyl, or —C(=O)—$R^S$.

In certain embodiments, $R^A$ is hydrogen. In some embodiments, $R^A$ is optionally substituted alkyl. In some embodiments, $R^A$ is optionally substituted $C_{1-6}$ alkyl. In some embodiments, $R^A$ is $C_{1-6}$ alkyl. In some embodiments, $R^A$ is methyl. In some embodiments, $R^A$ is ethyl, propyl, or butyl. In some embodiments, $R^A$ is optionally substituted alkenyl, e.g., $C_2$-$C_6$ alkenyl. In some embodiments, $R^A$ is optionally substituted heteroalkyl, e.g., $C_2$-$C_6$ heteroalkyl.

$R^A$ may include one or more $R^{S1}$. $R^{S1}$ may be optionally substituted aryl or optionally substituted heteroaryl. In some embodiments, $R^{S1}$ is optionally substituted aryl. In some embodiments, $R^{S1}$ is optionally substituted heteroaryl.

In certain embodiments, X is —$OR^A$ and —$OR^A$ is:

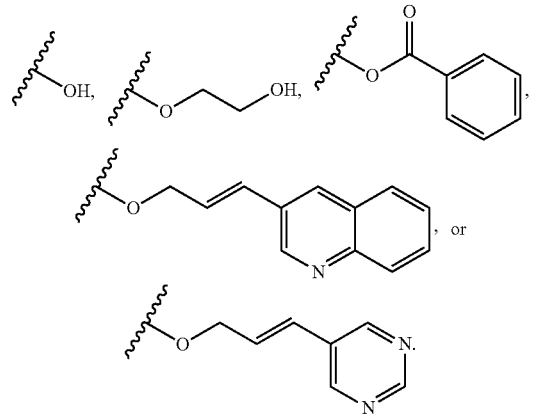

In certain embodiments, X is —NR$^B$—(CR$^x$R$^x$)$_t$-A-(R$^y$)$_q$.

In certain embodiments, R$^B$ is hydrogen, optionally substituted C$_1$-C$_6$ alkyl, optionally substituted C$_3$-C$_6$ cycloalkyl, or C(O)CH$_2$NR$^{x1}$R$^{y1}$. In certain embodiments, R$^B$ is hydrogen or C$_{1-3}$ alkyl. In some embodiments, R$^B$ is hydrogen. In certain embodiments, R$^B$ is optionally substituted C$_1$-C$_6$ alkyl. In some embodiments, R$^B$ is substituted C$_{1-3}$ alkyl. In some embodiments, R$^B$ is methyl. In some embodiments, R$^B$ is ethyl. In some embodiments, R$^B$ is propyl.

In certain embodiments, R$^B$ is optionally substituted C$_3$-C$_6$ cycloalkyl. In certain embodiments, R$^B$ is optionally substituted cyclopropyl. In certain embodiments, R$^B$ is optionally substituted cyclobutyl. In certain embodiments, R$^B$ is optionally substituted cyclopentyl. In certain embodiments, R$^B$ is optionally substituted cyclohexyl.

In certain embodiments, R$^B$ is C(O)CH$_2$NR$^{x1}$R$^{y1}$; and R$^{x1}$ and R$^{y1}$ are each independently hydrogen, optionally substituted C$_1$-C$_6$ alkyl, or optionally substituted C$_3$-C$_6$ cycloalkyl, or R$^{x1}$ and R$^{y1}$ together along with the nitrogen to which they are attached form a 4, 5, 6, or 7-membered optionally substituted ring containing up to two additional heteroatoms.

In certain embodiments, each occurrence of R$^x$ is independently hydrogen or C$_{1-3}$ alkyl. In some embodiments, each occurrence of R$^x$ is independently hydrogen, methyl, ethyl, or propyl. In some embodiments, each occurrence of R$^x$ is hydrogen.

In certain embodiments, R$^B$ is hydrogen and at least one occurrence of R$^x$ is hydrogen. In certain embodiments, R$^B$ is hydrogen and each occurrence of R$^x$ is hydrogen.

In certain embodiments, t is 0, 1, or 2. In certain embodiments, t is 0 or 1. In certain embodiments, t is 1 or 2. In certain embodiments, t is 0. In certain embodiments, t is 1. In certain embodiments, t is 2.

In certain embodiments, A is arylene, heteroarylene, heterocyclylene, cycloalkylene, alkylene, alkenylene, alkynylene, or a bond.

In certain embodiments, A is arylene. In certain embodiments, A is phenylene.

In certain embodiments, A is heteroarylene. In certain embodiments, A is pyridinylene. In certain embodiments, A is pyrazolylene. In certain embodiments, A is quinaxolylene. In certain embodiments, A is quinolinylene.

In certain embodiments, A is heterocyclylene. In certain embodiments, A is azetidinylene. In certain embodiments, A is pyrrolidinylene. In certain embodiments, A is piperidinylene. In certain embodiments, A is piperazinylene. In certain embodiments, A is morpholinylene. In certain embodiments, A is a 4-6 membered heterocyclylene comprising at least one oxygen atom and no nitrogen atoms. In certain embodiments, A is tetrahydropyranylene. In certain embodiments, A is dioxanylene. In certain embodiments, A is tetrahydrofuranylene. In certain embodiments, A is oxetanylene.

In certain embodiments, A is alkylene. In certain embodiments, A is C$_{1-20}$ alkylene. In certain embodiments, A is C$_{1-12}$ alkylene. In certain embodiments, A is C$_{6-12}$ alkylene. In certain embodiments, A is C$_{6-12}$ alkylene. In certain embodiments, A is alkenylene. In certain embodiments, A is C$_{2-12}$ alkenylene. In certain embodiments, A is alkynylene. In certain embodiments, A is C$_{2-12}$ alkynylene. In certain embodiments, A is C$_{2-6}$ alkynylene. In certain embodiments, A is propynylene.

In certain embodiments, A is cycloalkylene. In certain embodiments, A is C$_{3-8}$ cycloalkylene. In certain embodiments, A is C$_{3-6}$ cycloalkylene. In certain embodiments, A is C$_{3-5}$ cycloalkylene. In certain embodiments, A is C$_{3-4}$ cycloalkylene. In certain embodiments, A is cyclopropylene.

In certain embodiments, A is cyclobutylene. In certain embodiments, A is cyclopentylene. In certain embodiments, A is cyclohexylene. In certain embodiments, A is a bicyclic cycloalkylene. In certain embodiments, A is bicyclo[1.1.1]pentylene.

In certain embodiments, A is a bond.

In certain embodiments, each occurrence of R$^y$ is independently, hydrogen, C$_{1-6}$ alkyl, halogen, cyano, dialkylamino, haloalkyl, C(O)OC$_{1-3}$ alkyl, C(O)OH, C(O)CH$_2$NR$^{x1}$R$^{y1}$, C$_{1-6}$ alkylsulfonyl, heteroaryl, or heteroaryloxy. In certain embodiments, R$^y$ is hydrogen. In certain embodiments, each occurrence of R$^y$ is independently hydrogen or halogen. In certain embodiments, each occurrence of R$^y$ is independently hydrogen or C$_{1-6}$ alkyl. In certain embodiments, each occurrence of R$^y$ is independently hydrogen or cyano. In certain embodiments, each occurrence of R$^y$ is independently hydrogen or haloalkyl. In certain embodiments, each occurrence of R$^y$ is independently hydrogen or dialkylamino. In certain embodiments, each occurrence of R$^y$ is independently hydrogen or C$_{1-6}$ alkylsulfonyl. In certain embodiments, each occurrence of R$^y$ is independently hydrogen or heteroaryl. In certain embodiments, each occurrence of R$^y$ is independently hydrogen or heteroaryloxy. In certain embodiments, each occurrence of R$^y$ is independently hydrogen, Cl, Br, I, or F. In certain embodiments, each occurrence of R$^y$ is independently Cl, Br, I, or F. In certain embodiments, each occurrence of R$^y$ is independently Cl, Br, or F. In certain embodiments, each occurrence of R$^y$ is independently Cl or F. In certain embodiments, each occurrence of R$^y$ is F.

In certain embodiments, each occurrence of R$^y$ is independently, C(O)OC$_{1-3}$ alkyl, C(O)OH, or C(O)CH$_2$NR$^{x1}$R$^{y1}$; and R$^{x1}$ and R$^{y1}$ are each independently hydrogen, optionally substituted C$_1$-C$_6$ alkyl, or optionally substituted C$_3$-C$_6$ cycloalkyl, or R$^{x1}$ and R$^{y1}$ together along with the nitrogen to which they are attached form a 4, 5, 6, or 7-membered optionally substituted ring containing up to two additional heteroatoms. In certain embodiments, each occurrence of R$^y$ is C(O)OC$_{1-3}$ alkyl. In certain embodiments, each occurrence of R$^y$ is C(O)OH. In certain embodiments, each occurrence of R$^y$ is C(O)CH$_2$NR$^{x1}$R$^{y1}$; and R$^{x1}$ and R$^{y1}$ are each independently hydrogen, optionally substituted C$_1$-C$_6$ alkyl, or optionally substituted C$_3$-C$_6$ cycloalkyl, or R$^{x1}$ and R$^{y1}$ together along with the nitrogen to which they are attached form a 4, 5, 6, or 7-membered optionally substituted ring containing up to two additional heteroatoms.

In certain embodiments, q is 1, 2, or 3. In certain embodiments, q is 1 or 2. In certain embodiments, q is 2 or 3. In certain embodiments, q is 1. In certain embodiments, q is 2. In certain embodiments, q is 3.

In certain embodiments, A is a bond; t is 0, R$^B$ and R$^y$ together along with the nitrogen to which they are attached optionally form a 4, 5, 6, or 7-membered optionally substituted ring containing up to two additional heteroatoms.

In certain embodiments, X is

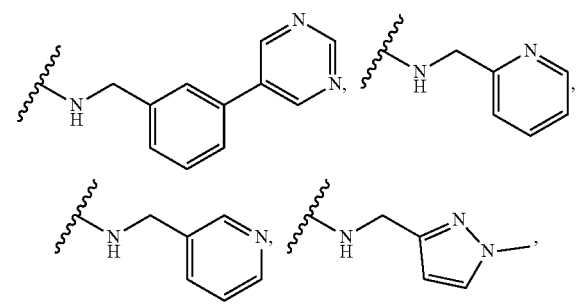

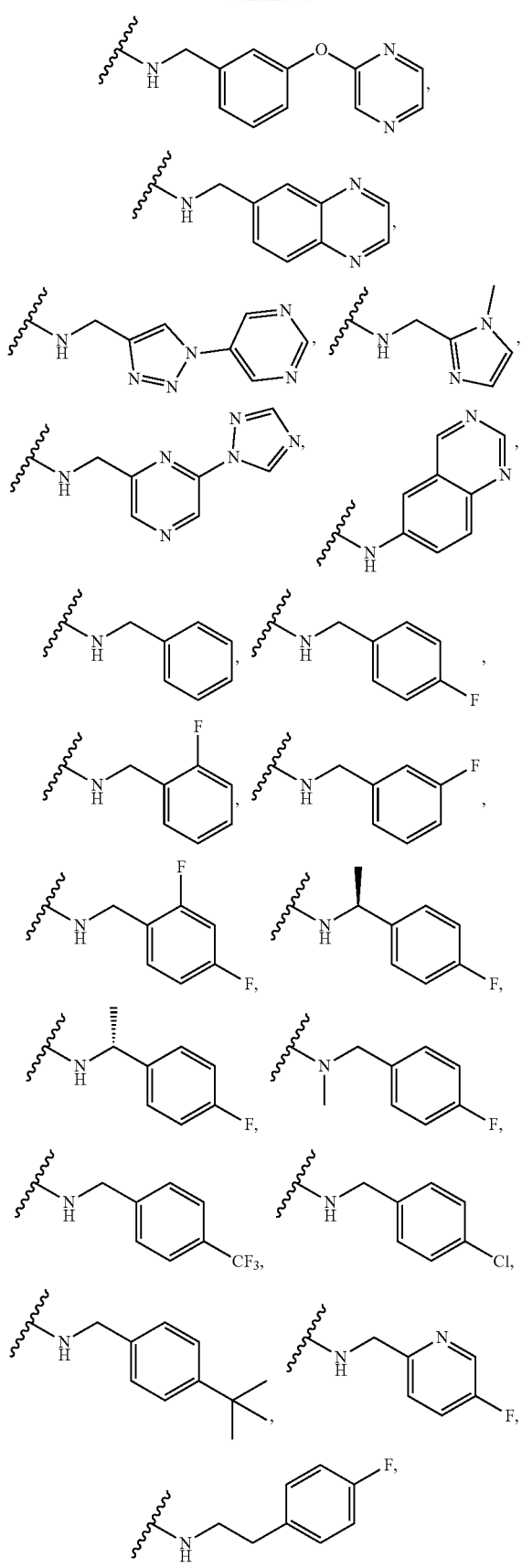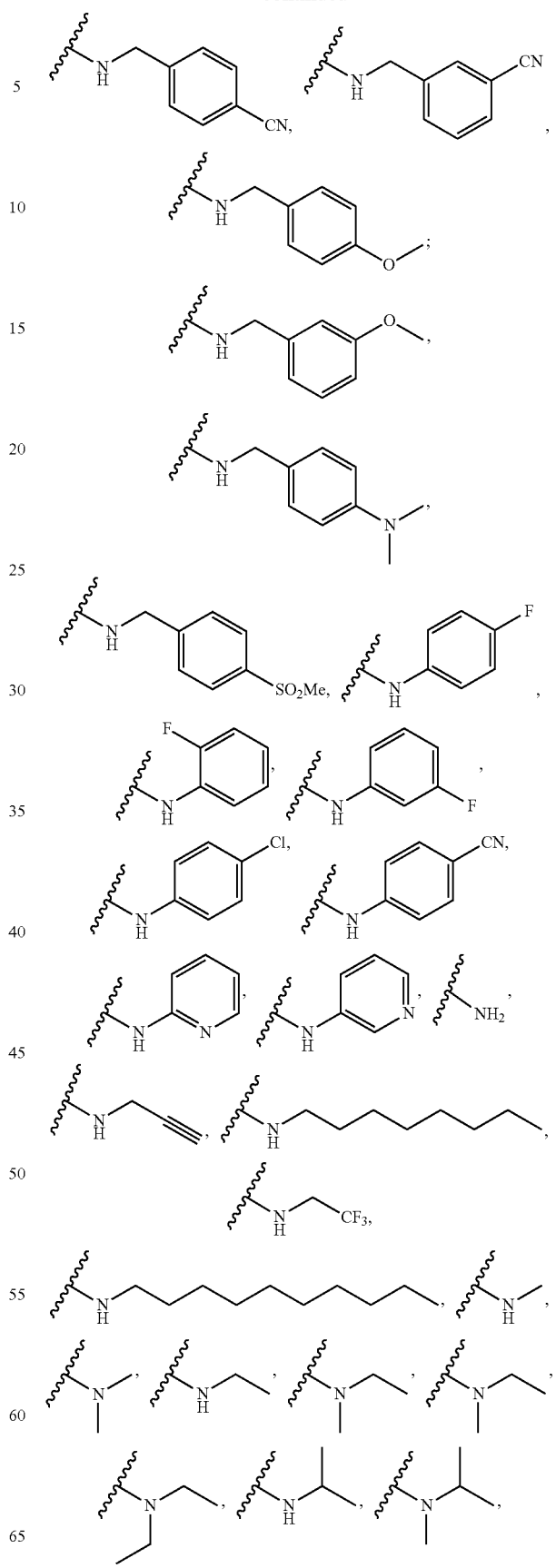

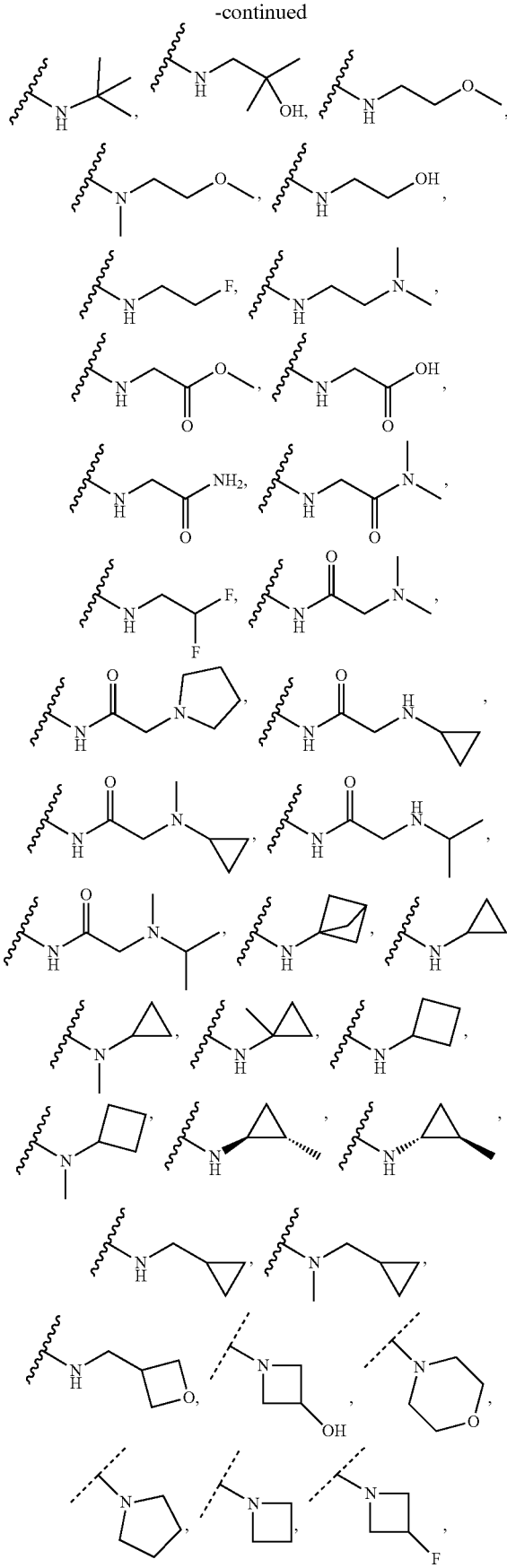
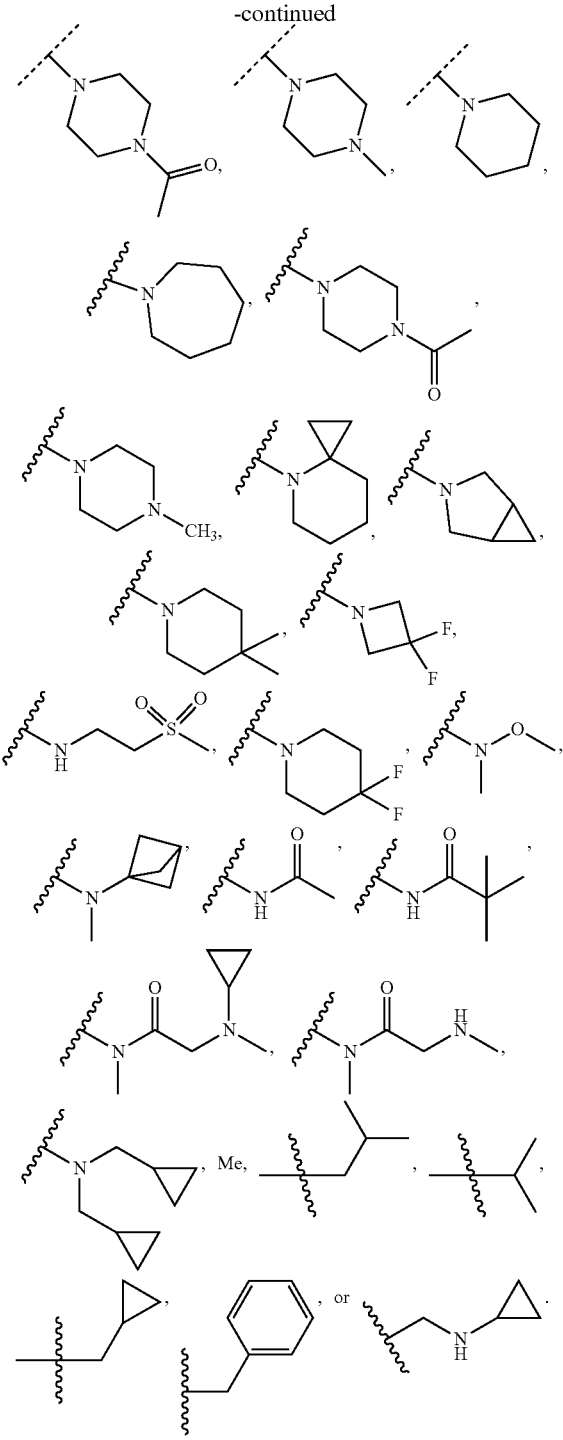
In certain embodiments, X is —NR$^B$—(CR$^x$R$^x$)$_t$-A-(R$^y$)$_q$, and —NR$^B$—(CR$^x$R$^x$)$_t$-A-(R$^y$)$_q$ is:
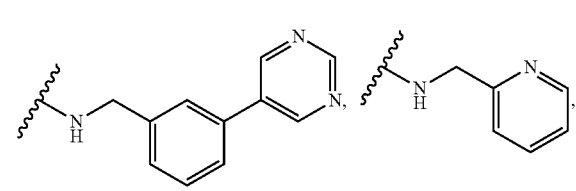

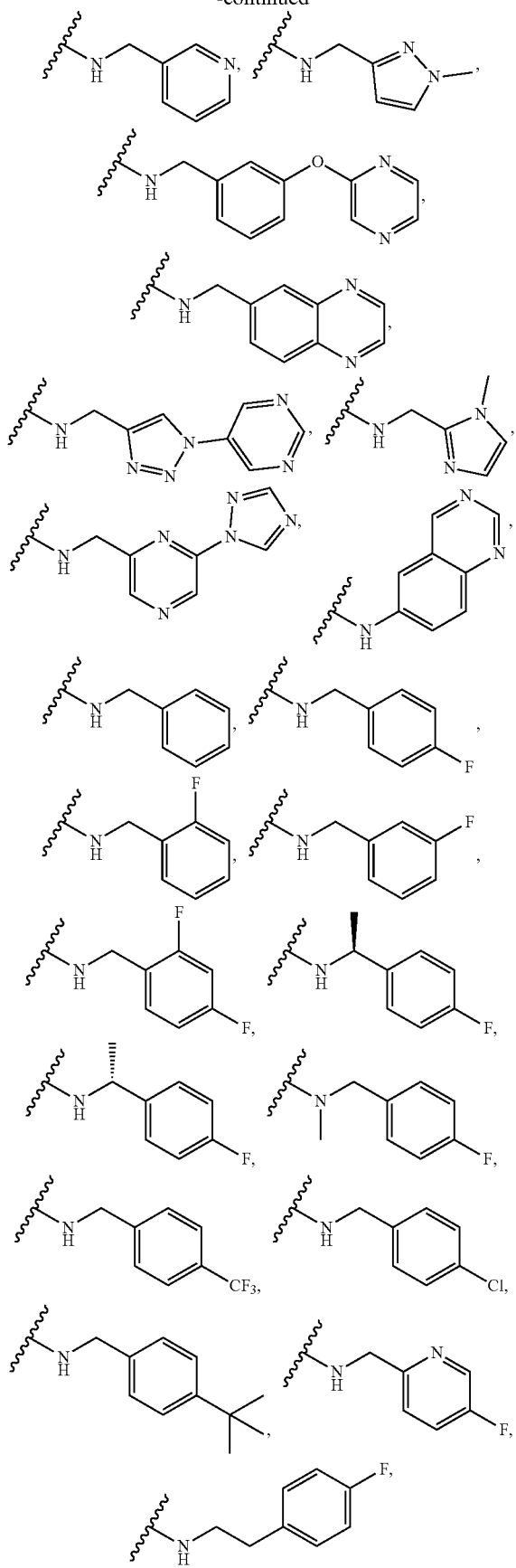
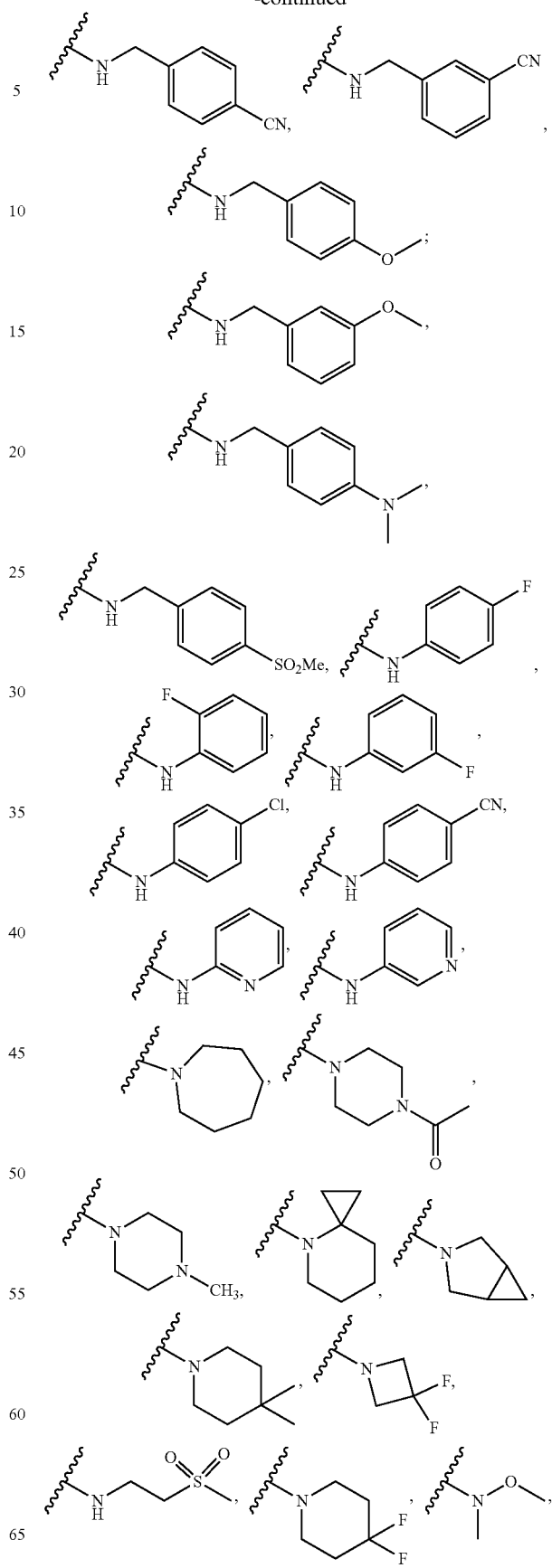

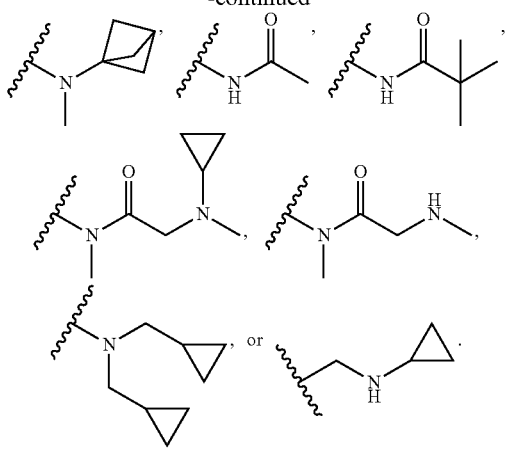
In certain embodiments, X is
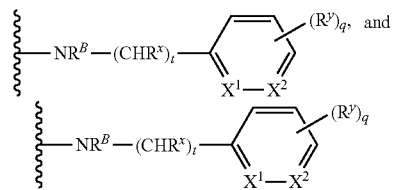
is:
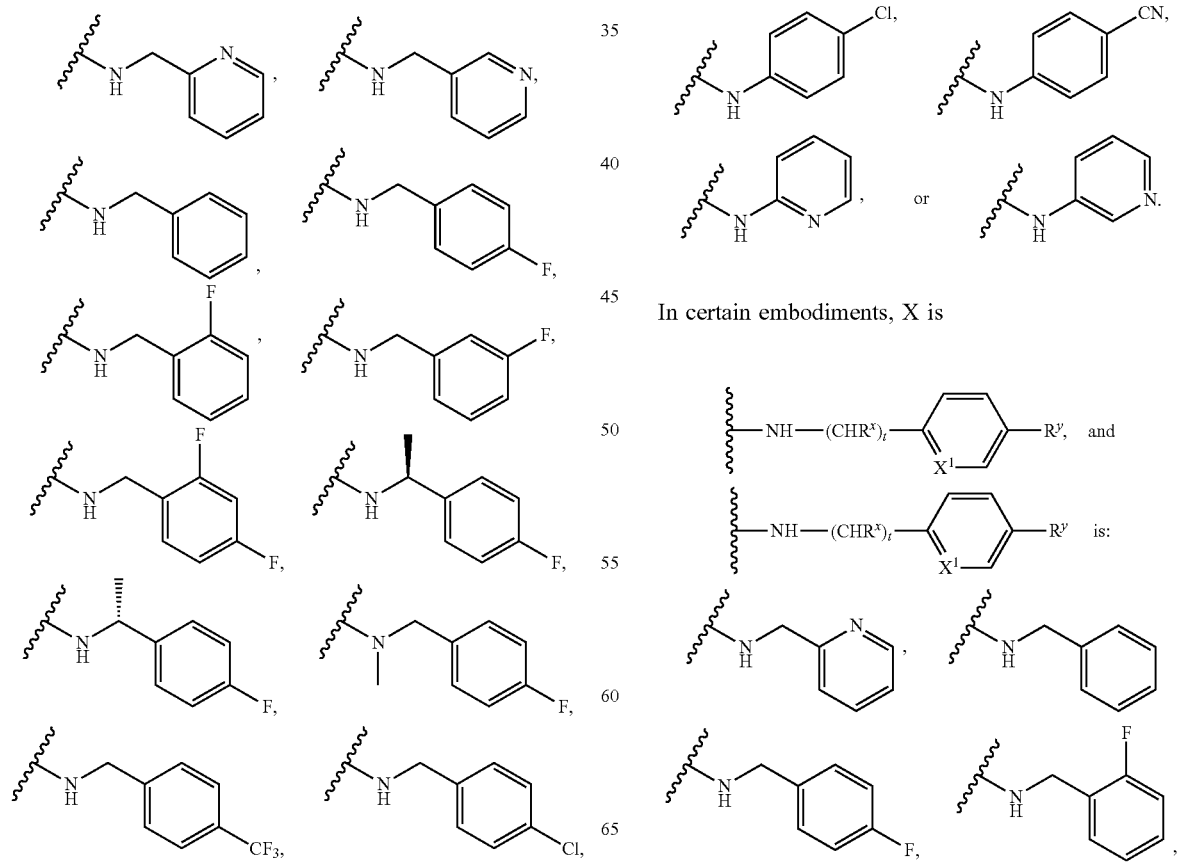
In certain embodiments, X is
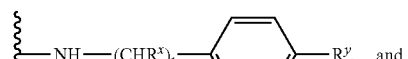
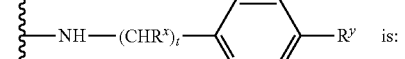
is:
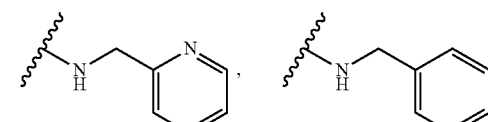
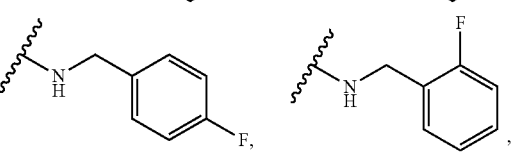

-continued
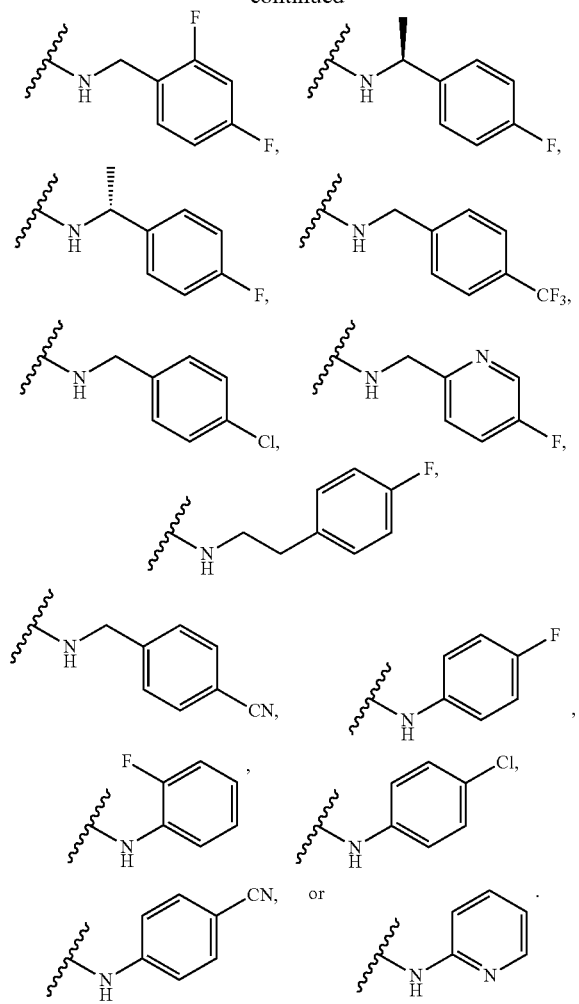
In certain embodiments, X is —NR$^B$—(CR$^x$R$^x$)$_t$-A-(R$^y$)$_q$, and —NR$^B$—(CR$^x$R$^x$)$_t$-A-(R$^y$)$_q$ is:
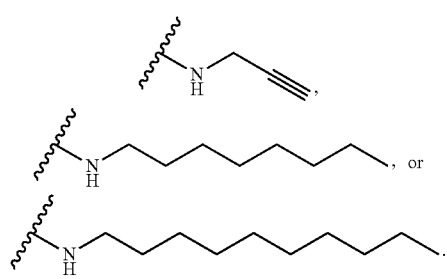
In certain embodiments, X is —NR$^B$—(CR$^x$R$^x$)$_t$-A-(R$^y$)$_q$, and —NR$^B$—(CR$^x$R$^x$)$_t$-A-(R$^y$)$_q$ is:
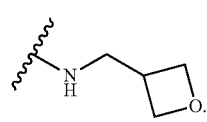
In certain embodiments, X is:
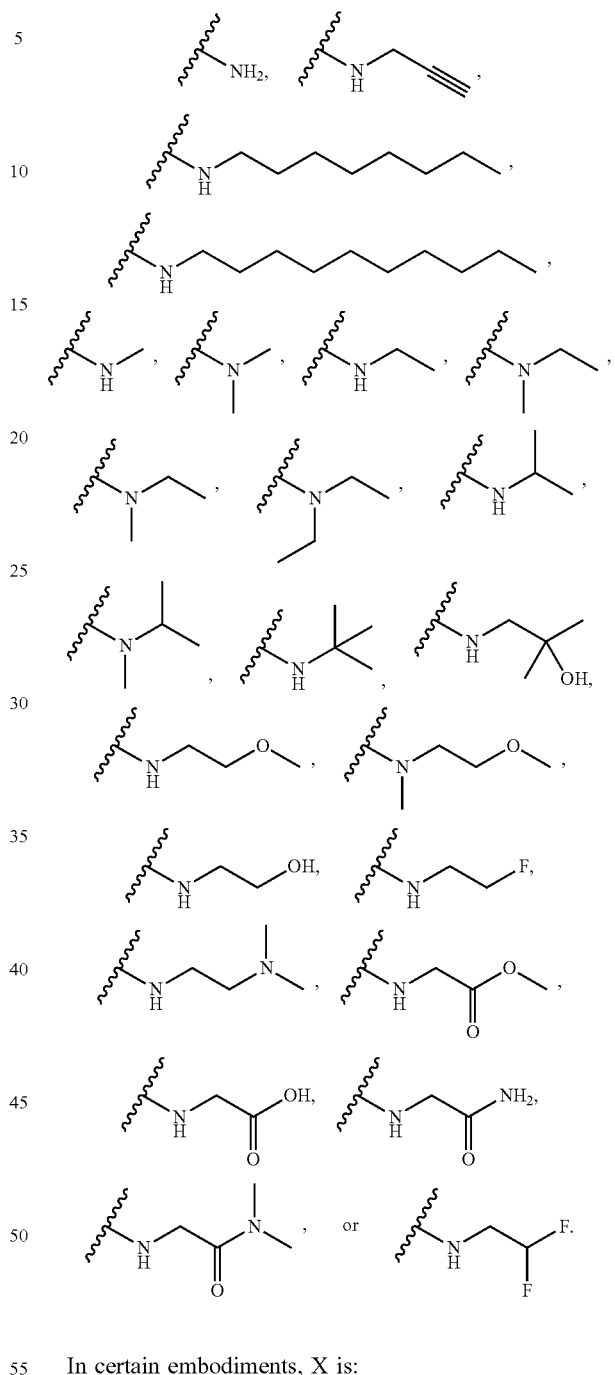
In certain embodiments, X is:
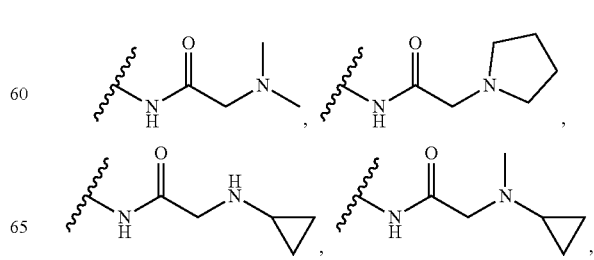

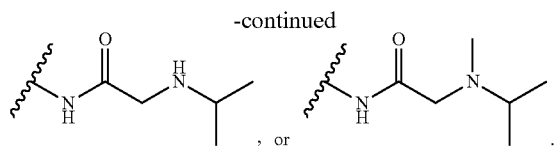, or

In certain embodiments, X is:

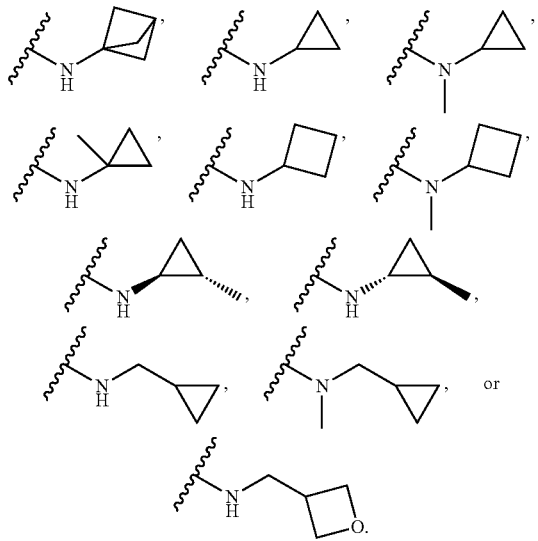

In certain embodiments, X is:

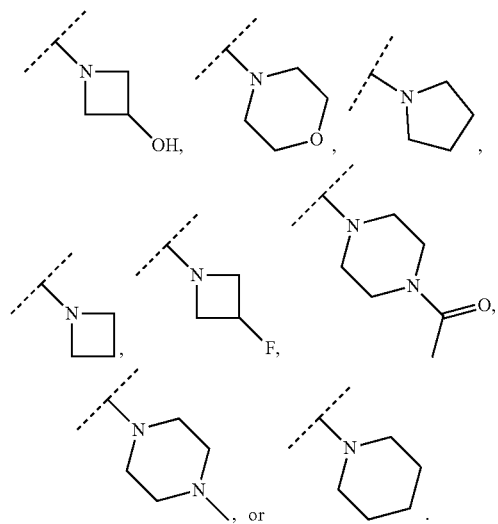

Group R³'

In certain embodiments, R³' is hydrogen, $C_{1-3}$ alkyl, OH, or oxo. In certain embodiments, R³' is hydrogen, $C_{1-3}$ alkyl, OH, or oxo; and n is 1. In certain embodiments, R³' is hydrogen or $C_{1-3}$ alkyl; and n is 0. In certain embodiments, R³' is hydrogen; and n is 0 or 1. In certain embodiments, R³' is hydrogen; and n is 0. In certain embodiments, R³' is hydrogen; and n is 1. In certain embodiments, R³' is OH or oxo; and n is 1. In certain embodiments, R³' is OH; and n is 1.

Groups $R^{S4a}$ and $R^{S4b}$

As generally defined herein, each of $R^{S4a}$ and $R^{S4b}$ may independently be hydrogen, halogen, optionally substituted $C_{1-3}$ alkyl, or $-OR^{SO}$. In certain embodiments, $R^{S4a}$ and $R^{S4b}$ are hydrogen. In certain embodiments, $R^{S4a}$ and $R^{S4b}$ are halogen. In certain embodiments, $R^{S4a}$ and $R^{S4b}$ are optionally substituted $C_{1-3}$ alkyl. In certain embodiments, $R^{S4a}$ and $R^{S4b}$ are $C_{1-3}$ alkyl. In certain embodiments, $R^{S4a}$ is hydrogen, and $R^{S4b}$ is halogen. In certain embodiments, $R^{S4a}$ is hydrogen, and $R^{S4b}$ is optionally substituted $C_{1-3}$ alkyl. In certain embodiments, $R^{S4a}$ is hydrogen, and $R^{S4b}$ is $C_{1-3}$ alkyl. In certain embodiments, $R^{S4a}$ is hydrogen, and $R^{S4b}$ is $-OR^{SO}$. In certain embodiments, $R^{S4b}$ is hydrogen, and $R^{S4a}$ is halogen. In certain embodiments, $R^{S4b}$ is hydrogen, and $R^{S4a}$ is optionally substituted $C_{1-6}$ alkyl. In certain embodiments, $R^{S4b}$ is hydrogen, and $R^{S4a}$ is $C_{1-6}$ alkyl. In certain embodiments, $R^{S4b}$ is hydrogen, and $R^{S4a}$ is $-OR^{SO}$.

In some embodiments, $R^{S4A}$ is hydrogen. In some embodiments, $R^{S4A}$ is $-F$. In some embodiments, $R^{S4a}$ is $-Cl$, $-Br$, or $-I$. In some embodiments, $R^{S4a}$ is optionally substituted alkyl. In some embodiments, $R^{S4a}$ is optionally substituted $C_{1-6}$ alkyl. In some embodiments, $R^{S4a}$ is $C_{1-6}$ alkyl. In some embodiments, $R^{S4a}$ is methyl. In some embodiments, $R^{S4a}$ is ethyl, propyl, or butyl. In certain embodiments, $R^{S4a}$ is $-OR^{SO}$. In certain embodiments, $R^{S4a}$ is $-OH$. In certain embodiments, $R^{S4a}$ is $-OR^{SO}$, and $R^{SO}$ is optionally substituted $C_{1-6}$ alkyl. In certain embodiments, $R^{S4a}$ is $-OR^{SO}$, and $R^{SO}$ is a carbohydrate. In certain embodiments, $R^{S4a}$ is $-OR^{SO}$, and $R^{SO}$ is a monosaccharide. In certain embodiments, $R^{S4a}$ is $-OR^{SO}$, and $R^{SO}$ is an oxygen protecting group. In some embodiments, $R^{S4b}$ is hydrogen. In some embodiments, $R^{S4b}$ is $-F$. In some embodiments, $R^{S4b}$ is $-Cl$, $-Br$, or $-I$. In some embodiments, $R^{S4b}$ is optionally substituted alkyl. In some embodiments, $R^{S4b}$ is optionally substituted $C_{1-6}$ alkyl. In some embodiments, $R^{S4b}$ is $C_{1-6}$ alkyl. In some embodiments, $R^{S4b}$ is methyl. In some embodiments, $R^{S4b}$ is ethyl, propyl, or butyl. In certain embodiments, $R^{S4b}$ is $-OR^{SO}$. In certain embodiments, $R^{S4b}$ is $-OH$. In certain embodiments, $R^{S4b}$ is $-OR^{SO}$, and $R^{SO}$ is optionally substituted $C_{1-6}$ alkyl. In certain embodiments, $R^{S4b}$ is $-OR^{SO}$, and $R^{SO}$ is a carbohydrate.

Group $R^{SN}$

As generally defined herein, each $R^{SN}$ of the sugar substituent $-N(R^{SN})_2$ may independently be hydrogen, optionally substituted $C_{1-6}$ alkyl, or a nitrogen protecting group, or two $R^{SN}$ may be joined to form an optionally substituted heterocyclyl or heteroaryl ring. In certain embodiments, at least one $R^{SN}$ is hydrogen. In certain embodiments, both $R^{SN}$ are joined to form an optionally substituted heterocyclyl ring. In certain embodiments, both $R^{SN}$ are joined to form an optionally substituted heteroaryl ring. In certain embodiments, both $R^{SN}$ are CM; alkyl. In certain embodiments, both $R^{SN}$ are $C_{1-6}$ alkyl. In certain embodiments, both $R^{SN}$ are methyl. In certain embodiments, both $R^{SN}$ are both ethyl, both propyl, or both butyl. In certain embodiments, both $R^{SN}$ are independently methyl, propyl, or butyl. In certain embodiments, both $R^{SN}$ are nitrogen protecting groups. In certain embodiments, both $R^{SN}$ are identical nitrogen protecting groups. In certain embodiments, one $R^{SN}$ is hydrogen, and the other $R^{SN}$ is optionally substituted $C_{1-6}$ alkyl. In certain embodiments, one $R^{SN}$ is hydrogen, and the other $R^{SN}$ is $C_{1-6}$ alkyl. In certain embodiments, one $R^{SN}$ is hydrogen, and the other $R^{SN}$ is methyl. In certain embodiments, one $R^{SN}$ is hydrogen, and the other $R^{SN}$ is ethyl, propyl, or butyl. In certain embodiments, one $R^{SN}$ is hydrogen, and the other $R^{SN}$ is a nitrogen protecting group. In certain embodiments, one $R^{SN}$ is hydrogen, and the other $R^{SN}$ is benzyl. In certain embodiments, both $R^{SN}$ are benzyl. In certain embodiments, one $R^{SN}$ is hydrogen, and the other $R^{SN}$ is alkoxycarbonyl (e.g., methoxycarbonyl, tert-butylcarbonyl). In certain embodiments, $R^{SN}$ is hydrogen, and the other $R^{SN}$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl.

Group $R^{SO}$

As generally defined herein, each $R^{SO}$ may independently be hydrogen, optionally substituted $C_{1-6}$ alkyl, a carbohydrate, or an oxygen protecting group. In some embodiments, $R^{SO}$ is hydrogen. In some embodiments, $R^{SO}$ is optionally substituted $C_{1-6}$ alkyl. In some embodiments, $R^{SO}$ is $C_{1-6}$ alkyl. In some embodiments, $R^{SO}$ is methyl. In some embodiments, $R^{SO}$ is ethyl, propyl, or butyl. In certain embodiments, $R^{SO}$ is an oxygen protecting group. In some embodiments, $R^{SO}$ is alkoxycarbonyl. In some embodiments, $R^{SO}$ is methoxycarbonyl. In some embodiments, $R^{SO}$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In some embodiments, $R^{SO}$ is a carbohydrate. In some embodiments, $R^{SO}$ is a monosaccharide. In some embodiments, $R^{SO}$ is benzoyl. In some embodiments, $R^{SO}$ is —C(=O)Ph.

Groups $R^{S6a}$ and $R^{S6b}$

As generally defined herein, $R^{S6a}$ and $R^{S6b}$ may independently be hydrogen, halogen, or optionally substituted $C_{1-6}$ alkyl. In certain embodiments, $R^{S6a}$ and $R^{S6b}$ are hydrogen. In certain embodiments, $R^{S6a}$ and $R^{S6b}$ are halogen. In certain embodiments, $R^{S6a}$ and $R^{S6b}$ are optionally substituted CHS alkyl. In certain embodiments, $R^{S6a}$ and $R^{S6b}$ are $C_{1-6}$ alkyl. In certain embodiments, $R^{S6a}$ is hydrogen, and $R^{S6b}$ is halogen. In certain embodiments, $R^{S6a}$ is hydrogen, and $R^{S6b}$ optionally substituted $C_{1-6}$ alkyl. In certain embodiments, $R^{S6a}$ is hydrogen, and $R^{S6b}$ $C_{1-6}$ alkyl. In some embodiments, $R^{S6a}$ is hydrogen. In some embodiments, $R^{S6a}$ is F. In some embodiments, $R^{S6a}$ is —Cl, —Br, or —I. In some embodiments, $R^{S6a}$ is optionally substituted alkyl. In some embodiments, $R^{S6a}$ is optionally substituted $C_{1-6}$ alkyl. In some embodiments, $R^{S6a}$ is $C_{1-6}$ alkyl. In some embodiments, $R^{S6a}$ is methyl. In some embodiments, $R^{S6a}$ is ethyl, propyl, or butyl. In some embodiments, $R^{S6b}$ is hydrogen. In some embodiments, $R^{S6b}$ is —F. In some embodiments, $R^{S6b}$ is —Cl, —Br, or —I. In some embodiments, $R^{S6b}$ is optionally substituted alkyl. In some embodiments, $R^{S6b}$ is optionally substituted $C_{1-6}$ alkyl. In some embodiments, $R^{S6b}$ is $C_{1-6}$ alkyl. In some embodiments, $R^{S6b}$ is methyl. In some embodiments, $R^{S6b}$ is ethyl, propyl, or butyl. In certain embodiments, $R^{S6a}$ is methyl, and $R^{S6b}$ is hydrogen. In certain embodiments, $R^{S6b}$ is methyl, and $R^{S6a}$ is hydrogen. In certain embodiments, the carbon to which $R^{S6a}$ and $R^{S6b}$ are attached is a stereocenter of the (R)-configuration. In certain embodiments, the carbon to which $R^{S6a}$ and $R^{S6b}$ are attached is a stereocenter of the (S)-configuration.

Groups $R^{1a}$ and $R^{1b}$

As generally defined herein, each of $R^{1a}$ and $R^{1b}$ is independently hydrogen, halogen, or optionally substituted alkyl. In certain embodiments, the carbon to which $R^{1a}$ and $R^{1b}$ are attached is a stereocenter of the (R)-configuration. In certain embodiments, the carbon to which $R^{1a}$ and $R^{1b}$ are attached is a stereocenter of the (S)-configuration.

In certain embodiments, at least one of $R^{1a}$ and $R^{1b}$ is hydrogen. In certain embodiments, both $R^{1a}$ and $R^{1b}$ are hydrogen. In certain embodiments, at least one of $R^{1a}$ and $R^{1b}$ is halogen; e.g. —F, —Cl, —Br, or I. In certain embodiments, both $R^{1a}$ and $R^{1b}$ are halogen; e.g. —F, —Cl, —Br, or I.

In certain embodiments, at least one instance of $R^{1a}$ and $R^{1b}$ is optionally substituted alkyl, e.g., optionally substituted $C_{1-6}$ alkyl optionally substituted $C_{1-2}$ alkyl, optionally substituted $C_{2-3}$ alkyl, optionally substituted $C_{1-3}$ alkyl, optionally substituted $C_{4-5}$ alkyl, or optionally substituted $C_{5-6}$ alkyl. In certain embodiments, at least one instance of $R^{1a}$ and $R^{1b}$ is —$CH_3$. In certain embodiments, both instances of $R^{1a}$ and $R^{1b}$ are —$CH_3$. In certain embodiments, at least one instance of $R^{1a}$ and $R^{1b}$ is alkyl substituted with one or more halogen atoms, e.g., optionally substituted haloalkyl; e.g., —$CF_3$, —$CF_2CF_3$, or —$CF_2H$. In certain embodiments, at least one of $R^{1a}$ and $R^{1b}$ is —$CH_2CHO$. In certain embodiments, $R^{1a}$ is methyl, and $R^{1b}$ is hydrogen.

Groups $R^{2a}$ and $R^{2b}$

As generally defined herein, each of $R^{2a}$ and $R^{2b}$ is independently hydrogen, halogen, or optionally substituted alkyl. In certain embodiments, the carbon to which $R^{2a}$ and $R^{2b}$ are attached is a stereocenter of the (R)-configuration. In certain embodiments, the carbon to which $R^{2a}$ and $R^{2b}$ are attached is a stereocenter of the (S)-configuration.

In certain embodiments, at least one instance of $R^{23}$ and $R^{2b}$ is hydrogen. In certain embodiments, both $R^{2a}$ and $R^{2b}$ are hydrogen. In certain embodiments, at least one of $R^{2a}$ and $R^{2b}$ is halogen; e.g. —F, —Cl, —Br, or I. In certain embodiments, both $R^{2a}$ and $R^{2b}$ are halogen; e.g. —F, —Cl, —Br, or I.

In certain embodiments, at least one instance of $R^{2a}$ and $R^{2b}$ is optionally substituted alkyl, e.g., optionally substituted $C_{1-6}$ alkyl optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, at least one instance of $R^{2a}$ and $R^{2b}$ is —$CH_3$. In certain embodiments, both instances of $R^{2a}$ and $R^{2b}$ are —$CH_3$. In certain embodiments, at least one instance of $R^{2a}$ and $R^{2b}$ is alkyl optionally substituted with one or more halogen atoms, e.g., optionally substituted haloalkyl; e.g., —$CF_3$, —$CF_2CF_3$, or —$CF_2H$. In certain embodiments, at least one of $R^{2a}$ and $R^{2b}$ is —$CH_2CHO$. In certain embodiments, $R^{2a}$ is hydrogen, and $R^{2b}$ is methyl.

Groups $R^{3a}$ and $R^4$

As generally defined herein, $R^{3a}$ is hydrogen, optionally substituted alkyl, optionally substituted alkenyl, optionally substituted alkynyl, or an oxygen protecting group. As generally defined herein, $R^4$ is hydrogen, halogen, or optionally substituted alkyl. In certain embodiments, the carbon to which —$OR^{3a}$ and $R^4$ are attached is a stereocenter of the (R)-configuration. The carbon to which —$OR^{3a}$ and $R^4$ are attached is a stereocenter of the (S)-configuration.

In certain embodiments, $R^4$ is optionally substituted alkyl, e.g., optionally substituted $C_{1-6}$ alkyl. In certain embodiments, at least one instance of $R^4$ is —$CH_3$. In certain embodiments, both instances of $R^{3a}$ and $R^4$ are —$CH_3$.

In certain embodiments, at least one instance of $R^{3a}$ and $R^4$ is optionally substituted alkenyl, e.g., optionally substituted $C_{2-6}$ alkenyl, optionally substituted $C_{2-3}$alkenyl, optionally substituted $C_{3-4}$ alkenyl, optionally substituted $C_{4-5}$ alkenyl, or optionally substituted $C_{5-6}$ alkenyl. In certain embodiments, at least one instance of $R^{3a}$ and $R^4$ is vinyl, allyl, or prenyl.

In certain embodiments, $R^{3a}$ is hydrogen. In certain embodiments, $R^{3a}$ is optionally substituted alkyl, e.g., optionally substituted $C_{1-6}$ alkyl. In certain embodiments, $R^{3a}$ is —$CH_3$. In certain embodiments, $R^{3a}$ is optionally substituted alkenyl, e.g., optionally substituted $C_{2-6}$ alkenyl. In certain embodiments, $R^{3a}$ is vinyl, allyl, or prenyl. In certain embodiments, $R^{3a}$ is an oxygen protecting group.

Groups $R^{5a}$ and $R^{5b}$

As generally defined herein, each instance of $R^{5a}$ and $R^{5b}$ is independently hydrogen, halogen, or optionally substituted alkyl. In certain embodiments, one instance of $R^{5a}$ and $R^{5b}$ is hydrogen, and the other of $R^{5a}$ and $R^{5b}$ is a non-hydrogen group. In certain embodiments, each instance of $R^{5a}$ and $R^{5b}$ is hydrogen. In certain embodiments, each instance of $R^{5a}$ and $R^{5b}$ is a non-hydrogen group. In certain embodiments, the carbon to which $R^{5a}$ and $R^{5b}$ is attached are a stereocenter of the (R)-configuration. In certain embodiments, the carbon to which $R^{5a}$ and $R^{5b}$ are attached is a stereocenter of the (S)-configuration.

In certain embodiments, at least one instance of $R^{5a}$ and $R^{5b}$ is optionally substituted alkyl, e.g., optionally substituted $C_{1-3}$ alkyl, optionally substituted $C_{1-2}$ alkyl, optionally substituted $C_{2-3}$ alkyl optionally substituted $C_{3-4}$ alkyl, optionally substituted $C_{4-5}$ alkyl, or optionally substituted $C_{1-3}$ alkyl. In certain embodiments, at least one instance of $R^{5a}$ and $R^{5b}$ is —$CH_3$. In certain embodiments, both instances of $R^{5a}$ and $R^{5b}$ are —$CH_3$. In certain embodiments, $R^{5a}$ is methyl, and $R^{5b}$ is hydrogen.

Groups $R^6$ and $R^{10}$

As generally defined herein, $R^6$ and $R^{10}$ are independently hydrogen, halogen, or optionally substituted alkyl. In certain embodiments, $R^6$ is hydrogen. In certain embodiments, $R^{10}$ is hydrogen. In certain embodiments, $R^6$ is hydrogen and $R^{10}$ is hydrogen. In certain embodiments, both of $R^6$ and $R^{10}$ are non-hydrogen groups. In certain embodiments, the carbon to which $R^6$ and $R^{10}$ are attached is a stereocenter of the (R)-configuration. In certain embodiments, the carbon to which $R^6$ and $R^{10}$ are attached is a stereocenter of the (S)-configuration.

In certain embodiments, at least one instance of $R^6$ and $R^{10}$ is optionally substituted alkyl; e.g., optionally substituted $C_{1-3}$ alkyl. In certain embodiments, at least one instance of $R^6$ and $R^{10}$ is —$CH_3$. In certain embodiments, at least one instance of $R^6$ and $R^{10}$ is —$CH_2CN$. In certain embodiments, at least one instance of $R^6$ and $R^{10}$ is —$CH_2C(=O)OR^{32}$, wherein $R^{32}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl.

In certain embodiments, at least one instance of $R^6$ and $R^{10}$ is halogen, e.g., fluoro, bromo, chloro, or iodo. In some embodiments, $R^6$ is fluoro. In some embodiments, $R^{10}$ is fluoro. In certain embodiments, $R^6$ is fluoro, and $R^{10}$ is methyl. In certain embodiments, $R^6$ is methyl, and $R^{10}$ is fluoro.

In certain embodiments, $R^6$ is:

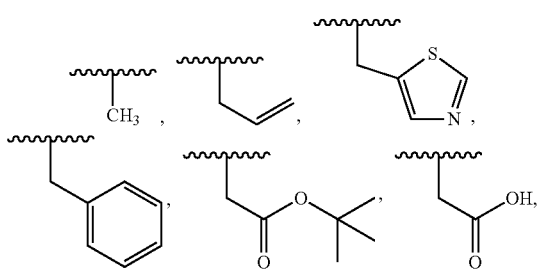

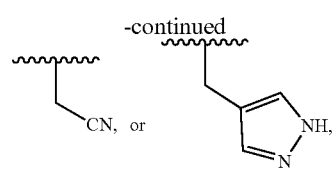

and $R^{10}$ is hydrogen or fluoro. In certain embodiments, $R^6$ is methyl, and $R^{10}$ is hydrogen.

Groups $R^{3a}$ and $R^6$ together

In certain embodiments, $R^{3a}$ and $R^6$ are joined to form an optionally substituted heterocyclyl ring. In certain embodiments, $R^{3a}$ and $R^6$ are joined to form an optionally substituted 6-10 membered heterocyclyl ring. In certain embodiments, $R^{3a}$ and $R^6$ are joined to form an optionally substituted 6-10 membered heterocyclyl ring, wherein the only heteroatom in the ring is the oxygen attached to $R^{3a}$. In certain embodiments, $R^{3a}$ and $R^6$ are joined to form a 6-membered heterocyclyl ring. In certain embodiments, $R^{3a}$ and $R^6$ are joined to form a 7-10 membered heterocyclyl ring, wherein $R^{3a}$ and $R^6$ are joined to form an optionally substituted 1-4 carbon linker.

Groups $R^{3a}$ and $R^{10}$ together

In certain embodiments, $R^{3a}$ and $R^{10}$ are joined to form an optionally substituted heterocyclyl ring. In certain embodiments, $R^{3a}$ and $R^{10}$ are joined to form an optionally substituted 6-10 membered heterocyclyl ring. In certain embodiments, $R^{3a}$ and $R^{10}$ are joined to form an optionally substituted 6-10 membered heterocyclyl ring, wherein the only heteroatom in the ring is the oxygen attached to $R^{3a}$. In certain embodiments, $R^{3a}$ and $R^{10}$ are joined to form a 6-membered heterocyclyl ring. In certain embodiments, $R^{3a}$ and $R^{10}$ are joined to form a 7-10 membered heterocyclyl ring, wherein $R^{3a}$ and $R^{10}$ are joined to form an optionally substituted 1-4 carbon linker.

Groups $R^{3a}$ and $R^S$ together

In certain embodiments, $R^{3a}$ and $R^S$ are joined to form an optionally substituted heterocyclyl ring. In certain embodiments, $R^{3a}$ and $R^S$ are joined to form an optionally substituted 10-15 membered heterocyclyl ring. In certain embodiments, $R^{3a}$ and $R^S$ are joined to form an optionally substituted 11-15 membered heterocyclyl ring. In certain embodiments, $R^{3a}$ and $R^S$ are joined to form an optionally substituted 11-14 membered heterocyclyl ring. In certain embodiments, $R^{3a}$ and $R^S$ are joined to form an optionally substituted 12-14 membered heterocyclyl ring. In certain embodiments, $R^{3a}$ and $R^S$ are joined to form an optionally substituted 11-membered heterocyclyl ring. In certain embodiments, $R^{3a}$ and $R^S$ are joined to form an optionally substituted 12-membered heterocyclyl ring. In certain embodiments, $R^{3a}$ and $R^S$ are joined to form an optionally substituted 13-membered heterocyclyl ring. In certain embodiments, $R^{3a}$ and $R^S$ are joined to form an optionally substituted 14-membered heterocyclyl ring. In certain embodiments, $R^{3a}$ and $R^S$ are joined to form a 11-15 membered heterocyclyl ring, wherein $R^{3a}$ and $R^S$ are joined to form an optionally substituted 2-6 carbon linker.

Group $R^7$

As generally defined herein, $R^7$ is hydrogen, halogen, optionally substituted alkyl, $C_2$-$C_6$-alkenyl, $C_2$-$C_6$-alkynyl, or $C_1$-$C_6$-alkoxy. In certain embodiments, $R^7$ is hydrogen, halogen, or optionally substituted alkyl. In certain embodiments, $R^7$ is hydrogen. However, in certain embodiments, $R^7$ is a non-hydrogen group, and the carbon to which $R^7$ is attached is a stereocenter of the (R)-configuration. In certain embodiments, $R^7$ is a non-hydrogen group, and the carbon to which $R^7$ is attached is a stereocenter of the (R)-configuration.

In certain embodiments, $R^7$ is optionally substituted alkyl, e.g., optionally substituted $C_{1-6}$ alkyl optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^7$ is —$CH_3$ or —$CH_2CH_3$.

Group $R^8$

As generally defined herein, $R^8$ is hydrogen, halogen, or optionally substituted $C_{1-6}$ alkyl. In certain embodiments, $R^8$ is hydrogen. In certain embodiments, $R^8$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^8$ is —$CH_3$ or —$CH_2CH_3$. In certain embodiments, $R^8$ is halogen, e.g., fluoro, bromo, chloro, or iodo.

Embodiments of Formula (I)

In certain embodiments, the compound of Formula (I) is a compound of Formula (I-a):

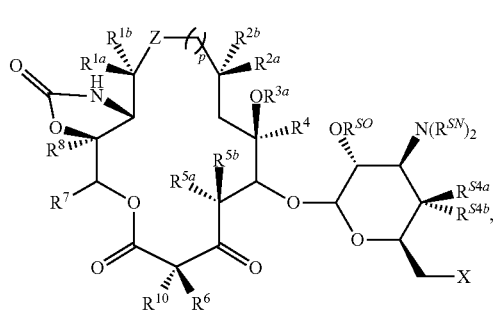

(I-a)

or a pharmaceutically acceptable salt thereof, wherein:

Z is —C(=O)— or —$NR^{Z2}$—;

$R^{Z2}$ is hydrogen, optionally substituted alkyl, acyl, or a nitrogen protecting group;

p is 0 or 1, provided that p is 0 when Z is —C(=O)—;

X is optionally substituted $C_{1-6}$ alkyl, —$OR^A$ or —$NR^B$—$(CR^xR^x)_t$-A-$(R^y)_q$;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen or $C_{1-3}$ alkyl;

each $R^x$ is independently hydrogen or $C_{1-3}$ alkyl;

A is arylene, heteroarylene, heterocyclylene, alkylene, cycloalkylene, alkenylene, or alkynylene;

each $R^y$ is independently, hydrogen, $C_{1-6}$ alkyl, $C_{1-6}$ alkoxy, halogen, hydroxyl, cyano, dialkylamino, haloalkyl, C(O)O$C_{1-3}$ alkyl, C(O)OH, C(O)$CH_2NR^{x1}R^{y1}$, C(O)$NR^{x1}R^{y1}$, C(O)$C_{1-6}$ alkyl, $C_{1-6}$ alkyl sulfonyl, heteroaryl, or heteroaryloxy;

t is 0, 1, or 2;

q is 1, 2, or 3;

each of $R^{S4a}$ and $R^{S4b}$ is independently hydrogen, halogen, optionally substituted $C_{1-6}$ alkyl, or —$OR^{SO}$;

each $R^{SN}$ is independently hydrogen, optionally substituted $C_{1-6}$ alkyl, or a nitrogen protecting group, or two $R^{SN}$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_{1-6}$ alkyl, or —$OR^{SO}$;

each $R^{SO}$ is independently hydrogen, optionally substituted $C_{1-6}$ alkyl, a carbohydrate, or an oxygen protecting group;

each of $R^{1a}$ and $R^{1b}$ is independently hydrogen, halogen, or optionally substituted alkyl;

each of $R^{2a}$ and $R^{2b}$ is independently hydrogen, halogen, or optionally substituted alkyl;

$R^{3a}$ is hydrogen, optionally substituted alkyl, optionally substituted alkenyl, optionally substituted alkynyl, or an oxygen protecting group;

$R^4$ is hydrogen, halogen, or optionally substituted alkyl;

each of $R^{5a}$ and $R^{5b}$ is independently hydrogen, halogen, or optionally substituted alkyl;

$R^6$ is hydrogen, halogen, or optionally substituted alkyl;

$R^{10}$ is hydrogen, halogen, or optionally substituted alkyl;

$R^7$ is hydrogen, halogen, or optionally substituted alkyl; and $R^8$ is hydrogen, halogen, or optionally substituted $C_{1-6}$ alkyl.

In certain embodiments, the compound of Formula (I) is a compound of Formula (I-a):

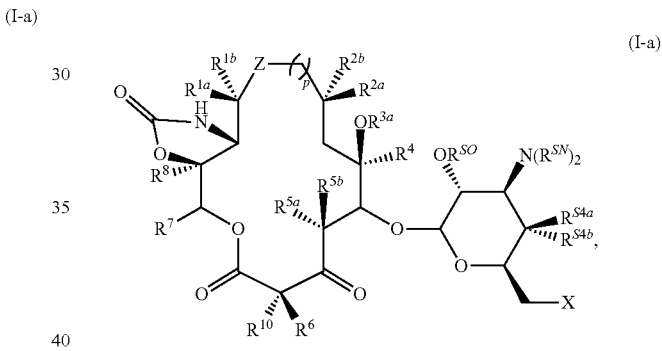

(I-a)

or a pharmaceutically acceptable salt thereof, wherein:

Z is —C(=O)— or —$NR^{Z2}$—;

$R^{Z2}$ is hydrogen, optionally substituted alkyl, acyl, or a nitrogen protecting group;

p is 0 or 1, provided that p is 0 when Z is —C(=O)—;

X is —$OR^A$ or —$NR^B$—$(CR^xR^x)_t$-A-$(R^y)_q$;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen or $C_{1-3}$ alkyl;

each $R^x$ is independently hydrogen or $C_{1-3}$ alkyl;

A is arylene, heteroarylene, heterocyclylene, alkylene, alkenylene, or alkynylene;

each $R^y$ is independently, hydrogen, $C_{1-6}$ alkyl, halogen, cyano, dialkylamino, haloalkyl, $C_{1-6}$ alkylsulfonyl, heteroaryl, or heteroaryloxy;

t is 0, 1, or 2;

q is 1, 2, or 3;

each of $R^{S4a}$ and $R^{S4b}$ is independently hydrogen, halogen, optionally substituted $C_{1-6}$ alkyl, or —$OR^{SO}$;

each $R^{SN}$ is independently hydrogen, optionally substituted $C_{1-6}$ alkyl, or a nitrogen protecting group, or two $R^{SN}$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_{1-6}$ alkyl, or —$OR^{SO}$;

each $R^{SO}$ is independently hydrogen, optionally substituted $C_{1-6}$ alkyl, a carbohydrate, or an oxygen protecting group;

each of $R^{1a}$ and $R^{1b}$ is independently hydrogen, halogen, or optionally substituted alkyl;

each of $R^{2a}$ and $R^{2b}$ is independently hydrogen, halogen, or optionally substituted alkyl;

$R^{3a}$ is hydrogen, optionally substituted alkyl, optionally substituted alkenyl, optionally substituted alkynyl, or an oxygen protecting group;

$R^4$ is hydrogen, halogen, or optionally substituted alkyl;

each of $R^{5a}$ and $R^{5b}$ is independently hydrogen, halogen, or optionally substituted alkyl;

$R^6$ is hydrogen, halogen, or optionally substituted alkyl;

$R^{10}$ is hydrogen, halogen, or optionally substituted alkyl;

$R^7$ is hydrogen, halogen, or optionally substituted alkyl; and $R^8$ is hydrogen, halogen, or optionally substituted $C_{1-6}$ alkyl.

In certain embodiments of the compound of Formula (I-a), Z is —C(=O)— or —$NR^{Z2}$—. Attached to group Z is a methylene (i.e., —$CH_2$—) group, which may be repeated 0 or 1 time, according to variable p. In certain embodiments, when Z is —C(=O)—, p is 0 to give a 14-membered ketolide. In certain embodiments, Z is —$NR^{Z2}$—, and p is 0 to give a 14-membered azaketolide. In certain embodiments, Z is —$NR^{Z2}$—, and p is 1 to give a 15-membered azaketolide. In certain embodiments, Z is —NH—, and p is 0. In certain embodiments, Z is —NH—, and p is 1.

In certain embodiments, the compound of Formula (I) is a compound of Formula (I-b):

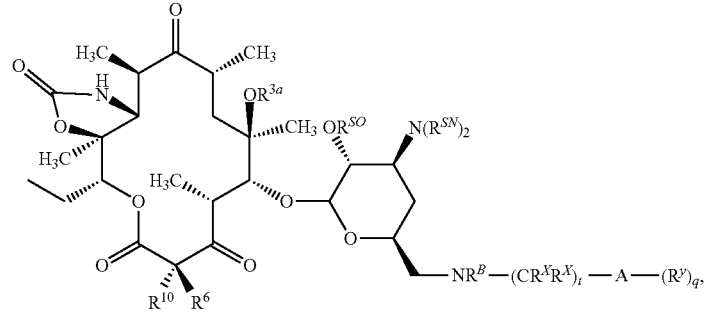

(I-b)

or a pharmaceutically acceptable salt thereof, wherein $R^{3a}$, $R^6$, $R^{10}$, $R^{SN}$, $R^{SO}$, $R^B$, $R^x$, t, q, A, and $R^y$ are as defined herein.

In certain embodiments, the compound of Formula (I) is a compound of Formula (I-c):

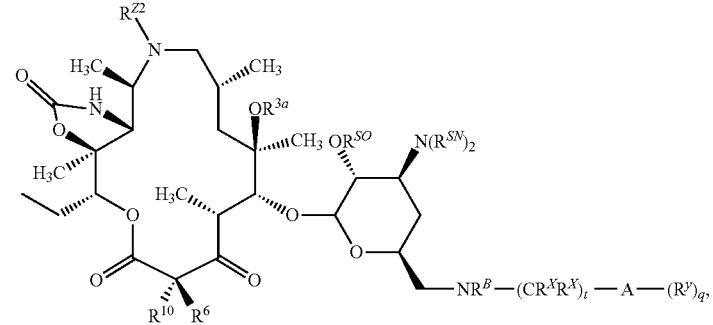

(I-c)

or a pharmaceutically acceptable salt thereof, wherein $R^{Z2}$, $R^{3a}$, $R^6$, $R^{10}$, $R^{SN}$, $R^{SO}$, $R^B$, $R^x$, t, q, A, and $R^y$ are as defined herein.

In certain embodiments, the compound of Formula (I) is a compound of Formula (I-d):

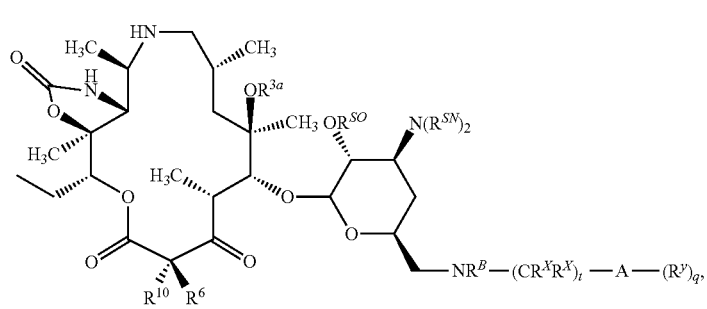

(I-d)

or a pharmaceutically acceptable salt thereof, wherein $R^{3a}$, $R^6$, $R^{10}$, $R^{SN}$, $R^{SO}$, $R^B$, $R^x$, t, q, A, and $R^y$ are as defined herein.

In certain embodiments, the compound of Formula (I) is a compound of Formula (I-e-i) or (I-e-ii):

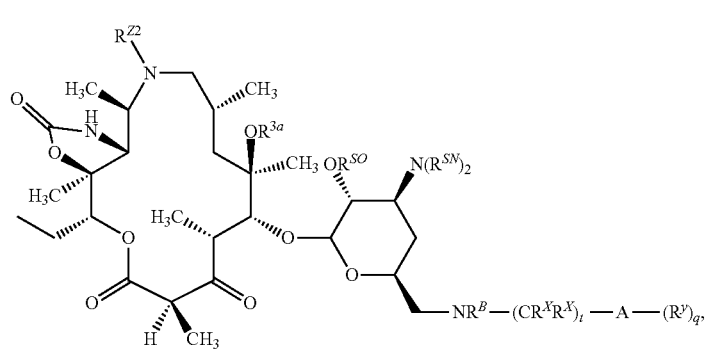

(I-e-i)

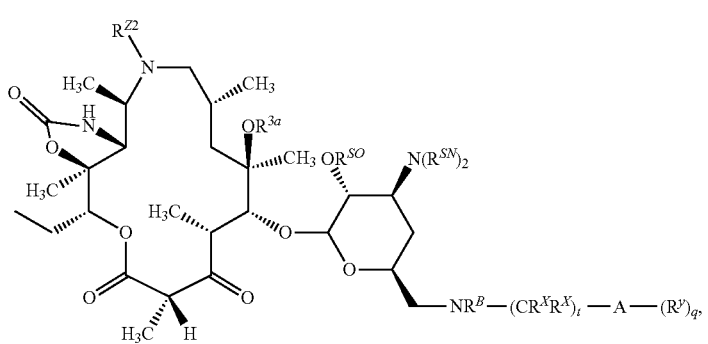

(I-e-ii)

or a pharmaceutically acceptable salt thereof, wherein $R^{Z2}$, $R^{3a}$, $R^{SN}$, $R^{SO}$, $R^B$, $R^x$, t, q, A, and $R^y$ are as defined herein.

In certain embodiments, the compound of Formula (I) is a compound of Formula (I-f-i) or (I-f-ii):

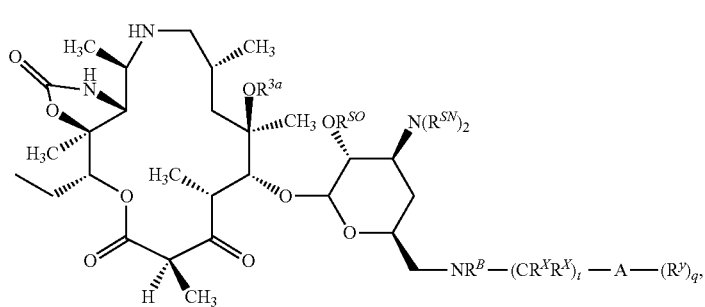
(I-f-i)

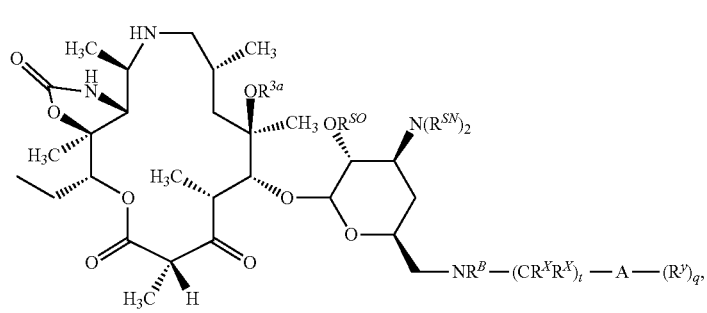
(I-f-ii)

or a pharmaceutically acceptable salt thereof, wherein $R^{3a}$, $R^{SN}$, $R^{SO}$, $R^B$, $R^x$, t, q, A, and $R^y$ are as defined herein.

In certain embodiments, the compound of Formula (I) is a compound of Formula (I-g-i) (I-g-ii):

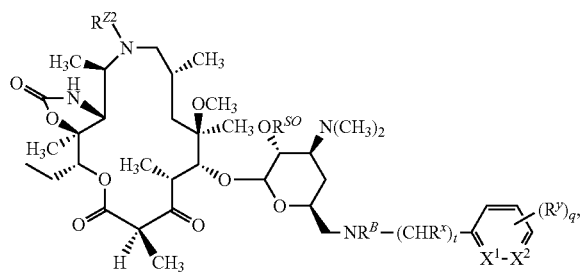
(I-g-i)

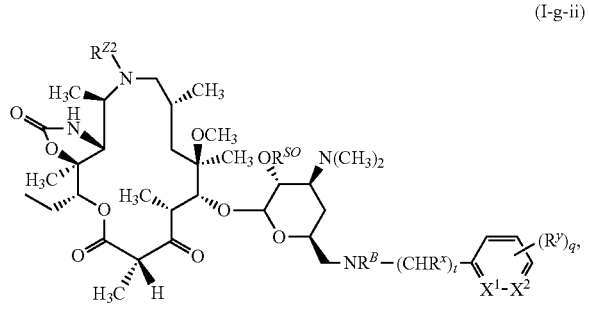
(I-g-ii)

or a pharmaceutically acceptable salt thereof, wherein:

$R^{X2}$ is hydrogen, optionally substituted alkyl, acyl, or a nitrogen protecting group;

$R^B$ is hydrogen or $C_{1-3}$ alkyl;

each $R^x$ is independently hydrogen or $C_{1-3}$ alkyl;

$X^1$ is N or $CR^y$;

$X^2$ is N or $CR^y$;

provided no more than one of $X^1$ and $X^2$ is N;

each $R^y$ is independently, hydrogen, halogen, cyano, alkoxy, or haloalkyl;

t is 0, 1, or 2;

q is 1 or 2; and $R^{SO}$ is as defined herein.

In certain embodiments, the compound of Formula (I) is a compound of Formula (I-h-i) or (I-h-ii):

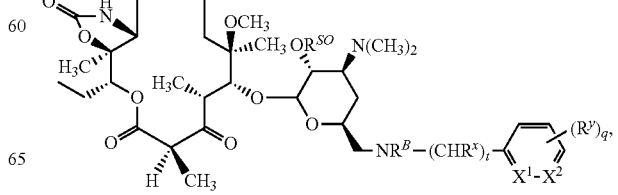
(I-h-i)

-continued (I-h-ii)

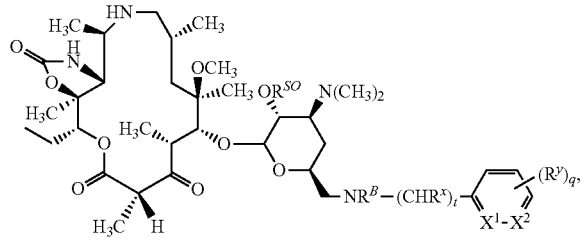

or a pharmaceutically acceptable salt thereof, wherein:
$R^B$ is hydrogen or $C_{1-3}$ alkyl;
each $R^x$ is independently hydrogen or $C_{1-3}$ alkyl;
$X^1$ is N or $CR^y$;
$X^2$ is N or $CR^y$;
provided no more than one of $X^1$ and $X^2$ is N;
each $R^y$ is, independently, hydrogen, halogen, cyano, alkoxy, or haloalkyl;
t is 0, 1, or 2;
q is 1 or 2; and
$R^{SO}$ is as defined herein.

In certain embodiments, the compound of Formula (I) is a compound of Formula (I-i-i) or (I-i-ii):

(I-i-i)

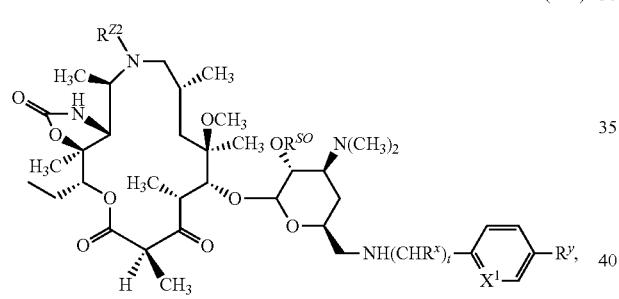

(I-i-ii)

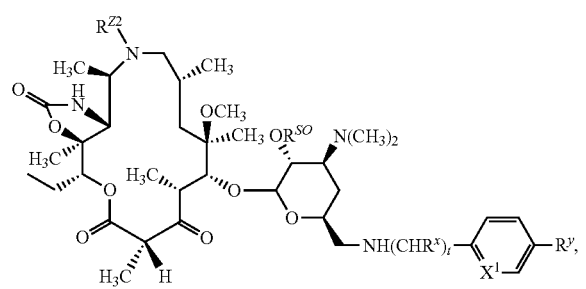

or a pharmaceutically acceptable salt thereof, wherein:
$R^{Z2}$ is hydrogen, optionally substituted alkyl, acyl, or a nitrogen protecting group;
each $R^x$ is independently hydrogen or $C_{1-3}$ alkyl;
$X^1$ is N or $CR^y$;
each $R^y$ is, independently, hydrogen, halogen, cyano, or haloalkyl;
t is 0, 1, or 2; and
$R^{SO}$ is as defined herein.

In certain embodiments, the compound of Formula (I) is a compound of Formula (I-j-i) or (I-j-ii):

(I-j-i)

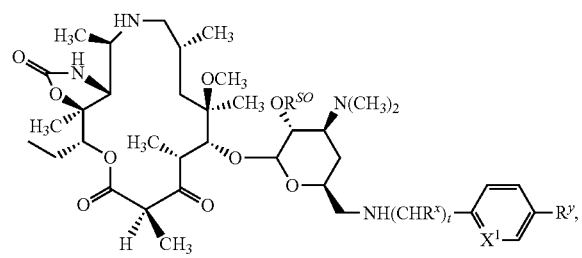

(I-j-ii)

or a pharmaceutically acceptable salt thereof, wherein:
each $R^x$ is independently hydrogen or $C_{1-3}$ alkyl;
$X^1$ is N or $CR^y$;
each $R^y$ is, independently, hydrogen, halogen, cyano, or haloalkyl;
t is 0, 1, or 2; and
$R^{SO}$ is as defined herein.

In certain embodiments, the compound of Formula (I) is a compound of Formula (I-k):

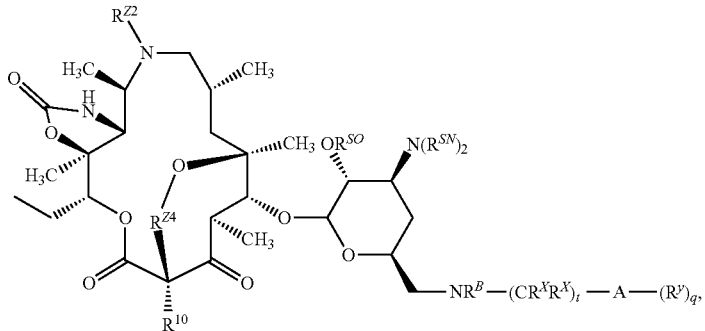

(I-k)

or a pharmaceutically acceptable salt thereof, wherein $R^{Z2}$, $R^{10}$, $R^{SN}$, $R^{SO}$, $R^B$, $R^x$, t, q, A, and $R^y$ are as defined herein; and $R^{Z4}$ is an optionally substituted alkylene, optionally substituted heteroalkylene, optionally substituted alkenylene, or optionally substituted alkynylene linker.

In certain embodiments, the compound of Formula (I) is a compound of Formula (I-l):

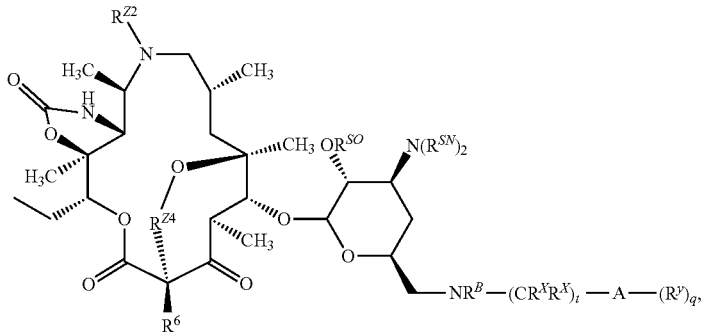

(I-l)

or a pharmaceutically acceptable salt thereof, wherein $R^{Z2}$, $R^6$, $R^{SN}$, $R^{SO}$, $R^B$, $R^x$, t, q, A, and $R^y$ are as defined herein; and $R^{Z4}$ is an optionally substituted alkylene, optionally substituted heteroalkylene, optionally substituted alkenylene, or optionally substituted alkynylene linker.

In certain embodiments, the compound of Formula (I) is a compound of Formula (I-m):

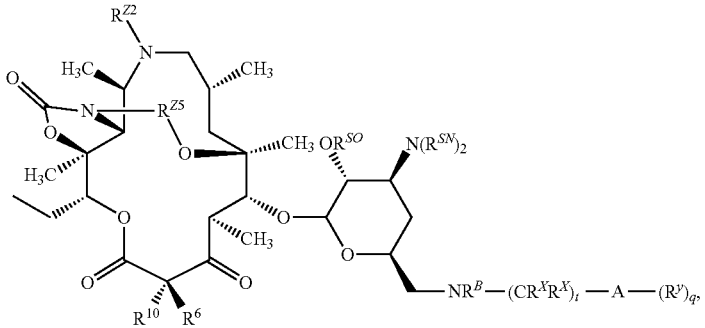

(I-m)

or a pharmaceutically acceptable salt thereof, wherein $R^{Z2}$, $R^6$, $R^{10}$, $R^{SN}$, $R^{SO}$, $R^B$, $R^x$, t, q, A, and $R^y$ are as defined herein; and $R^{Z5}$ is an optionally substituted alkylene, optionally substituted heteroalkylene, optionally substituted alkenylene, or optionally substituted alkynylene linker.

In certain embodiments, the compound of Formula (I) is a compound of Formula (II):

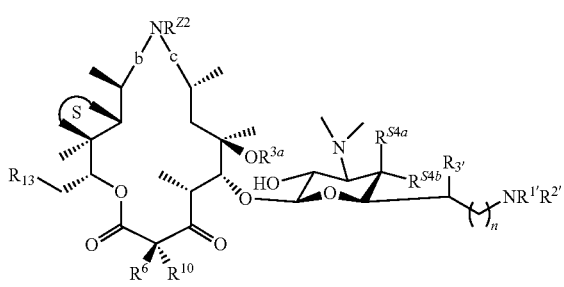

(II)

or a pharmaceutically acceptable salt thereof, wherein:
ring S is

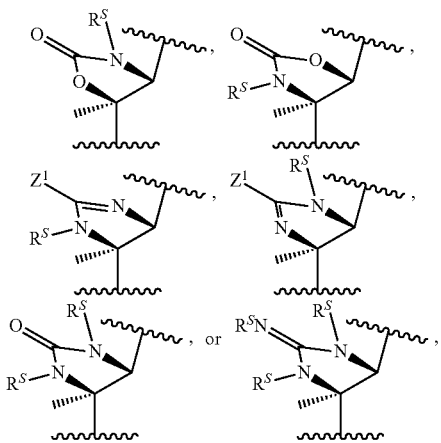

wherein $Z^1$ is $N(R^S)_2$ or $C(R^S)_3$ and each $R^S$ is independently H, $C_1$-$C_6$ alkyl, or $C_2$-$C_6$ alkenyl;
one of b or c is $CH_2$ and the other is a bond;
n is 0 or 1;
$R^6$ and $R^{10}$ are selected from H, $CH_3$, and F, wherein when $R^6$ is H, $R^{10}$ is $CH_3$, when $R^{10}$ is H, $R^6$ is $CH_3$, and when $R^{10}$ is F, $R^6$ is $CH_3$;
$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;
$R^{x1}$ and $R^{y1}$ are each independently selected from H, optionally substituted $C_1$-$C_6$ alkyl, optionally substituted $C_{1-6}$ alkoxy, $C(O)NR^{x1}R^{y1}$, $C(O)C_{1-6}$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;
$R^{3'}$ is H, OH, or oxo;
$R^{S4a}$ and $R^{S4b}$ are each independently selected from H, $CH_3$ and OH, wherein both $R^{S4a}$ and $R^{S4b}$ cannot be OH;

$R^{3a}$ is selected from H, $C_1$-$C_6$-alkyl, and $C_2$-$C_6$ alkenyl;
$R^{Z2}$ is selected from the group consisting of H and $C_1$-$C_6$-alkyl; and
$R^{13}$ is selected from H, $C_1$-$C_6$-alkyl, $C_2$-$C_6$-alkenyl, $C_2$-$C_6$-alkynyl, and $C_1$-$C_6$-alkoxy.

In certain embodiments, the compound of Formula (II) is a compound of Formula (II-a):

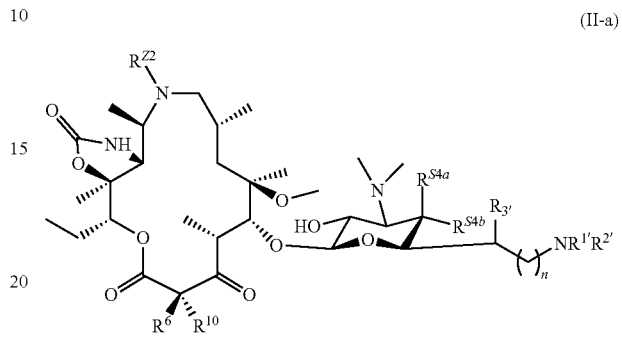

(II-a)

or a pharmaceutically acceptable salt thereof, wherein:
n is 0 or 1;
$R^6$ and $R^{10}$ are selected from H, $CH_3$, and F, wherein when $R^6$ is H, $R^{10}$ is $CH_3$, when $R^{10}$ is H, $R^6$ is $CH_3$, and when $R^{10}$ is F, $R^6$ is $CH_3$;
$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;
$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;
$R^{3'}$ is H, OH, or oxo;
$R^{S4a}$ and $R^{S4b}$ are each independently selected from H, $CH_3$ and OH, wherein both $R^{S4a}$ and $R^{S4b}$ cannot be OH; and
$R^{Z2}$ is selected from the group consisting of H and $C_1$-$C_6$ alkyl.

In another embodiment of a compound of Formula (II) and Formula (II-a), n is 0 and $R^{3'}$ is H.

In a further embodiment of a compound of Formula (II) and Formula (II-a), n is 1, and $R^{3'}$ is OH.

In a further embodiment of a compound of Formula (II) and Formula (II-a), n is 0, and $R^{3'}$ is oxo.

In a further embodiment of a compound of Formula (II) and Formula (II-a), n is 1, and $R^{3'}$ is oxo.

In a further embodiment of a compound of Formula (II) and Formula (II-a), $R^{1'}$ and $R^{2'}$ are selected from H and optionally substituted $C_1$-$C_6$ alkyl.

In a further embodiment of a compound of Formula (II) and Formula (II-a), $R^{1'}$ and $R^{2'}$ are selected from H and $C_1$-$C_6$ alkyl substituted with $OR_z$, halo, $C(O)OR_z$, $C(O)N(R_z)_2$, $N(R_z)_2$, or optionally substituted cycloalkyl; and each $R_z$ is independently H or optionally substituted $C_1$-$C_6$ alkyl.

In a further embodiment of a compound of Formula (II) and Formula (D-a), one of $R^{1'}$ and $R^{2'}$ is H, and the other of $R^{1'}$ and $R^{2'}$ is $C(O)CH_2NR^{x1}R^{y1}$. In a further embodiment, $R^{x1}$ and $R^{y1}$ are each independently selected from the group consisting of H, $C_1$-$C_6$ alkyl, and $C_1$-$C_6$ cycloalkyl, or $R^{x1}$ and $R^{y1}$ together along with the nitrogen to which they are attached form a 4, 5, 6, or 7-membered ring.

In a further embodiment of a compound of Formula (II) and Formula (II-a), $R^{1'}$ and $R^{2'}$ are each independently selected from the group consisting of H, $CH_3$, $CH_2CH_3$ isopropyl, tert-butyl,

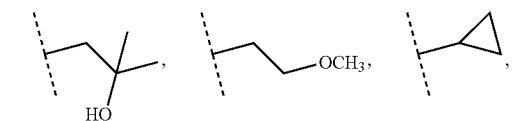

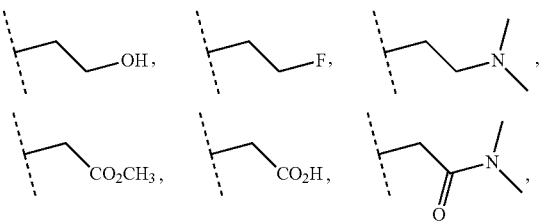

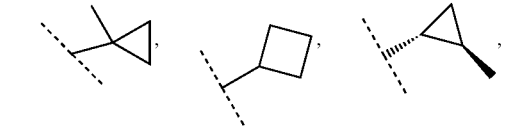

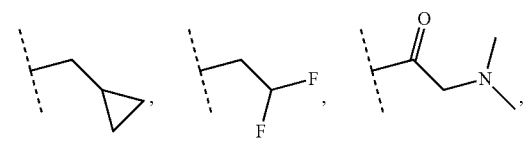

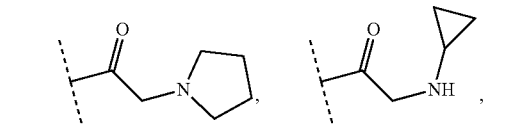

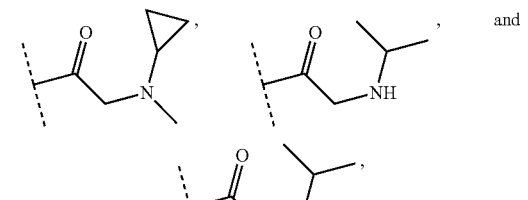

and

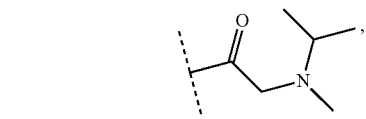

wherein "- - -" indicates the point of attachment.

In a further embodiment of a compound of Formula (II) and Formula (II-a), $R^{1'}$ and $R^{2'}$ together along with the nitrogen to which they are attached form an optionally substituted ring containing up to two additional heteroatoms, and wherein $NR^{1'}R^{2'}$ is selected from the group consisting of

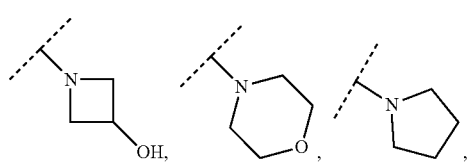

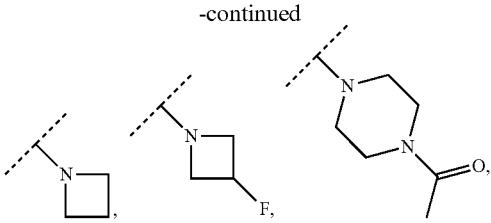

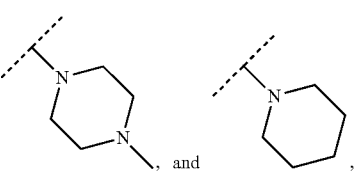

wherein "- - -" indicates the point of attachment.

In certain embodiments, the compound of Formula (II) is a compound of Formula (II-b):

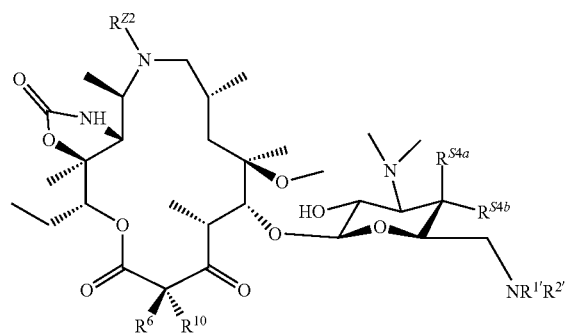

(II-b)

or a pharmaceutically acceptable salt thereof, wherein:

$R^6$ and $R^{10}$ are selected from H, $CH_3$, and F, wherein when $R^6$ is H, $R^{10}$ is $CH_3$, when $R^{10}$ is H, $R^6$ is $CH_3$, and when $R^{10}$ is F, $R^6$ is $CH_3$;

$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;

$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{S4a}$ and $R^{S4b}$ are each independently selected from H, $CH_3$ and OH, wherein both $R^{S4a}$ and $R^{S4b}$ cannot be OH; and $R^{Z2}$ is selected from the group consisting of H and $C_1$-$C_6$ alkyl.

In certain embodiments, the compound of Formula (II) is a compound of Formula (II-c):

(II-c)

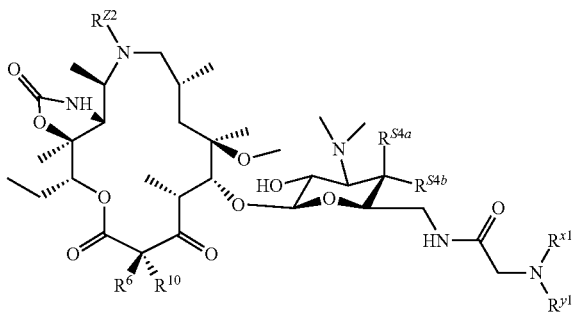

or a pharmaceutically acceptable salt thereof, wherein:

$R^6$ and $R^{10}$ are selected from H, $CH_3$, and F, wherein when $R^6$ is H, $R^{10}$ is $CH_3$, when $R^{10}$ is H, $R^6$ is $CH_3$, and when $R^{10}$ is F, $R^6$ is $CH_3$;

$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{S4a}$ and $R^{S4b}$ are each independently selected from H, $CH_3$ and OH, wherein both $R^{S4a}$ and $R^{S4b}$ cannot be OH; and $R^{Z2}$ is selected from the group consisting of H and $C_1$-$C_6$ alkyl.

In certain embodiments, the compound of Formula (II) is a compound of Formula (II-d):

(II-d)

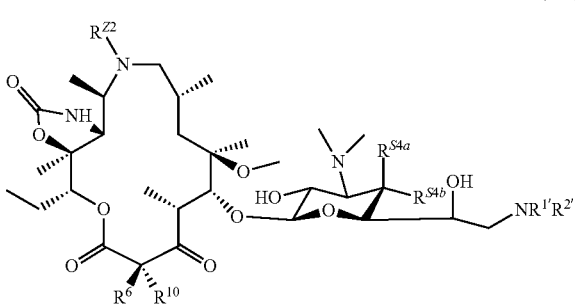

or a pharmaceutically acceptable salt thereof, wherein:

$R^6$ and $R^{10}$ are selected from H, $CH_3$, and F, wherein when $R^6$ is H, $R^{10}$ is $CH_3$, when $R^{10}$ is H, $R^6$ is $CH_3$, and when $R^{10}$ is F, $R^6$ is $CH_3$;

$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;

$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{S4a}$ and $R^{S4b}$ are each independently selected from H, $CH_3$ and OH, wherein both $R^{S4a}$ and $R^{S4b}$ cannot be OH; and $R^{Z2}$ is selected from the group consisting of H and $C_1$-$C_6$ alkyl.

In certain embodiments, the compound of Formula (II) is a compound of Formula (II-e):

(II-e)

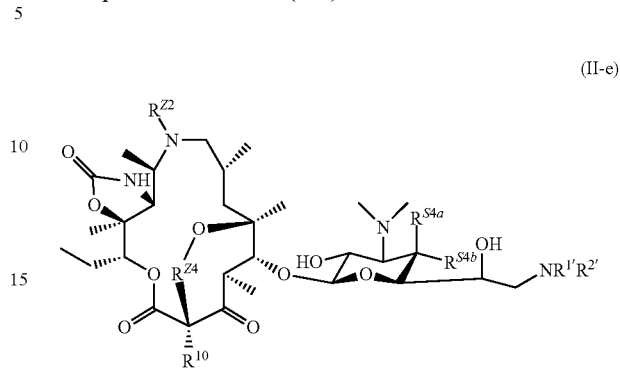

or a pharmaceutically acceptable salt thereof, wherein:

$R^{10}$ is selected from H, $CH_3$, and F;

$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;

$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{S4a}$ and $R^{S4b}$ are each independently selected from H, $CH_3$ and OH, wherein both $R^{S4a}$ and $R^{S4b}$ cannot be OH;

$R^{Z2}$ is selected from the group consisting of H and $C_1$-$C_6$ alkyl; and $R^{Z4}$ is an optionally substituted alkylene, optionally substituted heteroalkylene, optionally substituted alkenylene, or optionally substituted alkynylene linker.

In certain embodiments, the compound of Formula (II) is a compound of Formula (II-f):

(II-f)

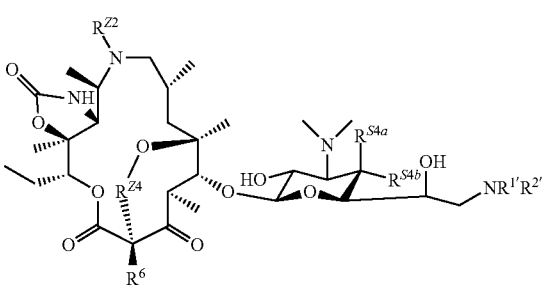

or a pharmaceutically acceptable salt thereof, wherein:

$R^6$ is selected from H, $CH_3$, and F;

$R^{1'}$ and $R^{2'}$ are each independently selected from H, optionally substituted $C_1$-$C_6$ alkyl, optionally substituted $C_3$-$C_6$ cycloalkyl, and $C(O)CH_2NR^{x1}R^{y1}$, or $R^{1'}$ and $R^{2'}$ together along with the nitrogen to which they are attached form a 4, 5, 6, or 7-membered optionally substituted ring containing up to two additional heteroatoms;

$R^{x1}$ and $R^{y1}$ are each independently selected from H, optionally substituted $C_1$-$C_6$ alkyl, and optionally substituted $C_1$-$C_6$ cycloalkyl, or $R^{x1}$ and $R^{y1}$ together along with the nitrogen to which they are attached form a 4, 5, 6, or 7-membered optionally substituted ring containing up to two additional heteroatoms;

$R^{S4a}$ and $R^{S4b}$ are each independently selected from H, $CH_3$ and OH, wherein both $R^{S4a}$ and $R^{S4b}$ cannot be OH;

$R^{Z2}$ is selected from the group consisting of H and $C_1$-$C_6$ alkyl; and $R^{Z4}$ is an optionally substituted alkylene, optionally substituted heteroalkylene, optionally substituted alkenylene, or optionally substituted alkynylene linker.

The disclosure also relates to epimeric mixtures at the C-2 position in compounds of formula II, when one of $R^6$ or $R^{10}$ is H and the other is $CH_3$. Epimerization may be prevented when $R^6$ is $CH_3$, and $R^{10}$ is F. In some embodiments, a mixture of compounds of formula II may be an epimeric mixture wherein $R^6$ and $R^{10}$ are in reversed positions.

Compounds of Formula (III) and (IV)

In another aspect, disclosed are compounds of Formula (III):

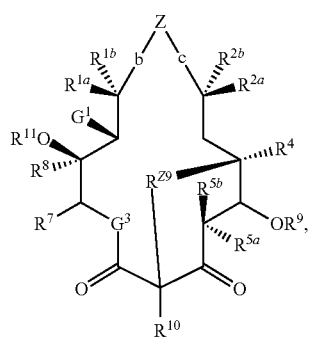

(III)

and pharmaceutically acceptable salts thereof, wherein:

Z is —C(=O)— or —$NR^{Z2}$—;

when Z is —$NR^{Z2}$—, one of b and c is $CH_2$ or —C(=O)—, and the other is a bond, or both b and c are a bond;

when Z is —C(=O)—, b and c are both a bond;

each instance of $R^{1a}$, $R^{1b}$, $R^{2a}$, and $R^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or wherein $R^{1a}$ and $R^{1b}$ or $R^{2a}$ and $R^{2b}$ can be taken together to form a carbonyl or

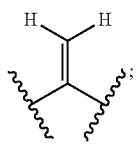 [SMILES: *C(*)=C]

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, guanidino, a nitrogen protecting group, —C(=O)$R^{Z8}$, —C(=O)N($R^{Z8}$)$_2$, or —C(=O)O$R^{Z8}$, or a group of formula:

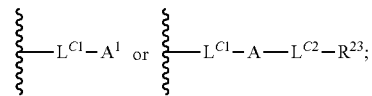

$R^{Z9}$ is optionally substituted heteroalkylene, optionally substituted heteroalkenylene, optionally substituted heteroalkynylene, optionally substituted alkylene, optionally substituted alkenylene, or optionally substituted alkynylene;

$R^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

$R^{5a}$ and $R^{5b}$ are each independently hydrogen, halogen, silyl, optionally substituted alkyl, optionally substituted carbocyclyl, or optionally substituted heterocyclyl;

$R^7$ and $R^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{Z8}$, —C(=O)O$R^{Z8}$, —C(=O)N($R^{Z8}$)$_2$, an oxygen protecting group, or a carbohydrate;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaryl, optionally substituted heteroaralkyl, —O$R^{Z8}$, —S$R^{Z8}$, —N($R^{Z8}$)$_2$, or acyl;

$G^3$ is —O—, —S—, or —N($R^{G1}$)—, wherein $R^{G1}$ is hydrogen, optionally substituted alkyl, or a nitrogen protecting group;

$G^1$ is —O$R^{12}$ or —N$R^{13}R^{14}$;

provided when $G^1$ is —O$R^{12}$, then $R^{11}$ and $R^{12}$ are joined as a group of formula —C(=O)— to provide a cyclic carbonate, or $R^{11}$ and $R^{12}$ are not joined, and $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, and $R^{12}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group, or a group of formula:

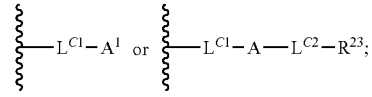

or provided when $G^1$ is —N$R^{13}R^{14}$, then $R^{11}$ and $R^{13}$ are joined as a group of formula —C(=O)— to provide a cyclic carbamate, or $R^{11}$ and $R^{13}$ are not joined, $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group, $R^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)$R^{Z8}$, or —C(=O)O$R^{Z8}$, or a group of formula:

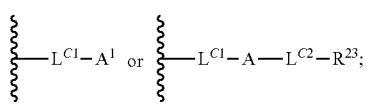

or $R^{13}$ and $R^{14}$ are joined to form an optionally substituted heterocyclyl or optionally substituted heteroaryl;

each instance of $L^{C1}$ and $L^{C2}$ is independently a bond, optionally substituted alkylene, optionally substituted alkenylene, optionally substituted alkynylene, optionally substituted heteroalkylene, optionally substituted heteroalkenylene, optionally substituted heteroalkynylene, or combinations thereof;

each instance of $A^1$ is independently a leaving group (LG), —SH, —OH, —NH$_2$, —NH—, NH$_2$, —N$_3$, —O—NH$_2$, —C(=O)$R^{X1}$,

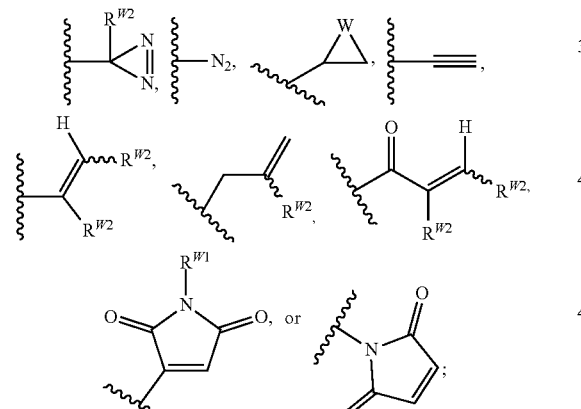

A is optionally substituted carbocyclyl, optionally substituted heterocyclyl, optionally substituted aryl, optionally substituted heteroaryl, —NH—, —NH—NH—, —NH—O—, —O—NH—, —S—, —O—,

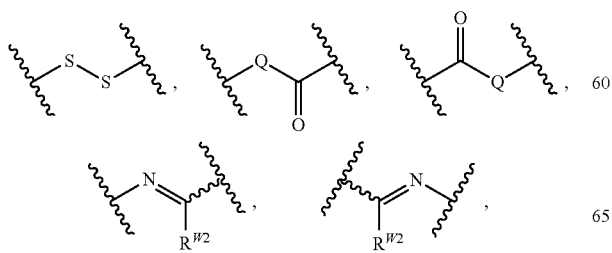

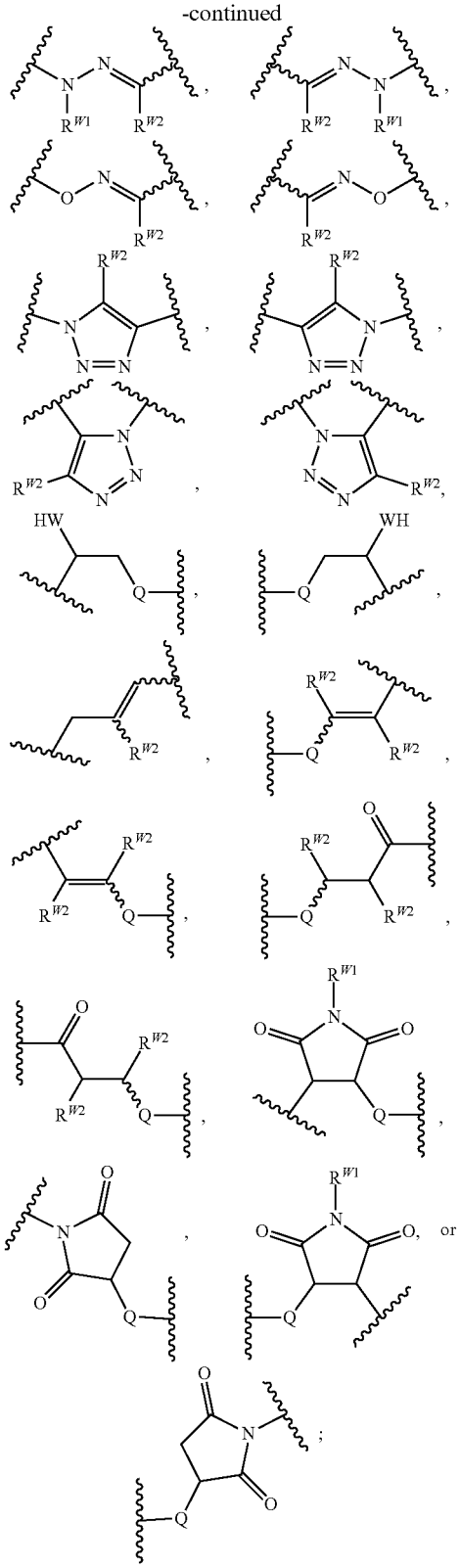

Q is —NH—, —NH—NH—, —O—NH—, —NH—O—, —S—, or —O—;
W is O, S, or NR$^{W1}$;
$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

$R^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two $R^{W2}$ groups are joined to form an optionally substituted cyclic moiety;

$R^{X1}$ is hydrogen, halogen, or $-OR^{X2}$, wherein $R^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

$R^{23}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocyclyl or optionally substituted heteroaryl ring.

In certain embodiments, the compound of Formula (III) is a compound of Formula (III-a):

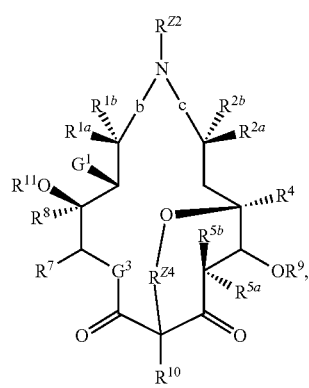

(III-a)

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-b-i) or Formula (III-b-ii):

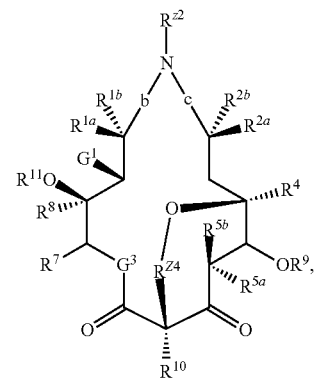

(III-b-i)

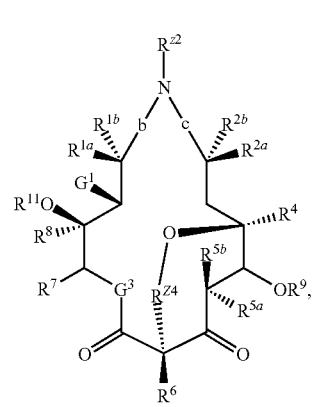

(III-b-ii)

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-c-i) or Formula (III-c-ii):

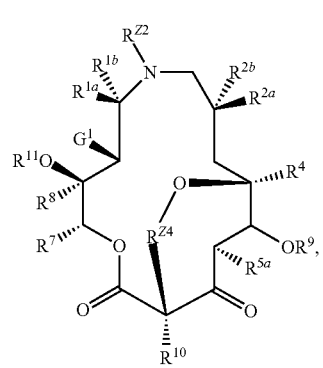

(III-c-i)

-continued (III-c-ii)

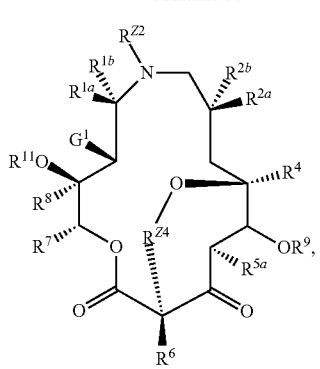

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-d-i) or Formula (III-d-i):

(III-d-i)

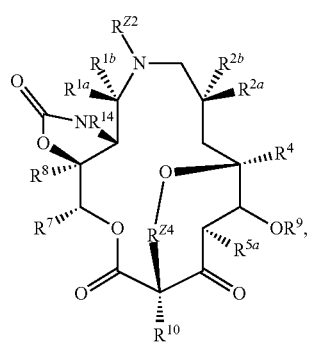

(III-d-ii)

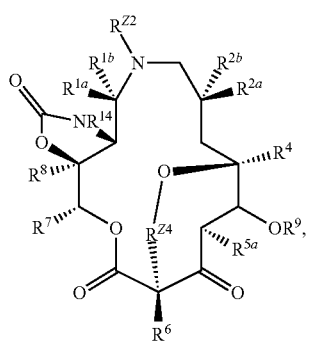

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-e-i) or Formula (III-e-ii):

(III-e-i)

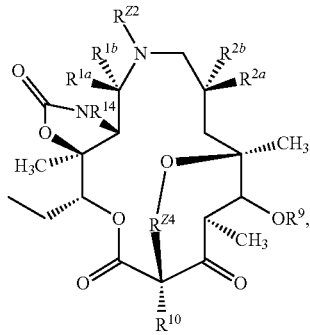

(III-e-ii)

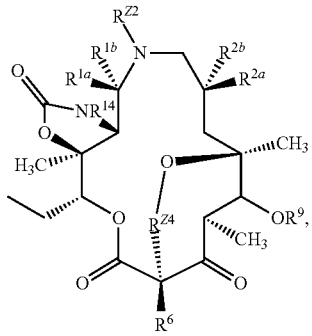

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-f-i) or Formula (III-f-ii):

(III-f-i)

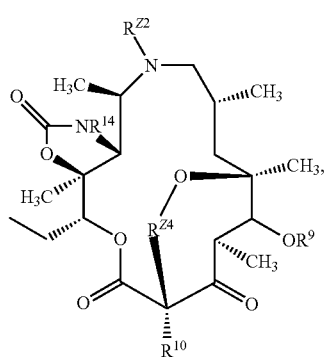

(III-f-ii)

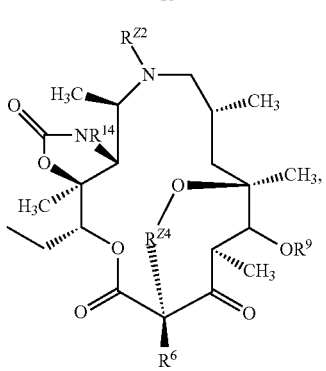

or a pharmaceutically acceptable salt thereof, wherein:

$R^{Z4}$ is optionally substituted heteroalkylene, optionally substituted alkylene, optionally substituted alkenylene, or optionally substituted alkynylene.

In certain embodiments, the compound of Formula (III) is a compound of Formula (III-g-i) or Formula (III-g-ii):

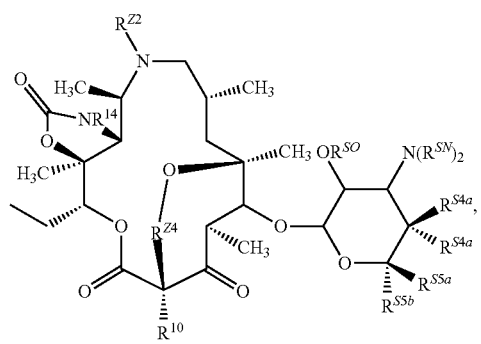

(III-g-i)

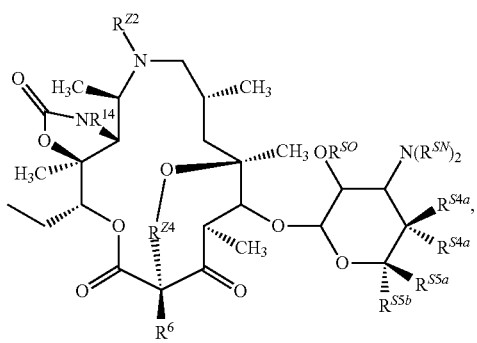

(III-g-ii)

or a pharmaceutically acceptable salt thereof, wherein:

$R^{Z4}$ is optionally substituted heteroalkylene, optionally substituted alkylene, optionally substituted alkenylene, or optionally substituted alkynylene;

each of $R^{S4a}$, $R^{S4b}$, $R^{S5a}$, and $R^{S5b}$ is independently hydrogen, optionally substituted alkyl, or $-OR^{SO}$;

each instance of $R^{SO}$ independently hydrogen, optionally substituted alkyl, optionally substituted alkenyl, optionally substituted heterocyclyl, or an oxygen protecting group; and $R^{SN}$ is independently hydrogen, optionally substituted alkyl, or a nitrogen protecting group; or optionally two $R^{SN}$ are taken with the intervening atoms to form a heterocyclic ring.

In certain embodiments, the compound of Formula (III) is a compound of Formula (III-h-i) or Formula (III-h-ii):

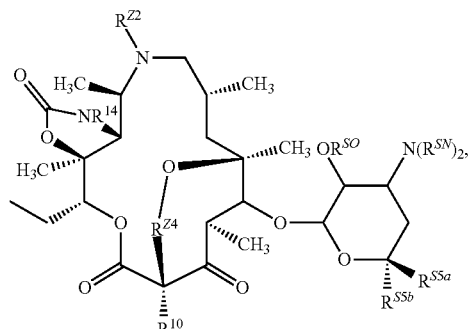

(III-h-i)

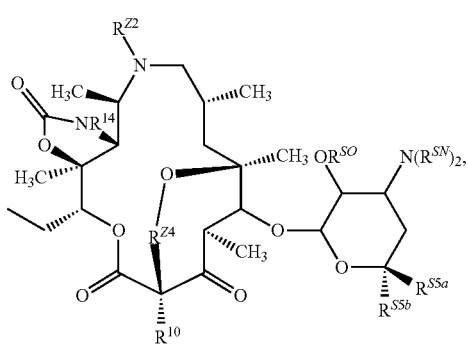

(III-h-ii)

or a pharmaceutically acceptable salt thereof, wherein:

$R^{Z4}$ is optionally substituted heteroalkylene, optionally substituted alkylene, optionally substituted alkenylene, or optionally substituted alkynylene;

each of $R^{S5a}$ and $R^{S5b}$ is independently hydrogen, optionally substituted alkyl, or $-OR^{SO}$;

each instance of $R^{SO}$ independently hydrogen, optionally substituted alkyl, optionally substituted alkenyl, optionally substituted heterocyclyl, or an oxygen protecting group; and $R^{SN}$ is independently hydrogen, optionally substituted alkyl, or a nitrogen protecting group; or optionally two $R^{SN}$ are taken with the intervening atoms to form a heterocyclic ring.

In certain embodiments, the compound of Formula (III) is a compound of Formula (III-i-i) or Formula (III-i-ii):

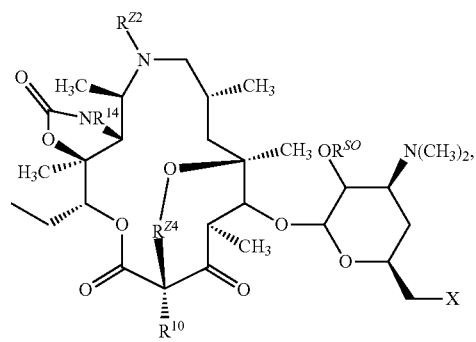

(III-i-i)

-continued (III-i-ii)

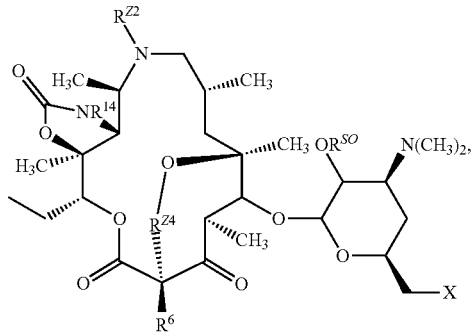

or a pharmaceutically acceptable salt thereof, wherein:

$R^{Z4}$ is optionally substituted heteroalkylene, optionally substituted alkylene, optionally substituted alkenylene, or optionally substituted alkynylene;

X is hydrogen, optionally substituted $C_{1-6}$ alkyl, —$OR^A$, or —$NR^B$—$(CR^xR^x)_t$-A-$(R^y)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, the compound of Formula (III) is a compound of Formula (III-j-i) or Formula (III-j-ii):

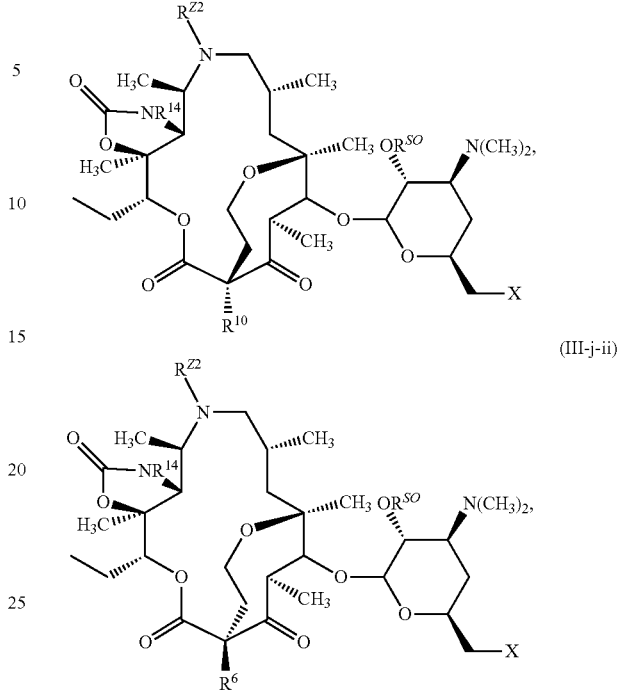

or a pharmaceutically acceptable salt thereof, wherein:

X is hydrogen, optionally substituted $C_{1-6}$ alkyl, —$OR^A$, or —$NR^B$—$(CR^xR^x)_t$-A-$(R^>)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, the compound of Formula (III) is a compound of Formula (III-k-i) or Formula (III-k-ii):

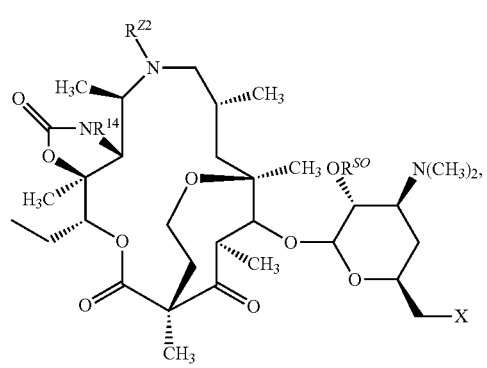

(III-k-i)

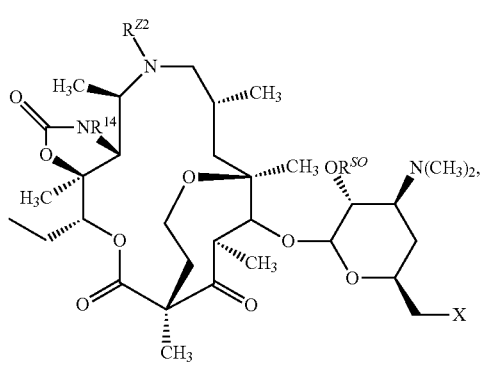

(III-k-ii)

or a pharmaceutically acceptable salt thereof, wherein:

X is hydrogen, optionally substituted CHS alkyl, —OR$^A$, or —NR$^B$—(CR$^x$R$^x$)$_t$-A-(R$^y$)$_q$;

t is 0, 1, or 2;

q is 1, 2, or 3;

R$^A$ is hydrogen, optionally substituted alkyl, optionally substituted heteroalkyl, optionally substituted alkenyl, or —C(=O)—R$^{S1}$;

R$^{S1}$ is optionally substituted aryl or optionally substituted heteroaryl;

R$^B$ is hydrogen, optionally substituted C$_1$-C$_6$ alkyl, optionally substituted C$_1$-C$_6$ cycloalkyl, or C(O)CH$_2$NR$^{x1}$R$^{y1}$;

each R$^x$ is independently hydrogen or C$_{1-3}$ alkyl;

A is arylene, heteroarylene, heterocyclylene, cycloalkylene, alkylene, alkenylene, alkynylene, or a bond;

each R$^y$ is independently, hydrogen, C$_{1-6}$ alkyl, C$_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, C$_{1-6}$ alkylsulfonyl, heteroaryl, or heteroaryloxy;

or when A is a bond and t is 0, R$^B$ and R$^y$ together along with the nitrogen to which they are attached optionally form a 4, 5, 6, or 7-membered optionally substituted ring containing up to two additional heteroatoms;

R$^{x1}$ and R$^{y1}$ are each independently hydrogen, optionally substituted C$_1$-C$_6$ alkyl, or optionally substituted C$_3$-C$_6$ cycloalkyl, or R$^{x1}$ and R$^{y1}$ together along with the nitrogen to which they are attached form a 4, 5, 6, or 7-membered optionally substituted ring containing up to two additional heteroatoms; and R$^{SO}$ is hydrogen, optionally substituted alkyl, optionally substituted alkenyl, optionally substituted heterocyclyl, or an oxygen protecting group.

In another aspect, disclosed are compounds of Formula (IV):

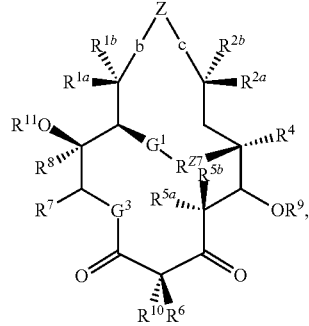

(IV)

and pharmaceutically acceptable salts thereof, wherein:

Z is —C(=O)— or —NR$^{Z2}$—;

when Z is —NR$^{Z2}$—, one of b and c is CH$_2$ or —C(=O)—, and the other is a bond, or both b and c are a bond;

when Z is —C(=O)—, b and c are both a bond;

each instance of R$^{1a}$, R$^{1b}$, R$^{2a}$, and R$^{2b}$ is independently hydrogen, halogen, carbonyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or wherein R$^{1a}$ and R$^{1b}$ or R$^{2a}$ and R$^{2b}$ can be taken together to form a carbonyl or

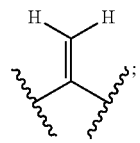

R$^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, guanidino, a nitrogen protecting group, —C(=O)R$^{Z8}$, —C(=O)N(R$^{Z8}$)$_2$, or —C(=O)OR$^{Z8}$, or a group of formula:

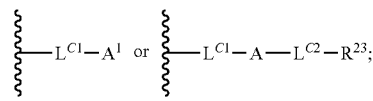

R$^{Z7}$ is optionally substituted heteroalkylene, optionally substituted heteroalkenylene, optionally substituted heteroalkynylene, optionally substituted alkylene, optionally substituted alkenylene, or optionally substituted alkynylene;

R$^4$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl;

R$^{5a}$ and R$^{5b}$ are each independently hydrogen, halogen, silyl, optionally substituted alkyl, optionally substituted carbocyclyl, or optionally substituted heterocyclyl;

R$^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl, —OR$^{Z8}$, —SR$^{Z8}$, —N(R$^{Z8}$)$_2$, or acyl;

R$^7$ and R$^8$ are each independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{Z8}$, —C(=O)OR$^{Z8}$, —C(=O)N(R$^{Z8}$)$_2$, an oxygen protecting group, or a carbohydrate;

R$^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, optionally substituted heteroaryl, optionally substituted heteroaralkyl, —OR$^{Z8}$, —SR$^{Z8}$, —N(R$^{Z8}$)$_2$, or acyl;

G$^3$ is —O—, —S—, or —N(R$^{G1}$)—, wherein R$^{G1}$ is hydrogen, optionally substituted alkyl, or a nitrogen protecting group;

G$^1$ is —O— or —NR$^{13}$—;

R$^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^{13}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, —C(=O)R$^{Z8}$, or —C(=O)OR$^{Z8}$, or a group of formula:

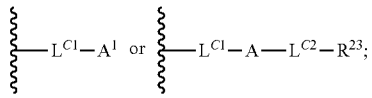

or R$^{11}$ and R$^{13}$ are joined as a group of formula —C(=O)— to provide a cyclic carbamate;

each instance of L$^{C1}$ and L$^{C2}$ is independently a bond, optionally substituted alkylene, optionally substituted alkenylene, optionally substituted alkynylene, optionally substituted heteroalkylene, optionally substituted heteroalkenylene, optionally substituted heteroalkynylene, or combinations thereof;

each instance of A$^1$ is independently a leaving group (LG), —SH, —OH, —NH$_2$, —NH—, NH$_2$, —N$_3$, —O—NH$_2$, —C(=O)R$^{X1}$,

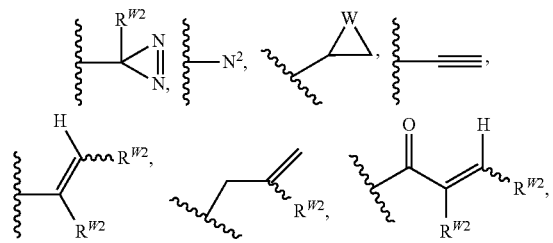

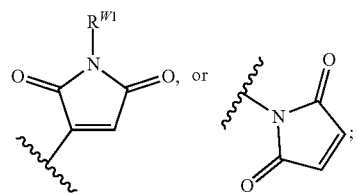

A is optionally substituted carbocyclyl, optionally substituted heterocyclyl, optionally substituted aryl, optionally substituted heteroaryl, —NH—, —NH—NH—, —NH—O—, —O—NH—, —S—, —O—,

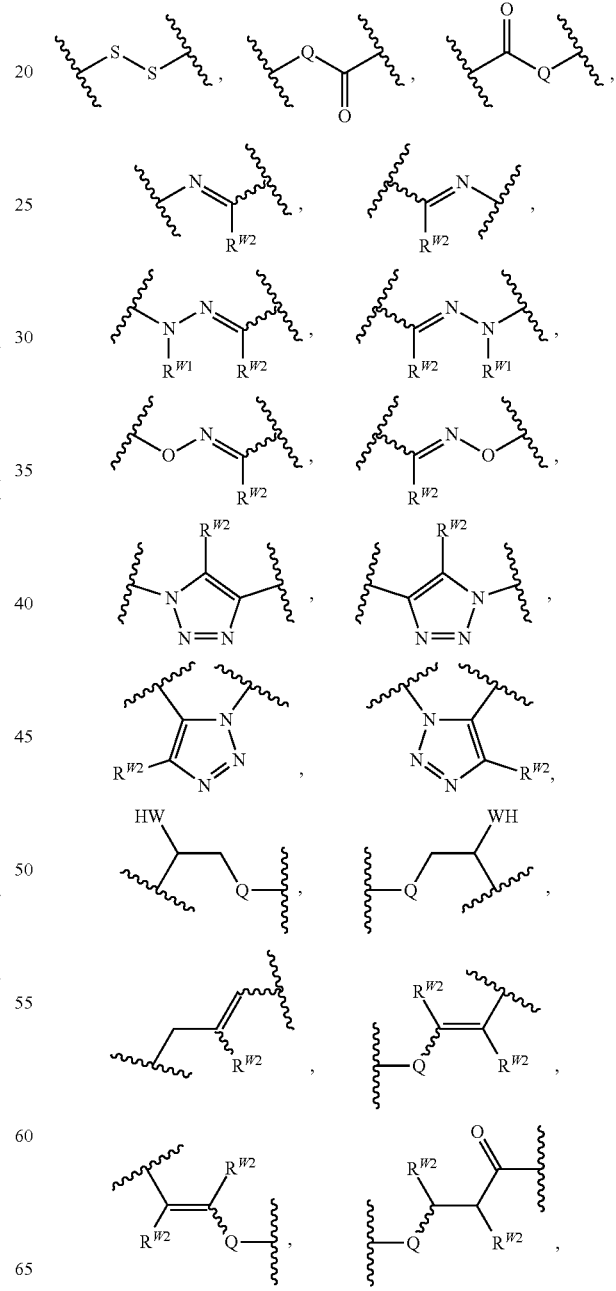

-continued

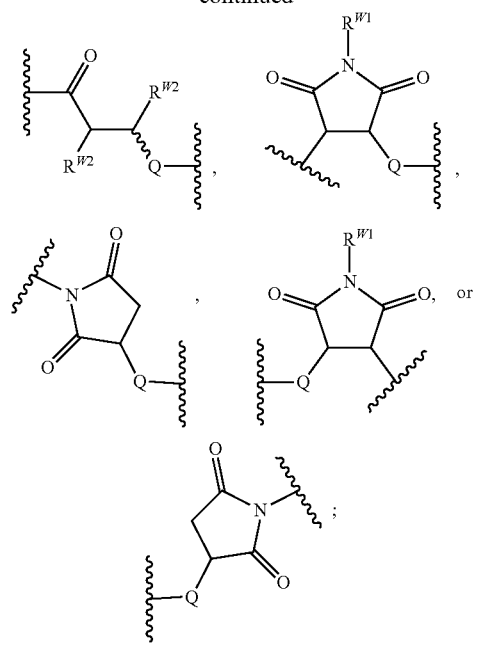

Q is —NH—, —NH—NH—, —O—NH—, —NH—O—, —S—, or —O—;

W is O, S, or $NR^{W1}$;

$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group;

$R^{W2}$ is hydrogen, optionally substituted alkyl; optionally substituted alkenyl; optionally substituted alkynyl; optionally substituted carbocyclyl; optionally substituted heterocyclyl; optionally substituted aryl; optionally substituted heteroaryl, or two $R^{W2}$ groups are joined to form an optionally substituted cyclic moiety;

$R^{X1}$ is hydrogen, halogen, or —$OR^{X2}$, wherein $R^{X2}$ is hydrogen; optionally substituted alkyl; optionally substituted alkyl; optionally substituted alkenyl; optionally substituted alkynyl; optionally substituted carbocyclyl; optionally substituted heterocyclyl; optionally substituted aryl; optionally substituted heteroaryl; or an oxygen protecting group;

$R^{23}$ is optionally substituted alkyl; optionally substituted alkenyl; optionally substituted alkynyl; optionally substituted carbocyclyl; optionally substituted heterocyclyl; optionally substituted aryl; or optionally substituted heteroaryl; and each instance of $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups are joined to form an optionally substituted heterocyclyl or optionally substituted heteroaryl ring.

In certain embodiments, the compound of Formula (IV) is a compound of Formula (IV-a):

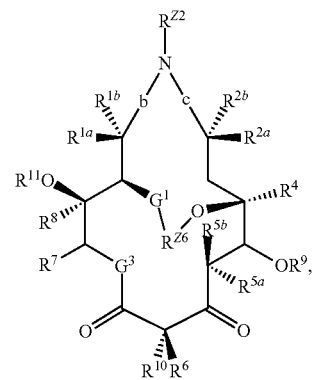

or a pharmaceutically acceptable salt thereof, wherein:
$R^{Z6}$ is optionally substituted heteroalkylene, optionally substituted alkylene, optionally substituted alkenylene, or optionally substituted alkynylene.

In certain embodiments, the compound of Formula (IV) is of Formula (IV-b):

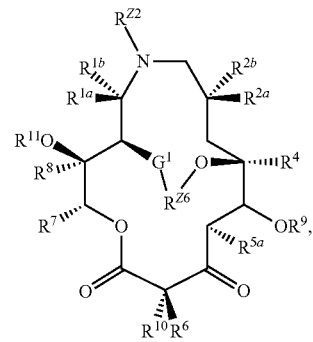

or a pharmaceutically acceptable salt thereof, wherein:
$R^{Z6}$ is optionally substituted heteroalkylene, optionally substituted alkylene, optionally substituted alkenylene, or optionally substituted alkynylene.

In certain embodiments, the compound of Formula (IV) is of Formula (IV-c):

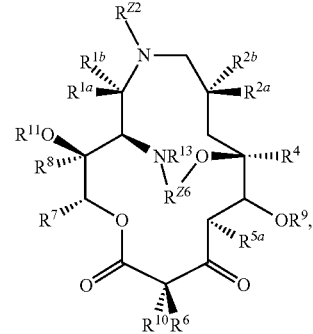

or a pharmaceutically acceptable salt thereof, wherein:
$R^{Z6}$ is optionally substituted heteroalkylene, optionally substituted alkylene, optionally substituted alkenylene, or optionally substituted alkynylene.

In certain embodiments, the compound of Formula (IV) is a compound of Formula (IV-d):

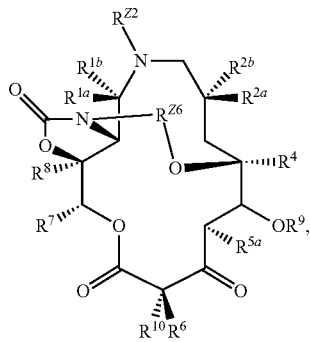

(IV-d)

or a pharmaceutically acceptable salt thereof, wherein:

$R^{Z6}$ is optionally substituted heteroalkylene, optionally substituted alkylene, optionally substituted alkenylene, or optionally substituted alkynylene.

In certain embodiments, the compound of Formula (IV) is a compound of Formula (IV-e):

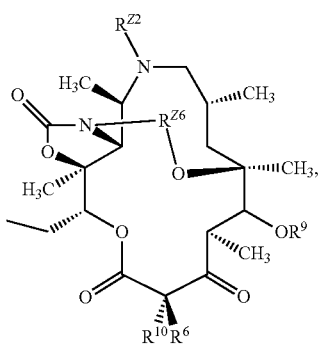

(IV-e)

or a pharmaceutically acceptable salt thereof, wherein:

$R^{Z6}$ is optionally substituted heteroalkylene, optionally substituted alkylene, optionally substituted alkenylene, or optionally substituted alkynylene.

In certain embodiments, the compound of Formula (IV) is a compound of Formula (IV-f):

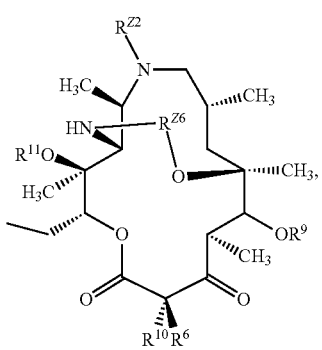

(IV-f)

or a pharmaceutically acceptable salt thereof, wherein:

$R^{Z6}$ is optionally substituted heteroalkylene, optionally substituted alkylene, optionally substituted alkenylene, or optionally substituted alkynylene.

In certain embodiments, the compound of Formula (IV) is a compound of Formula (IV-g):

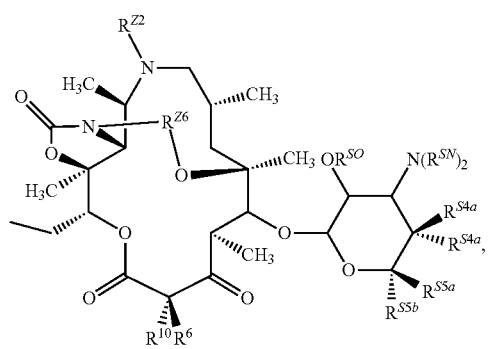

(IV-g)

or a pharmaceutically acceptable salt thereof, wherein:

$R^{Z6}$ is optionally substituted heteroalkylene, optionally substituted alkylene, optionally substituted alkenylene, or optionally substituted alkynylene;

each of $R^{S4a}$, $R^{S4b*}$, $R^{S5a}$, and $R^{S5b}$ is independently hydrogen, optionally substituted alkyl, or —$OR^{SO}$;

each instance of $R^{SO}$ is independently hydrogen, optionally substituted alkyl, optionally substituted alkenyl, optionally substituted heterocyclyl, or an oxygen protecting group; and $R^{SN}$ is independently hydrogen, optionally substituted alkyl, or a nitrogen protecting group; or optionally two $R^{SN}$ are taken with the intervening atoms to form a heterocyclic ring.

In certain embodiments, the compound of Formula (IV) is a compound of Formula (IV-h):

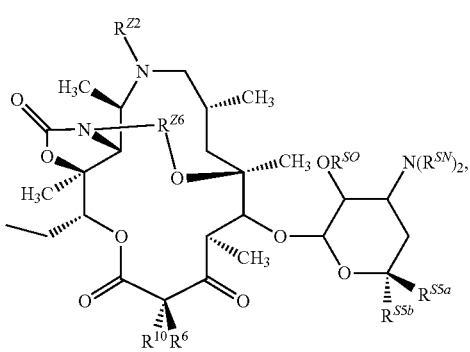

(IV-h)

or a pharmaceutically acceptable salt thereof, wherein:

$R^{Z6}$ is optionally substituted heteroalkylene, optionally substituted alkylene, optionally substituted alkenylene, or optionally substituted alkynylene;

each of $R^{S5a}$ and $R^{S5b}$ is independently hydrogen, optionally substituted alkyl, or —$OR^{SO}$;

each instance of $R^{SO}$ is independently hydrogen, optionally substituted alkyl, optionally substituted alkenyl, optionally substituted heterocyclyl, or an oxygen protecting group; and $R^{SN}$ is independently hydrogen, optionally substituted alkyl, or a nitrogen protecting group; or optionally two $R^{SN}$ are taken with the intervening atoms to form a heterocyclic ring.

In certain embodiments, the compound of Formula (IV) is a compound of Formula (IV-i):

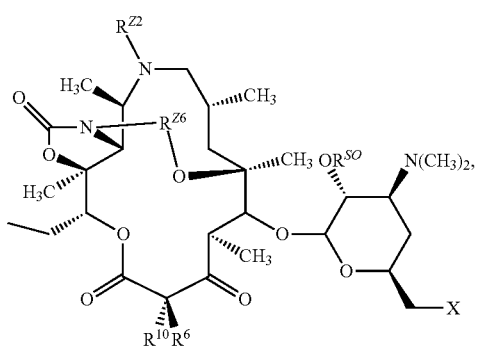

(IV-i)

or a pharmaceutically acceptable salt thereof, wherein:

$R^{Z6}$ is optionally substituted heteroalkylene, optionally substituted alkylene, optionally substituted alkenylene, or optionally substituted alkynylene;

X is hydrogen, optionally substituted CHS alkyl, —$OR^A$, or —$NR^B$—$(CR^xR^x)_t$-A-$(R^y)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, the compound of Formula (IV) is a compound of Formula (IV-j):

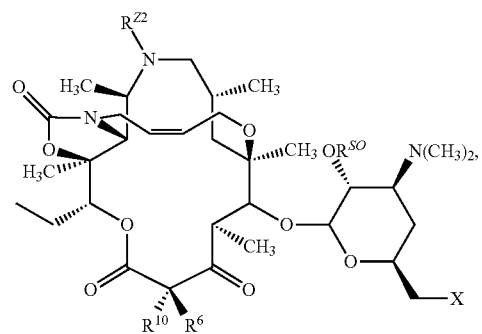

(IV-j)

or a pharmaceutically acceptable salt thereof, wherein:

X is hydrogen, optionally substituted $C_{1-6}$ alkyl, —$OR^A$, or —$NR^B$—$(CR^xR^x)_t$-A-$(R^y)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, the compound of Formula (IV) is a compound of Formula (IV-k):

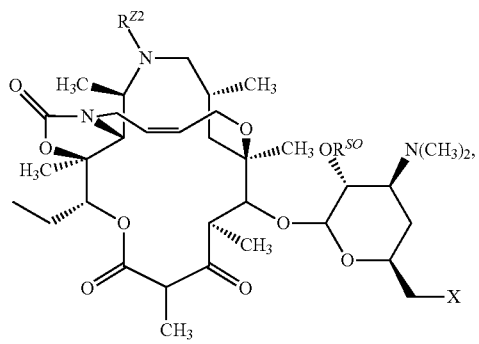

(IV-k)

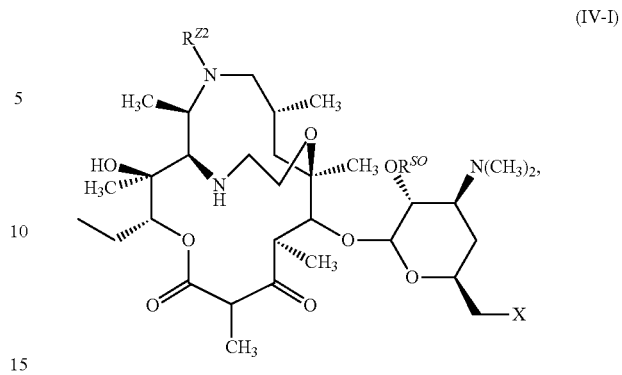

(IV-l)

or a pharmaceutically acceptable salt thereof, wherein:

X is hydrogen, optionally substituted $C_{1-6}$ alkyl, $-OR^A$, or $-NR^B-(CR^xR^x)_t-A-(R^y)_q$;

t is 0, 1, or 2;

q is 1, 2, or 3;

$R^A$ is hydrogen, optionally substituted alkyl, optionally substituted heteroalkyl, optionally substituted alkenyl, or $-C(=O)-R^{S1}$;

$R^{S1}$ is optionally substituted aryl or optionally substituted heteroaryl;

$R^B$ is hydrogen, optionally substituted $C_1-C_6$ alkyl, optionally substituted $C_1-C_6$ cycloalkyl, or $C(O)$ $CH_2NR^{x1}R^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, $C(O)OC_{1-3}$ alkyl, $C(O)OH$, $C(O)CH_2NR^{x1}R^{y1}$, $C(O)$ $NR^{x1}R^{y1}$, $C(O)C_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1-C_6$ alkyl, or optionally substituted $C_3-C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, the compound of Formula (IV) is a compound of Formula (IV-l):

or a pharmaceutically acceptable salt thereof, wherein:

X is hydrogen, optionally substituted $C_{1-6}$ alkyl, $-OR^A$, or $-NR^B-(CR^xR^x)_t-A-(R^y)_q$;

t is 0, 1, or 2;

q is 1, 2, or 3;

$R^A$ is hydrogen, optionally substituted alkyl, optionally substituted heteroalkyl, optionally substituted alkenyl, or $-C(=O)-R^{S1}$;

$R^{S1}$ is optionally substituted aryl or optionally substituted heteroaryl;

$R^B$ is hydrogen, optionally substituted $C_1-C_6$ alkyl, optionally substituted $C_1-C_6$ cycloalkyl, or $C(O)$ $CH_2NR^{x1}R^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, $C(O)OC_{1-3}$ alkyl, $C(O)OH$, $C(O)CH_2NR^{x1}R^{y1}$, $C(O)$ $NR^{x1}R^{y1}$, $C(O)C_{1-6}$ alkyl, $C_{1-6}$ alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1-C_6$ alkyl, or optionally substituted $C_3-C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments of Formula (III) and (IV), $R^9$ is of the formula:

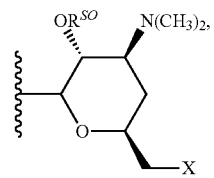

wherein:

X is hydrogen, optionally substituted $C_{1-6}$ alkyl, $-OR^A$, or $-NR^B-(CR^xR^x)_t-A-(R^y)_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, $C_{1-5}$ alkyl sulfonyl, heteroaryl, or heteroaryloxy;

or when A is a bond, and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, $R^9$ is of the formula:

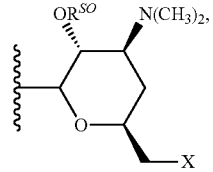

wherein:

X is optionally substituted $C_{1-6}$ alkyl, —OR$^A$, or —NR$^B$—(CR$^x$R$^x$)$_t$-A-(R$^y$)$_q$;

t is 0, 1, or 2;

q is 1, 2, or 3;

$R^A$ is hydrogen, optionally substituted alkyl, optionally substituted heteroalkyl, optionally substituted alkenyl, or —C(=O)—$R^{S1}$;

$R^{S1}$ is optionally substituted aryl or optionally substituted heteroaryl;

$R^B$ is hydrogen, optionally substituted $C_1$-$C_6$ alkyl, optionally substituted $C_1$-$C_6$ cycloalkyl, or C(O)CH$_2$NR$^{x1}$R$^{y1}$;

each $R^x$ is independently hydrogen or $C_{1-3}$ alkyl;

A is arylene, heteroarylene, heterocyclylene, cycloalkylene, alkylene, alkenylene, alkynylene, or a bond;

each $R^y$ is independently, hydrogen, $C_{1-6}$ alkyl, $C_{1-6}$ alkoxy, halogen, hydroxyl, cyano, dialkylamino, haloalkyl, C(O)OC$_{1-3}$ alkyl, C(O)OH, C(O)CH$_2$NR$^{x1}$R$^{y1}$, C(O)NR$^{x1}$R$^{y1}$, C(O)C$_{1-6}$ alkyl, C1-6 alkyl sulfonyl, heteroaryl, or heteroaryloxy;

or when A is a bond and t is 0, $R^B$ and $R^y$ together along with the nitrogen to which they are attached optionally form a 4, 5, 6, or 7-membered optionally substituted ring containing up to two additional heteroatoms;

$R^{x1}$ and $R^{y1}$ are each independently hydrogen, optionally substituted $C_1$-$C_6$ alkyl, or optionally substituted $C_3$-$C_6$ cycloalkyl, or $R^{x1}$ and $R^{y1}$ together along with the nitrogen to which they are attached form a 4, 5, 6, or 7-membered optionally substituted ring containing up to two additional heteroatoms; and $R^{SO}$ is hydrogen, optionally substituted alkyl, optionally substituted alkenyl, optionally substituted heterocyclyl, or an oxygen protecting group.

In certain embodiments, $R^9$ is of the formula:

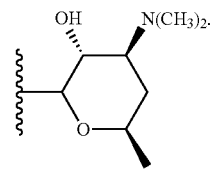 [SMILES: *C1O[C@H](C)C[C@H](N(C)C)[C@H]1O]

Exemplary Macrolides

Exemplary compounds of Formula (I) include, but are not limited to the compounds listed in Tables 1-10 and following, or pharmaceutically acceptable salts thereof.

TABLE 1

Examples of compounds of Formula (I)

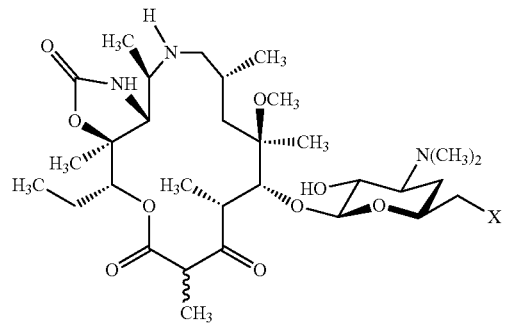

| X |
|---|
| 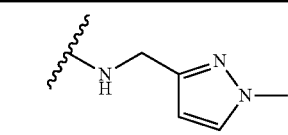 |
| 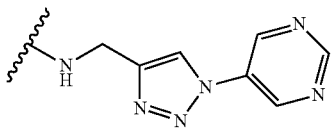 [SMILES: *NCc1cn(-c2cncnc2)nn1] |
| 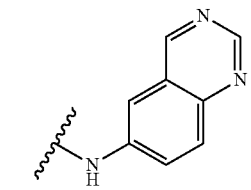 [SMILES: *Nc1ccc2ncncc2c1] |
| 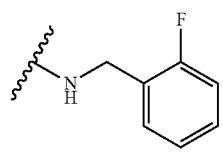 [SMILES: *NCc1ccccc1F] |

TABLE 1-continued
Examples of compounds of Formula (I)
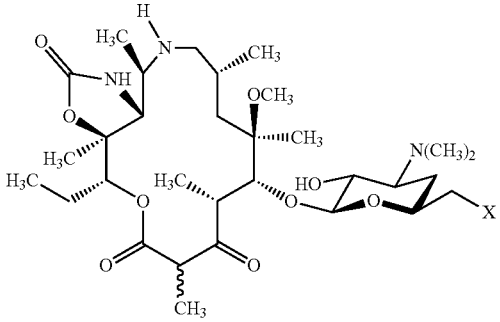
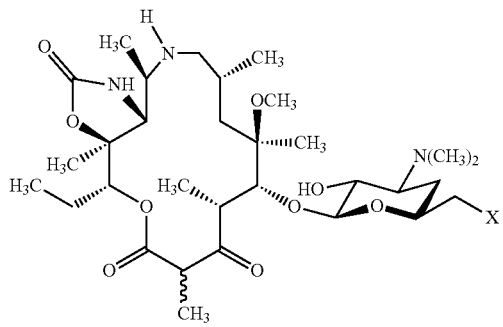

TABLE 1-continued

Examples of compounds of Formula (I)

TABLE 1-continued

Examples of compounds of Formula (I)

TABLE 1-continued
Examples of compounds of Formula (I)
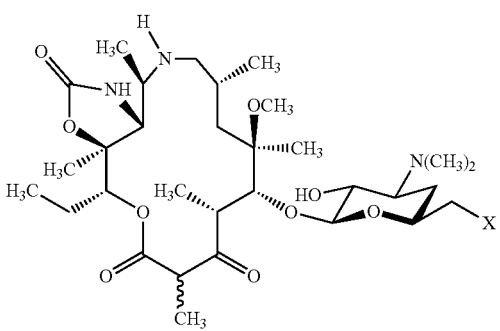
| 91 | 92 |
|---|---|
| X | X |

TABLE 1-continued
Examples of compounds of Formula (I)
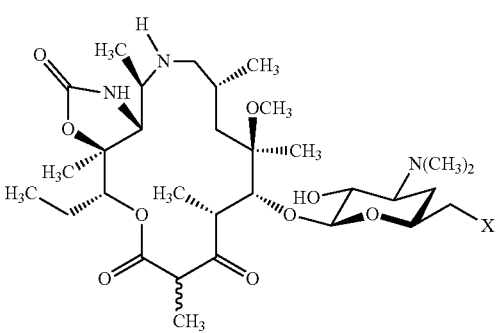
X
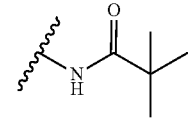
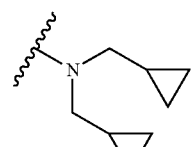
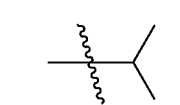 [SMILES: *C(C)C]
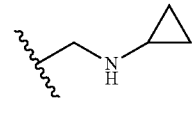 [SMILES: *CNC1CC1]
TABLE 2
Examples of compounds of Formula (I)
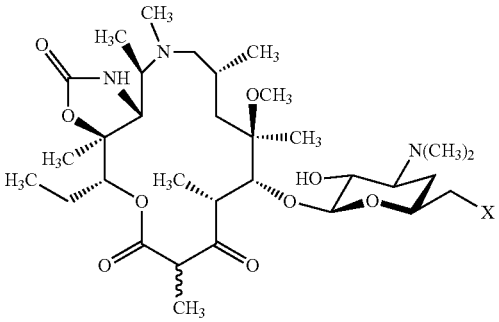
X
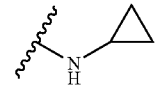
TABLE 2-continued
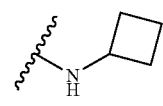
TABLE 3
Examples of compounds of Formula (I)
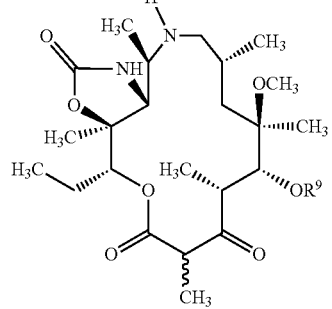
$R^9$
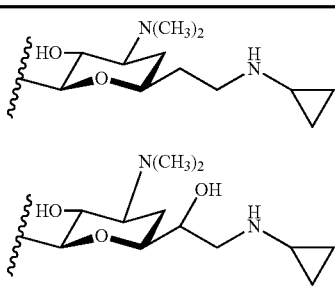
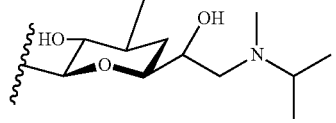
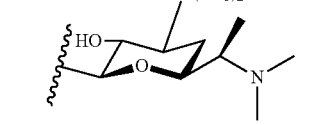
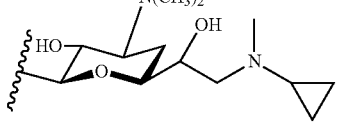
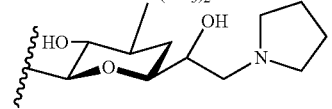
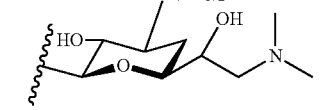

TABLE 3-continued
Examples of compounds of Formula (I)
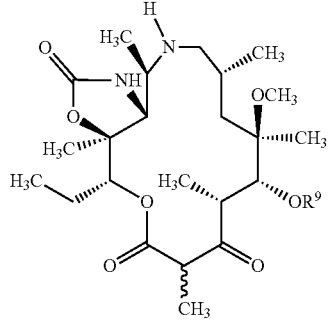
R⁹
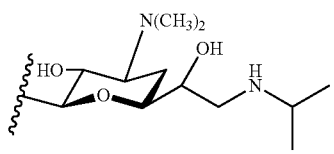
TABLE 4
Examples of compounds of Formula (I)
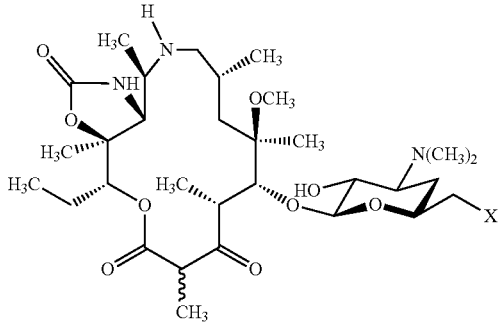
X
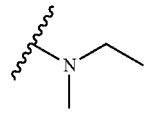
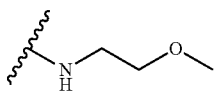
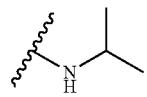
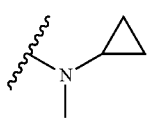
TABLE 4-continued
Examples of compounds of Formula (I)
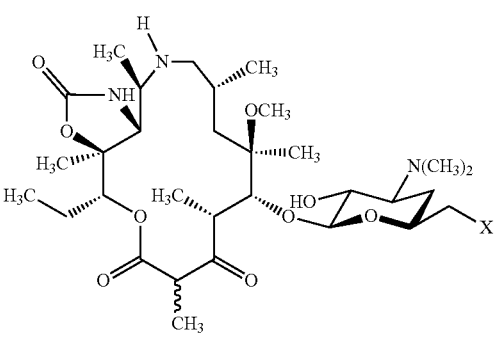
X
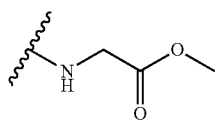 [SMILES: *NCC(=O)OC]
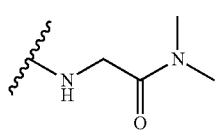 [SMILES: *NCC(=O)N(C)C]
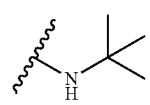
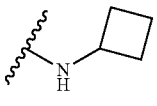
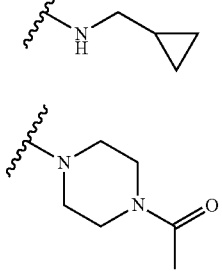
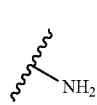
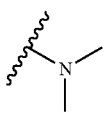
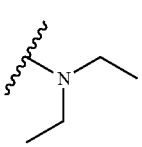

TABLE 4-continued
Examples of compounds of Formula (I)
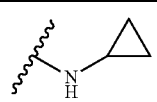
X
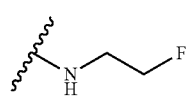
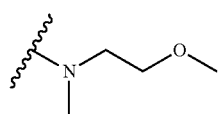
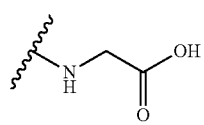
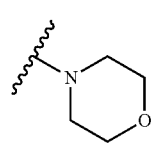
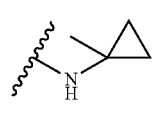
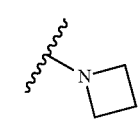
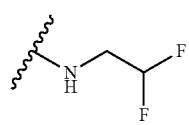 [SMILES: *NCC(F)F]
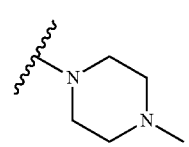 [SMILES: *N1CCN(C)CC1]
TABLE 4-continued
Examples of compounds of Formula (I)
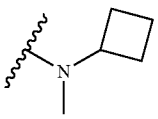 [SMILES: *N(C)C1CCC1]
X
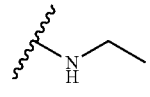
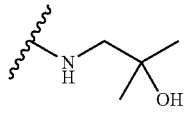
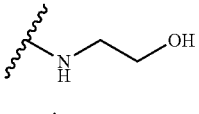
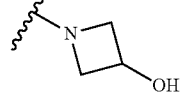
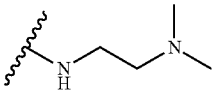
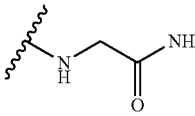
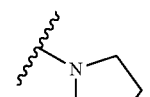
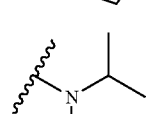
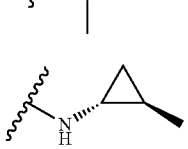

TABLE 4-continued
Examples of compounds of Formula (I)
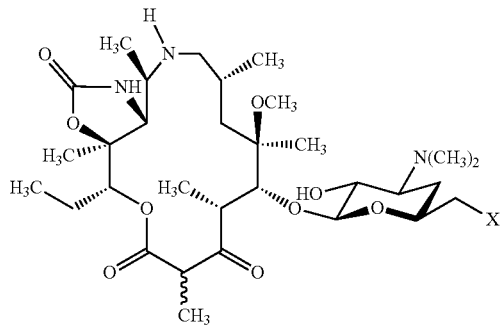
X
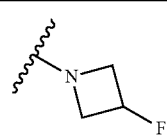
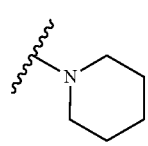 [SMILES: *N1CCCCC1]
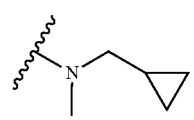 [SMILES: *N(C)CC1CC1]
TABLE 5
Examples of compounds of Formula (I)
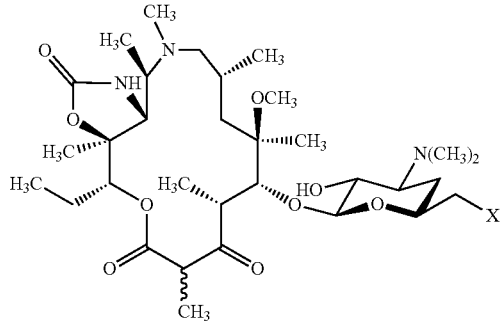
X
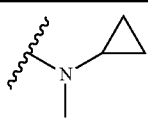
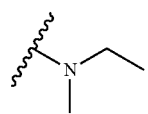 [SMILES: *N(C)CC]
TABLE 5-continued
Examples of compounds of Formula (I)
X
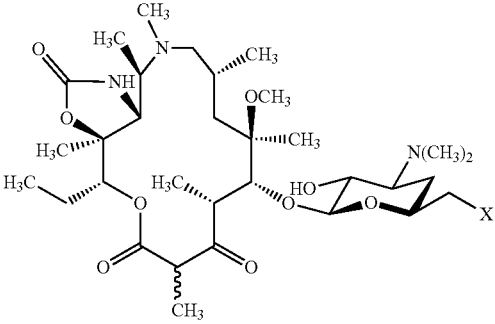
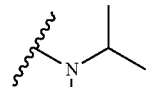
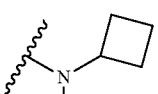
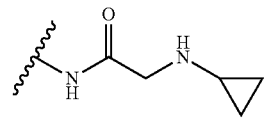 [SMILES: *NC(=O)CNC1CC1]
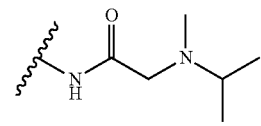 [SMILES: *NC(=O)CN(C)C(C)C]
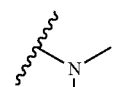
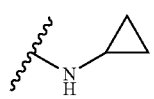
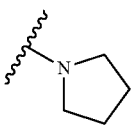
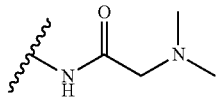 [SMILES: *NC(=O)CN(C)C]
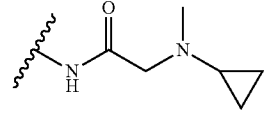 [SMILES: *NC(=O)CN(C)C1CC1]

TABLE 5-continued
Examples of compounds of Formula (I)
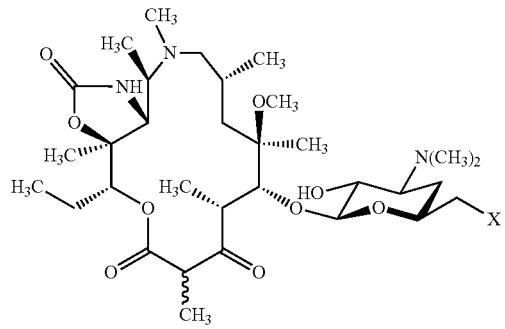
X
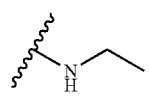 [SMILES: *NCC]
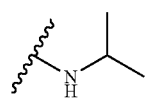 [SMILES: *NC(C)C]
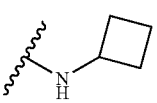 [SMILES: *NC1CCC1]
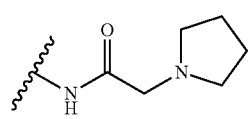 [SMILES: *NC(=O)CN1CCCC1]
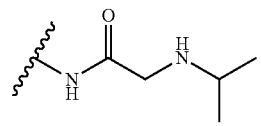 [SMILES: *NC(=O)CNC(C)C]
TABLE 6
Examples of compounds of Formula (I)
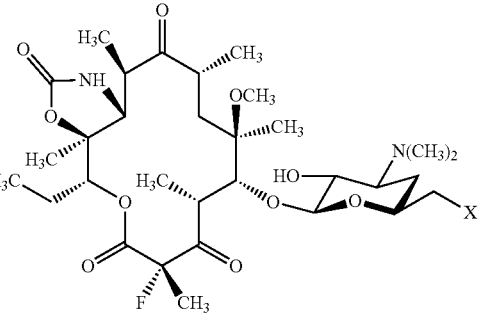
X
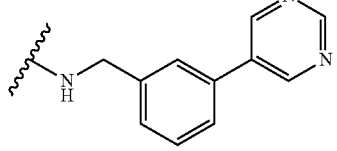
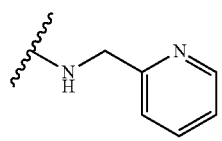 [SMILES: *NCc1ccccn1]
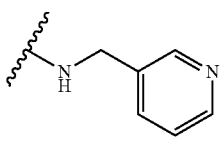 [SMILES: *NCc1cccnc1]
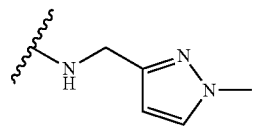 [SMILES: *NCc1ccn(C)n1]
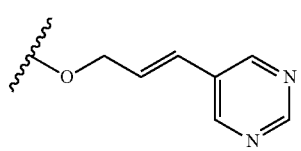 [SMILES: *OC/C=C/c1cncnc1]
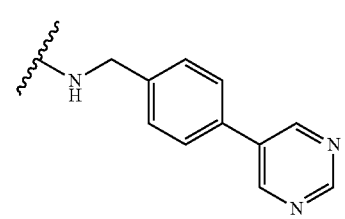 [SMILES: *NCc1ccc(-c2cncnc2)cc1]
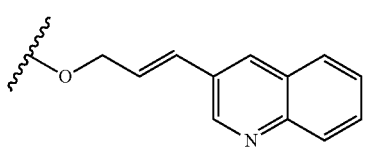 [SMILES: *OC/C=C/c1cnc2ccccc2c1]

TABLE 6-continued

Examples of compounds of Formula (I)

| Structure | |
|---|---|
| *(macrolide structure with F, CH3, OCH3, N(CH3)2, OH, X substituent)* | |

| X |
|---|
| —NH—C6H4—(pyrimidin-5-yl) |
| —O—CH2CH2—OH |

TABLE 7

Examples of compounds of Formulae (I) and (III)

*(macrolide structure with NMe2, OH, X substituent)*

| X |
|---|
| —OH |
| —NH—CH2—N(piperidinyl) |
| —NH—CH2—CF3 |
| —NH2 |

TABLE 7-continued

Examples of compounds of Formulae (I) and (III)

*(macrolide structure with NMe2, OH, X substituent)*

| X |
|---|
| —NH—CH2—(pyridin-3-yl) |
| —NH—cyclopropyl |
| —NH—CH(CH3)2 |
| —NH—CH2—cyclopropyl |
| —NH—(bicyclobutyl) |
| —CH3 |

TABLE 8
Examples of compounds of Formula (I) and (III)
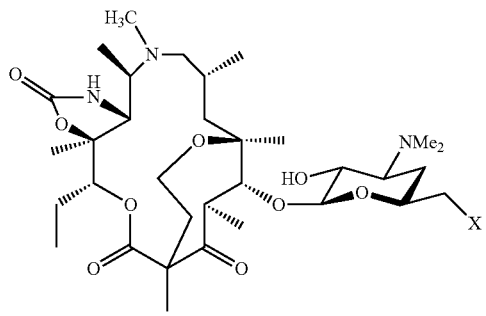
X
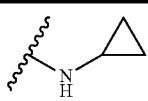
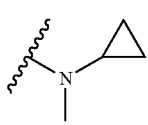 [SMILES: *N(C)C1CC1]
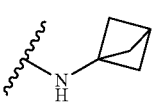 [SMILES: *NC12CC(C1)C2]
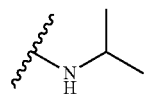
TABLE 9
Examples of compounds of Formula (III)
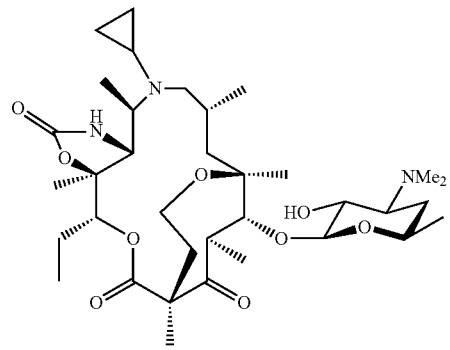
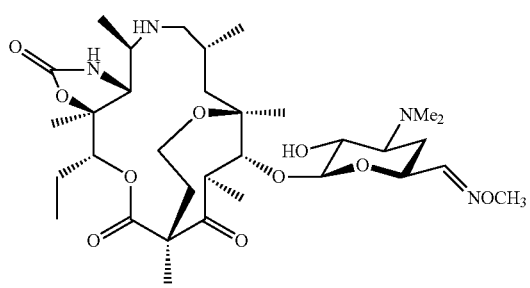
TABLE 9-continued
Examples of compounds of Formula (III)
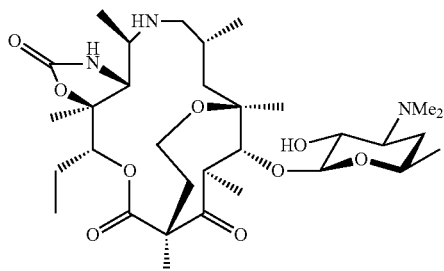
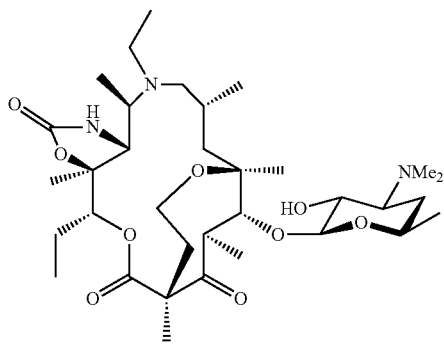
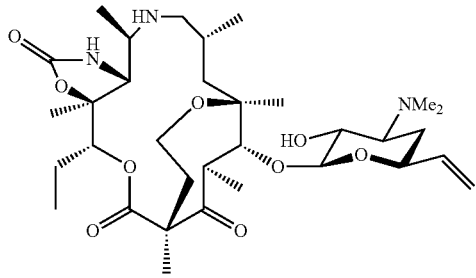
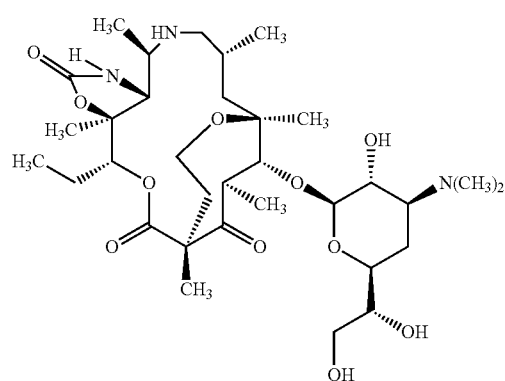

TABLE 9-continued
Examples of compounds of Formula (III)
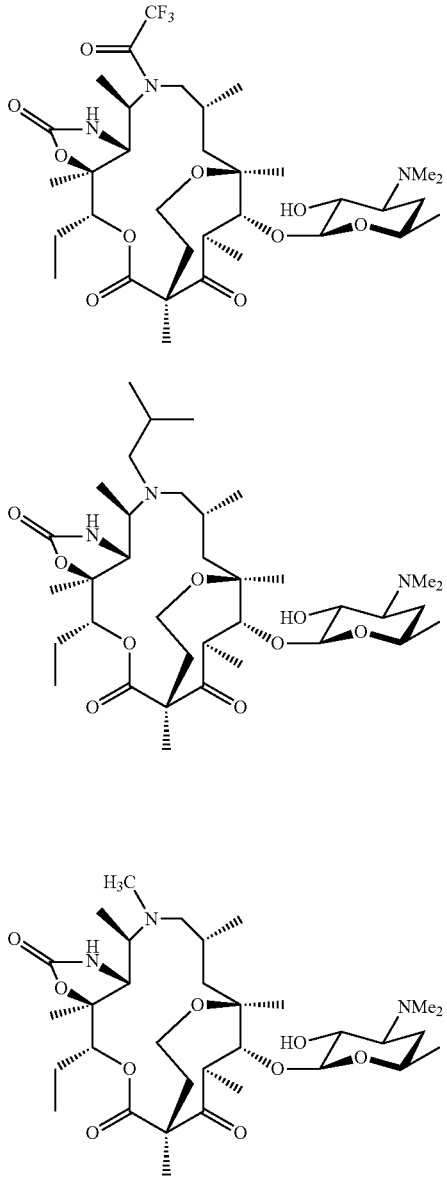
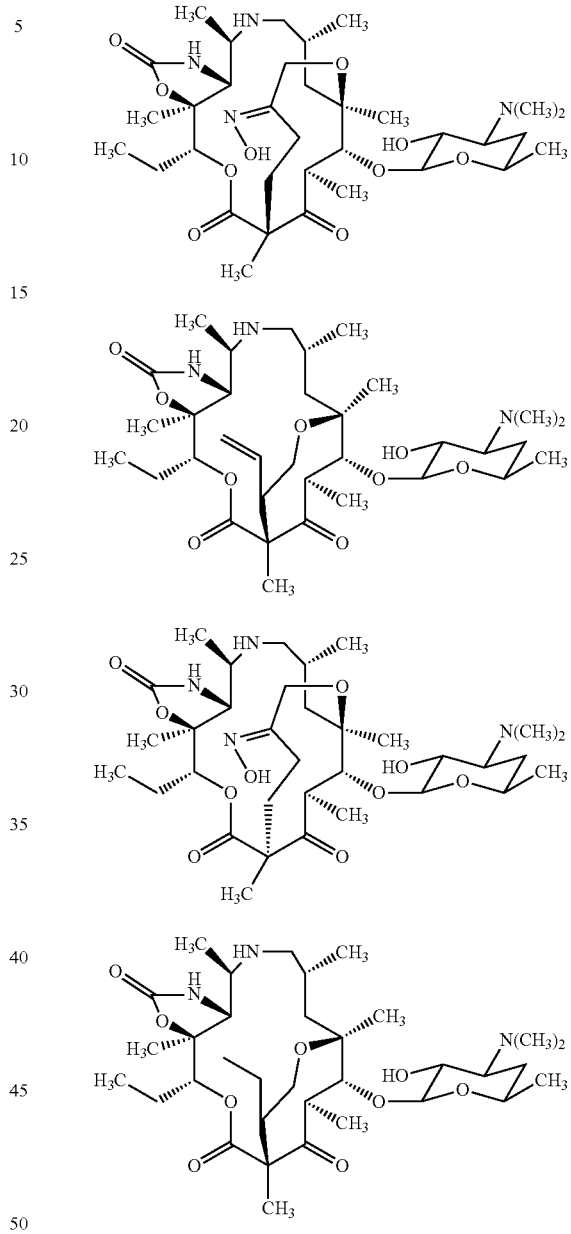
TABLE 10
Examples of compounds of Formula (IV)
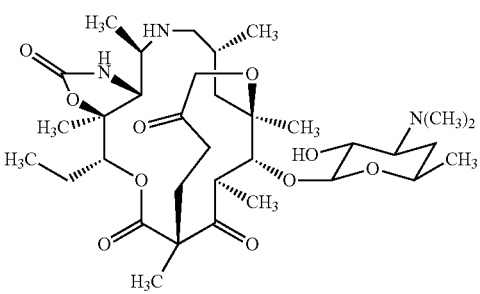
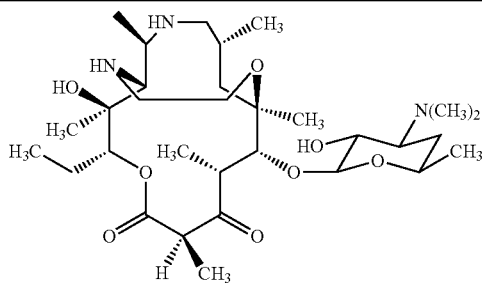

TABLE 10-continued

Examples of compounds of Formula (IV)

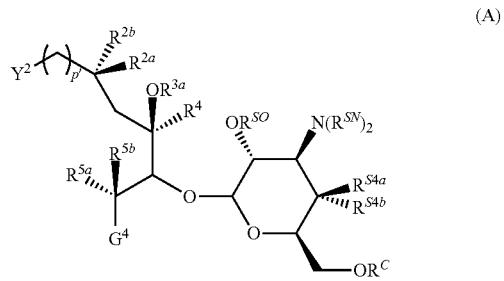

In an embodiment, the disclosed compounds or pharmaceutically acceptable salts thereof are in the (R)-configuration at C-2. In another embodiment, the disclosed compounds are in the (S)-configuration at C-2. In a further embodiment, the disclosed compounds are an epimeric mixture of C-2 (R)- and (S)-isomers.

The present disclosure also includes isotopically-labeled compounds, which are identical to those recited in Formula (I), Formula (II), Formula (III), and Formula (IV), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of Formula (I), Formula (II), Formula (III), and Formula (IV) of this invention and prodrugs thereof can generally be prepared by carrying out the procedures disclosed in the Schemes and/or in the Examples and Preparations below, by substituting a readily available isotopically-labeled reagent for a non-isotopically-labeled reagent.

Compounds of the invention can be prepared by readily available chemical methods such as described, for instance, in published international PCT application, WO 2014/165792.

Additional Formulae

Provided herein are certain intermediates that may be prepared during the preparation of a macrolide described herein. Such intermediates include the eastern half of a macrolide prior to coupling and uncyclized precursors prior to macrolactonization.

In one aspect, the present disclosure provides a macrolide eastern half intermediate of Formula (A):

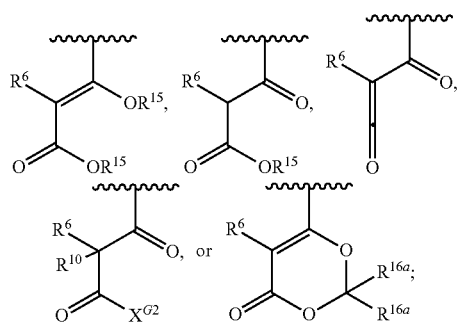

(A)

or salt thereof, wherein:

$R^{2a}$, $R^{2b}$, $R^{3a}$, $R^4$, $R^{5a}$, $R^{5b}$, $R^{S4a}$, $R^{S4b}$, $R^{SN}$, and $R^{SO}$ are as defined herein;

p' is 0, 1, or 2;

$Y^2$ is —$Z^4$H, —$CH_2NO_2$, -LG, —C(=O)$R^{Z3}$, —C(=O)O$R^{Z3}$, —C(=O)LG, —C(=O)CH=P($R^{P1}$)($R^{P2}$)($R^{P3}$), or —C(=O)$CH_2$P(=O)(O$R^{P2}$)(O$R^{P3}$);

LG is a leaving group;

$Z^4$ is —O—, —S—, or —$NR^{X2}$—;

$R^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{P1}$, $R^{1*2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl;

$G^4$ is of formula:

each instance of $X^{G2}$ is —$OR^{15}$, —$SR^{15}$, or —$N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In another aspect, the present disclosure provides an uncyclized macrolide intermediate of Formula (B):

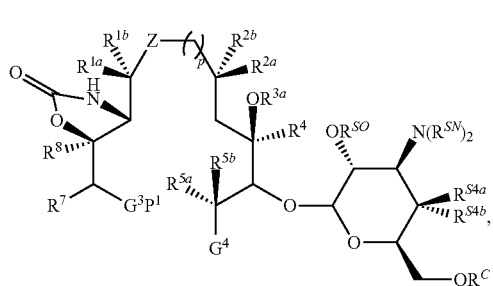

(B)

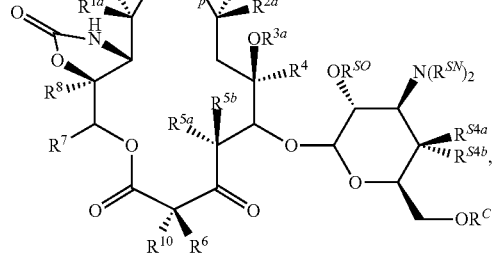

(C)

or salt thereof, wherein:

Z, p, $R^{1a}$, $R^{1b}$, $R^{Z8}$, $R^{2b}$, $R^{3a}$, $R^4$, $R^{5a}$, $R^{5b}$, $R^7$, $R^8$, $R^{S4a}$, $R^{S4b}$, $R^{SN}$, and $R^{SO}$ are as defined herein;

$R^C$ is —(C=O)Ph or —O-allyl, $P^1$ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group;

$G^4$ is of formula:

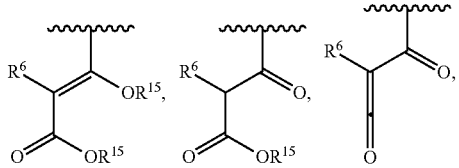

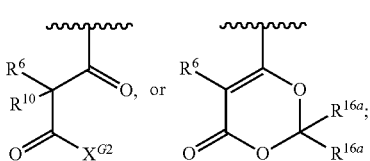

each instance of $X^{G2}$ is —$OR^{15}$, —$SR^{15}$, or —$N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In yet another aspect, the present disclosure provides an intermediate of Formula (C):

or salt thereof, wherein:

Z, $R^{1a}$, $R^{1b}$, $R^{Z8}$, $R^{2b}$, $R^{3a}$, $R^4$, $R^{5a}$, $R^{5b}$, $R^6$, $R^7$, $R^8$, $R^{S4a}$, $R^{S4b}$, $R^{SO}$, and $R^{SN}$ are as defined herein;

and $R^C$ is —(C=O)Ph or —O-allyl.

In another aspect, the present disclosure provides an intermediate of Formula (D):

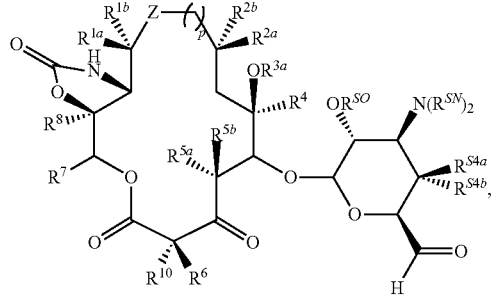

(D)

or salt thereof, wherein:

Z, $R^{1a}$, $R^{1b}$, $R^{Z8}$, $R^{2b}$, $R^{3a}$, $R^4$, $R^{5a}$, $R^{5b}$, $R^6$, $R^7$, $R^8$, $R^{S4a}$, $R^{S4b}$, $R^{SO}$, and $R^{SN}$ are as defined herein.

Preparation by Coupling and Macrolactonization

In certain embodiments, macrolides of the present disclosure are prepared by coupling an eastern half of Formula (A) and a western half of Formula (Z) to provide an uncyclized macrolide precursor of Formula (B) as depicted in Scheme 7, and the precursor of Formula (B) is cyclized to give an intermediate of Formula (C) as depicted in Scheme 2. The intermediate of Formula (C) can be deprotected and oxidized to provide an intermediate of Formula (D) as depicted in Scheme 3. The intermediate of Formula (D) can be reductively aminated to provide a macrolide of Formula (I-a), wherein X is —$NR^B$—$(CR^xR^x)_t$-A-$(R^y)_q$ as depicted in Scheme 4.

Exemplary methods that may be used in the preparation of a macrolide of the present disclosure are described below, and are not to be construed as limiting. Further description of the methods for preparation of the eastern and western halves, coupling of the halves, macrocyclization, and other methods for various steps in the preparation of the macrolides herein are described in PCT publications WO2014/165792 and WO2016/154591, which are both incorporated herein by reference in their entirety. The macrolides herein may be prepared by other methods of synthesis known in the art, and the procedures described herein may be modified or combined with other known methods.

Scheme 1
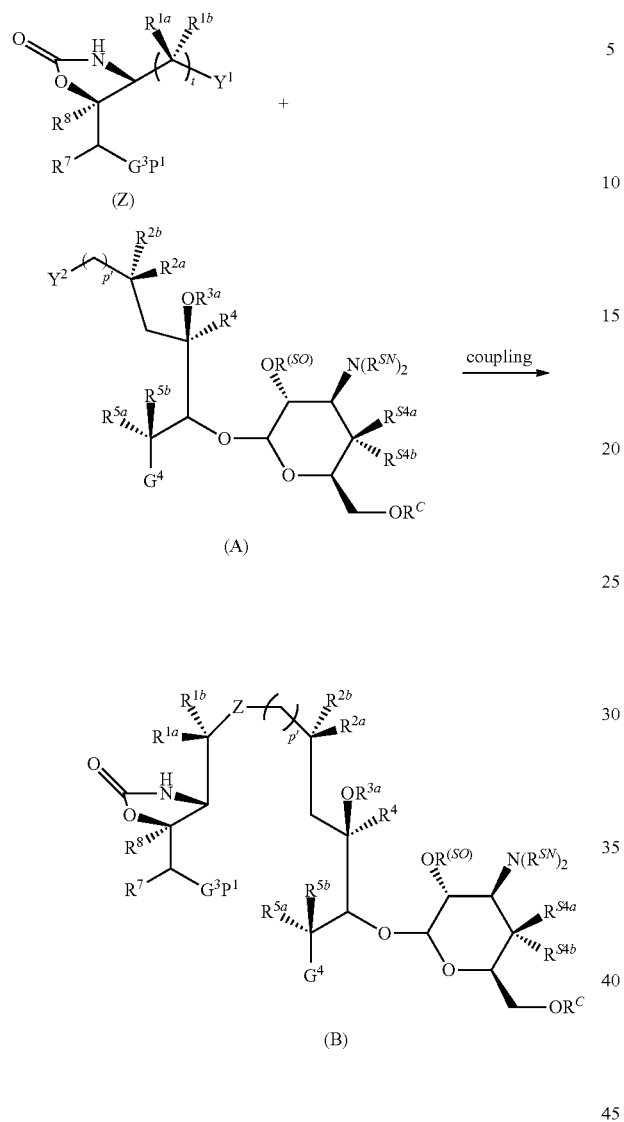
Scheme 2
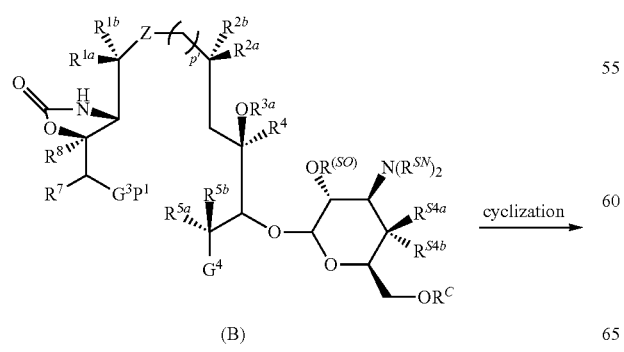
Scheme 3
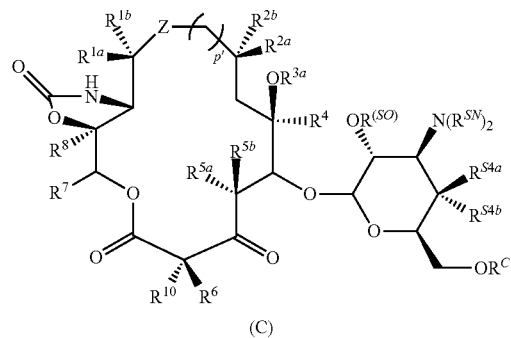
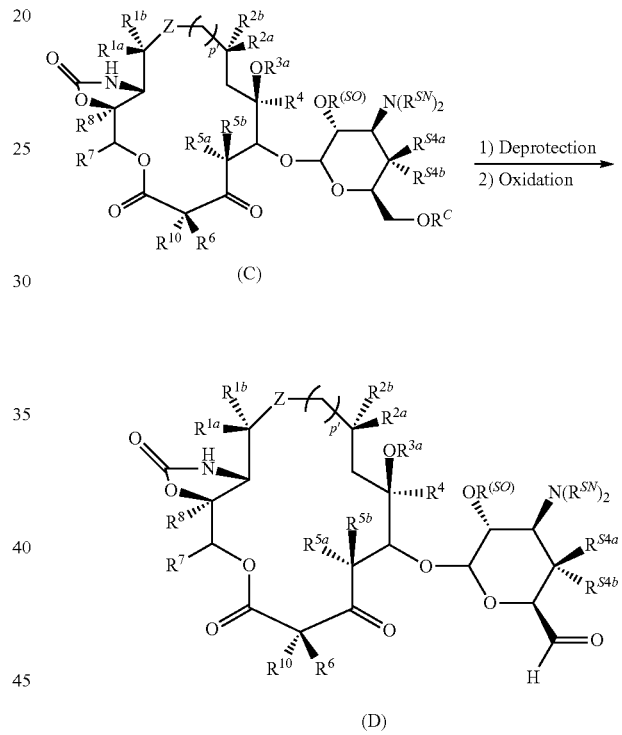
Scheme 4
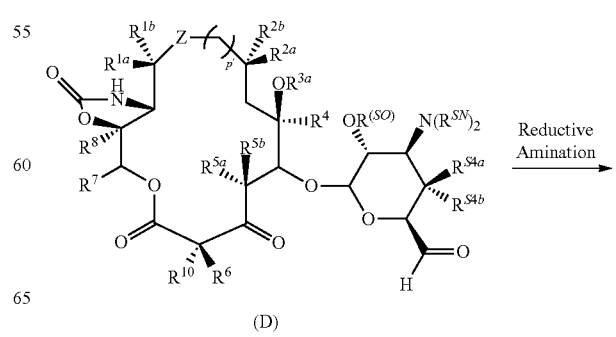

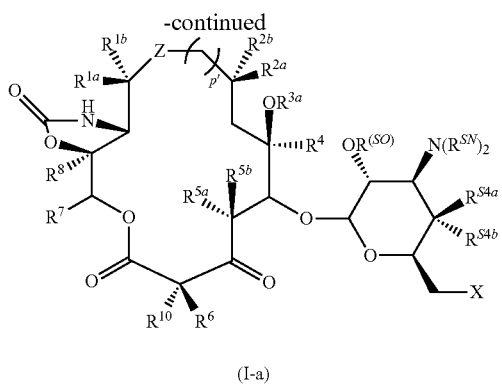

(I-a)

For all intermediates, Z, X, $R^{1a}$, $R^{1b}$, $R^{2a}$, $R^{2b}$, $R^{3a}$, $R^4$, $R^{5a}$, $R^{5b}$, $R^6$, $R^7$, $R^8$, $R^{S4a}$, $R^{S4b}$, $R^{SO}$, and $R^{SN}$ are as defined herein for a compound of Formula (I-a), unless otherwise stated.

Other variables depicted for intermediates and precursors are defined as follows:

$R^C$ is —(C=O)Ph or —O-allyl;
p' is 0, 1, or 2;
t is 0 or 1;
$Y^1$ is —$Z^4$H, —CH$_2$NO$_2$, -LG, —C(=O)$R^{Z3}$, —C(=O)O$R^{Z3}$, —C(=O)LG, or of formula:

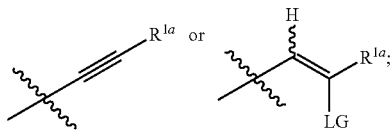

$Y^2$ is —$Z^4$H, —CH$_2$NO$_2$, -LG, —C(=O)$R^{Z3}$, —C(=O)O$R^{Z3}$, —C(=O)LG, —C(=O)CH=P($R^{P1}$)($R^{P2}$)($R^{P3}$), or —C(=O)CH$_2$P(=O)(O$R^{P2}$)(O$R^{P3}$);

LG is a leaving group;
$Z^4$ is —O—, —S—, or —N$R^{X2}$—;
$R^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{P1}$, $R^{P2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl;

$P^1$ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group;

$G^4$ is of formula:

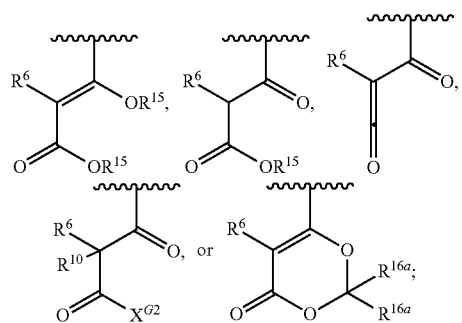

each instance of $X^{O2}$ is —O$R^{15}$, —S$R^{15}$, or —N($R^{15}$)$_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In another embodiment, compounds of Formula II-c may be prepared by reacting an amine with a compound of formula II-c-1 to yield a compound of Formula II-c, wherein P is a protecting group and X is a leaving group (Scheme 5).

Scheme 5

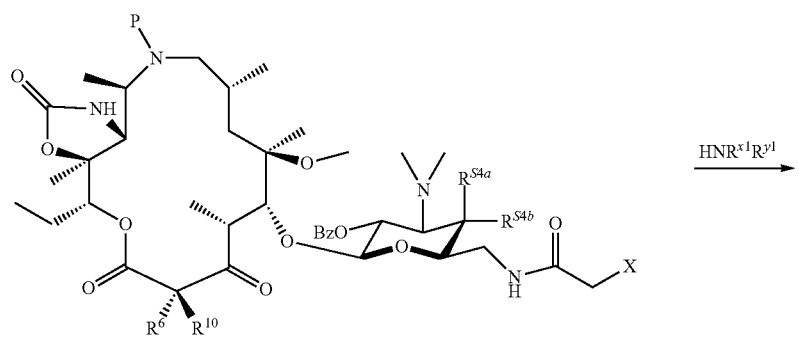

II-c-1

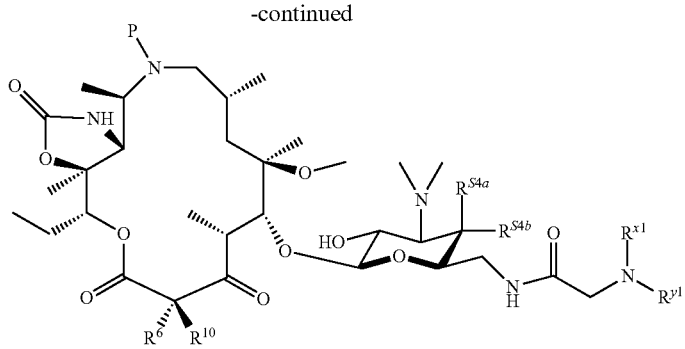

II-c

In another embodiment, compounds of Formula II-d may be prepared by reacting an amine with a compound of formula II-d-1 to yield a compound of Formula II-d, wherein P is a protecting group (Scheme 6).

Scheme 6

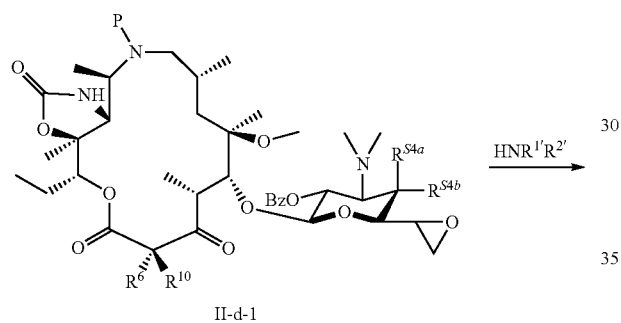

II-d-1

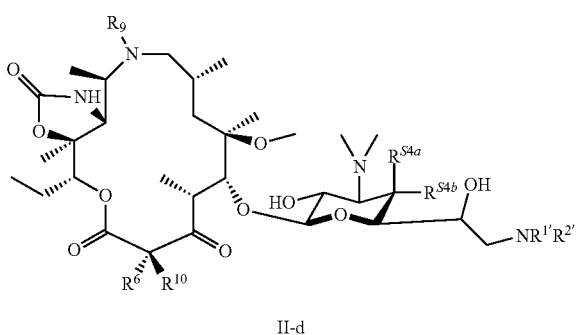

II-d

Preparation of a Modified Sugar

The present disclosure also provides methods of preparing a modified sugar. In certain embodiments, a compound of Formula (V) is prepared by thiolating a compound of Formula (V-a) as depicted in Scheme 7.

Scheme 7

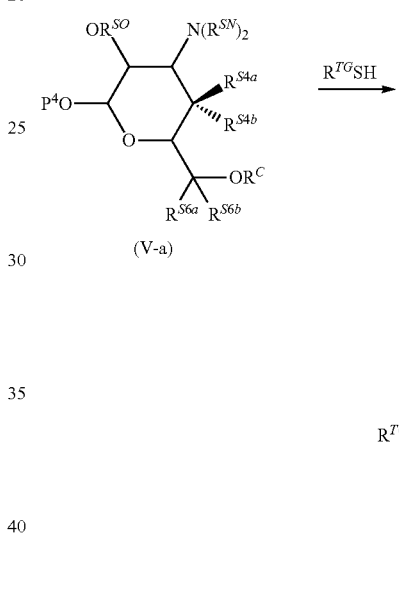

In certain embodiments, the method of preparing a compound of Formula (V) further comprises protecting or alkylating the compound of Formula (V-b) to provide the compound of Formula (V-a) as depicted in Scheme 8.

Scheme 8

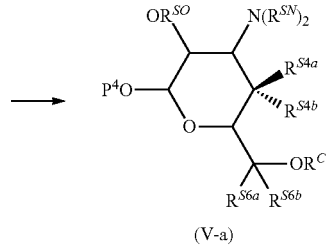

In certain embodiments, the method of preparing compounds of Formula (V) further comprises reducing and alkylating the compound of Formula (V-c) to provide the compound of Formula (V-b) as depicted in Scheme 9.

Scheme 9

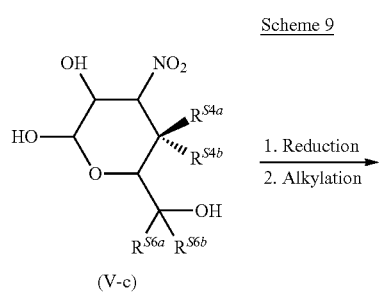

(V-c)

In certain embodiments, the compound of Formula (V) is deprotected to provide the compound of Formula (V'-a), and the compound of Formula (V'-a) is allylated to give the compound of Formula (V'-b) as depicted in Scheme 10.

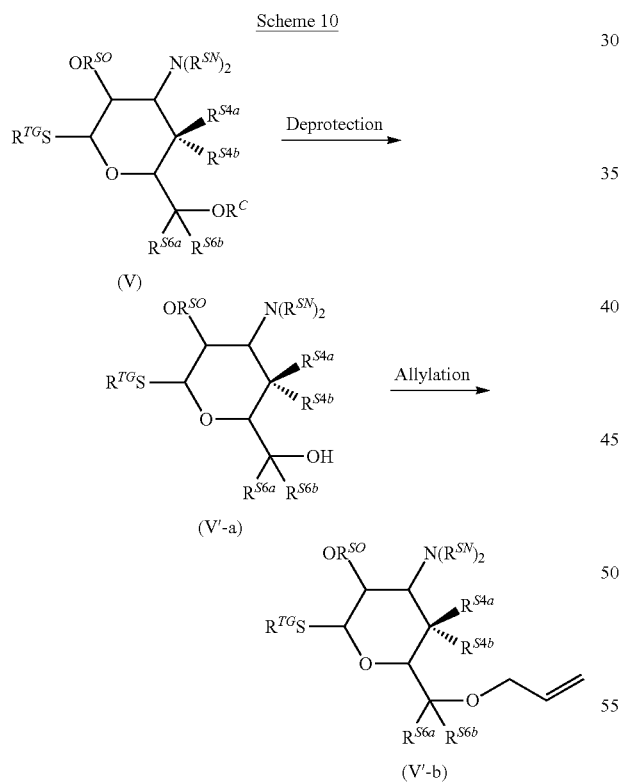

For each of the compounds and intermediates in Schemes 7-10,

P$^4$ is hydrogen, optionally substituted alkyl, or an oxygen protecting group;

R$^C$ is hydrogen, optionally substituted alkyl, optionally substituted heteroalkyl, optionally substituted alkenyl, optionally substituted carbocyclyl, optionally substituted carbocyclylalkyl, optionally substituted heterocyclyl, optionally substituted heterocyclylalkyl, optionally substituted aryl, optionally substituted arylalkyl, optionally substituted heteroaryl, optionally substituted heteroarylalkyl, —C(=O)-L$^{S2}$-R$^{S1}$, or an oxygen protecting group;

L$^{S2}$ is a bond, —NR$^{S1}$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

R$^{S1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two R$^{S1}$ groups attached to the same nitrogen atom are joined to form an optionally substituted heterocyclyl or heteroaryl ring;

each of R$^{S4a}$ and R$^{S4b}$ is independently hydrogen, halogen, optionally substituted C$_{1-6}$ alkyl, or —OR$^{SO}$;

each of R$^{S6a}$ and R$^{S6b}$ is independently hydrogen, halogen, or optionally substituted C$_{1-6}$ alkyl;

each R$^{SN}$ is independently hydrogen, optionally substituted C$_{1-6}$ alkyl, or a nitrogen protecting group, or two R$^{SN}$ groups attached to the same nitrogen atom are joined to form an optionally substituted heterocyclyl or heteroaryl ring;

each R$^{SO}$ is independently hydrogen, optionally substituted C$_{1-6}$ alkyl, a carbohydrate, or an oxygen protecting group; and R$^{TG}$ is methyl, ethyl, phenyl, pyrimidinyl, pyridinyl, benzothiazolyl, benzooxazolyl, or tetrazolyl.

In certain embodiments, R$^C$ is —(C=O)Ph.

In certain embodiments, each R$^{SN}$ is, independently, C$_{1-6}$ alkyl. In certain embodiments, each R$^{SN}$ is methyl.

In certain embodiments, R$^{SO}$ is —(C=O)Ph.

In certain embodiments, both R$^{S4a}$ and R$^{S4b}$ are hydrogen.

In certain embodiments, both R$^{S6a}$ and R$^{S6b}$ are hydrogen.

In certain embodiments, —SR$^{TG}$ is:

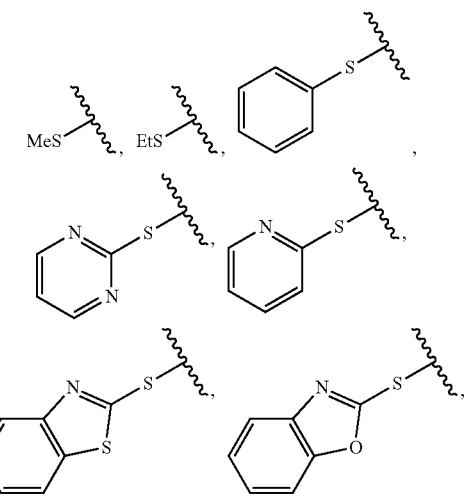

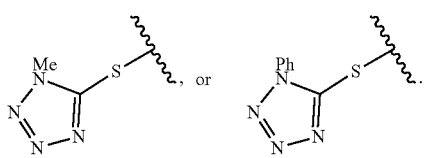, or

In certain embodiments, —SR$^{TG}$ is:

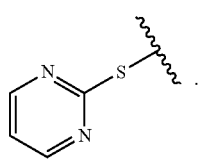 [SMILES: *Sc1ncccn1]

In certain embodiments, the compound of Formula (V) is of the formula:

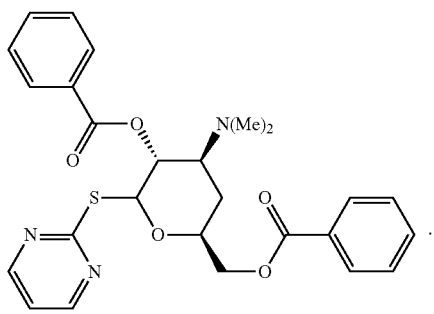

In certain embodiments, the compound of Formula (V'-b) is of the formula:

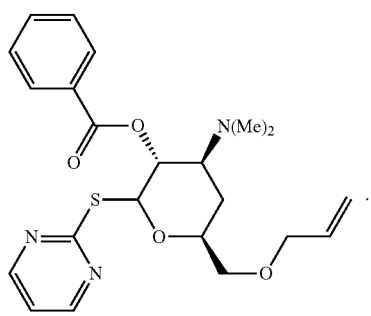

The modified sugar is typically attached to the macrolide framework during synthesis of the eastern half, but may also be attached at other stages of the preparation. The sugar may be attached by a glycosylation reaction between the hydroxyl group at the C5 position and a glycosyl donor as exemplified in Scheme 11. In certain embodiments, the modified sugar moiety is attached to the macrolide framework as a thioglycoside. In certain embodiments, substituents of the sugar are modified after glycosylation of the macrolide or macrolide precursor (e.g., eastern half). In certain embodiments, the sugar is not further modified after glycosylation of the macrolide or macrolide precursor.

Scheme 11

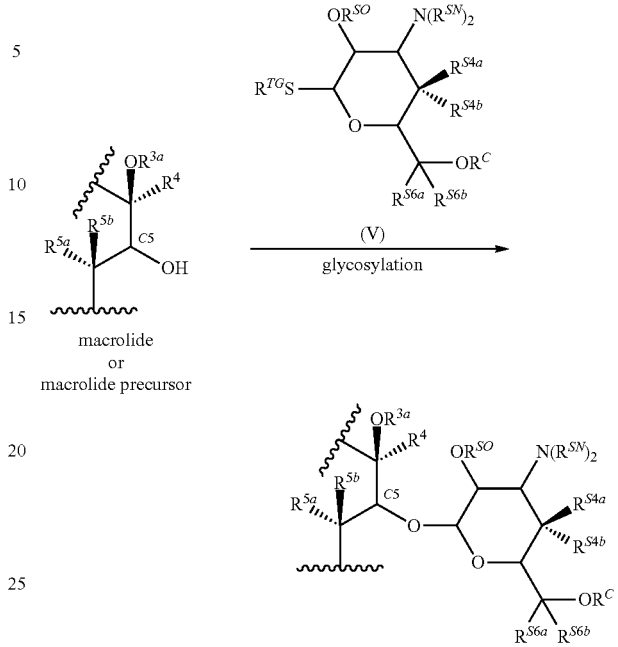

Pharmaceutical Compositions and Administration

The present disclosure provides pharmaceutical compositions comprising a macrolide as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21 st Edition (Lippincott Williams & Wilkins, 2005).

Pharmaceutical compositions described herein can be prepared by any method known in the art of pharmacology. In general, such preparatory methods include the steps of bringing the macrolide of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the macrolide of the present invention. The amount of the macrolide is generally equal to the dosage of the macrolide which would be administered to a subject and/or a convenient fraction of such a dosage such as, for example, one-half or one-third of such a dosage.

Relative amounts of the macrolide, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) macrolide.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the macrolides, the liquid dosage forms may comprise inert diluents commonly used in the art such as, for example, water or other solvents, solubilizing agents, and emulsifiers, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium.

Solid dosage forms for oral administration include capsules, tablets, pills, powders, and granules. In such solid dosage forms, the macrolide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethyl cellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Dosage forms for topical and/or transdermal administration of a macrolide of this invention may include ointments, pastes, creams, lotions, gels, powders, solutions, sprays, inhalants and/or patches. Generally, the macrolide is admixed under sterile conditions with a pharmaceutically acceptable carrier and/or any needed preservatives and/or buffers as can be required.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Macrolides provided herein are typically formulated in dosage unit form for ease of administration and uniformity of dosage. It will be understood, however, that the total daily amount of the macrolide will be decided by the attending physician within the scope of sound medical judgment. The specific therapeutically effective dose level for any particular subject will depend upon a variety of factors including the disease, disorder, or condition being treated and the severity of the disorder; the activity of the specific macrolide employed; the specific composition employed; the age, body weight, general health, sex and diet of the subject; the time of administration, route of administration, and rate of excretion of the specific macrolide employed; the duration of the treatment; drugs used in combination or coincidental with the specific macrolide employed; and like factors well known in the medical arts.

The macrolides and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general, the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

It will be also appreciated that a macrolide or composition, as described herein, can be administered in combination with one or more additional therapeutically active agents. The macrolide or composition can be administered concurrently with, prior to, or subsequent to, one or more additional therapeutically active agents. In general, each agent will be administered at a dose and/or on a time schedule determined for that agent. I will further be appreciated that the additional therapeutically active agent utilized in this combination can be administered together in a single composition or administered separately in different compositions. The particular combination to employ in a regimen will take into account compatibility of the inventive macrolide with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically active agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfopristin (Syndercid™).

Also encompassed by the invention are kits (e.g., pharmaceutical packs). The kits provided may comprise an inventive pharmaceutical composition or macrolide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or macrolide. In some embodiments, the inventive pharmaceutical composition or macrolide provided in the container and the second container are combined to form one unit dosage form.

Methods of Treatment and Uses

The present disclosure contemplates using macrolides of the present invention for the treatment of infectious diseases, for example, fungal, bacterial, viral, or parasitic infections, and for the treatment of inflammatory conditions. Macrolides are known to exhibit anti-bacterial activity as well as anti-parasitic activity. See, for example, Clark et al., *Bioorganic & Medicinal Chemistry Letters* (2000) 10:815-819 (anti-bacterial activity); and Lee et al., *J. Med. Chem.* (2011) 54:2792-2804 (anti-bacterial and anti-parasitic activity). Macrolides are also known to exhibit an anti-inflammatory effect. See, for example, Amsden, *Journal of Antimicrobial Chemotherapy* (2005) 55:10-21 (chronic pulmonary inflammatory syndromes).

Thus, as generally described herein, provided is a method of treating an infectious disease comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylactically effective amount. For example, in certain embodiments, the method prevents or reduces the likelihood of an infectious disease, e.g., in certain embodiments, the method comprises administering a macrolide of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In another aspect, provided is an in vitro method of inhibiting pathogenic growth comprising contacting an effective amount of the macrolide of the present invention with a pathogen (e.g., a bacteria, virus, fungus, or parasite) in a cell culture.

As used herein, "infectious disease" and "microbial infection" are used interchangeably, and refer to an infection with a pathogen, such as a fungus, bacteria, virus, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a macrolide of the present invention, or a pharmaceutically acceptable salt thereof, to a subject in need thereof.

In certain embodiments, the macrolide has a mean inhibitory concentration (MIC), with respect to a particular bacterium, of less than 50 mg/L, less than 25 mg/L, less than 20 mg/L, less than 10 mg/L, less than 5 mg/L, or less than 1 mg/L. In certain embodiments, the macrolide has a mean inhibitory concentration (MIC), with respect to a particular bacterium, of less than 64 mg/L, less than 32 mg/L, less than 16 mg/L, less than 8 mg/L, less than 4 mg/L, less than 2 mg/L or less than 1 mg/L.

In certain embodiments, the bacteria are susceptible (e.g., responds to) or resistant to known commercial macrolides, such as azithromycin, clindamycin, telithromycin, erythromycin, spiramycin, and the like. In certain embodiments, the bacteria is resistant to a known macrolide. For example, in certain embodiments, the bacteria is erythromycin resistant (ER).

In certain embodiments, the bacterial infection is resistant to other antibiotics (e.g., non-macrolide) therapy. For example, in certain embodiments, the pathogen is vancomycin resistant (VR). In certain embodiments, the pathogen is methicillin-resistant (MR), e.g., in certain embodiments, the bacterial infection is an methicillin-resistant *S. aureus* infection (a MRSA infection). In certain embodiments, the pathogen is quinolone resistant (QR). In certain embodiments, the pathogen is fluoroquinolone resistant (FR).

In certain embodiments, the bacteria has an efflux (e.g., mef, msr) genotype. In certain embodiments, the bacteria has a methyl a se (e.g., erm) genotype. In certain embodiments, the bacteria has a constitutive genotype. In certain embodiments, the bacteria has an inducible genotype.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum PlanctomycetesZVerrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a Gram positive bacteria.

In certain embodiments, the Gram positive bacteria is a bacteria of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casselijlavus*, and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. camous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentam, S. psuedointermedius, S. psudolugdemis, S. pulvereri, S. rostri, S. saccharolyticus, S. saprophyticus, S. schleiferi, S. sciuri, S. simiae, S. simulam, S. stepanovicii, S. succinus, S. vitulinus, S. warneri*, and *S. xylosus*. In certain embodiments, the *Staphylococcus* infection is an *S. aureus* infection. In certain embodiments, the *S. aureus* has an efflux (e.g., mef, msr) genotype. In certain embodiments, the *S. aureus* has a methylase (e.g., erm) genotype.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus *Streptococcus*, i.e., the bacterial infection is a *Streptococcus* infection. Exemplary *Streptococcus* bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans*, and *S. zooepidemicus*. In certain embodiments, the *Streptococcus* infection is an *S. pyogenes* infection. In certain embodiments, the *Streptococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacterial infection is an infection with a Gram negative bacteria.

In certain embodiments, the Gram negative bacteria is a bacteria of the phylum Proteobacteria and the genus *Escherichia*, i.e., the bacterial infection is an *Escherichia* infection. Exemplary *Escherichia* bacteria include, but are not limited to, *E. alhertii, E. blattae, E. coli, E. fergusonii, E. hermannii*, and *E. vulneris*. In certain embodiments, the *Escherichia* infection is an *E. coli* infection.

In certain embodiments, the Gram negative bacteria is a bacteria of the phylum Proteobacteria and the genus *Haemophilus*, i.e., the bacterial infection is a *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*. In certain embodiments, the *Haemophilus* infection is an *H. influenzae* infection.

In certain embodiments, the Gram negative bacteria is a bacteria of the phylum Proteobacteria and the family Enterobacteriaceae. Exemplary Enterobacteriaceae bacteria include, but are not limited to *Enterobacter aerogenes, Enterobacter cloacae, Proteus mirabilis, Proteus vulgaris, Serratia marcescens, Citrobacter freundii, Citrobacter koseri, Morganella morganii, Providencia stuartii* and *Providencia. rettgeri*.

In certain embodiments, the Gram negative bacteria is a bacteria of the phylum Proteobacteria and the genus *Acinetobacter*. i.e., the bacterial infection is an *Acinetobacter* infection. Exemplary *Acinetobacter* bacteria include, but are not limited to, *A. baumanii, A. haemolyticus*, and *A. lwoffii*. In certain embodiments, the *Acinetobacter* infection is an *A. baumanii* infection.

In certain embodiments, the Gram negative bacteria is a bacteria of the phylum Proteobacteria and the genus *Klebsiella*, i.e., the bacterial infection is a *Klebsiella* infection.

Exemplary *Klebsiella* bacteria include, but are not limited to, *K. granulomatis, K. oxytoca, K. michiganensis, K. pneumoniae,* K. quasi *pneumoniae*, and *K. variicola*. In certain embodiments, the *Klebsiella* infection is a *K. pneumoniae* infection.

In certain embodiments, the Gram negative bacteria is a bacteria of the phylum Proteobacteria and the genus *Pseudomonas*, i.e., the bacterial infection is a *Pseudomonas* infection. Exemplary *Pseudomonas* bacteria include, but are not limited to, *P. aeruginosa, P. oryzihabitans, P. plecoglissicida, P. syringae, P. putida*, and *P. fluoroscens*. In certain embodiments, the *Pseudomonas* infection is a *P. aeruginosa* infection.

In certain embodiments, the bacteria is an atypical bacteria, i.e., are neither Gram positive nor Gram negative.

In certain embodiments, the infectious disease is an infection with a parasitic infection. Thus, in certain embodiments, provided is a method of treating a parasitic infection comprising administering an effective amount of a macrolide of the present invention, or a pharmaceutically acceptable salt thereof, to a subject in need thereof.

In certain embodiments, the macrolide has a $IC_{50}$ (μM) with respect to a particular parasite, of less than 50 μM, less than 25 μM, less than 20 μM, less than 10 μM, less than 5 μM, or less than 1 uM. In certain embodiments, the macrolide has a $IC_{50}$ (mg/L) with respect to a particular parasite, of less than 64 mg/L, less than 32 mg/L, less than 16 mg/L, less than 8 mg/L, less than 4 mg/L, less than 2 mg/L, or less than 1 mg/L.

Exemplary parasites include, but are not limited to, *Trypanosoma* spp. (e.g., *Trypanosoma cruzi, Trypansosoma brucei), Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum), Crytosporidium* spp., *Isospora* spp., *Balantidium* spp., *Loa, Ascaris lumbricoides, Dirofilaria immitis*, and *Toxoplasma* ssp. (e.g. *T. gondii*).

As generally described herein, the present invention further a method of treating an inflammatory condition comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylactically effective amount. For example, in certain embodiments, the method prevents or reduces the likelihood of an inflammatory condition, e.g., in certain embodiments, the method comprises administering a macrolide of the present invention to a subject in need thereof in an amount sufficient to prevent or reduce the likelihood of an inflammatory condition. In certain embodiments, the subject is at risk to an inflammatory condition.

In another aspect, provided is an in vitro method of treating an inflammatory condition comprising contacting an effective amount of the macrolide of the present invention with an inflammatory cell culture.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, chronic pulmonary inflammatory syndromes (e.g., diffuse panbronchiolitis, cystic fibrosis, asthma, bronchiectasis, and chronic obstructive pulmonary disease).

Exemplary inflammatory conditions include, but are not limited to, inflammation associated with acne, anemia (e.g., aplastic anemia, haemolytic autoimmune anaemia), chronic pulmonary inflammatory syndromes (e.g., diffuse panbronchiolitis, cystic fibrosis, asthma, bronchiectasis, chronic obstructive pulmonary disease), arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), a gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo, and Wegener's granulomatosis.

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

Definitions

Chemical Terms

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. Stereochemistry of Carbon Compounds (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and === or === is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

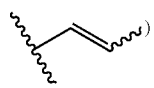

) may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C2-4 alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-4}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-6}$ carbocyclyl groups include, without limitation, the aforementioned $C_{3-8}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-4}$ carbocyclyl. In certain embodiments, the carbocyclyl group is a substituted $C_{3-4}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-4}$ cycloalkyl. In certain embodiments, the cycloalkyl group is a substituted $C_{3-4}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, aryl ene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(OR$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN($R^{bb}$)$_2$, =NN$R^{bb}$C(=O) $R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, C3-10 carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$.—N(O$R^{ee}$)$R^{ff}$, —SH, —S$R^{ee}$, —SS$R^{ee}$, C(=O)$R^{ee}$, —CO$_2$H, CO$_2$$R^{ee}$, OC(=O)$R^{ee}$, —OCO$_2$$R^{ee}$, —C(=O)N($R^{ff}$)$_2$, —OC(=O)N($R^{ff}$)$_2$, —NR$^{ff}$C(=O)$R^{ee}$, —NR$^{ff}$CO$_2$$R^{ee}$, —NR$^{ff}$C(=O)N($R^{ff}$)$_2$, C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —NR$^{ff}$C(=N$R^{ff}$)N($R^{ff}$)$_2$, —NR$^{ff}$SO$_2$$R^{ee}$, —SO$_2$N($R^{ff}$)$_2$, —SO$_2$$R^{ee}$, SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, C3-10 carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$. —NH($C_{1-6}$ alkyl)$_2$$^+$X$^-$.—NH$_2$($C_{1-6}$ alkyl)$^+$X$^-$.—NH$_3$$^+$X$^-$. —N(O$C_{1-6}$alkyl)($C_{1-6}$ alkyl), —N(OH)($C_{1-6}$ alkyl), —NH (OH), —SH, —S$C_{1-6}$ alkyl, SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N ($C_{1-6}$ alkyl)$_2$, —OC(=O)NH($C_{1-6}$ alkyl), —NHC(=O) ($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-3}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH) NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C (=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S) S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O) S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$X)$R^{aa}$, —OC(=N$R^{bb}$)N ($R^{bb}$)$_2$, —OS(=O)$R^{aa}$, —OSO$_2$$R^{aa}$, —OSi($R^{aa}$)$_3$, —OP ($R^{cc}$)$_2$, —OP($R^{cc}$)$_3$, —OP(=O)$_2$$R^{aa}$, —OP(=O)($R^{aa}$)$_2$, —OP(=O)(O$R^{cc}$)$_2$, —OP(=O)$_2$N($R^{bb}$)$_2$, and —OP(=O) (N$R^{bb}$)$_2$, wherein $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2$$R^{aa}$, —NHC(=O)N($R^{bb}$)$_2$, —NHC(=N$R^{bb}$)N($R^{bb}$)$_2$, —NHSO$_2$$R^{aa}$, —NHP(=O)(OR$^{cc}$)$_2$, and NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^+$. wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{bb}$ is as defined herein.

The term "acyl" refers to a group having the general formula —C(=O)R$^{X1}$, C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, herein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "silyl" refers to the group —Si(R$^{aa}$)$_3$, wherein R$^{aa}$ is as defined herein.

The term "oxo" refers to the group =O, and the term "thiooxo" refers to the group =S Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl) methyl carbamate, t-amyl carbamate, 5-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(AUV-dimethylcarboxamido)benzyl carbamate, 1,1-dimethyl-3-(AUV-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, M-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), Z-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacol methyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, Z-butyl, allyl, p-chlorophenyl, p-m ethoxy phenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (IMS), triethylsilyl (TES), triisopropylsilyl (TIPS), dimethylisopropylsilyl (IPDMS), diethylisopropylsilyl (DEEPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxy acetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, 5-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzyl sulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, herein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), $-OR^{aa}$ (when the O atom is attached to a carbonyl group, wherein $R^{aa}$ is as defined herein), $-O(C=O)R^{LG}$, or $-O(SO)_2R^{LG}$ (e.g., tosyl, mesyl, besyl), wherein $R^{LG}$ is optionally substituted alkyl, optionally substituted aryl, or optionally substituted heteroaryl. In some cases, the leaving group is a halogen. In some embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (tram) of the ring from the —CH$_2$OH side branch. The alternative form, in which the —CH$_2$OH substituent and the anomeric hydroxyl are on the same side (cis) of the plane of the ring, is called a P anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, gluceptate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenyl propionate, phosphate, pi crate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomologus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "administer," "administering," or "administration" refers to implanting, absorbing, ingesting, injecting, inhaling, or otherwise introducing a compound described herein, or a composition thereof, in or on a subject.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, postsurgical inflammation.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

As indicated previously, compounds of the invention can be prepared by readily available chemical methods such as described, for instance, in WO 2014/165792, the entire contents of which is incorporated by reference. Illustrative schemes are provided below.

Synthetic Method

The synthetic approach to constructing the macrolides of the present disclosure can be divided into three stages: 1) preparation of a modified desosamine donor (in the form of a thioglycoside) that contains one or a few diversifiable structural elements (e.g. a benzoyloxy group, an azide, etc.); 2) construction of the core macrolide scaffold and incorporation of the modified desosamine donor; 3) late-stage transformation of the diversifiable structural elements into a variety of substituents, concluding the synthesis and affording new antibiotic compounds.

Compounds where ring S is a oxazolidinone ring can be prepared as illustrated in Scheme 12.

Scheme 12

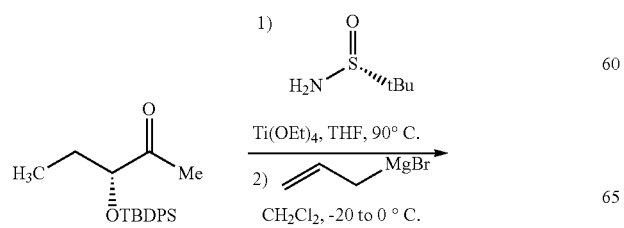

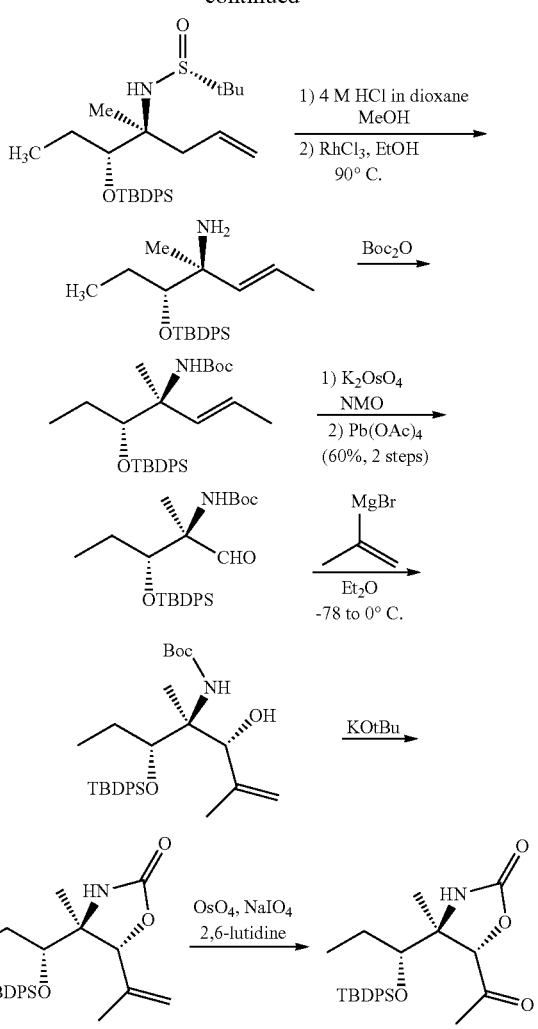

Compounds where ring S is a urea-containing ring can also be prepared as illustrated in Scheme 13.

Scheme 13.

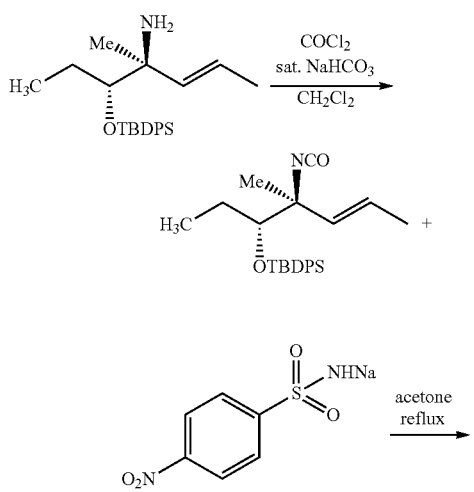

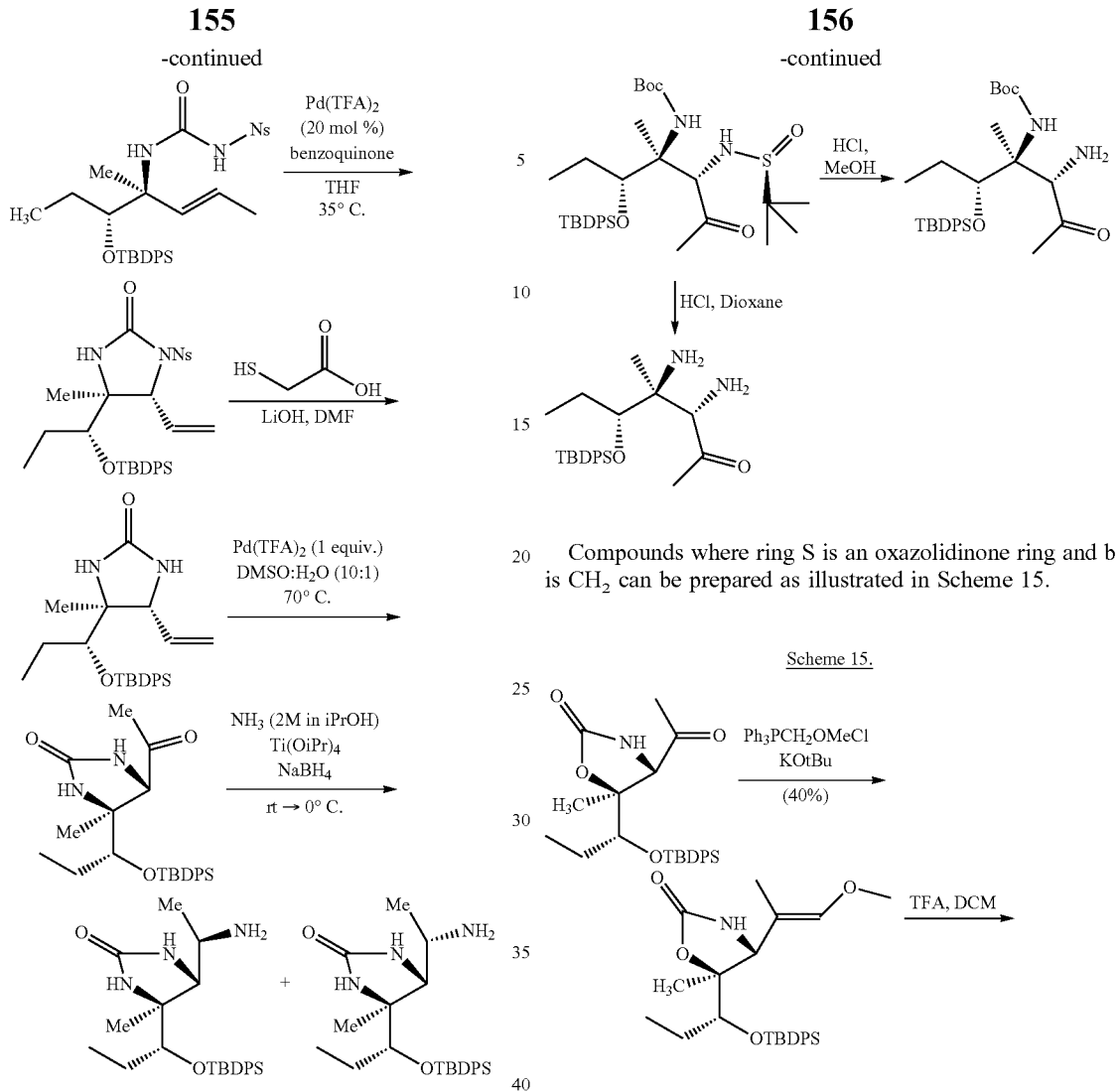
Compounds where ring S contains urea derivatives can also be prepared as illustrated in Scheme 14.
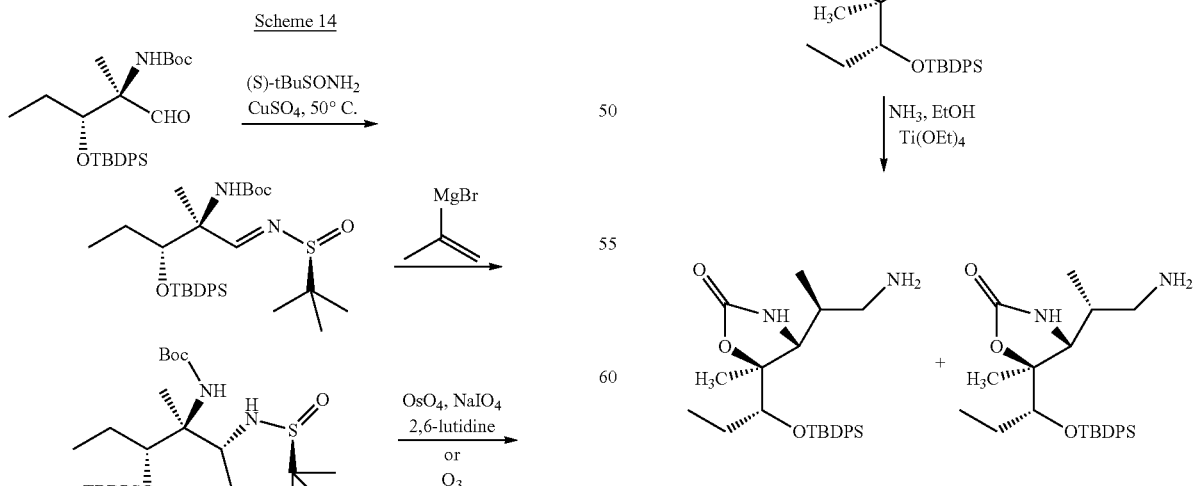
Compounds where ring S is an oxazolidinone ring and b is $CH_2$ can be prepared as illustrated in Scheme 15.
Compounds of formula II-b where n is 0, $R^{3'}$ is H, $R^{S4a}$ and $R^{S4b}$ are both H can be prepared as illustrated in in Scheme 16.

Scheme 16.
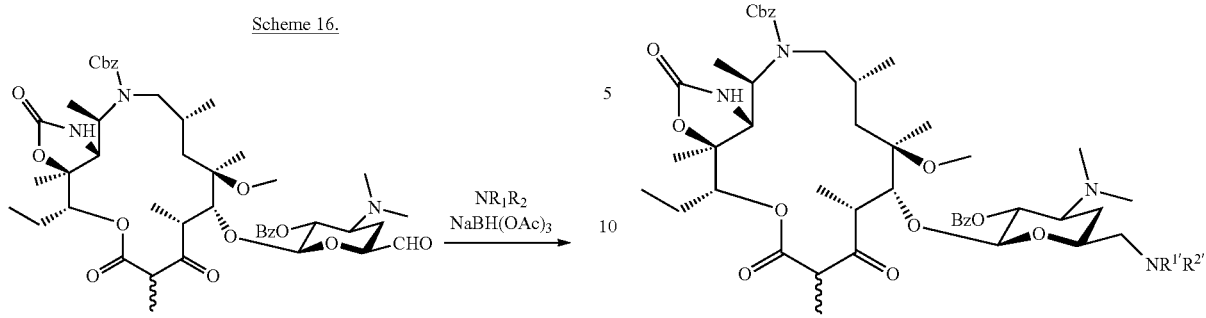
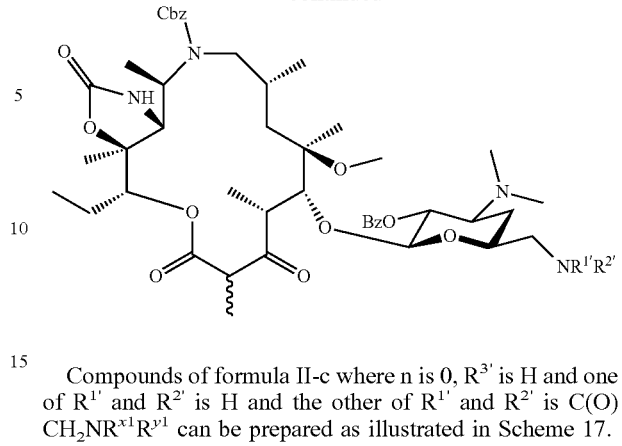
Compounds of formula II-c where n is 0, $R^{3'}$ is H and one of $R^{1'}$ and $R^{2'}$ is H and the other of $R^{1'}$ and $R^{2'}$ is $C(O)CH_2NR^{x1}R^{y1}$ can be prepared as illustrated in Scheme 17.
Scheme 17.
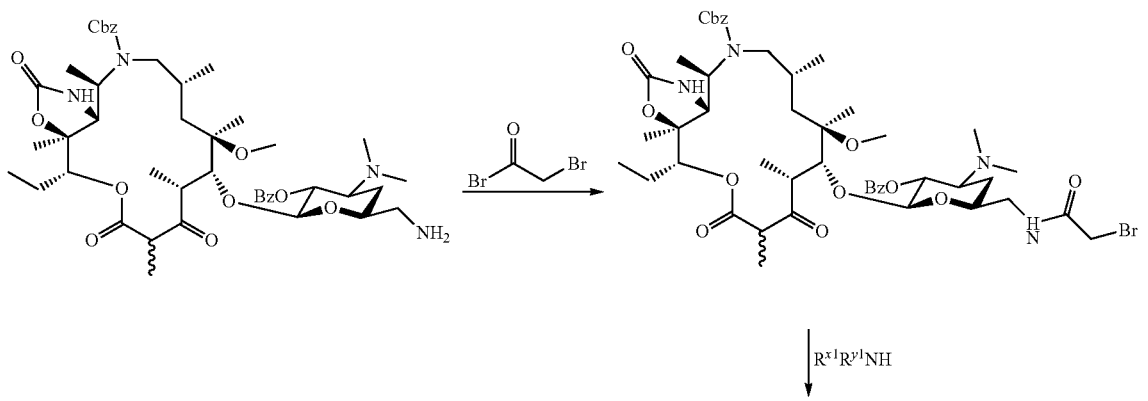
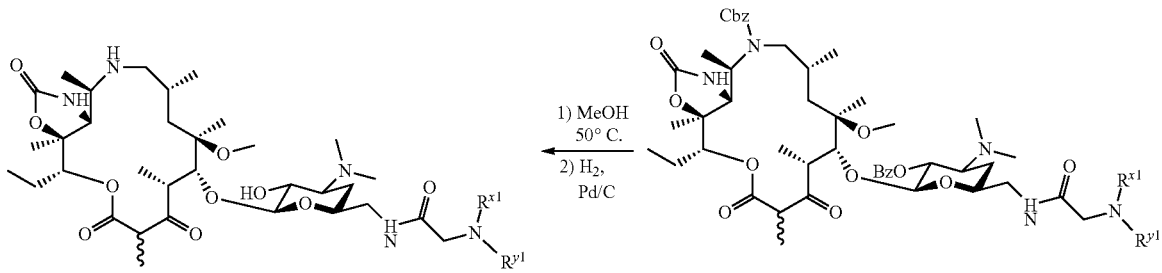

Compounds of formula n-d where n is 1, and R³' is OH can be prepared as illustrated in in Scheme 18.

Scheme 18.

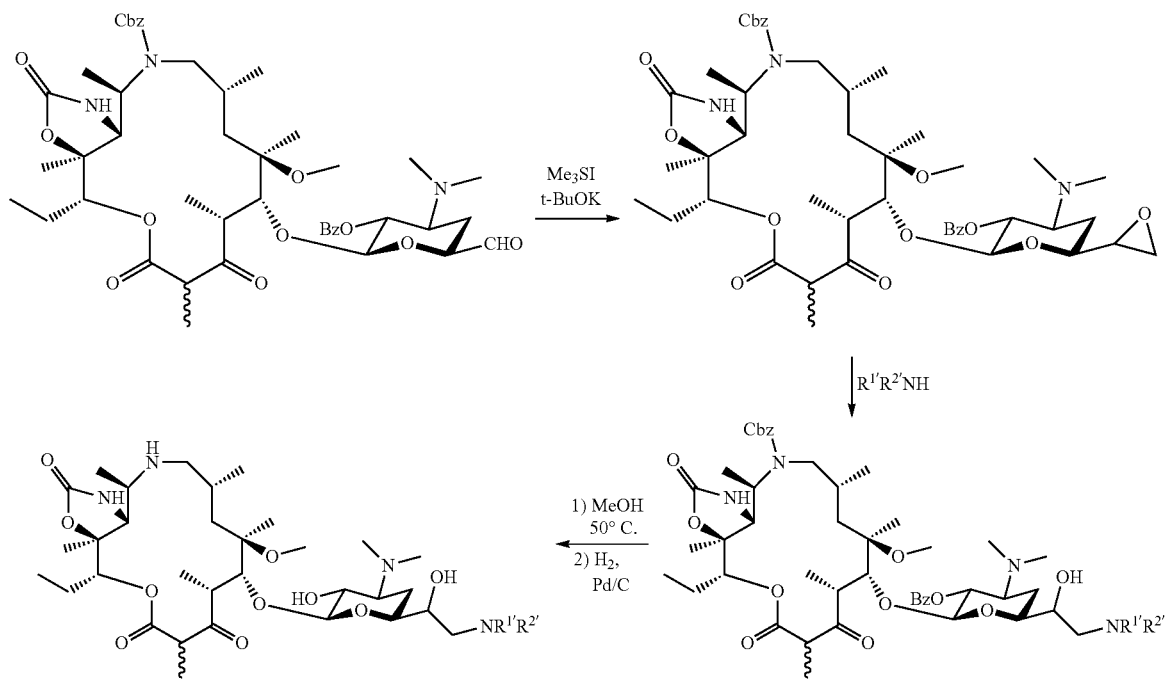

The synthesis of particular compounds are described below.

Synthesis of 6'-Modified Desosamine Thioglycosides

A three-step sequence to convert 3-nitro-3,4-dideoxyglucose to a 6'-benzoyloxy desosamine thioglycoside was employed (Scheme 19), which was used to introduce 6'-modified desosamine sugars to macrolide scaffolds. For the synthesis of 3-nitro-3,4-dideoxyglucose, see Zhang, Z.; Fukuzaki, T.; Myers, A. G. *Angew. Chem. Int. Ed.* 2016, 55, 523-527.

Scheme 19. Synthesis of 6'-benzoyloxy desosamine thioglycoside (4)

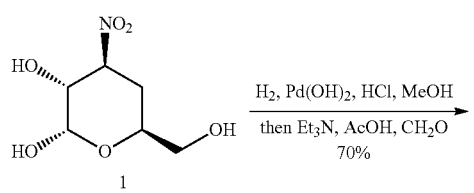

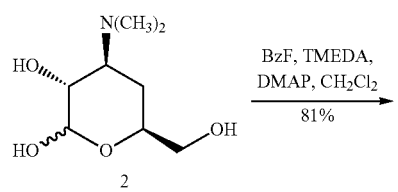

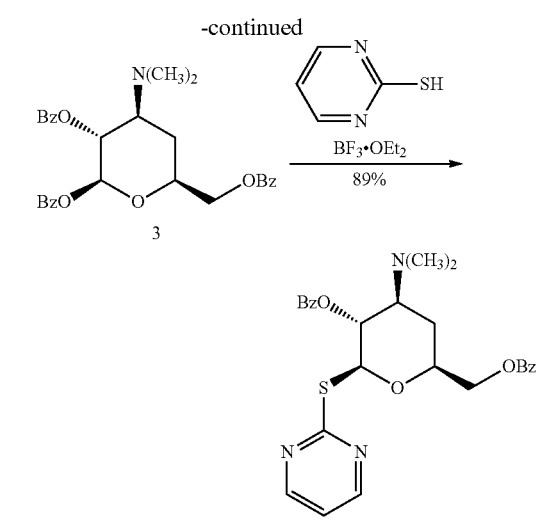

(3R,4S,6S)-4-(dimethylamino)-6-(hydroxymethyl) tetrahydro-2H-pyran-2,3-diol (2)

A 200-mL round-bottom flask was charged with a magnetic stir bar, (2S,3R,4S,6S)-6-(hydroxymethyl)-4-nitrotetrahydro-2H-pyran-2,3-diol (1.68 g, 8.70 mmol, 1 equiv), and hydrochloric acid in methanol (1.25 M, 27.8 mL, 4.0 equiv). 20 wt. % Palladium hydroxide on carbon (1.22 g, 1.74 mmol, 0.200 equiv) was added, then a rubber septum was affixed. The flask was evacuated (10 mmHg), then was flushed with argon. The evacuation-flush cycle was repeated twice with argon, then twice with hydrogen (balloon). The suspension was stirred at 23° C. under a hydrogen atmosphere (balloon pressure). After 41 h, additional 20 wt. % Palladium hydroxide on carbon (611 mg, 0.87 mmol, 0.100 equiv) was added and the suspension was stirred for 28 h. When TLC analysis indicated that full consumption of nitro sugar had occurred, trimethylamine (4.85 mL, 34.8 mmol, 4.0 equiv), acetic acid (1.49 mL, 26.1 mmol, 3.0 equiv), and formaldehyde solution in methanol (37 wt %, 2.23 mL, 2.50 equiv) were added sequentially. Stirring was continued for 2 h. The mixture was filtered through a thin pad of Celite® (10 g) and the filter cake was rinsed with methanol (30 mL). The filtrate was concentrated, and the residue was dissolved in methanol (100 mL). To the solution was added Amberlyst® A26 resin (OH form, 60 g). The slurry was stirred at 23° C. for 30 min, then was filtered through a sintered glass funnel (medium porosity). The resin was rinsed with methanol (100 mL), and the combined filtrate was concentrated to afford the title compound as a yellow oil (1.17 g, 70%, α:β approximately 1:2). $^1$H NMR (1:2 α:β anomeric mixture, 500 MHz, CD$_3$OD) α-anomer: δ 5.16 (d, 1H), 4.03 (m, 1H), 3.63-3.52 (m, 3H), 3.01 (ddd, 1H), 2.36 (s, 6H), 1.79-1.73 (m, 1H), 1.41-1.30 (m, 1H). β-anomer: δ 4.45 (d, 1H), 3.63-3.52 (m, 3H), 3.23 (dd, 1H), 2.66 (ddd, 1H), 2.35 (s, 6H), 1.79-1.73 (m, 1H), 1.41-1.30 (m, 1H). $^{13}$C NMR (1:2 α:β anomeric mixture, peaks are reported collectively, 126 MHz, CD$_3$OD) δ 99.6, 75.2, 73.4, 66.0, 65.8, 65.6, 40.8, 40.7, 27.2, 26.3. FTIR (neat), cm$^{-1}$: 3335 (br), 2928 (m), 2874 (s), 2833 (s), 1556 (s), 1456 (s), 1381 (s), 1723 (s), 1028 (m). HRMS (ESI): Calcd for (C$_8$H$_{18}$NO$_4$+H)$^+$: 192.1230; Found: 192.1234.

(2S,3R,4S,6S)-6-((benzoyloxy)methyl)-4-(dimethylamino)tetrahydro-2H-pyran-2,3-diyl dibenzoate (3)

A 200-mL round-bottom flask was charged with a magnetic stir bar, (3R,4S,6S)-4-(dimethylamino)-6-(hydroxymethyl)tetrahydro-2H-pyran-2,3-diol (1.10 g, 5.75 mmol, 1 equiv), and dichloromethane (57.5 mL). N,N,N',N'-tetramethylethylenediamine (4.34 ml, 28.8 mmol, 5 equiv), benzoyl fluoride (2.51 ml, 23.0 mmol, 4 equiv), and 4-dimethylaminopyridine (70.0 mg, 0.575 mmol, 0.1 equiv) were added sequentially at 0° C. After stirring for 47 h at 23° C., saturated aqueous sodium bicarbonate solution (50 mL) was added. The mixture was vigorously stirred for 30 min, then was extracted with dichloromethane (3×50 mL). The combined organic layers were dried over magnesium sulfate. The dried solution was concentrated, and the residue was purified by column chromatography (40 to 70% ethyl acetate/hexanes) to afford the title compound (2.35 g, 81%). $^1$H NMR (500 MHz, CDCl$_3$) δ 8.08 (d, 2H), 8.01 (d, 4H), 7.60-7.37 (m, 9H), 6.04 (d, 1H), 5.50 (dd, 1H), 4.47 (d, 1H), 4.18-4.13 (m, 1H), 3.16 (ddd, 1H), 2.39 (s, 6H), 2.06-2.01 (m, 1H), 1.78 (app q, 1H). $^{13}$C NMR (126 MHz, CDCl$_3$) δ 166.3, 165.5, 164.9, 133.4, 133.1, 133.0 130.0, 129.8, 129.7, 129.7, 128.9, 128.4, 128.3, 128.3, 94.2, 72.3, 70.1, 66.1, 63.0, 40.8, 26.4. FTIR (neat), cm$^{-1}$: 2982 (m), 2941 (m), 2872 (m), 1724 (s), 1603 (m), 1373 (m), 1316 (m), 1267 (s), 1240 (s), 1109 (s), 1043 (s), 1026 (s). HRMS (ESI): Calcd for (C$_{29}$H$_{29}$NO$_7$+Na)$^+$: 526.1836; Found: 526.1851.

Thioglycoside (4)

A 200-mL round-bottom flask was charged with a magnetic stir bar and Celite (3.0 g). The flask was heated with a gentle flame under vacuum (0.2 mmHg) for 2 min. After cooling to 23° C. in vacuo, the flask was flushed with argon and fitted with a rubber septum. A solution of (2S,3R,4S, 6S)-6-((benzoyloxy)methyl)-4-(dimethylamino)tetrahydro-2H-pyran-2,3-diyl dibenzoate (1.91 g, 3.79 mmol, 1 equiv) in 1,2-dichloroethane (37.9 mL) was transferred into the reaction flask via cannula. The septum was removed, and 2-mercaptopyrimidine (0.638 g, 5.69 mmol, 1.5 equiv) was added as a solid. After replacing the rubber septum, boron trifluoride ethyl etherate(1.92 mL, 15.2 mmol, 4.0 equiv) was added via syringe. The reaction mixture was heated to 60° C. and held at that temperature for 24 h with good magnetic stirring throughout. After cooling to 23° C., saturated aqueous sodium bicarbonate solution (40 mL) was added. The mixture was stirred for 30 min and filtered through a pad of Celite (10 g). The filtrate was extracted with dichloromethane (3×40 mL). The combined organic layers were dried over magnesium sulfate, and the dried solution was concentrated. The residue was purified by column chromatography over silica gel (40 to 70% ethyl acetate/hexanes) to afford the title compound as a pale yellow solid (1.67 g, 89%). TLC (70% ethyl acetate/hexanes): R$_f$=0.30 (UV, p-anisaldehyde). $^1$H NMR (500 MHz, CDCl$_3$) δ 8.40 (d, 2H), 8.04-8.01 (m, 4H), 7.60-7.51 (m, 2H), 7.45-7.39 (m, 4H), 6.90 (t, 1H), 5.85 (d, 1H), 5.42 (app t, 1H), 4.46 (dd, 1H), 4.40 (dd, 1H), 4.14-4.09 (m, 1H), 3.22-3.14 (m, 1H), 2.38 (s, 6H), 2.07-2.02 (m, 1H), 1.77 (app q, 1H). $^{13}$C NMR (126 MHz, CDCl$_3$) δ 170.3, 166.3, 165.5, 157.2, 133.0, 132.9, 130.1, 130.0, 129.9, 129.7, 128.3, 128.2, 117.0, 83.5, 68.8, 66.4, 64.9, 40.9, 27.2, 14.2. FTIR (neat), cm$^{-1}$: 2947 (m), 2968 (m), 2835 (m), 2787 (m), 1716 (s), 1562 (s), 1550 (s), 1451 (s), 1381 (s), 1265 (s), 1111 (s), 1097 (s), 1068 (s), 899 (s), 708 (s). HRMS (ESI): Calcd for (C$_{26}$H$_{27}$N$_3$O$_5$S+ Na)$^+$: 494.1744; Found: 494.1764.

This benzoyloxy group can be replaced with an allyloxy group in two steps (Scheme 10), affording a different desosamine sugar that was employed in the synthesis of another set of fully synthetic macrolides.

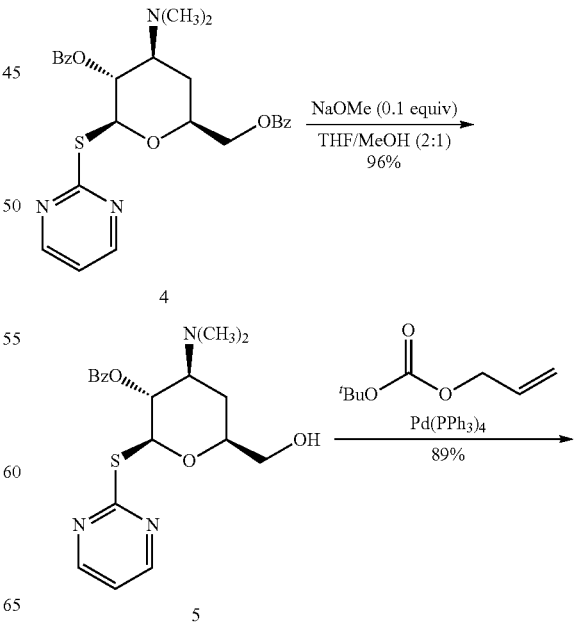

Scheme 20. Synthesis of 6'-allyloxy desosamine thioglycoside (6)

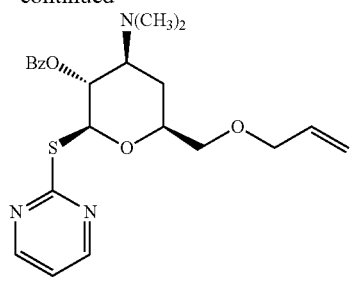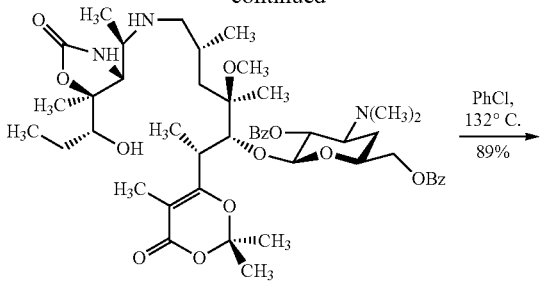

Incorporation of 6'-Modified Desosamines and Synthesis of Macrolide Scaffolds

As demonstrated by Scheme 13 and Table 7 below, glycosylation of a macrolide precursor with thioglycoside (4) gave access to an intermediate wherein facile functionalization of the benzoyloxy group at the 6'-position of the desosamine allowed generation of macrolides featuring diverse functional groups at the 6'-position.

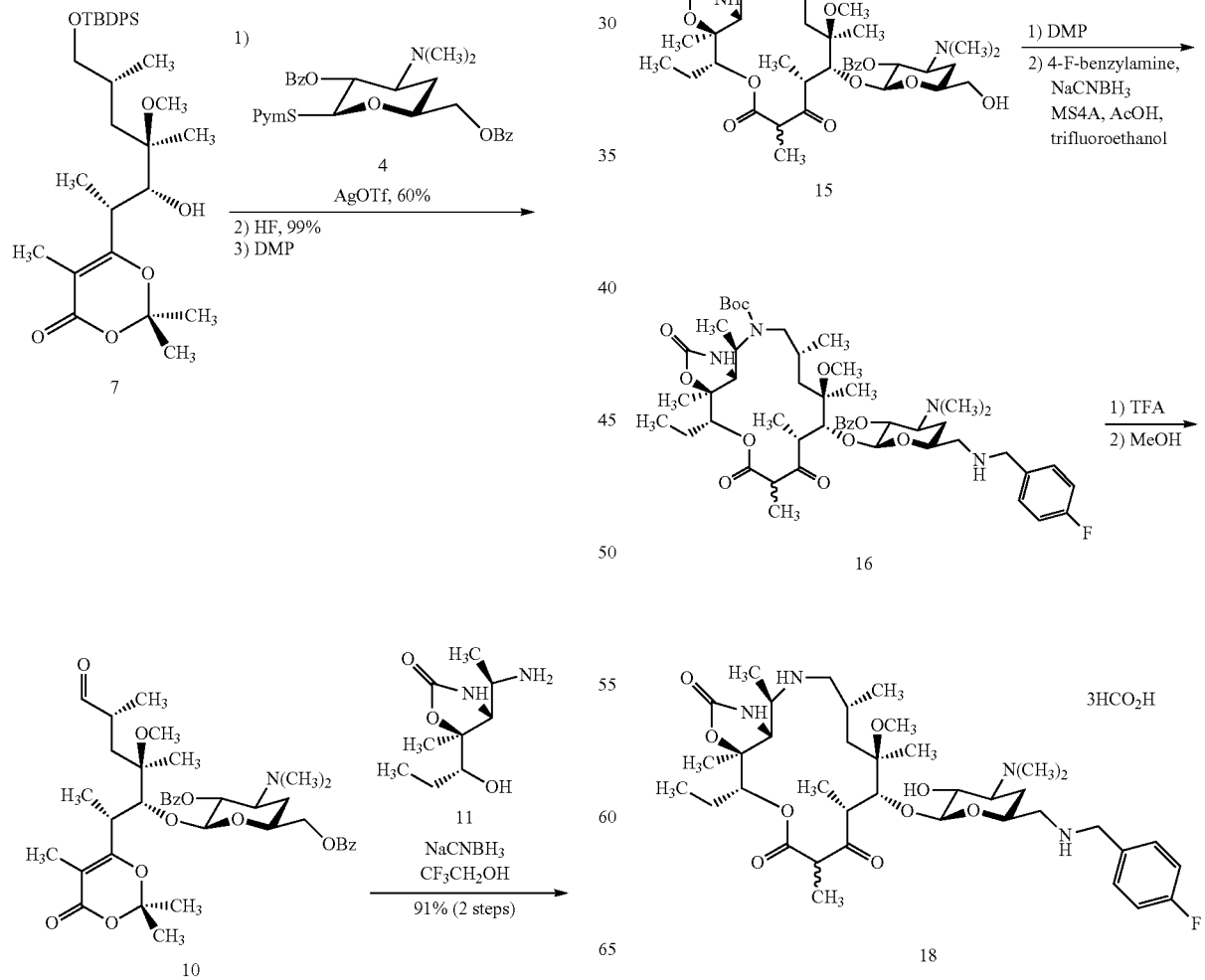

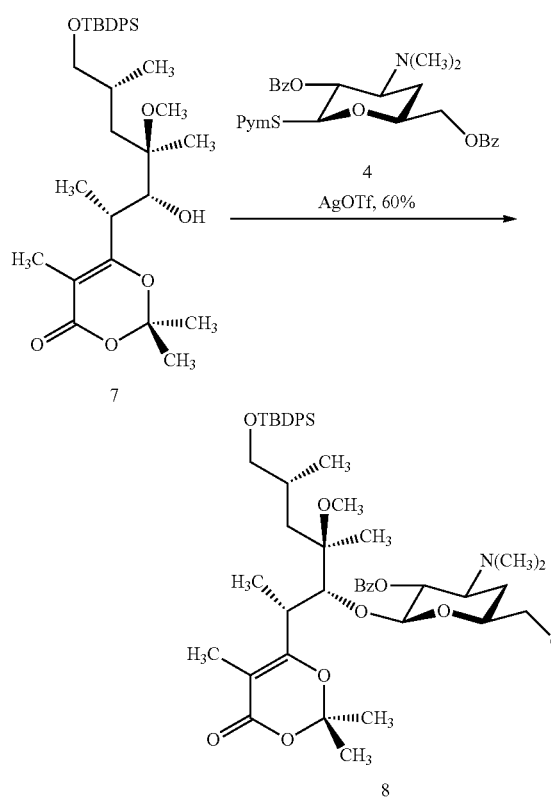

7

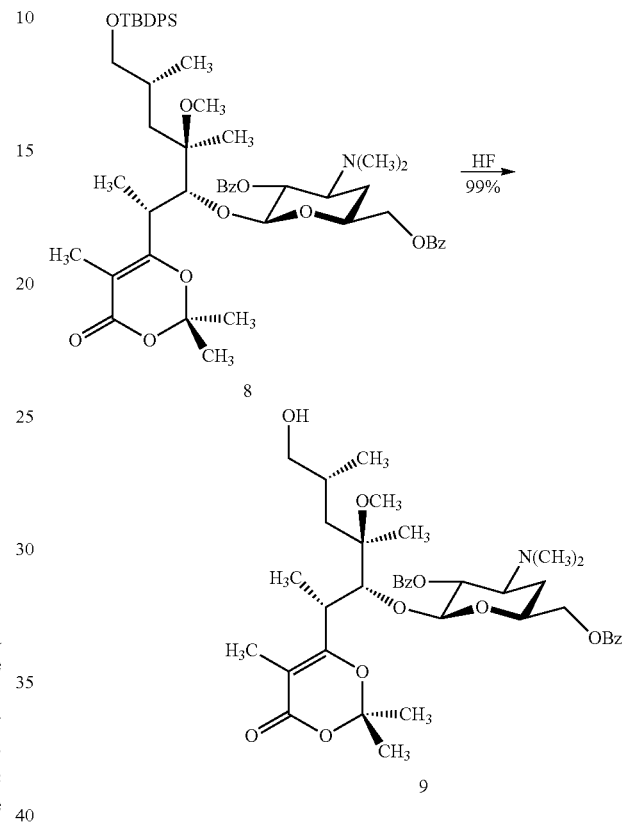

A 200-mL round-bottom flask was charged with grinded 4-Å molecular sieves (6.0 g, activated by a gentle flame under vacuum (0.2 mmHg) for 5 min, then cooling to 23° C. under dry argon). In a separate flask, a mixture of secondary alcohol 7 (1.68 g, 2.95 mmol, 1 equiv) and thioglycoside 4 (1.75 g, 3.54 mmol, 1.20 equiv) were dried by azeotropic distillation from benzene (3×20 mL) for 3 times. The residue was dissolved in dichloromethane (30 mL), and the resulting solution was transferred to the flask containing the molecular sieves via cannula. The suspension was cooled to −20° C. (ice-water bath), and silver(I) trifluoromethanesulfonate (1.90 g, 7.38 mmol, 2.5 equiv) was added in one portion. The mixture was stirred for 1 h at −20° C. to 0° C., and then warmed to room temperature. After 17 h, saturated aqueous sodium bicarbonate solution (10 mL) was added. The mixture was filtered through a pad of Celite, and the filter caking was rinsed with ethyl acetate (50 mL). The biphasic filtrate was partitioned, and the aqueous layer was extracted with ethyl acetate (2×30 mL). The combined organic layers were dried over magnesium sulfate, filtrated, and concentrated. The crude product was purified by flash column chromatography (80 to 100% ether/hexanes, then 20% ethyl acetate/ether) to afford the product (8) as a white foam (1.67 g, 60%). $^1$H NMR (500 MHz, CDCl$_3$) δ 8.06-8.02 (m, 4H), 7.68-7.65 (m, 4H), 7.60-7.55 (m, 2H), 7.46-7.32 (m, 10H), 5.17 (dd, 1H), 4.73 (d, 1H), 4.48 (dd, 1H), 4.43 (dd, 1H), 3.87-3.81 (m, 1H), 3.79 (d, 1H), 3.62 (dd, 1H), 3.36 (dd, 1H), 3.21 (ddd, 1H), 3.04-2.96 (m, 1H), 2.71 (s, 3H), 2.37 (s, 3H), 2.01-1.94 (m, 1H), 1.87-1.79 (m, 1H), 1.69 (s, 3H), 1.65 (s, 3H), 1.63-1.59 (m, 1H), 1.45 (s, 3H), 1.40 (dd, 1H), 1.20 (dd, 1H), 1.11 (s, 3H), 1.03 (s, 9H), 1.02-1.01 (m, 3H), 0.78 (d, 1H). $^{13}$C NMR (126 MHz, CDCl$_3$) δ 167.3, 166.1, 165.1, 162.8, 135.6, 134.3, 134.2, 133.4, 130.3, 129.6, 129.5, 129.4, 129.3, 128.5, 128.3, 127.4, 78.8, 77.2, 77.1, 71.6, 71.1, 69.1, 66.2, 63.4, 49.1, 40.8, 36.2, 34.0, 31.1, 30.3, 26.8, 25.6, 24.6, 20.1, 19.7, 19.3, 13.4, 9.6. FTIR (neat), cm$^{-1}$: 3068 (m), 3036 (m), 2976 (m), 2940 (m), 2866 (m), 2835 (m), 2781 (m), 1717 (s), 1562 (s), 1549 (s), 1450 (s), 1381 (s), 1265 (s), 1177 (s), 1097 (s), 1047 (s), 1028 (s), 899 (s), 748 (s), 708 (s). HRMS (ESI): Calcd for (C$_{55}$H$_{71}$NO$_{11}$Si+Na)$^+$: 950.4689; Found: 950.4672.

In a 100-mL plastic vial, 48% aqueous hydrofluoric acid (3.23 mL, 90.0 mmol, 100 equiv) was added via a plastic syringe to a solution of 8 (855 mg, 0.900 mmol, 1 equiv) in acetonitrile (9.0 mL) at 23° C. The mixture was stirred at 23° C. for 2 h, at which point TLC analysis indicated that full consumption of starting material had occurred. The reaction solution was transferred with a plastic pipet into a 500-mL Erlenmeyer flask containing saturated aqueous sodium bicarbonate solution (100 mL). After gas evolution had subsided, the mixture was extracted with ethyl acetate (3×50 mL). The combined organic layers were dried over magnesium sulfate, filtrated, and concentrated. The crude product was purified by flash column chromatography (15 to 30% acetone/hexanes) to afford the product (9) as a white foam (635 mg, 99%). $^1$H NMR (500 MHz, CDCl$_3$) δ 8.06-8.02 (m, 4H), 7.60-7.55 (m, 2H), 7.49-7.40 (m, 4H), 5.16 (dd, 1H), 4.75 (d, 1H), 4.51 (dd, 1H), 4.42 (dd, 1H), 3.90 (d, 1H), 3.90-3.83 (m, 1H), 3.53 (ddd, 1H), 3.40 (dd, 1H), 3.26-3.19 (m, 2H), 3.02-2.95 (m, 1H), 2.85 (s, 3H), 2.35 (s, 6H), 1.97-1.91 (m, 1H), 1.88-1.81 (m, 1H), 1.76 (s, 3H), 1.66 (s, 3H), 1.63 (s, 3H), 1.57-1.53 (m, 1H), 1.53-1.48 (m, 1H), 1.31-1.24 (m, 1H), 1.27 (s, 3H), 0.90 (d, 3H), 0.81 (d, 3H). $^{13}$C NMR (126 MHz, CDCl$_3$) δ 167.0, 166.0, 165.2, 143.4, 133.4, 133.0, 130.1, 129.6, 129.6, 129.4, 128.5, 128.3, 127.8, 104.4, 100.1, 99.8, 79.6, 77.2, 76.1, 71.5, 71.1, 68.3, 66.0, 63.2, 49.2, 40.8, 38.3, 33.9, 31.0, 26.6, 25.9, 24.3, 21.5, 19.8, 13.4, 9.7. FTIR (neat), cm$^{-1}$: 3430 (br), 2942 (m), 2874 (m), 2835 (m), 2785 (m), 1720 (s), 1641 (s), 1452 (s), 1379 (s), 1344 (s), 1267 (s), 1161 (s), 1109(s), 1087 (s), 1028 (s), 910 (s), 710 (s). HRMS (ESI): Calcd for $(C_{39}H_{53}NO_{11}+H)^{+}$: 712.3691; Found: 712.3669.

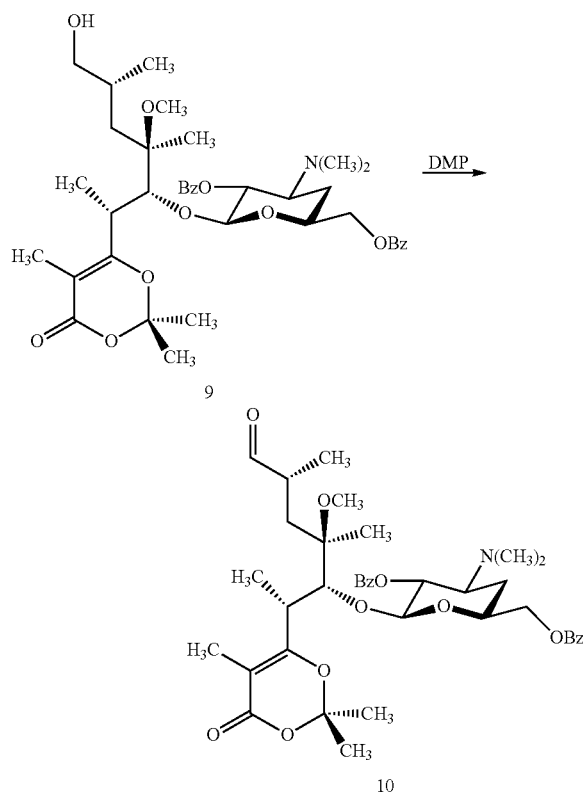

Dess-Martin periodinane (770 mg, 1.82 mmol, 1.6 equiv) was added to a solution of alcohol 9 (808 mg, 1.14 mmol, 1 equiv) in water-saturated dichloromethane (11.4 mL) in a 50-mL round-bottom flask that was immersed in a 22° C. water bath. After 90 min, the mixture was diluted with saturated aqueous sodium bicarbonate solution (10 mL), saturated aqueous sodium thiosulfate (10 mL), and ether (20 mL). The resulting cloudy mixture was stirred vigorously for 30 min, and the layers were separated. The aqueous layer was extracted with ether (3×20 mL). The organic layers were combined, and the resulting solution was washed with saturated sodium chloride solution (30 mL). The washed organic solution was dried over magnesium sulfate and concentrated to give the aldehyde 10 (806 mg) as a crude product (white foam). The crude product was used for next step without further purification. $^{1}$H NMR (500 MHz, CDCl$_{3}$) δ 9.28 (d, 1H), 8.06-8.01 (m, 4H), 7.60-7.54 (m, 2H), 7.49-7.39 (m, 4H), 5.14 (dd, 1H), 4.73 (d, 1H), 4.48 (dd, 1H), 4.43 (dd, 1H), 3.88-3.82 (m, 1H), 3.83 (d, 1H), 3.25-3.18 (m, 1H), 3.01-2.93 (m, 1H), 2.72 (s, 3H), 2.48-2.40 (m, 1H), 2.34 (s, 6H), 1.96-1.91 (m, 1H), 1.75 (s, 3H), 1.73-1.60 (m, 2H), 1.65 (s, 3H), 1.59 (s, 3H), 1.52 (dd, 1H), 1.22 (s, 3H), 1.03 (d, 3H), 0.83 (d, 3H). $^{13}$C NMR (126 MHz, CDCl$_{3}$) δ 204.4, 166.9, 166.0, 165.1, 162.6, 133.3, 132.9, 130.1, 129.5, 129.3, 128.4, 128.2, 104.3, 100.2, 99.6, 78.1, 76.7, 71.5, 71.1, 66.0, 63.2, 48.9, 41.7, 40.7, 37.1, 33.9, 26.2, 25.6, 24.3, 19.9, 15.4, 13.4, 9.6. FTIR (neat), cm$^{-1}$: 2940 (m), 2875 (m), 2834 (m), 2785 (m), 1717 (s), 1641 (s), 1452 (s), 1379 (s), 1354(s), 1267 (s), 1109(s), 1028 (s), 999 (s), 910 (s), 729 (s), 710 (s). HRMS (ESI): Calcd for $(C_{39}H_{51}NO_{11}+Na)^{+}$: 732.3354; Found: 732.3364.

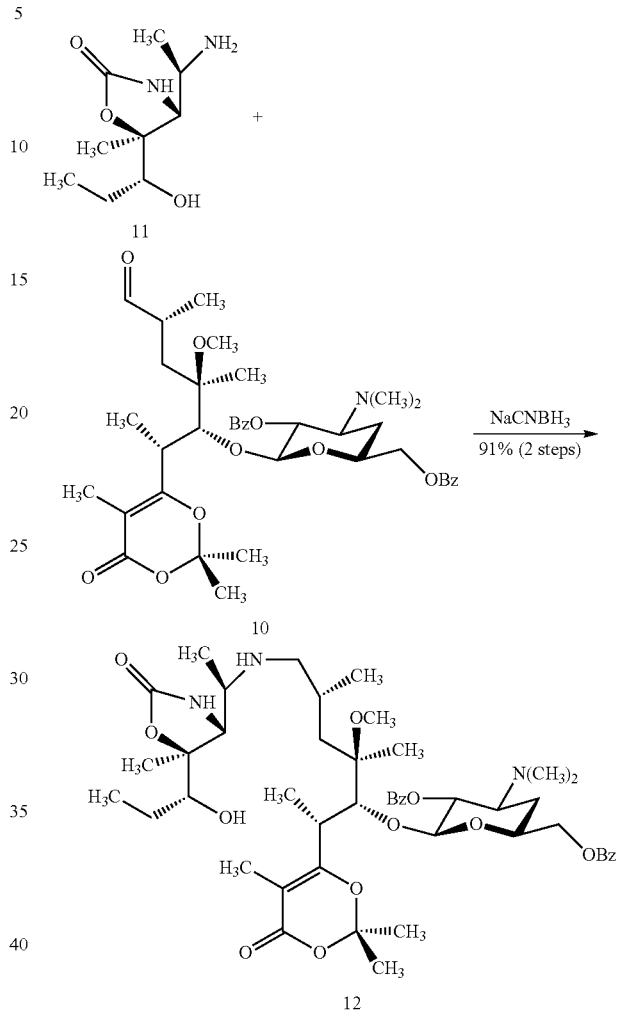

A solution of right-half aldehyde 10 (824 mg, 1.16 mmol, 1 equiv) in trifluoroethanol (11.0 mL) was transferred to the flask containing the left-half amine 11 (282 mg, 1.39 mmol, 1.2 equiv) via cannula. The solution was cooled to −20° C. (ice-salt bath). A solution of Sodium cyanoborohydride (146 mg, 2.32 mmol, 2.0 equiv) in trifluoroethanol (2.0 mL) was added dropwise via syringe. After 1 h, the reaction mixture was allowed to warm to 23° C., then was concentrated under reduced pressure. The residue was partitioned between dichloromethane (10 mL) and saturated aqueous sodium bicarbonate solution (10 mL). The aqueous layer was separated and further extracted with dichloromethane (2×10 mL). The combined organic layers were dried over sodium sulfate, and the dried solution was concentrated. The residue was purified by flash column chromatography (30% acetone-hexanes+0.5% 30% aqueous ammonium hydroxide solution) to afford the product 12 (944 mg, 91% in two steps) as a white foam. $^{1}$H NMR (500 MHz, CDCl$_{3}$) δ 8.05-8.01 (m, 4H), 7.60-7.55 (m, 2H), 7.48-7.39 (m, 4H), 5.13 (dd, 1H), 4.71 (d, 1H), 4.50 (dd, 1H), 4.41 (dd, 1H), 3.91-3.83 (m, 1H), 3.83 (d, 1H), 3.44 (d, 1H), 3.31 (d, 1H), 3.19-3.12 (m, 1H), 3.02-2.93 (m, 1H), 2.76 (s, 3H), 2.75-2.70 (m, 1H), 2.54-2.47 (m, 1H), 2.33 (s, 6H), 2.29 (dd, 1H), 1.96-1.90 (m, 1H), 1.84-1.75 (m, 1H), 1.75 (s, 3H), 1.74-1.68 (m, 1H), 1.66-1.54 (m, 2H), 1.64 (s, 3H), 1.60 (s, 3H), 1.37-1.28 (m, 1H), 1.23 (s, 3H), 1.20 (s, 3H), 1.11 (d, 3H), 1.09-1.04 (m, 1H), 1.01-0.94 (m, 5H), 0.83 (d, 3H). $^{13}$C NMR (126 MHz, CDCl$_3$) δ 167.4, 166.1, 165.2, 162.8, 160.7, 158.4, 133.4, 133.0, 130.2, 129.7, 129.1, 128.5, 128.3, 104.4, 100.5, 99.3, 87.5, 79.3, 77.7, 71.7, 71.2, 68.3, 66.2, 63.3, 53.0, 52.3, 49.1, 40.8, 36.6, 34.3, 31.9, 30.9, 28.5, 26.4, 26.1, 24.3, 23.9, 21.2, 19.8, 17.9, 13.9, 13.7, 11.0, 9.7. FTIR (neat), cm$^{-1}$: 3277 (br), 2974 (m), 2940 (m), 2875 (m), 2835 (m), 1751 (s), 1721 (s), 1640 (s), 1452 (s), 1379 (s), 1356 (s), 1267 (s), 1207 (s), 1109 (s), 1099 (s), 1069 (s), 1028 (s), 997 (s), 910 (s), 729 (s), 710 (s). HRMS (ESI): Calcd for (C$_{48}$H$_{69}$N$_3$O$_{13}$+H)$^+$: 896.4903; Found: 896.4871.

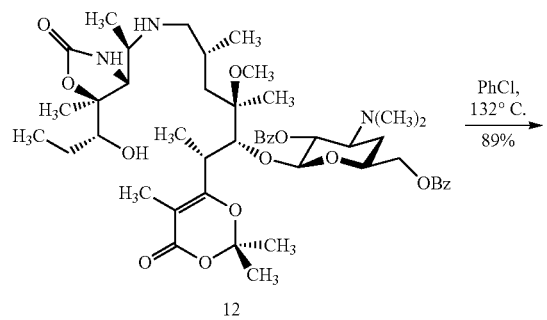

12

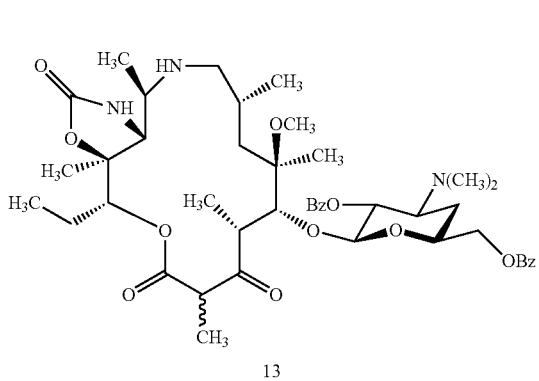

13

4.45 (d, 1H), 4.41 (dd, 1H), 4.06-4.00 (m, 1H), 3.72 (q, 1H), 3.31 (s, 1H), 3.04-2.97 (m, 1H), 2.92-2.85 (m, 1H), 2.82-2.77 (m, 1H), 2.74 (s, 3H), 2.61-2.56 (m, 1H), 2.35-2.30 (m, 1H), 2.31 (s, 6H), 1.98-1.89 (m, 2H), 1.78 (t, 1H), 1.06-1.51 (m, 2H), 1.44 (dd, 1H), 1.38-1.34 (m, 4H), 1.19 (s, 3H), 1.04 (d, 3H), 1.03-0.98 (m, 1H), 0.95 (d, 3H), 0.92 (d, 3H), 0.88 (t, 3H). $^{13}$C NMR (major epimer reported, 126 MHz, CDCl$_3$) δ 206.0, 171.0, 166.3, 165.1, 157.5, 133.2, 132.8, 130.3, 129.9, 129.7, 129.6, 128.4, 128.3, 100.5, 83.0, 78.3, 78.1, 74.6, 71.7, 71.1, 66.2, 63.4, 63.0, 57.4, 57.0, 49.9, 49.6, 45.1, 40.8, 40.7, 27.8, 26.1, 21.8, 21.7, 19.0, 14.1, 14.0, 13.7, 13.5, 10.3. FTIR (neat), cm$^{-1}$: 3316 (m), 3281 (m), 2974 (m), 2941 (m), 2878 (m), 2835 (m), 1755 (s), 1721 (s), 1452 (s), 1379 (s), 1316 (s), 1267 (s), 1177 (s), 1109(s), 1098 (s), 1069 (s), 991 (s), 910 (s), 729 (s), 710 (s). HRMS (ESI): Calcd for (C$_{45}$H$_{63}$N$_3$O$_{12}$+H)$^+$: 838.4485; Found: 838.4443.

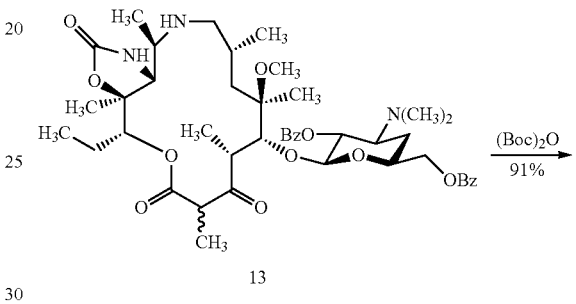

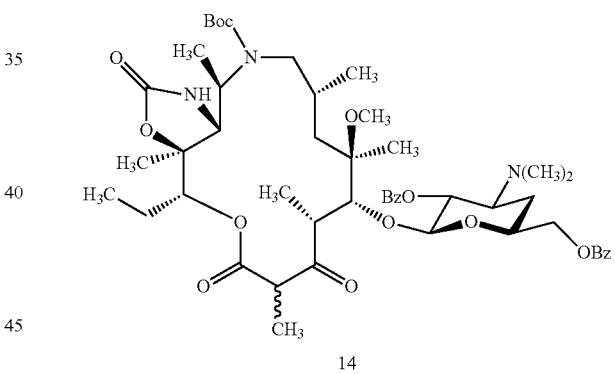

14

An oven-dried 3-L flask was charged with macrocyclization precursor 12 (588 mg, 0.656 mmol) and chlorobenzene (1.31 L). The flask was fitted with an oven-dried reflux condenser. The flask was evacuated (10 mmHg), then was flushed with argon. The evacuation-flush cycle was repeated twice with argon. The flask was then immersed in an oil bath preheated to 150° C. to allow a gentle reflux of the reaction solution. After 19 h, the heating bath was removed and the solution was allowed to cool to 23° C. The cooled solution was concentrated under reduced pressure (rotary evaporation, approximately 10 Torr, 40° C. water bath) and the residue was purified by flash column chromatography (2 to 5% methanol/dichloromethane+0.2 to 0.5% 30% aqueous ammonium hydroxide solution) to afford the product (13) as a white foam (490 mg, 89%). $^1$H NMR (2:1 ratio of C2-epimers, major epimer reported, 500 MHz, CDCl$_3$) δ 8.12-8.00 (m, 4H), 7.60-7.54 (m, 2H), 7.49-7.40 (m, 4H), 5.14 (dd, 1H), 5.08 (dd, 1H), 4.73 (d, 1H), 4.51 (dd, 1H), An oven-dried 10-mL flask was charged with macrolide amine 13 (220 mg, 0.263 mmol, 1 equiv) and Boc anhydride (1.0 mL, 4.31 mmol, 16.4 equiv). The mixture was heated to 60° C. After 2 h, the heating bath was removed and the mixture was allowed to cool to 23° C. The mixture was purified by flash column chromatography (30 to 100% ethyl acetate/hexanes) to afford the product (14) as a white foam (223 mg, 91%). $^1$H NMR (C2-epimers and N-Boc-rotamers mixture, 500 MHz, CDCl$_3$) δ 8.10-8.02 (m, 4H), 7.62-7.55 (m, 2H), 7.49-7.42 (m, 4H), 5.15-5.08 (m, 1H), 4.92-4.83 (m, 1H), 4.73-4.65 (m, 1H), 4.54-4.33 (m, 3H), 3.99-3.84 (m, 2H), 3.67 (s, 1H), 3.66-3.34 (m, 2H), 3.06-2.87 (m, 3H), 2.64 (s, 3H), 2.30 (s, 6H), 1.98-1.85 (m, 2H), 1.79-1.65 (m, 2H), 1.64-0.81 (m, 33H). FTIR (neat), cm$^{-1}$: 2976 (m), 2941 (m), 2880 (m), 2835 (m), 2785 (m), 1767 (s), 1724 (s), 1682 (s), 1452 (s), 1371 (s), 1267 (s), 1248 (s), 1155 (s), 1109 (s), 1099 (s), 1047 (s), 991 (s), 712 (s). HRMS (ESI): Calcd for (C$_{50}$H$_{71}$N$_3$O$_{14}$+H)$^+$: 938.5009; Found: 938.5013.

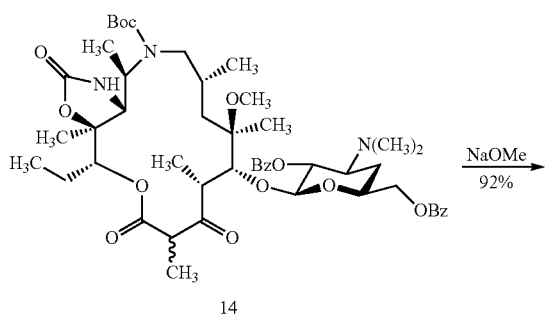

14

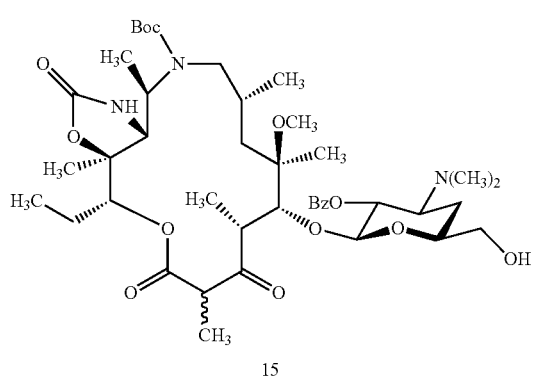

15

Sodium methoxide solution (25%, 0.018 mL, 0.078 mmol, 0.5 equiv) was added to a solution of 14 (157 mg, 0.157 mmol, 1 equiv) in 2:1 THF-methanol (1.5 mL) in a 10-mL round-bottom. After 2 h, the mixture was neutralized with 6 N hydrochloric acid solution (0.013 mL), and concentrated. The crude residue was purified by flash column chromatography (10% methanol/dichloromethane+0.5% 30% aqueous ammonium hydroxide solution) to afford the product (15) as a white foam (120 mg, 92%). $^1$H NMR (C2-epimers and N-Boc-rotamers mixture, 500 MHz, CDCl$_3$) δ 8.10-8.02 (m, 2H), 7.63-7.55 (m, 1H), 7.51-7.42 (m, 2H), 5.18-5.05 (m, 2H), 4.74-4.66 (m, 1H), 3.88-3.45 (m, 6H), 3.17-2.91 (m, 4H), 2.87 (s, 3H), 2.33 (s, 6H), 2.01-0.82 (m, 38H). FTIR (neat), cm$^{-1}$: 3349 (br), 2974 (m), 2940 (m), 2878 (m), 2837 (m), 2785 (m), 1761 (s), 1724 (s), 1454 (s), 1410 (s), 1368 (s), 1269 (s), 1249 (s), 1155 (s), 1113 (s), 1070 (s), 1028 (s), 737 (s), 712 (s). HRMS (ESI): Calcd for (C$_{43}$H$_{67}$N$_3$O$_{13}$+H)$^+$: 834.4747; Found: 834.4748.

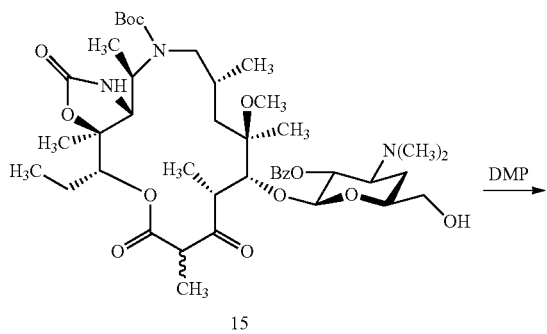

15

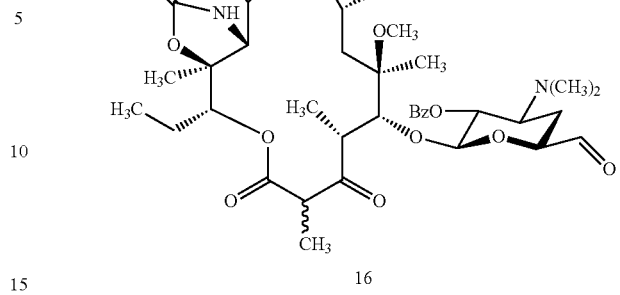

16

Dess-Martin periodinane (50.7 mg, 0.119 mmol, 2.0 equiv) was added to a solution of alcohol 15 (49.8 mg, 0.060 mmol, 1 equiv) in water-saturated dichloromethane (1.2 mL) in a 10-mL round-bottom flask. After 2 h, the mixture was diluted with saturated aqueous sodium bicarbonate solution (1 mL), saturated aqueous sodium thiosulfate (1 mL), and ethyl acetate (2 mL). The resulting cloudy mixture was stirred vigorously for 30 min, and the layers were separated. The aqueous layer was extracted with ethyl acetate (3×3 mL). The organic layers were combined, dried over magnesium sulfate, and concentrated to give the aldehyde 16 (49.8 mg) as a crude product (white foam). The crude product was used for next step without further purification.

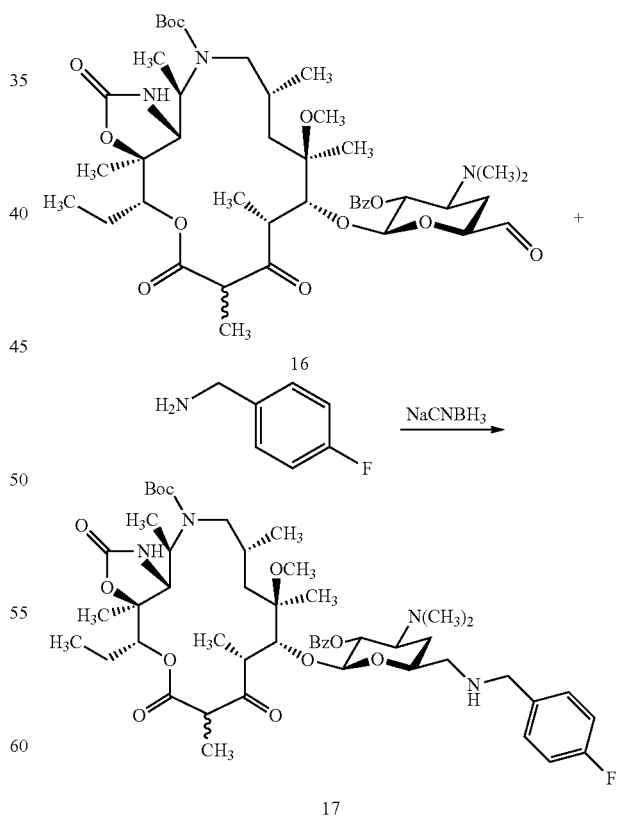

17

A 10-mL round-bottom flask was charged with aldehyde 16 (15.1 mg, 0.018 mmol, 1 equiv). Trifluoroethanol (0.37 mL), 4-Å molecular sieves (30 mg, activated by a gentle flame under vacuum (0.2 mmHg) for 5 min, then cooling to 23° C. under dry argon), 4-fluorobenzylamine (6.2 μL, 0.054 mmol, 3.0 equiv) and acetic acid (6.2 μL, 0.054 mmol, 3.0 equiv) were added sequentially. After 30 min, the suspension was cooled to −20° C. (ice-water bath), and sodium cyanoborohydride (3.4 mg, 0.054 mmol, 3.0 equiv) was added in one portion. After 30 min, saturated aqueous sodium bicarbonate solution (3 mL) was added. The mixture was extracted with 10% methanol/dichloromethane (3×3 mL). The combined organic layers were dried over magnesium sulfate, filtrated, and concentrated. The crude product (17) was used for next step without further purification.

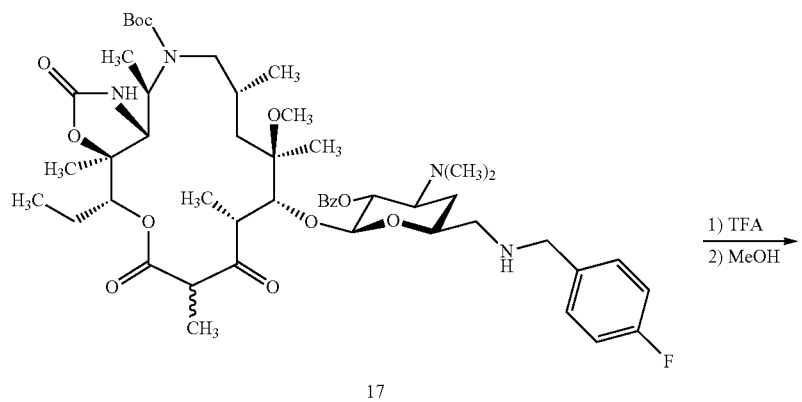

17

A 10-mL round-bottom flask was charged with crude 17 (0.018 mmol, 1 equiv), dichloromethane (0.5 mL) and trifluoroacetic acid (0.5 mL) was added. After 30 min, the mixture was concentrated and saturated aqueous sodium bicarbonate solution (3 mL) was added. The mixture was extracted with 10% methanol/dichloromethane (3×3 mL). The combined organic layers were dried over magnesium sulfate, filtrated, and concentrated. A 10-mL round-bottom flask was charged with crude product and methanol (2 mL). The flask was fitted with an oven-dried reflux condenser. The mixture was heated to reflux. After 6 h, the mixture was concentrated. The crude residue was purified by HPLC (10-30% acetonitrile/water+0.1% formic acid) to give 18 as a formate salt (8.8 mg, 56% in 4 steps). $^1$H NMR (500 MHz, CD$_3$OD) δ 8.27 (s, 3H), 7.53 (dd, 2H), 5.12 (dd, 1H), 4.62 (d, 1H), 4.53 (d, 1H), 4.33 (d, 1H), 4.24 (d, 1H), 4.21 (q, 1H), 4.15-4.08 (m, 1H), 3.60 (s, 1H), 3.58-3.48 (m, 3H), 3.32-3.17 (m, 3H), 3.11-3.05 (m, 1H), 3.04 (s, 3H), 2.84 (s, 6H), 2.56 (t, 1H), 2.15-2.10 (m, 1H), 2.00-1.88 (m, 2H), 1.85 (d, 1H), 1.78-1.66 (m, 2H), 1.63-1.57 (m, 1H), 1.56 (s, 3H), 1.39 (d, 3H), 1.36 (d, 3H), 1.35 (d, 3H), 1.34 (s, 3H), 1.09 (d, 3H), 0.99 (t, 3H). LCMS: Calcd for (C$_{38}$H$_{61}$FN$_4$O$_9$+H)$^+$: 737.4495; Found: 737.5.

(3aR,4R,7R,9R,10R,11R,13R,16R,16aS)-10-(((2S,3R,4S,6S)-6-((cyclopropylamino)methyl)-4-(dimethylamino)-3-hydroxytetrahydro-2H-pyran-2-yl)oxy)-16-ethyl-9-methoxy-4,7,9,11,13,16a-hexamethyldodecahydrooxazolo[5,4-c][1,6]oxaazacyclopentadecine-2,12,14(13H)-trione (Compound 19) was synthesized in an analogous fashion to macrolide 18.

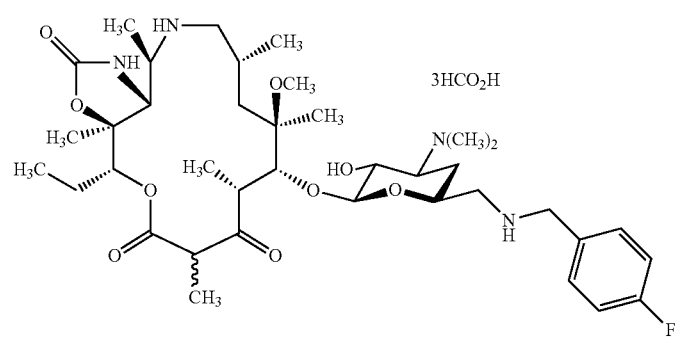

18

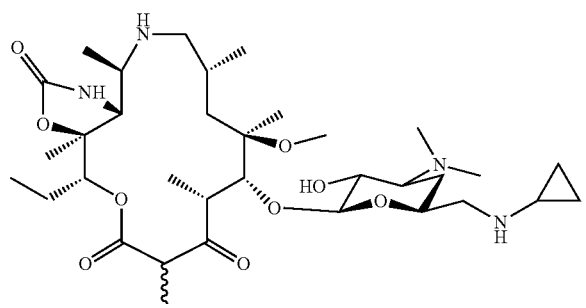

19

$^1$H NMR (400 MHz, Methanol-d$_4$) δ 8.46 (s, 2H), 5.08 (d, 10.0 Hz, 1H), 4.94-4.87 (m, 1H), 4.56-4.47 (m, 2H), 3.94-3.83 (m, 1H), 3.54-3.33 (m, 3H), 3.31-3.25 (m, 1H), 3.14-

2.96 (m, 3H), 3.08 (s, 3H), 2.75-2.83 (m, 6H) 2.52-2.42 (m, 1H), 2.42-2.31 (m, 1H), 2.09-1.98 (m, 1H), 1.98-1.81 (m, 2H), 1.79-1.48 (m, 5H), 1.54 (s, 3H), 1.39-1.28 (m, 9H), 1.29-1.20 (m, 4H) 1.17 (d, 1H), 1.05 (d, 3H), 1.03-0.95 (m, 2H), 0.93 (t, 3H), 0.64-0.53 (m, 2H), 0.51-0.39 (m, 2H); MS (ESI) m/z 669.4 (M+H).

The compounds listed in Table 11 were synthesized in an analogous fashion to macrolide 18.

TABLE 11

Exemplary Azaketolides

| Compound No. | Structure |
|---|---|
| 20 | 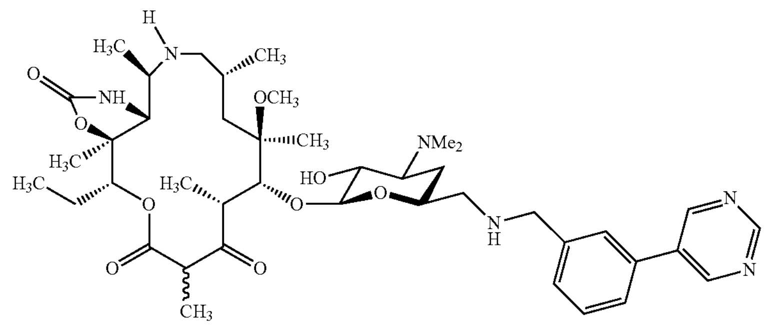 |
| 21 | 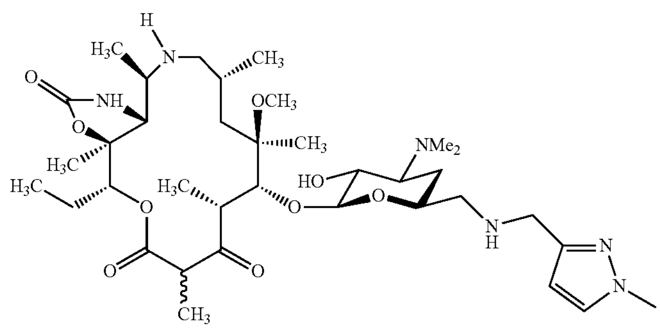 |
| 22 | 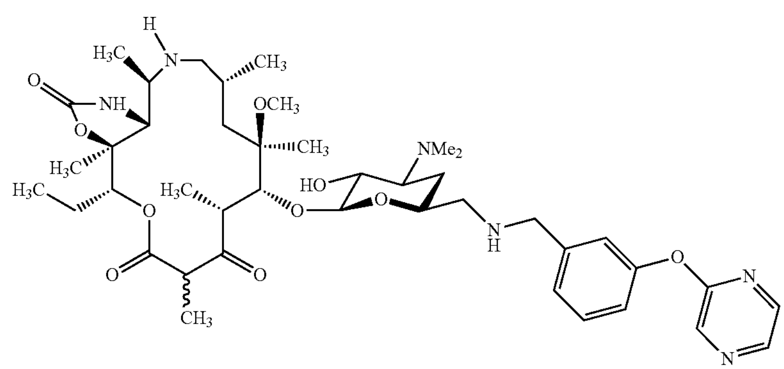 |
| 23 | 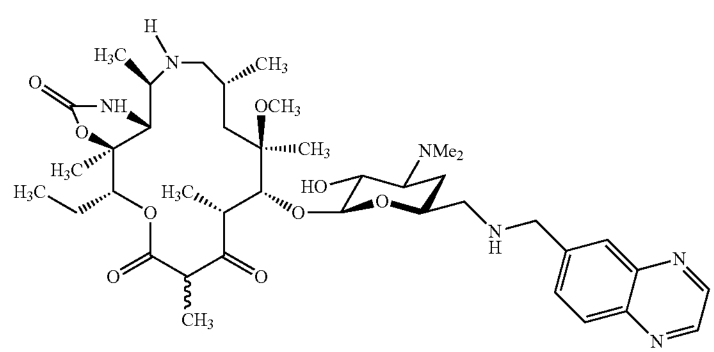 |

TABLE 11-continued

Exemplary Azaketolides

| Compound No. | Structure |
|---|---|
| 24 | 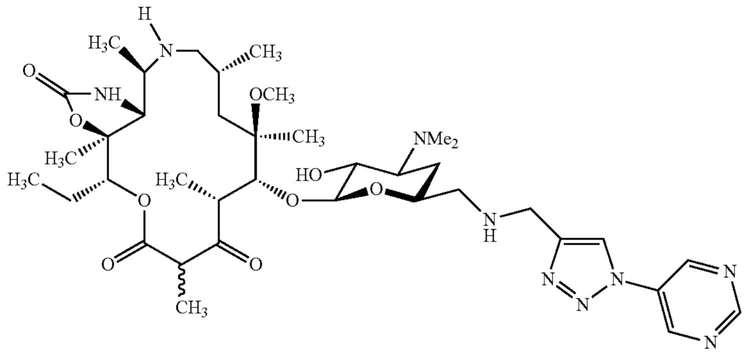 |
| 25 | 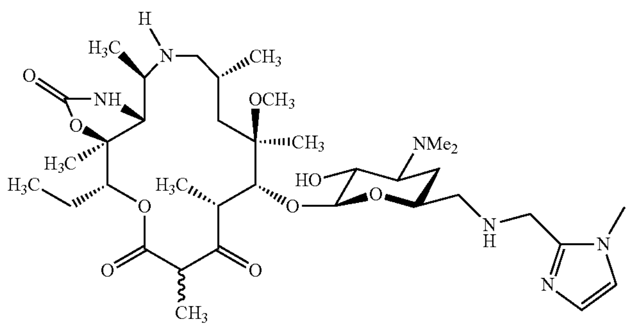 |
| 26 | 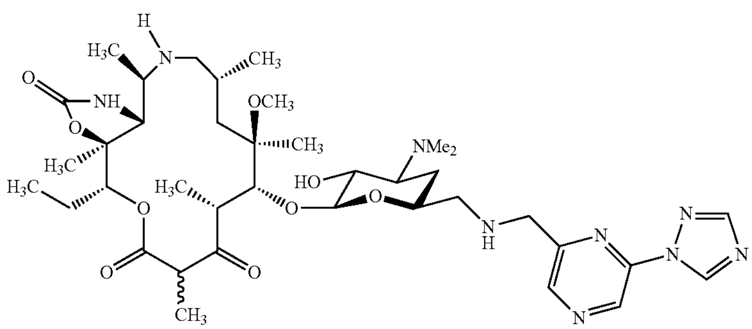 |
| 27 | 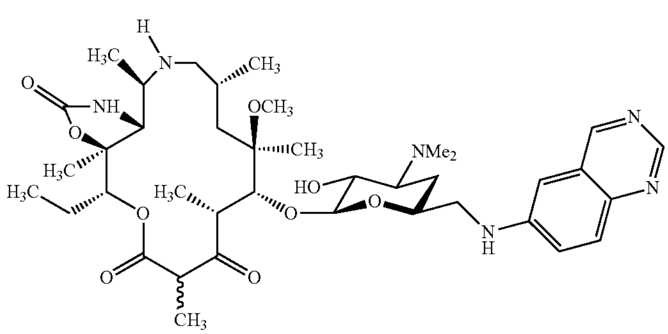 |

TABLE 11-continued

Exemplary Azaketolides

| Compound No. | Structure |
|---|---|
| 28 | 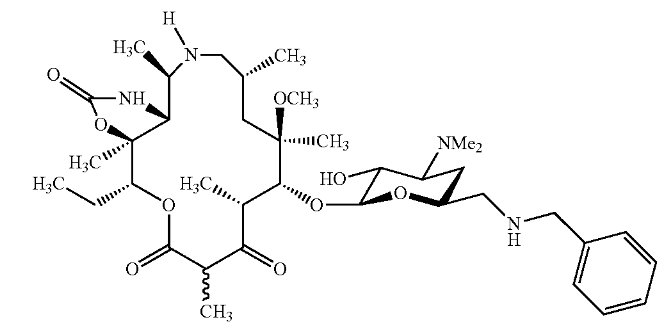 |
| 29 | 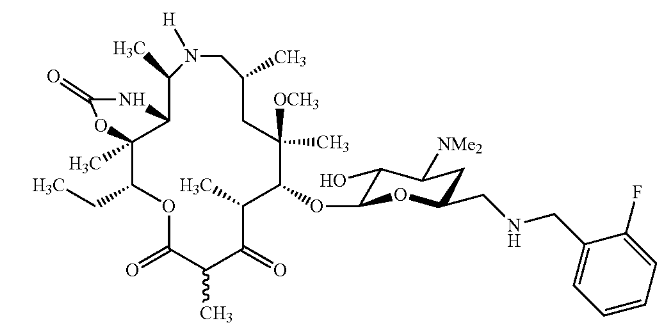 |
| 30 | 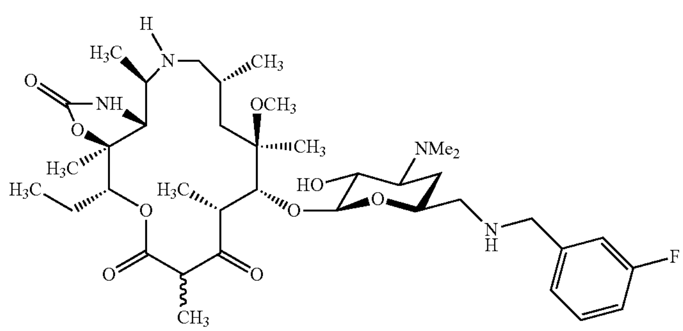 |
| 31 | 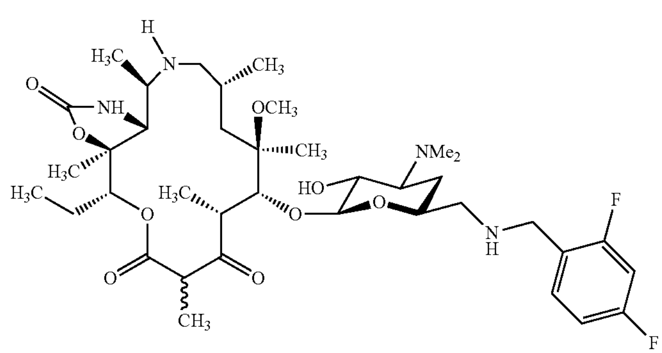 |

TABLE 11-continued

Exemplary Azaketolides

| Compound No. | Structure |
|---|---|
| 32 | 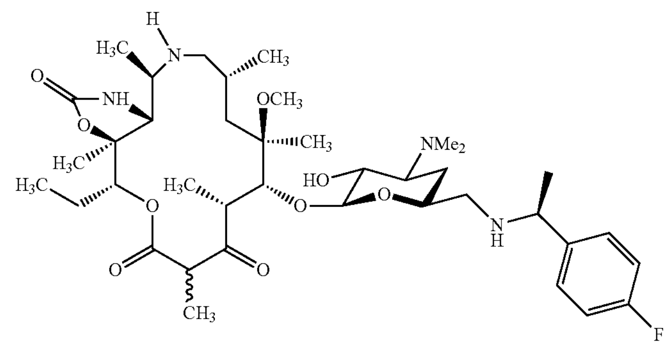 |
| 33 | 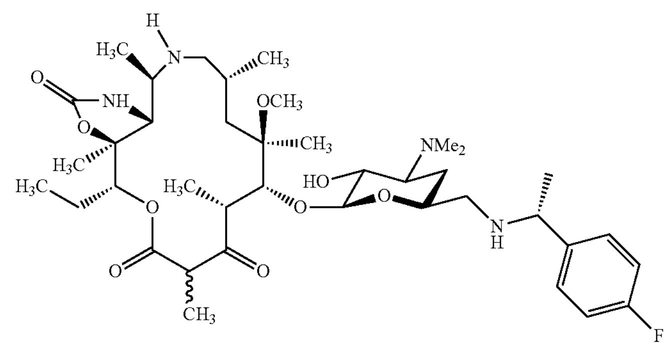 |
| 34 | 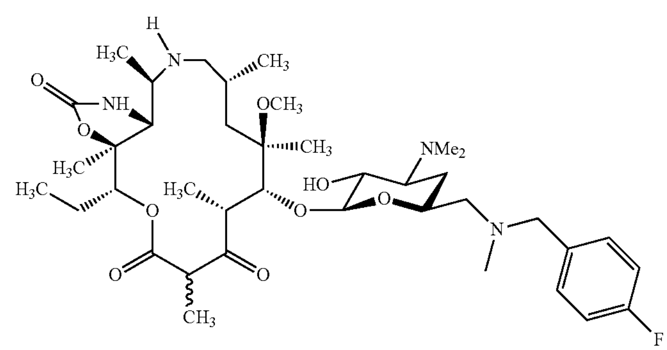 |
| 35 | 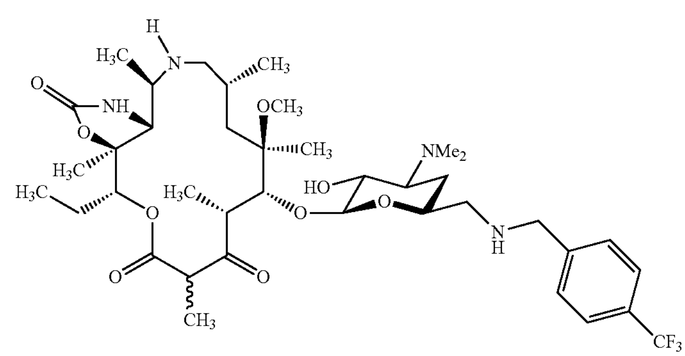 |

TABLE 11-continued

Exemplary Azaketolides

| Compound No. | Structure |
|---|---|
| 36 | 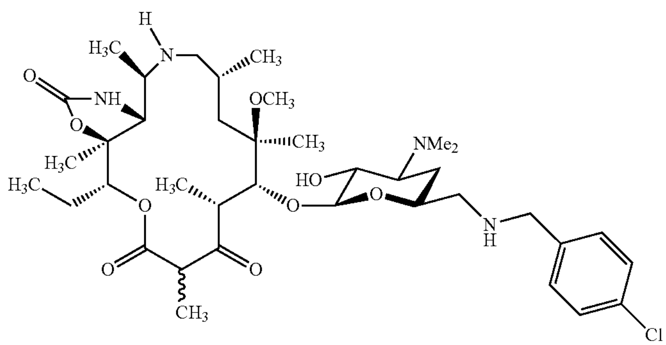 |
| 37 | 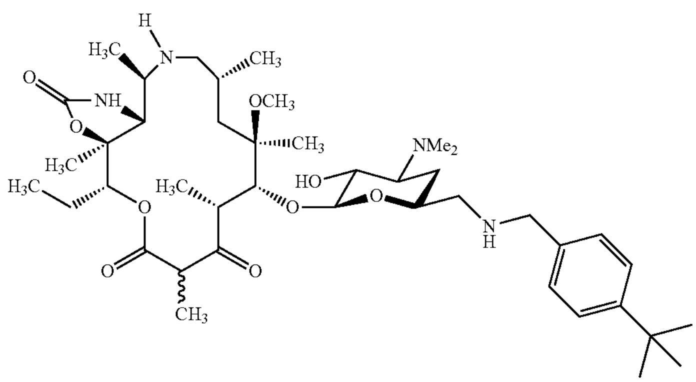 |
| 38 | 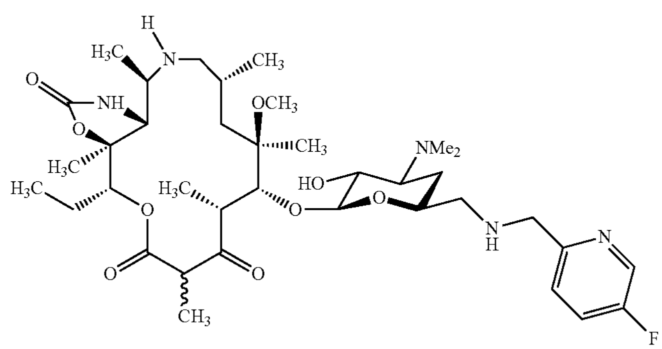 |
| 39 | 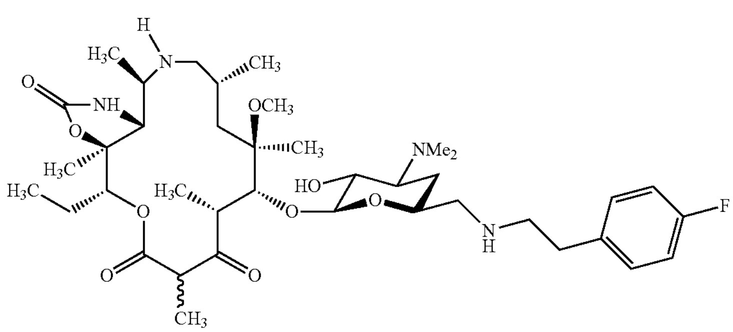 |

TABLE 11-continued

Exemplary Azaketolides

| Compound No. | Structure |
| --- | --- |
| 40 | 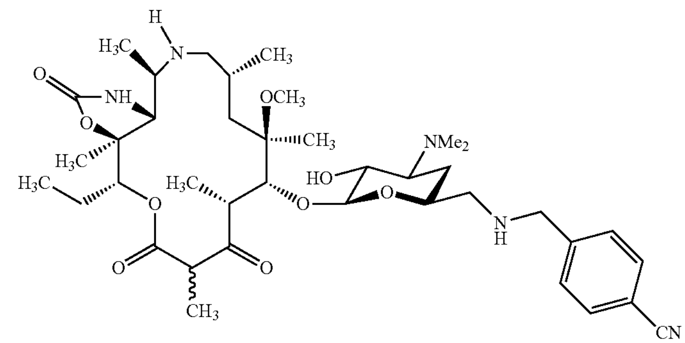 |
| 41 | 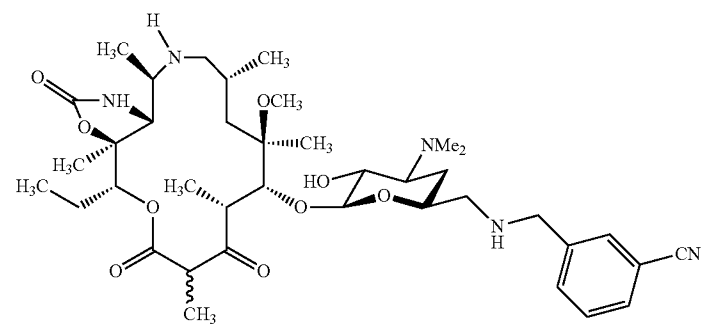 |
| 42 | 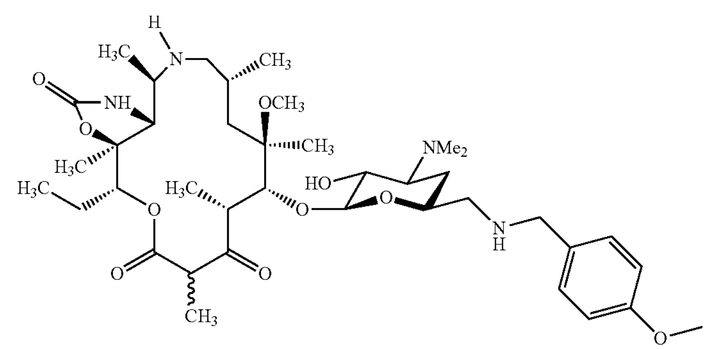 |
| 43 | 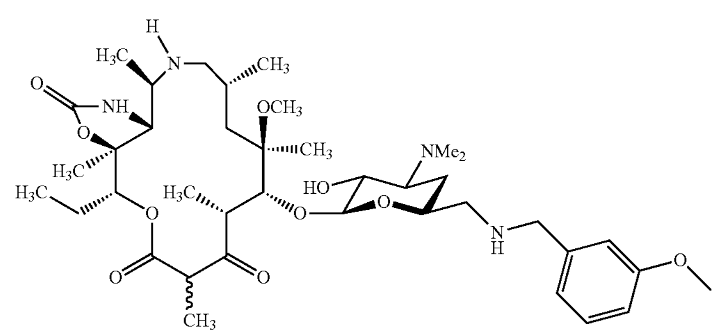 |

TABLE 11-continued

Exemplary Azaketolides

| Compound No. | Structure |
|---|---|
| 44 | 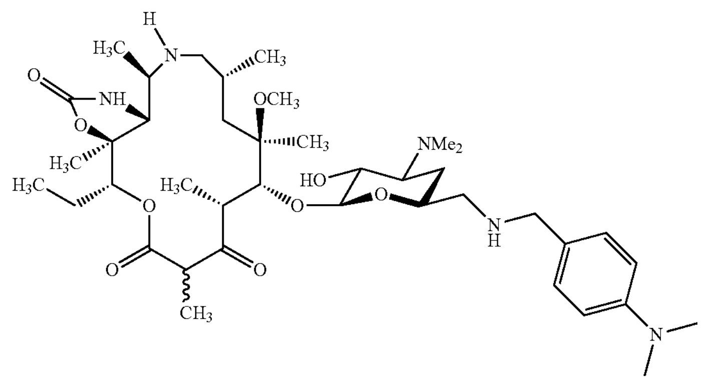 |
| 45 | 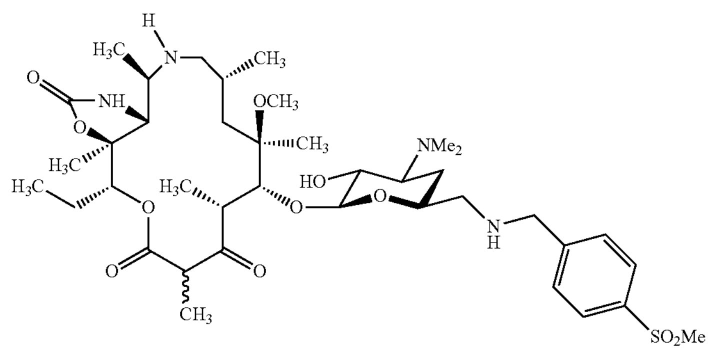 |
| 46 | 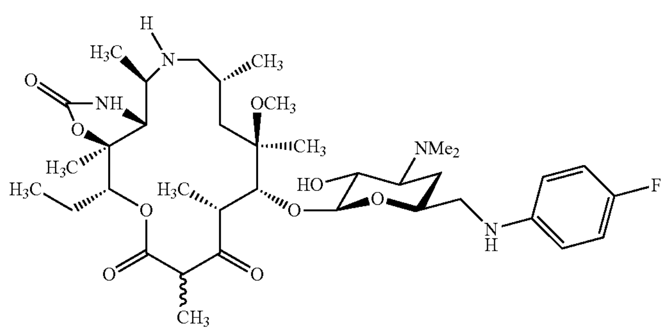 |
| 47 | 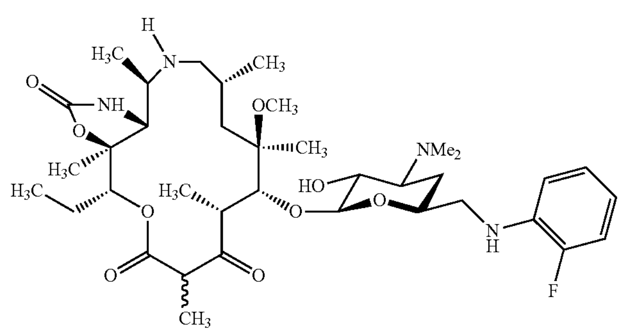 |

TABLE 11-continued

Exemplary Azaketolides

| Compound No. | Structure |
|---|---|
| 48 | *(structure shown)* |
| 49 | *(structure shown)* |
| 50 | *(structure shown)* |
| 51 | *(structure shown)* |

TABLE 11-continued

Exemplary Azaketolides

| Compound No. | Structure |
|---|---|
| 52 | 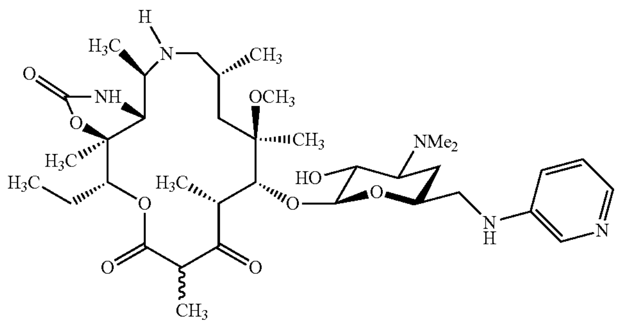 |
| 53 | 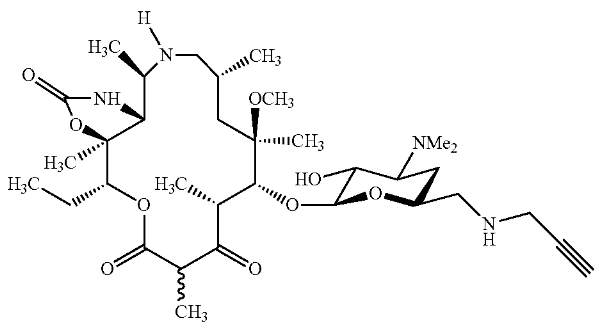 |
| 54 | 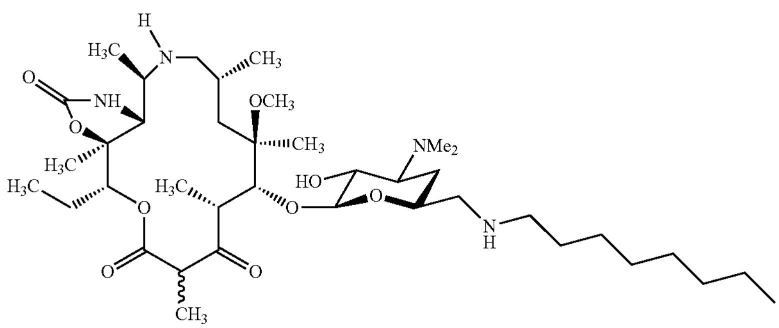 |
| 55 | 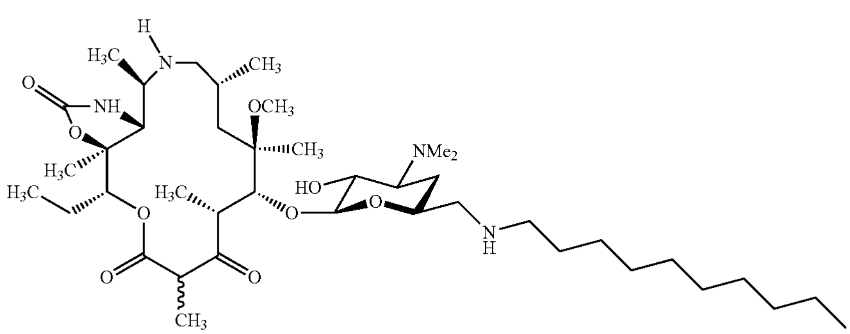 |

TABLE 11-continued
Exemplary Azaketolides
| Compound No. | Structure |
|---|---|
| 56 | 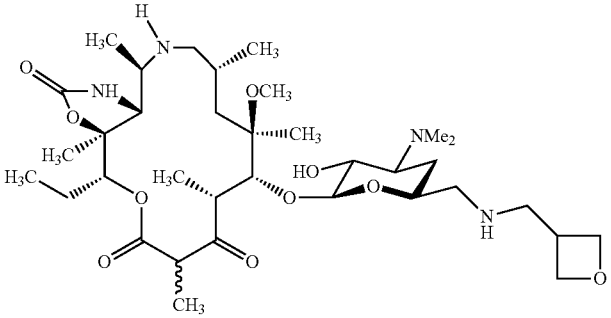 |
| 57 | 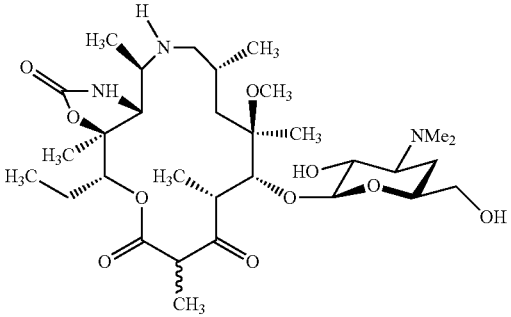 |
| 59 | 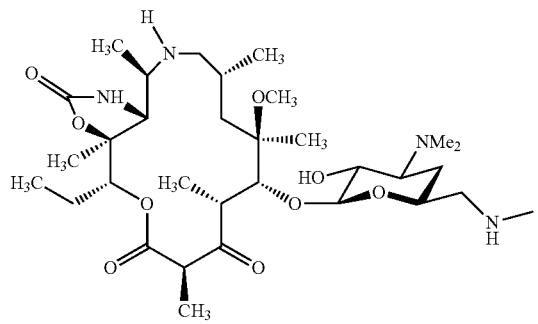 |
| 60 | 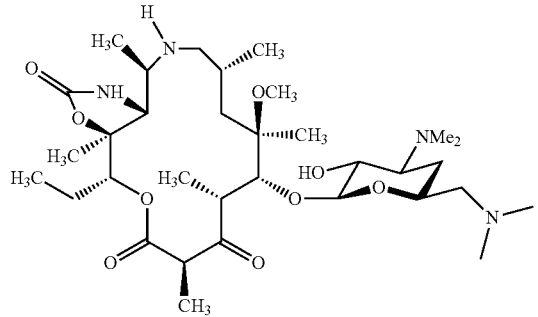 |

TABLE 11-continued

Exemplary Azaketolides

| Compound No. | Structure |
|---|---|
| 62 | 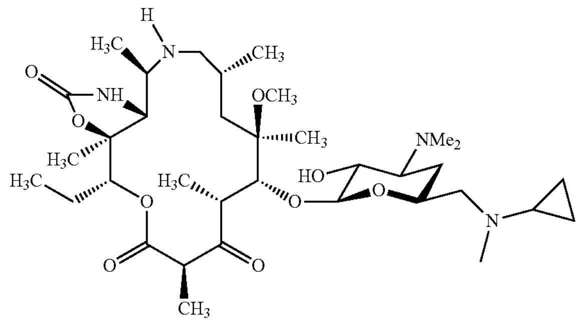 |
| 63 | 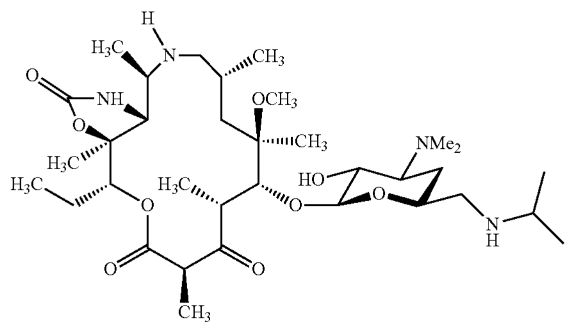 |
| 64 | 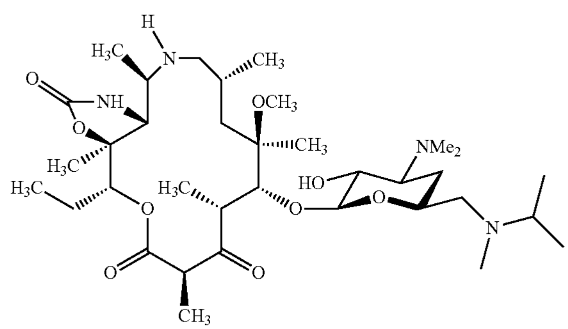 |
| 65 | 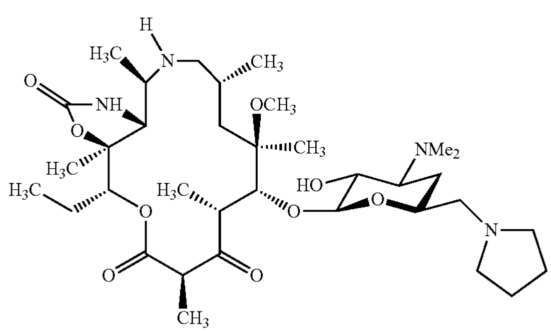 |

TABLE 11-continued

Exemplary Azaketolides

| Compound No. | Structure |
|---|---|
| 66 | 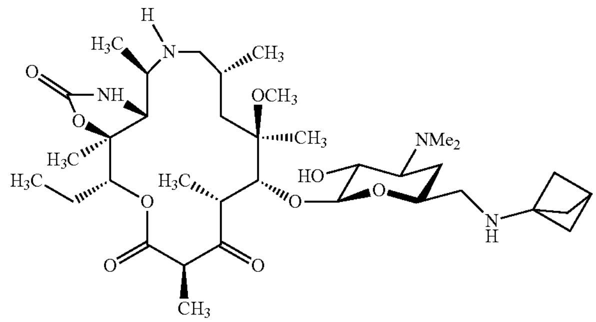 |
| 67 | 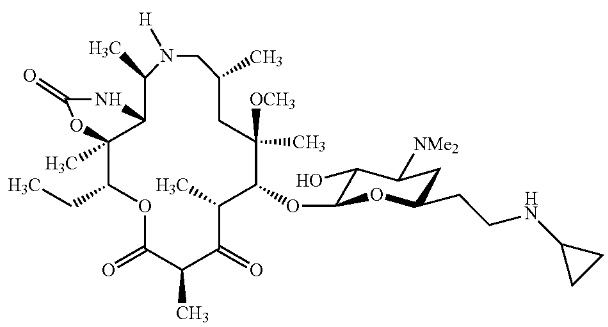 |
| 68 | 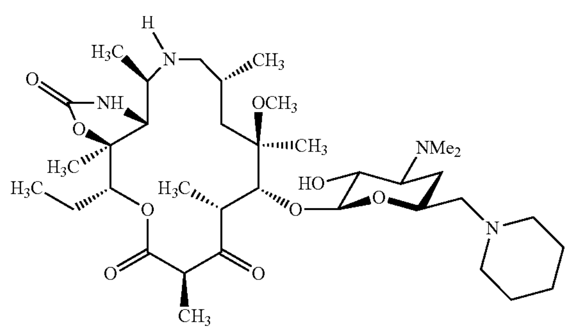 |
| 69 | 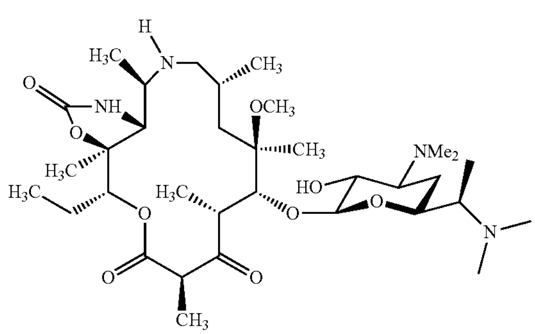 |

TABLE 11-continued

Exemplary Azaketolides

| Compound No. | Structure |
|---|---|
| 70 | 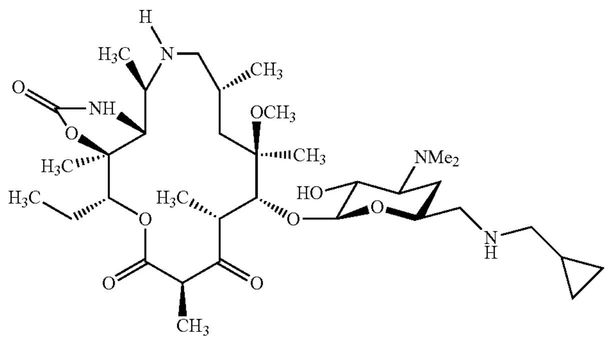 |
| 71 | 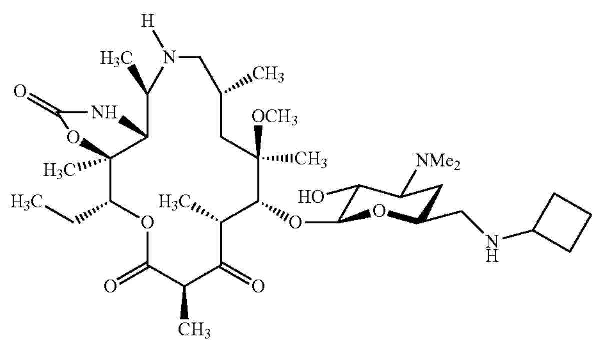 |
| 72 | 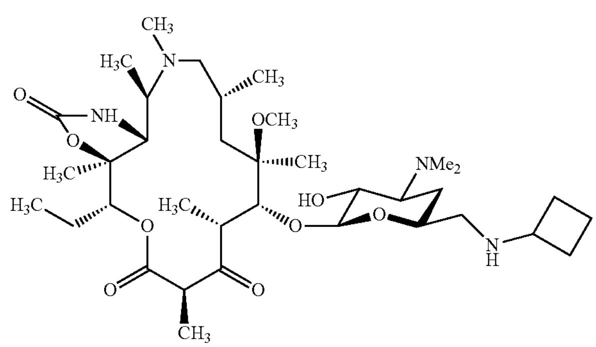 |
| 73 | 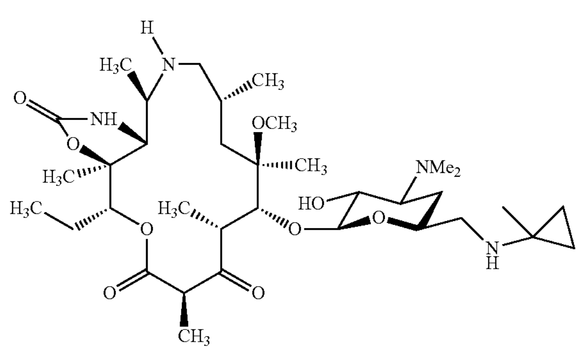 |

TABLE 11-continued

Exemplary Azaketolides

| Compound No. | Structure |
|---|---|
| 74 | 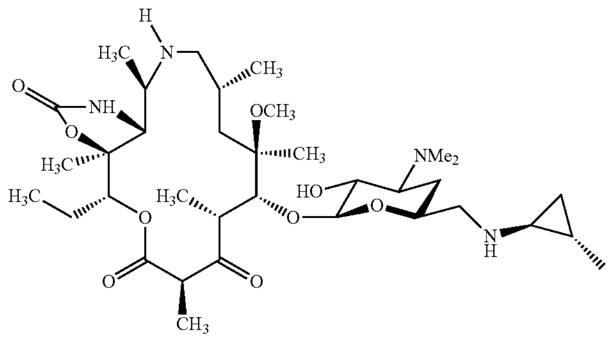 |
| 75 | 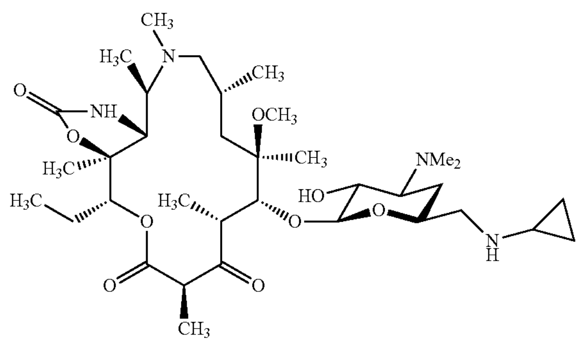 |
| 76 | 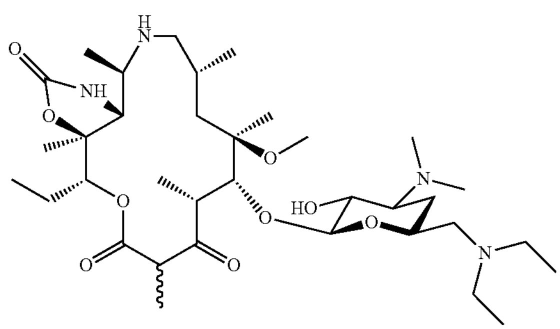 |
| 77 | 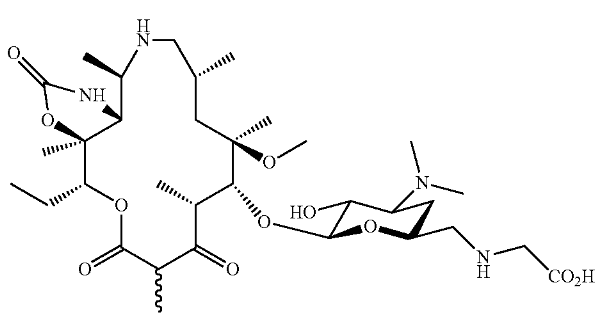 |

TABLE 11-continued

Exemplary Azaketolides

| Compound No. | Structure |
|---|---|
| 78 | 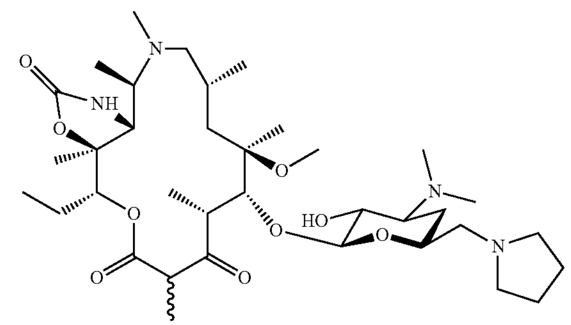 |
| 79 | 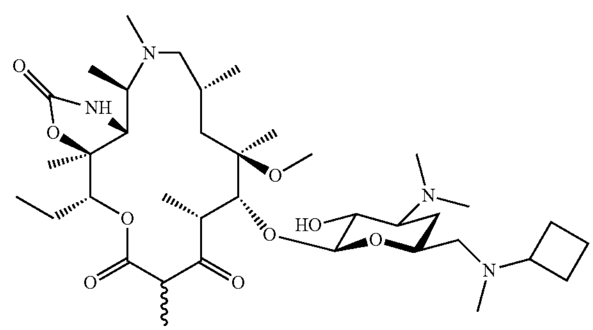 |
| 80 | 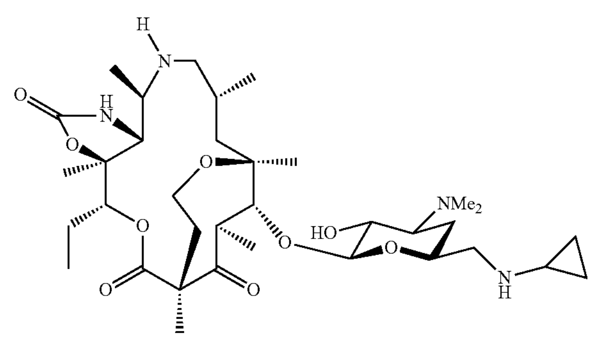 |

Additional exemplary macrolides shown in Table 12 were synthesized in analogous fashion to those described above, and by employing the methods described in Schemes 17 and/or 18.

TABLE 12

Exemplary Azaketolides

| Compound No. | Structure |
|---|---|
| 81 | 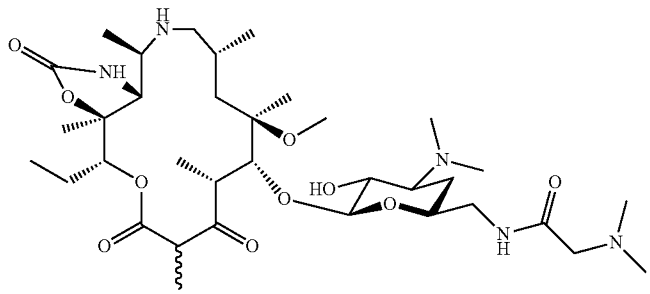 |
| 82 | 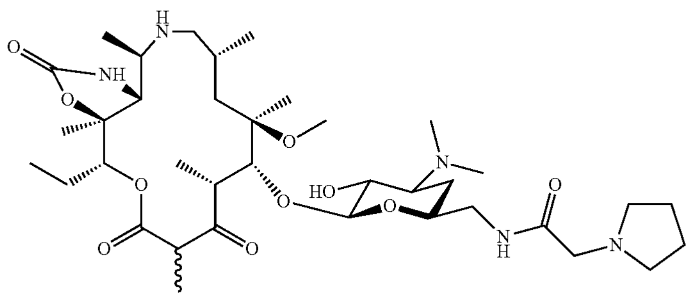 |
| 83 | 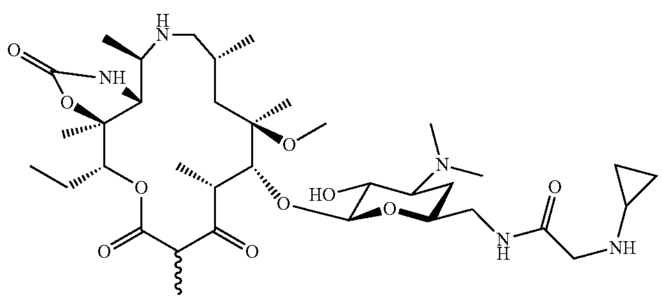 |
| 84 | 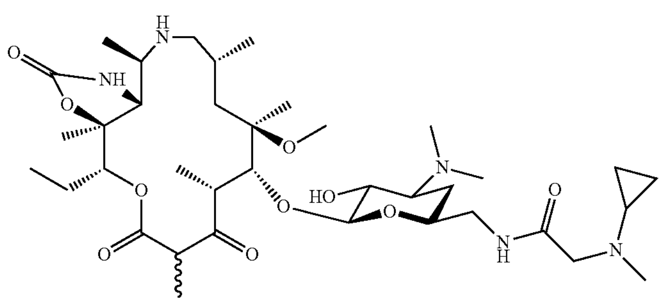 |
| 85 | 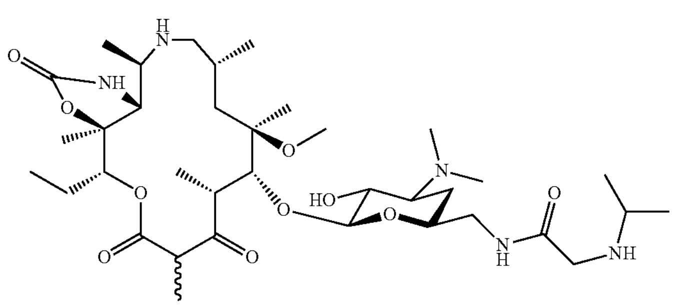 |

TABLE 12-continued

Exemplary Azaketolides

| Compound No. | Structure |
|---|---|
| 86 | 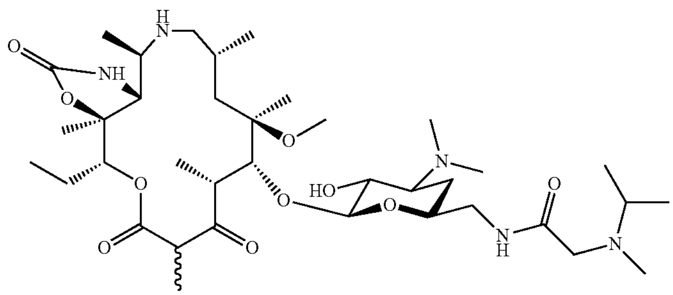 |
| 87 | 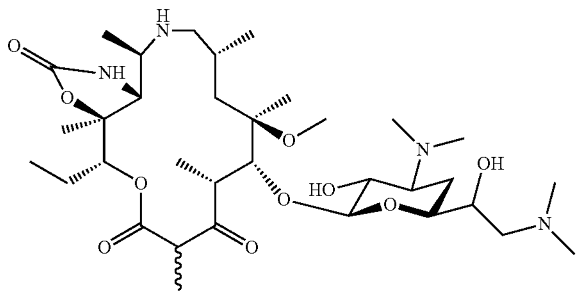 |
| 88 | 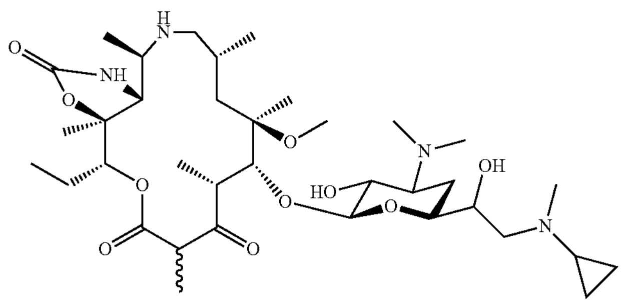 |
| 89 | 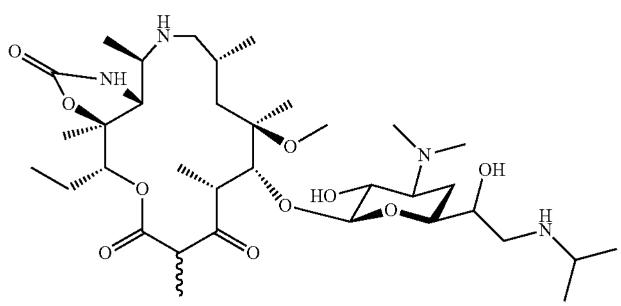 |
| 90 | 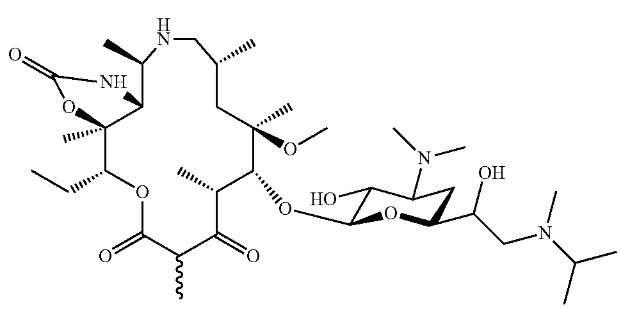 |

TABLE 12-continued

Exemplary Azaketolides

| Compound No. | Structure |
|---|---|
| 91 | 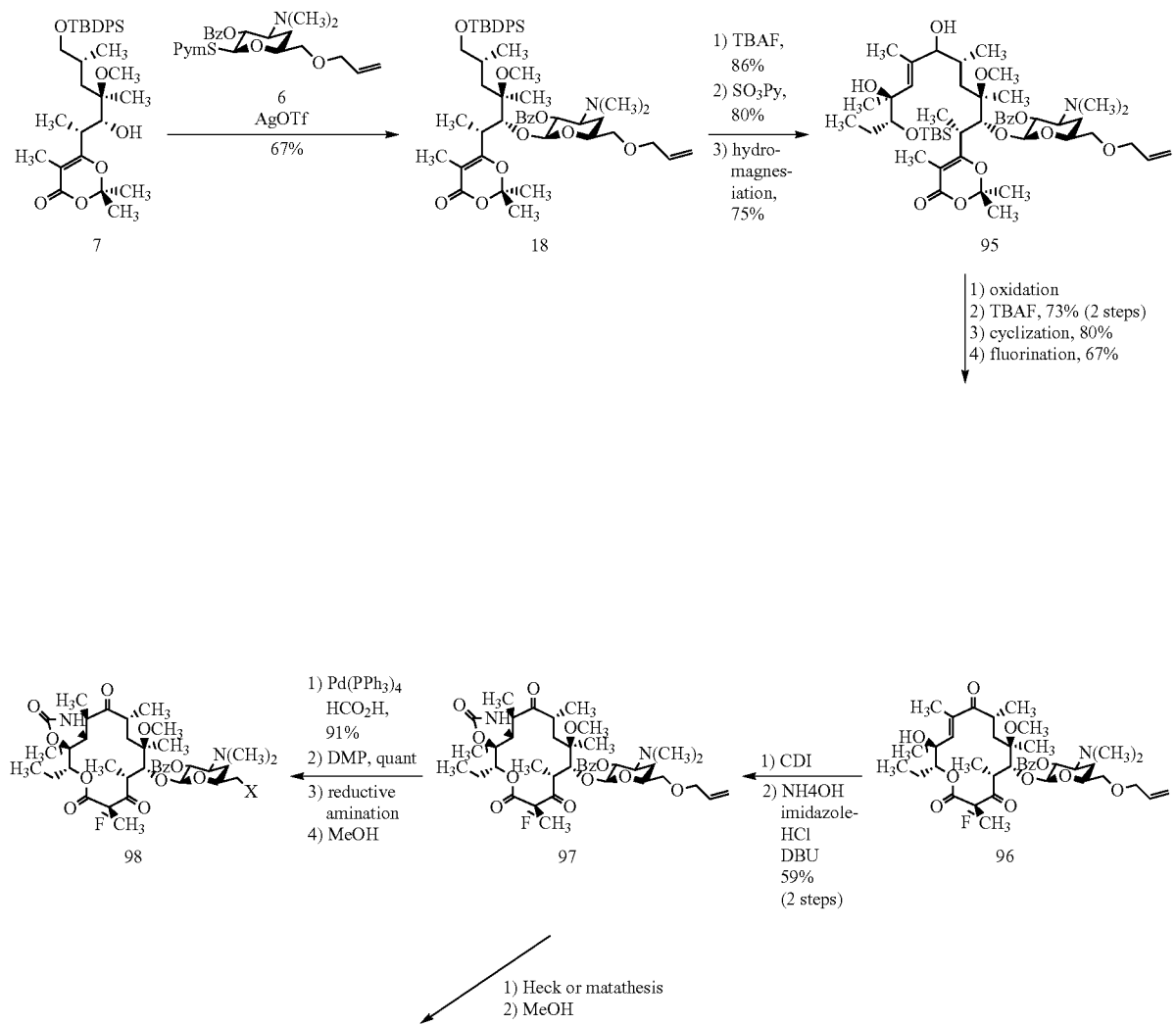 |

As demonstrated by Scheme 22 and Table 13 below, glycosylation of a macrolide precursor with thioglycoside (6) also gave access to intermediates wherein facile functionalization of the benzoyloxy group at the 6'-position of the desosamine allowed generation of macrolides featuring diverse functional groups at the 6'-position. In particular, ketolides of general structures 98 and 99 were realized as depicted in Table 13.

-continued
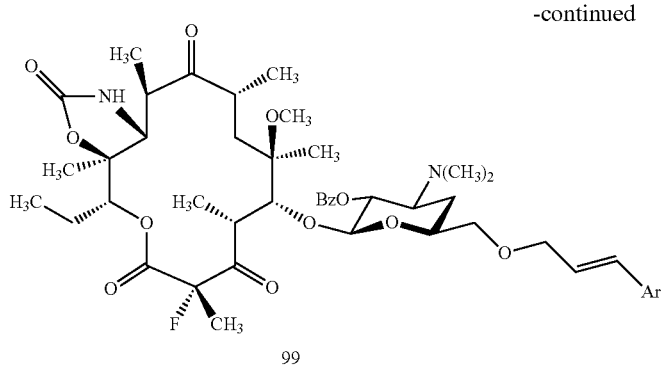
99
TABLE 13
Exemplary Azaketolides
| Compound No. | Structure |
|---|---|
| 92 | |
| 93 | |
| 94 | |

TABLE 13-continued

Exemplary Azaketolides

| Compound No. | Structure |
|---|---|
| 100 | 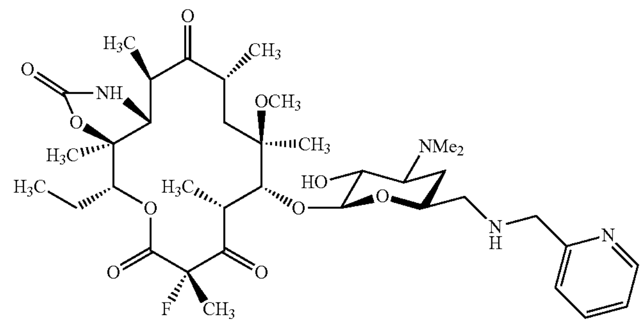 |
| 101 | 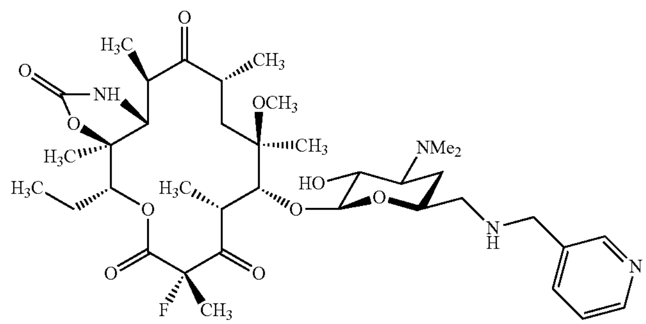 |
| 102 | 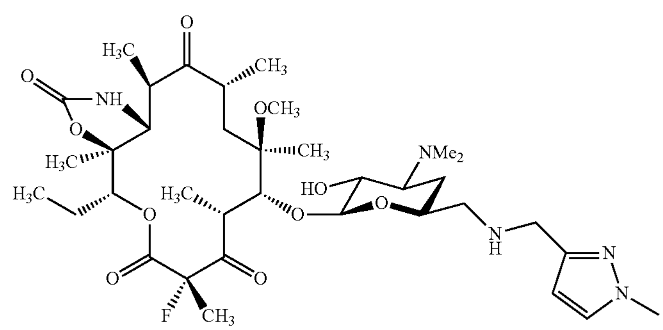 |
| 103 | 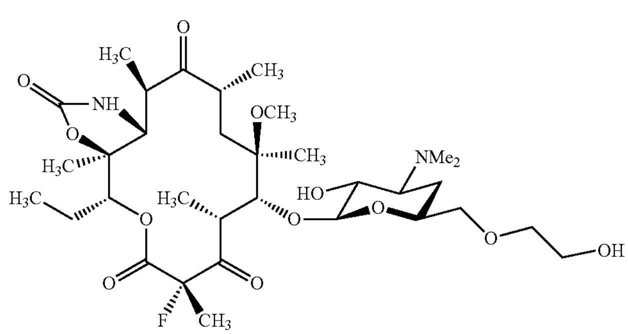 |

TABLE 13-continued
Exemplary Azaketolides
| Compound No. | Structure |
|---|---|
| 104 | 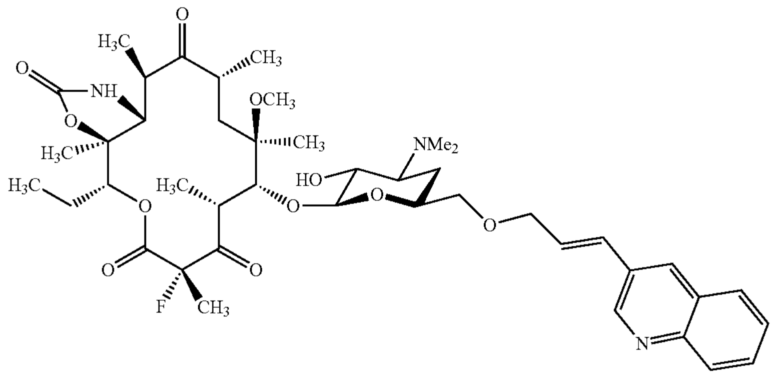 |
| 105 | 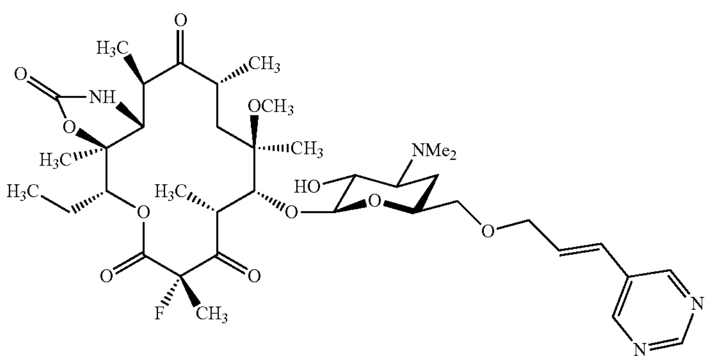 |
Compounds of Formula (I) may be synthesized using Schemes 23-35.
Scheme 23
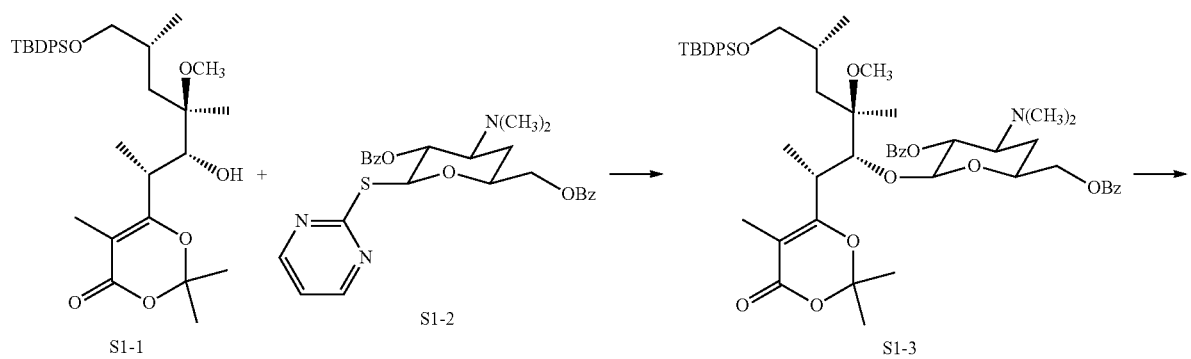

-continued
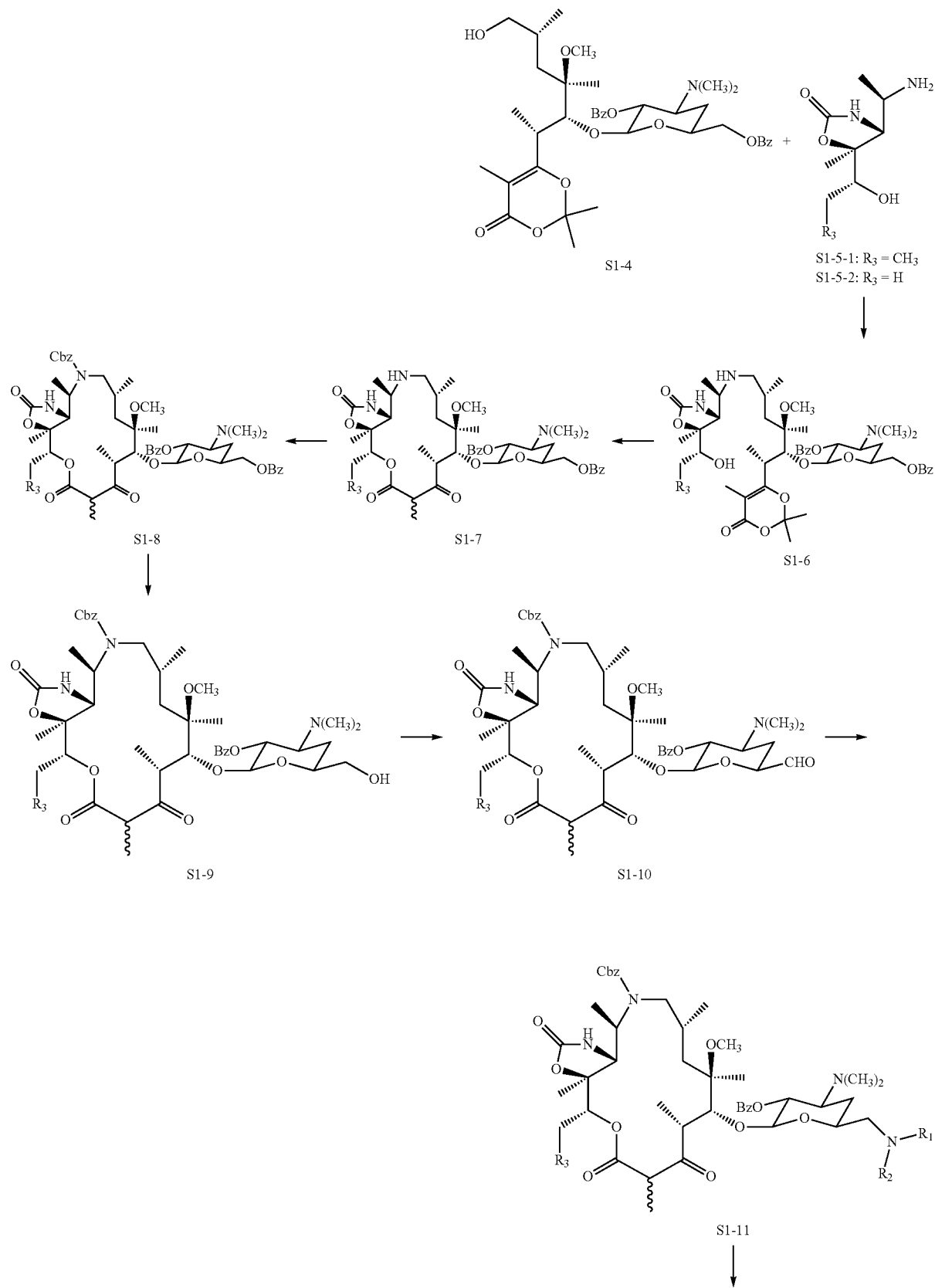

-continued

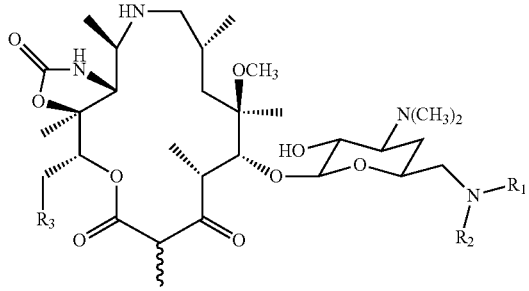

S1-12

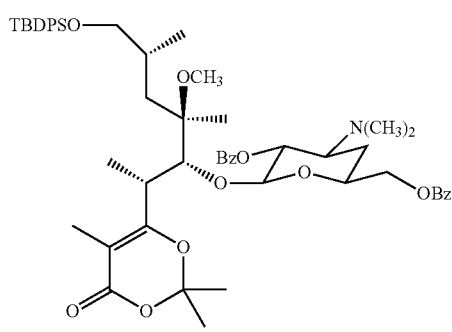

((2S,4S,5R,6S)-5-(benzoyloxy)-6-(((2R,3R,4R,6R)-7-((tert-butyldiphenylsilyl)oxy)-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)methyl benzoate (S1-3)

In a 100 mL flask was 5.8 g of powdered pre-activated 4 Å molecular sieves. The flask was flame dried under vacuum and allowed to cool to room temperature (rt), then backfilled with nitrogen. This process was repeated twice. Separately, S1-2 (6.00 g, 12.1 mmol) (Zhang, Z.; Fukuzaki, T.; and Myers, A. G. Synthesis of D-desosamine and analogs by rapid assembly of 3 amino sugars. *Angewandte Chemie Int. Ed. Eng*, 2016, 55, 523) and S1-1 (4.1 g, 7.2 mmol) (Seiple, I. B.; Zhang, Z.; Jakubec, P.; Langlois-Mercier, A.; Wright, P. M.; Hog, D. T.; Yabu, K.; Allu, S. R.; Fukuzaki, T.; Carlsen, P. N.; Kitamura, y.; Zhou, X.; Condakes, M. L.; Szczypinski, F. T.; Green, W. D.; and Myers, A. G. A platform for the discovery of synthetic macrolide antibiotics. *Nature*, 2016, 533, 338) were combined and concentrated from toluene containing dichloromethane (DCM), then dissolved in DCM (36 mL) and added to the flask via cannula. The mixture was stirred at 0° C. for 10 minutes. Silver triflate (5.88 g, 22.9 mmol) was added in one portion, and the resulting mixture was stirred in the slowly warming ice bath overnight. The reaction mixture was quenched with trimethylamine (5.0 mL, 3.63 g, 35.7 mmol) and stirred for 10 minutes, then filtered through a plug of Celite with the aid of DCM. The filtrate was partitioned between DCM and satd aq NaHCO₃ and a solid formed in the aqueous phase. The organic phase was separated and the aqueous phase was filtered and extracted 2× w/ DCM. The combined organic phases were dried over MgSO₄, filtered and concentrated, and the residue was purified on a silica gel column (elution with 25-75% EtOAc-heptanes) to yield recovered S1-1 as a pale yellow viscous oil (1.549 g, 39%) and the desired glycoside S1-3 as a white solid (2.967 g, 43%). MS (ESI+) m/z: 950.4 [M+H]⁺; NMR (400 MHz, Chloroform-d) δ 7.95 (dt, 1.5 Hz, 4H), 7.60-7.54 (m, 4H), 7.52-7.44 (m, 2H), 7.41-7.30 (m, 6H), 7.30-7.22 (m, 5H), 5.07 (dd, 7.6 Hz, 1H), 4.64 (d, 1H), 4.43-4.27 (m, 2H), 3.74 (s, 1H), 3.70 (d, 1H), 3.52 (dd, 1H), 3.27 (dd, 1H), 3.13 (td, 1H), 2.88 (td, 1H), 2.61 (s, 3H), 2.26 (s, 6H), 1.84 (ddd, 1H), 1.80-1.42 (m, 4H), 1.60 (s, 3H), 1.56 (s, 3H), 1.50 (s, 3H), 1.31 (dd, 1H), 1.19 (td, 1H), 1.13 (d, 1H), 1.09 (d, 1H), 1.02 (s, 3H), 0.94 (s, 9H), 0.92 (s, 1H), 0.69 (d, 3H).

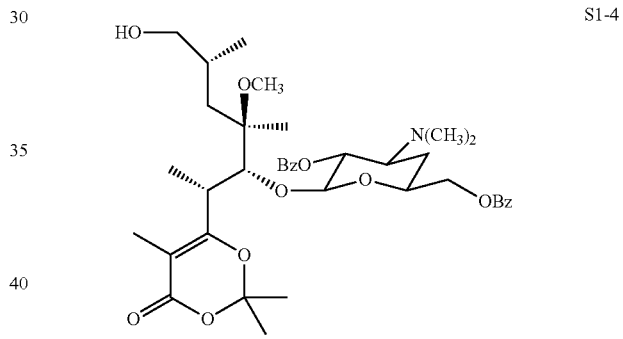

((2S,4S,5R,6S)-5-(benzoyloxy)-6-(((2R,3R,4R₁6R)-7-(hydroxy)-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)methyl Benzoate (S1-4)

S1-3 (2.967 g, 3.11 mmol) was dissolved in MeCN (12.4 mL) in a 100 mL plastic flask to give a yellow solution which was stirred at rt. Aqueous HF solution (48 wt %, 2.8 mL, 78 mmol) was added and the flask was sealed with parafilm and stirred overnight. The mixture was diluted with EtOAc and poured into satd aq NaHCO₃ and stirred for 5 minutes. The aqueous phase was extracted twice with EtOAc and the combined organic phases were dried over MgSO₄, filtered and concentrated. The residue was purified by column chromatography on 80 g of silica gel (elution with 0-10% MeOH-DCM+0.5% of 30% aq NH₄OH) to yield S1-4 as a yellow solid (2.204 g, 100%). MS (ESI+) m/z: 712.3 [M+H]⁺; ¹H NMR (400 MHz, Chloroform-d) δ 8.07-7.97 (m, 4H), 7.57 (t, 2H), 7.43 (dt, 5H), 5.16 (dd, 1H), 4.75 (d, 1H), 4.51 (dd, 1H), 4.42 (dd, 1H), 3.90 (d, 1H), 3.86 (s, 1H), 3.53 (d, 1H), 3.40 (s, 1H), 3.22 (td, 2H), 3.07-2.91 (m, 1H), 2.85 (s, 3H), 2.35 (s, 6H), 1.94 (dd, 1H), 1.84 (s, 1H), 1.76 (s, 3H), 1.74-1.46 (m, 5H), 1.66 (s, 3H), 1.63 (s, 3H), 1.26 (s, 6H), 0.90 (d, 3H), 0.81 (d, 3H).

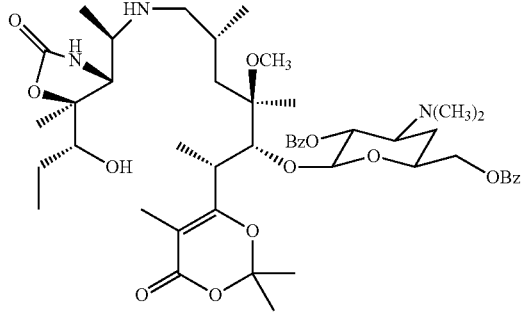

S1-6-1

In a 100 mL flask was a suspension of S1-4 (1.78 g, 2.50 mmol), powdered pre-activated molecular sieves (1.25 g) and N-methylmorpholine-N-oxide monohydrate (503 mg, 3.71 mmol) in DCM (22.5 mL) and acetonitrile (2.5 mL) which was stirred at rt for 25 minutes. Tetrapropylammonium perruthenate (44 mg, 0.13 mmol) was added and the suspension, now black, was stirred at rt for 2 hours. The mixture was concentrated and the residue was suspended in 2:1 MTBE:hexanes and filtered through a plug of Celite. The filter cake was washed several times with 2:1 MTBE:hexanes and the filtrates were concentrated to give the desired aldehyde intermediate as an off white solid (1.70 g) which was used without further purification. In a 100 mL flask the aldehyde was dissolved in MeOH (12 mL) and S1-5-1 (538 mg, 2.66 mmol) was added to give an orange solution which was stirred at rt. Ti(Oi-Pr)$_4$ was added over 30 seconds and stirred for 15 minutes. A small aliquot was added to a suspension of a small amount of NaBH$_4$ in MeOH and was analyzed by LC/MS and showed complete conversion. The reaction mixture was cooled in an ice bath for 10 minutes, then NaBH$_4$ was added in six roughly equal portions ca 4 minutes between each. When gas evolution ceased, 30% aqueous NH$_4$OH (3.5 mL) was added and stirred for 5 minutes, then the mixture was filtered through a pad of Celite with the aid of EtOAc. The filtrate was washed with brine, dried over MgSO$_4$, filtered and concentrated. The residue was purified on a 120 g SiO$_2$ column, elution with 0-6% MeOH-DCM to give S1-6-1 as a white solid (1.52 g, 71%). MS (ESI+) m/z: 710.3 [M+H]$^+$; $^1$H NMR (400 MHz, Chloroform-d) δ 8.04-7.83 (m, 4H), 7.49 (td, 2H), 7.35 (dt, 4H), 7.19 (dd, 3H), 7.14-7.04 (m, 3H), 5.05 (dd, 1H), 4.63 (d, 1H), 4.42 (dd, 1H), 4.33 (dd, 1H), 3.78 (s, 1H), 3.75 (d, 1H), 3.36 (dd, 1H), 3.24 (d, 1H), 3.14-3.02 (m, 1H), 2.88 (dq, 1H), 2.74-2.60 (m, 4H), 2.49-2.38 (m, 1H), 2.27 (d, 9H), 1.84 (dt, 1H), 1.77-1.43 (m, 4H), 1.68 (s, 3H), 1.56 (s, 3H), 1.52 (s, 3H), 1.31-1.09 (m, 4H), 1.16 (s, 3H), 1.13 (s, 3H), 1.03 (d, 3H), 0.99-0.85 (m, 6H), 0.76 (d, 3H).

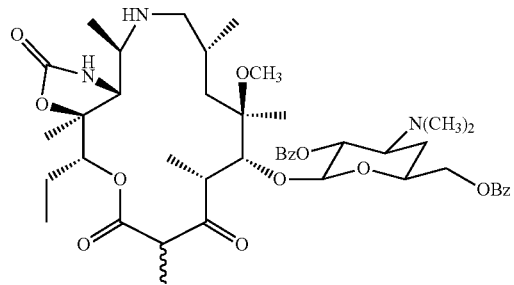

3-Descladinosyl-3-oxo-6-O-methyl-N9a-desmethyl-11,12-dideoxy-12,11-(oxycarbonylimino)-6'-benzoyloxy Azithromycin (S1-7-1)

S1-6-1 (1.52 g, 1.69 mmol) was concentrated twice from toluene in a 1 L flask. The flask was fitted with a reflux condenser and the condenser was flame dried under vacuum, allowed to cool and backfilled with nitrogen. Chlorobenzene (450 mL) was added via cannula and the flask was placed under mild vacuum and sonicated for 2 minutes, then backfilled with nitrogen. The degassing procedure was repeated, then the mixture was heated at a bath temperature of 155° C. for 16 hours and then at a bath temperature of 165° C. for 4 hours. The reaction was allowed to cool to rt and was concentrated. The residue was purified on 80 g of silica gel (elution with 0-10% MeOH-DCM+0.5% of 30% aq NH$_4$OH) to give S1-7-1 as a white solid (1.286 g, 91%). MS (ESI+) m/z: 419.8 [M+2H]$^{2+}$, 838.4 [M+H]$^+$; $^1$H NMR (400 MHz, Chloroform-d) δ 8.06-7.96 (m, 3H), 7.96-7.82 (m, 1H), 7.55-7.44 (m, 2H), 7.44-7.31 (m, 4H), 5.23 (s, 1H), 5.19-5.02 (m, 1H), 4.99 (dd, 1H), 4.68-4.54 (m, 1H), 4.43 (dd, 1H), 4.39-4.27 (m, 2H), 4.00-3.75 (m, 1H), 3.70-3.52 (m, 1H), 3.20 (d, 1H), 2.99-2.87 (m, 1H), 2.87-2.76 (m, 1H), 2.65 (s, 2H), 2.63 (s, 1H), 2.52-2.43 (m, 1H), 2.25 (s, 2H), 2.23 (s, 3H), 1.85 (ddq, 3H), 1.68 (t, 2H), 1.60-1.39 (m, 3H), 1.37-1.25 (m, 4H), 1.18 (s, 3H), 1.15-1.03 (m, 4H), 0.99 (d, 1H), 0.91 (t, 3H), 0.88-0.75 (m, 7H), 0.62-0.54 (m, 1H).

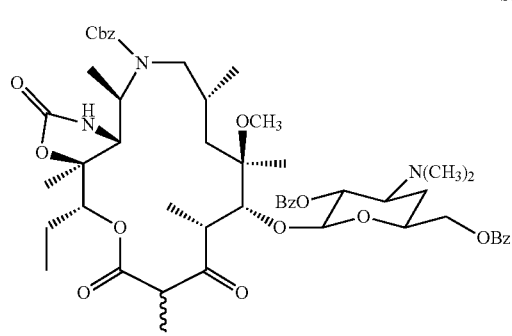

3-Descladinosyl-3-oxo-6-O-methyl-N9a-desmethyl-N9a-carbonylbenzyloxy-11,12-dideoxy-12,11-(oxycarbonylimino)-6'-benzoyloxy azithromycin (S1-8-1)

In a 50 mL flask was a solution of S1-7-1 (1.269 g, 1.50 mmol) in DCM (15 mL) to give a yellow solution which was stirred at rt. DIEA (0.80 mL, 0.59 g, 4.6 mmol) was added in one portion and stirred for 1 minute, then benzyl chloroformate (0.24 mL, 0.29 g, 1.67 mmol) was added drop wise over 90 seconds. The resulting mixture was stirred at rt for 2 hours. The reaction was diluted with DCM and poured into satd aq NH$_4$Cl. The aqueous phase was extracted with DCM and the combined organic phases were dried over MgSO$_4$, filtered and concentrated. The residue was purified on 80 g silica gel (elution with 0-5% MeOH-DCM) to give S1-8-1 as a white solid (1.216 g, 83%). MS (ESI+) m/z: 972.4 [M+H]$^+$. NMR (400 MHz, Chloroform-d) δ 8.05-7.88 (m, 5H), 7.55-7.44 (m, 3H), 7.44-7.20 (m, 11H), 5.14-4.73 (m, 5H), 4.61 (d, 1H), 4.33 (td, 3H), 3.84 (s, 2H), 3.67 (d, 1H), 3.48 (s, 1H), 2.85 (d, 2H), 2.77 (s, 1H), 2.51 (s, 3H), 2.30-2.24 (m, 1H), 2.22 (d, 6H), 1.81 (s, 1H), 1.53 (d, 3H), 1.45-1.32 (m, 2H), 1.24 (d, 3H), 1.22-1.02 (m, 13H), 0.95 (s, 2H), 0.78 (dt, 8H).

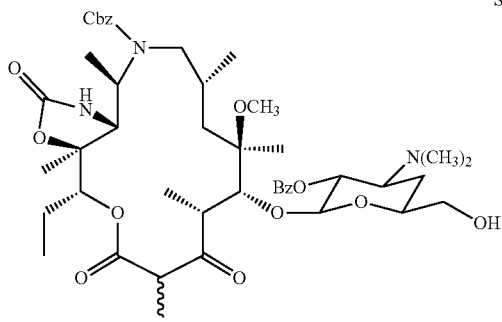

3-Descladinosyl-3-oxo-6-O-methyl-N9a-desmethyl-N9a-carbonylbenzyloxy-11,12-dideoxy-12,11-(oxycarbonylimino)-6'-hydroxy azithromycin (S1-9-1)

In a 50 mL vial was S1-8-1 (1.216 g, 1.24 mmol) in THF (8 mL) and MeOH (4 mL) to give a yellow solution which was stirred at rt. NaOMe (25 wt % in MeOH, 0.14 mL, 0.62 mmol) was added and the reaction was stirred at rt for 4.5 h. The reaction mixture was poured into satd aq NH$_4$Cl and extracted 3× with EtOAc. The combined organic phases were dried over MgSO$_4$, filtered and concentrated, and the residue was purified on 40 g silica gel (elution with 2-10% MeOH-DCM+0.5% of 30% aq NH$_4$OH) to give S1-9-1 as a white solid (0.957 g, 89%). MS (ESI+) m/z: 868.3 [M+H]$^+$ 1H NMR (400 MHz, Chloroform-d) δ 7.99-7.90 (m, 2H), 7.49 (t, 1H), 7.41-7.31 (m, 2H), 7.31-7.21 (m, 5H), 5.06-5.02 (m, 1H), 4.98 (dd, 2H), 4.61 (d, 1H), 3.69 (d, 1H), 3.57 (d, 2H), 3.51 (dd, 1H), 2.84 (ddd, 2H), 2.76 (s, 1H), 2.71 (s, 3H), 2.20 (s, 6H), 1.83-1.74 (m, 1H), 1.74-1.65 (m, 2H), 1.47-1.36 (m, 1H), 1.29-1.20 (m, 5H), 1.20-1.05 (m, 10H), 0.96 (d, 3H), 0.91-0.83 (m, 1H), 0.80 (t, 6H).

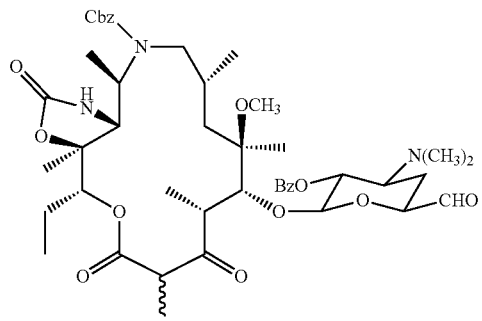

3-Descladinosyl-3-oxo-6-O-methyl-N9a-desmethyl-11,12-dideoxy-12,11-(oxycarbonylimino)-6'-oxo azithromycin (S1-10-1)

In a 20 mL vial was a solution of S1-9-1 (350 mg, 0.43 mmol) in DCM (5.8 mL) precooled at 0 C. DIEA (0.42 mL, 2.41 mmol) was added, followed by DMSO (0.17 mL, 2.41 mmol) and the mixture was stirred for 1 minute, then SO$_3$-pyridine complex (190 mg, 1.20 mmol) was added in one portion and the resulting mixture was stirred at 0° C. for 2 hours. The reaction mixture was diluted with EtOAc and washed twice with saturated, aqueous NaHCO$_3$, once with brine, dried over MgSO$_4$, filtered and concentrated to give crude S1-10-1 as white solid (364 mg). The material was used without further purification. MS (ESI+) m/z: 866.3 [M+H]$^+$, 884.3 [M+H$_2$O+H]$^+$.

106

3-Descladinosyl-3-oxo-6-O-methyl-N9a-desmethyl-11,12-dideoxy-12,11-(oxycarbonylimino)-6'-methyl-amino Azithromycin (106)

In a 5 mL vial was a solution of methylamine (2.0 M in THF, 40 μL, 80 μmol), acetic acid (6.9 μL, 120 μmol) and crude aldehyde S1-10-1 (35 mg, 40 μmol) in DCM to give a colorless solution which was stirred at rt for 30 min. NaBH(OAc)$_3$ (13 mg, 60 μmol) was added in one portion and the reaction was stirred at rt for 3.5 h. The reaction mixture was diluted with DCM and poured into satd aq NaHCO$_3$. The aqueous phase was extracted with DCM and the combined organic phases were dried over MgSO$_4$, filtered and concentrated. The residue was purified on 4 g of silica gel (elution with 0-10% MeOH-DCM+0.5% of 30% aq NH$_4$OH) to yield the desired amine. The residue was dissolved in MeOH (0.5 mL) and heated at 45° C. for 18 h. The reaction mixture was cooled, and aqueous HCl (3 M, 32

µL, 96 µmol) was added and the mixture was concentrated. The residue was placed under nitrogen and dissolved in 0.5 mL of MeOH, sonicated briefly under mild vacuum, then backfilled with nitrogen. Pd/C was added and the mixture was stirred under static hydrogen for 30 minutes, then was filtered through a syringe filter with the aid of methanol and concentrated. The residue was resubjected to the hydrogenation conditions, filtered through syringe filter and concentrated. The residue was purified by HPLC (5-30% MeCN-water-0.1% HCO$_2$H) to yield 106 as a triformate salt (10.0 mg, 34% over four steps from Example 1-6). MS (ESI+) m/z: 215.2 [M+3H]$^{3+}$, 322.2 [M+2H]$^{2+}$, 643.4 [M+H]$^+$; NMR (400 MHz, Methanol-d$_4$) δ 8.49 (s, 3H), 5.08 (d, 1H), 4.54 (d, 1H), 4.49 (d, 1H), 3.97 (s, 1H), 3.58-3.50 (m, 1H), 3.50-3.42 (m, 1H), 3.35 (s, 1H), 3.30-3.16 (m, 3H), 3.08 (d, 4H), 2.84 (s, 2H), 2.71 (d, 2H), 2.67 (s, 4H), 2.35 (t, 1H), 2.02 (d, 1H), 1.96-1.82 (m, 2H), 1.83-1.45 (m, 7H), 1.44-1.11 (m, 12H), 1.05 (d, 3H), 0.93 (t, 3H).

107

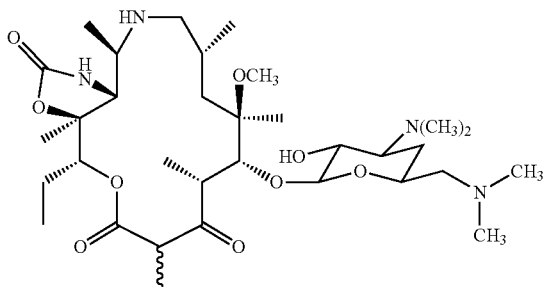

3-Descladinosyl-3-oxo-6-O-methyl-N9a-desmethyl-11,12-dideoxy-12,11-(oxycarbonylimino)-6'-dimethylamino Azithromycin (107)

Prepared according to the methods of 106, substituting dimethylamine gave 107 as a triformate salt (12.1 mg). MS (ESI+) m/z: 219.9 [M+3H]$^{3+}$; 329.3 [M+2H]$^{2+}$, 657.4 [M+H]$^+$; $^1$H NMR (400 MHz, Methanol-d$_4$) δ 8.48 (s, 3H), 5.08 (d, 1H), 4.53 (d, 1H), 4.48 (d, 1H), 3.98 (s, 1H), 3.51 (s, 1H), 3.49-3.43 (m, 1H), 3.35 (s, 1H), 3.26 (d, 1H), 3.08 (d, 5H), 3.01-2.89 (m, 2H), 2.72 (s, 11H), 2.32 (t, 1H), 2.01 (d, 1H), 1.88 (s, 2H), 1.81-1.42 (m, 7H), 1.34 (dd, 8H), 1.28-1.20 (m, 3H), 1.05 (d, 3H), 0.94 (q, 3H).

108

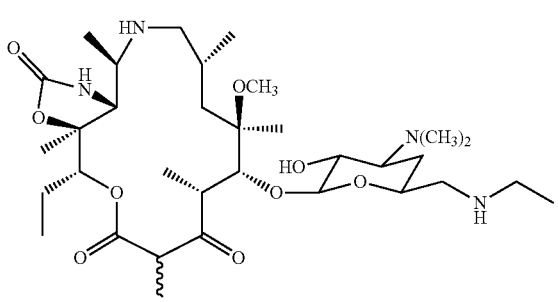

3-Descladinosyl-3-oxo-6-O-methyl-N9a-desmethyl-11,12-dideoxy-12,11-(oxycarbonylimino)-6'-ethylamino azithromycin (108)

Prepared according to the methods of 106, substituting ethylamine gave 108 as a bis-formate salt (18.92 mg). MS (ESI+) m/z: 219.8 [M+3H]$^{3+}$, 329.2 [M+2H]$^{2+}$, 657.4 [M+H]$^+$; $^1$H NMR (400 MHz, Methanol-d$_4$) δ 8.43 (s, 2H), 4.96 (dd, 1H), 4.46-4.37 (m, 1H), 4.32 (d, 1H), 3.87-3.74 (m, 1H), 3.36-3.28 (m, 2H), 3.28-3.22 (m, 1H), 3.15-2.98 (m, 6H), 2.94 (d, 5H), 2.89-2.72 (m, 2H), 2.70-2.57 (m, 1H), 2.47 (d, 5H), 2.07 (t, 1H), 1.95-1.73 (m, 3H), 1.59 (ddt, 3H), 1.45 (d, 5H), 1.38-1.20 (m, 13H), 1.20-1.10 (m, 3H), 1.05 (t, 4H), 0.91 (dd, 4H), 0.84 (q, 4H).

109

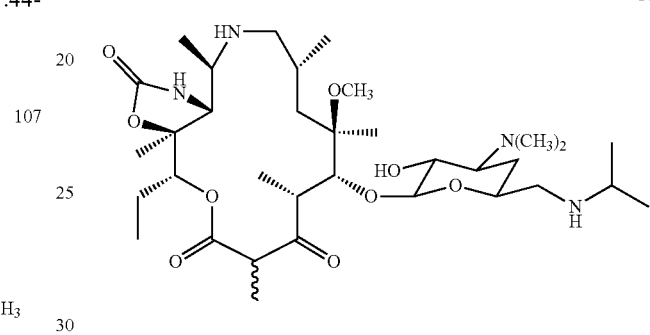

3-Descladinosyl-3-oxo-6-O-methyl-N9a-desmethyl-11,12-dideoxy-12,11-(oxycarbonylimino)-6'-isopropylamino Azithromycin (109)

Prepared according to the methods of 106, substituting isopropylamine gave 109 as a bis-formate salt (14.3 mg). MS (ESI+) m/z: 224.6 [M+3H]$^{3+}$; 336.3 [M+2H]$^{2+}$, 671.4 [M+H]$^+$; $^1$H NMR (400 MHz, Methanol-d$_4$) δ 8.47 (s, 2H), 5.08 (d, 1H), 4.87 (s, 23H), 4.54-4.47 (m, 2H), 3.97 (s, 1H), 3.68-3.60 (m, 1H), 3.55-3.44 (m, 2H), 3.38-3.20 (m, 7H), 3.10 (s, 4H), 2.69 (s, 5H), 2.38 (t, 1H), 2.06 (d, 1H), 1.89 (s, 1H), 1.77 (t, 1H), 1.66 (dd, 2H), 1.54 (s, 3H), 1.40-1.28 (m, 14H), 1.26 (d, 3H), 1.09-0.99 (m, 3H), 0.94 (q, 3H).

110

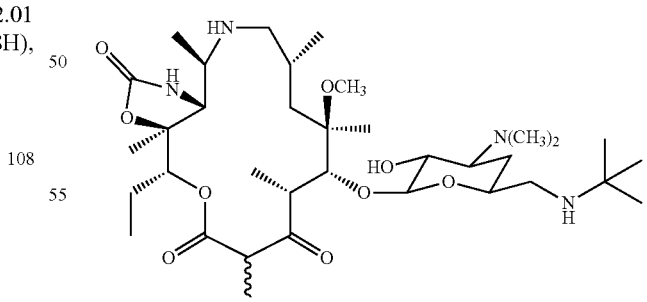

3-Descladinosyl-3-oxo-6-O-methyl-N9a-desmethyl-11,12-dideoxy-12,11-(oxycarbonylimino)-6'-tert-butylamino Azithromycin (110)

Prepared according to the methods of 106, substituting 1-methylcyclopropan-1-amine gave 110 as a tri-formate salt (5.1 mg) MS (ESI+) m/z: 229.5 [M+3H]$^{3+}$; 343.8 [M+2H]$^{2+}$, 686.4 [M+H]$^+$; $^1$H NMR (400 MHz, Methanol-d$_4$) δ 8.50 (s, 3H), 5.08 (d, 1H), 4.87 (s, 21H), 4.59-4.42 (m, 2H), 4.00 (s, 1H), 3.55 (s, 1H), 3.49 (d, 1H), 3.45-3.34 (m, 2H), 3.20 (s, 1H), 3.13-3.03 (m, 3H), 2.82 (d, 1H), 2.73 (s, 4H), 2.45 (t, 1H), 2.09 (d, 1H), 1.87 (dd, 3H), 1.77-1.46 (m, 7H), 1.39-1.26 (m, 12H), 1.10-0.99 (m, 5H), 0.93 (q, 3H).

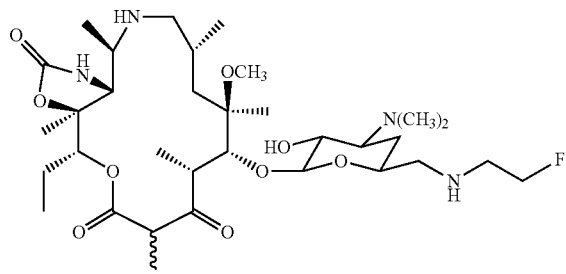

111

3-Descladinosyl-3-oxo-6-O-methyl-N9a-desmethyl-11,12-dideoxy-12,11-(oxycarbonylimino)-6'-(2-fluoroethylamino) Azithromycin (111)

Prepared according to the methods of 106, substituting 2-fluoroethylamine gave 111 as a tri-formate salt (11.2 mg) MS (ESI+) m/z: 225.9 [M+3H]$^{3+}$; 338.2 [M+2H]$^{2+}$, 675.4 [M+H]$^+$; $^1$H NMR (400 MHz, Methanol-d$_4$) δ 8.42 (s, 3H), 5.08 (d, 1H), 4.68 (s, 1H), 4.63-4.47 (m, 3H), 3.90 (s, 1H), 3.56-3.34 (m, 4H), 3.27-3.11 (m, 2H), 3.07 (s, 3H), 3.05-2.89 (m, 3H), 2.81 (d, 6H), 2.43 (t, 1H), 2.06 (d, 1H), 2.00-1.83 (m, 2H), 1.82-1.49 (m, 7H), 1.35 (dd, 8H), 1.28 (d, 3H), 1.06 (d, 3H), 0.94 (q, 3H).

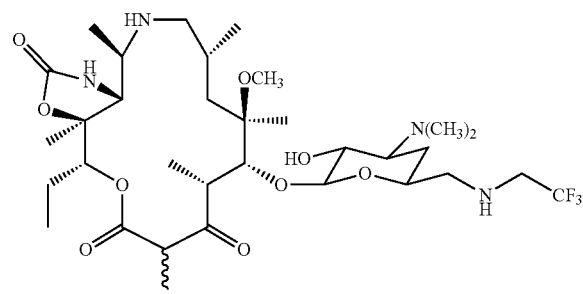

112

3-Descladinosyl-3-oxo-6-O-methyl-N9a-desmethyl-11,12-dideoxy-12,11-(oxycarbonylimino)-6'-(2-trifluoroethylamino) Azithromycin (112)

Prepared according to the methods of 106, substituting 2,2,2-trifluoroethylamine gave 112 as a mono-formate salt (14.89 mg). MS (ESI+) m/z: 237.8 [M+3H]$^{3+}$, 356.2 [M+2H]$^{2+}$, 711.4 [M+H]$^+$; $^1$H NMR (400 MHz, Methanol-d$_4$) δ 8.44 (s, 1H), 4.95 (dd, 1H), 4.44 (d, 1H), 4.30 (dd, 2H), 3.81 (d, 1H), 3.63-3.44 (m, 2H), 3.39-3.21 (m, 7H), 3.17 (d, 3H), 3.04-2.91 (m, 3H), 2.90 (d, 3H), 2.88 (s, 1H), 2.86-2.67 (m, 8H), 2.59 (td, 1H), 2.40 (d, 9H), 2.37-2.30 (m, 2H), 1.91 (dt, 2H), 1.85-1.70 (m, 4H), 1.67-1.57 (m, 3H), 1.60-1.48 (m, 3H), 1.47 (s, 2H), 1.43-1.28 (m, 7H), 1.28-1.20 (m, 9H), 1.20-1.06 (m, 8H), 1.00 (dd, 6H), 0.93-0.78 (m, 11H).

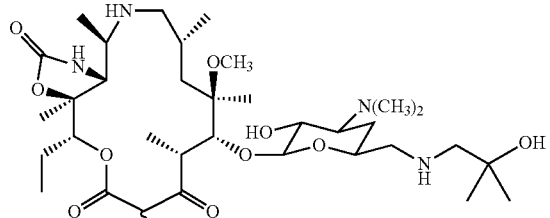

113

3-Descladinosyl-3-oxo-6-O-methyl-N9a-desmethyl-11,12-dideoxy-12,11-(oxycarbonylimino)-6'-(2-methylpropan-2-ol-amino) Azithromycin (113)

Prepared according to the methods of 106, substituting 1-amino-2-methylpropan-2-ol gave 113 as a bis-formate salt (12.1 mg) MS (ESI+) m/z: 234.6 [M+3H]$^{3+}$; 351.3 [M+2H]$^{2+}$, 701.4 [M+H]$^+$; $^1$H NMR (400 MHz, Methanol-d$_4$) δ 8.50 (s, 2H), 5.08 (d, 1H), 4.55 (d, 1H), 4.46 (d, 1H), 3.93 (d, 1H), 3.51-3.40 (m, 2H), 3.35 (s, 1H), 3.23-2.84 (m, 11H), 2.84-2.68 (m, 3H), 2.64 (s, 5H), 2.24 (t, 1H), 2.09-1.43 (m, 12H), 1.43-1.22 (m, 16H), 1.19 (d, 3H), 1.15 (d, 1H), 1.04 (d, 3H), 1.02-0.97 (m, 1H), 0.93 (t, 3H).

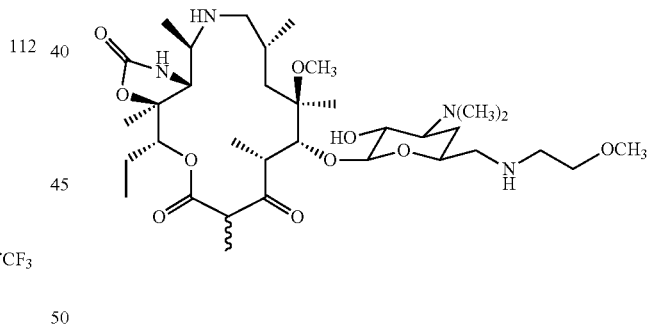

114

3-Descladinosyl-3-oxo-6-O-methyl-N9a-desmethyl-11,12-dideoxy-12,11-(oxycarbonylimino)-6'-(2-methoxyamino) Azithromycin (114)

Prepared according to the methods of 106, substituting 2-methoxyethylamine gave 114 as a tri-formate salt (13.2 mg). MS (ESI+) m/z: 229.9 [M+3H]$^{3+}$; 344.2 [M+2H]$^{2+}$, 687.4 [M+H]$^+$; $^1$H NMR (400 MHz, Methanol-d$_4$) δ 8.42 (s, 3H), 5.09 (d, 1H), 4.57-4.44 (m, 2H), 3.98 (s, 1H), 3.64 (t, 1H), 3.57-3.53 (m, 1H), 3.50 (dd, 1H), 3.45-3.26 (m, 3H), 3.38 (s, 3H), 3.25-2.99 (m, 4H), 3.10 (s, 3H) 2.77 (d, 6H), 2.42 (t, 1H), 2.05 (d, 1H), 1.90 (d, 2H), 1.79 (d, 1H), 1.72 (dd, 1H), 1.65 (s, 1H), 1.41-1.31 (m, 7H), 1.28 (d, 3H), 1.18 (d, 1H), 1.07 (d, 2H), 1.04-0.96 (m, 1H), 0.93 (t, 3H).

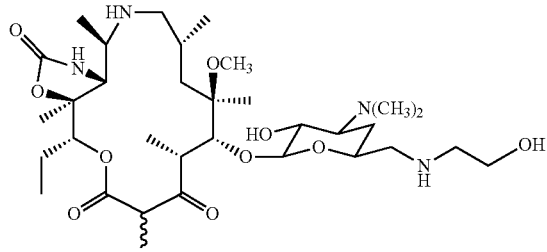

3-Descladinosyl-3-oxo-6-O-methyl-N9a-desmethyl-11,12-dideoxy-12,11-(oxycarbonylimino)-6'-(2-hydroxyethylamino) Azithromycin (115)

Prepared according to the methods of 106, substituting ethanolamine gave 115 as a tri-formate salt (12.9 mg). MS (ESI+) m/z: 225.2 [M+3H]$^{3+}$; 343.8 [M+2H]$^{2+}$, 673.4 [M+H]$^+$; $^1$H NMR (400 MHz, Methanol-d$_4$) δ 8.45 (s, 3H), 5.08 (d, 1H), 4.54 (d, 2H), 4.00 (d, 1H), 3.80 (s, 2H), 3.54 (s, 1H), 3.49 (d, 1H), 3.35 (s, 3H), 3.30-3.12 (m, 4H), 3.11-3.00 (m, 1H), 3.09 (s, 3H) 2.76 (d, 1H), 2.73 (s, 4H), 2.41 (t, 1H), 2.06 (d, 1H), 1.90 (s, 2H), 1.83-1.59 (m, 3H), 1.35 (d, 7H), 1.28 (d, 3H), 1.06 (d, 3H), 0.93 (t, 3H).

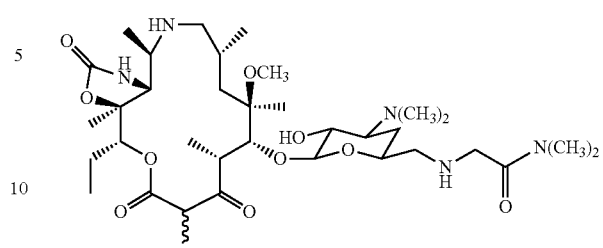

3-Descladinosyl-3-oxo-6-O-methyl-N9a-desmethyl-11,12-dideoxy-12,11-(oxycarbonylimino)-6'-(N—(N,N-dimethylacetamidyl)-amino) Azithromycin (117)

Prepared according to the methods of 106, substituting N,N-dimethylacetamide gave 117 as a triformate salt (15.1 mg). MS (ESI+) m/z: 238.9 [M+3H]$^{3+}$; 357.8 [M+2H]$^{2+}$, 714.4 [M+H]$^+$; $^1$H NMR (400 MHz, Methanol-d$_4$) δ 8.41 (s, 3H), 5.09 (d, 1H), 4.52 (d, 2H), 4.17 (d, 1H), 3.91 (d, 2H), 3.83-3.35 (m, 7H), 3.27-2.88 (m, 4H), 3.12 (s, 3H), 3.07 (s, 3H), 2.96 (s, 3H), 2.80 (d, 6H), 2.47 (t, 1H), 2.07 (d, 1H), 2.00-1.47 (m, 10H), 1.46-1.23 (m, 12H), 1.20 (d, 1H), 1.07 (d, 3H), 1.02 (d, 1H).

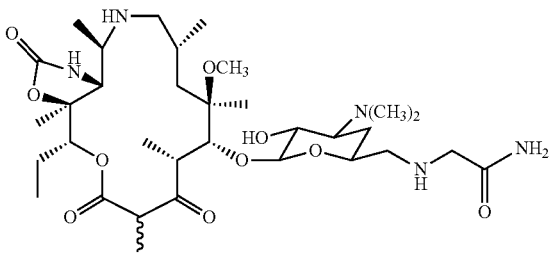

3-Descladinosyl-3-oxo-6-O-methyl-N9a-desmethyl-11,12-dideoxy-12,11-(oxycarbonylimino)-6'-(N-acetamidylamino) Azithromycin (116)

Prepared according to the methods of 106, substituting glycinamide gave 116 as a tri-formate salt (10.7 mg). MS (ESI+) m/z: 229.6 [M+3H]$^{3+}$; 337.3 [M+2H]$^{2+}$, 686.5 [M+H]$^+$; $^1$H NMR (400 MHz, Methanol-d$_4$) δ 8.44 (s, 3H), 5.08 (d, 1H), 4.53 (d, 2H), 3.55-3.34 (m, 5H), 3.16-3.00 (m, 2H), 3.08 (s, 3H), 2.90 (s, 2H), 2.81 (d, 6H), 2.38 (s, 1H), 2.04 (s, 1H), 1.89 (s, 2H), 1.82-1.58 (m, 4H), 1.44-1.29 (m, 8H), 1.29-1.19 (m, 4H), 1.17 (d, 1H), 1.05 (d, 3H), 0.93 (t, 3H).

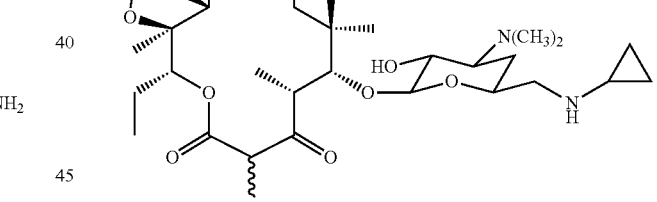

3-Descladinosyl-3-oxo-6-O-methyl-N9a-desmethyl-11,12-dideoxy-12,11-(oxycarbonylimino)-6'-cyclopropylamino Azithromycin (118)

Prepared according to the methods of 106, substituting cyclopropylamine gave 118 as a bis formate salt (201 mg, 40.7% over four steps from alcohol S) MS (ESI+) m/z: 223.8 [M+3H]$^{3+}$; 335.2 [M+2H]$^{2+}$, 669.4 [M+H]$^+$; $^1$H NMR (400 MHz, Methanol-d$_4$) δ 8.37 (s, 2H), 4.98 (dd, 1H), 4.49-4.37 (m, 2H), 4.11-3.94 (m, 1H), 3.88-3.81 (m, 1H), 3.49-3.28 (m, 4H), 3.19-3.06 (m, 1H), 3.06-2.93 (m, 6H), 2.97-2.85 (m, 1H), 2.72 (s, 2H), 2.71 (s, 5H), 2.53-2.38 (m, 2H), 2.03-1.91 (m, 1H), 1.87-1.65 (m, 2H), 1.69-1.54 (m, 1H), 1.58-1.45 (m, 2H), 1.45 (s, 3H), 1.35-1.15 (m, 13H), 1.11 (d, 1H), 1.00-0.78 (m, 7H), 0.62-0.44 (m, 4H).

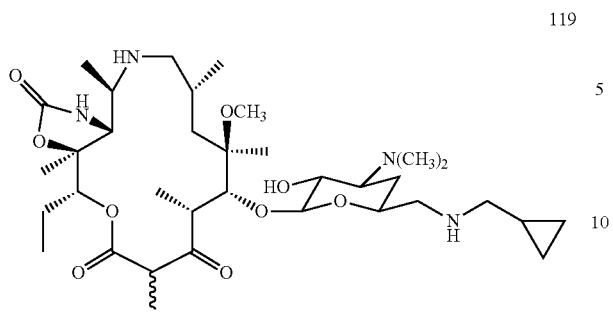

3-Descladinosyl-3-oxo-6-O-methyl-N9a-desmethyl-11,12-dideoxy-12,11-(oxycarbonylimino)-6'-(cyclopropylmethylamino) Azithromycin (119)

Prepared according to the methods of 106, substituting cyclopropylmethylamine gave 119 as a tri-formate salt (10.2 mg). MS (ESI+) m/z: 228.5 [M+3H]$^{3+}$, 342.8 [M+2H]$^{2+}$, 683.5 [M+H]$^{+}$; $^{1}$H NMR (400 MHz, Methanol-d$_4$) δ 8.52 (s, 3H), 5.07 (dd, 1H), 4.51-4.42 (m, 2H), 3.95 (t, 1H), 3.52 (d, 1H), 3.45 (dd, 1H), 3.17 (dd, 2H), 3.08 (d, 7H), 2.63 (s, 6H), 2.35 (t, 1H), 2.05-1.96 (m, 1H), 1.95-1.79 (m, 3H), 1.79-1.65 (m, 2H), 1.60-1.45 (m, 5H), 1.40-1.27 (m, 10H), 1.24 (dd, 3H), 1.05 (d, 4H), 0.92 (t, 4H), 0.73-0.63 (m, 2H), 0.42 (dd, 2H).

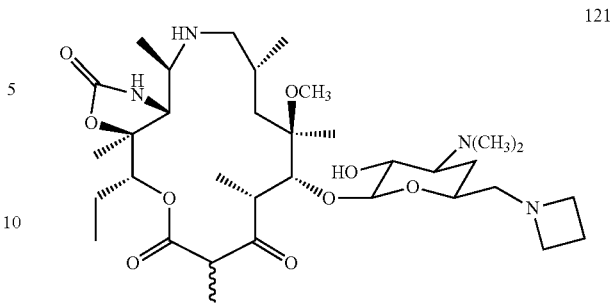

3-Descladinosyl-3-oxo-6-O-methyl-N9a-desmethyl-11,12-dideoxy-12,11-(oxycarbonylimino)-6'-(1-azetininyl) Azithromycin (121)

Prepared according to the methods of 106, substituting azetidine gave 121 as a bis-formate salt (9.6 mg). MS (ESI+) m/z: 223.8 [M+3H]$^{3+}$, 335.2 [M+2H]$^{2+}$, 669.4 [M+H]$^{+}$; $^{1}$H NMR (400 MHz, Methanol-d$_4$) δ 8.52 (s, 3H), 5.08 (d, 1H), 4.51 (s, 1H), 4.43 (d, 1H), 4.07 (d, 3H), 3.87 (s, 1H), 3.53 (s, 1H), 3.50-3.40 (m, 1H), 3.15 (d, 1H), 3.07 (s, 4H), 2.71 (s, 5H), 2.49-2.34 (m, 3H), 1.98 (d, 1H), 1.93-1.85 (m, 2H), 1.80 (d, 1H), 1.62 (d, 1H), 1.38-1.24 (m, 13H), 1.06 (d, 3H), 0.92 (t, 3H).

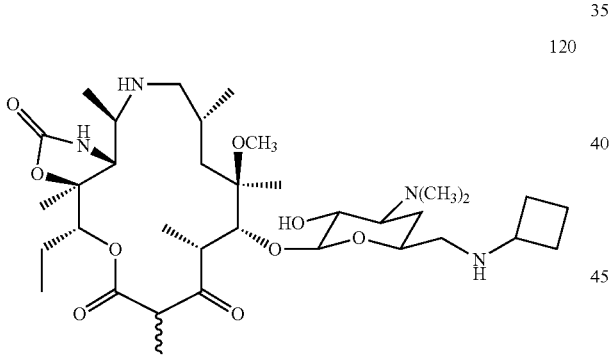

3-Descladinosyl-3-oxo-6-O-methyl-N9a-desmethyl-11,12-dideoxy-12,11-(oxycarbonylimino)-6'-cyclobutylamino Azithromycin (120)

Prepared according to the methods of 106, substituting cyclobutylamine gave 120 as a bis-formate salt (11.20 mg). MS (ESI+) m/z: 228.5 [M+3H]$^{3+}$, 342.2 [M+2H]$^{2+}$, 683.4 [M+H]$^{+}$; $^{1}$H NMR (400 MHz, Chloroform-d) δ 8.55 (s, 2H), 5.05 (d, 1H), 4.57 (d, 1H), 4.39 (d, 1H), 3.68 (s, 1H), 3.50 (d, 1H), 3.37 (d, 1H), 3.14-2.98 (m, 3H), 2.85 (s, 1H), 2.79 (s, 1H), 2.48 (s, 3H), 2.30 (s, 1H), 2.02 (t, 1H), 1.89 (d, 1H), 1.85 (s, 1H), 1.74 (dt, 4H), 1.62 (d, 1H), 1.45 (s, 3H), 1.35 (dd, 7H), 1.21 (d, 1H), 1.11 (dd, 3H), 1.04-0.89 (m, 5H).

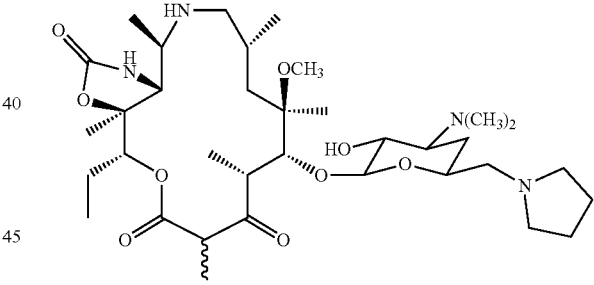

3-Descladinosyl-3-oxo-6-O-methyl-N9a-desmethyl-11,12-dideoxy-12,11-(oxycarbonylimino)-6'-(1-pyrrolodinyl) Azithromycin (122)

Prepared according to the methods of 106, substituting pyrrolidine gave 122 as a tri-formate salt (7.9 mg). MS (ESI+) m/z: 228.5 [M+3H]$^{3+}$, 342.2 [M+2H]$^{2+}$, 683.4 [M+H]$^{+}$, $^{1}$H NMR (400 MHz, Methanol-d$_4$) δ 8.48 (s, 3H), 5.08 (dd, 1H), 4.57-4.43 (m, 2H), 4.07 (d 1H), 3.66-3.34 (m, 9H), 3.26-3.17 (m, 1H), 3.15-2.95 (m, 1H), 3.07 (s, 3H), 2.77 (s, 6H), 2.49 (t, 1H), 2.08 (s, 5H), 1.91 (d, 1H), 1.89-1.78 (m, 2H), 1.77-1.64 (m, 2H), 1.57 (d, 1H), 1.38-1.28 (m, 11H), 1.06 (d, 3H), 0.91 (t, 3H).

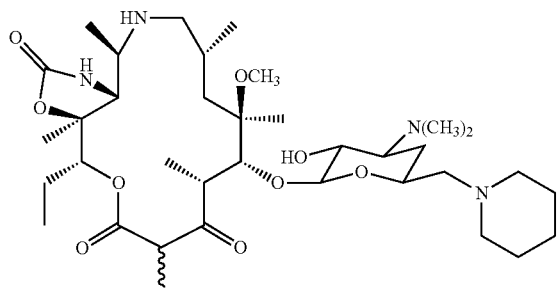

3-Desdadinosyl-3-oxo-6-O-methyl-N9a-desmethyl-11,12-dideoxy-12,11-(oxycarbonylimino)-6'-(1-piperidinyl) Azithromycin (123)

Prepared according to the methods of 106, substituting piperidine gave 123 as a bis-formate salt (6.8 mg). MS (ESI+) m/z: 233.1 [M+3H]$^{3+}$, 349.2 [M+2H]$^{2+}$, 697.4 [M+H]$^{+}$; $^1$H NMR (400 MHz, Chloroform-d) δ 8.54 (s, 2H), 5.10-5.02 (m, 1H), 4.54 (d, 1H), 4.40 (dd, 1H), 3.92 (d, 1H), 3.38 (dd, 2H), 3.31 (p, 10H), 3.07 (d, 1H), 3.01 (s, 3H), 2.99-2.89 (m, 2H), 2.83 (d, 3H), 2.54 (d, 6H), 2.05 (t, 1H), 1.88 (dd, 2H), 1.71 (s, 3H), 1.69-1.61 (m, 3H), 1.48-1.41 (m, 1H), 1.33 (d, 7H), 1.29 (s, 3H), 1.25-1.16 (m, 1H), 1.10 (d, 3H), 1.01 (d, 3H), 0.94 (dt, 4H).

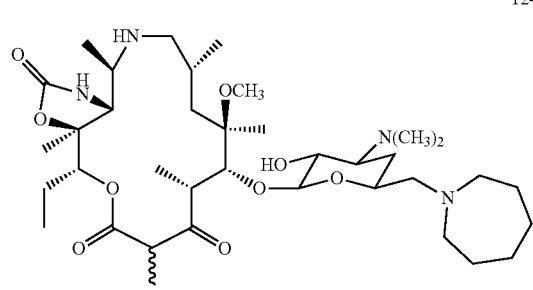

3-Desdadinosyl-3-oxo-6-O-methyl-N9a-desmethyl-11,12-dideoxy-12,11-(oxycarbonylimino)-6'-(1-azepanyl) Azithromycin (124)

Prepared according to the methods of 106, substituting azepane gave 124 as a bis-formate salt (15.83 mg). MS (ESI+) m/z: 237.8 [M+3H]$^{3+}$, 356.3 [M+2H]$^{2+}$, 711.5 [M+H]$^{+}$; $^1$H NMR (400 MHz, Methanol-d$_4$) δ 8.46-8.41 (m, 2H), 4.97 (dd, 1H), 4.85 (dd, 1H), 4.44-4.35 (m, 1H), 4.31 (dd, 1H), 3.39-3.22 (m, 6H), 3.21-3.06 (m, 8H), 3.05-2.83 (m, 8H), 2.59 (s, 3H), 2.55-2.51 (m, 1H), 2.49 (s, 5H), 2.41 (dd, 1H), 2.21-2.04 (m, 2H), 1.93 (d, 1H), 1.80 (ddq, 8H), 1.74-1.58 (m, 10H), 1.60-1.54 (m, 3H), 1.54-1.36 (m, 7H), 1.36-1.10 (m, 16H), 1.10-1.01 (m, 3H), 1.01-0.72 (m, 12H).

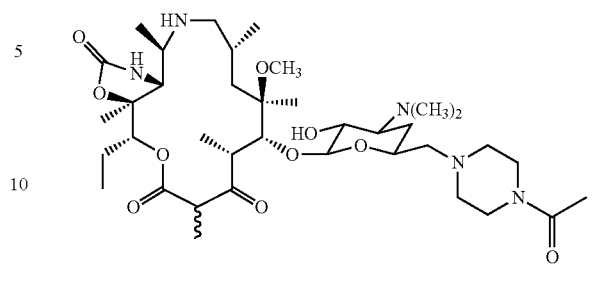

3-Descladinosyl-3-oxo-6-O-methyl-N9a-desmethyl-11,12-dideoxy-12,11-(oxycarbonylimino)-6'-(1-(4-acetyl)-piperazinyl) Azithromycin (125)

Prepared according to the methods of 106, substituting 1-acetylpiperazine gave 125 as a bis-formate salt (5.20 mg). MS (ESI+) m/z: 247.5 [M+3H]$^{3+}$, 370.8 [M+2H]$^{2+}$, 740.5 [M+H]$^{+}$; NMR (400 MHz, Methanol-d$_4$) δ 8.55 (s, 2H), 5.06 (dd, 1H), 4.57 (d, 1H), 4.40 (dd, 1H), 3.90 (d, 1H), 3.65-3.52 (m, 4H), 3.12-3.03 (m, 2H), 3.02 (s, 2H), 2.95-2.84 (m, 2H), 2.78 (t, 2H), 2.72 (dt, 3H), 2.65 (d, 1H), 2.62 (s, 1H), 2.59 (s, 5H), 2.09 (d, 4H), 1.95-1.86 (m, 2H), 1.72-1.61 (m, 2H), 1.44 (dd, 2H), 1.38-1.27 (m, 9H), 1.25-1.17 (m, 1H), 1.12 (dd, 3H), 1.00 (t, 3H), 0.98-0.88 (m, 3H).

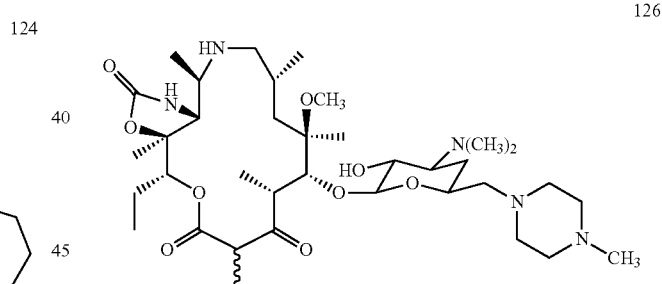

3-Descladinosyl-3-oxo-6-O-methyl-N9a-desmethyl-11,12-dideoxy-12,11-(oxycarbonylimino)-6'-(1-(4-methyl)-piperazinyl) Azithromycin (126)

Prepared according to the methods of 106, substituting 1-methylpiperazine gave 126 as a bis-formate salt (5.7 mg). MS (ESI+) m/z: 238.1 [M+3H]$^{3+}$, 356.7 [M+2H]$^{2+}$, 712.4 [M+H]$^{+}$; $^1$H NMR (400 MHz, Methanol-d$_4$) δ 8.54 (s, 2H), 5.05 (dd, 1H), 4.53 (d, 1H), 4.40 (dd, 1H), 3.85-3.64 (m, 1H), 3.44-3.35 (m, 2H), 3.12-2.83 (m, 6H), 2.71-2.53 (m, 11H), 2.36 (d, 3H), 2.17-1.98 (m, 1H), 1.96-1.86 (m, 2H), 1.79-1.40 (m, 7H), 1.37-1.28 (m, 7H), 1.25-1.08 (m, 4H), 1.04-0.89 (m, 5H).

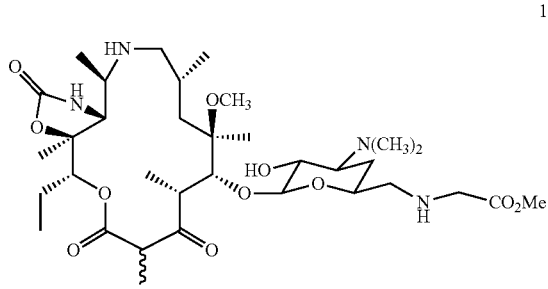

127

3-Descladinosyl-3-oxo-6-O-methyl-N9a-desmethyl-11,12-dideoxy-12,11-(oxycarbonylimino)-6'-(methyl aminomethylcarboxylate) Azithromycin (127)

Prepared according to the methods of 106, substituting glycine methyl ester gave 127 as a tri-formate salt (0.6 mg). MS (ESI+) m/z: 701.4 [M+H]$^+$. $^1$H NMR (400 MHz, Methanol-d$_4$) δ 8.56 (s, 3H), 5.06 (d, 2H), 4.58 (s, 1H), 4.40 (d, 1H), 3.73 (d, 3H), 3.65-3.36 (m, 4H), 3.05 (s, 3H), 2.95-2.73 (m, 5H), 2.48 (s, 5H), 1.35 (d, 7H), 1.08 (d, 3H), 1.01 (d, 3H), 0.93 (t, 3H).

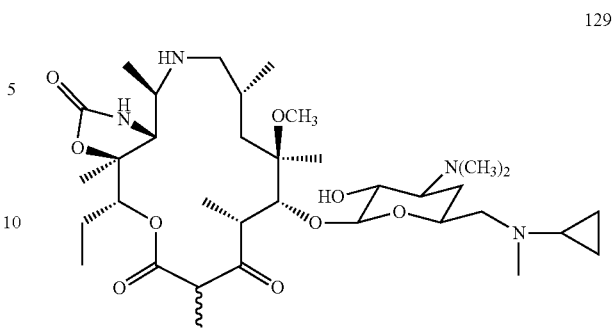

129

3-Descladinosyl-3-oxo-6-O-methyl-N9a-desmethyl-11,12-dideoxy-12,11-(oxycarbonylimino)-6'-(N-methylcyclopropylamino) Azithromycin (129)

Prepared according to the methods of 106, substituting N-methylcyclopropylamine gave 129 as a tri-formate salt (10.5 mg). MS (ESI+) m/z: 228.6 [M+3H]$^{3+}$, 342.3 [M+2H]$^{2+}$, 683.4 [M+H]$^+$. $^1$H NMR (400 MHz, Methanol-d$_4$) δ 8.45 (s, 3H), 5.08 (d, 1H), 4.54 (d, 1H), 4.51 (d, 1H), 3.96 (s, 1H), 3.59-3.37 (m, 4H), 3.35 (s, 1H), 3.15 (dd, 2H), 3.04 (d, 4H), 2.84 (d, 2H), 2.81 (d, 6H), 2.55 (s, 3H), 2.37 (t, 1H), 2.10-1.61 (m, 8H), 1.44-1.29 (m, 10H), 1.29-1.21 (m, 4H), 1.05 (d, 3H), 0.96-0.90 (m, 3H), 0.55 (d, 2H), 0.44 (d, 3H).

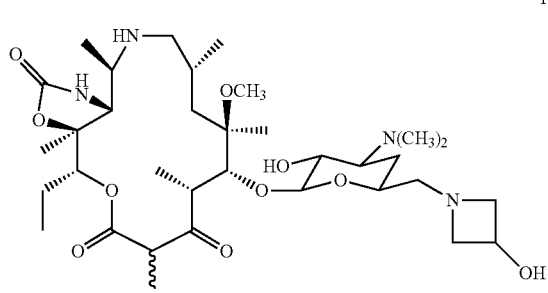

128

3-Descladinosyl-3-oxo-6-O-methyl-N9a-desmethyl-11,12-dideoxy-12,11-(oxycarbonylimino)-6'-(3-hydroxy-1-azetidinyl) Azithromycin (128)

Prepared according to the methods of 106, substituting 3-hydroxyazetidine gave 128 as a tri-formate salt (14.1 mg). MS (ESI+) m/z: 229.9 [M+3H]$^{3+}$, 343.3 [M+2H]$^{2+}$, 685.4 [M+H]$^+$. $^1$H NMR (400 MHz, Methanol-d$_4$) δ 8.42 (s, 3H), 5.09 (d, 1H), 4.53 (d, 2H), 4.46 (d, 1H), 4.27-4.06 (m, 2H), 3.84 (s, 1H), 3.66-3.33 (m, 6H), 3.24-2.97 (m, 7H), 2.77 (s, 6H), 2.44 (t, 1H), 2.10-1.59 (m, 7H), 1.36 (d, 6H), 1.33 (d, 3H), 1.29 (d, 3H), 1.07 (d, 3H), 0.93 (t, 3H).

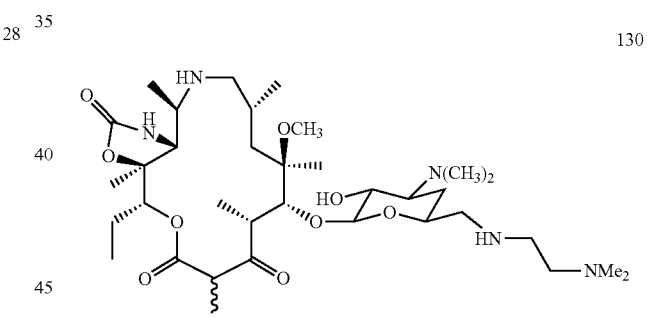

130

3-Descladinosyl-3-oxo-6-O-methyl-N9a-desmethyl-11,12-dideoxy-12,11-(oxycarbonylimino)-6'-[(2-dimethylamino)ethylamino]Azithromycin (130)

Prepared according to the methods of 106, substituting 2-dimethylaminoethylamine gave 130 as a tri-formate salt (9.4 mg). MS (ESI+) m/z: 234.3 [M+3H]$^{3+}$, 350.8 [M+2H]$^{2+}$, 700.5 [M+H]$^+$. $^1$H NMR (400 MHz, Methanol-d$_4$) δ 8.47 (s, 3H), 5.07 (d, 1H), 4.50 (d, 2H), 3.87 (s, 1H), 3.54-3.42 (m, 2H), 3.35 (s, 1H), 3.19-2.92 (m, 11H), 2.78 (s, 6H), 2.73 (s, 6H), 2.37 (s, 1H), 2.05 (d, 1H), 1.89 (s, 2H), 1.80-1.45 (m, 8H), 1.43-1.28 (m, 10H), 1.25 (d, 4H), 1.05 (d, 3H), 0.93 (t, 3H).

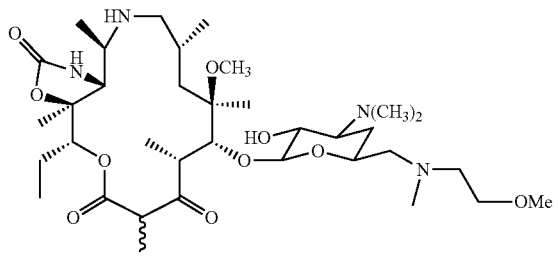

3-Descladinosyl-3-oxo-6-O-methyl-N9a-desmethyl-11,12-dideoxy-12,11-(oxycarbonylimino)-6'-[N-(methyl)-2-methoxyethylamino]Azithromycin (131)

Prepared according to the methods of 106, substituting N-methyl-2-methoxyethylamine gave 131 as a tri-formate salt (7.7 mg). MS (ESI+) m/z: 234.6 [M+3H]$^{3+}$, 351.3 [M+2H]$^{2+}$, 701.4 [M+H]$^+$. $^1$H NMR (400 MHz, Methanol-d$_4$) δ 8.47 (s, 3H), 5.08 (d, 1H), 4.52 (d, 1H), 4.48 (d, 1H), 4.00 (s, 1H), 3.61 (t, 2H), 3.58-3.39 (m, 3H), 3.36 (d, 4H), 3.17-2.99 (m, 7H), 2.96 (d, 2H), 2.75 (s, 6H), 2.65 (s, 2H), 2.34 (t, 1H), 2.03 (s, 1H), 1.88 (s, 3H), 1.79-1.43 (m, 8H), 1.39-1.27 (m, 10H), 1.25 (d, 3H), 1.05 (d, 3H), 0.93 (t, 3H).

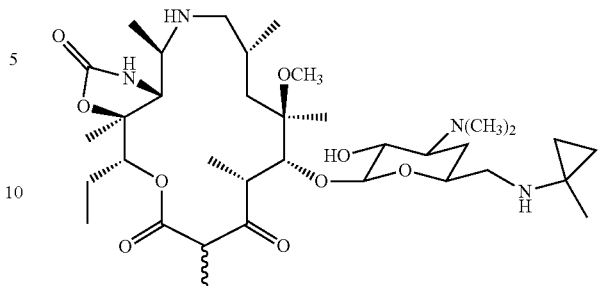

3-Descladinosyl-3-oxo-6-O-methyl-N9a-desmethyl-11,12-dideoxy-12,11-(oxycarbonylimino)-6'-(1-methyl-1-cyclopropylamino) Azithromycin (133)

Prepared according to the methods of 106, substituting 1-methyl-1-aminocyclopropane gave 133 as a tri-formate salt (2.0 mg). MS (ESI+) m/z: 229.5 [M+3H]$^{3+}$, 343.3 [M+2H]$^{2+}$, 684.4 [M+H]$^+$. $^1$H NMR (400 MHz, Methanol-d$_4$) δ 8.40 (s, 3H), 5.09 (dd, 1H), 4.57-4.43 (m, 2H), 3.93 (d, 1H), 3.76-3.60 (m, 5H), 3.57 (s, 1H), 3.53-3.37 (m, 3H), 3.27-3.16 (m, 1H), 3.15-2.94 (m, 5H), 2.83 (s, 6H), 2.79-2.53 (m, 7H), 2.49 (t, 1H), 2.07 (d, 1H), 1.90 (dd, 2H), 1.84-1.57 (m, 4H), 1.34 (ddd, 12H), 1.07 (d, 3H), 0.96-0.89 (m, 3H).

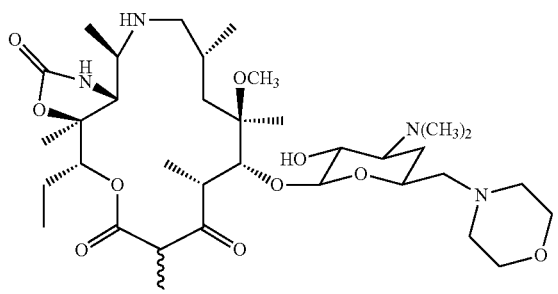

3-Descladinosyl-3-oxo-6-O-methyl-N9a-desmethyl-11,12-dideoxy-12,11-(oxycarbonylimino)-6'-(1-morpholino) Azithromycin (132)

Prepared according to the methods of 106, substituting morpholine gave 132 as a tri-formate salt (5.4 mg). MS (ESI+) m/z: 233.9 [M+3H]$^{3+}$, 350.3 [M+2H]$^{2+}$, 699.4 [M+H]$^+$. $^1$H NMR (400 MHz, Methanol-d$_4$) δ 8.40 (s, 3H), 5.09 (dd, 1H), 4.57-4.43 (m, 2H), 3.93 (d, 1H), 3.76-3.60 (m, 5H), 3.57 (s, 1H), 3.53-3.37 (m, 3H), 3.27-3.16 (m, 1H), 3.15-2.94 (m, 5H), 2.83 (s, 6H), 2.79-2.53 (m, 7H), 2.49 (t, 1H), 2.07 (d, 1H), 1.90 (dd, 2H), 1.84-1.57 (m, 4H), 1.34 (ddd, 12H), 1.07 (d, 3H), 0.96-0.89 (m, 3H).

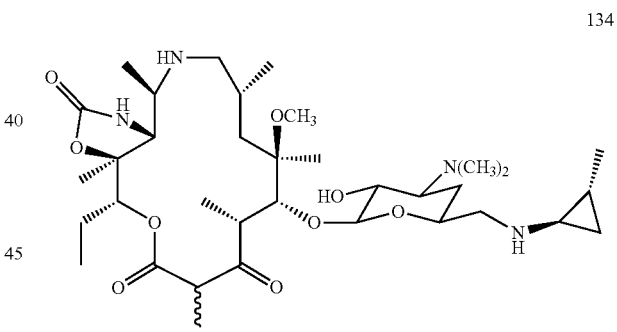

3-Descladinosyl-3-oxo-6-O-methyl-N9a-desmethyl-11,12-dideoxy-12,11-(oxycarbonylimino)-6'-((1"R,2"R)-2"-methylcyclopropyl)amino Azithromycin (134)

Prepared according to the methods of 106, substituting (1R,2R)-2-methylcyclopropan-1-amine gave 134 as a bis-formate salt (2.3 mg). MS (ESI+) m/z: 228.5 [M+3H]$^{3+}$, 342.3 [M+2H]$^{2+}$, 683.5 [M+H]$^+$; $^1$H NMR (400 MHz, Methanol-d$_4$) δ 8.55 (s, 2H), 5.05 (d, 1H), 4.66-4.49 (m, 1H), 4.45-4.32 (m, 1H), 3.92 (s, 1H), 3.72 (s, 1H), 3.16-2.93 (m, 4H), 2.80 (d, 5H), 2.44 (s, 6H), 2.16-1.76 (m, 5H), 1.76-1.46 (m, 6H), 1.46-0.87 (m, 24H), 0.79 (s, 1H), 0.68-0.47 (m, 1H), 0.31 (q, 1H).

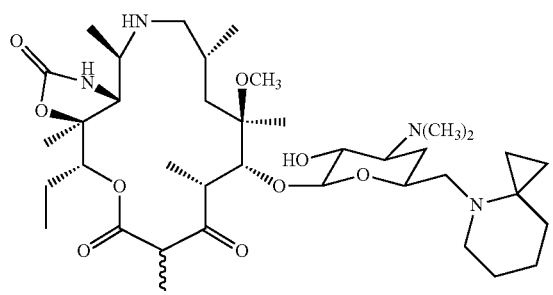

3-Descladinosyl-3-oxo-6-O-methyl-N9a-desmethyl-11,12-dideoxy-12,11-(oxycarbonylimino)-6'-(4"-azaspiro[2".5"]octanyl)amino Azithromycin (135)

Prepared according to the methods of 106, substituting 4-azaspiro[2.5]octane gave 135 as a mono-formate salt (11.22 mg). MS (ESI+) m/z: 241.8 [M+3H]$^{3+}$, 362.2 [M+2H]$^{2+}$, 723.4 [M+H]$^+$; $^1$H NMR (400 MHz, Methanol-d$_4$) δ 8.45 (s, 1H), 4.94 (dd, 1H), 4.42 (d, 1H), 4.24 (d, 2H), 3.48 (t, 1H), 3.26 (dd, 2H), 3.17-2.62 (m, 16H), 2.41 (d, 9H), 1.96-1.68 (m, 5H), 1.68-1.12 (m, 32H), 1.11-0.71 (m, 15H), 0.67-0.39 (m, 3H), 0.39-0.20 (m, 3H).

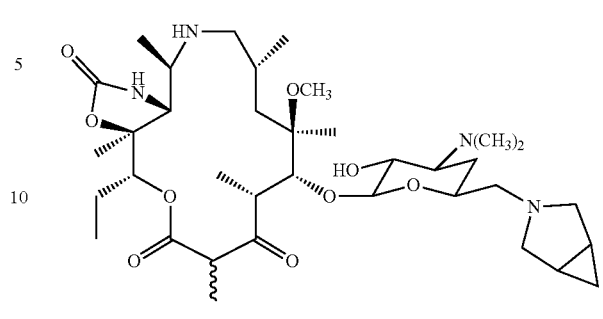

3-Descladinosyl-3-oxo-6-O-methyl-N9a-desmethyl-11,12-dideoxy-12,11-(oxycarbonylimino)-6'-azabicyclo[3.1.0]hexan-3"-ylamino Azithromycin (137)

Prepared according to the methods of 106, substituting 3-azabicyclo[3.1.0]hexane gave 137 as a mono-formate salt (13.37 mg). MS (ESI+) m/z: 232.5 [M+3H]$^{3+}$, 348.2 [M+2H]$^{2+}$, 695.4 [M+H]$^+$; $^1$H NMR (400 MHz, Methanol-d$_4$) δ 8.45 (s, 1H), 4.95 (dd, 1H), 4.49-4.42 (m, 1H), 4.31-4.21 (m, 1H), 3.59 (t, 1H), 3.31-3.05 (m, 17H), 3.05-2.87 (m, 6H), 2.83 (d, 1H), 2.79-2.69 (m, 2H), 2.69-2.62 (m, 1H), 2.56 (d, 2H), 2.50 (dd, 3H), 2.42 (d, 8H), 1.95-1.69 (m, 5H), 1.67-1.43 (m, 5H), 1.41 (s, 3H), 1.39-1.06 (m, 18H), 1.06-0.72 (m, 12H), 0.58 (dq, 1H), 0.37-0.22 (m, 1H). $^1$

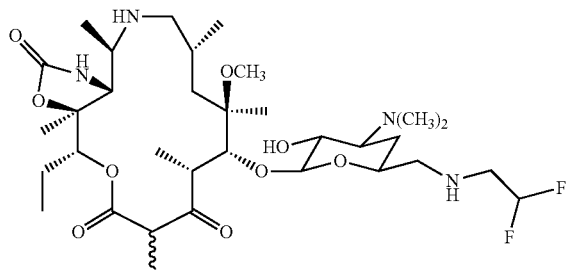

3-Descladinosyl-3-oxo-6-O-methyl-N9a-desmethyl-11,12-dideoxy-12,11-(oxycarbonylimino)-6'-difluoroethylamino Azithromycin (136)

Prepared according to the methods of 106, substituting 2,2-difluoroethylamine gave 136 as a bis-formate salt (5.4 mg). MS (ESI+) m/z: 231.8 [M+3H]$^{3+}$, 347.2 [M+2H]$^{2+}$, 693.4 [M+H]$^+$; $^1$H NMR (400 MHz, Methanol-d$_4$) δ 8.54 (s, 2H), 5.94 (dt, 1H), 5.06 (dd, 1H), 4.54 (d, 1H), 4.43 (d, 1H), 3.73 (dd, 1H), 3.41 (dq, 2H), 3.15-3.02 (m, 4H), 3.00 (d, 4H), 2.92-2.80 (m, 3H), 2.60 (d, 6H), 2.21-2.00 (m, 1H), 1.90 (dtd, 2H), 1.72-1.60 (m, 2H), 1.59-1.39 (m, 5H), 1.38-1.27 (m, 8H), 1.21 (d, 1H), 1.17-1.08 (m, 3H), 1.04-0.88 (m, 6H).

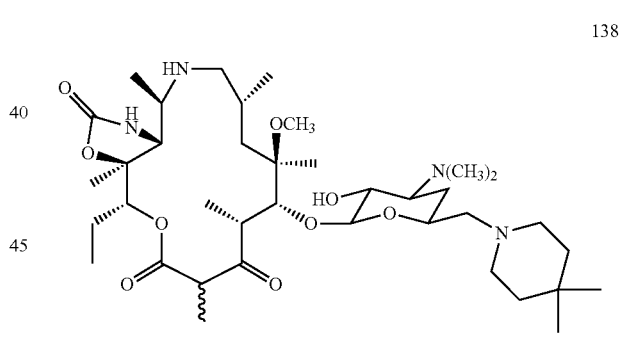

3-Desdadinosyl-3-oxo-6-O-methyl-N9a-desmethyl-11,12-dideoxy-12,11-(oxycarbonylimino)-6'-(4",4"-dimethylpiperidin-1-yl) Azithromycin (138)

Prepared according to the methods of 106, substituting 4,4-dimethylpiperidine gave 138 as a mono-formate salt (14.67 mg). MS (ESI+) m/z: 242.5 [M+3H]$^{3+}$, 363.3 [M+2H]$^{2+}$, 725.5 [M+H]$^+$; $^1$H NMR (400 MHz, Methanol-d$_4$) δ 8.45 (s, 1H), 4.96 (dd, 1H), 4.47-4.23 (m, 3H), 3.85-3.76 (m, 1H), 3.59-3.45 (m, 1H), 3.34-3.21 (m, 5H), 3.20-3.08 (m, 2H), 2.99 (ddd, 1H), 2.96-2.81 (m, 7H), 2.79-2.65 (m, 6H), 2.64-2.32 (m, 12H), 2.11 (dd, 1H), 1.96-1.70 (m, 5H), 1.67-1.45 (m, 6H), 1.45-1.36 (m, 8H), 1.36-1.15 (m, 16H), 1.15-1.07 (m, 2H), 1.07-0.89 (m, 12H), 0.86 (t, 6H), 0.85-0.74 (m, 4H).

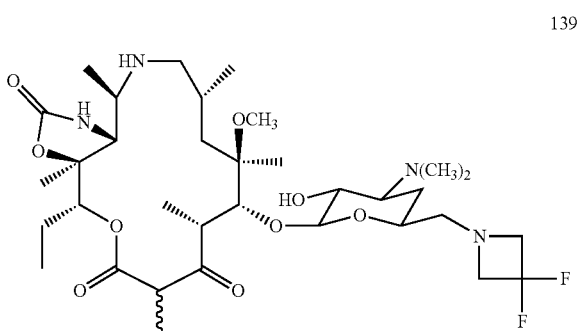

3-Descladinosyl-3-oxo-6-O-methyl-N9a-desmethyl-11,12-dideoxy-12,11-(oxycarbonylimino)-6'-(3",3"-difluoroazetidinyl) Azithromycin (139)

Prepared according to the methods of 106, substituting 3,3-difluoroazetidine gave 139 as a mono-formate salt (9.63 mg). MS (ESI+) m/z: 236.0 [M+3H]$^{3+}$, 353.4 [M+2H]$^{2+}$, 705.3 [M+H]$^{+}$; $^{1}$H NMR (400 MHz, Methanol-d$_4$) δ 8.45 (s, 1H), 4.96 (dd, 1H), 4.45 (d, 1H), 4.21 (d, 1H), 3.87-3.75 (m, 1H), 3.68 (dd, 3H), 3.64-3.51 (m, 3H), 3.30-3.23 (m, 2H), 3.05-2.94 (m, 2H), 2.92 (d, 4H), 2.81-2.57 (m, 6H), 2.40 (d, 8H), 1.91 (t, 1H), 1.85-1.68 (m, 3H), 1.67-1.49 (m, 4H), 1.44 (d, 5H), 1.30 (dd, 2H), 1.28-1.19 (m, 11H), 1.19-1.00 (m, 4H), 0.98 (d, 3H), 0.93-0.78 (m, 9H).

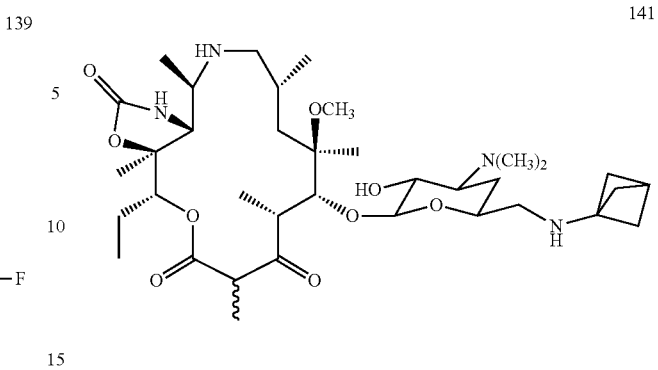

3-Descladinosyl-3-oxo-6-O-methyl-N9a-desmethyl-11,12-dideoxy-12,11-(oxycarbonylimino)-6'-(bicyclo[1.1.1]pentanylamino) Azithromycin (141)

Prepared according to the methods of 106, substituting bicyclo[1.1.1]pentan-1-amine gave 141 as a bis-formate salt (14.06 mg). MS (ESI+) m/z: 232.5 [M+3H]$^{3+}$, 348.2 [M+2H]$^{2+}$, 695.4 [M+H]$^{+}$; $^{1}$H NMR (400 MHz, Methanol-d$_4$) δ 8.44 (s, 2H), 4.96 (dd, 1H), 4.45-4.31 (m, 2H), 4.01 (q, 1H), 3.63 (dd, 1H), 3.56-3.49 (m, 1H), 3.34 (dt, 3H), 3.13 (t, 4H), 3.06-2.83 (m, 9H), 2.78 (dd, 1H), 2.68 (dd, 4H), 2.60 (d, 9H), 2.42 (d, 1H), 2.34 (d, 2H), 2.13 (t, 1H), 1.92 (s, 1H), 1.89 (s, 1H), 1.76 (tt, 12H), 1.59 (ddd, 3H), 1.47 (s, 2H), 1.41 (d, 6H), 1.32-1.16 (m, 12H), 1.16-0.99 (m, 8H), 0.96-0.78 (m, 10H).

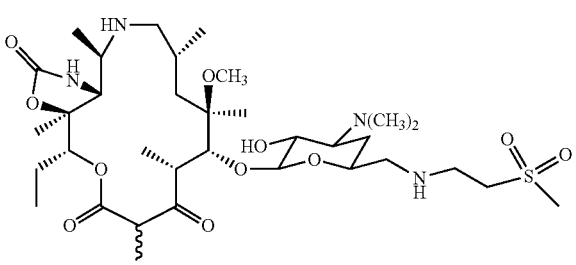

3-Descladinosyl-3-oxo-6-O-methyl-N9a-desmethyl-11,12-dideoxy-12,11-(oxycarbonylimino)-6'-2"-(methylsulfonyl)ethan-1"-amino Azithromycin (140)

Prepared according to the methods of 106, substituting 2-(methylsulfonyl)ethan-1-amine gave 140 as a mono-formate salt (10.67 mg). MS (ESI+) m/z: 245.8 [M+3H]$^{3+}$, 368.2 [M+2H]$^{2+}$, 735.4 [M+H]$^{+}$; $^{1}$H NMR (400 MHz, Methanol-d$_4$) δ 8.45 (s, 1H), 4.96 (dd, 1H), 4.45 (d, 1H), 4.34 (dd, 1H), 3.85 (d, 1H), 3.79-3.69 (m, 1H), 3.66 (s, 1H), 3.35-3.21 (m, 13H), 3.18-3.06 (m, 2H), 3.06-3.00 (m, 3H), 2.94 (q, 9H), 2.87-2.61 (m, 6H), 2.53 (d, 8H), 1.94 (dt, 2H), 1.84-1.73 (m, 3H), 1.64 (s, 1H), 1.63-1.50 (m, 3H), 1.43 (d, 7H), 1.31-1.05 (m, 17H), 1.01 (t, 4H), 0.94-0.76 (m, 9H).

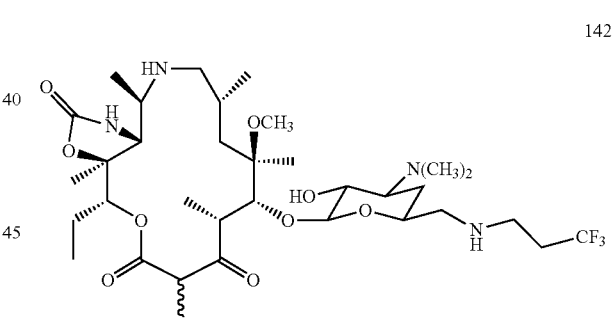

3-Descladinosyl-3-oxo-6-O-methyl-N9a-desmethyl-11,12-dideoxy-12,11-(oxycarbonylimino)-6'-trifluoropropylamino Azithromycin (142)

Prepared according to the methods of 106, substituting 3,3,3-trifluoropropan-1-amine gave 142 as a mono-formate salt (12.78 mg). MS (ESI+) m/z: 242.5 [M+3H]$^{3+}$, 363.3 [M+2H]$^{2+}$, 725.3 [M+H]$^{+}$; $^{1}$H NMR (400 MHz, Methanol-d$_4$) δ 8.44 (s, 1H), 4.95 (dd, 1H), 4.44 (d, 1H), 4.31 (dd, 1H), 3.62 (dd, 1H), 3.16 (q, 1H), 3.04-2.93 (m, 2H), 2.93-2.80 (m, 7H), 2.80-2.71 (m, 4H), 2.69 (d, 3H), 2.41 (s, 2H), 2.40 (s, 5H), 2.33 (ddt, 3H), 2.33-2.20 (m, 2H), 1.89 (q, 2H), 1.79 (dddd, 3H), 1.60 (ddd, 2H), 1.57-1.48 (m, 2H), 1.48-1.25 (m, 8H), 1.25-1.21 (m, 7H), 1.18 (s, 4H), 1.11 (q, 2H), 1.00 (dd, 4H), 0.85 (dt, 9H).

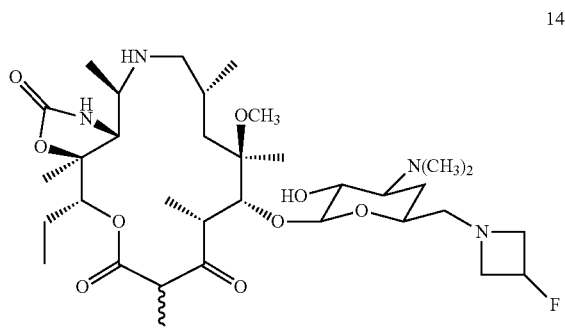 [SMILES: CC[C@H]1OC(=O)C(C)C(=O)[C@H](C)[C@@H](OC2OC(CN(C)C)CC(N(C)C)C2O)[C@](C)(OC)C[C@@H](C)CN[C@H](C)[C@H]2NC(=O)O[C@@]21C]

3-Descladinosyl-3-oxo-6-O-methyl-N9a-desmethyl-11,12-dideoxy-12,11-(oxycarbonylimino)-6'-(3"-fluoroazetidin-1"-yl) Azithromycin (143)

Prepared according to the methods of 106, substituting 3-fluoroazetidine gave 143 as a bis-formate salt (6.2 mg). MS (ESI+) m/z: 233.1 [M+3H]$^{3+}$, 349.2 [M+2H]$^{2+}$, 687.4 [M+H]$^+$; $^1$H NMR (400 MHz, Methanol-d$_4$) δ 8.55 (s, 2H), 5.06 (dd, 1H), 4.70-4.51 (m, 1H), 4.37 (dd, 1H), 4.01-3.52 (m, 2H), 3.52-3.38 (m, 1H), 3.18-2.66 (m, 5H), 2.55 (d, 3H), 2.16-1.60 (m, 4H), 1.60-1.26 (m, 7H), 1.26-0.79 (m, 6H).

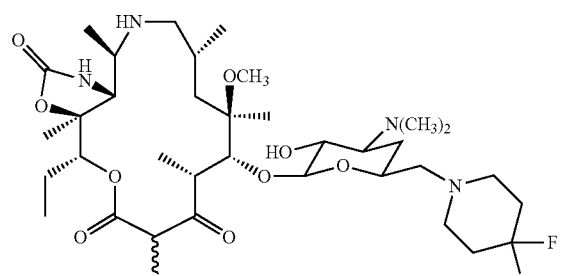

3-Descladinosyl-3-oxo-6-O-methyl-N9a-desmethyl-11,12-dideoxy-12,11-(oxycarbonylimino)-6'-(4",4"-difluoropiperidin-1"-yl) Azithromycin (144)

Prepared according to the methods of 106, substituting 4,4-difluoropiperidine gave 144 as a mono-formate salt (8.90 mg). MS (ESI+) m/z: 245.1 [M+3H]$^{3+}$, 367.2 [M+2H]$^{2+}$, 733.4 [M+H]$^+$; $^1$H NMR (400 MHz, Methanol-d$_4$) δ 8.42 (s, 1H), 4.96 (dd, 1H), 4.47-4.40 (m, 1H), 4.33 (dd, 1H), 3.86-3.78 (m, 1H), 3.76 (d, 1H), 3.67-3.59 (m, 1H), 3.38-3.23 (m, 3H), 3.20-3.05 (m, 4H), 3.04-2.89 (m, 5H), 2.89-2.73 (m, 5H), 2.73-2.50 (m, 15H), 2.45 (d, 1H), 2.03-1.73 (m, 10H), 1.67-1.46 (m, 6H), 1.42 (s, 4H), 1.35 (d, 1H), 1.34-1.12 (m, 14H), 1.12-0.98 (m, 5H), 0.96-0.78 (m, 8H).

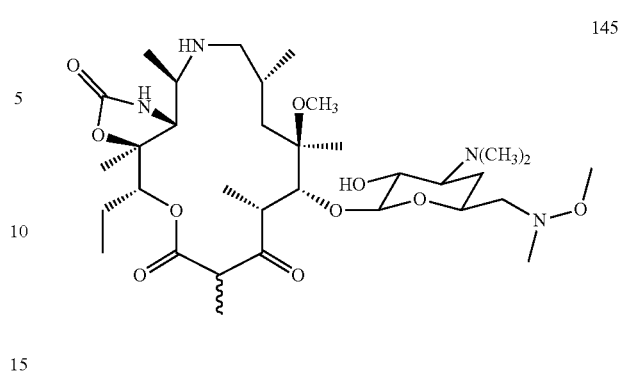

3-Descladinosyl-3-oxo-6-O-methyl-N9a-desmethyl-11,12-dideoxy-12,11-(oxycarbonylimino)-6'-(methoxy(methyl)amino Azithromycin (145)

Prepared according to the methods of 106, substituting N,O-dimethylhydroxylamine gave 145 as a bis-formate salt (1.27 mg). MS (ESI+) m/z: 337.2 [M+2H]$^{2+}$, 673.4 [M+H]$^+$; $^1$H NMR (400 MHz, Methanol-d$_4$) δ 8.44 (s, 2H), 4.94 (dd, 1H), 4.45 (d, 1H), 4.35 (dd, 1H), 4.21 (q, 1H), 3.84 (s, 1H), 3.74 (d, 1H), 3.62-3.53 (m, 1H), 3.48 (s, 2H), 3.43 (s, 1H), 3.37-3.22 (m, 4H), 3.16 (q, 2H), 3.09 (s, 1H), 2.98 (dt, 2H), 2.90 (d, 4H), 2.81-2.61 (m, 4H), 2.58 (d, 5H), 2.52 (d, 6H), 2.04-1.88 (m, 3H), 1.85-1.74 (m, 2H), 1.65 (s, 1H), 1.58 (ddd, 2H), 1.53-1.41 (m, 5H), 1.37 (d, 2H), 1.33-1.23 (m, 7H), 1.20 (d, 8H), 1.10 (q, 2H), 1.02 (t, 4H), 0.93-0.76 (m, 8H).

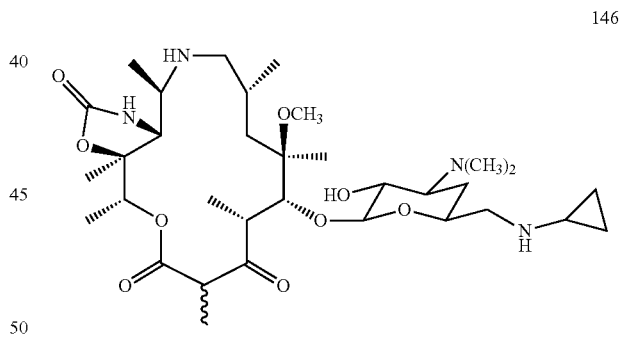

3-Descladinosyl-3-oxo-6-O-methyl-N9a-desmethyl-11,12-dideoxy-12,11-(oxycarbonylimino)-6'-cyclopropylamino-13-methyl Azithromycin (146)

Prepared according to the methods of 106, substituting S1-5-2 and cyclopropylamine, gave 146 as a bis-formate salt. MS (ESI+) m/z: 655.1 [M+H]$^+$; $^1$H NMR (400 MHz, Methanol-d$_4$) δ 5.07 (q, 1H), 4.60 (d, 1H), 4.42 (d, 1H), 4.16 (d, 2H), 3.82 (s, 1H), 3.73 (s, 1H), 3.58 (s, 2H), 3.53-3.39 (m, 2H), 3.25 (s, 3H), 3.07 (s, 4H), 2.93 (s, 4H), 2.83 (s, 3H), 2.23 (d, 1H), 2.13 (s, 1H), 1.77 (s, 3H), 1.56 (s, 3H), 1.44-1.30 (m, 14H), 1.11 (d, 3H), 1.02 (d, 4H).

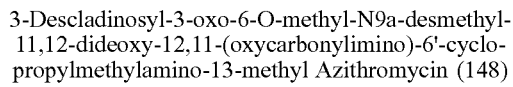

3-Descladinosyl-3-oxo-6-O-methyl-N9a-desmethyl-11,12-dideoxy-12,11-(oxycarbonylimino)-6'-cyclopropylmethylamino-13-methyl Azithromycin (148)

Prepared according to the methods of 106, substituting S1-5-2 and cyclopropylmethylamine, gave 148 as a bis-formate salt. MS (ESI+) m/z: 669.1 [M+H]$^+$; $^1$H NMR (400 MHz, Methanol-d$_4$) δ 8.47 (s, 2H), 5.15 (q, 1H), 4.53 (d, 1H), 4.43 (d, 1H), 4.19-3.95 (m, 2H), 3.63 (d, 1H), 3.58-3.47 (m, 2H), 3.46 (dd, 1H), 3.45-3.34 (m, 1H), 3.32-3.24 (m, 1H), 3.23-3.05 (m, 6H), 3.01 (s, 1H), 2.82 (d, 6H), 2.58 (t, 1H), 2.15 (d, 1H), 1.96 (s, 1H), 1.82-1.61 (m, 3H), 1.58 (d, 3H), 1.45-1.33 (m, 6H), 1.37-1.23 (m, 8H), 1.25-1.10 (m, 3H), 1.06 (dd, 3H), 0.73 (dq, 2H), 0.55-0.38 (m, 2H).

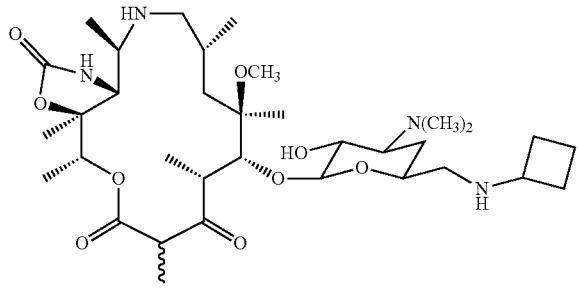

3-Descladinosyl-3-oxo-6-O-methyl-N9a-desmethyl-11,12-dideoxy-12,11-(oxycarbonylimino)-6'-cyclobutylamino-13-methyl Azithromycin (147)

Prepared according to the methods of 106, substituting S1-5-2 and cyclobutylamine, gave 147 as a bis-formate salt. MS (ESI+) m/z: 669.1 [M+H]$^+$; $^1$H NMR (400 MHz, Methanol-d$_4$) δ 5.09 (q, 1H), 4.61 (d, 1H), 4.43 (d, 1H), 4.18 (q, 1H), 4.05 (q, 2H), 3.83 (q, 1H), 3.75 (d, 1H), 3.59 (t, 2H), 3.32-3.23 (m, 2H), 3.27-3.15 (m, 1H), 3.10 (s, 3H), 2.89 (d, 7H), 2.32 (ddd, 4H), 2.15 (s, 1H), 1.98 (ddd, 3H), 1.81-1.70 (m, 3H), 1.58 (s, 3H), 1.59-1.32 (m, 16H), 1.12 (d, 3H).

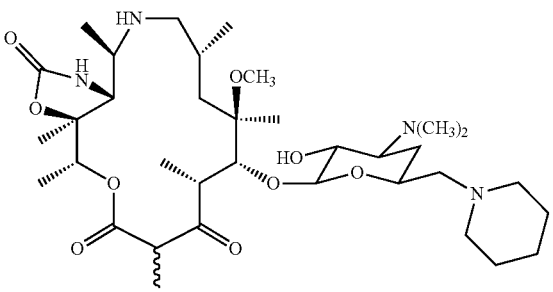

3-Descladinosyl-3-oxo-6-O-methyl-N9a-desmethyl-11,12-dideoxy-12,11-(oxycarbonylimino)-6'-piperidinyl-13-methyl Azithromycin (149)

Prepared according to the methods of 106, substituting S1-5-2 and piperidine, gave 149 as a bis-formate salt. MS (ESI+) m/z: 683.1 [M+H]$^+$; $^1$H NMR (400 MHz, Methanol-d$_4$) δ 8.48 (s, 2H), 5.13 (q, 1H), 4.51 (d, 1H), 4.43 (d, 1H), 4.22-4.10 (m, 2H), 3.61 (d, 1H), 3.59-3.40 (m, 2H), 3.39 (s, 2H), 3.36-3.23 (m, 2H), 3.24-3.16 (m, 1H), 3.20-3.07 (m, 1H), 3.03 (s, 3H), 2.81 (s, 6H), 2.55 (t, 1H), 2.18-2.01 (m, 2H), 1.96-1.81 (m, 2H), 1.87 (s, 4H), 1.80-1.63 (m, 4H), 1.59 (s, 3H), 1.45-1.25 (m, 14H), 1.30-1.18 (m, 2H), 1.05 (dd, 4H).

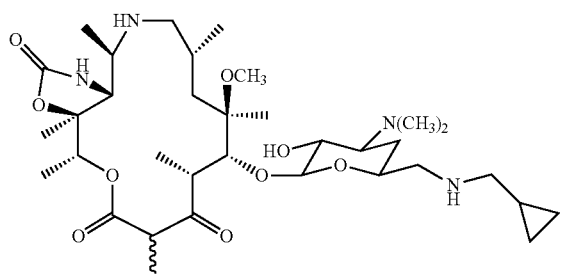

TABLE 14

Exemplary Azaketolides.

| Compound No. | Structure |
|---|---|
| 106 | 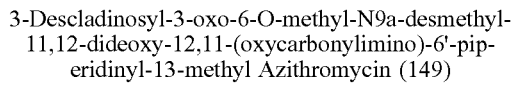 |

TABLE 14-continued

Exemplary Azaketolides.

| Compound No. | Structure |
|---|---|
| 107 | *(structure image)* |
| 108 | *(structure image)* |
| 109 | *(structure image)* |
| 110 | *(structure image)* |
| 111 | *(structure image)* |

TABLE 14-continued

Exemplary Azaketolides.

| Compound No. | Structure |
|---|---|
| 112 | 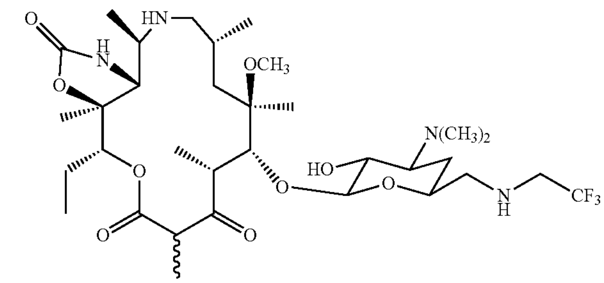 [SMILES: CC[C@H]1OC(=O)C(C)C(=O)[C@H](C)[C@@H](OC2OC(CNCC(F)(F)F)CC(N(C)C)C2O)[C@](C)(OC)C[C@@H](C)CN[C@H](C)[C@H]2NC(=O)O[C@@]21C] |
| 113 | 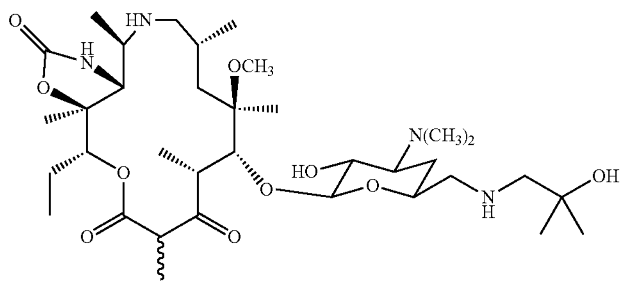 [SMILES: CC[C@H]1OC(=O)C(C)C(=O)[C@H](C)[C@@H](OC2OC(CNCC(C)(C)O)CC(N(C)C)C2O)[C@](C)(OC)C[C@@H](C)CN[C@H](C)[C@H]2NC(=O)O[C@@]21C] |
| 114 | 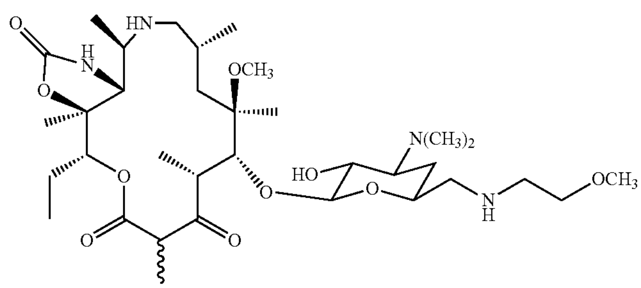 [SMILES: CC[C@H]1OC(=O)C(C)C(=O)[C@H](C)[C@@H](OC2OC(CNCCOC)CC(N(C)C)C2O)[C@](C)(OC)C[C@@H](C)CN[C@H](C)[C@H]2NC(=O)O[C@@]21C] |
| 115 | 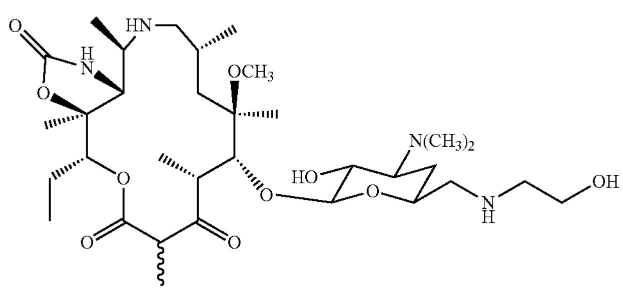 [SMILES: CC[C@H]1OC(=O)C(C)C(=O)[C@H](C)[C@@H](OC2OC(CNCCO)CC(N(C)C)C2O)[C@](C)(OC)C[C@@H](C)CN[C@H](C)[C@H]2NC(=O)O[C@@]21C] |
| 116 | 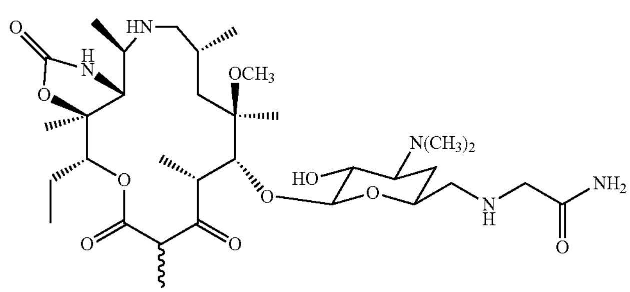 [SMILES: CC[C@H]1OC(=O)C(C)C(=O)[C@H](C)[C@@H](OC2OC(CNCC(N)=O)CC(N(C)C)C2O)[C@](C)(OC)C[C@@H](C)CN[C@H](C)[C@H]2NC(=O)O[C@@]21C] |

TABLE 14-continued

Exemplary Azaketolides.

| Compound No. | Structure |
|---|---|
| 117 | 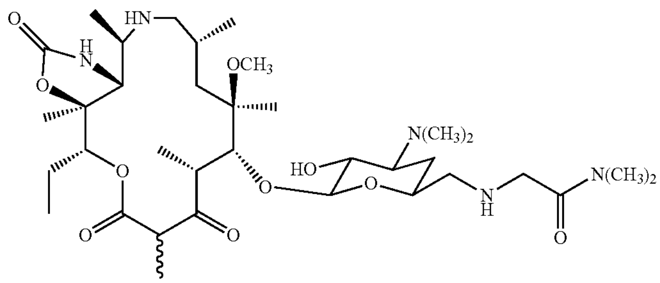 [SMILES: CC[C@H]1OC(=O)C(C)C(=O)[C@H](C)[C@@H](OC2OC(CNCC(=O)N(C)C)CC(N(C)C)C2O)[C@](C)(OC)C[C@@H](C)CN[C@H](C)[C@H]2NC(=O)O[C@@]21C] |
| 118 | 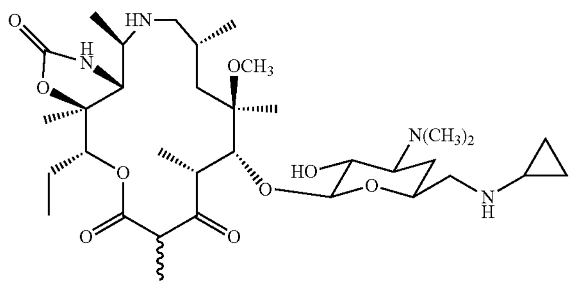 [SMILES: CC[C@H]1OC(=O)C(C)C(=O)[C@H](C)[C@@H](OC2OC(CNC3CC3)CC(N(C)C)C2O)[C@](C)(OC)C[C@@H](C)CN[C@H](C)[C@H]2NC(=O)O[C@@]21C] |
| 119 | 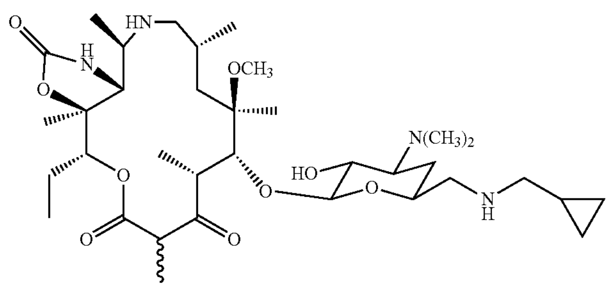 [SMILES: CC[C@H]1OC(=O)C(C)C(=O)[C@H](C)[C@@H](OC2OC(CNCC3CC3)CC(N(C)C)C2O)[C@](C)(OC)C[C@@H](C)CN[C@H](C)[C@H]2NC(=O)O[C@@]21C] |
| 120 | 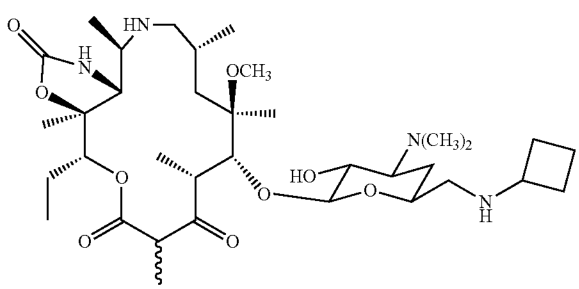 [SMILES: CC[C@H]1OC(=O)C(C)C(=O)[C@H](C)[C@@H](OC2OC(CNC3CCC3)CC(N(C)C)C2O)[C@](C)(OC)C[C@@H](C)CN[C@H](C)[C@H]2NC(=O)O[C@@]21C] |
| 121 | 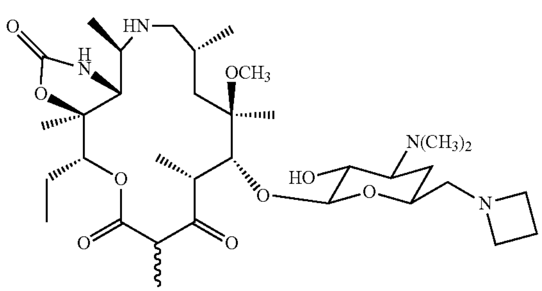 [SMILES: CC[C@H]1OC(=O)C(C)C(=O)[C@H](C)[C@@H](OC2OC(CN3CCC3)CC(N(C)C)C2O)[C@](C)(OC)C[C@@H](C)CN[C@H](C)[C@H]2NC(=O)O[C@@]21C] |

TABLE 14-continued
Exemplary Azaketolides.
| Compound No. | Structure |
|---|---|
| 122 | 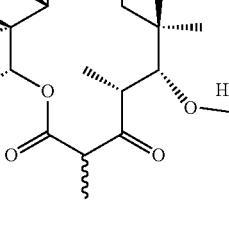 |
| 123 | 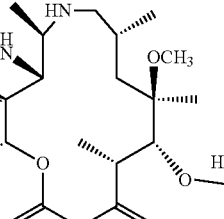 |
| 124 | 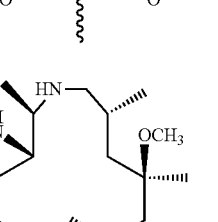 |
| 125 | 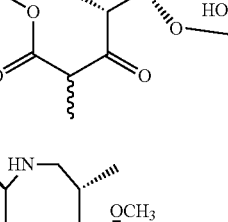 |
| 126 | 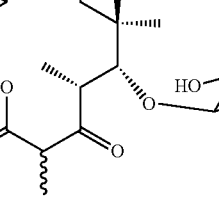 |

TABLE 14-continued

Exemplary Azaketolides.

| Compound No. | Structure |
| --- | --- |
| 127 | 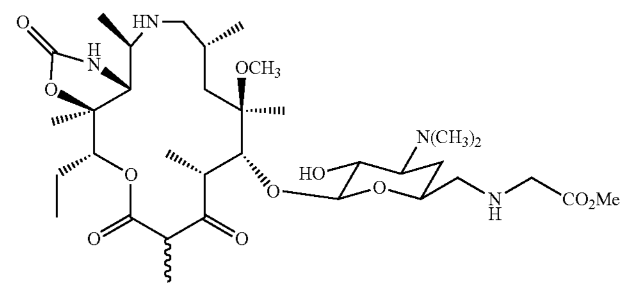 [SMILES: CC[C@H]1OC(=O)C(C)C(=O)[C@H](C)[C@@H](OC2OC(CNCC(=O)OC)CC(N(C)C)C2O)[C@](C)(OC)C[C@@H](C)CN[C@H](C)[C@H]2NC(=O)O[C@@]21C] |
| 128 | 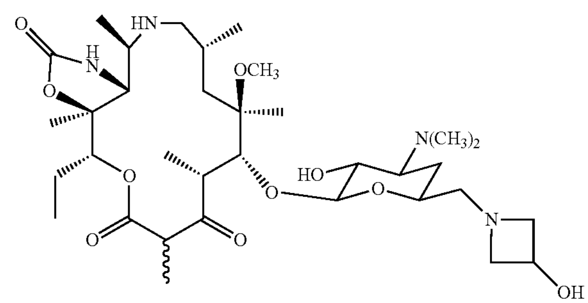 [SMILES: CC[C@H]1OC(=O)C(C)C(=O)[C@H](C)[C@@H](OC2OC(CN3CC(O)C3)CC(N(C)C)C2O)[C@](C)(OC)C[C@@H](C)CN[C@H](C)[C@H]2NC(=O)O[C@@]21C] |
| 129 | 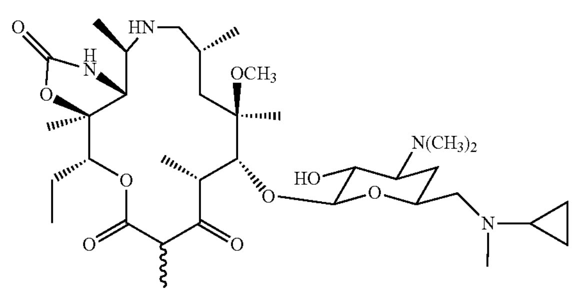 [SMILES: CC[C@H]1OC(=O)C(C)C(=O)[C@H](C)[C@@H](OC2OC(CN(C)C3CC3)CC(N(C)C)C2O)[C@](C)(OC)C[C@@H](C)CN[C@H](C)[C@H]2NC(=O)O[C@@]21C] |
| 130 | 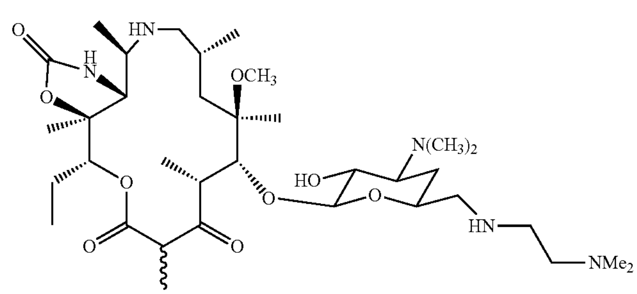 [SMILES: CC[C@H]1OC(=O)C(C)C(=O)[C@H](C)[C@@H](OC2OC(CNCCN(C)C)CC(N(C)C)C2O)[C@](C)(OC)C[C@@H](C)CN[C@H](C)[C@H]2NC(=O)O[C@@]21C] |
| 131 | 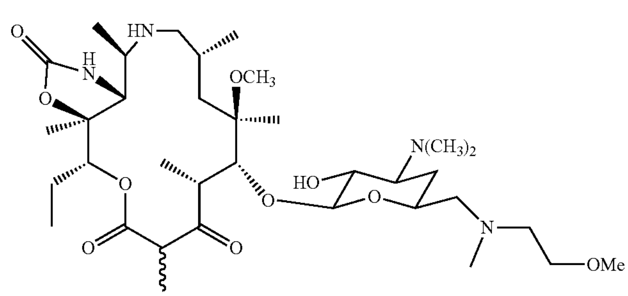 [SMILES: CC[C@H]1OC(=O)C(C)C(=O)[C@H](C)[C@@H](OC2OC(CN(C)CCOC)CC(N(C)C)C2O)[C@](C)(OC)C[C@@H](C)CN[C@H](C)[C@H]2NC(=O)O[C@@]21C] |

TABLE 14-continued

Exemplary Azaketolides.

| Compound No. | Structure |
|---|---|
| 132 | 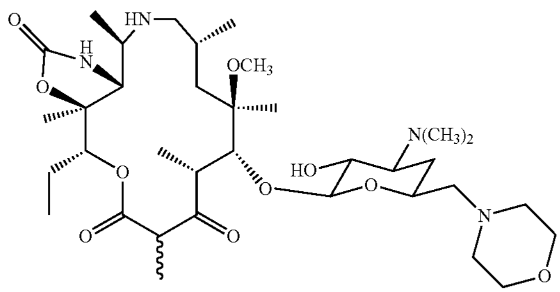 [SMILES: CC[C@H]1OC(=O)C(C)C(=O)[C@H](C)[C@@H](OC2OC(CN3CCOCC3)CC(N(C)C)C2O)[C@](C)(OC)C[C@@H](C)CN[C@H](C)[C@H]2NC(=O)O[C@@]21C] |
| 133 | 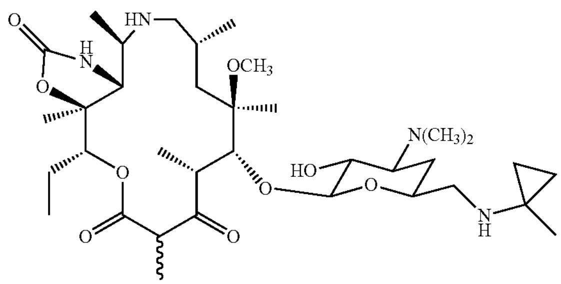 [SMILES: CC[C@H]1OC(=O)C(C)C(=O)[C@H](C)[C@@H](OC2OC(CNC3(C)CC3)CC(N(C)C)C2O)[C@](C)(OC)C[C@@H](C)CN[C@H](C)[C@H]2NC(=O)O[C@@]21C] |
| 134 | 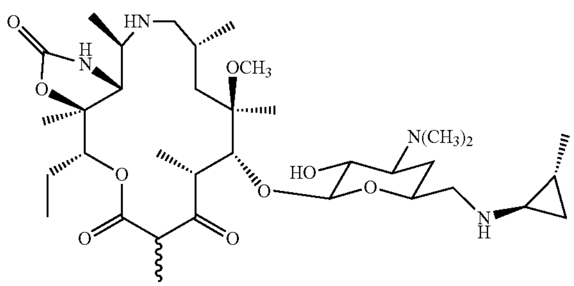 [SMILES: CC[C@H]1OC(=O)C(C)C(=O)[C@H](C)[C@@H](OC2OC(CN[C@@H]3C[C@H]3C)CC(N(C)C)C2O)[C@](C)(OC)C[C@@H](C)CN[C@H](C)[C@H]2NC(=O)O[C@@]21C] |
| 135 | 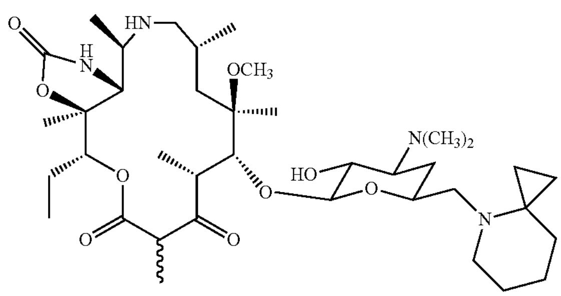 [SMILES: CC[C@H]1OC(=O)C(C)C(=O)[C@H](C)[C@@H](OC2OC(CN3CCCCC34CC4)CC(N(C)C)C2O)[C@](C)(OC)C[C@@H](C)CN[C@H](C)[C@H]2NC(=O)O[C@@]21C] |
| 136 | 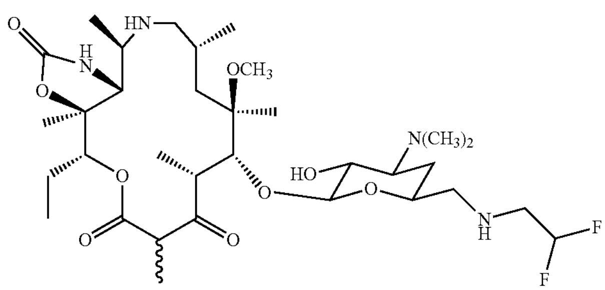 [SMILES: CC[C@H]1OC(=O)C(C)C(=O)[C@H](C)[C@@H](OC2OC(CNCC(F)F)CC(N(C)C)C2O)[C@](C)(OC)C[C@@H](C)CN[C@H](C)[C@H]2NC(=O)O[C@@]21C] |

TABLE 14-continued

Exemplary Azaketolides.

| Compound No. | Structure |
|---|---|
| 137 | 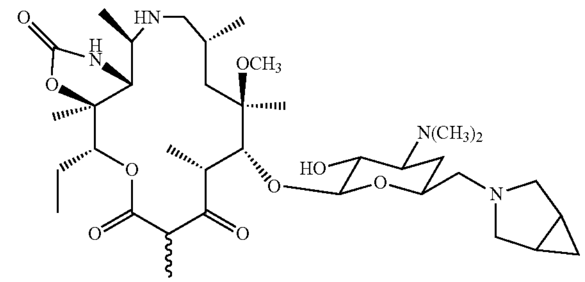 [SMILES: CC[C@H]1OC(=O)C(C)C(=O)[C@H](C)[C@@H](OC2OC(CN3CC4CC4C3)CC(N(C)C)C2O)[C@](C)(OC)C[C@@H](C)CN[C@H](C)[C@H]2NC(=O)O[C@@]21C] |
| 138 | 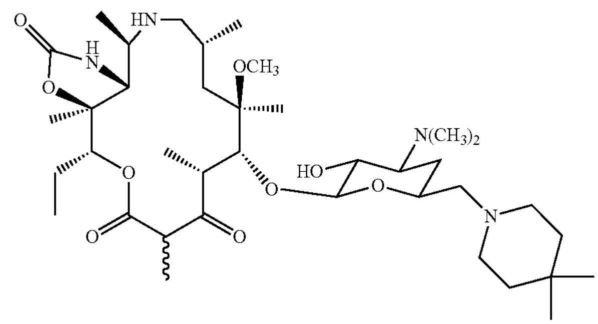 [SMILES: CC[C@H]1OC(=O)C(C)C(=O)[C@H](C)[C@@H](OC2OC(CN3CCC(C)(C)CC3)CC(N(C)C)C2O)[C@](C)(OC)C[C@@H](C)CN[C@H](C)[C@H]2NC(=O)O[C@@]21C] |
| 139 | 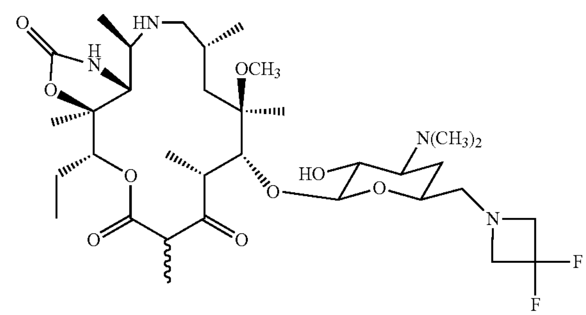 [SMILES: CC[C@H]1OC(=O)C(C)C(=O)[C@H](C)[C@@H](OC2OC(CN3CC(F)(F)C3)CC(N(C)C)C2O)[C@](C)(OC)C[C@@H](C)CN[C@H](C)[C@H]2NC(=O)O[C@@]21C] |
| 140 | 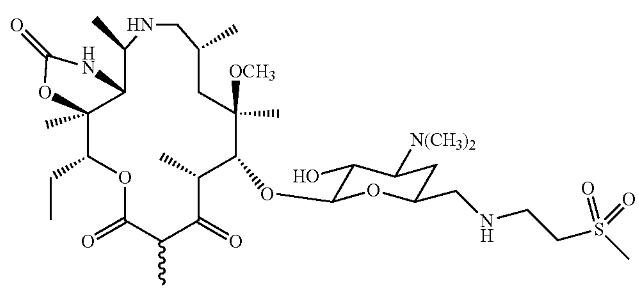 [SMILES: CC[C@H]1OC(=O)C(C)C(=O)[C@H](C)[C@@H](OC2OC(CNCCS(C)(=O)=O)CC(N(C)C)C2O)[C@](C)(OC)C[C@@H](C)CN[C@H](C)[C@H]2NC(=O)O[C@@]21C] |
| 141 | 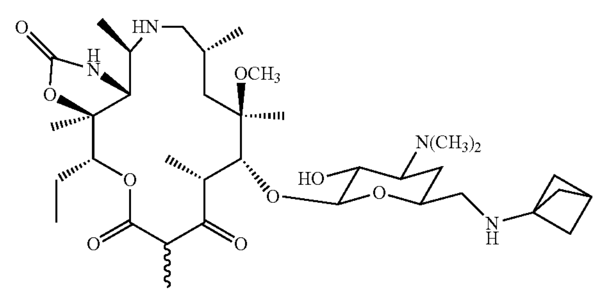 [SMILES: CC[C@H]1OC(=O)C(C)C(=O)[C@H](C)[C@@H](OC2OC(CNC34CC(C3)C4)CC(N(C)C)C2O)[C@](C)(OC)C[C@@H](C)CN[C@H](C)[C@H]2NC(=O)O[C@@]21C] |

TABLE 14-continued

Exemplary Azaketolides.

| Compound No. | Structure |
|---|---|
| 142 | *(structure image)* |
| 143 | *(structure image)* |
| 144 | *(structure image)* |
| 145 | *(structure image)* |
| 146 | *(structure image)* |

TABLE 14-continued
Exemplary Azaketolides.
| Compound No. | Structure |
|---|---|
| 147 | 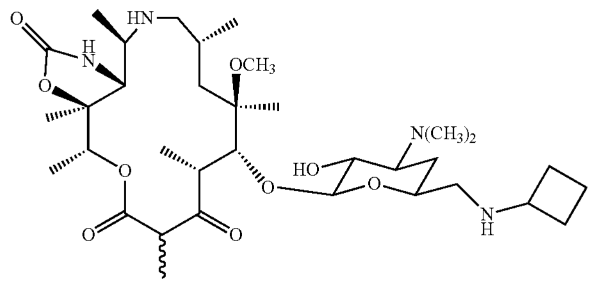 [SMILES: CO[C@]1(C)C[C@@H](C)CN[C@H](C)[C@H]2NC(=O)O[C@]2(C)[C@@H](C)OC(=O)C(C)C(=O)[C@H](C)[C@H]1OC1OC(CNC2CCC2)CC(N(C)C)C1O] |
| 148 | 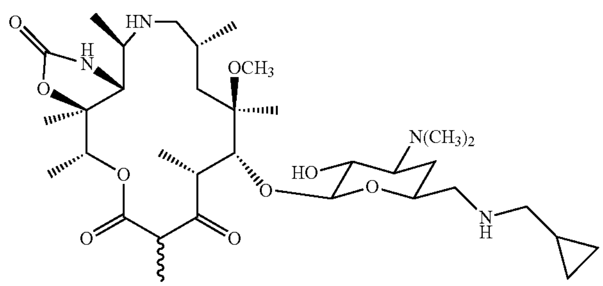 [SMILES: CO[C@]1(C)C[C@@H](C)CN[C@H](C)[C@H]2NC(=O)O[C@]2(C)[C@@H](C)OC(=O)C(C)C(=O)[C@H](C)[C@H]1OC1OC(CNCC2CC2)CC(N(C)C)C1O] |
| 149 | 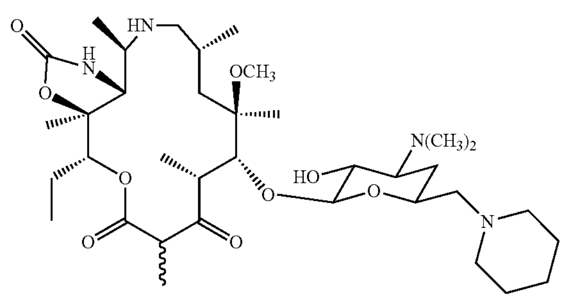 [SMILES: CC[C@H]1OC(=O)C(C)C(=O)[C@H](C)[C@@H](OC2OC(CN3CCCCC3)CC(N(C)C)C2O)[C@](C)(OC)C[C@@H](C)CN[C@H](C)[C@H]2NC(=O)O[C@@]21C] |
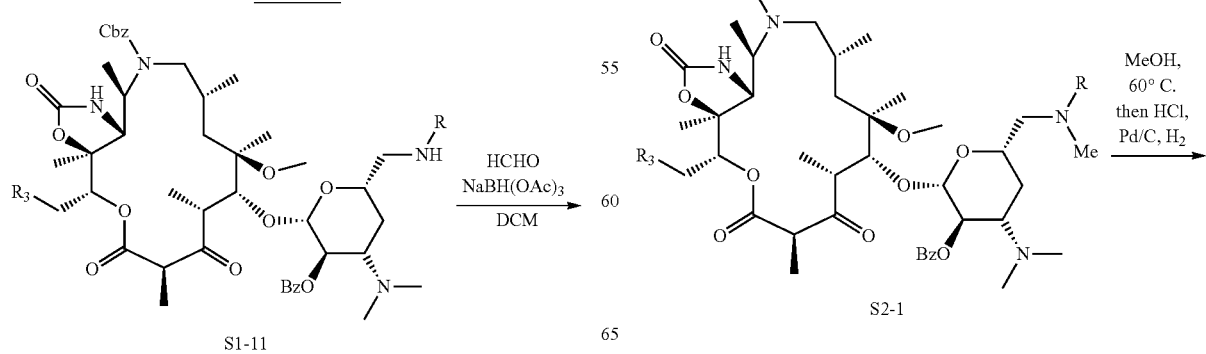
Scheme 24.
-continued

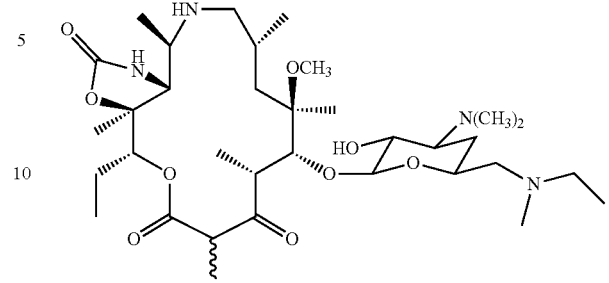

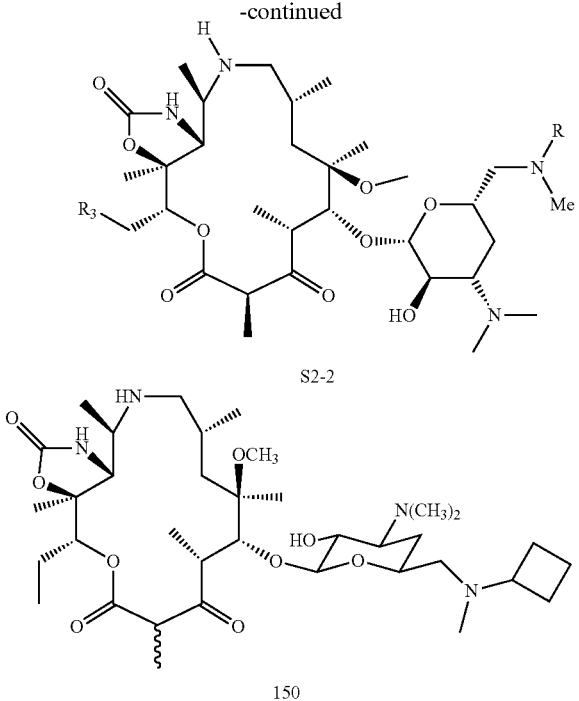

150

3-Descladinosyl-3-oxo-6-O-methyl-N9a-desmethyl-
11,12-dideoxy-12,11-(oxycarbonylimino)-6'-methyl-
cyclobutylamino Azithromycin (150)

In a 5 mL vial was a solution of amine S1-11 (35 mg, 38 μmol) and NaBH(OAc)$_3$ (2 equiv., 16 mg, 76 μmol) in DCM (1 mL) was added at rt. Formaldehyde (100 equiv, 0.11 mL, 3.8 mmol, aqueous solution) was added dropwise to give a colorless solution which was stirred at rt until LC/MS indicated complete consumption of starting material (10 min). The reaction mixture was diluted with DCM and poured into satd aq NaHCO$_3$. The aqueous phase was extracted with DCM and the combined organic phases were dried over MgSO$_4$, filtered and concentrated. The residue was purified on 4 g of silica gel (elution with 0-10% MeOH-DCM+0.5% of 30% aq NH$_4$OH) to yield amine S2-1. Then amine S2-1 was dissolved in MeOH (0.5 mL) and heated at 60° C. until LC/MS indicated complete consumption of starting material (16 hours). The reaction mixture was cooled, and aqueous HCl (12 M, 3 equiv, 10 μL) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% HCO$_2$H) to yield 150 as a bis formate salt (10.78 mg, 36% over four steps). MS (ESI+) m/z: 233.1 [M+3H]$^{3+}$, 349.2 [M+2H]$^{2+}$, 697.4 [M+H]$^+$; $^1$H NMR (400 MHz, Methanol-d$_4$) δ 8.52 (s, 2H), 5.08 (dd, 1H), 4.59-4.52 (m, 1H), 4.47 (d, 1H), 3.93 (t, 1H), 3.52-3.32 (m, 10H), 3.26 (d, 2H), 3.21-3.00 (m, 7H), 2.75 (d, 10H), 2.59 (d, 1H), 2.54 (s, 3H), 2.34-2.15 (m, 4H), 2.04 (d, 1H), 2.01 (s, 1H), 1.98 (s, 1H), 1.91 (ddd, 2H), 1.83 (s, 1H), 1.76 (d, 2H), 1.74-1.65 (m, 3H), 1.65-1.45 (m, 7H), 1.44-1.13 (m, 16H), 1.10-0.89 (m, 8H).

151

3-Descladinosyl-3-oxo-6-O-methyl-N9a-desmethyl-
11,12-dideoxy-12,11-(oxycarbonylimino)-6'-methyl-
ethylamino Azithromycin (151)

Prepared according to the methods of 150, substituting ethylamine gave 151 as a bis-formate salt (15.38 mg). MS (ESI+) m/z: 224.5 [M+3H]$^{3+}$, 336.2 [M+2H]$^{2+}$, 671.4 [M+H]$^+$; $^1$H NMR (400 MHz, Methanol-d$_4$) δ 8.43 (s, 2H), 4.96 (dd, 1H), 4.44 (d, 1H), 4.33 (dd, 1H), 3.81 (d, 1H), 3.35-3.24 (m, 2H), 3.04-2.98 (m, 2H), 2.98-2.72 (m, 10H), 2.53 (d, 11H), 2.43-2.31 (m, 1H), 1.99 (t, 1H), 1.92-1.75 (m, 3H), 1.68-1.52 (m, 3H), 1.44 (d, 5H), 1.36 (dd, 1H), 1.25 (d, 6H), 1.23-1.03 (m, 11H), 1.02 (d, 3H), 0.97-0.78 (m, 8H).

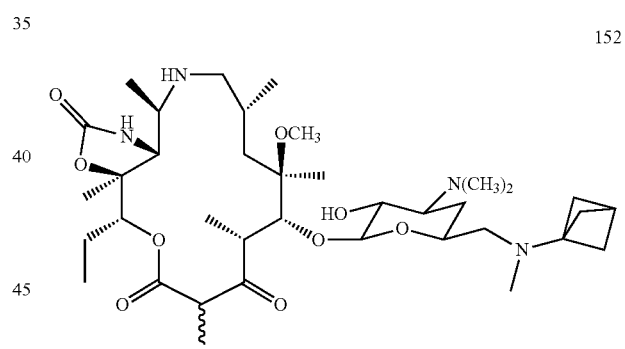

3-Descladinosyl-3-oxo-6-O-methyl-N9a-desmethyl-
11,12-dideoxy-12,11-(oxycarbonylimino)-6'-bicyclo
[1.1.1]pentanylmethylamino Azithromycin (152)

Prepared according to the methods of 150, substituting bicyclo[1.1.1]pentan-1-amine gave 152 as a bis-formate salt (7.85 mg). MS (ESI+) m/z: 237.1 [M+3H]$^{3+}$, 355.2 [M+2H]$^{2+}$, 709.4 [M+H]$^+$; $^1$H NMR (400 MHz, Methanol-d$_4$) δ 8.43 (s, 2H), 4.95 (dd, 1H), 4.44 (d, 1H), 4.37-4.28 (m, 1H), 3.65 (t, 1H), 3.37-3.22 (m, 3H), 3.19-3.09 (m, 2H), 3.09-2.94 (m, 2H), 2.91 (d, 5H), 2.79 (ddd, 2H), 2.59 (d, 10H), 2.54-2.45 (m, 2H), 2.33 (d, 5H), 2.21 (s, 2H), 2.04 (t, 1H), 1.96-1.79 (m, 3H), 1.72 (d, 11H), 1.64-1.51 (m, 3H), 1.48-1.36 (m, 6H), 1.36-1.18 (m, 12H), 1.18-0.98 (m, 8H), 0.86 (dt, 9H).

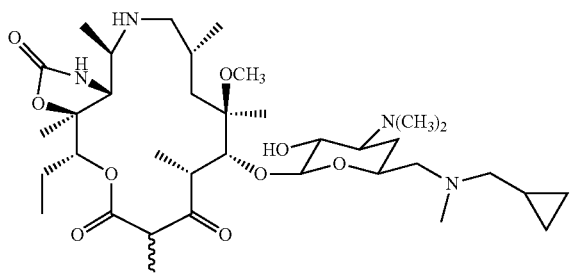

3-Descladinosyl-3-oxo-6-O-methyl-N9a-desmethyl-11,12-dideoxy-12,11-(oxycarbonylimino)-6'-methyl-cyclopropylmethylamino Azithromycin (153)

Prepared according to the methods of 150, substituting cyclopropylmethylamine gave 153 as a bis-formate salt (13.44 mg). MS (ESI+) m/z: 233.1 [M+3H]$^{3+}$, 349.2 [M+2H]$^{2+}$, 697.4 [M+H]$^+$; $^1$H NMR (400 MHz, Methanol-$d_4$) δ 8.51 (s, 2H), 5.10 (dd, 1H), 4.51-4.45 (m, 2H), 4.08 (q, 1H), 3.56 (d, 1H), 3.48 (dd, 1H), 3.42-3.32 (m, 3H), 3.32-3.19 (m, 6H), 3.19-3.11 (m, 1H), 3.09 (s, 3H), 3.07 (d, 1H), 3.04 (d, 2H), 2.93 (s, 3H), 2.80 (d, 1H), 2.73 (s, 5H), 2.69 (d, 1H), 2.41 (t, 1H), 2.08-2.00 (m, 1H), 1.99-1.48 (m, 9H), 1.42-1.30 (m, 9H), 1.29 (d, 3H), 1.25-1.12 (m, 1H), 1.12-0.94 (m, 5H), 0.93 (d, 2H), 0.79-0.62 (m, 2H), 0.40 (dq, 2H).

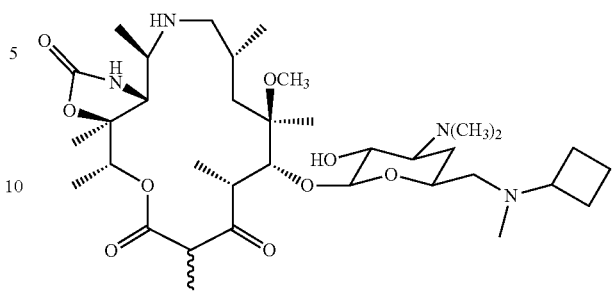

3-Descladinosyl-3-oxo-6-O-methyl-N9a-desmethyl-11,12-dideoxy-12,11-(oxycarbonylimino)-6'-methyl-cyclobutylamino-13-methyl Azithromycin (155)

Prepared according to the methods of 150, substituting S1-11-2 and cyclobutylamine, gave 155 as a bis-formate salt. MS (ESI+) m/z: 683.2 [M+H]$^+$, $^1$H NMR (400 MHz, Methanol-$d_4$) δ 8.45 (s, 2H), 5.14 (q, 1H), 4.56 (dd, 1H), 4.47 (d, 1H), 4.20-4.05 (m, 2H), 3.72 (p, 1H), 3.63 (d, 1H), 3.52 (qd, 3H), 3.24-3.12 (m, 3H), 3.10-2.91 (m, 1H), 3.04 (s, 3H), 2.82 (d, 8H), 2.66-2.55 (m, 1H), 2.30 (d, 3H), 2.19 (dq, 3H), 1.98 (s, 1H), 1.90-1.79 (m, 1H), 1.82-1.63 (m, 3H), 1.57 (d, 3H), 1.44-1.20 (m, 16H), 1.06 (dd, 3H).

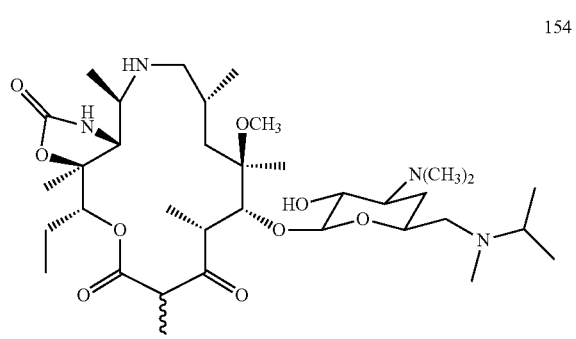 [SMILES: CC[C@H]1OC(=O)C(C)C(=O)[C@H](C)[C@@H](OC2OC(CN(C)C(C)C)CC(N(C)C)C2O)[C@](C)(OC)C[C@@H](C)CN[C@H](C)[C@H]2NC(=O)O[C@@]21C]

3-Desdadinosyl-3-oxo-6-O-methyl-N9a-desmethyl-11,12-dideoxy-12,11-(oxycarbonylimino)-6'-isopropylmethylamino Azithromycin (154)

Prepared according to the methods of 150, substituting isopropylamine gave 154 as a bis-formate salt (5.6 mg). MS (ESI+) m/z: 229.1 [M+3H]$^{3+}$, 343.2 [M+2H]$^{2+}$, 685.4 [M+H]$^+$; $^1$H NMR (400 MHz, Methanol-$d_4$) δ 8.50 (s, 3H), 5.07 (dd, 1H), 4.48 (dd, 3H), 4.23-4.02 (m, 2H), 3.86-3.78 (m, 1H), 3.55 (s, 2H), 3.54-3.42 (m, 4H), 3.23-3.10 (m, 3H), 3.08 (s, 5H), 2.84 (s, 4H), 2.76 (d, 11H), 2.48 (t, 2H), 2.09 (d, 2H), 1.94-1.78 (m, 5H), 1.75-1.63 (m, 4H), 1.39-1.17 (m, 44H), 1.04 (dd, 6H), 0.91 (t, 9H).

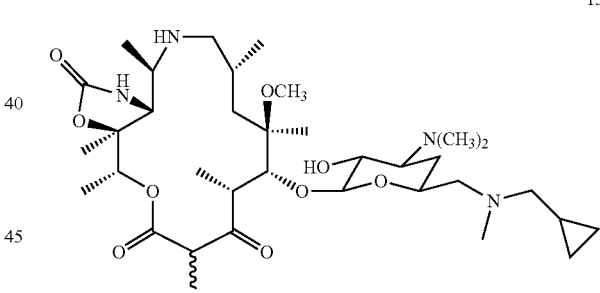

3-Desdadinosyl-3-oxo-6-O-methyl-N9a-desmethyl-11,12-dideoxy-12,11-(oxycarbonylimino)-6'-methyl-cyclopropylmethyl-13-methyl Azithromycin (156)

Prepared according to the methods of 150, substituting S1-11-2 and cyclopropylmethylamine, gave 156 as a bis-formate salt. MS (ESI+) m/z: 683.1 [M+H]$^+$; $^1$H NMR (400 MHz, Methanol-$d_4$) δ 8.45 (s, 2H), 5.16 (q, 1H), 4.52 (d, 1H), 4.43 (d, 1H), 4.15 (tt, 2H), 3.63 (d, 1H), 3.60-3.33 (m, 4H), 3.25-3.12 (m, 3H), 3.09-2.93 (m, 6H), 2.91 (s, 1H), 2.83 (d, 6H), 2.59 (t, 1H), 2.13 (d, 1H), 1.96 (s, 1H), 1.84-1.61 (m, 3H), 1.58 (d, 3H), 1.44-1.30 (m, 14H), 1.27 (d, 1H), 1.25-1.14 (m, 2H), 1.06 (dd, 3H), 0.83-0.70 (m, 2H), 0.47 (tp, 2H).

TABLE 15

Exemplary Azaketolides.

| Compound No. | Structure |
| --- | --- |
| 150 | 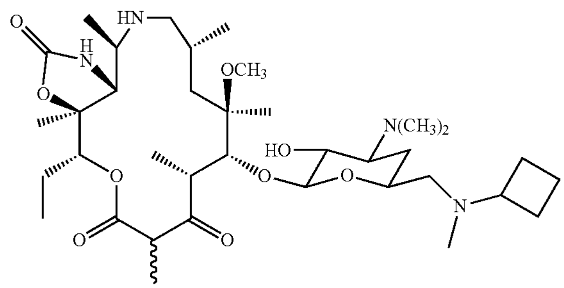 [SMILES: CC[C@H]1OC(=O)C(C)C(=O)[C@H](C)[C@@H](OC2OC(CN(C)C3CCC3)CC(N(C)C)C2O)[C@](C)(OC)C[C@@H](C)CN[C@H](C)[C@H]2NC(=O)O[C@@]21C] |
| 151 | 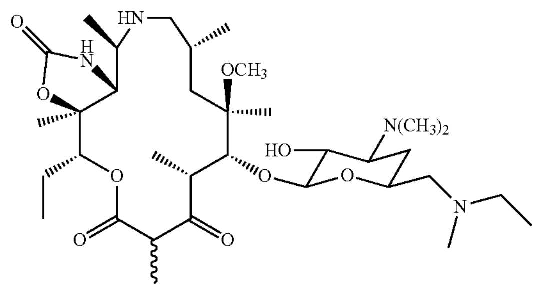 [SMILES: CC[C@H]1OC(=O)C(C)C(=O)[C@H](C)[C@@H](OC2OC(CN(C)CC)CC(N(C)C)C2O)[C@](C)(OC)C[C@@H](C)CN[C@H](C)[C@H]2NC(=O)O[C@@]21C] |
| 152 | 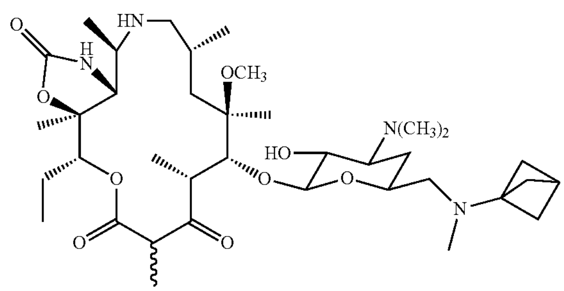 [SMILES: CC[C@H]1OC(=O)C(C)C(=O)[C@H](C)[C@@H](OC2OC(CN(C)C34CC(C3)C4)CC(N(C)C)C2O)[C@](C)(OC)C[C@@H](C)CN[C@H](C)[C@H]2NC(=O)O[C@@]21C] |
| 153 | 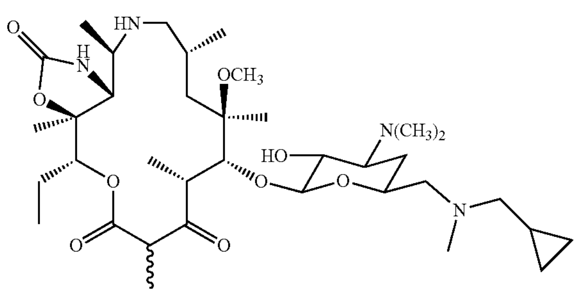 [SMILES: CC[C@H]1OC(=O)C(C)C(=O)[C@H](C)[C@@H](OC2OC(CN(C)CC3CC3)CC(N(C)C)C2O)[C@](C)(OC)C[C@@H](C)CN[C@H](C)[C@H]2NC(=O)O[C@@]21C] |
| 154 | 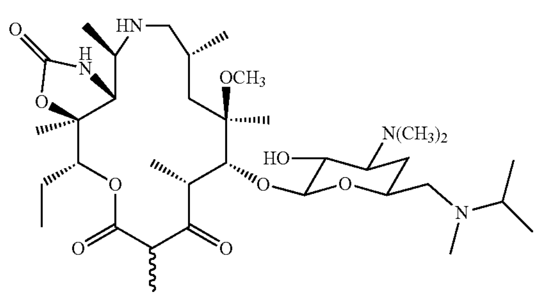 [SMILES: CC[C@H]1OC(=O)C(C)C(=O)[C@H](C)[C@@H](OC2OC(CN(C)C(C)C)CC(N(C)C)C2O)[C@](C)(OC)C[C@@H](C)CN[C@H](C)[C@H]2NC(=O)O[C@@]21C] |

TABLE 15-continued

Exemplary Azaketolides.

| Compound No. | Structure |
|---|---|
| 155 | 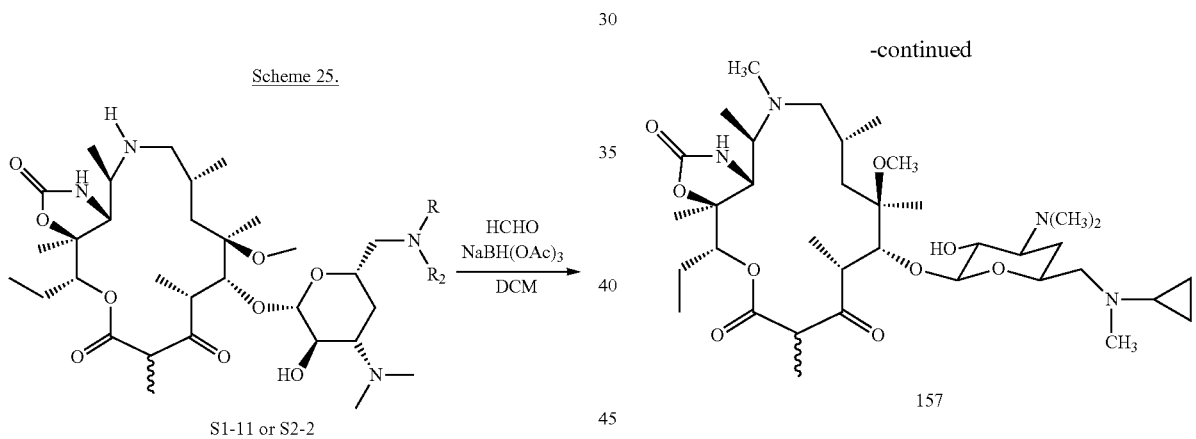 |
| 156 | 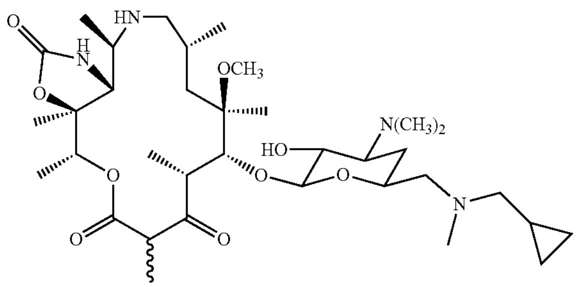 [SMILES: CO[C@]1(C)C[C@@H](C)CN[C@H](C)[C@H]2NC(=O)O[C@]2(C)[C@@H](C)OC(=O)C(C)C(=O)[C@H](C)[C@H]1OC1OC(CN(C)CC2CC2)CC(N(C)C)C1O] |

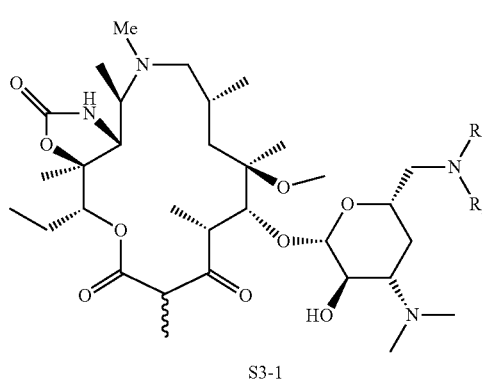

Scheme 25.

3-Descladinosyl-3-oxo-6-O-methyl-11,12-dideoxy-12,11-(oxycarbonylimino)-6'-[N-(methyl)cyclopropylamino]Azithromycin (157)

In a 5 mL vial was a solution of 129 tri formate salt (6.2 mg, 7.6 μmol) in 0.25 mL of DCM. Formaldehyde (36 μL, 37 wt % in water, 360 μmol) was added followed by sodium triacetoxyborohydride (10.7 mg, 50.7 μmol) and the mixture was stirred at rt for 3.5 hr. The reaction mixture was diluted with DCM and poured into satd aq $NaHCO_3$. The aqueous phase was extracted twice with DCM and the combined organic phases were dried over $MgSO_4$, filtered and concentrated. The residue was purified by HPLC (elution with 5-20% MeCN-water-0.1% Formic acid) and lyophilized to give 157 tri-formate salt as a white solid (2.6 mg, 41%). MS (ESI+) m/z: 233.3 $[M+3H]^{3+}$, 349.4 $[M+2H]^{2+}$, 697.5 $[M+H]^+$. $^1H$ NMR (400 MHz, Methanol-$d_4$) δ 8.36 (s, 3H), 4.55-4.43 (m, 2H), 4.09 (s, 1H), 3.98 (s, 1H), 3.66 (d, 1H), 3.53-3.41 (m, 3H), 3.03 (s, 2H), 2.87 (s, 3H), 2.83 (s, 6H), 2.58 (s, 3H), 2.10-1.91 (m, 5H), 1.76 (dt, 2H), 1.61 (d, 5H), 1.43-1.26 (m, 9H), 1.26-1.11 (m, 4H), 1.05-0.92 (m, 7H), 0.61-0.38 (m, 4H).

158

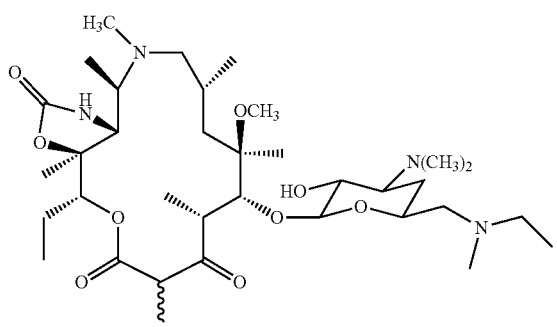

3-Descladinosyl-3-oxo-6-O-methyl-11,12-dideoxy-12,11-(oxycarbonylimino)-6'-ethylmethylamino Azithromycin (158)

Prepared according to the methods of 157 from S2-2-2 gave 158 as a tri-formate salt (1.6 mg, 54%). MS (ESI+) m/z: 229.3 [M+3H]$^{3+}$, 343.5 [M+2H]$^{2+}$, 685.4 [M+H]$^+$; $^1$H NMR (400 MHz, Methanol-d$_4$) δ 8.45 (s, 3H), 4.62 (s, 1H), 4.39 (dd, 1H), 3.98 (d, 1H), 3.86-3.72 (m, 1H), 3.72-3.51 (m, 1H), 3.52-3.11 (m, 3H), 3.11-2.12 (m, 19H), 2.08-1.45 (m, 11H), 1.45-0.67 (m, 23H).

159

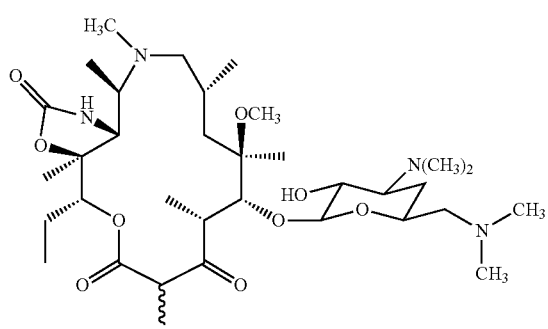

3-Descladinosyl-3-oxo-6-O-methyl-11,12-dideoxy-12,11-(oxycarbonylimino)-6'-dimethylamino Azithromycin (159)

Prepared according to the methods of 157 from 107 gave 159 as a tri-formate salt (1.52 mg, 48%). MS (ESI+) m/z: 224.5 [M+3H]$^{3+}$, 336.2 [M+2H]$^{2+}$, 671.4 [M+H]$^+$; $^1$H NMR (400 MHz, Methanol-d$_4$) δ 8.44 (s, 3H), 4.40 (dd, 1H), 4.04-3.95 (m, 1H), 3.78 (d, 1H), 3.66 (d, 1H), 3.58 (d, 1H), 3.36-3.23 (m, 4H), 2.95-2.82 (m, 2H), 2.81-2.66 (m, 4H), 2.63-2.52 (m, 6H), 2.49 (s, 2H), 2.39 (td, 2H), 2.33 (s, 3H), 1.98 (t, 2H), 1.87 (s, 2H), 1.86-1.80 (m, 1H), 1.77 (s, 1H), 1.68 (d, 1H), 1.64-1.57 (m, 1H), 1.56 (s, 1H), 1.51 (s, 4H), 1.29-1.14 (m, 11H), 1.10-0.94 (m, 6H), 0.94-0.76 (m, 10H).

160

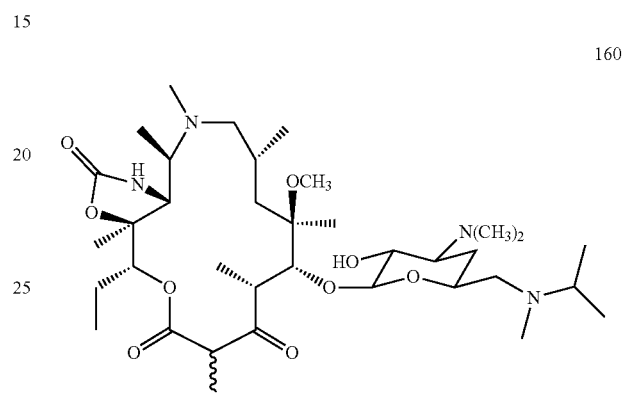

3-Desdadinosyl-3-oxo-6-O-methyl-9a-desmethyl-11,12-dideoxy-12,11-(oxycarbonylimino)-6'-isopropylmethylamino Azithromycin (160)

Prepared according to the methods of 157 from S2-2-5 gave 160 as a bis-formate salt (1.52 mg, 48%). MS (ESI+) m/z: 233.8 [M+3H]$^{3+}$, 350.2 [M+2H]$^{2+}$, 699.4 [M+H]$^+$; $^1$H NMR (400 MHz, Methanol-d$_4$) δ 8.44 (s, 2H), 4.64 (s, 1H), 4.40 (dd, 2H), 4.25 (s, 1H), 3.98 (d, 1H), 3.86-3.76 (m, 2H), 3.63 (d, 1H), 3.58 (d, 1H), 3.30 (d, 2H), 3.17 (s, 2H), 2.97 (s, 1H), 2.89 (d, 5H), 2.78 (s, 2H), 2.70 (d, 2H), 2.59-2.46 (m, 12H), 2.38 (d, 3H), 2.23 (d, 2H), 1.97 (s, 3H), 1.87 (s, 4H), 1.68 (d, 3H), 1.54 (d, 6H), 1.41 (s, 1H), 1.30-1.15 (m, 20H), 1.13 (s, 5H), 1.10-0.99 (m, 10H), 0.98-0.84 (m, 13H), 0.82 (t, 4H), 0.78 (d, 1H).

TABLE 16

| Exemplary Azaketolides. | |
| --- | --- |
| Compound No. | Structure |
| 157 | |

TABLE 16-continued
Exemplary Azaketolides.
| Compound No. | Structure |
|---|---|
| 158 | 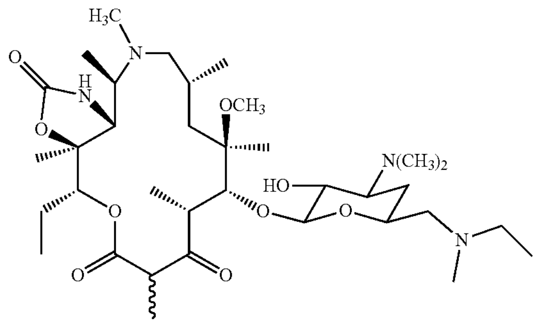 [SMILES: CC[C@H]1OC(=O)C(C)C(=O)[C@H](C)[C@@H](OC2OC(CN(C)CC)CC(N(C)C)C2O)[C@](C)(OC)C[C@@H](C)CN(C)[C@H](C)[C@H]2NC(=O)O[C@@]21C] |
| 159 | 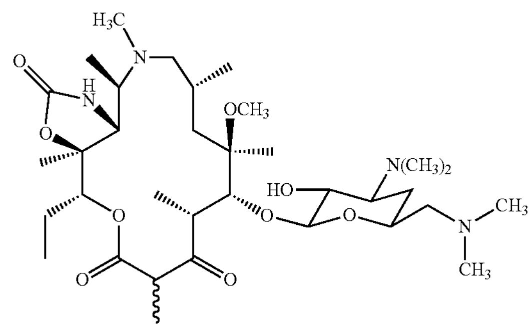 [SMILES: CC[C@H]1OC(=O)C(C)C(=O)[C@H](C)[C@@H](OC2OC(CN(C)C)CC(N(C)C)C2O)[C@](C)(OC)C[C@@H](C)CN(C)[C@H](C)[C@H]2NC(=O)O[C@@]21C] |
| 160 | 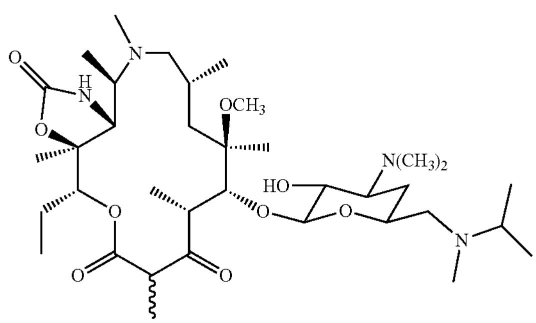 [SMILES: CC[C@H]1OC(=O)C(C)C(=O)[C@H](C)[C@@H](OC2OC(CN(C)C(C)C)CC(N(C)C)C2O)[C@](C)(OC)C[C@@H](C)CN(C)[C@H](C)[C@H]2NC(=O)O[C@@]21C] |
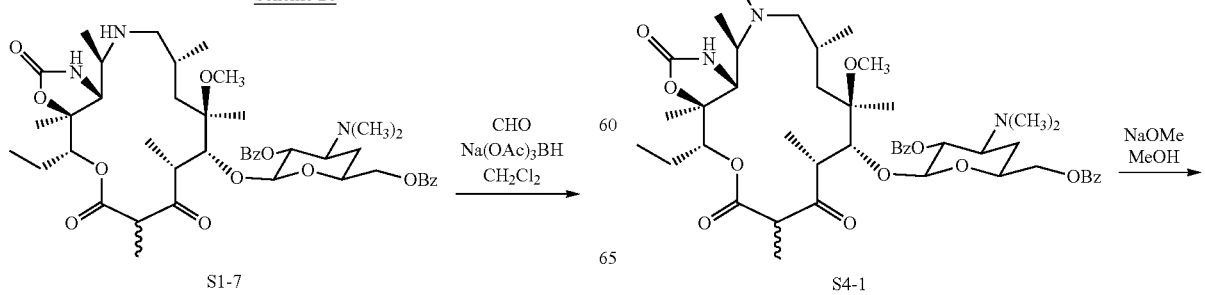
Scheme 26

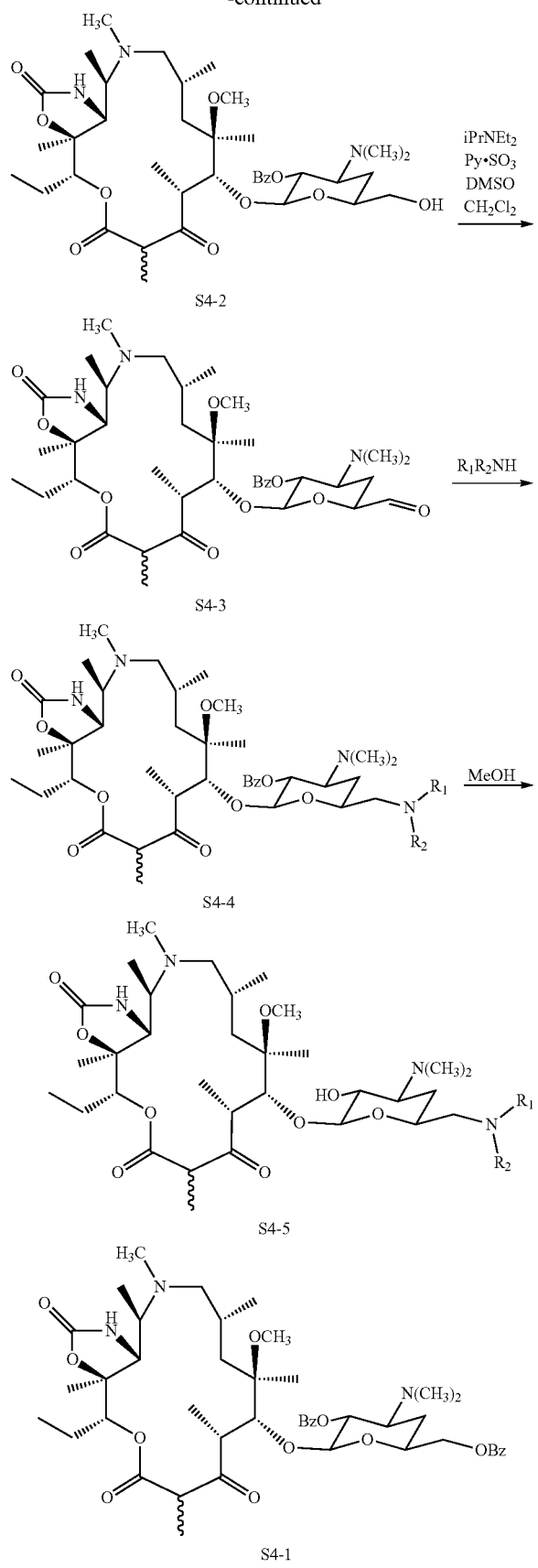

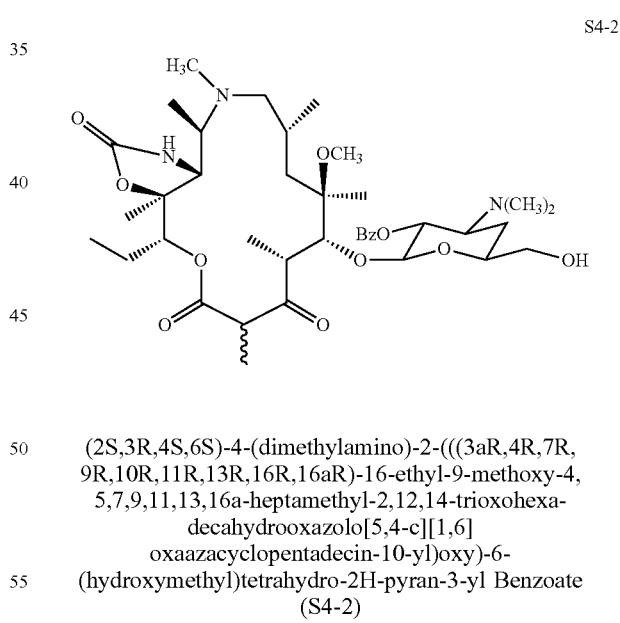

((2S,4S,5R,6S)-5-(benzoyloxy)-4-(dimethylamino)-6-(((3aR,4R,7R,9R,10R,11R,13R,16R,16aR)-16-ethyl-9-methoxy-4,5,7,9,11,13,16a-heptamethyl-2,12,14-trioxohexadecahydrooxazolo[5,4-c][1,6]oxaazacyclopentadecin-10-yl)oxy)tetrahydro-2H-pyran-2-yl)methyl Benzoate (S4-1)

A solution of S1-7-1 (250 mg, 0.3 mmol) in dichloromethane (3 mL) was added with formaldehyde (0.24 mL, 3 mmol) followed by sodium triacetoxyborohydride (126 mg, 0.6 mmol). The reaction mixture was stirred at room temperature for 30 mins, at which point LC/MS indicated complete conversion of starting material to the desired mass. The reaction mixture was partitioned between dichloromethane and sat. aq. NaHCO₃, the organic layer was dried over sodium sulfate, filtered and concentrated in vacuo. Crude residue was purified by silica gel chromatography (ISCO 12 g column, 0-10% MeOH/CH₂Cl₂, 0.5% NH₄OH) to give S4-1 as a white solid (251 mg, 99%). MS (ESI+) m/z: 426.8 $[M+2H]^{2+}$, 852.4 $[M+H]^+$; ¹H NMR (400 MHz, Chloroform-d) δ 8.14-7.99 (m, 4H), 7.63-7.52 (m, 2H), 7.45 (dtd, 4H), 5.97 (s, 0.5H), 5.89 (s, 0.5H), 5.25-5.07 (m, 1H), 4.78-4.71 (m, 0.5H), 4.70-4.64 (m, 1H), 4.60 (dd, 0.5H), 4.52-4.35 (m, 2H), 4.27 (d, 0.5H), 4.16 (q, 0.5H), 4.02-3.84 (m, 1H), 3.79-3.65 (m, 1.5H), 3.55 (d, 0.5H), 3.15-2.91 (m, 2H), 2.89-2.74 (m, 1H), 2.74-2.59 (m, 3H), 2.50 (d, 0.5H), 2.32 (d, 6H), 2.21 (td, 0.5H), 2.14-2.00 (m, 1H), 1.96-1.85 (m, 3.5H), 1.81 (s, 1H), 1.79-1.68 (m, 1.5H), 1.61 (qd, 2H), 1.52-1.41 (m, 2H), 1.41-1.30 (m, 1H), 1.30-1.20 (m, 3H), 1.17 (s, 3H), 1.09 (d, 2H), 1.04-0.88 (m, 9H), 0.86 (d, 2H), 0.63 (t, 1.5H), 0.52 (ddt, 0.5H).

(2S,3R,4S,6S)-4-(dimethylamino)-2-(((3aR,4R,7R,9R,10R,11R,13R,16R,16aR)-16-ethyl-9-methoxy-4,5,7,9,11,13,16a-heptamethyl-2,12,14-trioxohexadecahydrooxazolo[5,4-c][1,6]oxaazacyclopentadecin-10-yl)oxy)-6-(hydroxymethyl)tetrahydro-2H-pyran-3-yl Benzoate (S4-2)

In a 20 mL vial was added a solution of S4-1 (252 mg, 0.3 mmol) in 3 mL of 2:1 THF:MeOH which was stirred at rt. NaOMe (25% in MeOH, 0.034 mL, 0.15 mmol) was added and the resulting mixture was stirred at rt. After 90 mins LC/MS showed complete conversion of the starting material to the desired mass. The reaction was quenched by the addition of sat. aq NH*Cl and ethyl acetate. The organic layer was separated and washed with brine. The washed solution was dried over sodium sulfate, filtered and concentrated in vacuo. Crude was purified by silica gel chromatography (ISCO 12 g column, 0-10% MeOH/CH$_2$Cl$_2$, 0.5% NH$_4$OH) to give S4-2 as a white solid (162 mg, 0.22 mmol, 74%). MS (ESI+) m/z. 374.8 [M+2H]$^{2+}$, 748.4 [M+H]$^+$; $^1$H NMR (400 MHz, Chloroform-d) δ 8.10-8.02 (m, 2H), 7.64-7.51 (m, 1H), 7.46 (dd, 2H), 5.61 (s, 1H), 5.19-5.07 (m, 1H), 4.69 (d, 1H), 4.59 (dd, 1H), 4.16 (q, 1H), 3.83-3.69 (m, 3H), 3.69-3.57 (m, 2H), 3.12 (d, 1H), 3.06-2.93 (m, 1H), 2.81 (s, 3H), 2.51 (d, 1H), 2.37 (dd, 1H), 2.30 (s, 6H), 2.00-1.89 (m, 1H), 1.82 (s, 3H), 1.80-1.72 (m, 2H), 1.62 (q, 2H), 1.29 (s, 3H), 1.15 (s, 3H), 1.10 (d, 3H), 1.00-0.96 (m, 3H), 0.94 (dt, 6H), 0.63 (t, 3H), 0.52 (ddt, 1H).

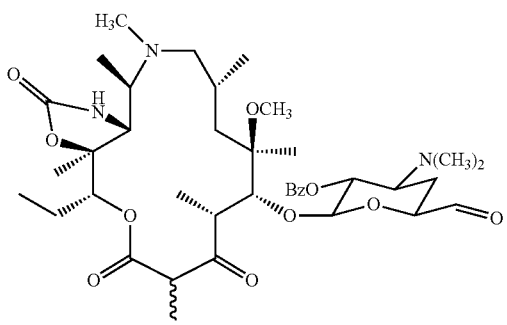

S4-3

(2R,3R,4S,6S)-4-(dimethylamino)-2-(((3aR,4R,7R,9R,10R,11R,13R,16R,16aR)-16-ethyl-9-methoxy-4,5,7,9,11,13,16a-heptamethyl-2,12,14-trioxohexadecahydrooxazolo[5,4-c][1]oxa[6]azacyclopentadecin-10-yl)oxy)-6-formyltetrahydro-2H-pyran-3-yl benzoate (S4-3)

A solution of S4-2 (162 mg, 0.21 mmol) in dichloromethane (2 mL) was cooled in an ice-water bath. DIEA (0.22 mL, 1.29 mmol) was added, followed by dimethyl sulfoxide (0.09 mL, 1.29 mmol) and the mixture was stirred for 1 minute, then SO$_3$-pyridine complex (103 mg, 0.65 mmol) was added in one portion and the resulting mixture was stirred at 0° C. The reaction was complete by LC/MS after 1 hour. The reaction was diluted with ethyl acetate and washed sat. aq NaHCO$_3$, brine, dried over MgSO$_4$, filtered and concentrated in vacuo to give a title compound as white solid (140 mg, 0.19 mmol, 87%). The crude S4-3 was used in the next step without further purification. MS (ESI+) m/z: 382.8 [M+H$_2$O+2H]$^{2+}$.

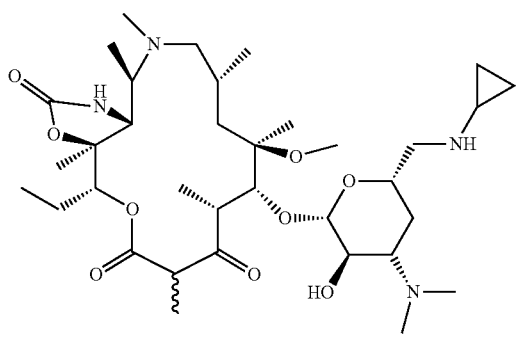

161

3-Descladinosyl-3-oxo-6-O-methyl-11,12-dideoxy-12,11-(oxycarbonylimino)-6'-cyclopropylamino Azithromycin (161)

A solution of S4-3 (28 mg, 0.04 mmol) in dichloromethane (0.5 mL) was added with cyclopropylamine (5.19 uL, 0.08 mmol) followed by acetic acid (6.4 uL, 0.1 mmol). Sodium triacetoxylborohydride (11.9 mg, 0.06 mmol) was added sequentially and the reaction mixture was stirred at room temperature. Upon completion by UPLC, the reaction mixture was diluted with dichloromethane and poured into sat. aq. NaHCO$_3$. The aqueous phase was extracted with dichloromethane and the combined organic extracts were dried over sodium sulfate, filtered and concentrated in vacuo. The residue was purified with by silica gel chromatography (ISCO 4 g column, 0-10% MeOH/CH$_2$Cl$_2$, 0.5% NH$_4$OH) to give reductive amination product as a white foam (20 mg, 0.03 mmol, 68%). MS (ESI+) m/z: 263.2 [M+3H]$^{3+}$, 394.3 [M+2H]$^{2+}$, 786.4 [M+H]$^+$; This product was dissolved in methanol (0.5 mL) and heated at 60° C. until LC/MS indicated complete consumption of starting material (16 hours). The reaction mixture was cooled and concentrated in vacuo. The residue was purified by HPLC (MeCN-water-0.1% HCO$_2$H) to yield 161 as a bis-formate salt (3.52 mg, 20%). MS (ESI+) m/z: 228.5 [M+3H]$^{3+}$, 342.3 [M+2H]$^{2+}$, 683.4 [M+H]$^+$; $^1$H NMR (400 MHz, Chloroform-d) δ 8.51 (s, 1H), 4.74 (ddd, 0.5H), 4.56-4.49 (m, 1H), 4.37 (t, 1H), 4.13-3.97 (m, 1H), 3.86 (d, 1H), 3.67 (d, 1H), 3.48 (dt, 1H), 3.41-3.33 (m, 1H), 3.24 (s, 1H), 2.98 (s, 2H), 2.90 (d, 4H), 2.77 (s, 7H), 2.52-2.36 (m, 1.5H), 2.30 (t, 0.5H), 2.21-1.92 (m, 6H), 1.91-1.66 (m, 3H), 1.58 (d, 3H), 1.34 (s, 2H), 1.32-1.20 (m, 6H), 1.20-1.11 (m, 3H), 1.11-0.96 (m, 7H), 0.93 (dd, 3H), 0.64-0.51 (m, 2H), 0.51-0.34 (m, 2H).

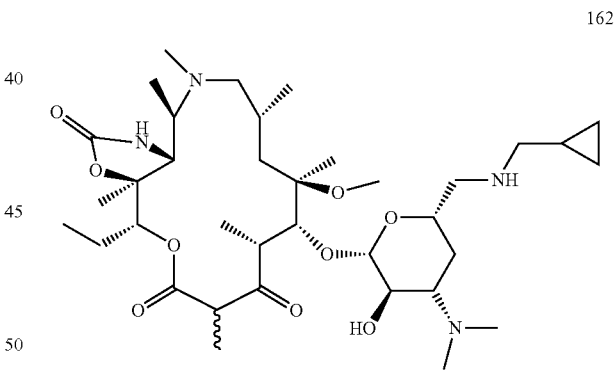

162

3-Descladinosyl-3-oxo-6-O-methyl-11,12-dideoxy-12,11-(oxycarbonylimino)-6'-cyclopropylmethylamino Azithromycin (162)

Prepared according to the methods of 161, substituting cyclopropylamine gave 162. MS (ESI+) m/z: 233.3 [M+3H]$^{3+}$, 349.4 [M+2H]$^{2+}$, 696.4 [M+H]$^+$; 1H NMR (400 MHz, Methanol-d$_4$) δ 8.49 (s, 3H), 4.74 (dd, 0.5H), 4.63 (d, 0.5H), 4.54 (dd, 1H), 4.36 (d, 1H), 4.16-3.86 (m, 2H), 3.68 (d, 1H), 3.51 (dt, 1H), 3.47-3.36 (m, 1H), 3.29-3.19 (m, 2H), 3.15-3.06 (m, 4H), 3.05-2.94 (m, 1H), 2.91 (s, 1H), 2.79 (s, 6H), 2.48 (dd, 0.5H), 2.28 (d, 2H), 2.09 (t, 2H), 1.94 (d, m, 2H), 1.83-1.66 (m, 3H), 1.63 (d, 3H), 1.33 (dd, 8H), 1.22-1.08 (m, 5H), 1.05-0.93 (m, 7H), 0.70 (d, 2H), 0.52-0.35 (m, 2H).

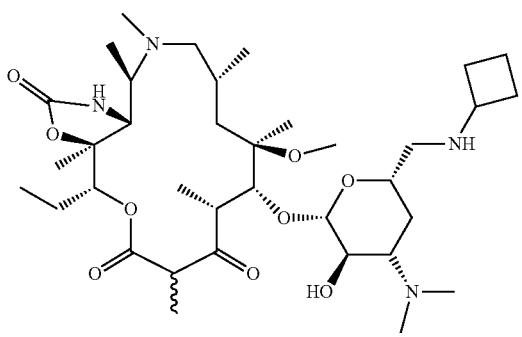

163

3-Descladinosyl-3-oxo-6-O-methyl-11,12-dideoxy-12,11-(oxycarbonylimino)-6'-cyclobutylamino Azithromycin (163)

Prepared according to the methods of 161, substituting cyclobutylamine gave 163. MS (ESI+) m/z: 233.3 [M+3H]³⁺, 349.3 [M+2H]²⁺, 697.4 [M+H]⁺; ¹H NMR (400 MHz, Methanol-d₄) δ 8.51 (s, 2H), 4.74 (m, 0.5H), 4.55 (t, 1H), 4.43-4.30 (m, 1H), 4.14-4.00 (m, 0.6H), 3.90 (d, 0.4H), 3.87-3.70 (m, 2H), 3.68 (d, 0.5H), 3.60-3.41 (m, 1.5H), 3.24 (m, 1H), 3.05 (s, 2H), 3.01-2.94 (m, 1H), 2.91 (s, 2H), 2.80 (d, 0.5H), 2.72 (d, 6H), 2.48 (dd, 1H), 2.34 (d, 2H), 2.24-1.94 (m, 8H), 1.94-1.76 (m, 5H), 1.76-1.50 (m, 5H), 1.40-1.25 (m, 7H), 1.25-1.12 (m, 3H), 1.12-0.87 (m, 9H).

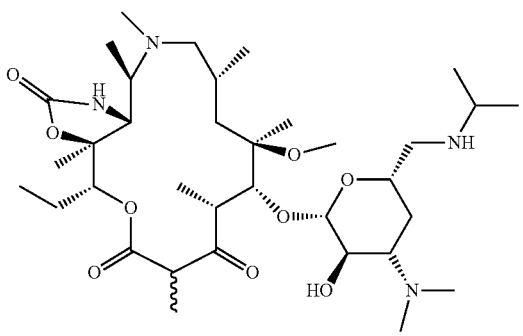

164

3-Descladinosyl-3-oxo-6-O-methyl-11,12-dideoxy-12,11-(oxycarbonylimino)-6'-isopropylamino Azithromycin (164)

Prepared according to the methods of 161, substituting isopropylamine gave 164. MS (ESI+) m/z: 229.2 [M+3H]³⁺, 343.3 [M+2H]²⁺, 685.4 [M+H]⁺; ¹H NMR (400 MHz, Methanol-d₄) δ 8.53 (s, 2H), 4.76-4.67 (m, 0.4H), 4.57 (d, 0.4H), 4.54-4.47 (m, 0.6H), 4.35 (t, 1H), 4.17-4.00 (m, 0.6H), 3.87 (m, 1.4H), 3.67 (d, 0.6H), 3.53-3.39 (m, 1.6H), 3.27-3.09 (m, 4H), 3.03 (s, 3H), 2.90 (s, 1.6H), 2.80 (d, 0.4H), 2.64 (d, 6H), 2.53-2.34 (m, 1H), 2.19-1.90 (m, 6H), 1.88-1.66 (m, 3H), 1.66-1.50 (m, 4H), 1.36-1.23 (m, 13H), 1.20-1.11 (m, 3H), 1.01 (dt, 6H), 0.94 (t, 3H).

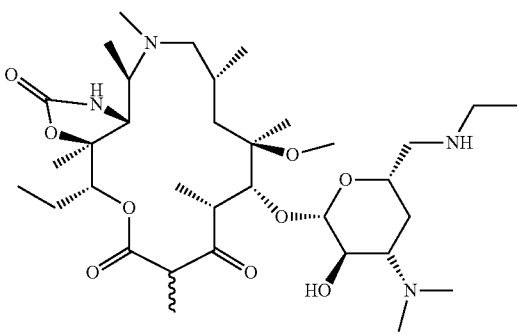

165

3-Descladinosyl-3-oxo-6-O-methyl-11,12-dideoxy-12,11-(oxycarbonylimino)-6'-ethylamino Azithromycin (165)

Prepared according to the methods of 161. substituting ethylamine gave 165. MS (ESI+) m/z: 224.5 [M+3H]³⁺, 336.3 [M+2H]²⁺, 671.4 [M+H]⁺; ¹H NMR (400 MHz. Methanol-d₄) δ 8.52 (s, 2H). 4.73 (dd, 0.6H), 4.59 (d, 0.4H), 4.54 (d, 0.6H), 4.36 (d, 1H), 4.09 (t, 0.4H), 3.99-3.82 (m, 1.6H), 3.68 (d, 0.6H), 3.53-3.41 (m, 1.4H), 3.27-3.12 (m, 5H), 3.05 (s, 4H), 2.90 (s, 2H), 2.80 (d, 1H), 2.70 (s, 7H), 2.48 (dd, 1H), 2.25-2.00 (m, 5H), 1.97 (s, 2H), 1.91-1.66 (m, 3H), 1.62 (d, 5H), 1.37-1.26 (m, 12H), 1.22-1.13 (m, 3H), 1.07-0.90 (m, 10H).

TABLE 17

Exemplary Azaketolides.

| Compound No. | Structure |
|---|---|
| 161 | 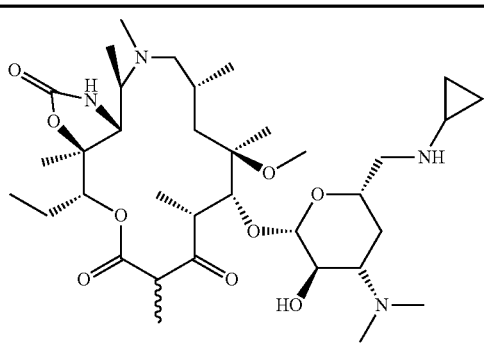 |

TABLE 17-continued

Exemplary Azaketolides.

| Compound No. | Structure |
| --- | --- |
| 162 | 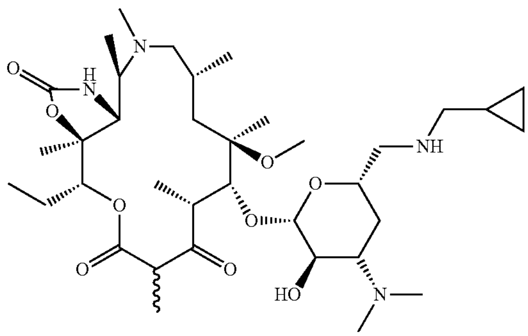 |
| 163 | 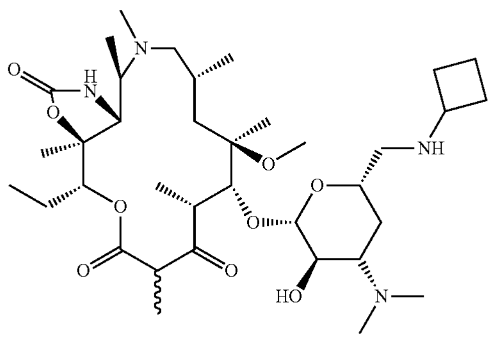 |
| 164 | 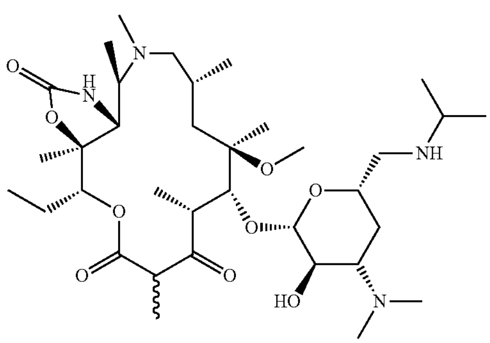 |
| 165 | 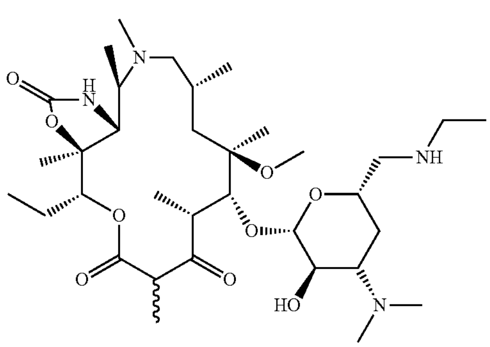 |

Scheme 27.

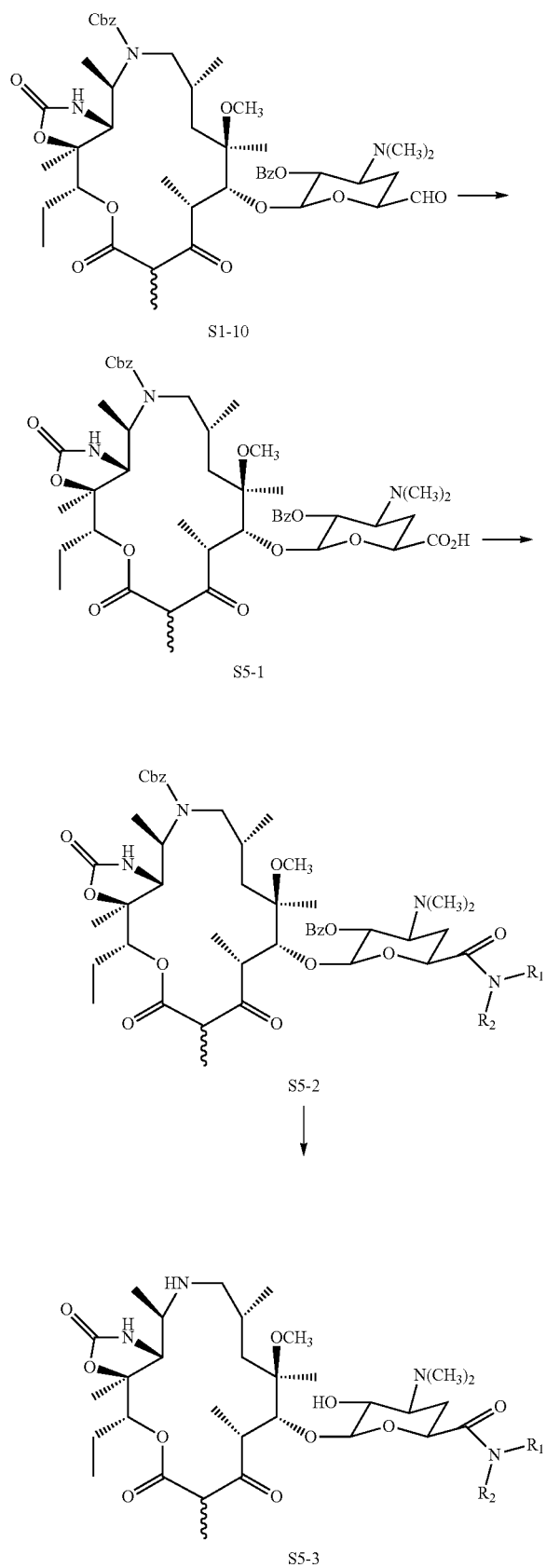

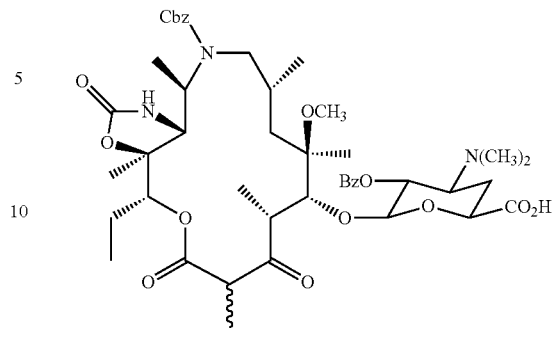

3-Descladinosyl-3-oxo-6-O-methyl-N9a-desmethyl-N9a-carbonylbenzyloxy-11,12-dideoxy-12,11-(oxy-carbonylimino)-5'-desmethyl-5'-carboxyl Azithromycin (S5-1)

In a 20 mL vial was a solution of S1-10-1 (35 mg, 40.4 µmol) in tBuOH (0.2 mL) and THF (0.1 mL) which was stirred at rt and 2-methyl-2-butene (100 µL, 942 µmol) was added. A solution of sodium chlorite (11 mg, 121 µmol) and NaH$_2$PO$_4$ (70 mg, 448 µmol) in water (0.2 mL) was added and the resulting mixture was stirred at rt for 1 hr. The reaction mixture was concentrated at 50 torr and the resulting suspension was diluted with EtOAc and poured into satd aq sodium sulfite. The aqueous phase was extracted 3× w/ EtOAc, then the combined organic phases were dried over Na$_2$SO$_4$, filtered, concentrated to give crude S5-1 as a white solid (30 mg, used as is). MS (ESI+) m/z: 882.2 [M+H]$^+$.

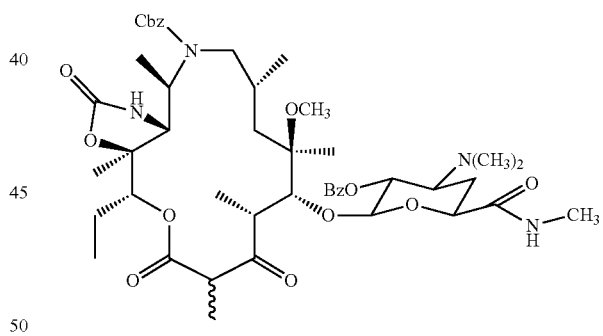

3-Descladinosyl-3-oxo-6-O-methyl-N9a-desmethyl-N9a-carbonylbenzyloxy-11,12-dideoxy-12,11-(oxy-carbonylimino)-5'-desmethyl-5'-(N-methylcarboxamido) Azithromycin (S5-2-1)

In a 5 mL vial was a solution of S5-1 (34 mg, 38.5 µmol) in DMF (0.5 mL) which was cooled to 0° C. 1-[Bis(dimethylamino)methylene]-1H-1,2,3-triazolo[4,5-b]pyridinium 3-oxide hexafluorophosphate (HATU) (22 mg, 58 µmol), then DIEA (20 µL, 114 µmol) were added and the resulting mixture was stirred for 3 minutes, then amine (20 µL, 2.0 M in THF, 40 µmol) was added, and the mixture was stirred at 0° C. for 90 minutes. The reaction mixture was diluted with EtOAc and washed 2× w/ NaHCO$_3$ and 1× w/ brine, dried over Na$_2$SO$_4$, filtered and concentrated. The residue was purified by column chromatography on silica gel (elution with 0-10% MeOH-DCM+0.5% of 30% aq NH₄OH) to give S5-2-1 as a gold film (30 mg, used as is). MS (ESI+) m/z: 895.0 [M+H]⁺.

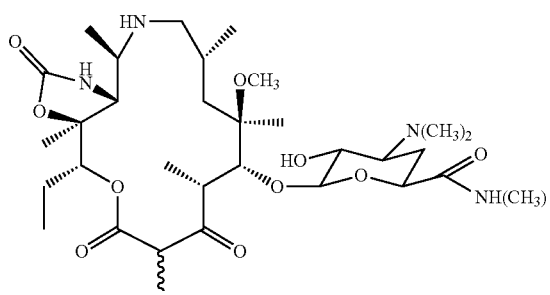

166

3-Descladinosyl-3-oxo-6-O-methyl-N9a-desmethyl-11,12-dideoxy-12,11-(oxycarbonylimino)-5'-desmethyl-5'-(N-methylcarboxamido) Azithromycin (166)

S5-2-1 (30 mg) was dissolved in MeOH (1.0 mL) and heated at 60° C. for 3 h, then allowed to cool. The solution was treated with aqueous HCl (3.0 M, 23 μL, 69 μmol) and concentrated. The residue was placed under nitrogen, dissolved in MeOH (0.5 mL) and degassed by sonication. 5% Pd/C was added and the vial was purged and backfilled with hydrogen 5×, then stirred under static hydrogen for 2 h, then filtered through a syringe filter with the aid of MeOH and concentrated. The hydrogenation process was repeated once more, and the resulting residue was purified by HPLC (elution with 5-40% MeCN-water-0.1% HCO₂H) to give 166 as a formate salt (4.7 mg, 11% over 5 steps from S1-9). MS (ESI+) m/z: 329.4 [M+2H]²⁺, 657.4 [M+H]⁺; ¹H NMR (400 MHz, Methanol-d₄) δ 8.40 (s, 1H), 4.95 (dd, 1H), 4.46-4.39 (m, 2H), 4.03 (dd, 1H), 3.40-3.23 (m, 3H), 3.16 (d, 2H), 3.04-2.90 (m, 5H), 2.82 (dd, 1H), 2.73 (s, 3H), 2.71 (d, 1H), 2.63 (d, 1H), 2.59 (s, 1H), 2.56 (s, 5H), 2.18 (ddd, 1H), 2.07 (t, 1H), 1.79 (dtd, 2H), 1.68 (d, 1H), 1.65-1.50 (m, 4H), 1.50-1.34 (m, 2H), 1.42 (s, 3H) 1.33-1.17 (m, 10H), 1.19 (s, 1H), 1.16-1.08 (m, 2H), 1.04 (dd, 3H), 0.92 (d, 3H), 0.84 (t, 4H).

167

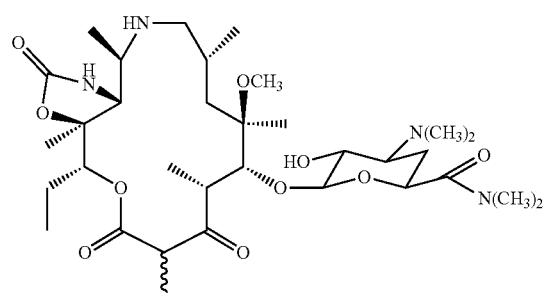

3-Descladinosyl-3-oxo-6-O-methyl-N9a-desmethyl-11,12-dideoxy-12,11-(oxycarbonylimino)-5'-desmethyl-5'-(N,N-dimethylcarboxamido) Azithromycin (167)

Prepared according to the methods of 166, substituting dimethylamine gave 167 as a formate salt (6.1 mg). MS (ESI+) m/z: 336.4 [M+2H]²⁺, 671.4 [M+H]⁺; ¹H NMR (400 MHz, Methanol-d₄) δ 8.54 (s, 1H), 5.06 (dd, 1H), 4.60 (d, 1H), 4.57-4.42 (m, 2H), 3.56-3.35 (m, 4H), 3.19-3.05 (m, 3H), 3.02 (d, 6H), 2.93-2.80 (m, 2H), 2.62 (s, 6H), 2.08-1.81 (m, 5H), 1.81-1.56 (m, 4H), 1.50-1.12 (m, 14H), 1.10 (d, 3H), 1.01 (d, 3H), 0.93 (t, 3H).

168

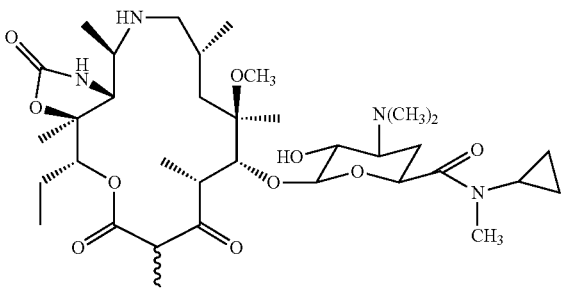

3-Descladinosyl-3-oxo-6-O-methyl-N9a-desmethyl-11,12-dideoxy-12,11-(oxycarbonylimino)-5'-desmethyl-5'-(N,N-cyclopropyl(methyl)carboxamido) Azithromycin (168)

Prepared according to the methods of 167, substituting cyclopropyl(methyl)amine gave 168 as a formate salt (4.6 mg). MS (ESI+) m/z: 349.4 [M+2H]²⁺, 697.5 [M+H]⁺; ¹H NMR (400 MHz, Methanol-d₄) δ 8.55 (s, 1H), 5.04 (dd, 1H), 4.66-4.43 (m, 2H), 4.11 (q, 1H), 3.52-3.40 (m, 2H), 3.20-3.03 (m, 4H), 2.98 (d, 6H), 2.83 (ddd, 3H), 2.57 (s, 6H), 2.06-1.80 (m, 5H), 1.80-1.56 (m, 4H), 1.45-1.11 (m, 14H), 1.10-0.80 (m, 4H), 1.08 (d, 3H), 1.00 (d, 3H), 0.93 (t, 3H), 0.67-0.57 (m, 0.4H).

TABLE 18

Exemplary Azaketolides.

| Compound No. | Structure |
|---|---|
| 166 | 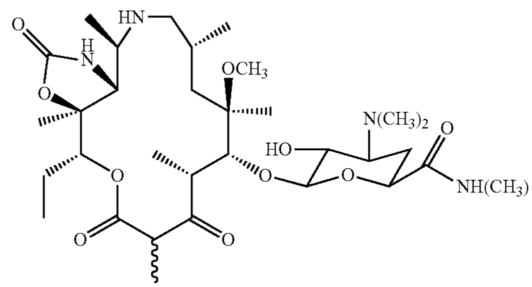 |
| 167 | 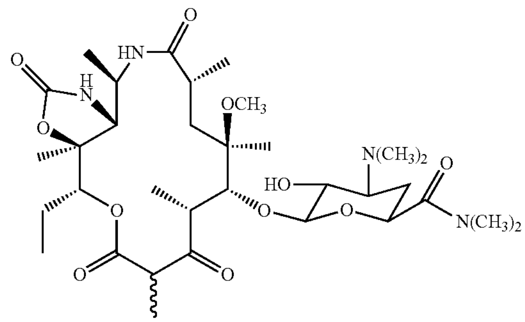 [SMILES: CC[C@H]1OC(=O)C(C)C(=O)[C@H](C)[C@@H](OC2OC(C(=O)N(C)C)CC(N(C)C)C2O)[C@](C)(OC)C[C@@H](C)C(=O)N[C@H](C)[C@H]2NC(=O)O[C@@]21C] |
| 168 | 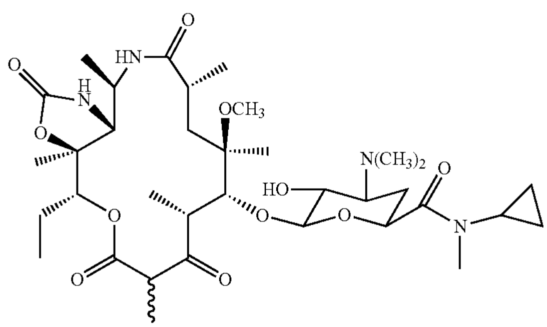 [SMILES: CC[C@H]1OC(=O)C(C)C(=O)[C@H](C)[C@@H](OC2OC(C(=O)N(C)C3CC3)CC(N(C)C)C2O)[C@](C)(OC)C[C@@H](C)C(=O)N[C@H](C)[C@H]2NC(=O)O[C@@]21C] |
| 193 | 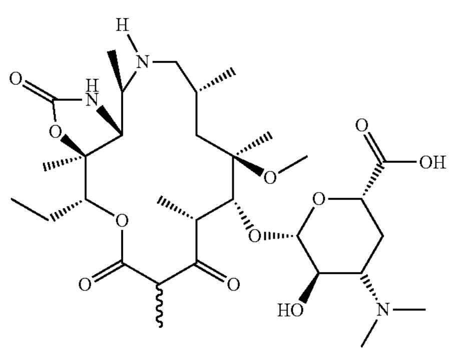 |

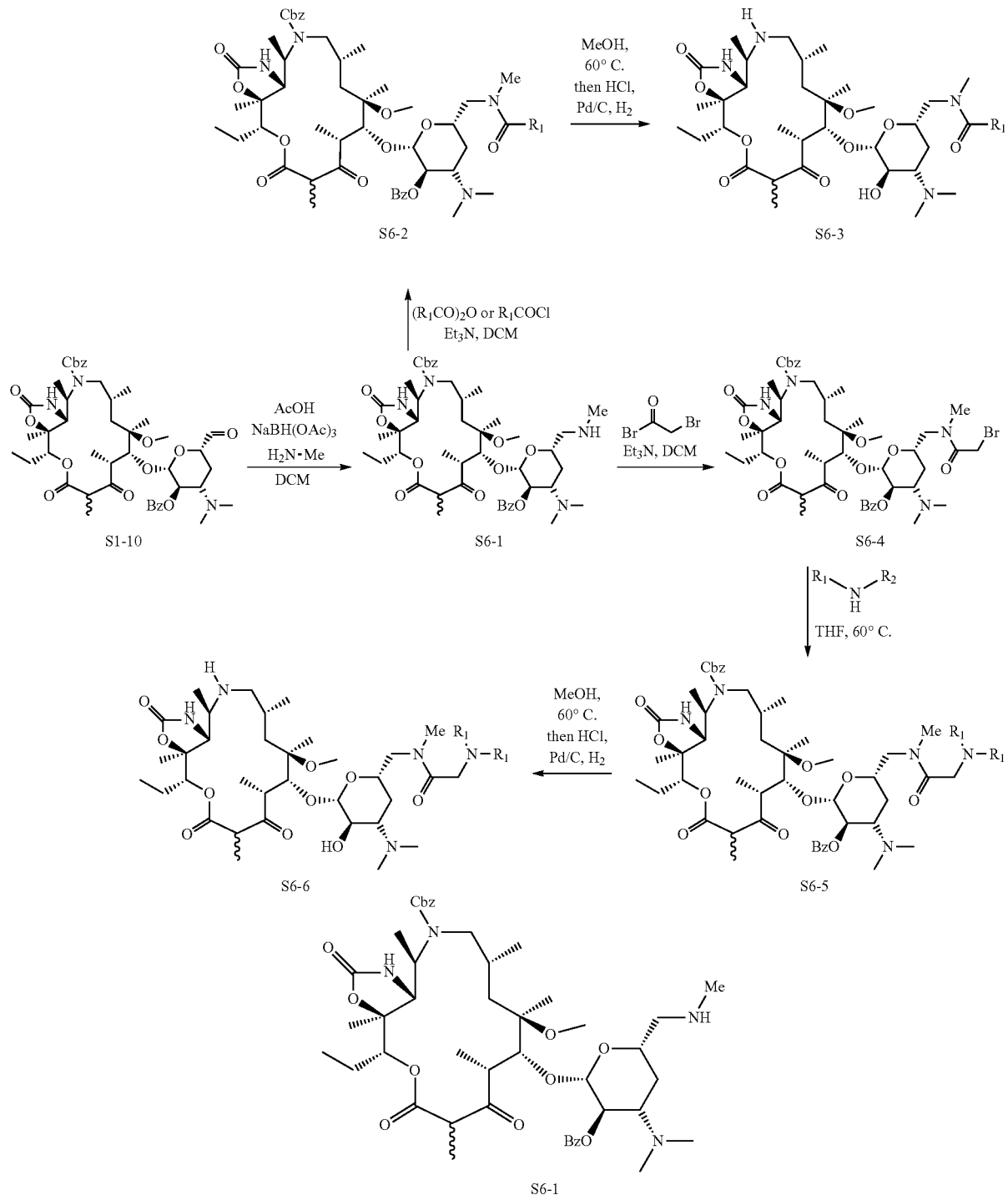

Scheme 28.

3-Descladinosyl-3-oxo-6-O-methyl-N9a-desmethyl-N9a-carbonylbenzyloxy-11,12-dideoxy-12,11-(oxy-carbonylimino)-5'-benzoyloxy-6'-(methylamino) Azithromycin (S6-1)

In a 5 mL vial was a solution of methyl amine (2M in THF, 2 equiv, 0.18 mL, 0.37 mmol), acetic acid (3 equiv, 0.031 mL, 0.55 mmol) and crude aldehyde S1-10 (1 equiv, 160 mg, 0.18 mmol) in DCM to give a colorless solution which was stirred at rt for 30 min. NaBH(OAc)$_3$ (1.5 equiv, 58.5 mg, 0.28 mmol) was added in one portion and the reaction was stirred at rt until LC/MS indicated complete consumption of starting material (2 hours). The reaction mixture was diluted with DCM and poured into satd aq NaHCO$_3$. The aqueous phase was extracted with DCM and the combined organic phases were dried over MgSO$_4$, filtered and concentrated. The residue was purified on 4 g of silica gel (elution with 0-10% MeOH-DCM+0.5% of 30% aq NH$_4$OH) to yield S6-1 (108 mg, 0.12 mmol, 66.6% yield).

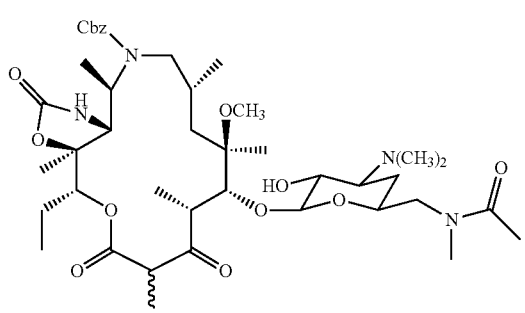

S6-2-1

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-(N-methylacetamido) Azithromycin (S6-2-1)

To a solution of the amine S6-1 (1 equiv, 20 mg, 0.023 mmol) in DCM was added Et$_3$N (3 equiv, 9.4 µL, 0.068 mmol) and Ac$_2$O (1.5 equiv, 3.2 µL, 0.034 mmol) at rt. The reaction mixture was stirred at rt for 1 h. LCMS shows full conversion of the starting material. The reaction mixture was diluted with DCM and poured into satd aq NaHCO$_3$. The aqueous phase was extracted with DCM and the combined organic phases were dried over MgSO$_4$, filtered and concentrated. The residue was purified on 4 g of silica gel (elution with 0-10% MeOH-DCM+0.5% of 30% aq NH$_4$OH) to yield the desired product S6-2-1 (18.8 mg, 90.3% yield).

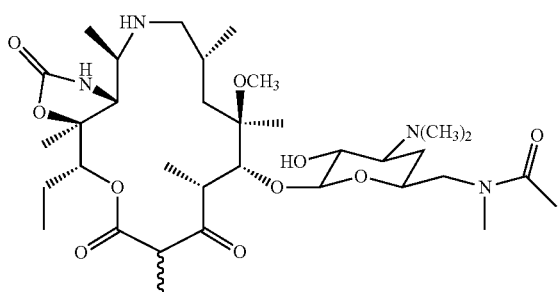

169

3-Descladinosyl-3-oxo-6-O-methyl-N9a-desmethyl-11,12-dideoxy-12,11-(oxycarbonylimino)-6'-(N-methyl-N-acetylamino) Azithromycin (169)

Compound S6-2-1 was dissolved in MeOH (0.5 mL) and heated at 60° C. until LC/MS indicated complete consumption of starting material (16 hours). The reaction mixture was cooled, and aqueous HCl (12 M, 3 equiv, 5 µL) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% HCO$_2$H) to give 169 as a bis-formate salt (7.4 mg, 50%). MS (ESI+) m/z: 343.2 [M+2H]$^{2+}$, 685.4 [M+H]$^+$; $^1$H NMR (400 MHz, Methanol-d$_4$) δ 8.43 (s, 1H), 4.96 (dd, 1H), 4.50 (d, 1H), 4.42 (d, 1H), 4.22 (dd, 1H), 3.85-3.39 (m, 4H), 3.38-3.24 (m, 3H), 3.14 (s, 2H), 3.11-2.92 (m, 7H), 2.91 (s, 1H), 2.89-2.77 (m, 3H), 2.66-2.50 (m, 8H), 2.09-1.92 (m, 5H), 1.86-1.75 (m, 3H), 1.68-1.63 (m, 1H), 1.62-1.50 (m, 3H), 1.49-1.35 (m, 6H), 1.32 (dd, 2H), 1.27-1.04 (m, 14H), 1.04-0.99 (m, 4H), 0.94-0.78 (m, 8H).

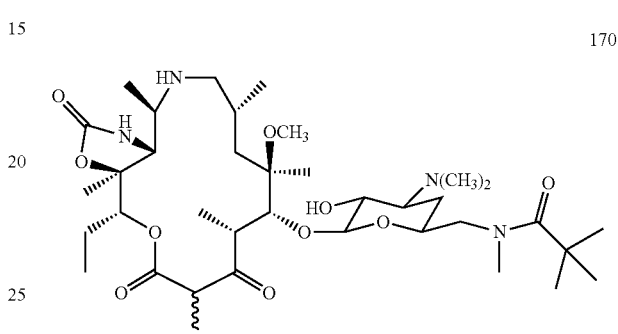

170

3-Descladinosyl-3-oxo-6-O-methyl-N9a-desmethyl-11,12-dideoxy-12,11-(oxycarbonylimino)-6'-(N-methyl-N-pivaloylamino) Azithromycin (170)

Prepared according to the methods of 169, substituting pivaloyl chloride gave 170 as a mono-formate salt (10.14 mg). MS (ESI+) m/z: 364.2 [M+2H]$^{2+}$, 727.4 [M+H]$^+$; $^1$H NMR (400 MHz, Methanol-d$_4$) δ 8.44 (s, 1H), 4.96 (dd, 1H), 4.48 (d, 1H), 4.21 (d, 1H), 3.84-3.64 (m, 3H), 3.33-3.23 (m, 6H), 3.04-2.85 (m, 7H), 2.82-2.70 (m, 3H), 2.51 (d, 1H), 2.47 (s, 7H), 1.90 (t, 2H), 1.84-1.74 (m, 3H), 1.67-1.50 (m, 4H), 1.41 (s, 4H), 1.39-1.33 (m, 1H), 1.33-1.16 (m, 28H), 1.11 (s, 1H), 1.09-0.95 (m, 5H), 0.93-0.78 (m, 9H).

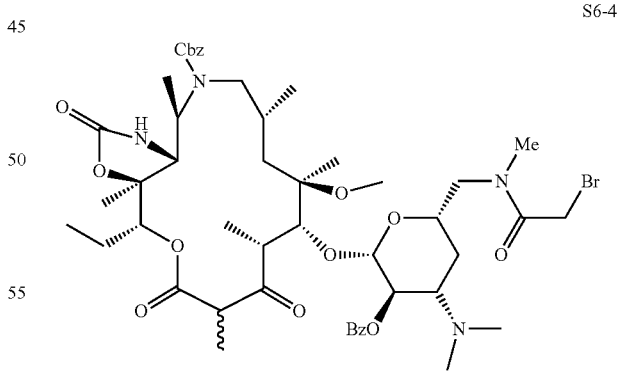

S6-4

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-(2-bromo-N-methylacetamido) Azithromycin (S6-4)

To a solution of S6-1 (1 equiv, 66 mg, 0.075 mmol) in DCM (2 mL) was added Et$_3$N (3 equiv, 31 µL, 0.22 mmol)

and bromoacetyl bromide (1.2 equiv, 9.8 μL, 0.11 mmol) at 0° C. The reaction mixture was stirred at rt for 1 h. LCMS shows full conversion of the starting material. The reaction mixture was diluted with DCM and poured into satd aq NaHCO$_3$. The aqueous phase was extracted with DCM and the combined organic phases were dried over MgSO$_4$, filtered and concentrated. The crude product was used in the next step without further purification.

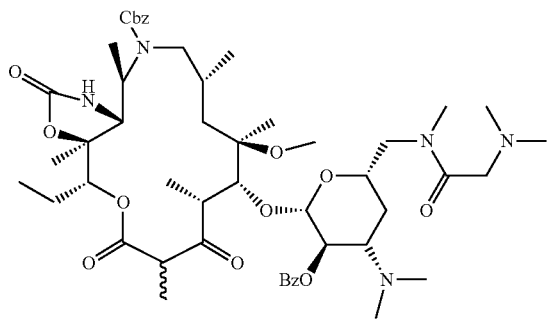

S6-5-1

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-((2-(dimethylamino)-N-methylacetamido) Azithromycin (S6-5-1)

The crude S6-4 was dissolved in THF (1 mL) and dimethylamine (2M in THF, 2 equiv, 0.42 mL, 0.018 mmol) was added. The reaction mixture was heated at 60° C. for 2 h. LCMS shows full conversion of the starting materials. The reaction mixture was concentrated and used in the next step without further purification.

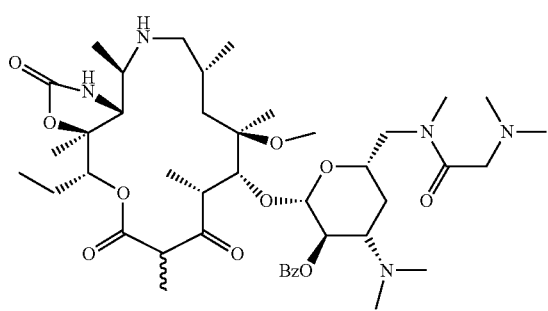

171

3-Descladinosyl-3-oxo-6-O-methyl-N9a-desmethyl-11,12-dideoxy-12,11-(oxycarbonylimino)-6'-N-methyl-2"-dimethylamino-acetamide Azithromycin (171)

The crude S6-5-1 (1 equiv, 14 mg. 0.014 mmol) was dissolved in MeOH (0.5 mL) and heated at 60° C. until LC/MS indicated complete consumption of starting material (16 hours). The reaction mixture was cooled, and aqueous HCl (12 M, 3 equiv, 3.6 μL) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% HCO$_2$H) to give 171 as a bis-formate salt (5.08 mg, 49%). MS (ESI+) m/z: 243.5 [M+3H]$^{3+}$, 364.7 [M+2H]$^{2+}$, 728.4 [M+H]$^+$; $^1$H NMR (400 MHz, Methanol-d$_4$) δ 8.53 (s, 2H), 3.91 (d, 3H), 3.49 (d, 3H), 3.22 (s, 3H), 3.13 (d, 3H), 3.06 (d, 6H), 2.69 (d, 3H), 2.38 (t, 1H), 2.05 (q, 1H), 1.99-1.83 (m, 3H), 1.83-1.67 (m, 2H), 1.59 (d, 2H), 1.55 (s, 4H), 1.51 (d, 1H), 1.40-1.31 (m, 12H), 1.31-1.15 (m, 8H), 1.10-0.89 (m, 9H).

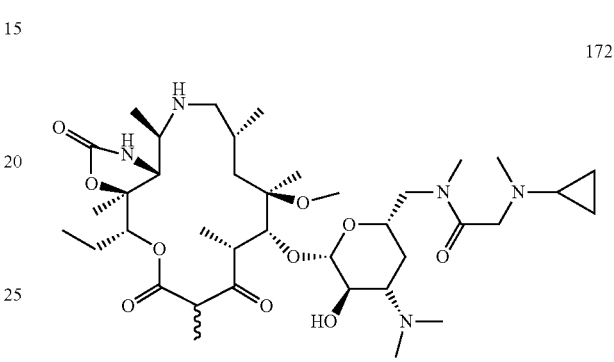

172

3-Descladinosyl-3-oxo-6-O-methyl-N9a-desmethyl-11,12-dideoxy-12,11-(oxycarbonylimino)-6'-(N-methyl-N-(2-cyclopropylamino)acetylamino) Azithromycin (172)

Prepared according to the methods of 171, substituting N-cyclopropyl,N-methyl amine gave 172 as a bis-formate salt (1.68 mg). MS (ESI+) m/z: 247.5 [M+3H]$^{3+}$, 370.7 [M+2H]$^{2+}$, 740.4 [M+H]$^+$; $^1$H NMR (400 MHz, Methanol-d$_4$) δ 8.44 (s, 2H), 4.96 (dt, 1H), 4.50 (d, 1H), 4.39 (dd, 1H), 4.19 (dd, 2H), 4.10 (d, 1H), 3.91 (dd, 1H), 3.84-3.66 (m, 3H), 3.66-3.42 (m, 5H), 3.30 (qt, 5H), 3.17 (s, 1H), 3.11 (s, 2H), 3.02 (s, 2H), 3.01-2.85 (m, 7H), 2.77 (dd, 2H), 2.46 (d, 7H), 2.20 (s, 1H), 2.15 (d, 1H), 1.92 (q, 2H), 1.80 (ddd, 3H), 1.65-1.48 (m, 4H), 1.48-1.39 (m, 4H), 1.39-1.27 (m, 5H), 1.23 (dd, 6H), 1.22-1.07 (m, 11H), 1.00 (dd, 5H), 0.90 (dd, 4H), 0.82 (t, 5H), 0.45-0.28 (m, 5H).

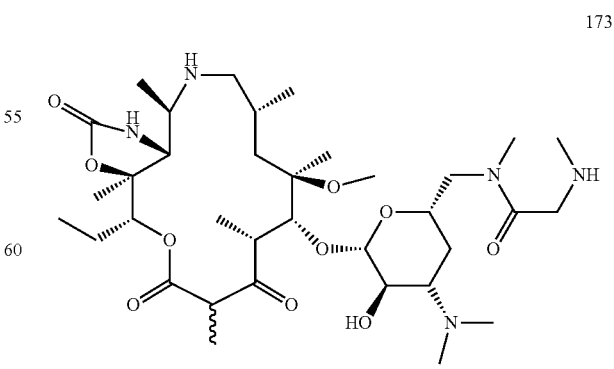

173

3-Descladinosyl-3-oxo-6-O-methyl-N9a-desmethyl-11,12-dideoxy-12,11-(oxycarbonylimino)-6'-N-methyl-2''-methylamino-acetamide Azithromycin (173)

Prepared according to the methods of 171, substituting methylamine gave 173 as a bis-formate salt (4.17 mg). MS (ESI+) m/z: 238.8 [M+3H]$^{3+}$, 357.7 [M+2H]$^{2+}$, 714.4 [M+H]$^{+}$; $^1$H NMR (400 MHz, Methanol-d$_4$) δ 8.38 (s, 2H), 4.96 (dd, 1H), 4.47 (d, 1H), 4.27 (dd, 2H), 3.94 (s, 1H), 3.86-3.75 (m, 2H), 3.65-3.57 (m, 1H), 3.43 (s, 1H), 3.35 (d, 3H), 3.29-3.24 (m, 1H), 3.17-3.03 (m, 6H), 2.94 (d, 5H), 2.73 (d, 1H), 2.66-2.51 (m, 9H), 2.15 (t, 2H), 2.06 (s, 1H), 1.91 (d, 2H), 1.78 (td, 3H), 1.67-1.55 (m, 3H), 1.53-1.40 (m, 5H), 1.36 (s, 1H), 1.31-0.99 (m, 22H), 0.93 (dd, 4H), 0.82 (t, 5H).

TABLE 19

Exemplary Azaketolides.

| Compound No. | Structure |
|---|---|
| 169 | 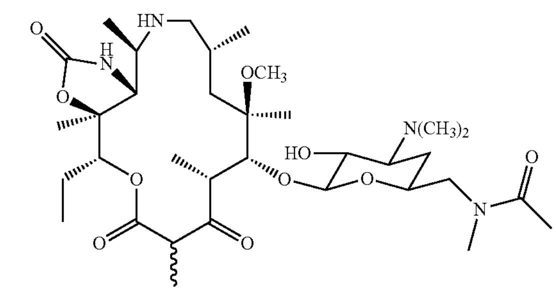 [SMILES: CC[C@H]1OC(=O)C(C)C(=O)[C@H](C)[C@@H](OC2OC(CN(C)C(C)=O)CC(N(C)C)C2O)[C@](C)(OC)C[C@@H](C)CN[C@H](C)[C@H]2NC(=O)O[C@@]21C] |
| 170 | 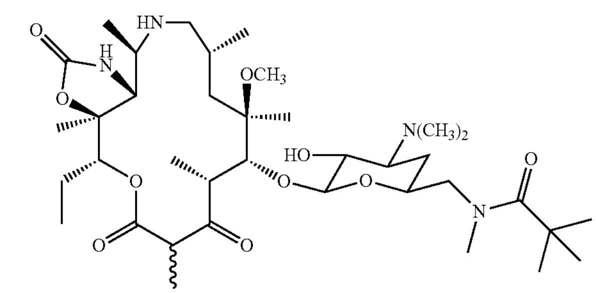 [SMILES: CC[C@H]1OC(=O)C(C)C(=O)[C@H](C)[C@@H](OC2OC(CN(C)C(=O)C(C)(C)C)CC(N(C)C)C2O)[C@](C)(OC)C[C@@H](C)CN[C@H](C)[C@H]2NC(=O)O[C@@]21C] |
| 171 | 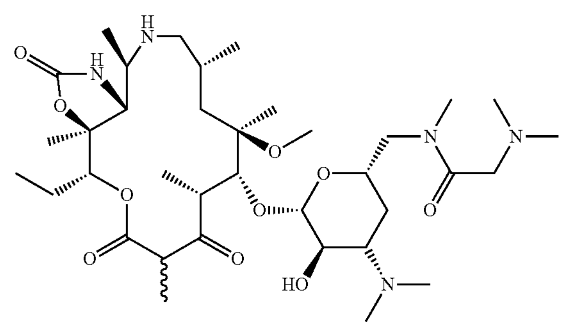 |
| 172 | 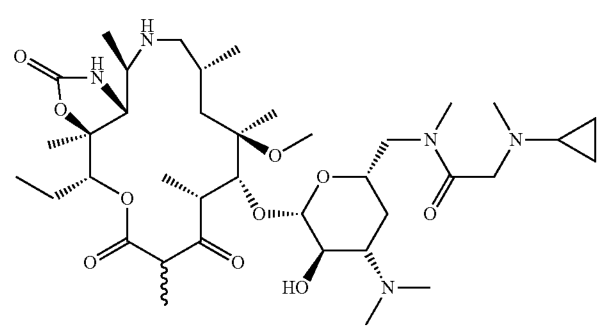 |

TABLE 19-continued
Exemplary Azaketolides.
| Compound No. | Structure |
|---|---|
| 173 | 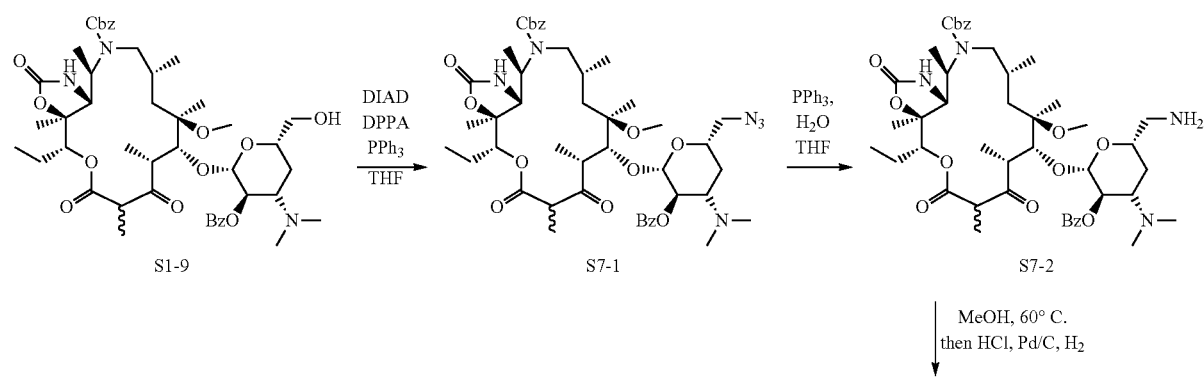 |
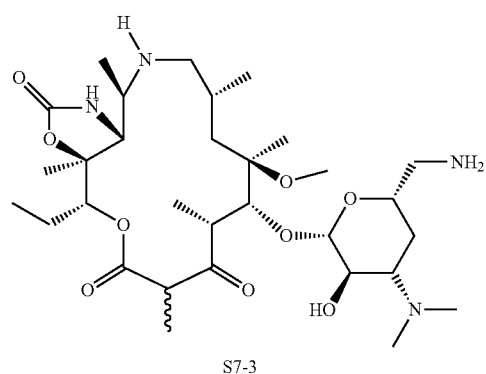

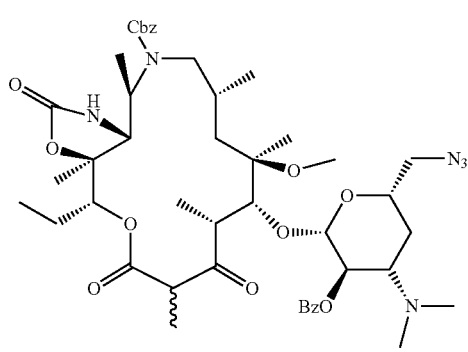

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-azido Azithromycin (S7-1)

To a solution of the substrate S1-9 (1 equiv, 12 mg, 0.0134 mmol) in dry THF (1 mL) was added $PPh_3$ (1.5 equiv, 5.4 mg, 0.021 mmol) and DPPA (1.4 equiv, 4.2 mg, 0.019 mmol). Then diisopropyl azodicarboxylate (DIAD) (1.2 equiv, 3.2 μL, 0.016 mmol) was added dropwise at rt. The reaction mixture was stirred at rt for 2 h. LCMS shows full conversion of the starting materials and the reaction was quenched by adding saturated aqueous $NaHCO_3$. The aqueous layer was extracted with DCM and combined organic layers were dried and concentrated and purified by a 4 g silica gel column (0-10% MeOH/DCM, 0.5% $NH_4OH$) to give S7-1 as a white solid (6 mg, 71% yield).

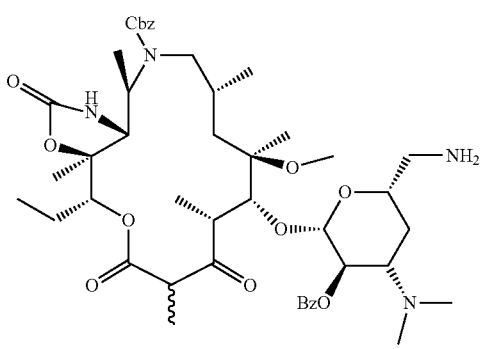

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-amino Azithromycin (S7-2)

Azide S7-1 (1 equiv, 6 mg, 0.0095 mmol) was dissolved in THF (0.5 mL) and $PPh_3$ (3 equiv, 7.5 mg, 0.028 mmol) and $H_2O$ (20 equiv, 3.4 μL, 0.019 mmol) were added. The reaction mixture was then heated at 55° C. for 8 h. LCMS shows full conversion of the starting materials and the reaction was quenched by adding saturated aqueous $NaHCO_3$. The aqueous layer was extracted with DCM and combined organic layers were dried and concentrated and purified by a 4 g silica gel column (0-16% MeOH/DCM, 0.5% $NH_4OH$) to give the amine as a white solid (2.3 mg, 28% yield).

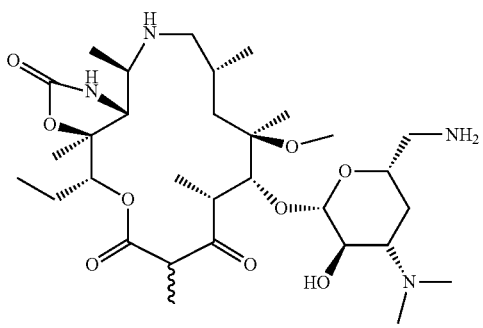

3-Descladinosyl-3-oxo-6-O-methyl-N9a-desmethyl-11,12-dideoxy-12,11-(oxycarbonylimino)-11-methyl-6'-amino Azithromycin (174)

Amine S7-2 (1 equiv, 2.3 mg, 0.0027 mmol) was dissolved in MeOH (0.5 mL) and heated at 60° C. until LC/MS indicated complete consumption of starting material (16 hours). The reaction mixture was cooled, and aqueous HCl (12 M, 3 equiv) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% $HCO_2H$) to yield 174 as a bis formate salt (0.8 mg, 10% in three steps). MS (ESI+) m/z: 210.5 $[M+3H]^{3+}$, 315.2 $[M+2H]^{2+}$, 629.4 $[M+H]^+$; $^1H$ NMR (400 MHz, Chloroform-d) δ 8.55 (s, 4H), 4.63-4.52 (m, 1H), 4.42 (d, 1H), 3.63 (d, 2H), 3.52-3.39 (m, 1H), 3.24-2.38 (m, 14H), 2.15-1.78 (m, 4H), 1.78-1.40 (m, 7H), 1.39-1.17 (m, 9H), 1.17-0.78 (m, 8H).

TABLE 20

Exemplary Azaketolides.

| Compound No. | Structure |
|---|---|
| 174 | 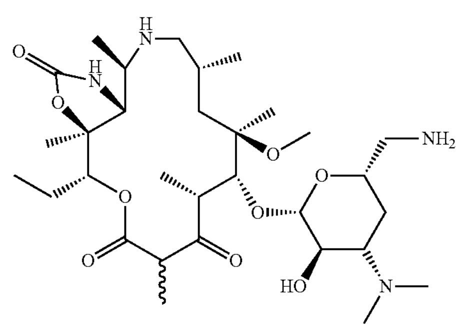 |

Scheme 30.

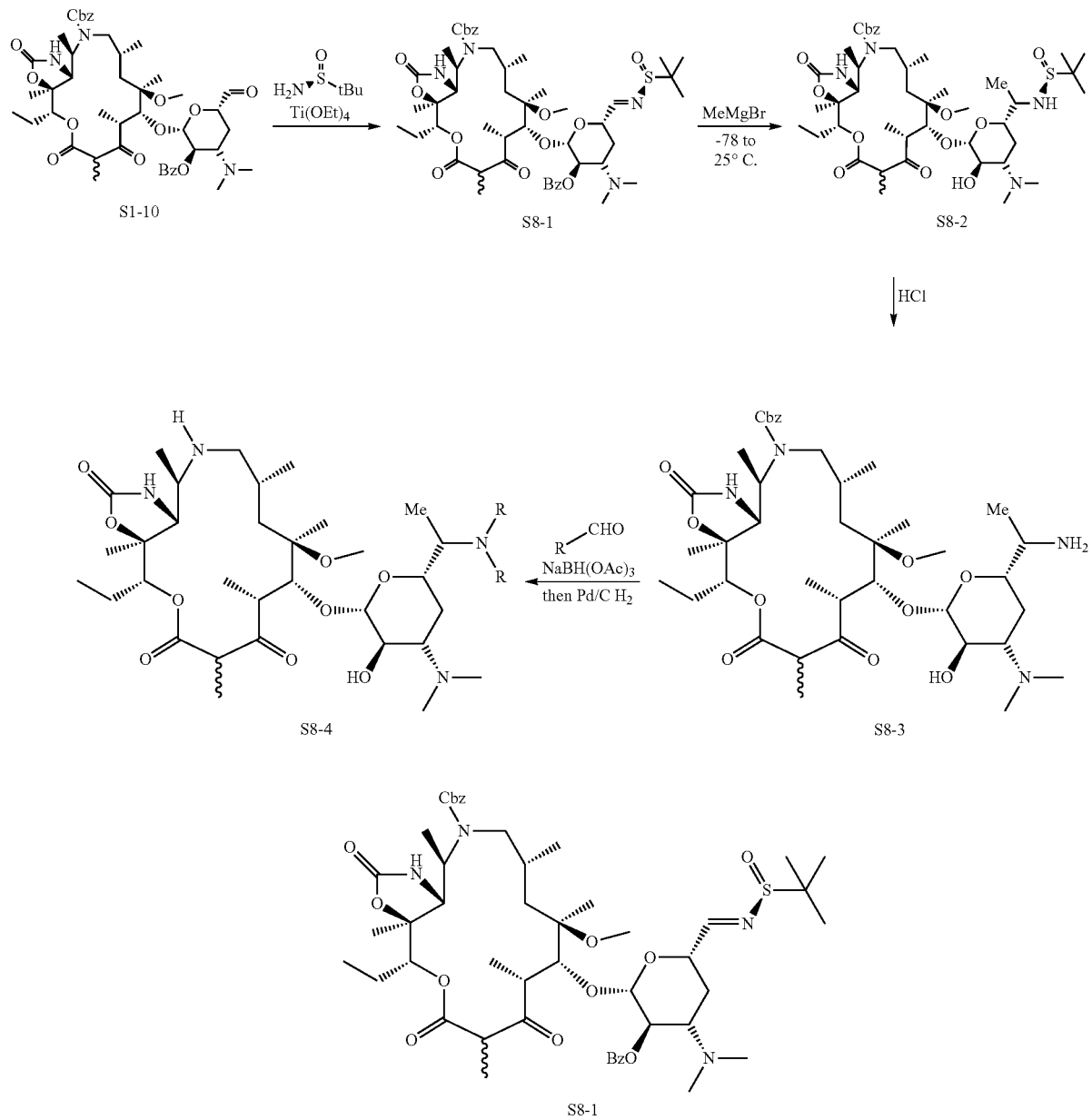

3-Descladinosyl-3-oxo-6-O-methyl-N9a-desmethyl-N9a-carbonylbenzyloxy-11,12-dideoxy-12,11-(oxycarbonylimino)-5'-benzoyloxy-6'-(((S)-tert-butylsulfinyl)imino) Azithromycin (S8-1)

To a solution of the aldehyde S1-10 (1 equiv, 33 mg, 0.038 mmol), amine (3 equiv, 13.8 mg, 0.11 mmol) in THF (2 mL) was added Ti(OEt)$_4$ (6 equiv, 52 mg, 0.23 mmol) at rt. The reaction mixture was stirred at rt for 30 min. LCMS shows the reaction was complete. The reaction mixture was diluted with DCM and washed with saturated aqueous NaHCO$_3$ solution. The aqueous layer was extracted with DCM and the combined organic layers were dried over MgSO$_4$, filtered and concentrated. The mixture was purified on 4 g of silica gel, elution with 0-10% MeOH-DCM-0.5% NH$_4$OH.

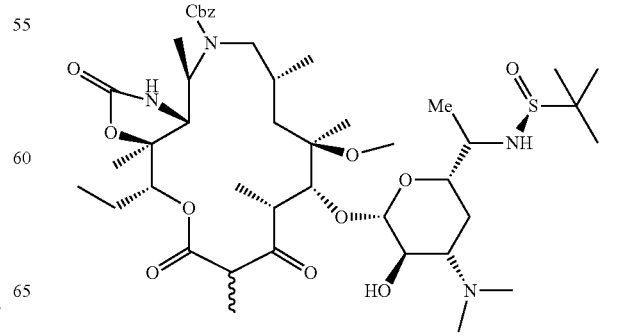

S8-2

3-Descladinosyl-3-oxo-6-O-methyl-N9a-desmethyl-N9a-carbonylbenzyloxy-11,12-dideoxy-12,11-(oxycarbonylimino)-6'-desmethyl-6'-((R)-1-(((S)-tert-butylsulfinyl)amino)ethyl) Azithromycin (S8-2)

The sulfinimine S8-1 (1 equiv, 29 mg, 0.030 mmol) was dissolved in DCM (1 mL) under $N_2$ atmosphere and was cooled to −78° C. MeMgBr (3.0 M in $Et_2O$, 10 equiv, 0.1 mL, 0.30 mmol) was added dropwise. The reaction mixture was allowed to stir at rt slowly. LCMS shows full conversion the starting materials after 2 h. The reaction was quenched with saturated aqueous $NH_4Cl$ and the aqueous layer was extracted with DCM. The combined organic layers were combined, dried and concentrated. The crude mixture was then dissolved in MeOH and heated at 55° C. for 16 h. LCMS shows two diastereomers are formed with a ratio of 3:2. The mixture was concentrated and used in the next step without further purification.

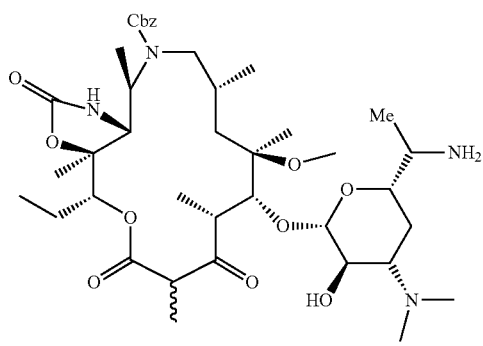

S8-3

3-Descladinosyl-3-oxo-6-O-methyl-N9a-desmethyl-N9a-carbonylbenzyloxy-11,12-dideoxy-12,11-(oxycarbonylimino)-6'-desmethyl-6'-((R)-1-aminoethyl) Azithromycin (S8-3)

The crude S8-2 was dissolved in MeOH and HCl in dioxane (4M, 2 equiv, 0.015 mL, 0.06 mmol) was added. The reaction mixture was stirred at rt for 2 h. LCMS shows full conversion of the SM and the reaction mixture was concentrated and purified on 4 g of silica gel (0-16% MeOH in DCM with 0.5% $NH_4OH$). The desired product was isolated as a white foam (13 mg) in 49% yield in two steps. MS (ESI+) m/z: 777.5 $[M+H]^+$.

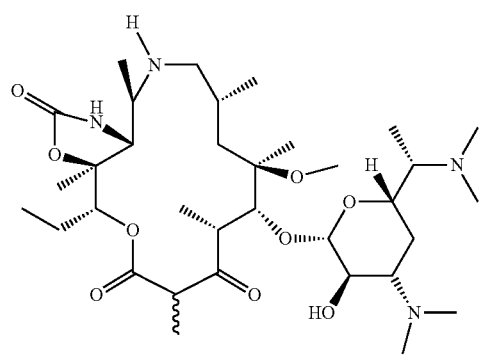

175

3-Descladinosyl-3-oxo-6-O-methyl-N9a-desmethyl-11,12-dideoxy-12,11-(oxycarbonylimino)-6'-((S)-(dimethylamino)ethyl) Azithromycin (175)

In a 5 mL vial was a solution of amine S8-3 (19.5 mg, 0.025 mmol) and formaldehyde (100 equiv, 0.2 mL, 2.5 mmol) in DCM (1 mL) to give a colorless solution which was stirred at rt for 30 min. $NaBH(OAc)_3$ (2.5 equiv, 13.2 mg, 0.0625 mmol) was added in one portion and the reaction was stirred at rt until LC/MS indicated complete consumption of starting material (10 min). The reaction mixture was diluted with DCM and poured into satd aq $NaHCO_3$. The aqueous phase was extracted with DCM and the combined organic phases were dried over $MgSO_4$, filtered and concentrated. The residue was purified on 4 g of silica gel (elution with 0-10% MeOH-DCM+0.5% of 30% aq $NH_4OH$) to yield the desired amine. The pure amine was dissolved in MeOH, and aqueous HCl (12 M, 3 equiv) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% $HCO_2H$) to yield the desired products, which is the minor isomer of S8-2, as a tri-formate salt (2.79 mg, 73%). MS (ESI+) m/z: 224.5 $[M+3H]^{3+}$, 336.2 $[M+2H]^{2+}$, 671.4 $[M+H]^+$; $^1H$ NMR (400 MHz, Methanol-$d_4$) δ 8.44 (s, 3H), 4.97 (dd, 1H), 4.47 (d, 1H), 4.27 (d, 1H), 3.73-3.63 (m, 1H), 3.39-3.29 (m, 3H), 3.29-3.23 (m, 1H), 3.19-3.06 (m, 3H), 3.02-2.89 (m, 6H), 2.86 (d, 1H), 2.75 (d, 1H), 2.65 (s, 6H), 2.57 (d, 3H), 2.52 (s, 5H), 2.46 (s, 1H), 2.40 (s, 1H), 2.37 (d, 1H), 2.05 (t, 1H), 1.93 (d, 1H), 1.86 (d, 1H), 1.79 (ddd, 2H), 1.68 (s, 1H), 1.66-1.50 (m, 4H), 1.47 (d, 1H), 1.43 (s, 3H), 1.41-1.32 (m, 2H), 1.32-1.13 (m, 19H), 1.13-1.01 (m, 6H), 1.01-0.73 (m, 10H).

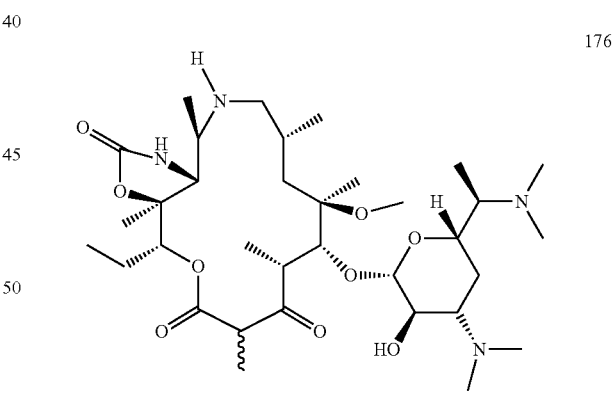

176

3-Descladinosyl-3-oxo-6-O-methyl-N9a-desmethyl-11,12-dideoxy-12,11-(oxycarbonylimino)-6'-((R)-(dimethylamino)ethyl) Azithromycin (176)

Prepared according to the methods of 175, using formaldehyde and the major isomer from S8-2, gave 176 as a tri-formate salt (4.48 mg). MS (ESI+) m/z: 224.5 $[M+3H]^{3+}$, 336.2 $[M+2H]^{2+}$, 671.4 $[M+H]^+$; $^1H$ NMR (400 MHz, Methanol-$d_4$) δ 8.44 (s, 3H), 4.97 (dd, 1H), 4.47-4.34 (m, 2H), 3.88 (d, 1H), 3.41-3.27 (m, 3H), 3.19-3.08 (m, 4H), 3.00-2.85 (m, 6H), 2.61 (d, 14H), 2.55-2.47 (m, 1H), 2.44 (s, 1H), 2.18 (t, 1H), 1.97-1.84 (m, 2H), 1.82-1.75 (m, 2H), 1.68-1.51 (m, 4H), 1.51-1.34 (m, 6H), 1.31-1.18 (m, 16H), 1.18-1.00 (m, 6H), 0.94 (d, 4H), 0.91-0.78 (m, 5H).

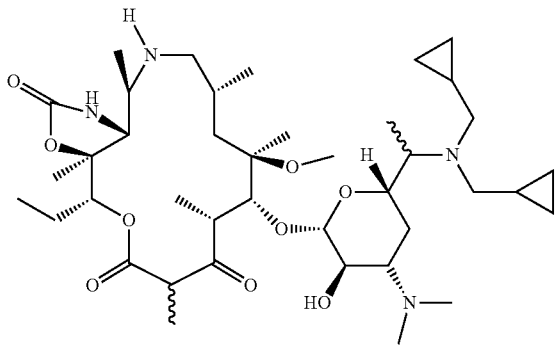

3-Descladinosyl-3-oxo-6-O-methyl-N9a-desmethyl-11,12-dideoxy-12,11-(oxycarbonylimino)-6'-((R,S)-(dicyclopropylmethylamino)ethyl) Azithromycin (177)

Prepared according to the methods of 175, using cyclopropylcarboxaldehyde gave 177 as a bis-formate salt (1.74 mg, 59%). MS (ESI+) m/z: 251.2 [M+3H]$^{3+}$, 376.2 [M+2H]$^{2+}$, 751.5 [M+H]$^{+}$; $^{1}$H NMR (400 MHz, Methanol-d$_4$) δ 8.45 (s, 2H), 5.00-4.92 (m, 1H), 4.36-4.27 (m, 1H), 4.01 (d, 1H), 3.76 (d, 1H), 3.34-3.24 (m, 2H), 2.94 (d, 5H), 2.87 (s, 1H), 2.77 (t, 3H), 2.60 (s, 1H), 2.51 (s, 1H), 2.46-2.41 (m, 4H), 1.93 (d, 1H), 1.89 (s, 1H), 1.79 (dd, 2H), 1.66-1.50 (m, 3H), 1.48 (t, 1H), 1.42 (s, 3H), 1.36-1.17 (m, 13H), 1.15-1.06 (m, 2H), 1.06-0.96 (m, 5H), 0.91 (s, 2H), 0.90-0.78 (m, 6H), 0.56 (d, 3H), 0.22 (s, 2H), 0.09 (s, 1H).

3-Descladinosyl-3-oxo-6-O-methyl-N9a-desmethyl-11,12-dideoxy-12,11-(oxycarbonylimino)-6'-((R,S)-(cyclopropylmethylamino)ethyl) Azithromycin (178)

Prepared according to the methods of 175, using cyclopropylcarboxaldehyde gave 178 as a bis-formate salt (5.25 mg, 85%). MS (ESI+) m/z: 233.1 [M+3H]$^{3+}$, 349.2 [M+2H]$^{2+}$, 697.4 [M+H]$^{+}$; $^{1}$H NMR (400 MHz, Methanol-d$_4$) δ 8.45 (s, 3H), 4.97 (dt, 1H), 4.47-4.28 (m, 2H), 3.81 (dd, 1H), 3.40-3.26 (m, 3H), 3.05-2.94 (m, 7H), 2.90 (d, 2H), 2.77 (t, 1H), 2.50 (dd, 7H), 2.16-2.05 (m, 1H), 1.90 (d, 1H), 1.80 (qd, 2H), 1.71 (s, 1H), 1.60 (ddd, 3H), 1.48 (d, 2H), 1.43 (s, 3H), 1.37 (d, 2H), 1.31-1.00 (m, 22H), 0.97-0.84 (m, 6H), 0.82 (d, 3H), 0.57 (dd, 2H), 0.28 (td, 2H).

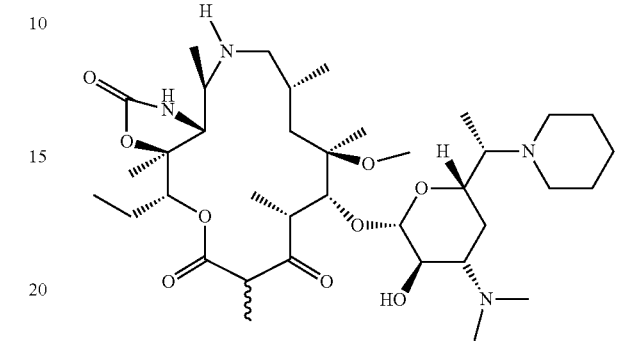

3-Descladinosyl-3-oxo-6-O-methyl-N9a-desmethyl-11,12-dideoxy-12,11-(oxycarbonylimino)-6'-((S)-1-(piperidin-1-yl)ethyl) Azithromycin (179)

Prepared according to the methods of 175, using glutaraldehyde gave 179 as a bis-formate salt (1.05 mg, 63%). MS (ESI+) m/z: 237.8 [M+3H]$^{3+}$, 356.2 [M+2H]$^{2+}$, 711.4 [M+H]$^{+}$; $^{1}$H NMR (400 MHz, Methanol-d$_4$) δ 8.42 (s, 2H), 4.96 (dd, 1H), 4.39-4.30 (m, 1H), 3.99-3.90 (m, 1H), 3.32 (dd), 3.18-3.06 (m, 3H), 3.01-2.94 (m, 1H), 2.91 (s, 2H), 2.83 (d, 1H), 2.57 (d, 1H), 2.48 (d, 3H), 2.06-1.91 (m, 2H), 1.84-1.76 (m, 1H), 1.72 (s, 2H), 1.68-1.62 (m, 1H), 1.57 (t, 3H), 1.49 (d, 1H), 1.43 (s, 2H), 1.39-1.17 (m, 13H), 1.13 (s, 1H), 1.07-0.95 (m, 3H), 0.95-0.76 (m, 6H), 0.65 (t, 1H).

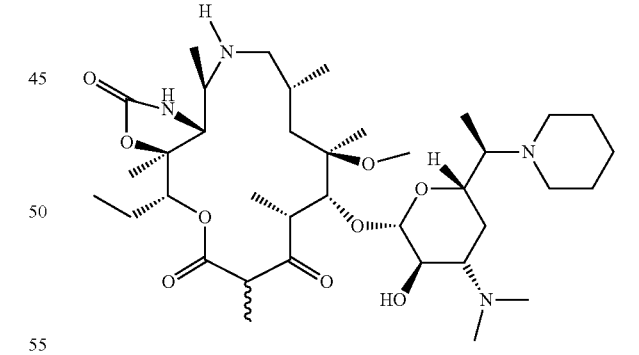

3-Descladinosyl-3-oxo-6-O-methyl-N9a-desmethyl-11,12-dideoxy-12,11-(oxycarbonylimino)-6'-((R)-1-(piperidin-1-yl)ethyl) Azithromycin (180)

Prepared according to the methods of 175, using glutaraldehyde gave 180 as a bis-formate salt (1.25 mg, 75%). MS (ESI+) m/z: 237.8 [M+3H]$^{3+}$, 356.2 [M+2H]$^{2+}$, 711.4 [M+H]$^{+}$; $^{1}$H NMR (400 MHz, Methanol-d$_4$) δ 8.46 (s, 3H), 4.96 (s, 1H), 4.45 (s, 1H), 4.24 (d, 1H), 3.73 (s, 1H), 3.63-3.42 (m, 2H), 3.31 (dd, 4H), 2.98 (s, 2H), 2.91 (s, 1H), 2.84 (d, 1H), 2.47 (s, 2H), 2.29-2.19 (m, 1H), 2.02 (t, 1H), 1.96-1.83 (m, 2H), 1.72 (s, 2H), 1.67-1.59 (m, 2H), 1.59-1.47 (m, 4H), 1.46 (s, 1H), 1.43 (s, 2H), 1.38 (s, 1H), 1.37-1.13 (m, 25H), 1.04 (d, 4H), 0.96-0.87 (m, 3H), 0.87-0.75 (m, 7H), 0.67 (dt, 2H).

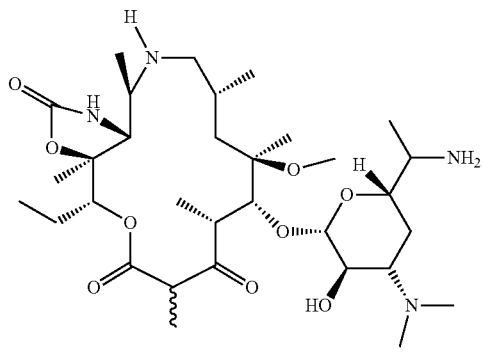

181

3-Desdadinosyl-3-oxo-6-O-methyl-N9a-desmethyl-11,12-dideoxy-12,11-(oxycarbonylimino)-6'-aminoethyl Azithromycin. (181)

The pure amine S8-3 (3.8 mg, 0.005 mmol) was dissolved in MeOH, and aqueous HCl (12 M, 3 equiv, 1 µL, 0.015 mmol) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% HCO$_2$H) to yield the desired products (1.0 mg, 48% yield). MS (ESI+) m/z: 215.1 [M+3H]$^{3+}$, 322.2 [M+2H]$^{2+}$, 643.4 [M+H]$^+$; $^1$H NMR (400 MHz, Methanol-d$_4$) δ 8.44 (s, 2H), 4.99-4.92 (m, 1H), 4.45 (dd, 1H), 4.29 (dd, 1H), 3.56-3.46 (m, 1H), 3.34-3.24 (m, 2H), 3.17 (s, 4H), 3.04-2.85 (m, 5H), 2.84-2.72 (m, 3H), 2.57 (s, 1H), 2.43 (d, 4H), 1.97 (s, 1H), 1.80 (q, 2H), 1.67-1.45 (m, 4H), 1.41 (s, 2H), 1.36 (s, 1H), 1.28 (s, 3H), 1.26-1.17 (m, 11H), 1.15-0.97 (m, 6H), 0.94-0.76 (m, 7H).

TABLE 21

Exemplary Azaketolides.

| Compound No. | Structure |
|---|---|
| 175 | 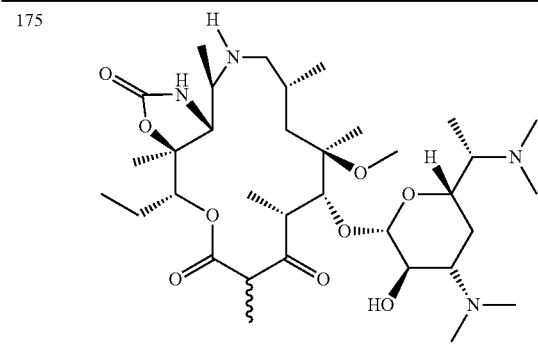 |
| 176 | 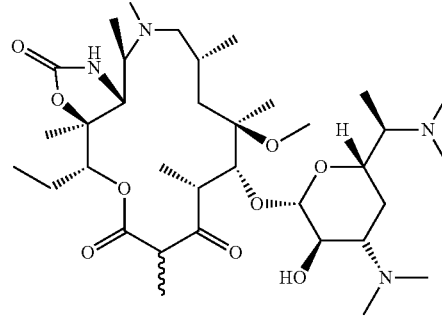 |
| 177 | 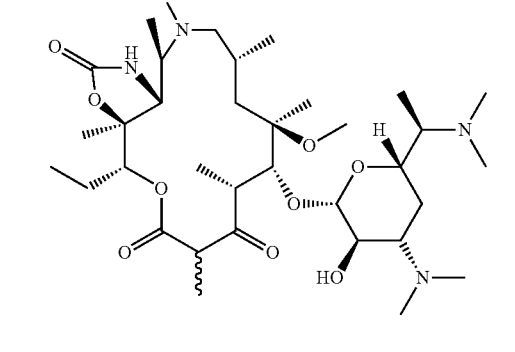 |
| 178 | 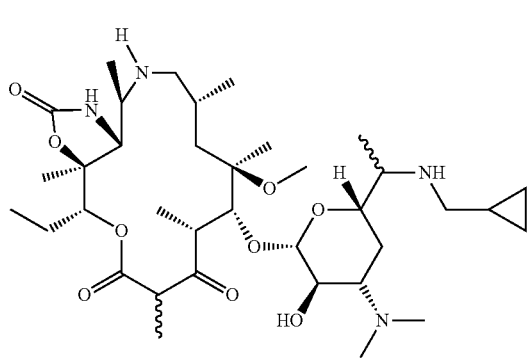 |
| 179 | 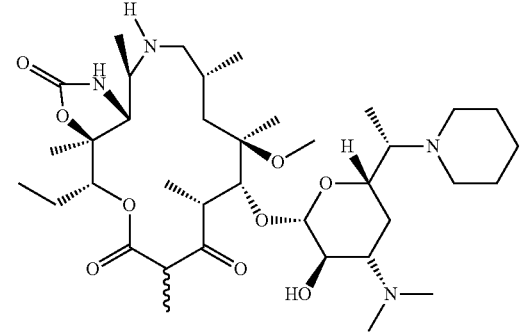 |

TABLE 21-continued

Exemplary Azaketolides.

| Compound No. | Structure |
|---|---|
| 180 | 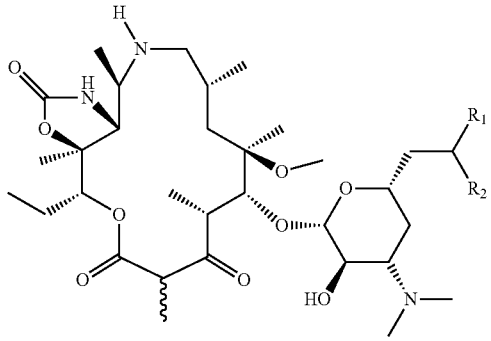 |
| 181 | 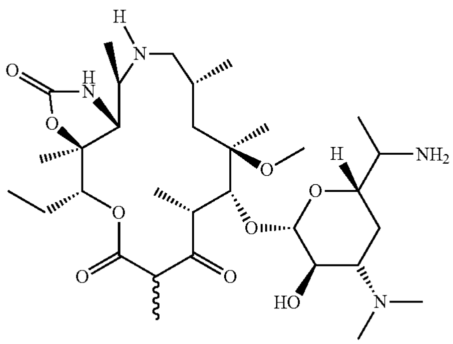 |

Scheme 31.

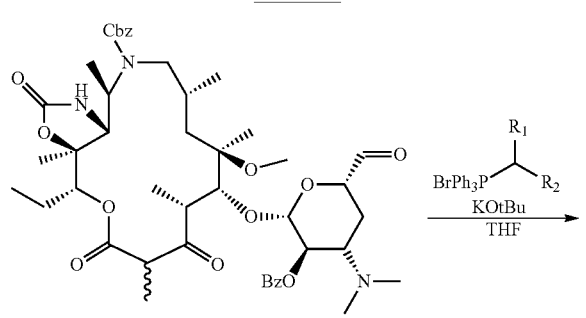

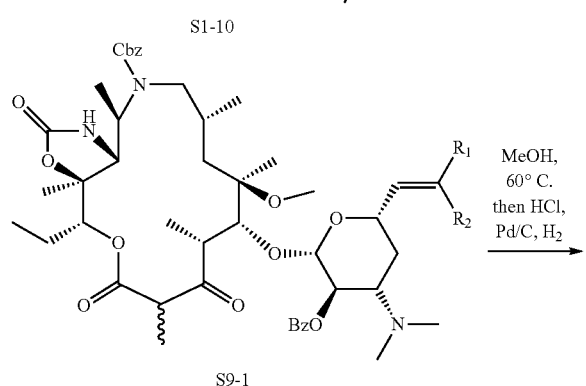

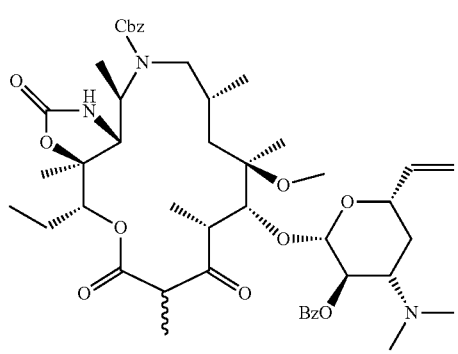

3-Descladinosyl-3-oxo-6-O-methyl-8-oxo-N9a-desmethyl-N9a-carbonylbenzyloxy-11,12-dideoxy-12,11-(oxycarbonylimino)-6'-ethenyl Azithromycin (S9-1-1)

In a 5 mL flask was a suspension of methyltriphenylphosphonium bromide (90.3 mg, 253 µmol) in 0.5 mL of THF which was cooled at 0° C. Potassium tert-butoxide solution (1.0 M in THF, 0.23 mL, 230 µmol) was added and the resulting mixture was stirred at 0° C. for 30 min. A solution of S1-10-1 (100 mg, 115 µmol) in THF (0.4 mL) was added and the resulting mixture was stirred at 0° C. for 30 minutes, and then at rt for 1 h. The reaction mixture was diluted with EtOAc and poured into satd aq NH$_4$Cl. The organic phase was extracted twice with EtOAc, then the combined organic phases were dried over Na$_2$SO$_4$, filtered and concentrated. The residue was partially purified on a 12 g silica gel column, elution with 0-10% MeOH-DCM-0.5% of 30% aq NH$_4$OH to yield a white solid consisting of the desired product and triphenylphosphine oxide (133 mg) which was used without further purification. MS (ESI+) m/z: 864.3 [M+H]$^+$.

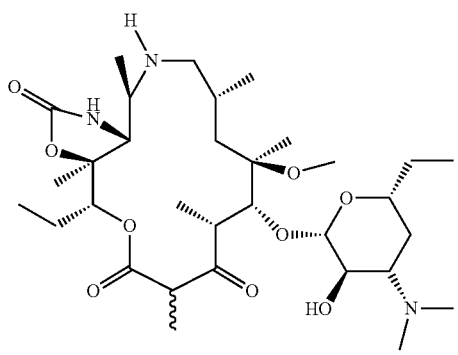

3-Descladinosyl-3-oxo-6-O-methyl-N9a-desmethyl-11,12-dideoxy-12,11-(oxycarbonylimino)-5'-desmethyl-5'-ethyl Azithromycin (182)

In a 5 mL flask was a solution of S-9-1-1 (30 mg) in MeOH (1.0 mL) which was heated at 45° C. for 16 h, then allowed to cool to rt. The mixture was treated with aqueous HCl (1.0 M, 60 µL, 60 µmol) and concentrated. The residue was placed under nitrogen, dissolved in MeOH (0.5 mL) and degassed by sonication. 5% Pd/C was added and the vial was purged and backfilled with hydrogen 5×, then stirred under static hydrogen for 2 h, then filtered through a syringe filter with the aid of MeOH and concentrated. The hydrogenation process was repeated once more, and the resulting residue was purified by HPLC (elution with 5-40% MeCN-water-0.1% HCO2H) to give 182 as a formate salt (5.7 mg, 33% over 3 steps from S1-9). MS (ESI+) m/z: 314.7 [M+2H]$^{2+}$, 628.3 [M+H]$^+$; $^1$H NMR (400 MHz, Methanol-d$_4$): δ 8.55 (s, 1H), 5.06 (dd, 1H), 4.55 (d, 1H), 4.44 (dd, 1H), 4.11 (q, 1H), 3.53 (dt, 1H), 3.48-3.38 (m, 2H), 3.24 (td, 1H), 3.15-2.96 (m, 5H), 2.90 (ddd, 1H), 2.74 (d, 6H), 2.16 (t, 1H), 2.03-1.82 (m, 2H), 1.78-1.66 (m, 3H), 1.66-1.56 (m, 2H), 1.56-1.45 (m, 4H), 1.48-1.30 (m, 9H), 1.27-0.89 (m, 15H).

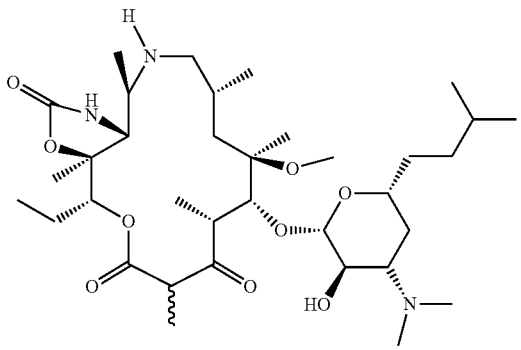

3-Descladinosyl-3-oxo-6-O-methyl-N9a-desmethyl-11,12-dideoxy-12,11-(oxycarbonylimino)-6'-isobutyl Azithromycin (183)

Prepared according to the methods of 182, using isobutyltriphenylphosphonium bromide gave 183 MS as a bis-formate salt (1.69 mg). (ESI+) m/z: 335.7 [M+2H]$^{2+}$, 670.4 [M+H]$^+$; $^1$H NMR (400 MHz, Methanol-d$_4$) δ 8.45 (s, 2H), 4.52-4.42 (m, 1H), 4.32-4.17 (m, 1H), 3.46-3.26 (m, 3H), 3.21 (p, 28H), 3.03-2.93 (m, 1H), 2.89 (d, 3H), 2.72 (dd, 2H), 2.44 (s, 3H), 1.91 (t, 1H), 1.83-1.75 (m, 2H), 1.62-1.52 (m, 3H), 1.52-1.43 (m, 3H), 1.41 (s, 3H), 1.37-1.14 (m, 12H), 1.14-0.95 (m, 5H), 0.95-0.73 (m, 11H).

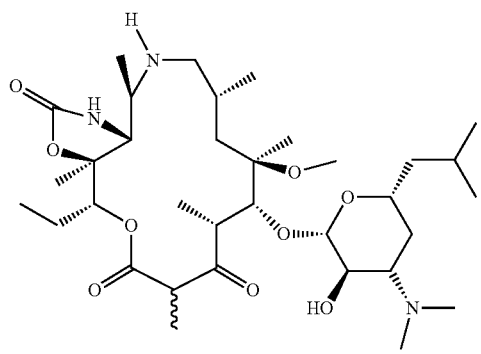

3-Desdadinosyl-3-oxo-6-O-methyl-N9a-desmethyl-11,12-dideoxy-12,11-(oxycarbonylimino)-6'-isopropyl Azithromycin (184)

Prepared according to the methods of 182, using isopropylltriphenylphosphonium bromide gave 184 as a bis-formate salt (1.6 mg, 31% in two steps). MS (ESI+) m/z: 328.7 [M+2H]$^{2+}$, 656.4 [M+H]$^+$; $^1$H NMR (400 MHz, Methanol-d$_4$) δ 8.45 (s, 2H), 4.96 (s, 1H), 4.47 (d, 1H), 4.24 (d, 1H), 4.02-3.71 (m, 2H), 3.49 (d, 1H), 3.27 (d, 2H), 3.04-2.92 (m, 2H), 2.91-2.82 (m, 4H), 2.70 (dd, 4H), 2.61-2.52 (m, 1H), 2.35 (s, 6H), 1.93-1.74 (m, 5H), 1.68 (t, 2H), 1.62-1.55 (m, 2H), 1.54-1.46 (m, 3H), 1.44 (s, 1H), 1.41 (s, 2H), 1.38 (s, 2H), 1.34-1.16 (m, 17H), 1.14-1.05 (m, 3H), 0.89 (ddt, 23H).

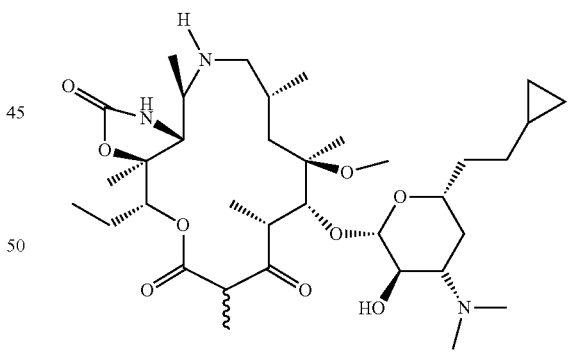

3-Descladinosyl-3-oxo-6-O-methyl-N9a-desmethyl-11,12-dideoxy-12,11-(oxycarbonylimino)-6'-cyclopropylmethyl Azithromycin (185)

Prepared according to the methods of 182, using cyclopropylmethyltriphenylphosphonium bromide gave 185 as a bis-formate salt (2.3 mg, 37% in two steps). MS (ESI+) m/z: 334.7 [M+2H]$^{2+}$, 668.4 [M+H]$^+$; $^1$H NMR (400 MHz, Methanol-d$_4$) δ 8.45 (s, 2H), 4.94 (d, 1H), 4.43 (d, 1H), 4.25 (dd, 1H), 3.87-3.75 (m, 1H), 3.48 (q, 1H), 3.45-3.38 (m, 1H), 3.30-3.22 (m, 3H), 3.03-2.82 (m, 5H), 2.81-2.63 (m, 4H), 2.47 (s, 1H), 2.39 (s, 5H), 1.98-1.83 (m, 2H), 1.78 (ddd, 3H), 1.64-1.48 (m, 6H), 1.47 (s, 2H), 1.41 (s, 4H), 1.33 (d, 2H), 1.31-1.16 (m, 13H), 1.15-0.97 (m, 4H), 0.96 (d, 2H), 0.93-0.78 (m, 8H), 0.68 (td, 1H), 0.44-0.28 (m, 2H), −0.09 (ddd, 1H).

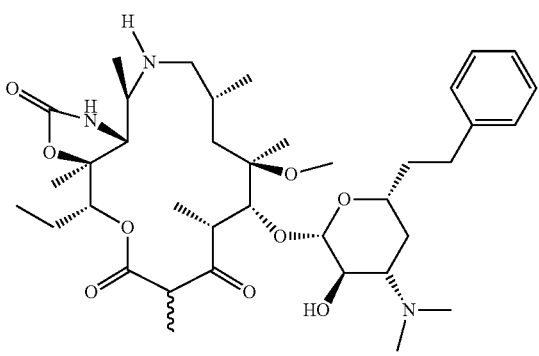

3-Descladinosyl-3-oxo-6-O-methyl-N9a-desmethyl-11,12-dideoxy-12,11-(oxycarbonylimino)-6'-benzyl Azithromycin (186)

Prepared according to the methods of 182, using benzyltriphenylphosphonium bromide gave 186 as a bis-formate salt (7.81 mg, 58% in two steps). MS (ESI+) m/z: 352.7 [M+2H]$^{2+}$, 704.4 [M+H]$^{+}$; $^1$H NMR (400 MHz, Methanol-d$_4$) δ 8.44 (s, 1H), 7.26-7.19 (m, 4H), 7.19-7.11 (m, 1H), 7.09 (ddt, 1H), 4.96 (dd, 1H), 4.56 (d, 1H), 4.37-4.26 (m, 1H), 3.42 (t, 1H), 3.37-3.24 (m, 3H), 3.11-2.97 (m, 2H), 2.96 (s, 3H), 2.93-2.65 (m, 6H), 2.53 (d, 8H), 2.04-1.71 (m, 7H), 1.69-1.55 (m, 3H), 1.55-1.45 (m, 2H), 1.45-1.33 (m, 6H), 1.33-1.25 (m, 8H), 1.24 (s, 3H), 1.14-1.07 (m, 1H), 1.02 (dd, 4H), 0.97-0.79 (m, 8H).

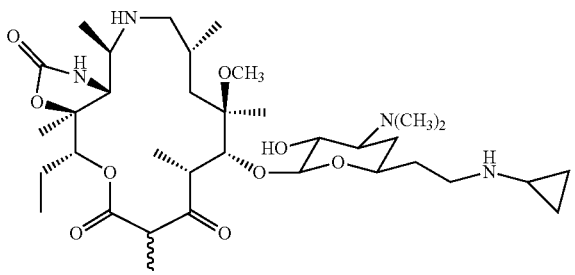

3-Descladinosyl-3-oxo-6-O-methyl-N9a-desmethyl-11,12-dideoxy-12,11-(oxycarbonylimino)-5'-desmethyl-5'-(2-(aminocyclopropyl)ethyl) Azithromycin (187)

In a 5 mL vial was (methoxy)methyltriphenylphosphonium chloride (42 mg, 122 μmol) in THF (0.5 mL) to give a white suspension which was cooled to 0° C. KOtBu (1.0 M in THF, 117 μL, 117 μmol) was added and the orange solution was stirred at 0° C. for 30 minutes. A solution of aldehyde S1-10-1 (51 mg, 59 μmol) in THF (0.5 mL) was added and the mixture was stirred at 0° C. for 9 h. The reaction mixture was diluted with EtOAc and poured into satd aq NaHCO$_3$. The aqueous phase was extracted 3× with EtOAc and the combined organic phases were dried over Na$_2$SO$_4$, filtered and concentrated. The residue was purified on 4 g of silica gel, elution with 0-15% MeOH-DCM-NH$_4$OH to give 31 mg colorless oil which contained a mixture of the intermediate alkene and triphenylphosphine oxide. The residue was dissolved in THF (0.35 mL) and water (0.1 mL) and was stirred at rt. TFA (50 μL, 654 μL) was added and the mixture was stirred at rt for 17 hrs, then concentrated. The residue was dissolved in MeOH (0.5 mL) to give a solution which was stirred at rt, then cyclopropylamine (5 μL, 72 μmol) was added and the mixture was stirred for 3 minutes, then NaBH(OAc)$_3$ (10 mg, 47 μmol) was added in one portion and the mixture was stirred at rt for 3 hours. Additional amine (20 μL, 288 μmol) and NaBH(OAc)$_3$ (20 mg, 576 μmol) were added, then AcOH (20 μL, 350 μmol) was added and the mixture was stirred for 75 minutes, then diluted with EtOAc and poured into satd NaHCO$_3$. The aqueous phase was extracted 3× w/ EtOAc and the combined organic phases were dried over Na$_2$SO$_4$, filtered and concentrated. The crude was purified on 4 g silica gel, 0-10% MeOH-DCM-0.5% NH$_4$OH to give 18 mg yellow solid. This solid was dissolved in MeOH (0.5 mL) and heated at 60° C. for 3.5 h. The reaction mixture was treated with aq HCl (1.0 M, 60 μL, 60 μmol) and concentrated. The residue was dissolved in 0.5 mL of MeOH and the atmosphere purged with nitrogen 5×. 5% Pd/C (5 mg) was added, then the vial was purged with hydrogen 5×, and stirred at rt under static H$_2$ for 2.5 h. The mixture was filtered through a syringe filter with the aid of methanol and concentrated. The residue was purified by HPLC, elution with 5-30% MeCN-water-0.1% formic acid to give 29 as a white solid, bis-formate salt (6.8 mg, 15%). MS (ESI+) m/z: 228.5 [M+3H]$^{3+}$, 342.3 [M+2H]$^{2+}$, 683.3 [M+H]$^{+}$; $^1$H NMR (400 MHz, Methanol-d$_4$) δ 8.54 (s, 2H), 5.08 (dd, 1H), 4.55 (d, 1H), 4.42 (d, 1H), 3.93 (d, 1H), 3.74-3.57 (m, 1H), 3.51-3.39 (m, 3H), 3.30-3.19 (m, 2H), 3.19-3.08 (m, 5H), 3.07 (s, 3H), 3.06-2.97 (m, 3H), 2.73 (s, 3H), 2.71 (s, 6H), 2.53-2.40 (m, 2H), 2.24 (t, 1H), 2.08-1.97 (m, 2H), 1.97-1.86 (m, 4H), 1.86-1.80 (m, 1H), 1.78-1.64 (m, 3H), 1.64-1.45 (m, 8H), 1.41-1.28 (m, 12H), 1.27-1.11 (m, 8H), 1.04 (d, 3H), 1.02-0.96 (m, 3H), 0.94 (t, 3H), 0.74-0.59 (m, 6H).

TABLE 22
Exemplary Azaketolides.
| Compound No. | Structure |
|---|---|
| 182 | 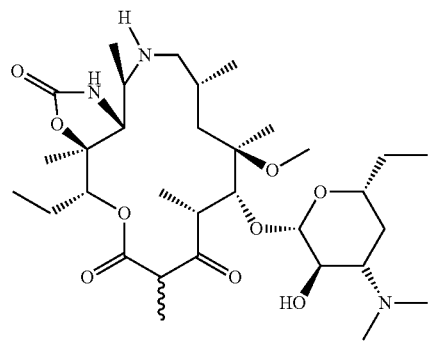 |
| 183 | 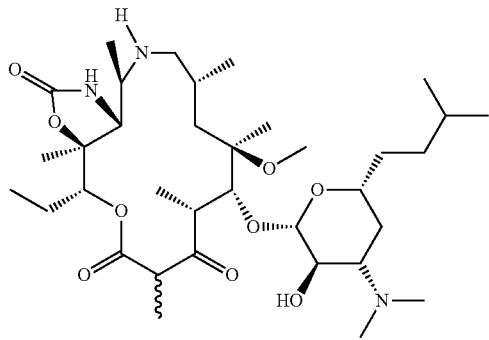 |
| 184 | 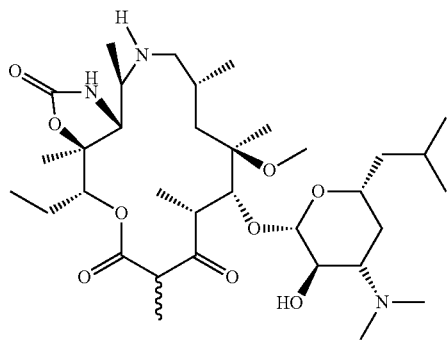 |
| 185 | 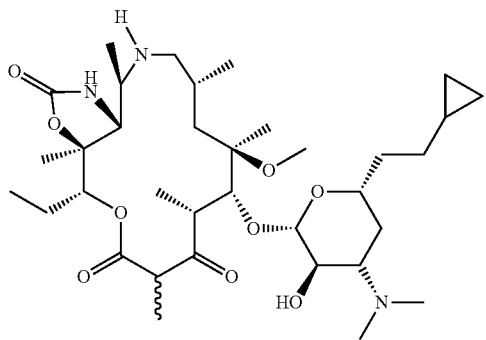 |

TABLE 22-continued

Exemplary Azaketolides.

| Compound No. | Structure |
|---|---|
| 186 | 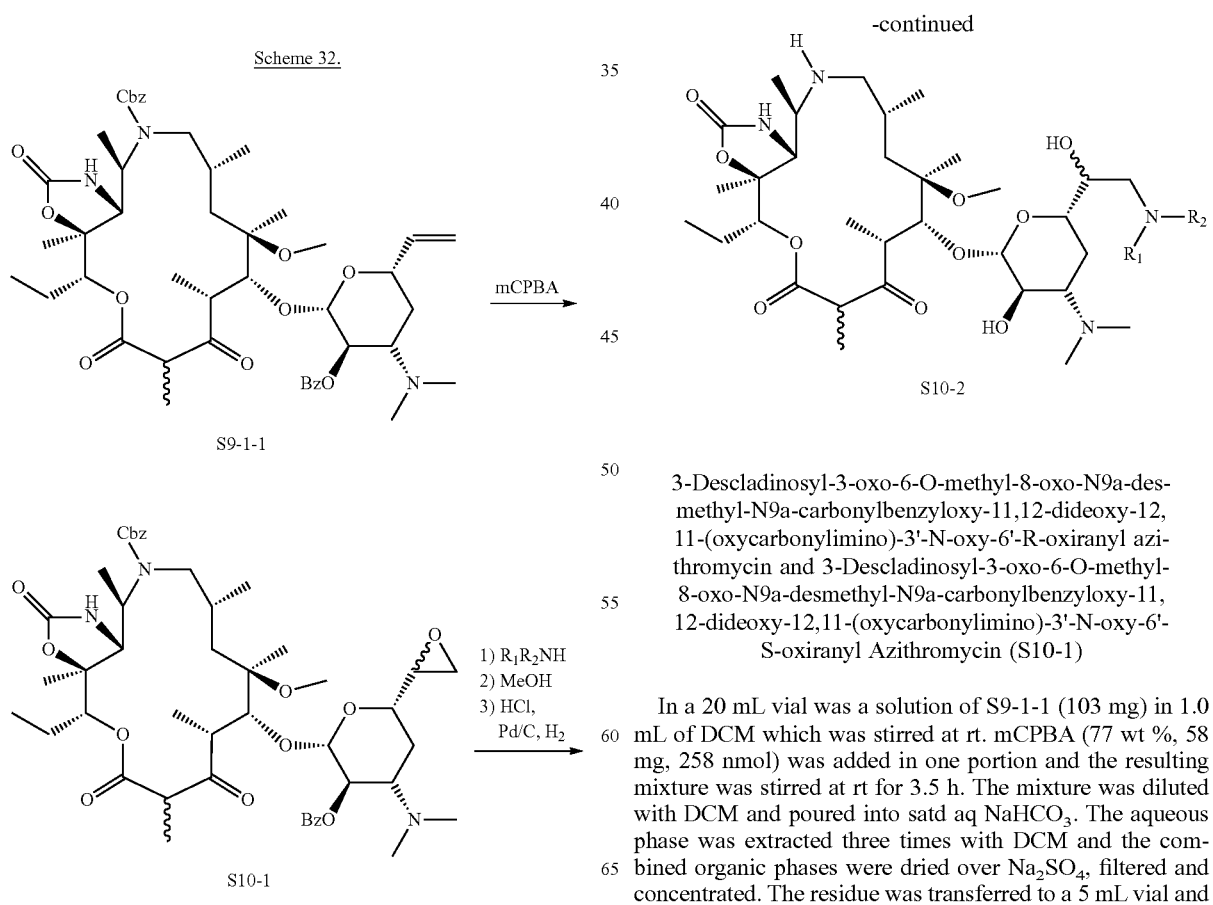 |
| 187 | 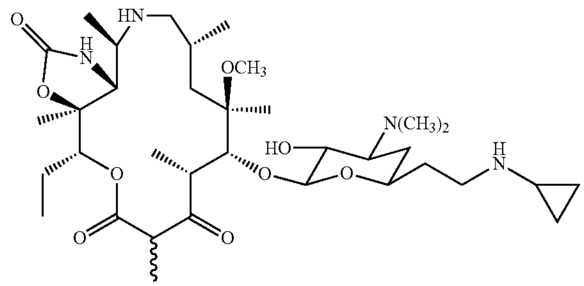 [SMILES: CC[C@H]1OC(=O)C(C)C(=O)[C@H](C)[C@@H](OC2OC(CCNC3CC3)CC(N(C)C)C2O)[C@](C)(OC)C[C@@H](C)CN[C@H](C)[C@H]2NC(=O)O[C@@]21C] |

3-Descladinosyl-3-oxo-6-O-methyl-8-oxo-N9a-desmethyl-N9a-carbonylbenzyloxy-11,12-dideoxy-12,11-(oxycarbonylimino)-3'-N-oxy-6'-R-oxiranyl azithromycin and 3-Descladinosyl-3-oxo-6-O-methyl-8-oxo-N9a-desmethyl-N9a-carbonylbenzyloxy-11,12-dideoxy-12,11-(oxycarbonylimino)-3'-N-oxy-6'-S-oxiranyl Azithromycin (S10-1)

In a 20 mL vial was a solution of S9-1-1 (103 mg) in 1.0 mL of DCM which was stirred at rt. mCPBA (77 wt %, 58 mg, 258 nmol) was added in one portion and the resulting mixture was stirred at rt for 3.5 h. The mixture was diluted with DCM and poured into satd aq $NaHCO_3$. The aqueous phase was extracted three times with DCM and the combined organic phases were dried over $Na_2SO_4$, filtered and concentrated. The residue was transferred to a 5 mL vial and dissolved in 200 μL of EtOH and cyclopropylamine (50 μL, 722 µmol) was added which was stirred at rt while amine was added. The resulting mixture was stirred at rt for 15 h, then at 60° C. for 4.5 h. The reaction mixture was allowed to cool and concentrated. The residue was dissolved in DCM and mCPBA (77 wt %, 91 mg, 407 µmol) was added and the mixture was stirred for 16 h. The reaction mixture was diluted with DCM and poured into satd aq NaHCO$_3$ and the aqueous phase was extracted three times DCM. The combined organic phases were dried over Na$_2$SO$_4$, filtered and concentrated to yield the crude 6' epoxide, 4'-dimethyl-amino-N-oxide (40 mg) which was used without further purification. MS (ESI+) m/z: 849.3 [M+H]$^+$.

188

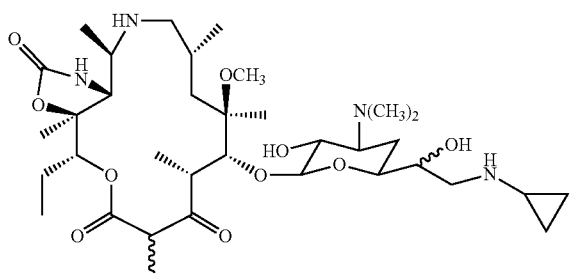

3-Descladinosyl-3-oxo-6-O-methyl-8-oxo-N9a-desmethyl-11,12-dideoxy-12,11-(oxycarbonylimino)-6'-hydroxy-6'-cyclopropylaminomethyl Azithromycin (188)

In a 5 mL flask was a solution of S10-1 in 200 uL of EtOH and cyclopropylamine (50 µL, 722 µmol). The resulting mixture was heated at 40° C. for 2.5 h. The reaction mixture was concentrated to give crude amino alcohol. The residue was dissolved in 0.5 mL of MeOH under nitrogen in a 5 mL vial. 5% Pd/C (10 mg, 4.6 µmol Pd) was added and hydrogen was actively bubbled through the solution for 30 minutes, then the mixture was stirred under a static hydrogen atmosphere for 17 h. The mixture was filtered through a syringe filter and concentrated. The residue was purified by HPLC, elution with 5-30% MeCN-DCM-0.1% formic acid to give 188 as a white solid, penta-formate complex, as a mixture of stereoisomers at C6' (1.6 mg, 2% yield over three steps from S9-1-1). MS (ESI+) m/z: 699.2 [M+H]$^+$. $^1$H NMR (400 MHz, Methanol-d$_4$) δ 8.39 (s, 5H), 4.97 (dd, 1H), 4.41 (t, 1H), 4.40-4.31 (m, 1H), 3.98-3.83 (m, 1H), 3.73 (dd, 1H), 3.65-3.48 (m, 1H), 3.47-3.32 (m, 3H), 2.99 (s, 3H), 2.97-2.92 (m, 1H), 2.69 (d, 6H), 2.57-2.37 (m, 1H), 2.29 (t, 1H), 1.84-1.69 (m, 2H), 1.57-1.45 (m, 2H), 1.44 (s, 3H), 0.97-0.93 (m, 3H), 0.83 (t, 3H), 0.71-0.53 (m, 5H).

TABLE 23

Exemplary Azaketolides.

| Compound No. | Structure |
|---|---|
| 188 | 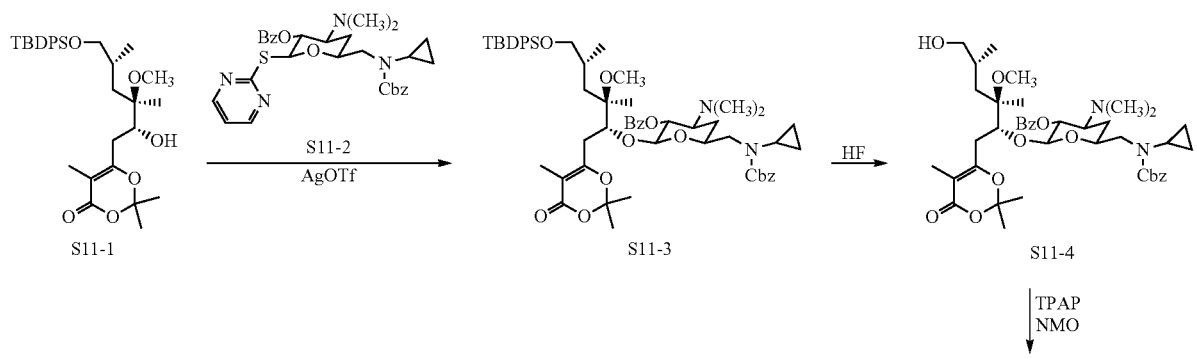 |

Scheme 33.

((2S,4S,5R,6S)-5-(benzoyloxy)-6-<((2R,3R,4R,6R)-7-((tert-butyldiphenylsilyl)oxy)-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)(N-carbonylbenzyloxy)cyclopropylaminomethyl Benzoate (S11-3)

In a 25 mL flask were powdered 4 Å molecular sieves (1.35 g) which were flame dried under vacuum twice. Meanwhile, a mixture of S11-1 (3.45 g, 2.02 mmol) and S11-2 (1.55 g, 2.62 mmol) were azeotroped twice from toluene. The residue was dissolved in DCM and transferred to the flask and rinsed in (total 15 mL DCM). The resulting mixture was stirred at 0° C. for 15 minutes, then silver triflate (1.34 g, 5.25 mmol) was added in one portion, the flask was covered with foil and stirred in the slowly warming ice bath for 16 h. Triethylamine (1.4, 10 mmol) was added and the mixture was stirred at rt for 15 minutes, then filtered through a plug of Celite with the aid of DCM. The filtrate was poured into satd aq NaHCO$_3$ and the aqueous phases were extracted 2× w/ DCM concentrated dried over Na$_2$SO$_4$, filtered and concentrated. The filtrate was purified on 80 g of silica gel, elution with 0-100% EtOAc-hexanes to give S11-3 as a yellow solid (1.14 g, 54%). $^1$H NMR (400 MHz, Chloroform-d) δ 8.05-7.99 (m, 2H), 7.67 (ddd, 4H), 7.59-7.51 (m, 1H), 7.51-7.29 (m, 14H), 5.26-5.03 (m, 3H), 4.69 (d, 1H), 3.82 (d, 1H), 3.75 (d, 1H), 3.62 (dd, 1H), 3.53 (d, 1H), 3.37 (dd, 2H), 3.29-3.17 (m, 1H), 2.92 (d, 1H), 2.84 (s, 3H), 2.72-2.62 (m, 1H), 2.30 (s, 6H), 1.90-1.76 (m, 2H), 1.63 (d, 6H), 1.44 (dd, 2H), 1.28 (t, 1H), 1.24-1.15 (m, 1H), 1.13 (s, 3H), 1.03 (s, 11H), 0.79 (d, 6H), 0.66 (d, 2H).

((2S,4S,5R,6S)-5-(benzoyloxy)-6-(((2R,3R,4R,6R)-7-(hydroxy)-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)(N-carbonylbenzyloxy)cyclopropylaminomethyl Benzoate (S11-4)

In a 15 mL polypropylene tube was a solution of S11-3 (1.14 g, 1.11 mmol) in 4 mL of MeCN which was stirred at rt then HF (50 wt % in water, 0.77 mL, 22.2 mmol) was added. The reaction mixture was stirred at rt for 18 h, then diluted with EtOAc and poured into satd aq NaHCO$_3$. The aqueous phase was extracted three times with EtOAc and the combined organic phases were washed with brine and dried over Na$_2$SO$_4$. The crude product was purified on 24 g of silica gel, elution with 0-10% MeOH-DCM-0.5% of 30% aq NH$_4$OH to give S11-4 as a pale yellow solid (768 mg, 89%). $^1$H NMR (400 MHz, Chloroform-d) δ 8.08-7.96 (m, 2H), 7.63-7.54 (m, 1H), 7.53-7.46 (m, 1H), 7.46-7.36 (m, 6H), 7.36-7.29 (m, 1H), 5.24-5.05 (m, 4H), 4.75 (d, 1H), 3.95 (d, 1H), 3.80 (s, 1H), 3.56-3.48 (m, 2H), 3.48-3.42 (m, 1H), 3.37 (s, 1H), 3.31-3.20 (m, 2H), 3.17 (d, 1H), 3.04 (s, 3H), 2.66 (p, 1H), 2.42 (s, 6H), 2.37-2.31 (m, 1H), 1.98 (s, 1H), 1.86 (ddt, 1H), 1.79 (s, 3H), 1.58-1.42 (m, 3H), 1.30 (s, 3H), 1.28-1.20 (m, 1H), 0.90 (d, 3H), 0.84-0.74 (m, 7H), 0.64 (d, 1H).

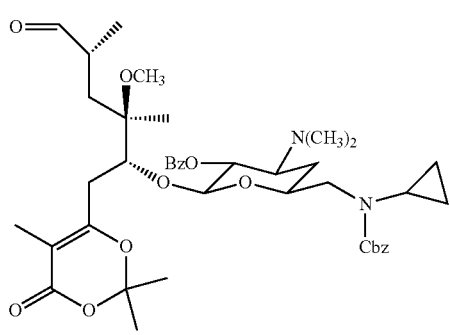

S11-5

((2S,4S,5R,6S)-5-(benzoyloxy)-6-(((2R,3R,4R,6R)-7-oxo-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)(N-carbonylbenzyloxy)cyclopropylaminomethyl Benzoate (S11-5)

In a 20 mL vial were powdered 4 Å molecular sieves (125 mg) which were flame dried under vacuum twice. A solution of N-methylmorpholine-N-oxide hydrate (51.9 mg, 384 µmol) and S11-4 (200 mg, 256 µmol) in 0.2 mL of MeCN and 1.8 mL of DCM was added and stirred at rt for 15 minutes, then tetrapropylammonium perruthenate (4.5 mg, 12.8 µmol) was added and the mixture was stirred at rt for 2 h. Additional tetrapropylammonium perruthenate (0.9 mg, 2.6 µmol), 4 Å molecular sieves (25 mg) and N-methylmorpholine-N-oxide hydrate (10 mg, 76 µmol) were added. The mixture was stirred at rt for 1 h, then concentrated and the residue was dissolved in 2:1 MTBE heptanes and filtered through a plug of Celite and concentrated to give the crude S11-5 (139 mg) as a white solid which was used without further purification. MS (ESI+) m/z: 779.5 [M+H]$^+$.

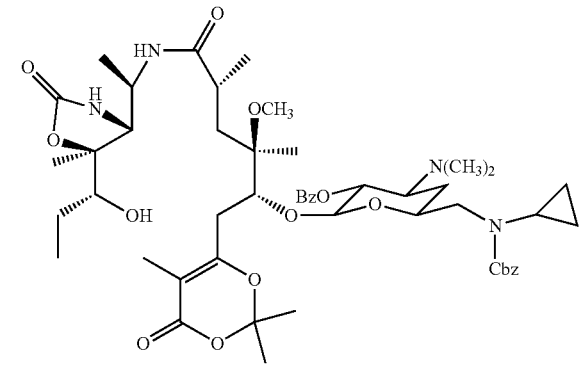

S11-6

((2S,4S,5R,6S)-5-(benzoyloxy)-6-(((2R,3R,4R,6R)-7-carboxyl-4-methoxy-4,6-dimethyl-2-(2,2,5-trimethyl-4-oxo-4H-1,3-dioxin-6-yl)heptan-3-yl)oxy)-4-(dimethylamino)tetrahydro-2H-pyran-2-yl)(N-carbonylbenzyloxy)cyclopropylaminomethyl Benzoate (S11-6)

S11-5 was transferred to a 20 mL vial along with 2-methyl-2-butene (0.66 mL, 6.19 mmol) in 1.5 mL of tBuOH at rt. A solution of monobasic sodium hydrogen phosphate (211 mg, 1.76 mmol) and sodium chlorite (48 mg, 0.53 mmol) in 1.5 mL of water was added and the biphasic mixture was stirred vigorously at room temperature for 1.5 h. The mixture was diluted with EtOAc and poured into saturated sodium sulfite. The aqueous phase was extracted three times with EtOAc, then the combined organic phases were washed with brine, dried over Na$_2$SO$_4$, filtered and concentrated to give the crude acid (155 mg) as a white solid which was used without further purification. MS (ESI+) m/z: 795.3 [M+H]$^+$. The crude acid was dissolved in 1.5 mL of DMF and S1-5-1 (39 mg, 194 µmol) was added and the mixture was cooled at 0° C. N,N-Diisopropylethylamine (61.5 µL, 354 µmol) was added followed by HATU (67.3 mg, 177 µmol), and the resulting solution was removed from the bath and stirred at rt for 1 h. The reaction mixture was poured into EtOAc and satd aq NaHCO$_3$ and the organic phase was washed with water 3× and then with brine, dried over Na$_2$SO$_4$, filtered and concentrated. The residue was purified on 4 g of silica gel, elution with 0-10% MeOH-DCM+0.5% of 30% aq NH$_4$OH, to give S11-6 as a colorless oil (74 mg) which was used without further purification. MS (ESI+) m/z: 490.4 [M+2H]$^{2+}$.

S11-7

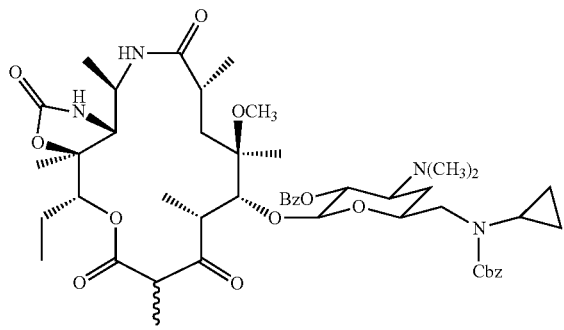

3-Descladinosyl-3-oxo-6-O-methyl-8-oxo-N9a-desmethyl-11,12-dideoxy-12,11-(oxycarbonylimino)-2'-O-benzoyl-6'-(N-carbonylbenzyloxy)cyclopropylamino Azithromycin (S11-7)

S11-6 was transferred to a 50 mL round-bottomed flask and azeotroped twice from toluene and then dissolved in 22 mL of chlorobenzene. The atmosphere was purged 3× with nitrogen and the flask was sonicated under vacuum for 1 minute, then backfilled with nitrogen and purged again. The resulting mixture was heated at a gentle reflux (block temperature 142° C.) for 18 h. The reaction mixture was concentrated and the residue purified on silica, eluting with 0-20% MeOH-DCM-0.5% NH$_4$OH, to give the S11-7 as a yellow solid (58 mg, 25% over four steps). MS (ESI+) m/z: 921.4 [M+H]$^+$.

189

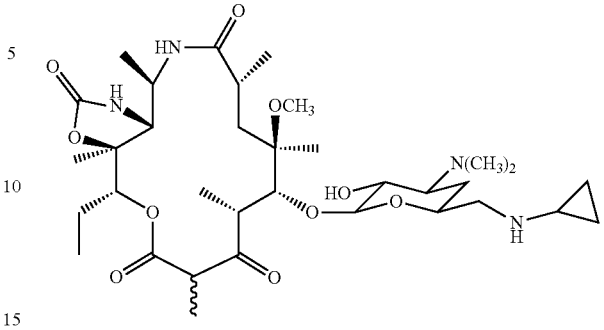

3-Descladinosyl-3-oxo-6-O-methyl-8-oxo-N9a-desmethyl-11,12-dideoxy-12,11-(oxycarbonylimino)-6'-cyclopropylamino Azithromycin (189)

In a 20 mL vial was a solution of S11-7 in 2 mL of MeOH which was heated at 60° C. for 9.5 h. The reaction mixture was cooled to rt and treated with HCl (3 M in water, 46 µL, 140 µmol) and concentrated. The residue was dissolved in 1 mL of MeOH and purged with nitrogen. 5% Pd/C was added and hydrogen was streamed through for 5 minutes then the mixture was stirred under static hydrogen for 4 hours. The mixture was filtered through a syringe filter with the aid of MeOH and concentrated. The residue was purified by HPLC 5-50% MeCN—H2O-0.1% formic acid and the clean fractions were lyophilized to give 189 as a bis-formate salt (13.4 mg, 28% over two steps). White solid. MS (ESI+) m/z: 342.3 [M+2H]$^{2+}$. $^1$H NMR (400 MHz, Methanol-d$_4$) δ 8.51 (s, 2H), 7.69 (d, 1H), 4.53 (d, 1H), 4.28 (t, 1H), 4.18 (d, 1H), 4.04 (q, 1H), 3.88 (dd, 1H), 3.57-3.35 (m, 4H), 3.10-2.94 (m, 2H), 2.82 (s, 6H), 2.81 (s, 3H), 2.57-2.30 (m, 3H), 2.18-1.99 (m, 1H), 1.84 (dpd, 1H), 1.76-1.55 (m, 2H), 1.52 (s, 3H), 1.43 (q, 4H), 1.31 (d, 7H), 1.23-1.15 (m, 1H), 1.12 (d, 3H), 1.08 (d, 3H), 0.92 (t, 3H), 0.65 (p, 2H), 0.59-0.45 (m, 2H).

TABLE 24

Exemplary Azaketolides.

| Compound No. | Structure |
|---|---|
| 189 | ![structure] |

Scheme 34.
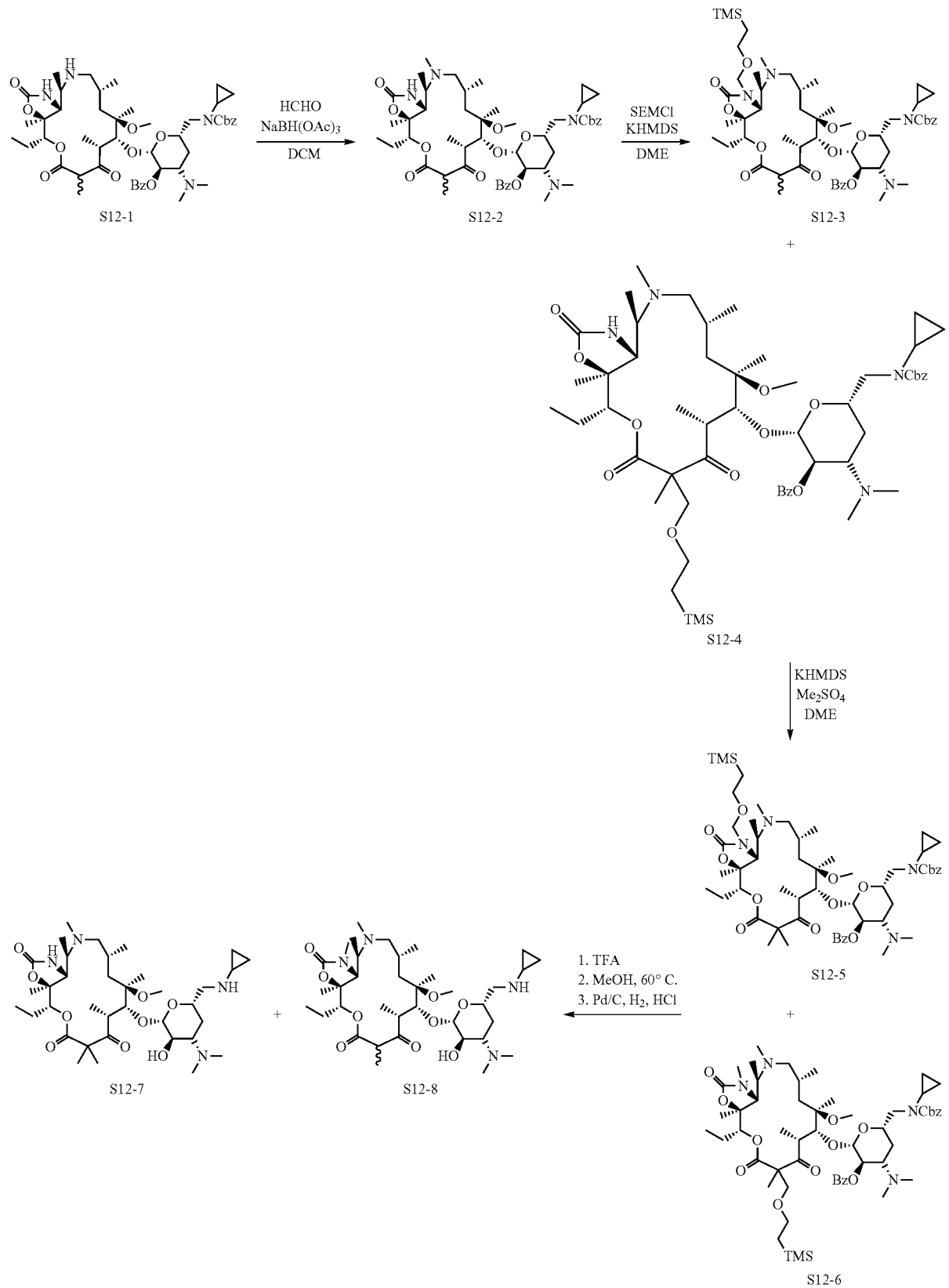

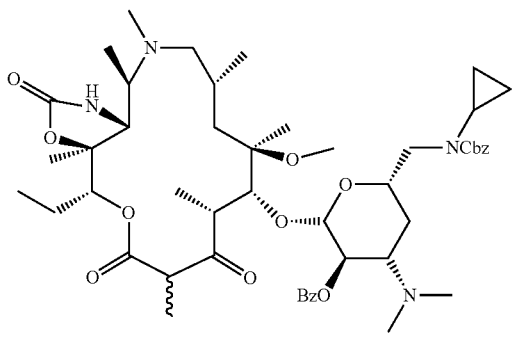

S12-2

3-Descladinosyl-3-oxo-6-O-methyl-11,12-dideoxy-12,11-(oxycarbonylimino)-2'-O-benzoyl-6'-(N-carbonylbenzyloxy)cyclopropylamino Azithromycin (S12-2)

The substrate S12-1 (1 equiv, 30 mg, 0.033 mmol) was dissolved in DCM (0.5 mL) and NaBH(OAc)₃ (2 equiv, 13.9 mg, 0.066 mmol) was added dropwise at rt. HCHO solution (100 equiv, 26.6 μL, 3.3 mmol) was added. The reaction mixture was stirred at rt for 10 min. Then the reaction was quenched by adding saturated aqueous NaHCO₃. The aqueous layer was extracted with DCM and combined organic layers were dried and concentrated and purified by a 12 g silica gel column (0-10% MeOH/DCM, 0.5% NH₄OH) to give desired product as a white foam (29.8 mg, 98% yield). MS (ESI+) m/z: 481.2 [M+2H]²⁺, 961.5 [M+H]⁺.

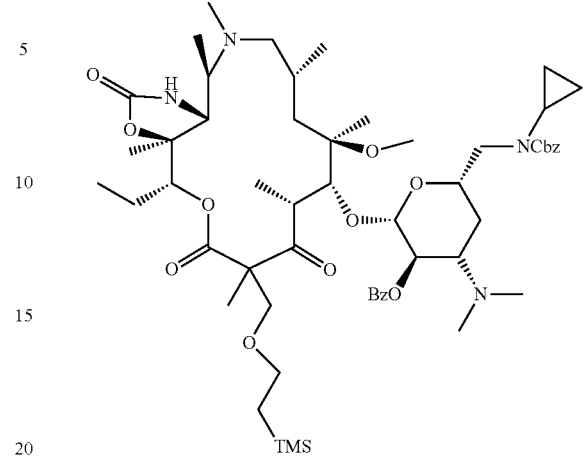

S12-4

3-Descladinosyl-3-oxo-6-O-methyl-11,12-dideoxy-12,11-(oxycarbonylimino)-11-(2"-(trimethylsilyl)ethoxy)methyl) 2'-O-benzoyl-6'-(N-carbonylbenzyloxy)cyclopropylamino Azithromycin (S12-3) and 2-(2"-(Trimethylsilyl)ethoxy)methyl)-3-descladinosyl-3-oxo-6-O-methyl-11,12-dideoxy-12,11-(oxycarbonylimino)-2'-O-benzoyl-6'-(N-carbonylbenzyloxy)cyclopropylamino Azithromycin (S12-4)

The substrate S12-2 (27 mg, 0.029 mmol) was dissolved in DME (0.5 mL) under N₂ and cooled at −40° C. KHMDS (1M in THF, 1.5 equiv, 44 μL, 0.044 mmol) was added dropwise and the reaction mixture was stirred for 30 min. SEMCl (1.2 equiv, 6.2 μL, 0.035 mmol) was added and the reaction mixture was allowed to warm to −10° C. LCMS shows full conversion and the reaction mixture was quenched by adding saturated aqueous NaHCO₃. The aqueous layer was extracted with DCM and combined organic layers were dried and concentrated and purified by a 12 g silica gel column (0-10% MeOH/DCM, 0.5% NH₄OH). The product was a mixture of S12-3 and S12-4 (23 mg, 67% yield).

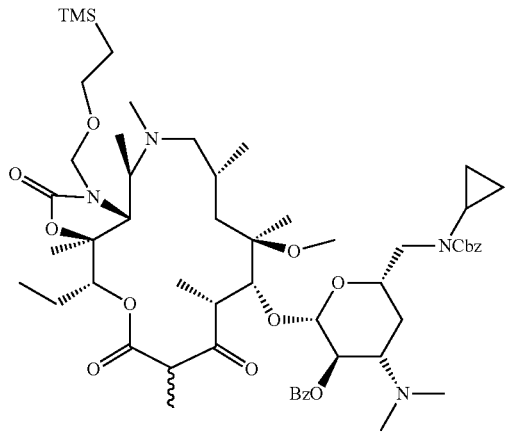

S12-3

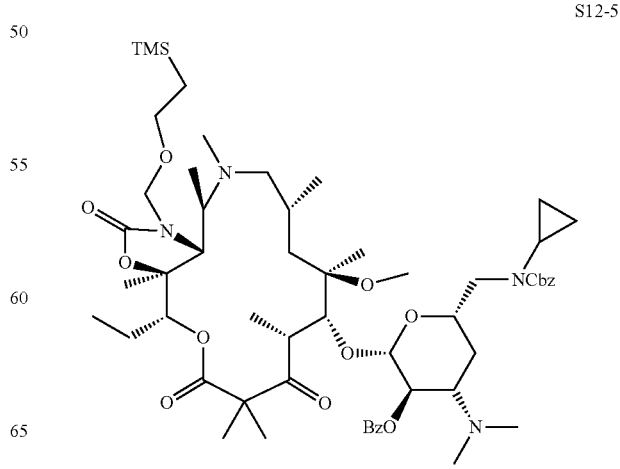

S12-5

S12-6

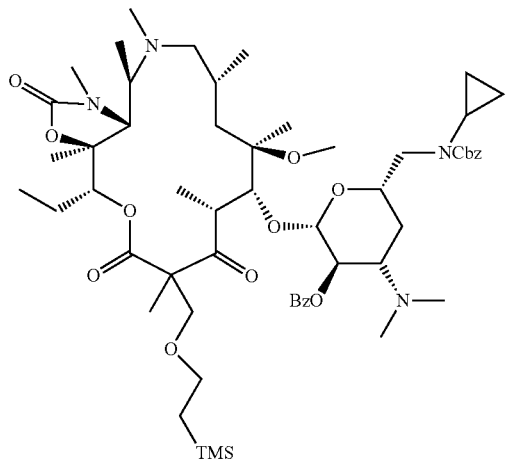

2-Methyl-3-descladinosyl-3-oxo-6-O-methy 1-11,
12-dideoxy-12,11-(oxycarbonylimino)-11-(2"-(trimethylsilyl)ethoxy)methyl) 2'-O-benzoyl-6'-(N-carbonylbenzyloxy)cyclopropylamino azithromycin (S12-5) and 2-(2"-(Trimethylsilyl)ethoxy)methyl)-2-methyl-3-descladinosyl-3-oxo-6-O-methyl-11,12-dideoxy-12,11-(oxycarbonylimino)-2'-O-benzoyl-6'-(N-carbonylbenzyloxy)cyclopropylamino Azithromycin (S12-6)

The mixture of S12-3 and S12-4 (23 mg, 0.0196 mmol) was dissolved in DME (0.5 mL) under $N_2$ and cooled at −40° C. KHMDS (1 M in THF, 1.5 equiv, 29.4 µL, 0.029 mmol) was added drop wise and the reaction mixture was stirred for 30 min. $Me_2SO_4$ (2 equiv, 3.7 µL, 0.040 mmol) was added and the reaction mixture was allowed to warm to −10° C. LCMS shows full conversion and the reaction mixture was quenched by adding saturated aqueous $NaHCO_3$. The aqueous layer was extracted with DCM and combined organic layers were dried and concentrated and purified by a 12 g silica gel column (0-10% MeOH/DCM, 0.5% $NH_4OH$). The product was a mixture of S12-5 and S12-6 (15 mg, 70% yield).

190

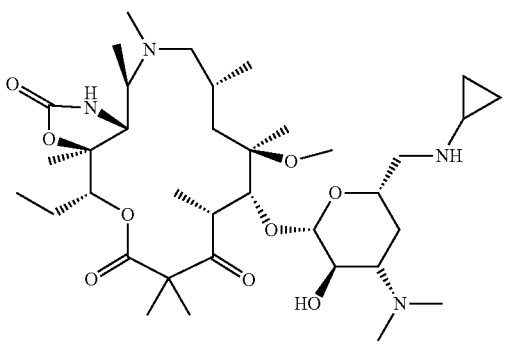

2-Methyl-3-descladinosyl-3-oxo-6-O-methyl-N9a-desmethyl-11,12-dideoxy-12,11-(oxycarbonylimino)-6'-cylcopropylamino Azithromycin (190)

The mixture of S12-5 and S12- was dissolved in TFA and stirred for 5 min. Then the reaction mixture was diluted with DCM and quenched by adding saturated aqueous $NaHCO_3$. The aqueous layer was extracted with DCM and combined organic layers were dried and concentrated. The mixture was dissolved in MeOH (0.5 mL) and heated at 60° C. until LC/MS indicated complete consumption of starting material (16 hours). The reaction mixture was cooled, and aqueous HCl (12 M, 3 equiv, 4 µL, 0.042 mmol) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% $HCO_2H$) to yield 190 (0.94 mg, 10% in four steps) and 191 (1.27 mg, 13% in four steps). Data for 190: MS (ESI+) m/z: 233.1 $[M+3H]^{3+}$, 349.2 $[M+2H]^{2+}$, 697.5 $[M+H]^+$; $^1H$ NMR (400 MHz, Methanol-$d_4$) δ 8.53 (s, 3H), 4.60 (s, 2H), 4.42-4.01 (m, 1H), 3.91-3.60 (m, 1H), 3.57-3.36 (m, 1H), 3.23-2.61 (m, 6H), 2.51-1.92 (m, 4H), 1.72-1.39 (m, 3H), 1.40-1.25 (m, 4H), 1.16 (d, 1H), 1.06-0.94 (m, 3H), 0.48 (d, 2H).

191

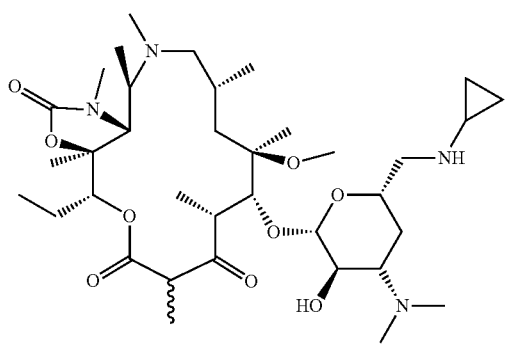

3-Descladinosyl-3-oxo-6-O-methyl-N9a-desmethyl-11,12-dideoxy-12,11-(oxycarbonylimino)-11-methyl-6'-cylcopropylamino Azithromycin (191)

MS (ESI+) m/z: 233.1 $[M+3H]^{3+}$, 349.2 $[M+2H]^{2+}$, 697.5 $[M+H]^+$; $^1H$ NMR (400 MHz, Methanol-$d_4$) δ 8.55 (s, 3H), 4.47 (d, 1H), 4.37 (dd, 1H), 4.08 (s, 1H), 3.85 (d, 1H), 3.73-3.43 (m, 3H), 3.13 (dd, 3H), 3.05-2.71 (m, 9H), 2.39-1.78 (m, 12H), 1.22-0.85 (m, 16H), 0.45 (d, 6H).

TABLE 21
Exemplary Azaketolides.
| Compound No. | Structure |
|---|---|
| 190 | 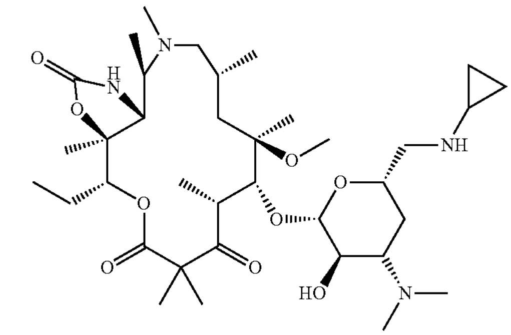 |
| 191 | |
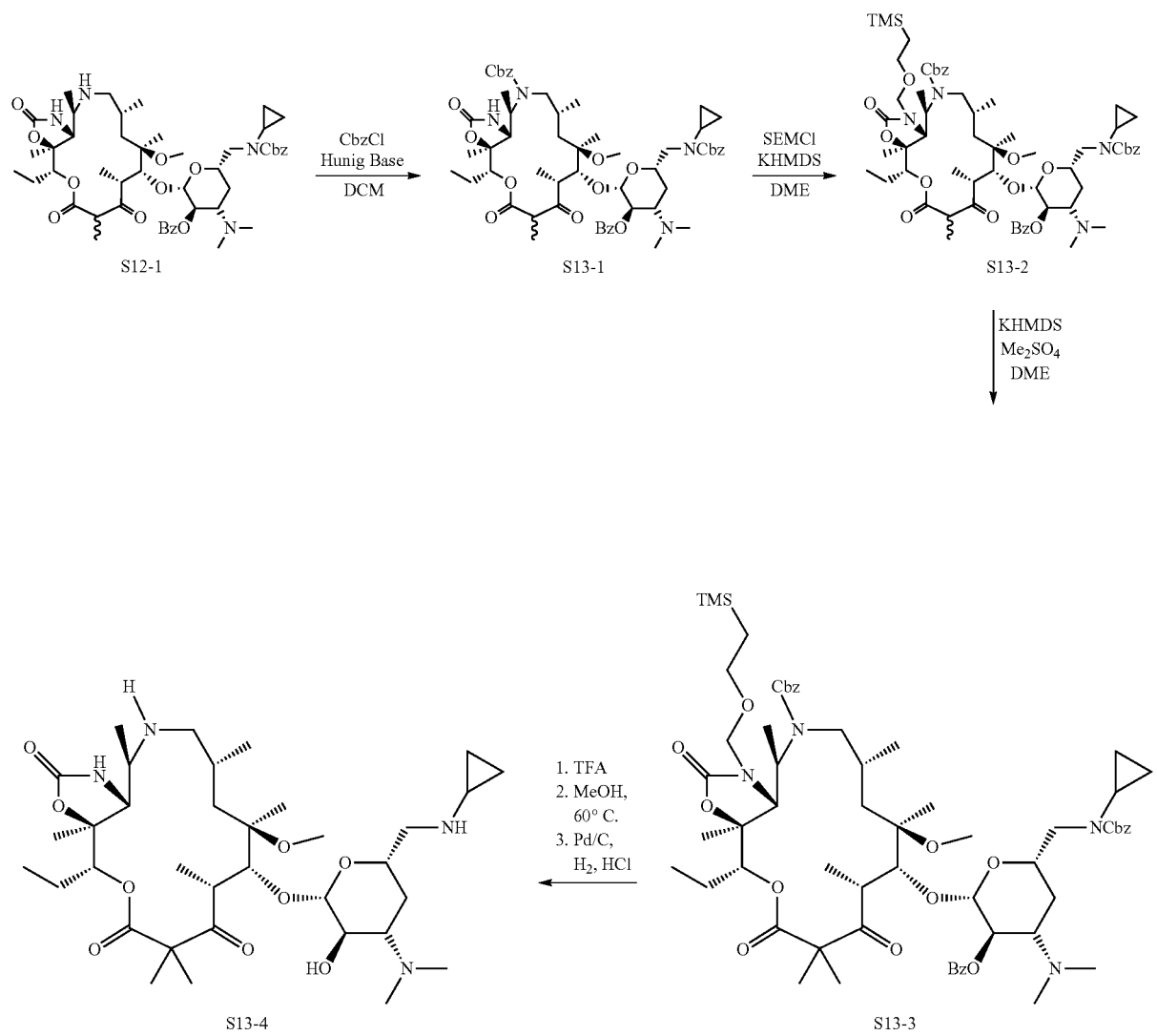
Scheme 35.

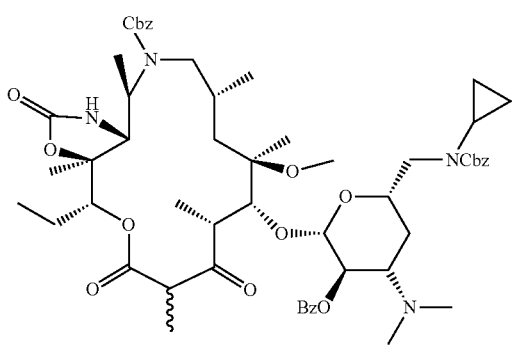

3-Descladinosyl-3-oxo-6-O-methyl-N9a-carbonyl-benzyloxy-11,12-dideoxy-12,11-(oxycarbonylimino)-2'-O-benzoyl-6'-(N-carbonylbenzyloxy)cyclopropylamino Azithromycin (S13-1)

The substrate S12-1 (30 mg, 0.033 mmol) and Hunig's base (3 equiv, 17.1 µL, 0.1 mmol) were dissolved in DCM (0.5 mL) and CbzCl (1.1 equiv, 5.2 µL, 0.036 mmol) was added drop wise at 0° C. The reaction mixture was stirred at 0° C. for 2 h. Then the reaction was quenched by adding saturated aqueous NaHCO₃. The aqueous layer was extracted with DCM and combined organic layers were dried and concentrated and purified by a 12 g silica gel column (0-10% MeOH/DCM, 0.5% NH₄OH) to give the desire product as a white foam (27 mg, 90% yield). MS (ESI+) m/z: 1041.5 [M+H]$^+$.

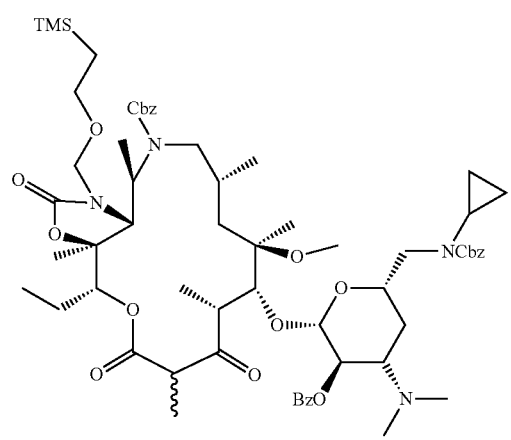

3-Descladinosyl-3-oxo-6-O-methyl-N9a-carbonyl-benzyloxy-11,12-dideoxy-12,11-(oxycarbonylimino)-11-(2''-(trimethylsilyl)ethoxy)methyl) 2'-O-benzoyl-6'-(N-carbonylbenzyloxy)cyclopropylamino Azithromycin (S13-2)

The substrate S13-1 (1 equiv, 27 mg, 0.026 mmol) was dissolved in DME (0.5 mL) under N₂ and cooled at −40° C. KHMDS (1M in THF, 1.5 equiv, 38.8 µL, 0.039 mmol) was added drop wise and the reaction mixture was stirred for 30 min. SEMCl (1.2 equiv, 5.5 µL, 0.031 mmol) was added and the reaction mixture was allowed to warm to −10° C. LCMS shows full conversion and the reaction mixture was quenched by adding saturated aqueous NaHCO₃. The aqueous layer was extracted with DCM and combined organic layers were dried and concentrated and purified by a 12 g silica gel column (0-10% MeOH/DCM, 0.5% NH₄OH) to give the desired product as a white foam (23 mg, 75% yield). MS (ESI+) m/z: 1171.6 [M+H]$^+$.

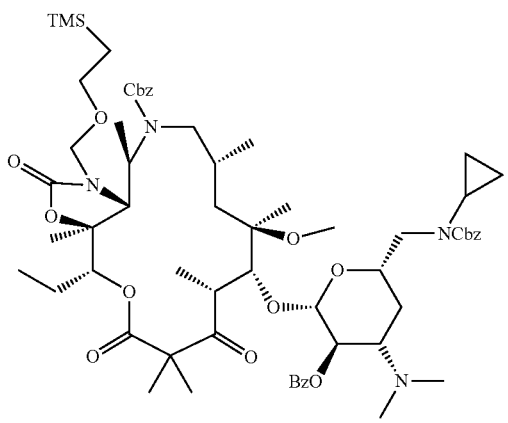

2-Methyl-3-descladinosyl-3-oxo-6-O-methyl-N9a-carbonylbenzyloxy-11,12-dideoxy-12,11-(oxycarbonylimino)-11-(2''-(trimethylsilyl)ethoxy)methyl) 2'-O-benzoyl-6'-(N-carbonylbenzyloxy)cyclopropylamino Azithromycin (S13-3)

The substrate S13-2 (23 mg, 0.0196 mmol) was dissolved in DME (0.5 mL) under N₂ and cooled at −40° C. KHMDS (1M in THF, 1.5 equiv, 29.4 µL, 0.029 mmol) was added dropwise and the reaction mixture was stirred for 30 min. Me₂SO₄ (2 equiv, 3.7 µL, 0.039 mmol) was added and the reaction mixture was allowed to warm to −10° C. LCMS shows full conversion and the reaction mixture was quenched by adding saturated aqueous NaHCO₃. The aqueous layer was extracted with DCM and combined organic layers were dried and concentrated and purified by a 12 g silica gel column (0-10% MeOH/DCM, 0.5% NH₄OH) to give the desired product as a white foam (15 mg, 68% yield). MS (ESI+) m/z: 1185.6 [M+H]$^+$.

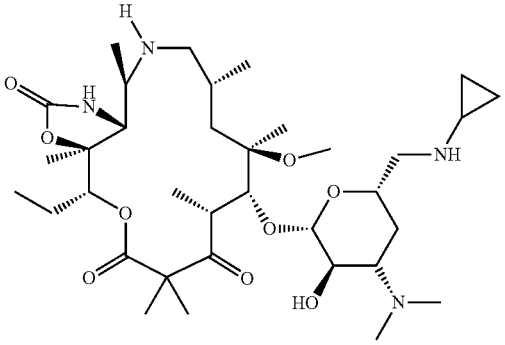

192

2-Methyl-3-descladinosyl-3-oxo-6-O-methy 1-N9a-desmethyl-11,12-dideoxy-12,11-(oxycarbonylimino)-6'-cylcopropylamino Azithromycin (192)

The substrate S13-3 (15 mg, 0.012 mmol) was dissolved in TFA and stirred for 5 min. Then the reaction mixture was diluted with DCM and quenched by adding saturated aqueous NaHCO₃. The aqueous layer was extracted with DCM and combined organic layers were dried and concentrated. The mixture was dissolved in MeOH (0.5 mL) and heated at 60° C. until LC/MS indicated complete consumption of starting material (16 h). The reaction mixture was cooled, and aqueous HCl (12 M, 3 equiv, 3 μL, 0.036 mmol) was added. The reaction mixture was sonicated briefly under mild vacuum, then backfilled with nitrogen. Pd/C was added and the mixture was stirred under streaming hydrogen for 10 minutes, then under static hydrogen until LC/MS indicated complete consumption of starting material. The reaction mixture was filtered through a syringe filter with the aid of methanol and concentrated. The residue was purified by HPLC (MeCN-water-0.1% HCO₂H) to yield the desired products. (1.62 mg, 16% in four steps). MS (ESI+) m/z: 228.5 [M+3H]³⁺, 342.2 [M+2H]²⁺, 683.4 [M+H]⁺; ¹H NMR (400 MHz, Methanol-d₄) δ 8.52 (s, 3H), 4.29 (d, 1H), 3.88 (s, 1H), 3.75-3.35 (m, 6H), 3.22-2.69 (m, 16H), 2.51-2.19 (m, 2H), 2.10-1.12 (m, 32H), 1.12-0.85 (m, 9H), 0.64-0.35 (m, 5H).

TABLE 26

Exemplary Azaketolides.

| Compound No. | Structure |
|---|---|
| 192 | 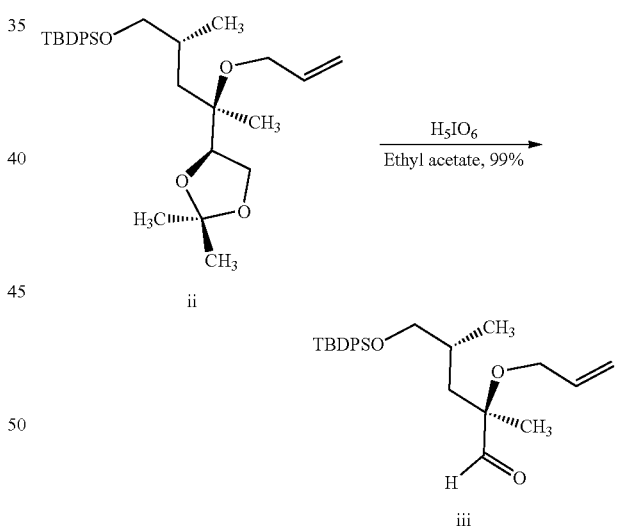 |

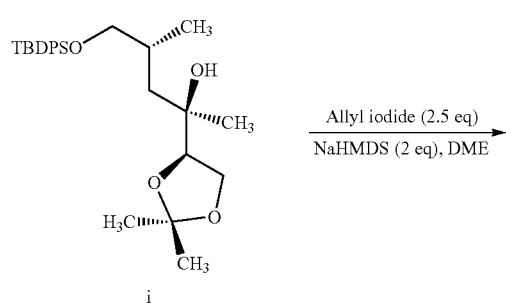

3-Iodoprop-1-ene (9 mL, 99 mmol, freshly passed through basic aluminium oxide) was added to a stirred solution of (2R,4R)-5-((tert-butyldiphenylsilyl)oxy)-2-((R)-2,2-dimethyl-1,3-dioxolan-4-yl)-4-methylpentan-2-ol (15 g, 32.8 mmol) in DME (114 mL) at rt. The reaction flask was placed in water bath at rt. A solution of NaHMDS 1 M in THF (65.7 ml, 65.7 mmol) was added drop wise (20 mL per 1 h) by using syringe pump over 3 h. TLC (15% ethyl acetate in hexanes) indicated 90% conversion. The reaction was stirred further for 2 h at rt. The reaction was quenched with aqueous ammonium chloride solution (60 mL), aqueous sodium thiosulfate solution (60 mL). The mixture was extracted with ether (100 ML×3). The combined organic layer was washed with brine (50 mL), dried over sodium sulfate and concentrated. The crude product was purified by column (0-10% ethyl acetate in hexanes) to yield compound ii as a colorless oil (14.3 g, 97% yield).

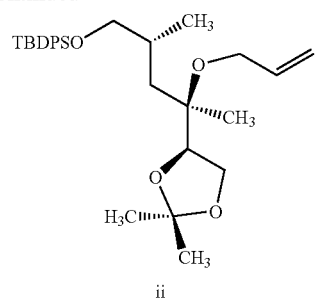

Periodic acid (10.32 g, 45.3 mmol, 1.5 equiv) was added in one portion to a solution of acetonide compound ii (15 g, 30.2 mmol, 1 equiv) in ethyl acetate (151 mL) at 23° C. The mixture was vigorously stirred for 1.5 h. TLC analysis (15% ethyl acetate-hexanes) indicated that full consumption of starting material had occurred, then was diluted with hexanes (200 mL). The suspension was passed through a short pad of silica gel (10 cm), eluting with 50% ethyl acetate-hexanes (300 mL). The combined filtrate was concentrated to afford the aldehyde iii as a colorless oil (12.72 g, 99%).

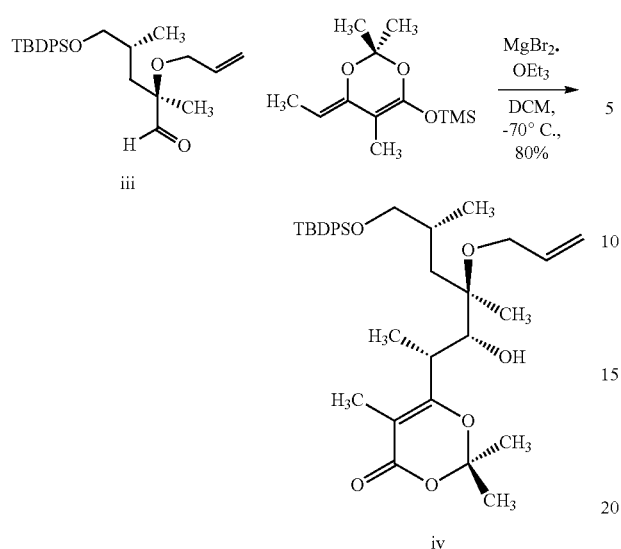

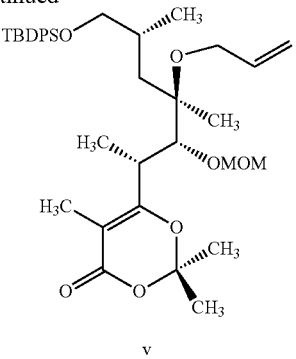

Magnesium bromide diethyl etherate (38.9 g, 151 mmol) was added to a solution of (2R,4R)-2-(allyloxy)-5-((tert-butyldiphenylsilyl)oxy)-2,4-dimethylpentanal iii (12.8 g, 30.1 mmol) in dichloromethane (250 mL) at −10° C. (ice-salt bath). After stirring at that temperature for 10 min, the suspension was cooled to −70° C. by means of an immersion cooler. (Z)-((4-ethylidene-2,2,5-trimethyl-4H-1,3-dioxin-6-yl)oxy)trimethylsilane (15.38 g, 60.3 mmol, 2.00 equiv) was added drop wise via syringe. Magnesium bromide etherate did not fully dissolve during the reaction. After 18 h, TLC analysis (50% ethyl acetate-hexanes) indicated that full consumption of starting material had occurred. Ether (100 mL), water (100 mL) and saturated aqueous ammonium chloride solution (100 mL) were added to the slurry, and the mixture was vigorously stirred for 10 min. The layers were separated, and the aqueous layer was extracted with ether (2×100 mL). The combined organic layers were washed with saturated sodium chloride solution and the washed solution was dried over magnesium sulfate. The dried solution was filtered, and the filtrate was concentrated. The residue was purified by column chromatography (combiflash, 220 g column, 0-10-30% ethyl acetate in hexanes over 50 min) afford mixture of diastereomers (8:1 dr). The mixture was again purified by column (combiflash, 220 g column, 0-2%-10% over 50 min acetone in DCM) afford pure diastereomer iv (less polar isomer) as a foaming solid (14.3 g, 80%).

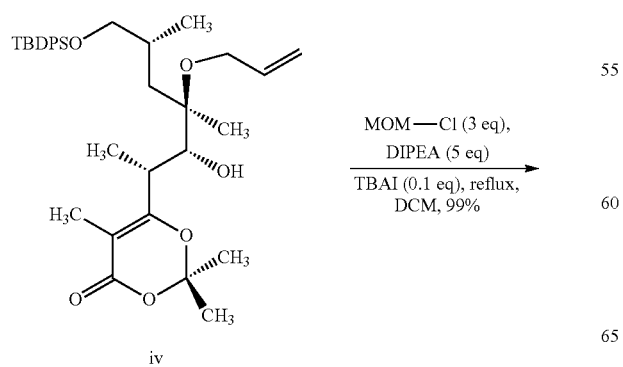

Diisopropylethylamine (11.27 mL, 64.6 mmol, 6.00 equiv) and tetrabutylammonium iodide (0.397 g, 1.07 mmol, 0.1 equiv) were added sequentially to a solution of aldol adduct iv (6.40 g, 10.76 mmol, 1 equiv) in dichloromethane (53.8 mL) in a 200-mL round-bottom flask at 23° C. The reaction vessel was cooled to 0° C. in an ice-water cooling bath and Chloromethyl methyl ether (2.45 mL, 32.3 mmol, 3 equiv) was added dropwise. The vessel was equipped with a dry reflux condenser and refluxed for 16 h. The reaction mixture was washed with water (20 mL), aqueous layer was back extracted with dichloromethane (20 mL). The combined organic layer was dried over sodium sulfate, filtered and concentrated. The crude product was purified by column chromatography on silica gel (20% ethyl acetate in hexanes) afford product v as pale-yellow oil (6.8 g, 99%).

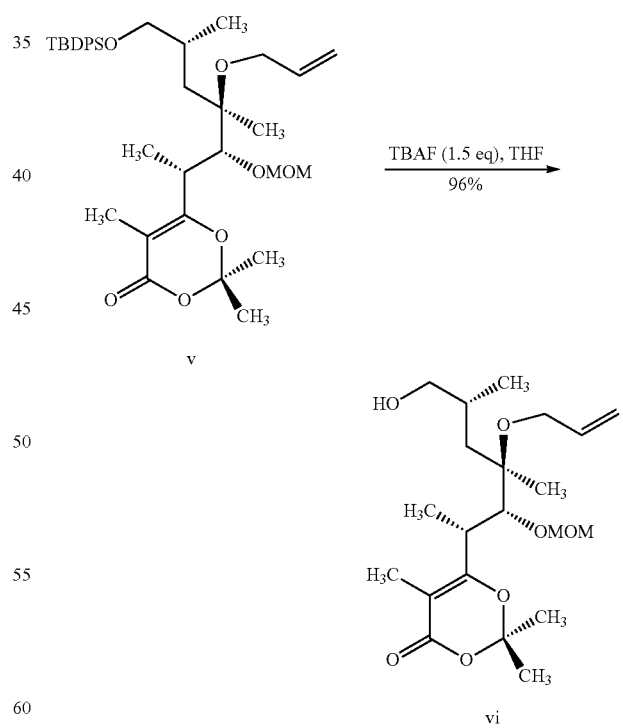

Tetrabutylammonium fluoride (1.0 M solution in tetrahydrofuran, 21.29 ml, 21.29 mmol, 2 equiv) was added dropwise to a solution of TBS-protected aldol adduct v (6.80 g, 10.64 mmol, 1 equiv) in tetrahydrofuran (53.20 ml) at 0° C. The mixture was allowed to warm to 23° C., and was stirred at this temperature for 15 h. The product solution was concentrated. The resulting brown oily residue was purified by column chromatography over silica gel (10%-?50% ethyl acetate-hexanes) to provide alcohol vi as a pale-yellow oil (4.10 g, 96%).

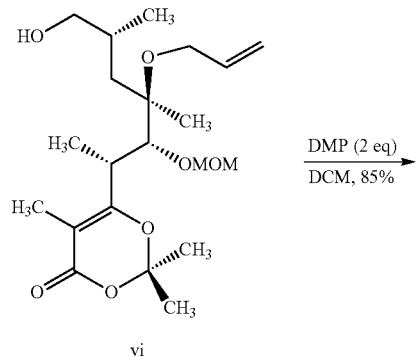

Dess-Martin periodinane (3.03 g, 7.14 mmol, 1.3 equiv) was added to a solution of alcohol vi (2.20 g, 5.49 mmol, 1 equiv) in water-saturated dichloromethane (27.5 mL) in a 200-mL round-bottom flask that was immersed in a 22° C. water bath. After 90 min, the mixture was diluted with saturated aqueous sodium bicarbonate solution (15 mL) and ether (20 mL). The mixture was stirred vigorously for 5 min, at which point saturated aqueous sodium thiosulfate (20 mL) was added. The resulting cloudy mixture was stirred vigorously for 1 h, and the layers were separated. The aqueous layer was extracted with ether (3×10 mL). The organic layers were combined, and the resulting solution was washed with 1:1 saturated aqueous sodium bicarbonate: saturated aqueous sodium thiosulfate (20 mL), then with saturated sodium chloride solution (20 mL). The washed organic solution was dried with sodium sulfate, and the dried solution was filtered. The filtrate was concentrated and the resulting residue was purified by chromatography over silica gel (0-30% ethyl acetate-hexanes) to provide acyclic MOM protected aldehyde vii (1.85 g, 85% yield) as a white foam.

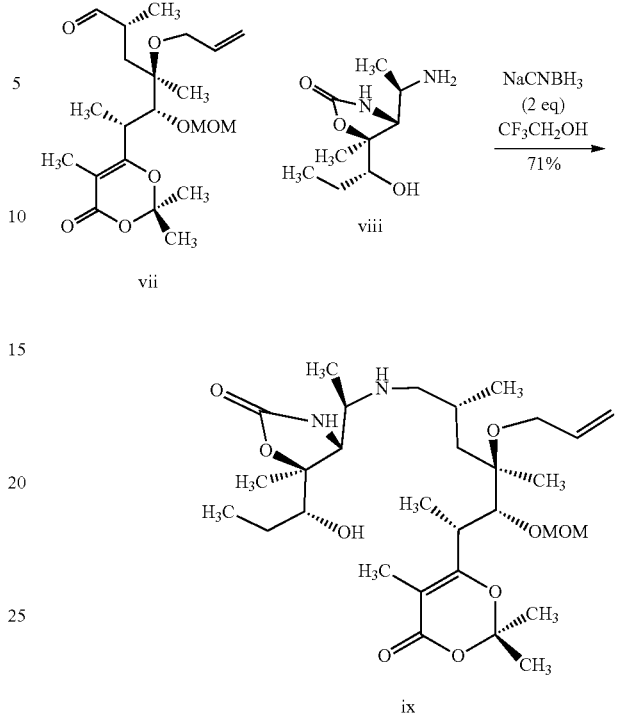

Sodium cyanoborohydride (0.583 g, 9.28 mmol, 2.00 equiv) was added in one portion to a solution of left-half amine vii (0.939 g, 4.64 mmol, 1 equiv) in trifluoroethanol (10 mL) at −15° C. (ice-salt bath). A solution of right-half aldehyde viii (1.85 g, 4.64 mmol, 1 equiv) in trifluoroethanol (3.0 mL) was added dropwise via syringe. The transfer was quantitated with the same solvent (2×1.5 mL). After 2 h, TLC analysis (40% acetone in hexanes+0.5% Et3N) indicated that full consumption of the aldehyde had occurred. The reaction mixture was allowed to warm to 23° C., then was concentrated under reduced pressure. The residue was partitioned between dichloromethane (20 mL) and saturated aqueous sodium bicarbonate solution (15 mL). The aqueous layer was separated and further extracted with dichloromethane (2×10 mL). The combined organic layers were dried over sodium sulfate, and the dried solution was concentrated. The residue was purified by column chromatography (30% acetone-hexanes+0.3% triethylamine) to afford the product ix (1.93 g, 71%) as a white foam.

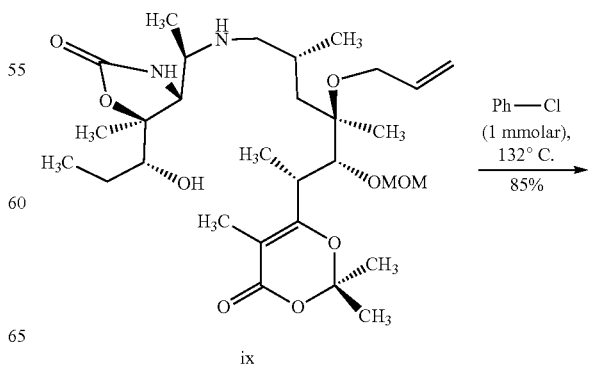

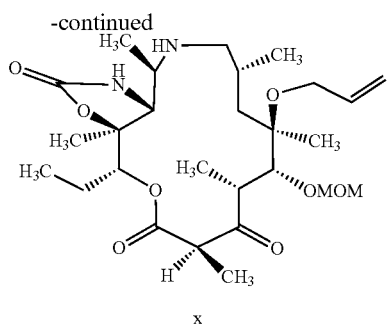

x

An oven-dried 5-L flask was charged with macrocyclization precursor ix (1.56 g, 2.28 mmol) and chlorobenzene (3000 mL). The flask was fitted with an oven-dried reflux condenser. Dry argon was bubbled through the solution via a 22-gauge needle for 15 min. The flask was then immersed in an oil bath preheated to 150° C. to allow a gentle reflux of the reaction solution. After 16 h, the heating bath was removed and the solution was allowed to cool to 23° C. The cooled solution was concentrated under reduced pressure (rotary evaporation, 10 Torr, 40° C. water bath) and the residue was purified by flash column chromatography (20% acetone in hexanes) to afford the product x as a white foam (1.20 g, 85%).

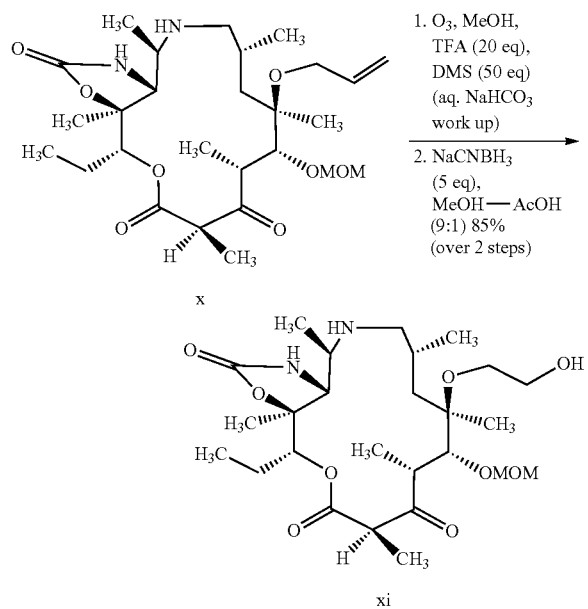

Trifluoracetic acid (0.326 mL, 4.23 mmol, 10 equiv) was added to a stirred solution of allyl macrolide x (0.223 g, 0.423 mmol, 1 equiv) in methanol (1 mL) and dichloromethane (3 mL) at −78° C. Ozone was bubbled through the above solution at −78° C. for 2 min till stable blue color attains. The solution was degassed with nitrogen for 5 min to remove excess ozone in it. Dimethyl sulfide (1.566 mL, 21.17 mmol, 50 equiv) was added and stirred for 30 min at −78° C. Dry ice-acetone bath was removed, the reaction was quenched with saturated aqueous sodium bicarbonate (6 mL) and warmed to rt. The layers were mixed vigorously, then were separated. The aqueous layer was extracted with dichloromethane (2×10 mL), and the combined organic layer was washed with brine (10 mL), filtered through a pad of sodium sulfate. The filtrate was concentrated under reduced pressure, and the crude (232 mg) was subjected to the next reaction without further purification.

The crude aldehyde (242 mg) was dissolved in 9:1 methanol:acetic acid (2.2 mL) and sodium cyanoborohydride (160 mg, 2.54 mmol, 6 equiv) was added at rt. The reaction was stirred at rt for 15 h. LC-Ms indicated complete conversion to product. The reaction was concentrated under reduced pressure. The residue was partitioned between dichloromethane (15 mL) and saturated aqueous sodium bicarbonate solution (10 mL). The aqueous layer was separated and further extracted with dichloromethane (2×10 mL). The combined organic layers were dried over sodium sulfate, and the dried solution was concentrated. The residue was purified by column chromatography (40% acetone-hexanes+1% triethylamine) to afford the product xi (0.210 g, 85% over 2 steps) as a white foam.

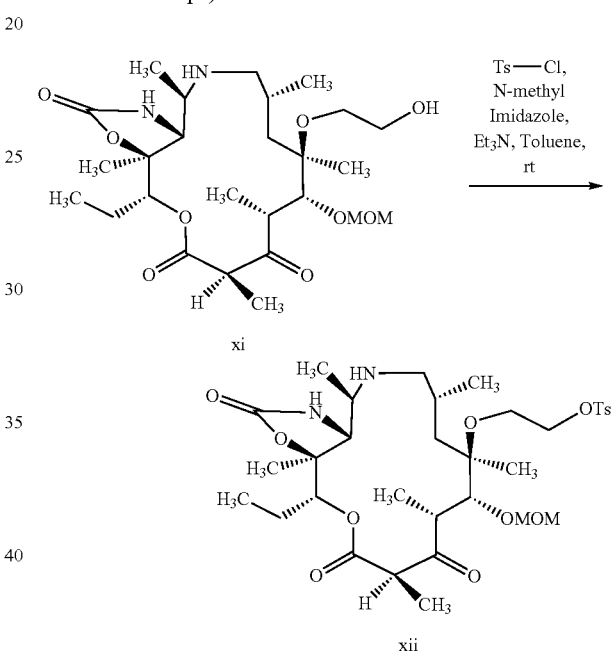

Triethylamine (0.378 mL, 2.71 mmol, 5.00 equiv) and N-methylimidazole (0.064 mL, 0.814 mmol, 1.5 equiv) were added sequentially to a solution of alcohol xi (0.288 g, 0.543 mmol, 1 equiv) in toluene (4.14 mL) in a 25-mL round-bottom flask at 23° C. p-toluenesulfonyl chloride (0.155 g, 0.814 mmol, 1.5 equiv) was added in one portion at rt. The resulting pale-yellow reaction mixture was stirred for 1 h at rt. TLC (40% acetone in hexanes+0.5% triethylamine) indicated full consumption of the alcohol had occurred. The reaction was diluted with aqueous sodium bicarbonate solution (5 mL) and ethyl acetate (10 mL). The mixture was stirred vigorously for 10 minutes, and the resulting biphasic mixture was transferred to a 30-mL separatory funnel. The layers were separated, and the aqueous layer was extracted with ethyl acetate (2×10 mL). The organic layers were combined and the resulting solution was washed with saturated sodium chloride solution (10 mL). The washed organic solution was dried with sodium sulfate, and the dried solution was filtered. The filtrate was concentrated to afford xii as a pale-yellow foaming solid (510 mg). The crude product was subjected to the next reaction without further purification.

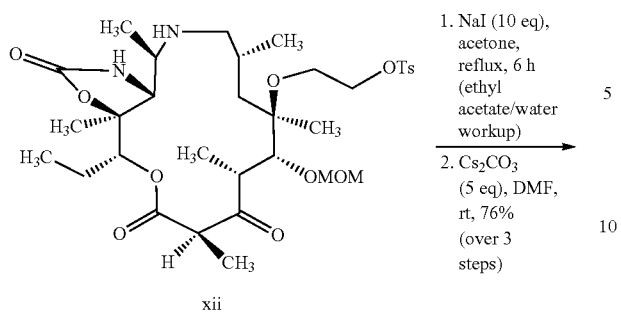

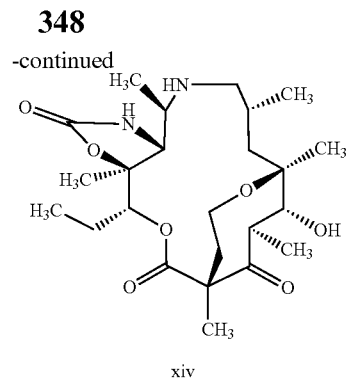

xii

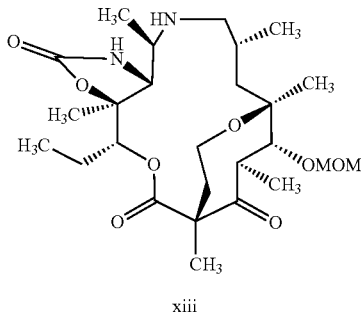

xiii

6 N aqueous hydrochloric acid (4.500 mL, 27.0 mmol, 25.0 equiv) was added to a solution of xiii (0.554 g, 1.081 mmol, 1 equiv) in methanol (3.60 mL) at 0° C. Ice-water bath was removed and the mixture stirred at 23° C. for 12 h, at which point LC-MS indicated that full consumption of starting material had occurred. The reaction was concentrated under reduced pressure. The residue was dissolved in methanol (10 mL) and quenched with solid sodium bicarbonate (6 g, 66 equiv). The mixture was diluted with dichloromethane (50 mL) and stirred for 30 min. The mixture was filtered through a pad of Celite, and the filter caking was rinsed with 2% methanol in dichloromethane (100 mL). The filtrate was concentrated. The crude product was purified by flash column chromatography ((7% methanol-dichloromethane+1% triethylamine) to afford the product (xiv) as a white solid (0.436 g, 86%).

The crude tosylate (510 mg) was dissolved in acetone (2 mL) and sodium iodide (1.22 g, 8.15 mmol, 15 equiv with respect to xii) was added at rt. The flask was fitted with an oven-dried reflux condenser and refluxed for 6 h. TLC (40% acetone in hexanes+0.5% triethylamine) indicated full consumption of the aldehyde had occurred. The reaction was cooled to rt and concentrated under reduced pressure. The residue was partitioned between ethyl acetate (20 mL) and water (20 mL). The aqueous layer was separated and further extracted with ethyl acetate (2×10 mL). The combined organic layers were dried over sodium sulfate, and the dried solution was concentrated. The crude iodo compound was dissolved in N,N-dimethyl formamide (6 mL) and cesium carbonate (0.885 g, 2.72 mmol, 5 equiv with respect to xii) was added at rt. The resulting reaction mixture was stirred at rt for 4 h. The reaction was concentrated under reduced pressure. The residue was partitioned between ethyl acetate (30 mL) and water (10 mL). The aqueous layer was separated and further extracted with ethyl acetate (2×10 mL). The combined organic layers were dried over sodium sulfate, and the dried solution was concentrated. The residue was purified by column chromatography (30%-40% acetone-hexanes+0.5% triethylamine) to afford the product xiii (0.199 g, 76% over 3 steps) as a white foam.

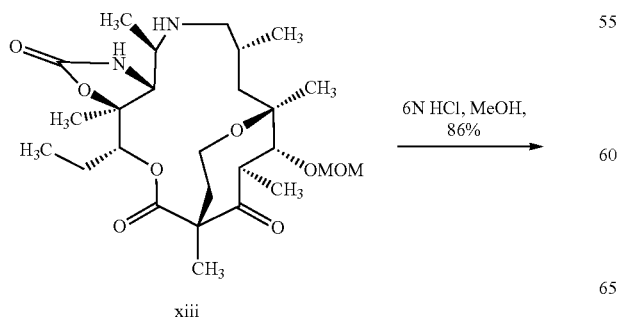

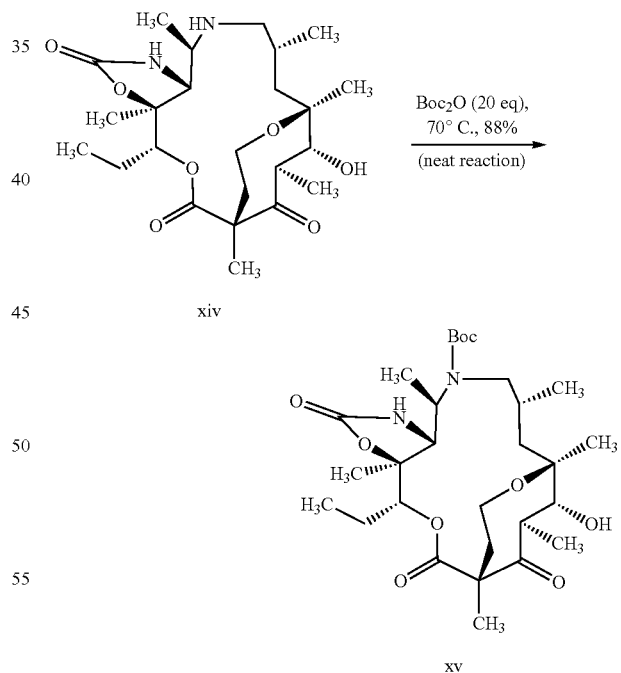

Boc-anhydride (3.80 mL, 16.37 mmol, 17.9 equiv) was added to a flask containing strapped macrolide xiv (0.428 g, 0.913 mmol, 1 equiv). The flask was shield with a rubber septum. The vessel and its contents were then heated by means of a 70° C. oil bath. The reaction mixture was maintained at 70° C. for 4 to 5 h (till clear solution appeared). The solution was allowed to cool to 23° C., then was concentrated. The crude residue was purified by column chromatography over silica gel (10% acetone in hexanes, 30% acetone in hexanes+0.5% triethylamine) to afford xv as a white foam (0.455 g, 88%).

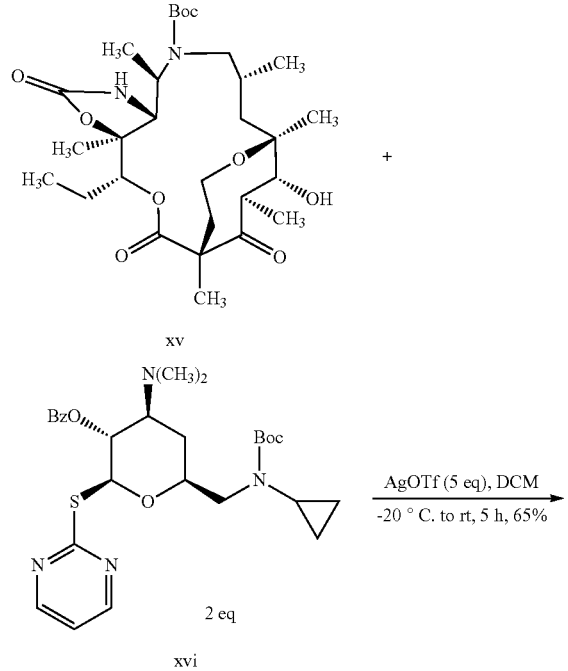

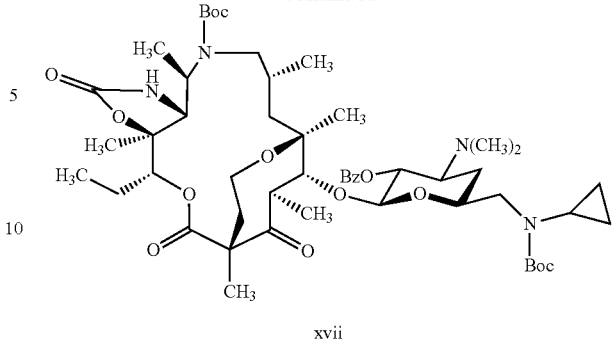

4-Å Molecular sieves (1.2 g, activated by heating at 200° C. under 0.1 Torr for 16 h, then cooling to 23° C. under dry argon) was added to a stirred solution of macrolide xv (0.455 g, 0.80 mmol, 1 equiv) and thioglycoside xvi (0.846 g, 1.60 mmol, 2.00 equiv) in dichloromethane (8.0 mL) at rt. The mixture was cooled to −20° C., after 10 min, silver trifluoromethanesulfonate (1.233 g, 4.80 mmol, 6.00 equiv) was added in one portion. The slurry was allowed to stir for 1 h and then warm to 23° C. After 18 h, saturated aqueous sodium bicarbonate solution (5 mL) was added. The suspension was filtered through a thin pad of Celite (2 mm). The filter cake was rinsed with dichloromethane (30 mL). The combined biphasic filtrate was partitioned, and the organic layer was dried over sodium sulfate. The dried solution was concentrated under reduced pressure and the residue was purified by column chromatography (7→15% acetone-dichloromethane) to afford two products as a white foam (6:1 β:α anomers 76%, less polar product xvii (major) 0.485 g (61.5%)).

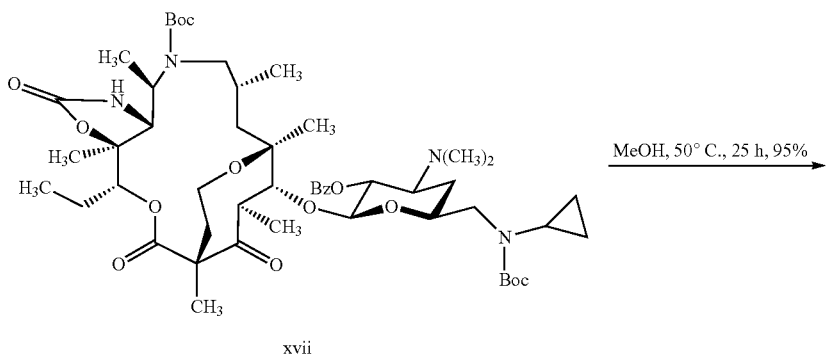

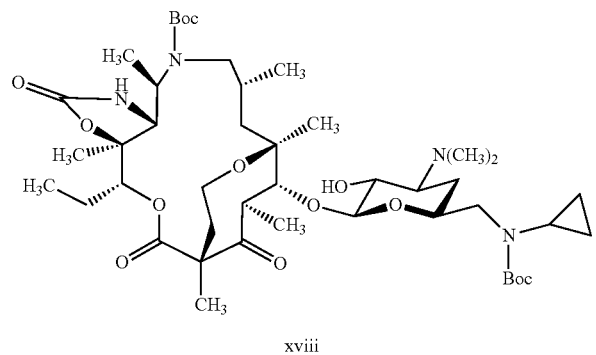

A stirred solution of xvii (0.120 g, 0.122 mmol) and dry methanol (3 mL) was heated to 50° C. in an oil bath for 23 h, at which point TLC (40% acetone in hexanes+0.5% triethylamine) indicated that full consumption of starting material had occurred. The reaction was concentrated directly under reduced pressure. The crude was purified by column (20-35% acetone in hexanes+0.5% Et₃N) afford product xviii (102 mg, 95%) as foaming solid.

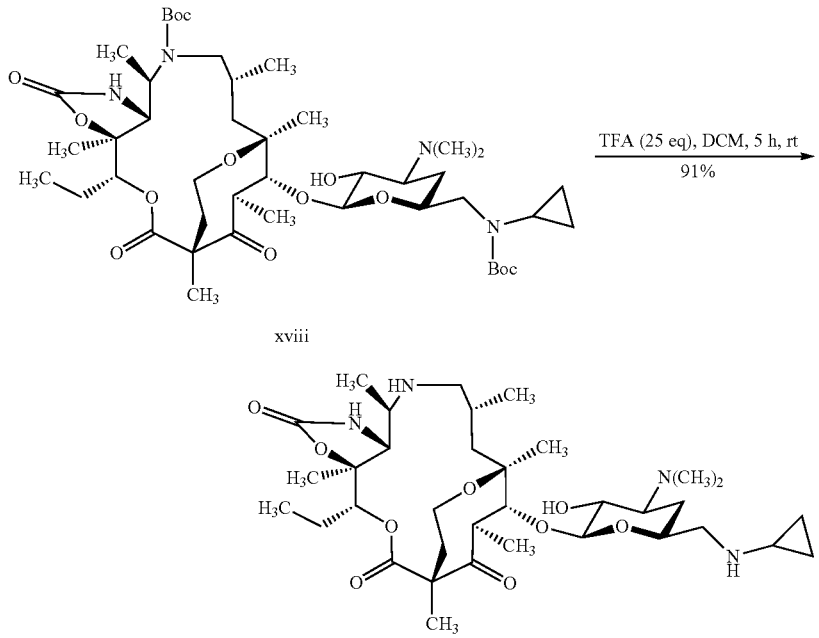

Compound xviii (0.102 g, 0.116 mmol, 1 equiv) was dissolved in dichloromethane (2 mL) and the solution was cooled to 0° C. in an ice-water bath. After 10 min, trifluoroacetic acid (0.223 mL, 2.89 mmol, 25 equiv) was added dropwise at 0° C. After 10 min, the ice-water bath removed, warmed to rt and stirred for 5 h, at which point LC-MS indicated that full consumption of starting material had occurred. The reaction was concentrated under reduced pressure. The residue was partitioned between dichloromethane (15 mL) and saturated aqueous sodium bicarbonate solution (20 mL). The aqueous layer was separated and further extracted with dichloromethane (4×15 mL). The combined organic layers were dried over sodium sulfate, and the dried solution was concentrated. The residue was purified by column chromatography (5% methanol in DCM+ 0.5% 30% aqueous ammonium hydroxide solution) to afford 80 (0.071 g, 91%) as a white amorphous solid.

The following compounds were synthesized in analogous fashion to the procedures employed for the synthesis of compound 80. Compounds obtained as the C-2 epimer were isolated in the final reaction step of the sequence.

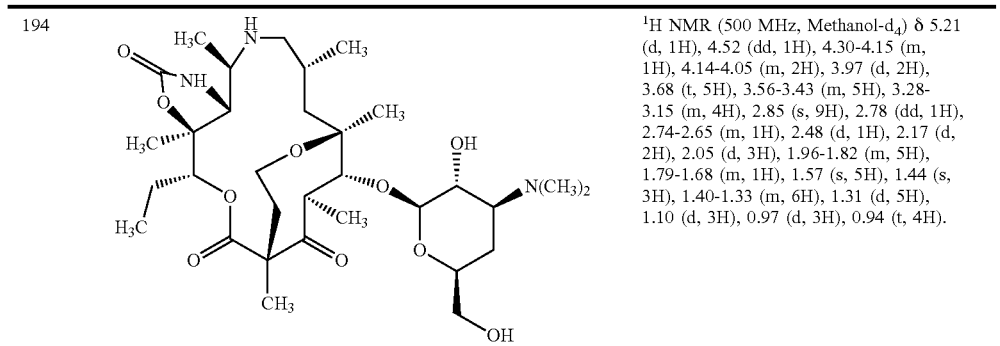

194

$^1$H NMR (500 MHz, Methanol-d$_4$) δ 5.21 (d, 1H), 4.52 (dd, 1H), 4.30-4.15 (m, 1H), 4.14-4.05 (m, 2H), 3.97 (d, 2H), 3.68 (t, 5H), 3.56-3.43 (m, 5H), 3.28-3.15 (m, 4H), 2.85 (s, 9H), 2.78 (dd, 1H), 2.74-2.65 (m, 1H), 2.48 (d, 1H), 2.17 (d, 2H), 2.05 (d, 3H), 1.96-1.82 (m, 5H), 1.79-1.68 (m, 1H), 1.57 (s, 5H), 1.44 (s, 3H), 1.40-1.33 (m, 6H), 1.31 (d, 5H), 1.10 (d, 3H), 0.97 (d, 3H), 0.94 (t, 4H).

| | | |
|---|---|---|
| 195 | 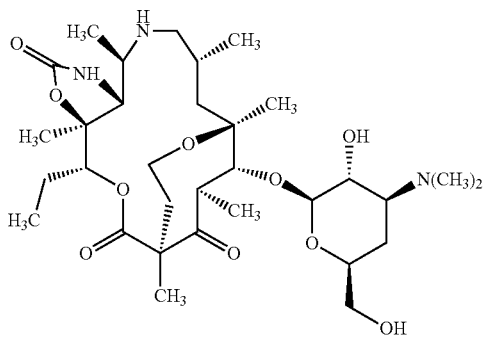 [SMILES: CC[C@H]1OC(=O)[C@@]2(C)CCO[C@](C)(C[C@@H](C)CN[C@H](C)[C@H]3NC(=O)O[C@@]31C)[C@H](O[C@@H]1O[C@H](CO)C[C@H](N(C)C)[C@H]1O)[C@@H](C)C2=O] | ¹H NMR (500 MHz, Methanol-d₄) δ 5.15 (d, 1H), 4.57-4.47 (m, 1H), 4.19 (d, 1H), 4.10 (td, 1H), 3.66 (d, 4H), 3.53 (d, 1H), 3.49 (d, 4H), 3.24 (s, 4H), 3.16 (s, 2H), 2.81 (s, 6H), 2.72 (d, 1H), 2.31 (d, 1H), 2.21 (dd, 1H), 2.18-2.10 (m, 1H), 2.06-1.99 (m, 1H), 1.88 (dd, 1H), 1.72 (d, 3H), 1.61-1.55 (m, 7H), 1.46 (d, 3H), 1.39 (s, 4H), 1.31 (s, 6H), 1.07 (d, 3H), 1.01-0.92 (m, 6H). |
| 196 | 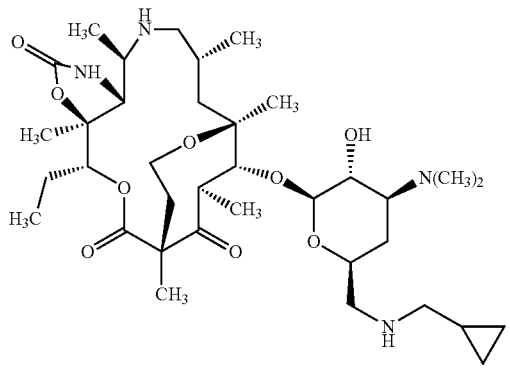 [SMILES: CC[C@H]1OC(=O)[C@]2(C)CCO[C@](C)(C[C@@H](C)CN[C@H](C)[C@H]3NC(=O)O[C@@]31C)[C@H](O[C@@H]1O[C@H](CNCC3CC3)C[C@H](N(C)C)[C@H]1O)[C@@H](C)C2=O] | ¹H NMR (600 MHz, Methanol-d₄) δ 5.11 (s, 1H), 4.61 (s, 1H), 4.48 (d, 1H), 4.07 (d, 2H), 3.75 (d, 2H), 3.17 (s, 3H), 2.99 (d, 2H), 2.69 (s, 1H), 2.63 (d, 2H), 2.52 (s, 5H), 2.32-2.07 (m, 3H), 2.06-1.78 (m, 3H), 1.77-1.58 (m, 5H), 1.54 (d, 6H), 1.46-1.34 (m, 11H), 1.00 (d, 3H), 0.96 (d, 3H), 0.91 (dt, 6H), 0.59 (d, 2H), 0.24 (s, 2H), 0.09 (s, 1H). |
| 197 | 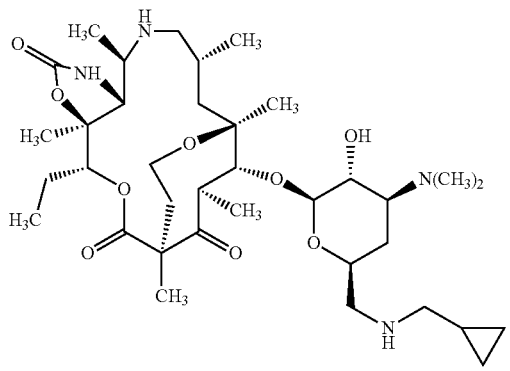 [SMILES: CC[C@H]1OC(=O)[C@@]2(C)CCO[C@](C)(C[C@@H](C)CN[C@H](C)[C@H]3NC(=O)O[C@@]31C)[C@H](O[C@@H]1O[C@H](CNCC3CC3)C[C@H](N(C)C)[C@H]1O)[C@@H](C)C2=O] | ¹H NMR (600 MHz, Methanol-d₄) δ 5.26-5.14 (m, 1H), 4.75 (s, 1H), 4.61 (s, 1H), 4.56 (d, 1H), 4.20 (d, 1H), 4.07 (d, 2H), 4.01-3.92 (m, 2H), 3.69 (td, 2H), 3.53-3.45 (m, 6H), 3.17 (s, 3H), 3.12 (t, 1H), 3.04 (t, 1H), 2.96 (dd, 4H), 2.81-2.73 (m, 6H), 2.66 (s, 5H), 2.47 (d, 1H), 2.02 (t, 1H), 1.93-1.81 (m, 7H), 1.73 (dd, 1H), 1.55 (s, 4H), 1.46-1.36 (m, 9H), 1.24 (d, 12H), 1.07 (d, 3H), 0.96 (d, 3H), 0.90 (dq, 9H), 0.64 (d, 2H), 0.32 (s, 2H), 0.09 (s, 1H). |
| 198 | 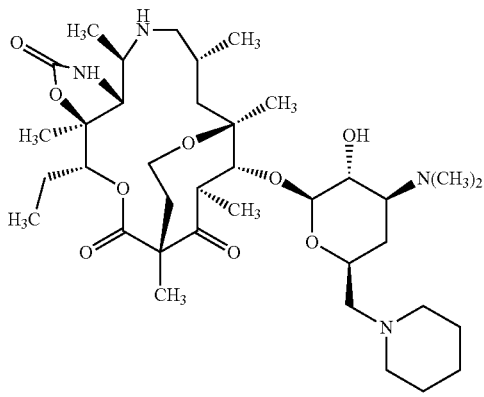 [SMILES: CC[C@H]1OC(=O)[C@]2(C)CCO[C@](C)(C[C@@H](C)CN[C@H](C)[C@H]3NC(=O)O[C@@]31C)[C@H](O[C@@H]1O[C@H](CN3CCCCC3)C[C@H](N(C)C)[C@H]1O)[C@@H](C)C2=O] | ¹H NMR (600 MHz, Methanol-d₄) δ 5.11 (dd, 1H), 4.68 (d, 1H), 4.46 (d, 1H), 4.13 (d, 1H), 4.10-4.00 (m, 1H), 3.78 (s, 2H), 3.48 (d, 1H), 3.17 (d, 3H), 3.04 (d, 1H), 2.64 (d, 11H), 2.20 (d, 2H), 2.04-1.90 (m, 2H), 1.86 (dd, 1H), 1.71-1.60 (m, 7H), 1.53 (d, 10H), 1.40 (d, 3H), 1.30 (d, 13H), 1.01 (d, 3H), 0.95 (d, 4H), 0.92 (t, 4H). |

| | | |
|---|---|---|
| 199 | 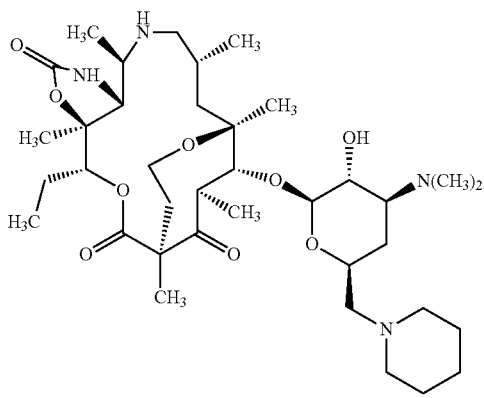 [SMILES: CC[C@H]1OC(=O)[C@@]2(C)CCO[C@](C)(C[C@@H](C)CN[C@H](C)[C@H]3NC(=O)O[C@@]31C)[C@H](O[C@@H]1O[C@H](CN3CCCCC3)C[C@H](N(C)C)[C@H]1O)[C@@H](C)C2=O] | ¹H NMR (600 MHz, Methanol-d₄) δ 5.20 (dd, 1H), 4.75 (s, 2H), 4.63-4.47 (m, 2H), 4.20 (dd, 1H), 4.12-4.01 (m, 2H), 3.96 (t, 1H), 3.88 (t, 1H), 3.79-3.55 (m, 1H), 3.51-3.46 (m, 2H), 3.25-3.15 (m, 6H), 2.75 (dd, 1H), 2.64 (d, 12H), 2.45 (d, 1H), 2.02 (t, 1H), 1.84 (s, 5H), 1.75-1.61 (m, 5H), 1.55 (s, 3H), 1.49 (d, 2H), 1.39 (s, 3H), 1.35 (d, 4H), 1.14 (dd, 1H), 1.07 (d, 3H), 0.96 (d, 3H), 0.92 (t, 4H). |
| 200 | 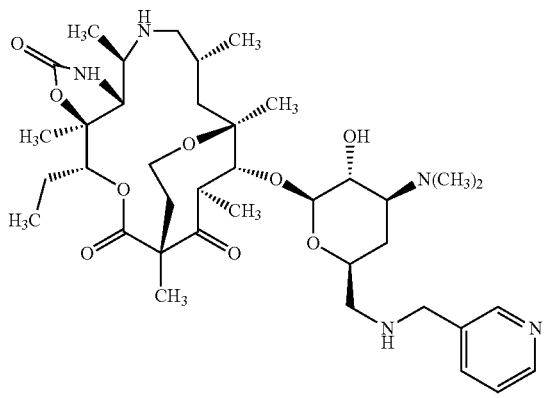 [SMILES: CC[C@H]1OC(=O)[C@]2(C)CCO[C@](C)(C[C@@H](C)CN[C@H](C)[C@H]3NC(=O)O[C@@]31C)[C@H](O[C@@H]1O[C@H](CNCc3cccnc3)C[C@H](N(C)C)[C@H]1O)[C@@H](C)C2=O] | ¹H NMR (600 MHz, Methanol-d₄) δ 8.46 (d, 3H), 7.86 (d, 1H), 7.44 (dd, 1H), 5.10 (dd, 1H), 4.68 (d, 1H), 4.46 (d, 1H), 4.07 (d, 1H), 4.04-3.95 (m, 1H), 3.93-3.82 (m, 2H), 3.76-3.61 (m, 3H), 3.47 (d, 1H), 3.40 (d, 3H), 3.22-3.00 (m, 2H), 2.78 (d, 2H), 2.62 (s, 7H), 2.18 (d, 2H), 1.98 (t, 1H), 1.94-1.80 (m, 2H), 1.67 (t, 2H), 1.60 (s, 1H), 1.53 (d, 8H), 1.41 (d, 3H), 1.28 (d, 6H), 1.00 (d, 3H), 0.97-0.91 (m, 6H). |
| 201 | 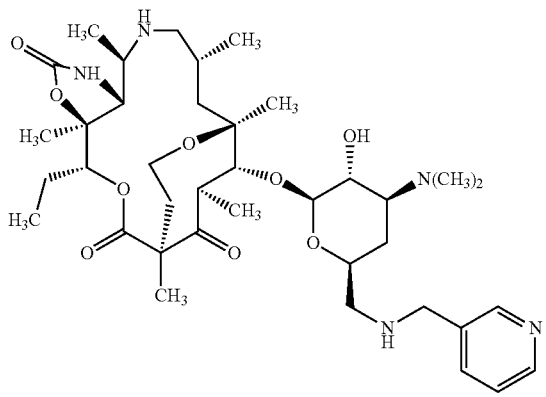 [SMILES: CC[C@H]1OC(=O)[C@@]2(C)CCO[C@](C)(C[C@@H](C)CN[C@H](C)[C@H]3NC(=O)O[C@@]31C)[C@H](O[C@@H]1O[C@H](CNCc3cccnc3)C[C@H](N(C)C)[C@H]1O)[C@@H](C)C2=O] | ¹H NMR (600 MHz, Methanol-d₄) δ 8.46 (s, 2H), 7.87 (d, 1H), 7.44 (t, 1H), 5.19 (d, 1H), 4.61 (s, 1H), 4.49 (d, 1H), 4.23-4.15 (m, 1H), 4.01 (d, 2H), 3.91 (dq, 3H), 3.77 (t, 1H), 3.69 (d, 1H), 3.64 (s, 1H), 3.23-3.16 (m, 5H), 2.82 (d, 2H), 2.74 (dd, 1H), 2.66 (s, 8H), 2.46 (d, 1H), 2.00 (t, 1H), 1.94 (d, 1H), 1.91-1.85 (m, 1H), 1.83 (s, 4H), 1.71 (d, 1H), 1.54 (s, 4H), 1.36-1.33 (m, 6H), 1.12 (dd, 1H), 1.07 (d, 3H), 0.95-0.88 (m, 8H). |
| 202 | 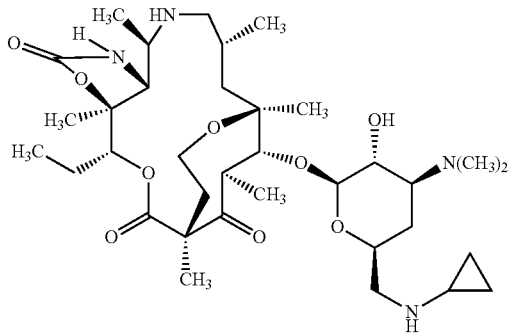 | ¹H NMR (600 MHz, Methanol-d₄) δ 5.19 (dd, 1H), 4.70-4.50 (m, 1H), 4.30 (d, 1H), 4.17 (td, 1H), 4.01 (dd, 1H), 3.85 (d, 1H), 3.70 (d, 1H), 3.49 (h, 2H), 3.15 (dq, 2H), 2.94 (dd, 1H), 2.83 (s, 4H), 2.65-2.40 (m, 2H), 2.24-2.13 (m, 1H), 2.09 (d, 1H), 1.95-1.75 (m, 2H), 1.75-1.64 (m, 2H), 1.59 (d, 4H), 1.53 (d, 2H), 1.42 (s, 2H), 1.26 (d, 2H), 1.03 (d, 2H), 0.95 (t, 2H), 0.80-0.62 (m, 3H). |

| | | |
|---|---|---|
| 203 | 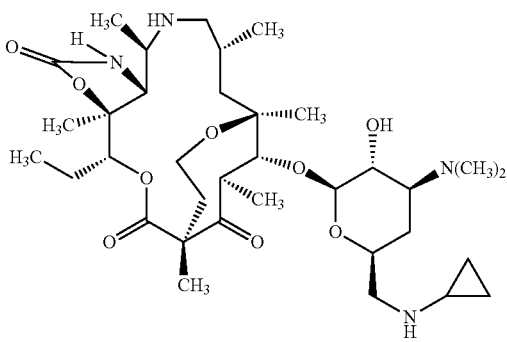 | ¹H NMR (500 MHz, Methanol-d₄) δ 5.19 (dd, 1H), 4.49 (d, 1H), 4.20 (p, 1H), 4.10-4.01 (m, 2H), 3.93 (dt, 2H), 3.75-3.63 (m, 1H), 3.53-3.36 (m, 2H), 3.20 (dd, 3H), 2.91-2.81 (m, 2H), 2.75 (dd, 1H), 2.65 (s, 6H), 2.47 (d, 1H), 2.26 (dq, 1H), 2.02 (t, 1H), 1.97-1.86 (m, 2H), 1.84 (s, 4H), 1.71 (ddd, 1H), 1.55 (s, 5H), 1.40 (s, 3H), 1.35 (d, 4H), 1.14 (dd, 2H), 1.07 (d, 4H), 0.96 (d, 3H), 0.90 (q, 6H), 0.53 (td, 2H), 0.38 (dd, 2H). |
| 204 | 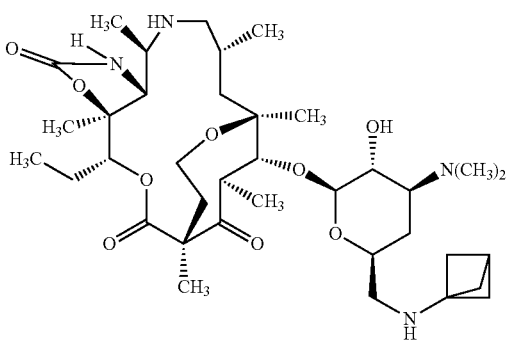 | ¹H NMR (500 MHz, Methanol-d₄) δ 5.11 (d, 1H), 4.58 (s, 1H), 4.43 (d, 1H), 4.05 (dd, 2H), 3.80 (d, 1H), 3.65-3.53 (m, 1H), 3.46 (d, 2H), 3.14 (s, 1H), 3.07-2.81 (m, 2H), 2.71 (d, 2H), 2.65-2.57 (m, 1H), 2.52 (s, 5H), 2.43 (s, 1H), 2.29-2.14 (m, 2H), 1.96 (t, 1H), 1.89-1.78 (m, 8H), 1.68 (d, 2H), 1.60 (s, 1H), 1.54 (d, 7H), 1.41 (d, 4H), 1.33 (s, 4H), 0.99 (d, 3H), 0.97-0.93 (m, 4H), 0.93-0.88 (m, 5H). |
| 205 | 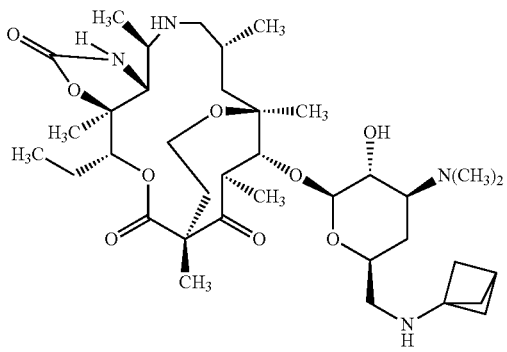 | ¹H NMR (500 MHz, Methanol-d₄) δ 5.27-5.10 (m, 1H), 4.58 (s, 1H), 4.47 (d, 1H), 4.19 (q, 1H), 4.05 (t, 2H), 3.94 (dt, 2H), 3.61 (dd, 1H), 3.50 (d, 2H), 3.41-3.34 (m, 2H), 3.26-3.00 (m, 2H), 2.80-2.72 (m, 3H), 2.70-2.62 (m, 1H), 2.58 (s, 6H), 2.45 (d, 2H), 2.02 (t, 1H), 1.94-1.79 (m, 12H), 1.77-1.66 (m, 1H), 1.55 (s, 3H), 1.50-1.41 (m, 1H), 1.39 (s, 3H), 1.35 (d, 4H), 1.15 (dd, 2H), 1.07 (d, 3H), 0.96 (d, 3H), 0.93-0.85 (m, 6H). |
| 206 | 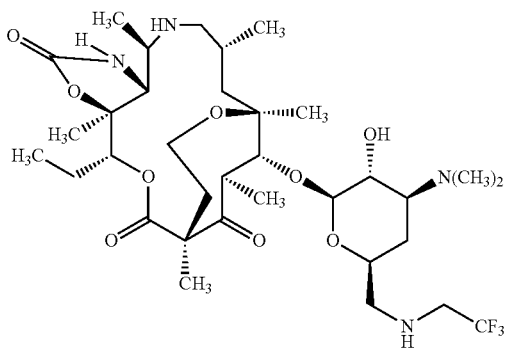 | ¹H NMR (500 MHz, Methanol-d₄) δ 5.11 (dd, 1H), 4.58 (s, 1H), 4.45 (d, 1H), 4.16-3.97 (m, 2H), 3.88-3.74 (m, 1H), 3.62 (dd, 1H), 3.46 (d, 2H), 3.42-3.35 (m, 1H), 3.05 (d, 1H), 2.86 (d, 2H), 2.61 (d, 7H), 2.24-2.17 (m, 2H), 2.04-1.80 (m, 3H), 1.66 (dd, 3H), 1.54 (d, 8H), 1.41 (d, 3H), 1.33 (s, 4H), 1.00 (d, 3H), 0.96-0.93 (m, 4H), 0.93-0.87 (m, 6H). |

| | | |
|---|---|---|
| 207 | 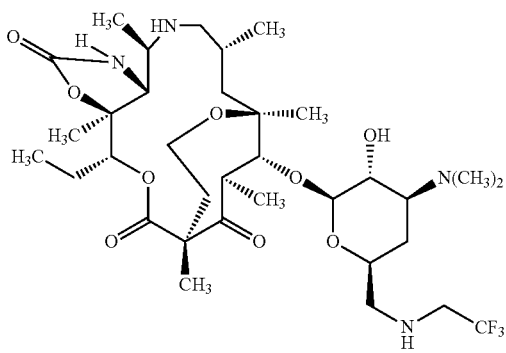 | ¹H NMR (500 MHz, Methanol-d₄) δ 5.25-5.10 (m, 1H), 4.58 (s, 1H), 4.48 (d, 1H), 4.20 (p, 1H), 4.10-4.00 (m, 2H), 4.00-3.84 (m, 2H), 3.68-3.58 (m, 1H), 3.48 (d, 2H), 3.36 (dd, 3H), 3.24 (d, 1H), 3.19-3.10 (m, 1H), 3.04 (s, 1H), 2.88 (d, 2H), 2.75 (dd, 1H), 2.70-2.62 (m, 1H), 2.57 (s, 5H), 2.45 (d, 1H), 2.02 (t, 1H), 1.88 (dd, 2H), 1.84 (d, 4H), 1.72 (ddd, 1H), 1.55 (s, 4H), 1.39 (s, 3H), 1.36 (d, 3H), 1.15 (dd, 2H), 1.07 (d, 3H), 0.95 (d, 3H), 0.94-0.86 (m, 5H). |
| 208 | 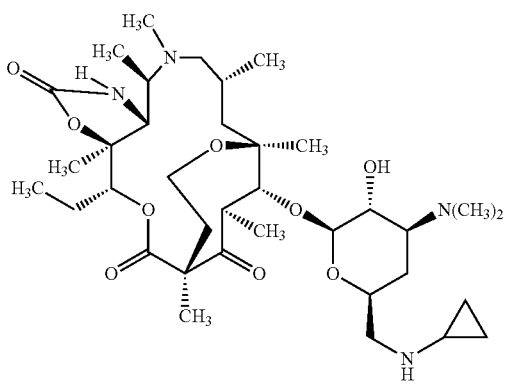 | ¹H NMR (600 MHz, Methanol-d₄) δ 5.19 (dd, 1H), 4.57 (d, 1H), 4.26-4.00 (m, 2H), 3.88 (d, 4H), 3.57-3.36 (m, 3H), 3.05 (d, 3H), 2.82 (s, 9H), 2.60-2.39 (m, 5H), 2.27 (d, 3H), 2.12-1.96 (m, 3H), 1.89 (ddd, 3H), 1.81-1.66 (m, 2H), 1.59 (d, 7H), 1.48 (d, 3H), 1.42 (s, 3H), 1.23 (d, 3H), 1.01 (d, 3H), 0.95 (t, 3H), 0.71-0.53 (m, 4H). |
| 209 | 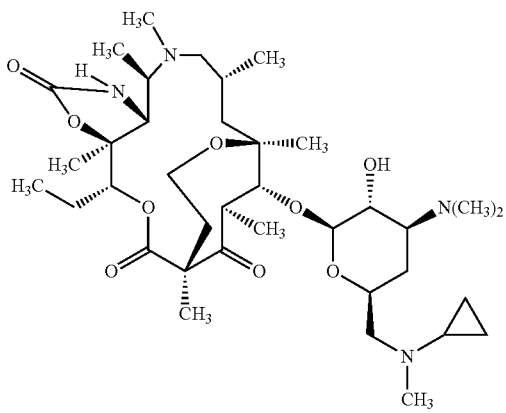 | ¹H NMR (500 MHz, Methanol-d₄) δ 5.16 (dd, 1H), 4.50 (d, 1H), 4.15 (d, 1H), 3.98 (s, 2H), 3.86-3.58 (m, 2H), 3.53-3.36 (m, 3H), 2.81 (s, 7H), 2.74-2.56 (m, 3H), 2.43 (s, 7H), 2.05-1.85 (m, 5H), 1.81 (tt, 1H), 1.72 (ddq, 2H), 1.59 (s, 3H), 1.56-1.50 (m, 4H), 1.42 (d, 3H), 1.37 (s, 3H), 1.16 (dd, 3H), 1.02-0.89 (m, 6H), 0.59-0.49 (m, 2H), 0.48-0.36 (m, 2H). |
| 210 | 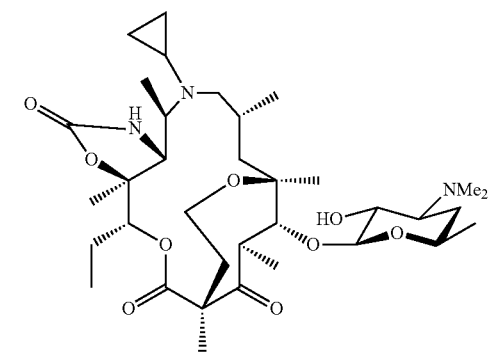 | ¹H NMR (600 MHz, Methanol-d₄) δ 8.36 (s, 2H), 5.18 (dd, 1H), 4.45 (dd, 1H), 4.30 (s, 1H), 3.79 (dd, 2H), 3.75-3.67 (m, 1H), 3.56-3.38 (m, 4H), 3.14 (d, 1H), 2.82 (s, 5H), 2.64-2.58 (m, 1H), 2.52 (d, 1H), 2.27 (t, 1H), 2.13 (p, 1H), 2.05-2.00 (m, 1H), 1.87 (dd, 2H), 1.80 (s, 1H), 1.73-1.62 (m, 2H), 1.53 (q, 2H), 1.42 (d, 3H), 1.38 (s, 3H), 1.33-1.21 (m, 10H), 1.10 (d, 3H), 0.93 (td, 3H), 0.85 (d, 3H), 0.56 (q, 2H), 0.43 (t, 2H). |

| | | |
|---|---|---|
| 211 | 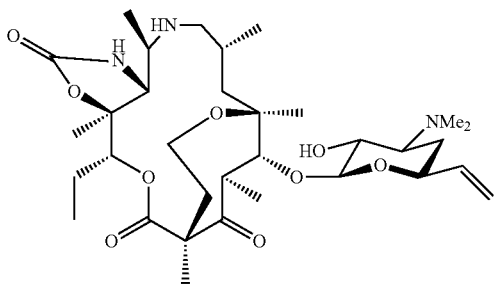 | ¹H NMR (600 MHz, Methanol-d₄) δ 8.53-8.50 (m, 1H), 5.92 (dddd, 1H), 5.35 (dq, 1H), 5.18 (dd, 1H), 5.14-5.08 (m, 1H), 4.59 (s, 2H), 4.54 (dd, 1H), 4.07 (dq, 2H), 3.82-3.76 (m, 1H), 3.50-3.42 (m, 2H), 3.31 (s, 12H), 3.29 (s, 5H), 3.09 (d, 1H), 2.71 (s, 2H), 2.67-2.62 (m, 1H), 2.24-2.16 (m, 2H), 2.03 (q, 2H), 1.91-1.81 (m, 1H), 1.71 (d, 1H), 1.65-1.62 (m, 1H), 1.59-1.50 (m, 5H), 1.43 (d, 2H), 1.37 (d, 2H), 1.28 (s, 1H), 1.02 (dd, 2H), 0.98-0.85 (m, 5H). |
| 212 | 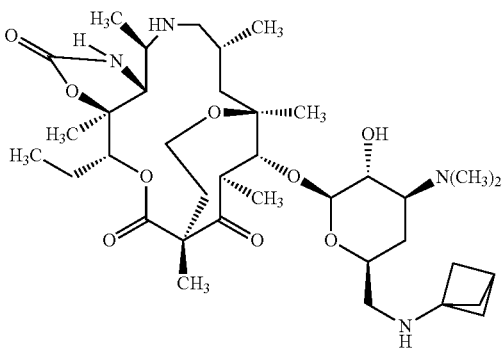 | ¹H NMR (600 MHz, Methanol-d₄) δ 8.51 (s, 2H), 5.12 (d, 1H), 4.59 (s, 1H), 4.48 (d, 1H), 4.13 (s, 1H), 3.67 (dd, 1H), 3.44 (d, 1H), 3.34 (s, 1H), 2.78-2.72 (m, 2H), 2.71 (s, 3H), 2.43 (s, 1H), 1.97 (d, 1H), 1.95 (s, 1H), 1.86-1.78 (m, 4H), 1.75-1.67 (m, 2H), 1.57 (s, 1H), 1.54 (t, 2H), 1.47 (s, 1H), 1.30 (s, 2H), 1.03 (d, 1H), 1.01 (s, 1H), 0.93 (h, 4H). |
| 213 | 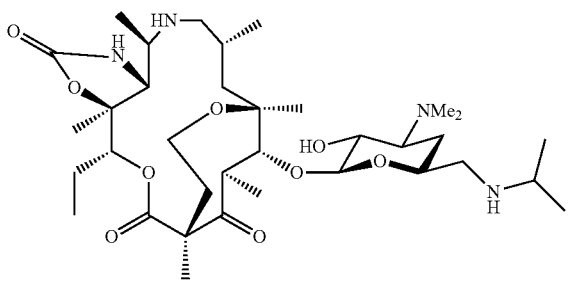 | ¹H NMR (600 MHz, Methanol-d₄) δ 8.47 (s, 3H), 5.15 (d, 1H), 4.59 (d, 1H), 4.21 (d, 1H), 4.10 (s, 1H), 3.91 (s, 1H), 3.58 (s, 1H), 3.46 (d, 1H), 3.35-3.32 (m, 2H), 3.30 (s, 13H), 3.20 (d, 1H), 3.09 (s, 1H), 2.80-2.74 (m, 1H), 2.71 (s, 3H), 2.32 (s, 1H), 2.25 (q, 2H), 2.04 (d, 1H), 1.86 (dd, 1H), 1.78-1.70 (m, 2H), 1.69 (q, 1H), 1.62-1.58 (m, 2H), 1.57 (s, 3H), 1.53-1.46 (m, 3H), 1.43 (s, 1H), 1.39 (s, 3H), 1.30 (t, 5H), 1.12 (d, 2H), 1.01-0.91 (m, 5H). |
| 214 | 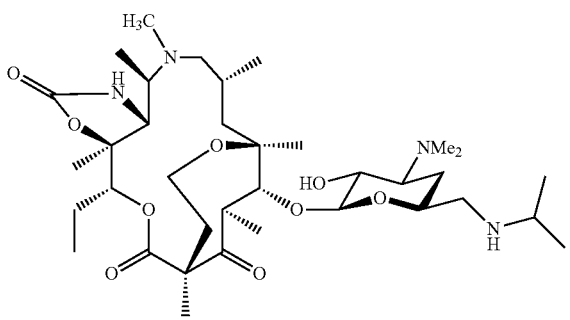 | |
| 215 | 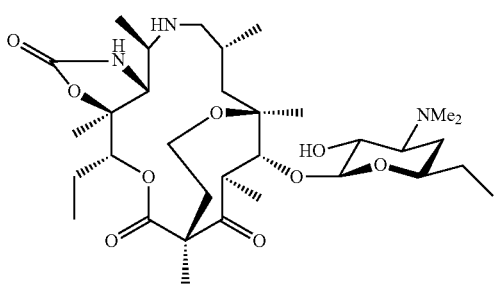 | ¹H NMR (600 MHz, Methanol-d₄) δ 8.43 (s, 1H), 5.16 (dd, 1H), 4.50 (d, 1H), 4.16-4.08 (m, 2H), 3.87 (ddd, 1H), 3.60 (d, 1H), 3.55-3.45 (m, 2H), 3.45-3.36 (m, 2H), 3.24 (dq, 1H), 2.82 (d, 5H), 2.80 (d, 1H), 2.37-2.26 (m, 2H), 2.21 (ddd, 1H), 2.02 (ddd, 1H), 1.85 (dtd, 2H), 1.81-1.72 (m, 2H), 1.72-1.66 (m, 2H), 1.66-1.58 (m, 3H), 1.57 (s, 4H), 1.55-1.51 (m, 1H), 1.47 (d, 3H), 1.39 (s, 2H), 1.33-1.27 (m, 1H), 1.14 (d, 2H), 1.06-0.98 (m, 5H), 0.94 (t, 3H). |

| # | Structure | NMR |
|---|---|---|
| 216 | | ¹H NMR (600 MHz, Methanol-d₄) δ 8.34 (s, 1H), 7.42 (d, 1H), 6.76 (d, 1H), 5.17 (dd, 2H), 4.82-4.76 (m, 2H), 4.60 (dd, 3H), 4.33-4.27 (m, 1H), 4.21-4.10 (m, 4H), 3.88 (s, 5H), 3.83 (s, 2H), 3.61 (s, 2H), 3.51 (dt, 5H), 3.19 (t, 3H), 2.82 (d, 10H), 2.40 (d, 1H), 2.39-2.32 (m, 3H), 2.31-2.26 (m, 2H), 2.22-2.14 (m, 3H), 1.87 (dt, 3H), 1.78 (s, 2H), 1.75 (d, 1H), 1.72 (d, 1H), 1.71-1.68 (m, 2H), 1.66 (d, 1H), 1.64-1.57 (m, 11H), 1.49 (dd, 5H), 1.38 (d, 5H), 1.28 (s, 1H), 1.16 (d, 5H), 1.01 (dd, 5H), 0.94 (t, 5H). |
| 217 | | ¹H NMR (600 MHz, Methanol-d₄) δ 8.28 (s, 1H), 5.20 (dd, 1H), 4.55 (d, 1H), 4.29 (d, 1H), 4.18 (td, 1H), 3.98 (dd, 1H), 3.78-3.59 (m, 6H), 3.52-3.42 (m, 2H), 3.19-3.11 (m, 1H), 2.97-2.91 (m, 1H), 2.85 (s, 5H), 2.63 (dd, 1H), 2.50 (ddd, 1H), 2.26-2.20 (m, 1H), 2.16 (dd, 1H), 1.86 (dddd, 2H), 1.79 (dd, 1H), 1.77-1.57 (m, 8H), 1.53 (d, 3H), 1.40 (s, 2H), 1.25 (d, 3H), 1.03 (d, 3H), 0.95 (t, 3H). |
| 218 | | ¹H NMR (600 MHz, Methanol-d₄) δ 8.43 (s, 3H), 5.24 (s, 1H), 5.16 (d, 2H), 4.60 (d, 2H), 4.48 (s, 1H), 4.22 (d, 2H), 4.12 (s, 1H), 3.95 (dd, 2H), 3.91-3.88 (m, 1H), 3.62 (s, 1H), 3.49 (dd, 2H), 3.38 (s, 1H), 3.28 (s, 2H), 3.24-3.18 (m, 3H), 3.08 (s, 1H), 2.83 (d, 2H), 2.76 (s, 3H), 2.39 (t, 2H), 2.20 (dd, 2H), 2.06 (d, 1H), 1.86 (dd, 2H), 1.81-1.73 (m, 3H), 1.70 (dq, 2H), 1.63 (s, 1H), 1.58 (d, 6H), 1.50 (d, 2H), 1.40 (s, 2H), 1.33-1.27 (m, 2H), 1.17 (d, 2H), 1.01 (d, 2H), 0.94 (t, 3H). |
| 219 | | ¹H NMR (600 MHz, Methanol-d₄) δ 8.46 (s, 1H), 5.15 (dd, 1H), 4.49 (d, 1H), 4.14-4.06 (m, 2H), 3.88 (ddd, 1H), 3.73 (dqd, 1H), 3.58 (d, 1H), 3.45 (dd, 1H), 3.37 (tdd, 2H), 3.23 (dq, 1H), 2.80 (s, 5H), 2.78 (dd, 1H), 2.35-2.17 (m, 3H), 2.02 (ddd, 1H), 1.86 (dqd, 1H), 1.71 (dddd, 3H), 1.61 (d, 1H), 1.57 (s, 3H), 1.56-1.48 (m, 4H), 1.46 (d, 3H), 1.37 (s, 3H), 1.31 (d, 3H), 1.12 (d, 3H), 0.99 (d, 3H), 0.94 (t, 3H). |
| 220 | | ¹H NMR (600 MHz, Methanol-d₄) δ 8.35 (s, 1H), 5.15 (dd, 1H), 4.51 (t, 1H), 4.13-4.04 (m, 1H), 3.73 (dt, 1H), 3.59 (td, 1H), 3.48-3.43 (m, 1H), 3.40 (dd, 1H), 3.30 (d, 4H), 2.84-2.81 (m, 5H), 2.12-2.01 (m, 2H), 1.63 (s, 1H), 1.58-1.48 (m, 6H), 1.46-1.41 (m, 4H), 1.38 (d, 4H), 1.34-1.26 (m, 5H), 1.05-0.96 (m, 3H), 0.92 (d, 2H), 0.85 (d, 1H). |

| | | |
|---|---|---|
| 221 | 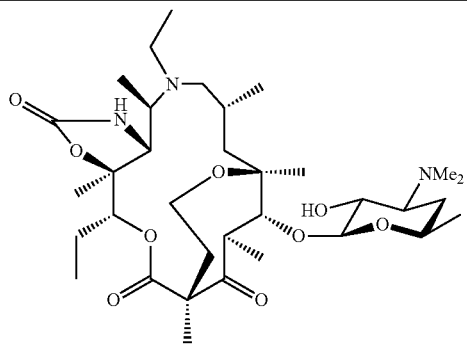 | ¹H NMR (600 MHz, Methanol-d₄) δ 8.43 (s, 2H), 5.19 (dd, 1H), 4.44 (d, 1H), 4.05 (s, 1H), 4.00 (d, 1H), 3.88-3.85 (m, 1H), 3.71 (dqd, 1H), 3.47 (dd, 1H), 3.41 (ddd, 1H), 2.98 (s, 1H), 2.85 (s, 1H), 2.83 (s, 5H), 2.28 (d, 1H), 2.03 (ddd, 1H), 1.97 (d, 1H), 1.88 (dtd, 1H), 1.83 (d, 1H), 1.67 (ddq, 1H), 1.57-1.47 (m, 7H), 1.40 (s, 3H), 1.37 (d, 3H), 1.31 (d, 3H), 1.23 (d, 5H), 1.00 (d, 3H), 0.94 (t, 3H). |
| 222 | 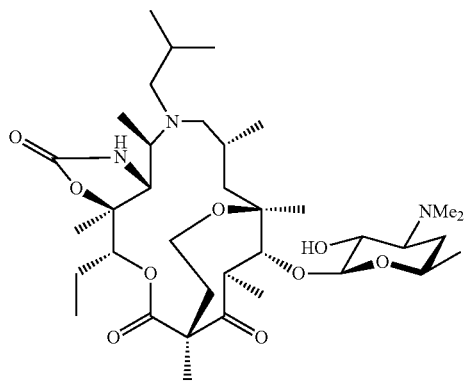 | ¹H NMR (600 MHz, Methanol-d₄) δ 5.14 (dd, 1H), 4.44 (d, 1H), 4.33 (s, 1H), 3.84 (d, 1H), 3.77-3.67 (m, 2H), 3.56 (dt, 1H), 3.45 (dd, 1H), 3.35 (d, 1H), 3.31 (s, 11H), 2.97 (q, 1H), 2.78 (s, 4H), 2.34-2.28 (m, 1H), 2.26 (d, 1H), 2.15 (dd, 1H), 1.99 (t, 2H), 1.90 (dtd, 2H), 1.79 (d, 1H), 1.70-1.61 (m, 3H), 1.51 (q, 3H), 1.43 (s, 3H), 1.38 (s, 2H), 1.35-1.22 (m, 10H), 1.20 (s, 1H), 1.01 (d, 3H), 0.97-0.91 (m, 5H), 0.88 (d, 2H), 0.79 (d, 2H). |
| 223 | 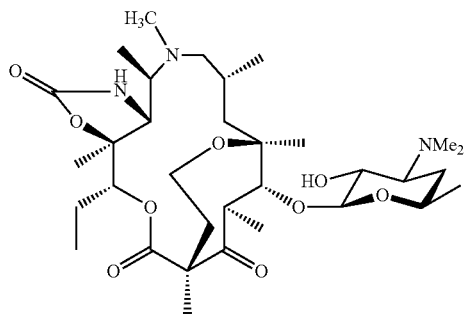 | ¹H NMR (600 MHz, Methanol-d₄) δ 8.53 (s, 1H), 5.12-5.07 (m, 1H), 4.42 (d, 1H), 4.17 (s, 1H), 3.86 (s, 1H), 3.78 (s, 1H), 3.69-3.66 (m, 1H), 3.41-3.33 (m, 3H), 3.14 (s, 1H), 3.02 (s, 1H), 2.64 (s, 3H), 2.25 (s, 1H), 2.10 (s, 1H), 1.99-1.90 (m, 3H), 1.77 (s, 1H), 1.71 (ddd, 2H), 1.57 (s, 2H), 1.43 (d, 3H), 1.27 (d, 6H), 1.03 (s, 1H), 0.94 (q, 5H), 0.89 (d, 3H). |
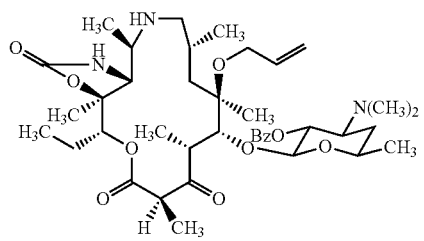
xix
O₃, TFA (20 eq), DMS (50 eq), MeOH
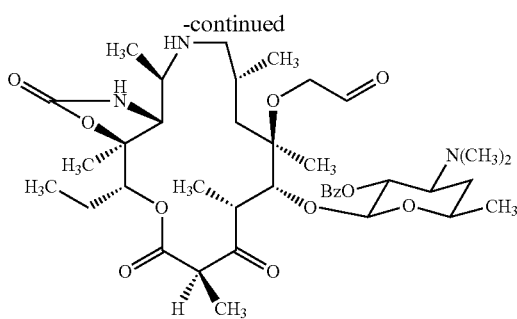
xx Trifluoracetic acid (0.839 mL, 10.89 mmol, 50 equiv) was added to a stirred solution of xix (0.270 g, 0.363 mmol, 1 equiv) in methanol (10 mL) at −78° C. Ozone was bubbled through the above solution at −78° C. for 2 min till stable blue color attains. The solution was degassed with nitrogen for 5 min to remove excess ozone in it. Dimethyl sulfide (1.342 mL, 18.15 mmol, 50 equiv) was added and stirred for 30 min at −78° C. Dry ice-acetone bath was removed, the reaction was warmed to rt. The reaction mixture was concentrated directly. The residue was suspended in DCM (10 mL) quenched with saturated aqueous sodium bicarbonate (6 mL). The layers were mixed vigorously, then were separated. The aqueous layer was extracted with dichloromethane (2×10 mL), and the combined organic layer was washed with brine (10 mL), filtered through a pad of sodium sulfate. The filtrate was concentrated under reduced pressure, and the crude xx (0.271 g, 100%) was subjected to the next reaction without further purification.

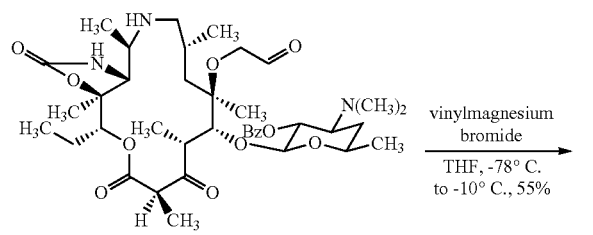

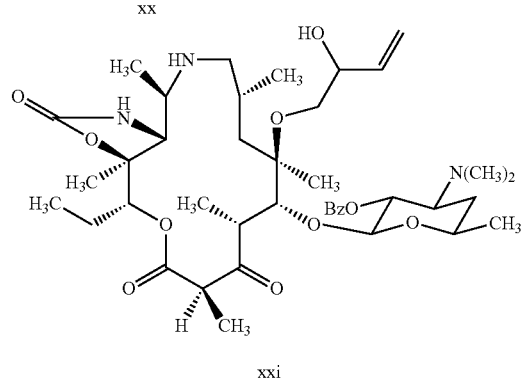

The crude aldehyde xx (0.27 g, 0.362 mmol, 1 eq) was dissolved in THF (5 mL) and cooled to −78° C. Vinylmagnesium bromide solution, 1.0 M in THF (1.08 mL, 1.086 mmol, 3 eq) was added dropwise over 15 min. The reaction mixture was stirred for 6 h at −78° C., and then warmed to −10° C. The reaction was quenched with aqueous ammonium chloride solution (5 mL). The reaction was warmed to rt. The mixture was extracted with ethyl acetate (10 mL×3). The organic layers were combined and the resulting solution was washed with saturated sodium chloride solution (10 mL). The washed organic solution was dried with sodium sulfate, filtered and the filtrate was concentrated afford pale-brown foaming solid. The crude product was purified by column chromatography (3%-5% methanol-dichloromethane+0.5% 30% aqueous ammonium hydroxide) to provide xxi (154 mg, 55%) as half-white powder.

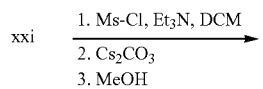

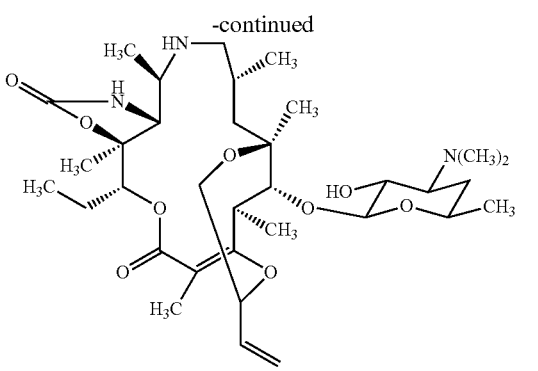

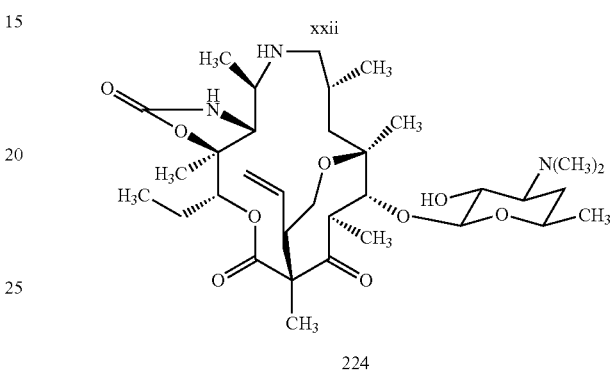

Triethylamine (0.077 mL, 0.549 mmol, 5 eq) and mesyl chloride (0.010 mL, 0.132 mmol, 1.2 equiv) were added sequentially to a solution of xxi (0.085 g, 0.110 mmol, 1 equiv) in DCM (5 mL) at −15° C. The reaction mixture was stirred at −15° C. for 30 min, at which point LC-MS indicated that full consumption of starting material had occurred. The reaction was quenched with aqueous sodium bicarbonate solution (1 mL) and warmed to rt. The layers were separated, aqueous layer was extracted with dichloromethane (5 mL×2). The combined organic layer was washed with brine (10 mL), dried over sodium sulfate and concentrated to afford half-white foaming solid. The crude product was subjected to the next reaction without further purification.

The crude mesylate compound was dissolved in N,N-dimethyl formamide (6 mL) and cesium carbonate (0.180 g, 0.550 mmol, 5 equiv with respect to xxi) was added at rt. The resulting reaction mixture was stirred at rt for 4 h, at which point LC-MS indicated that full consumption of starting material had occurred. The reaction was concentrated under reduced pressure. The residue was partitioned between ethyl acetate (10 mL) and water (5 mL). The aqueous layer was separated and further extracted with ethyl acetate (2×5 mL). The combined organic layers were dried over sodium sulfate, and the dried solution was concentrated. The residue was subjected to methanolysis in anhydrous methanol at 60° C. for 15 h and then concentrated directly. The residue was purified by Prep-HPLC to provide 224. $^1$H NMR (600 MHz, Methanol-$d_4$) δ 5.57 (ddd, 1H), 5.40 (dd, 1H), 5.27 (dd, 1H), 5.18 (dd, 1H), 4.59 (d, 1H), 4.30 (s, 1H), 4.24 (d, 1H), 3.95 (t, 1H), 3.89 (dd, 1H), 3.82 (q, 1H), 3.77 (dqd, 1H), 3.47 (d, 1H), 3.45-3.39 (m, 1H), 3.34 (s, 1H), 3.25-3.16 (m, 1H), 3.12 (dq, 1H), 2.95 (dd, 1H), 2.89 (s, 2H), 2.84 (dd, 1H), 2.79 (s, 2H), 2.04 (ddd, 1H), 1.97 (d, 1H), 1.90-1.78 (m, 2H), 1.69 (ddq, 1H), 1.57 (d, 2H), 1.56-1.50 (m, 5H), 1.50 (s, 2H), 1.44 (s, 2H), 1.33 (d, 6H), 1.06 (d, 2H), 1.00 (t, 2H).

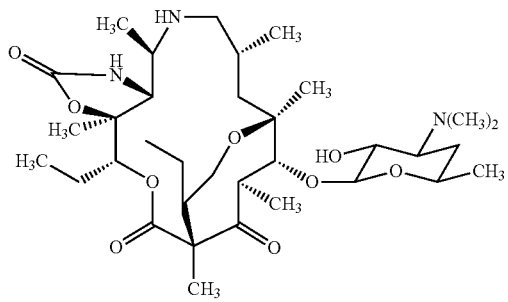

225

Compound 225 was synthesized in analogous fashion to the procedures employed for the synthesis of compound 224. NMR (600 MHz, Methanol-d$_4$) δ 8.47 (s, 1H), 4.93 (dd, 1H), 4.41 (d, 1H), 4.16 (d, 1H), 4.01-3.93 (m, 1H), 3.78 (d, 1H), 3.71 (dd, 2H), 3.45 (dd, 1H), 3.38 (t, 2H), 3.31 (s, 14H), 2.84 (ddq, 3H), 2.80 (s, 4H), 2.76 (t, 1H), 2.10-2.05 (m, 1H), 2.05-2.02 (m, 1H), 2.01 (d, 1H), 1.93 (t, 1H), 1.72 (ddd, 2H), 1.67 (s, 1H), 1.60 (s, 2H), 1.57-1.48 (m, 2H), 1.38 (s, 2H), 1.33-1.24 (m, 7H), 1.20 (d, 2H), 1.11 (d, 4H), 0.98 (t, 3H), 0.94 (d, 2H), 0.88 (t, 3H).

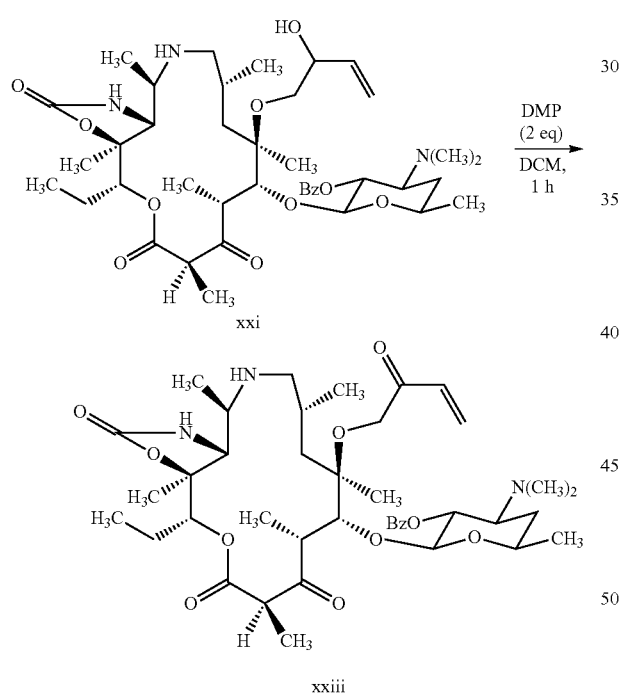

Dess-Martin periodinane (0.060 g, 0.150 mmol, 2 equiv) was added to a solution of xxi (0.050 g, 0.075 mmol, 1 equiv) in water-saturated dichloromethane (3 mL) in a 20-mL round-bottom flask that was immersed in a 22° C. water bath. After 1 h, the mixture was diluted with saturated aqueous sodium bicarbonate solution (1 mL) and ether (2 mL). The mixture was stirred vigorously for 5 min, at which point saturated aqueous sodium thiosulfate (1 mL) was added. The resulting cloudy mixture was stirred vigorously for 1 h, and the layers were separated. The aqueous layer was extracted with ether (3×3 mL). The organic layers were combined, and the resulting solution was washed with 1:1 saturated aqueous sodium bicarbonate: saturated aqueous sodium thiosulfate (2 mL), then with saturated sodium chloride solution (2 mL). The washed organic solution was dried with sodium sulfate, and the dried solution was filtered. The filtrate was concentrated and the resulting residue was subjected to the next reaction without further purification.

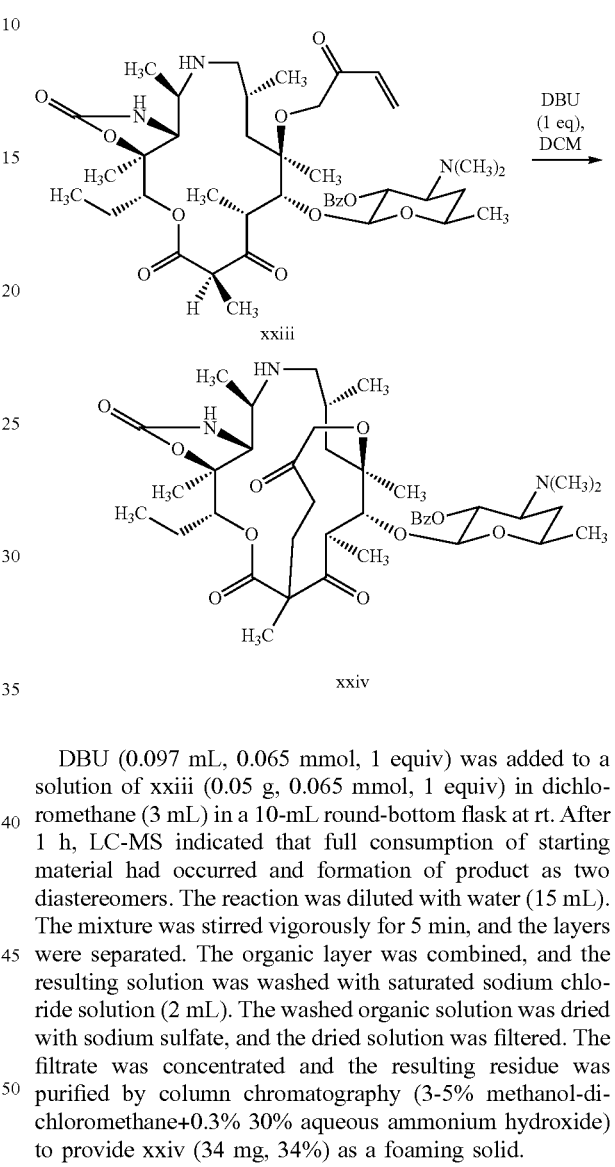

DBU (0.097 mL, 0.065 mmol, 1 equiv) was added to a solution of xxiii (0.05 g, 0.065 mmol, 1 equiv) in dichloromethane (3 mL) in a 10-mL round-bottom flask at rt. After 1 h, LC-MS indicated that full consumption of starting material had occurred and formation of product as two diastereomers. The reaction was diluted with water (15 mL). The mixture was stirred vigorously for 5 min, and the layers were separated. The organic layer was combined, and the resulting solution was washed with saturated sodium chloride solution (2 mL). The washed organic solution was dried with sodium sulfate, and the dried solution was filtered. The filtrate was concentrated and the resulting residue was purified by column chromatography (3-5% methanol-dichloromethane+0.3% 30% aqueous ammonium hydroxide) to provide xxiv (34 mg, 34%) as a foaming solid.

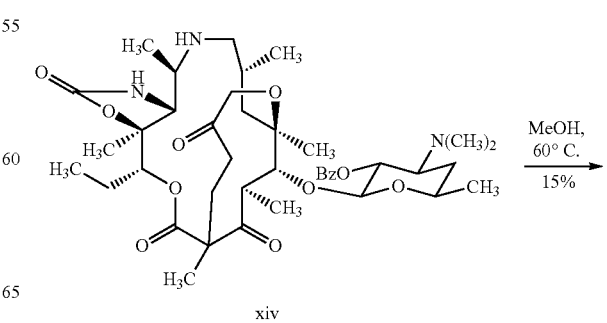

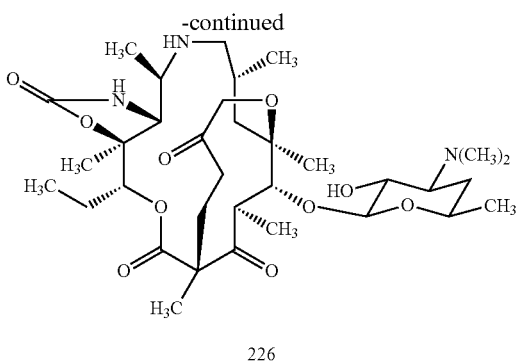

226

Compound xiv (0.010, 0.013 mmol, 1 equiv) was dissolved in anhydrous methanol (3 mL) and heated to 60° C. for 15 h. LC-MS indicated that full consumption of starting material had occurred. The reaction was concentrated directly under reduced pressure. The crude residue was purified by prep-HPLC to afford 226 (1.3 mg, 15%). $^1$H NMR (600 MHz, Methanol-$d_4$) δ 8.49 (s, 2H), 5.04 (dt, 1H), 4.43 (d, 1H), 4.16 (d, 1H), 3.78 (dd, 1H), 3.73 (q, 2H), 3.59 (d, 1H), 3.46 (ddd, 1H), 2.86-2.82 (m, 1H), 2.78 (d, 6H), 2.54 (t, 1H), 2.29 (q, 1H), 2.23 (d, 1H), 2.03-1.93 (m, 4H), 1.85-1.74 (m, 2H), 1.63 (s, 1H), 1.58 (d, 2H), 1.56-1.47 (m, 2H), 1.44 (d, 3H), 1.35 (s, 3H), 1.34-1.28 (m, 8H), 1.28-1.24 (m, 2H), 1.17 (dd, 2H), 1.13 (d, 3H), 1.02 (t, 3H), 0.96 (d, 3H).

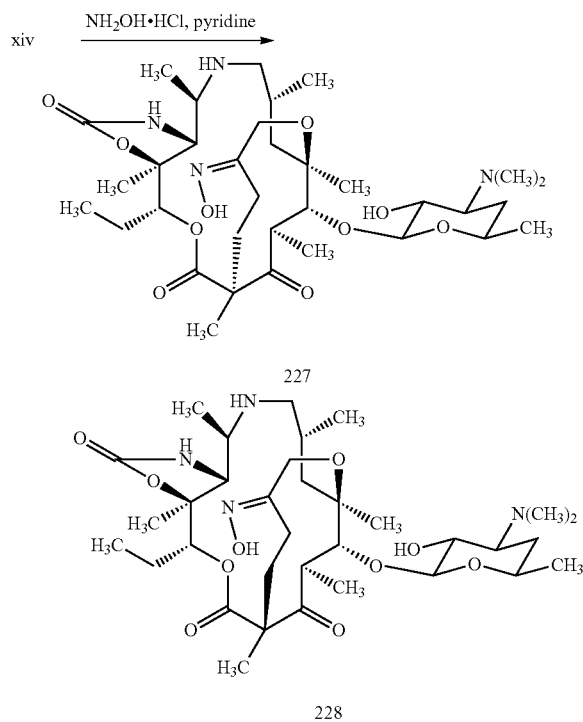

NH$_2$OH·HCl (0.018 g, 0.026 mmol) was added to xiv (10 mg, 0.013 mmol) in trifluoroethanol (2 mL) at 0° C. The reaction mixture was stirred for 1.5 h at 0° C. LC-MS indicated complete consumption of starting material occurred. The reaction was concentrated. The residue was dissolved in anhydrous methanol (2 mL) and heated to 50° C. for 15 h. The reaction mixture was concentrated. The crude product was purified by prep-HPLC, affording 227 (22%) and 228 (13%).

227: $^1$H NMR (600 MHz, Methanol-$d_4$) δ 8.28 (s, 2H), 4.46 (td, 1H), 4.29 (d, 1H), 4.17 (d, 1H), 4.01-3.93 (m, 1H), 3.85 (d, 1H), 3.74 (td, 1H), 3.69 (t, 1H), 3.51-3.38 (m, 2H), 3.27 (s, 1H), 2.87 (d, 1H), 2.83 (d, 4H), 2.25-2.17 (m, 2H), 2.03-1.91 (m, 2H), 1.89-1.83 (m, 1H), 1.83-1.75 (m, 1H), 1.74 (d, 1H), 1.61-1.52 (m, 4H), 1.47 (s, 1H), 1.40 (s, 1H), 1.37 (s, 1H), 1.32 (dd, 3H), 1.29-1.17 (m, 4H), 1.17-1.07 (m, 3H), 1.06-0.92 (m, 5H).

228: $^1$H NMR (600 MHz, Methanol-$d_4$) δ 8.31 (s, 3H), 4.67 (d, 2H), 4.28 (s, 1H), 4.00 (d, 2H), 3.47-3.44 (m, 2H), 3.36-3.30 (m, 21H), 3.29 (dt, 16H), 3.07 (s, 1H), 2.83 (s, 4H), 2.83 (s, 2H), 2.73 (d, 2H), 2.67 (s, 1H), 2.26 (d, 2H), 2.09-2.01 (m, 3H), 1.78 (d, 1H), 1.59 (d, 2H), 1.31 (dd, 9H), 1.21-1.11 (m, 7H), 1.05-0.98 (m, 5H), 0.97 (d, 2H).

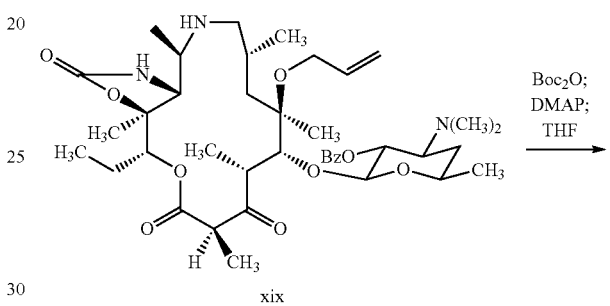

Boc-anhydride (257 µl, 1.109 mmol) was added to a stirred solution of xix (165 mg, 0.222 mmol) and DMAP (27.1 mg, 0.222 mmol) in THF (1109 µl) at room temperature. The reaction mixture was stirred for 24 h at room temperature. After 24 h, the reaction was concentrated and residue was purified by column (20% acetone in hexanes+ 0.5% Et$_3$N). The aqueous layer was extracted with dichloromethane (2×10 mL), and the combined organic layer was washed with brine (10 mL), filtered through a pad of sodium sulfate. The filtrate was concentrated under reduced pressure, and the crude xxv (0.271 g, 100%) was subjected to the next reaction without further purification.

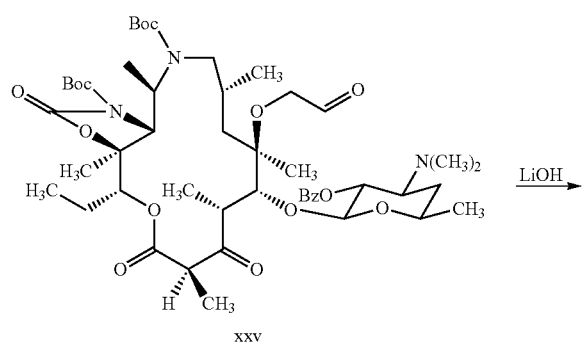

xxv

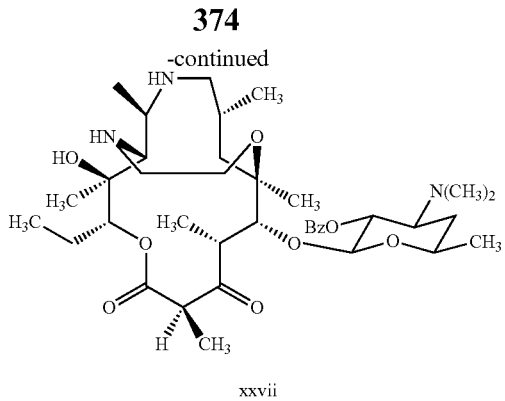

xxvii

TFA (0.034 ml, 0.436 mmol) was added to a stirred solution of xxvi (20 mg, 0.022 mmol) in methanol (2 ml) at −78° C. Ozone gas was bubbled through the solution for 3-4 min until a stable blue color solution appeared, then nitrogen gas was bubbled for 2 min until a clear solution could be observed. DMS (0.081 ml, 1.089 mmol) was added at −78° C. and stirred for 30 min at −78° C. Then the reaction was warmed to rt and concentrated with a stream of nitrogen. The residue was dissolved in DCM (2 mL) and TFA (0.1 mL) was added at room temperature and stirred at room temperature. After 1 h, the reaction was diluted with methanol (1 mL), and sodium cyanoborohydride (2.74 mg, 0.044 mmol) was added at room temperature. The reaction mixture was stirred at room temperature for 30 min and was then diluted with DCM (2 mL), aq. sodium bicarbonate sol (2 mL), and stirred for 30 min at rt. The layers were separated, aqueous layer was extracted with DCM (10 mL×2). The combined organic layers were dried over sodium sulfate and concentrated to afford xxvii as a white foaming solid.

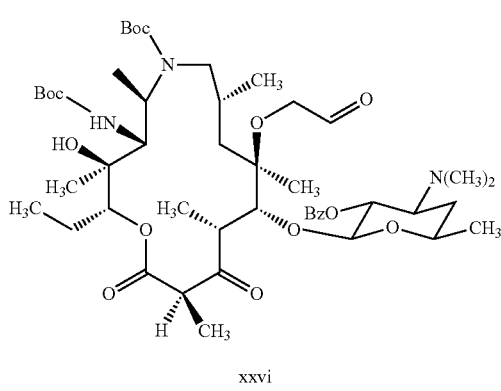

xxvi

Lithium hydroxide (95 mg, 3.97 mmol) was added to a stirred mixture of xxv (150 mg, 0.159 mmol) in THF (530 μl), MeOH (530 μl) and water (530 μl) at room temperature. The resulting suspension was stirred at room temperature. After 5 h of stirring the reaction was diluted with DCM (20 mL) and water (2 mL). The layers were separated and aqueous layer was extracted with DCM (10 mL×2). The combined organic layer was dried over Na₂SO₄, concentrated. The crude product was purified by column (7-10% methanol+1% NH₄OH in DCM) to provide compound xxvi (55% yield).

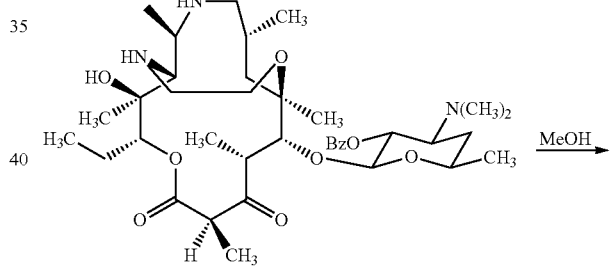

xxvii

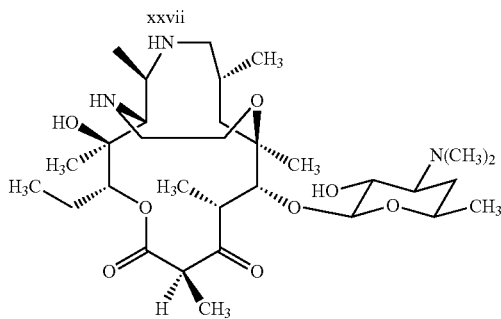

229

Figure 2:
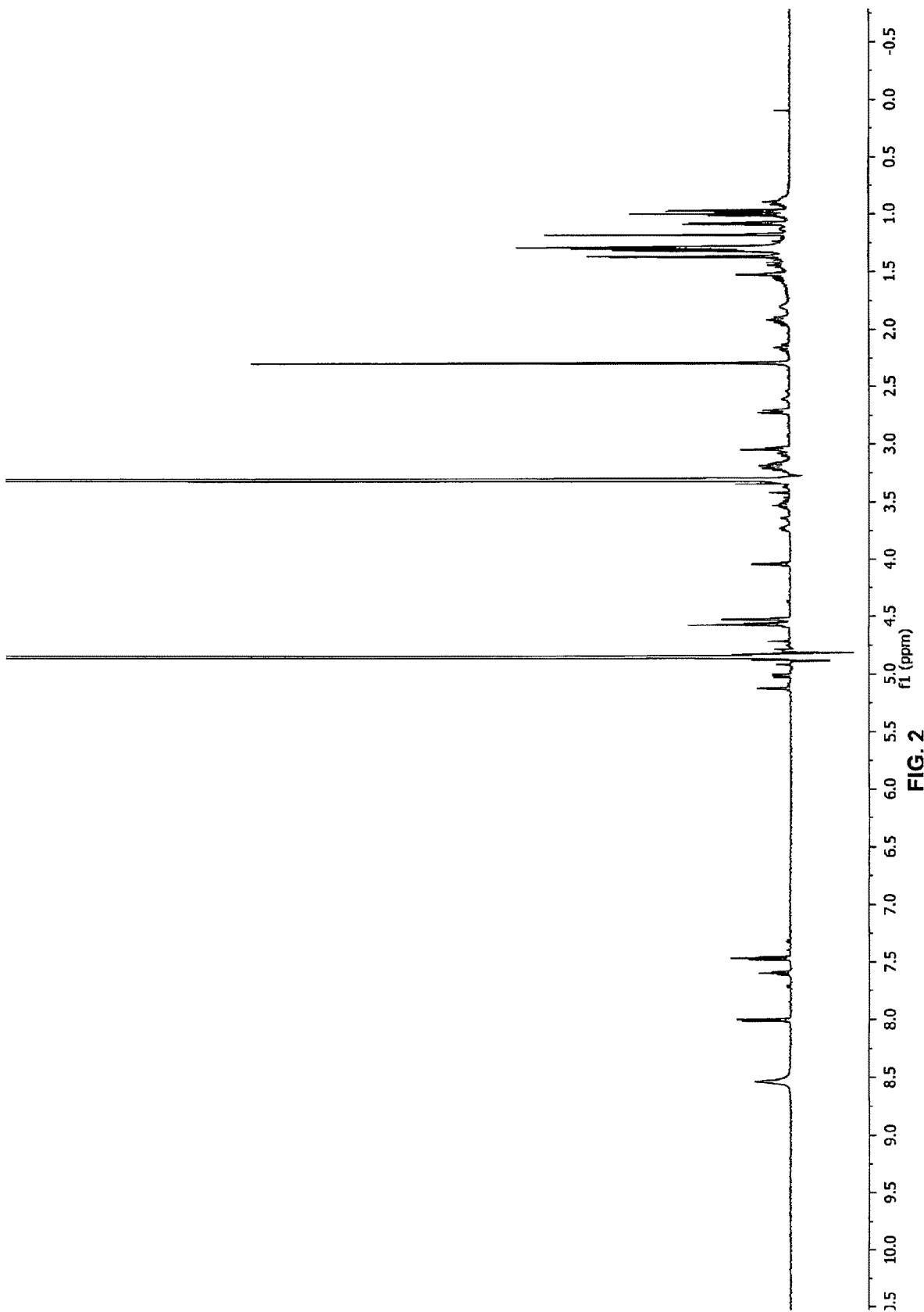
FIG. 2 is the $^1$H NMR spectrum of exemplary compound 229.

A stirred solution of xxvii (10 mg, 0.014 mmol) in methanol (2 mL, 49.4 mmol) was heated to 55° C. and kept under stirring overnight. LCMS analysis indicated complete conversion. The reaction mixture was concentrated directly. The residue was dissolved in 0.1% HCOOH in water (1 mL), purified by reverse phase HPLC (0→30% acetonitrile-water+0.1% formic acid over 30 min) to provide 229 (58% over 3 steps; NMR in FIG. 2)

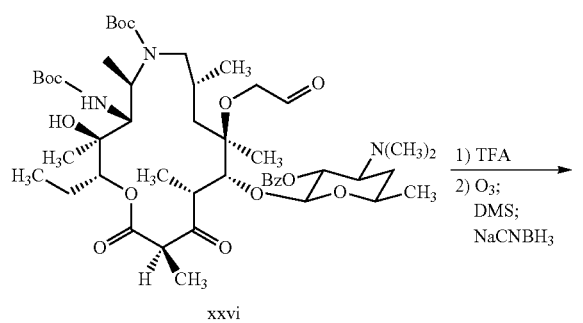

xxvi

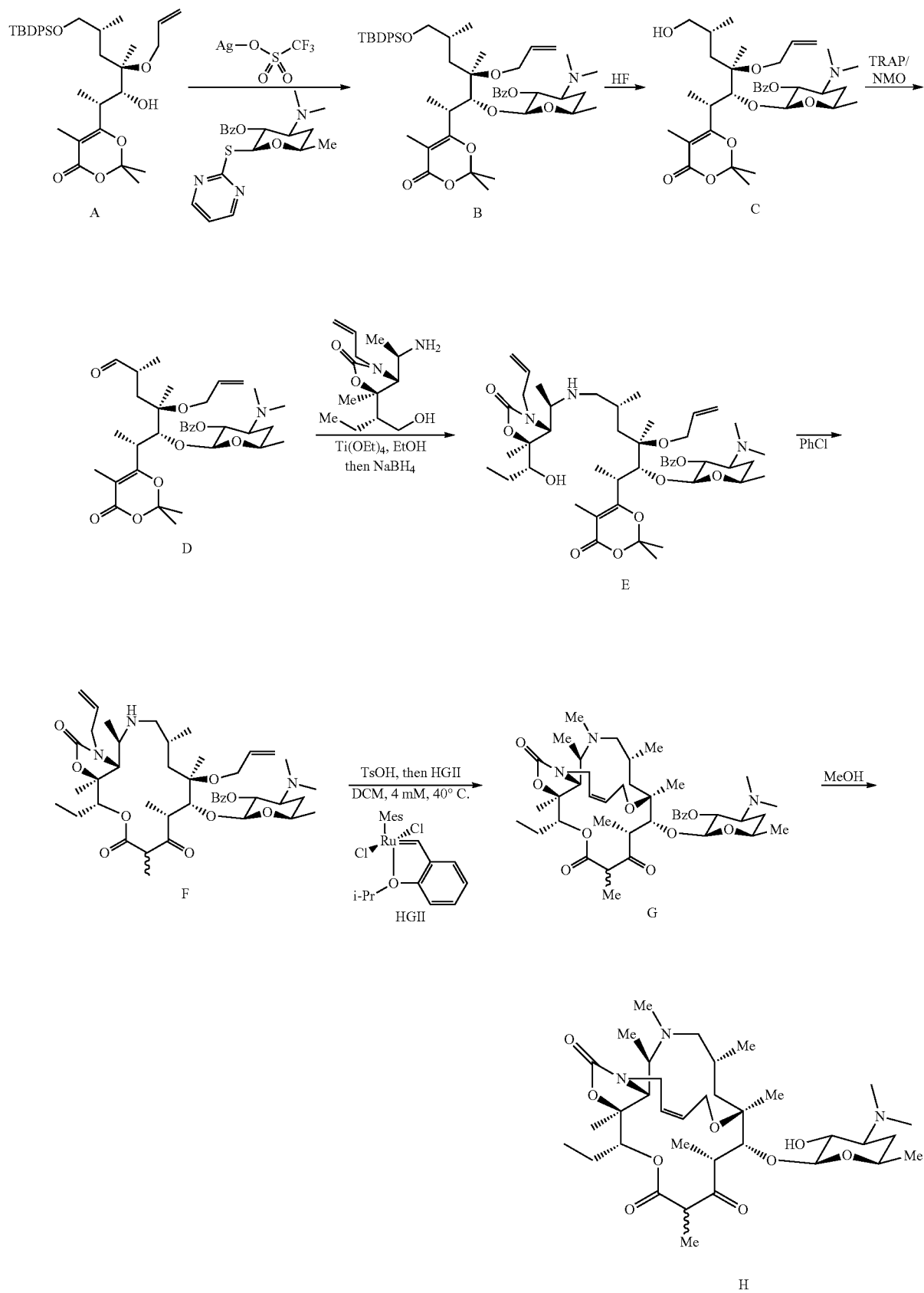
Scheme 36

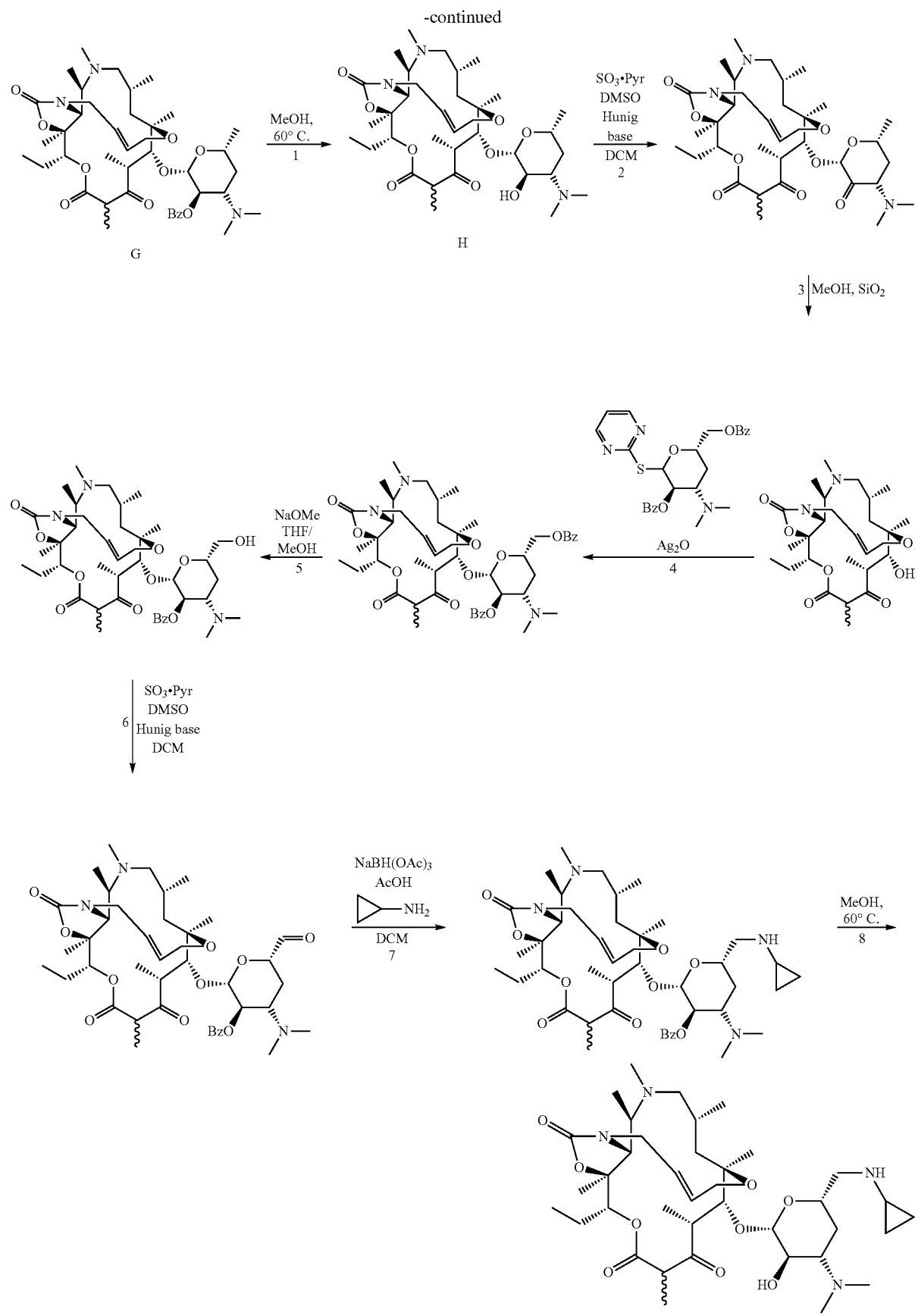

Synthesis of 3-Descladinosyl-3-oxo-6-O-methyl-N9a-desmethyl-11,12-dideoxy-12,11-(oxycarbonylimino)-6,11-(Z-2-butenyl)-6'-cyclopropylamino azithromycin. (Compound 230)

Compounds A-H were synthesized according to methods and procedures readily available to the skilled artisan.

Step 1.

The substrate was dissolved in MeOH and heated at 60° C. until LC/MS indicated complete consumption of starting material. The reaction mixture was concentrated used in the next step without further purification.

Step 2.

In a vial was a solution of alcohol in DCM precooled at 0° C. DIEA (6 equiv) was added, followed by DMSO (6 equiv) and the mixture was stirred for 1 minute, then $SO_3$-pyridine complex (3 equiv) was added in one portion and the resulting mixture was stirred at 0° C. for 2 hours. The reaction mixture was diluted with EtOAc and washed twice with satd aq $NaHCO_3$, once with brine, dried over $MgSO_4$, filtered and concentrated to give the desired crude aldehyde as white solid. The resulting product was used as is in step 4.

Step 3.

The crude product from step 2 was dissolved in MeOH and silica gel was added. The reaction mixture was heated at 55° C. for overnight. LCMS shows full conversion of the starting materials. The reaction mixture was filtered through a short plug with 10% MeOH in DCM and the residue was concentrated and purified by a silica gel column (0-8% MeOH in DCM with 0.5% $NH_4OH$)

Step 4.

In a flask was powdered preactivated 4 Å molecular sieves. The flask was flame dried under vacuum and allowed to cool to rt, then backfilled with nitrogen. This process was repeated twice. Separately, sugar donor (2 equiv) and alcohol from step 3 were combined and concentrated from toluene containing DCM, then dissolved in DCM and added to the flask via cannula. The mixture was stirred at 0° C. for 10 minutes. Silver triflate (3 equiv) was added in one portion, and the resulting mixture was stirred in the slowly warming ice bath overnight. The reaction mixture was quenched with trimethylamine (5 equiv) and stirred for 10 minutes, then filtered through a plug of Celite with the aid of DCM. The filtrate was partitioned between DCM and satd aq $NaHCO_3$ and a solid formed in the aqueous phase. The organic phase was separated and the aqueous phase was filtered and extracted 2x w/ DCM. The combined organic phases were dried over $MgSO_4$, filtered and concentrated, and the residue was purified on a silica gel column (0-10% MeOH in DCM with 0.5% $NH_4OH$) to yield desired glycoside as a white solid.

Step 5.

In a vial was benzoyl ester from step 4 in THF and MeOH (2:1) to give a yellow solution which was stirred at rt. NaOMe (25 wt % in MeOH, 0.5 equiv) was added and the reaction was stirred at rt for 4.5 h. The reaction mixture was poured into satd aq $NH_4Cl$ and extracted 3x with EtOAc. The combined organic phases were dried over $MgSO_4$, filtered and concentrated, and the residue was purified on a silica gel (elution with 2-10% MeOH-DCM+0.5% of 30% aq $NH_4OH$) to give the desired alcohol as a white solid.

Step 6.

In a 20 mL vial was a solution of alcohol from step 5 in DCM precooled at 0° C. DIEA (6 equiv) was added, followed by DMSO (6 equiv) and the mixture was stirred for 1 minute, then $SO_3$-pyridine complex (3 equiv) was added in one portion and the resulting mixture was stirred at 0° C. for 2 hours. The reaction mixture was diluted with EtOAc and washed twice with satd aq $NaHCO_3$, once with brine, dried over $MgSO_4$, filtered and concentrated to give the desired crude aldehyde as white solid. The resulting product was used as is in step 7.

Step 7.

In a 5 mL vial was a solution of amine (2 equiv), acetic acid (3 equiv) and crude aldehyde (1 equiv) in DCM to give a colorless solution which was stirred at rt for 30 min. $NaBH(OAc)_3$ (1.5 equiv) was added in one portion and the reaction was stirred at rt until LC/MS indicated complete consumption of starting material (2 hours). The reaction mixture was diluted with DCM and poured into satd aq $NaHCO_3$. The aqueous phase was extracted with DCM and the combined organic phases were dried over $MgSO_4$, filtered and concentrated. The residue was purified on 4 g of silica gel (elution with 0-10% MeOH-DCM+0.5% of 30% aq $NH_4OH$) to yield the desired amine.

Step 8.

The product from step 7 was dissolved in MeOH (0.5 mL) and heated at 60° C. until LC/MS indicated complete consumption of starting material. The reaction mixture was filtered through a syringe filter with the aid of methanol and concentrated. The residue was purified by HPLC (MeCN-water-0.1% HCO2H) to yield the desired products.

3-Desdadinosyl-3-oxo-6-O-methyl-N9a-desmethyl-11,12-dideoxy-12,11-(oxycarbonylimino)-6,11-(Z-2-butenyl)-6'-cyclopropylamino Azithromycin. (Compound 230)

(5.13 mg, 8% in eight steps). MS (ESI+) m/z: 241.3 $[M+3H]^{3+}$, 361.2 $[M+2H]^2$ 721.4 $[M+H]^+$; $^1H$ NMR (400 MHz, Methanol-$d_4$) δ 5.81 (t, 1H), 5.34 (d, 1H), 4.82 (s, 2H), 4.17 (d, 1H), 4.05 (t, 1H), 3.97-3.84 (m, 2H), 3.76 (d, 2H), 3.67-3.53 (m, 2H), 3.50-3.37 (m, 3H), 3.11 (q, 3H), 2.88 (s, 1H), 2.73 (d, 6H), 2.63-2.52 (m, 1H), 2.48 (s, 1H), 2.40 (s, 1H), 2.28 (d, 4H), 2.19 (d, 1H), 2.05-1.98 (m, 2H), 1.98-1.89 (m, 2H), 1.81 (s, 1H), 1.79-1.66 (m, 2H), 1.59-1.45 (m, 3H), 1.35 (dd, 5H), 1.28 (d, 5H), 1.27-1.09 (m, 17H), 1.04 (dd, 3H), 0.99-0.94 (m, 5H), 0.93 (s, 1H), 0.91-0.75 (m, 7H), 0.65 (q, 2H), 0.59 (s, 1H), 0.51 (s, 2H), 0.40 (d, 1H).

There are currently no macrolides that target serious infections caused by Gram-negative pathogens, in particular tissue based urinary tract infections (UTIs) that are often responsible for recurrent UTI infections. The strength of the macrolide class of antibiotics would be their good safety profile, iv/oral dosage forms and their excellent tissue distribution. However, a limitation of existing macrolide antibiotics to achieve Gram-negative activity can be rationalized by their inherent physicochemical properties (MW>750, Log D7.4>1) that results in limited penetration into Gram-negative bacteria and a high propensity for efflux. By utilizing a fully synthetic platform the macrolide framework can be re-engineered in a modular way allowing for useful physicochemical properties and Gram-negative activity.

While there has been extensive work around the macrolide scaffold since the discovery of erythromycin in 1952, the semisynthetic chemistry involved is inherently limiting. Additionally, a focus on Gram-positive activity has led to modifications that are generally counterproductive for Gram-negative activity, including the addition of large, lipophilic groups on the periphery of the molecule which enhance target affinity but limit permeability through the Gram-negative outer membrane. This technology platform enables, for the first time, a modular approach to construct novel 14- and 15-membered azaketolides that are essentially impossible to be prepared by traditional semisynthesis. This includes access to previously unexplored or underexplored positions on the scaffold, introduction of novel functional groups, and major core modifications. The scaffold can be dissected into two major fragments, each of which is prepared from the simple building blocks A-F (FIG. 1).

Modifications within these building blocks allows for introduction of novelty and replacement of entire portions of the molecule. A mix-and-match strategy can then be employed by combining successful modifications in different building blocks into one molecule.

Biological Assay Results

Minimum inhibitory concentrations (MICs) for macrolides described herein were determined for *E. coli* strain MP-4, *K. pneumoniae* strain MP-548, *P. aeruginosa* strain MP-3, *A. baumannii* strain MP-15, and *S. aureus* strain MP-12 using similar test procedures as published in US Pat. Pub. No. 2017/0305953. MIC data is represented as "+++" for values less than or equal to 4 mg/L, "++" for values of greater than or equal to 8 mg/L and less than 32 mg/L, and "+" for values of 32 mg/L or greater. ND indicates no data for a particular compound. CLSI standard procedures for broth dilution MIC determination were used. Data for exemplary compounds described herein is shown in Table 27.

TABLE 27

MIC values for selected macrolides.

| Compound No. | MIC against E. coli (MP-4) | MIC against K. pneumoniae (MP-548) | MIC against P. aeruginosa (MP-3) | MIC against A. baumannii (MP-15) | MIC against S. aureus (MP-12) |
|---|---|---|---|---|---|
| 92 | + | + | + | + | +++ |
| 93 | + | + | + | + | +++ |
| 94 | + | + | + | ++ | +++ |
| 100 | ++ | + | + | + | +++ |
| 101 | + | + | + | + | +++ |
| 102 | ++ | + | + | + | +++ |
| 103 | + | + | + | + | +++ |
| 104 | + | + | + | ++ | +++ |
| 105 | + | + | + | + | +++ |
| 20 | +++ | + | + | + | + |
| 21 | + | + | + | + | + |
| 22 | ++ | + | + | + | + |
| 23 | +++ | + | + | + | + |
| 53 | +++ | ++ | + | + | + |
| 57 | ++ | + | + | + | + |
| 18 | +++ | ++ | + | + | + |
| 24 | + | + | + | + | + |
| 25 | + | + | + | + | + |
| 26 | + | + | + | + | + |
| 27 | ++ | + | + | + | + |
| 28 | +++ | + | + | + | + |
| 29 | +++ | + | + | + | + |
| 30 | +++ | + | + | + | + |
| 31 | +++ | + | + | + | + |
| 32 | +++ | + | + | + | + |
| 33 | +++ | + | + | + | + |
| 34 | ++ | + | + | ++ | + |
| 35 | +++ | + | + | ++ | + |
| 36 | +++ | + | + | + | + |
| 37 | + | + | + | + | + |
| 38 | +++ | + | + | + | + |
| 39 | +++ | + | + | + | + |
| 40 | +++ | + | + | + | + |
| 41 | +++ | + | + | + | + |
| 42 | +++ | + | + | + | + |
| 43 | +++ | + | + | + | + |
| 44 | +++ | + | + | + | + |
| 45 | + | + | + | + | + |
| 46 | +++ | ++ | + | + | ++ |
| 47 | +++ | ++ | + | + | ++ |
| 48 | ++ | + | + | + | ++ |
| 49 | ++ | + | + | + | ++ |
| 50 | ++ | + | + | + | + |
| 51 | +++ | ++ | + | + | + |
| 52 | +++ | ++ | + | + | + |
| 54 | ++ | + | + | + | + |
| 55 | ++ | + | + | + | + |
| 56 | ++ | + | + | + | + |
| 80 | +++ | +++ | ++ | ++ | +++ |
| 115 | + | + | + | + | + |
| 146 | + | + | + | + | + |
| 121 | ++ | + | + | + | + |
| 132 | +++ | ++ | + | + | ++ |
| 186 | +++ | ++ | + | ++ | +++ |
| 192 | +++ | + | + | + | + |
| 113 | ++ | + | + | + | + |

TABLE 27-continued

MIC values for selected macrolides.

| Compound No. | MIC against E. coli (MP-4) | MIC against K. pneumoniae (MP-548) | MIC against P. aeruginosa (MP-3) | MIC against A. baumannii (MP-15) | MIC against S. aureus (MP-12) |
|---|---|---|---|---|---|
| 111 | +++ | +++ | + | + | + |
| 149 | +++ | + | + | + | + |
| 147 | ++ | + | + | + | + |
| 171 | +++ | + | + | + | + |
| 124 | +++ | ++ | + | + | + |
| 159 | +++ | ++ | + | + | + |
| 127 | +++ | ++ | + | + | + |
| 150 | ++ | + | + | + | + |
| 108 | ++ | + | + | + | + |
| 136 | +++ | ++ | + | + | ++ |
| 125 | + | + | + | + | + |
| 174 | + | + | + | + | + |
| 161 | +++ | +++ | + | ++ | ++ |
| 179 | +++ | ++ | + | + | + |
| 112 | +++ | ++ | + | ++ | +++ |
| 188 | + | + | + | + | + |
| 152 | + | + | + | ++ | ++ |
| 109 | ++ | + | + | + | + |
| 131 | +++ | ++ | + | + | + |
| 164 | +++ | ++ | + | + | + |
| 153 | +++ | + | + | + | + |
| 154 | +++ | ++ | + | + | + |
| 168 | + | + | + | + | + |
| 193 | + | + | + | + | + |
| 116 | +++ | + | + | + | + |
| 158 | +++ | ++ | + | + | + |
| 137 | +++ | ++ | + | ++ | + |
| 135 | +++ | ++ | + | +++ | ++ |
| 184 | +++ | ++ | + | ++ | +++ |
| 114 | +++ | ++ | + | + | + |
| 106 | ++ | + | + | + | + |
| 128 | + | + | + | + | + |
| 130 | + | + | + | + | + |
| 148 | + | + | + | + | + |
| 133 | +++ | ++ | + | ++ | ++ |
| 134 | +++ | +++ | + | ++ | + |
| 166 | ++ | + | + | + | + |
| 126 | +++ | ++ | + | + | + |
| 162 | +++ | ++ | + | + | + |
| 181 | ++ | + | + | + | + |
| 139 | +++ | ++ | + | ++ | ++ |
| 169 | + | + | + | + | + |
| 140 | + | + | + | + | + |
| 145 | ++ | ++ | + | + | + |
| 141 | +++ | +++ | + | ++ | ++ |
| 176 | + | + | + | + | + |
| 177 | ++ | + | + | + | + |
| 190 | + | + | + | + | + |
| 165 | +++ | ++ | + | + | + |
| 156 | + | + | + | + | + |
| 122 | +++ | ++ | + | + | + |
| 110 | +++ | ++ | + | + | + |
| 155 | +++ | ++ | + | ++ | + |
| 167 | + | + | + | + | + |
| 182 | +++ | ++ | + | ++ | ++ |
| 117 | + | + | + | + | + |
| 180 | ND | ND | ND | ND | ND |
| 175 | +++ | ++ | + | + | + |
| 178 | +++ | ++ | + | + | + |
| 191 | +++ | ++ | + | + | + |
| 129 | +++ | ++ | + | ++ | ++ |
| 163 | +++ | +++ | + | + | + |
| 151 | +++ | ++ | + | + | + |
| 138 | +++ | + | + | + | + |
| 119 | +++ | ++ | ND | + | + |
| 143 | +++ | ++ | + | + | ++ |
| 123 | +++ | ++ | + | + | + |
| 142 | +++ | ++ | + | + | ++ |
| 170 | ++ | + | + | + | + |
| 183 | ++ | + | + | ++ | ++ |
| 185 | ++ | + | + | ++ | ++ |
| 189 | + | + | + | + | + |
| 118 | +++ | +++ | + | + | ++ |

TABLE 27-continued

MIC values for selected macrolides.

| Compound No. | MIC against E. coli (MP-4) | MIC against K. pneumoniae (MP-548) | MIC against P. aeruginosa (MP-3) | MIC against A. baumannii (MP-15) | MIC against S. aureus (MP-12) |
|---|---|---|---|---|---|
| 157 | +++ | ++ | + | ++ | ++ |
| 120 | +++ | +++ | + | + | + |
| 187 | +++ | +++ | + | + | + |
| 144 | +++ | ++ | + | ++ | ++ |
| 160 | +++ | + | + | + | + |
| 172 | + | + | + | + | + |
| 173 | + | + | + | + | + |
| 194 | + | + | + | + | + |
| 195 | + | + | + | + | + |
| 196 | ++ | + | + | + | + |
| 197 | + | + | + | + | + |
| 198 | +++ | ++ | + | + | ++ |
| 199 | + | + | + | + | + |
| 200 | ++ | + | + | + | ++ |
| 201 | + | + | + | + | + |
| 202 | +++ | +++ | + | ++ | +++ |
| 203 | ND | ND | + | ND | + |
| 204 | +++ | +++ | + | ++ | +++ |
| 205 | ND | ND | ND | ND | + |
| 206 | +++ | ++ | + | + | +++ |
| 207 | ND | ND | ND | ND | + |
| 208 | +++ | +++ | + | ++ | +++ |
| 209 | +++ | +++ | + | ++ | +++ |
| 210 | ++ | + | + | + | +++ |
| 211 | +++ | +++ | + | +++ | +++ |
| 212 | +++ | ++ | + | ++ | +++ |
| 213 | +++ | +++ | + | + | +++ |
| 214 | +++ | +++ | + | + | +++ |
| 215 | ND | ND | ND | ND | ND |
| 216 | ND | ND | ND | ND | ND |
| 217 | ND | ND | ND | ND | ND |
| 218 | ++ | + | + | + | ++ |
| 219 | +++ | +++ | + | ++ | +++ |
| 220 | + | + | + | + | + |
| 221 | +++ | +++ | + | + | +++ |
| 222 | ND | ND | ND | ND | ++ |
| 223 | +++ | +++ | + | ++ | +++ |
| 224 | + | + | + | + | + |
| 225 | ND | ND | ND | ND | + |
| 226 | + | + | + | + | + |
| 227 | + | + | + | + | + |
| 228 | + | + | + | + | + |
| 229 | + | + | + | + | + |
| 230 | ND | ND | ND | ND | + |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound which is:

| Compound No. | Structure |
|---|---|
| 18 | 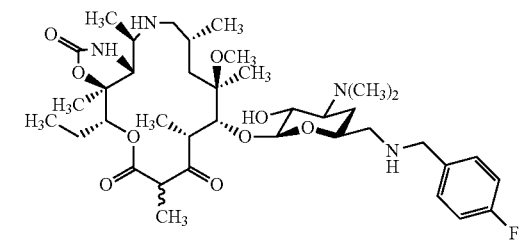 |
| 19 | 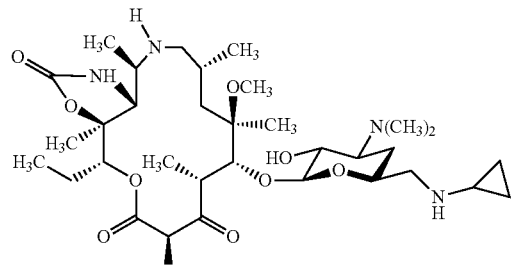 |
| 20 | 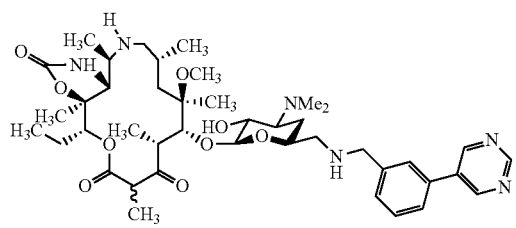 |
| 21 | 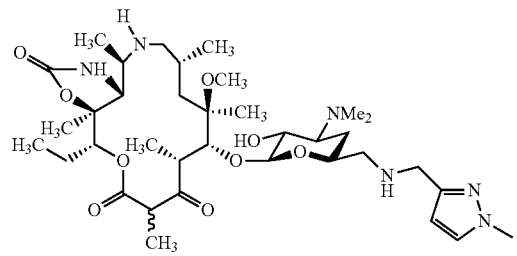 |
| 22 | 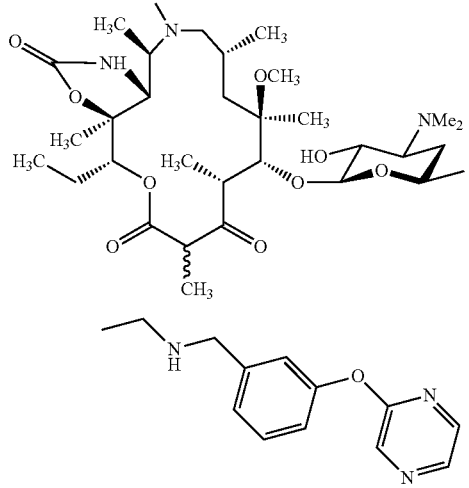 |
| 23 | 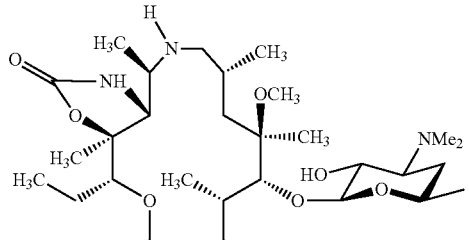<br>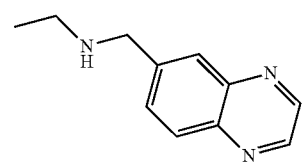 |

389
-continued

| Compound No. | Structure |
|---|---|
| 24 | 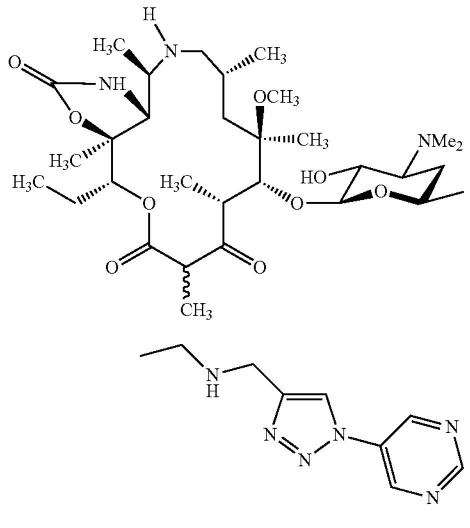 |
| 25 | 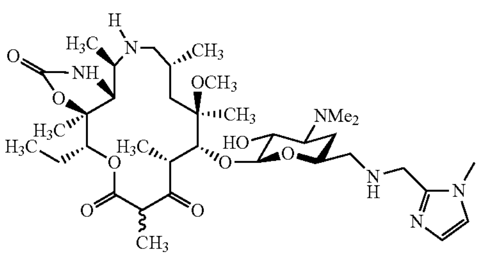 |
| 26 | 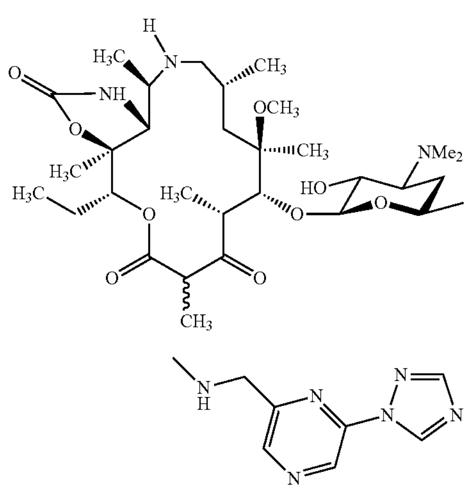 |

390
-continued

| Compound No. | Structure |
|---|---|
| 27 | 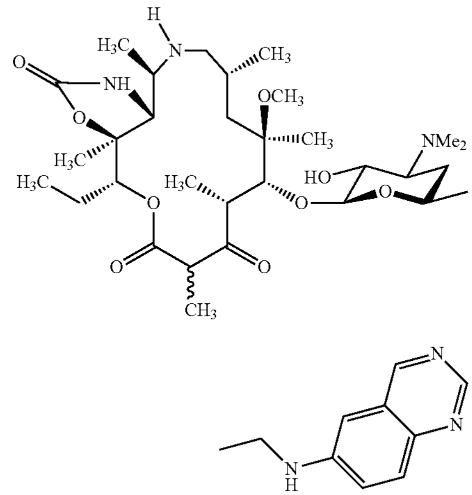 |
| 28 | 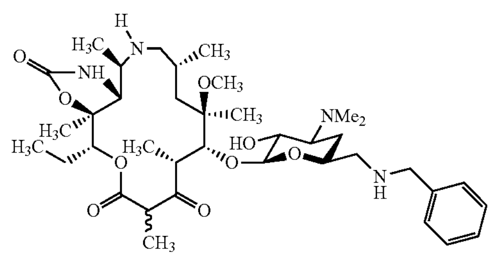 |
| 29 | 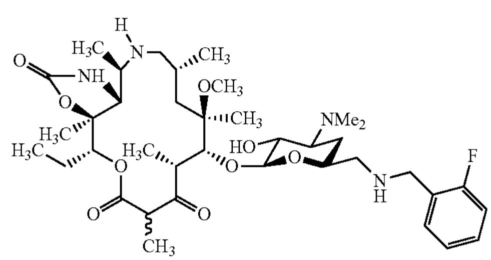 |
| 30 | 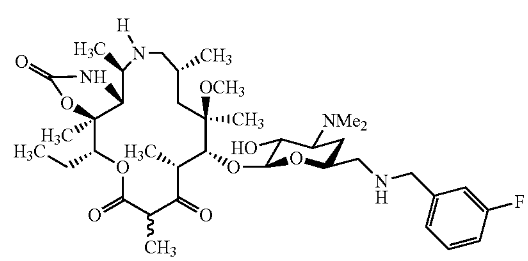 |
| 31 | 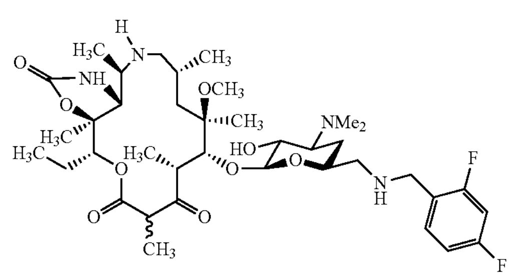 |

| Compound No. | Structure |
|---|---|
| 32 | 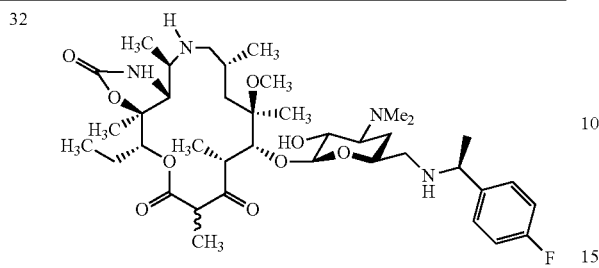 |
| 33 | 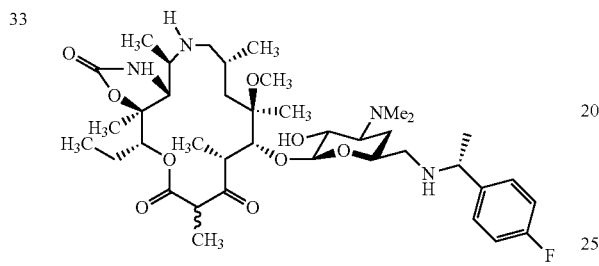 |
| 34 | 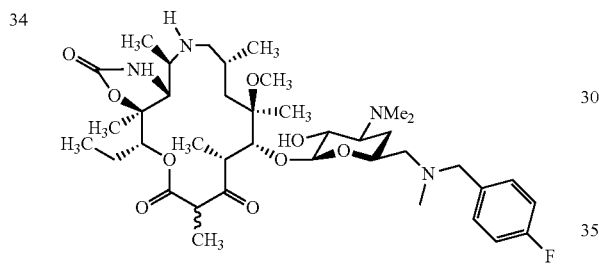 |
| 35 | 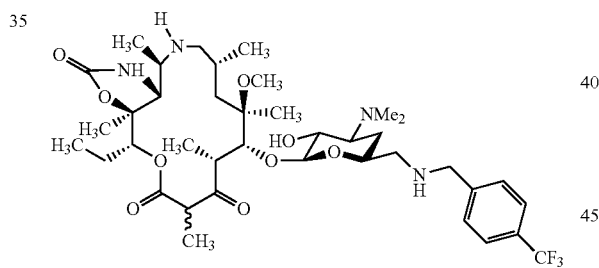 |
| 36 | 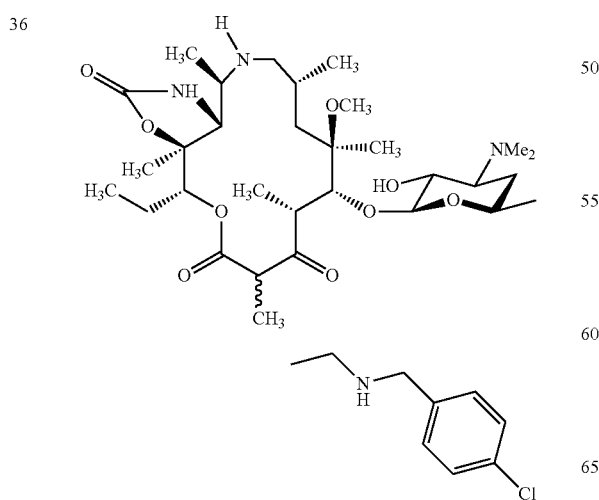 |
| Compound No. | Structure |
|---|---|
| 37 | 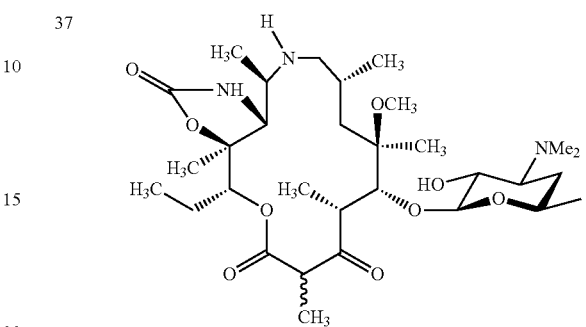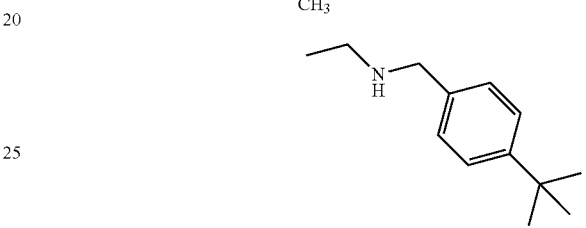 |
| 38 | 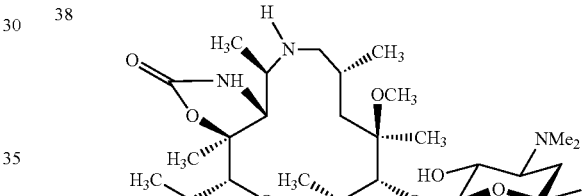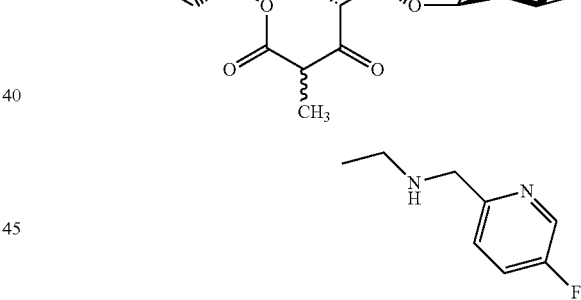 |
| 39 | 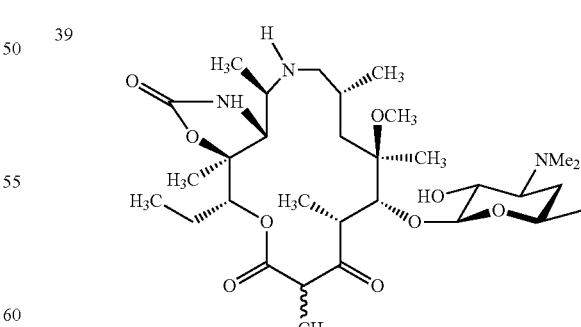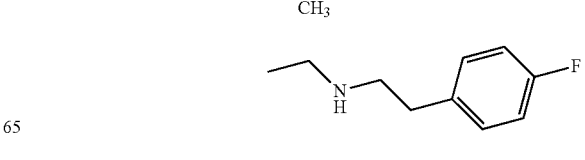 |

| Compound No. | Structure |
|---|---|
| 40 | (macrolide structure with 4-cyanobenzyl ethylamine substituent) |
| 41 | (macrolide structure with 3-cyanobenzyl ethylamine substituent) |
| 42 | (macrolide structure with 4-methoxybenzyl ethylamine substituent) |
| 43 | (macrolide structure with 3-methoxybenzyl ethylamine substituent) |
| 44 | (macrolide structure with 4-(dimethylamino)benzyl ethylamine substituent) |
| 45 | (macrolide structure with 4-(methylsulfonyl)benzyl ethylamine substituent) |

| Compound No. | Structure |
|---|---|
| 46 | (chemical structure: macrolide with 4-fluoroanilino-ethyl substituent) |
| 47 | (chemical structure: macrolide with 2-fluoroanilino-ethyl substituent) |
| 48 | (chemical structure: macrolide with 3-fluoroanilino-ethyl substituent) |
| 49 | (chemical structure: macrolide with 4-chloroanilino-ethyl substituent) |
| 50 | (chemical structure: macrolide with 4-cyanoanilino-ethyl substituent) |

| Compound No. | Structure |
|---|---|
| 51 | (chemical structure: macrolide with 2-pyridyl-ethylamino substituent) |
| 52 | (chemical structure: macrolide with 3-pyridyl-ethylamino substituent) |
| 53 | (chemical structure: macrolide with propargylamino-methyl substituent) |

-continued

| Compound No. | Structure |
|---|---|
| 54 | (macrolide structure with ethylaminooctyl side chain) |
| 55 | (macrolide structure with ethylaminodecyl side chain) |
| 56 | (macrolide structure with oxetanylmethylamino side chain) |
| 59 | (macrolide structure with methylamino side chain) |

-continued

| Compound No. | Structure |
|---|---|
| 62 | (macrolide structure with N-cyclopropyl-N-methylamino side chain) |
| 63 | (macrolide structure with isopropylamino side chain) |
| 64 | (macrolide structure with N-isopropyl-N-methylamino side chain) |
| 65 | (macrolide structure with pyrrolidinyl side chain) |
| 66 | (macrolide structure with cyclobutylamino side chain) |

| Compound No. | Structure |
|---|---|
| 67 | 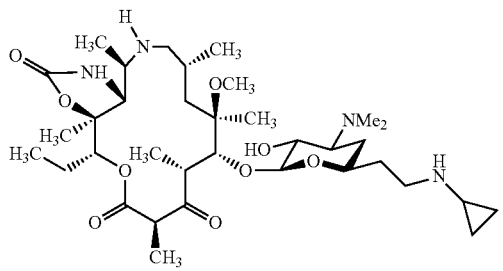 |
| 68 | 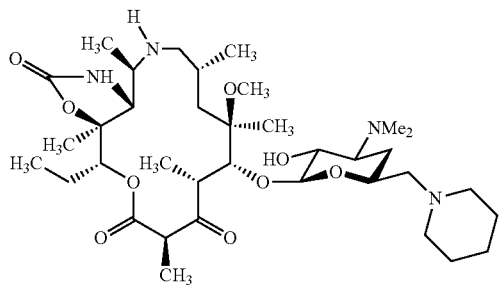 |
| 69 | 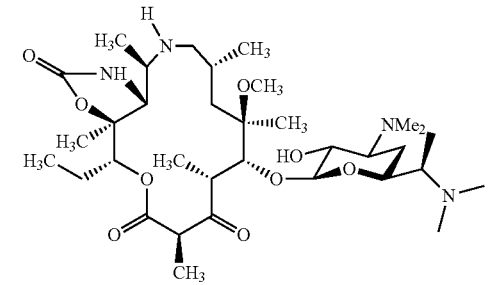 |
| 70 | 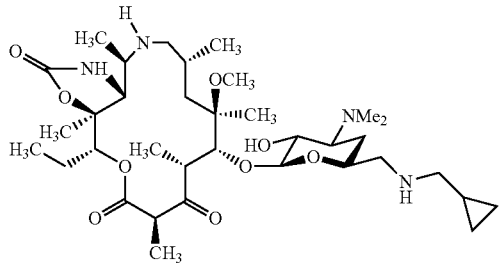 |
| 71 | 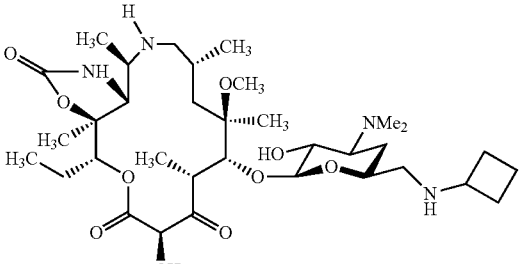 |
| Compound No. | Structure |
|---|---|
| 72 | 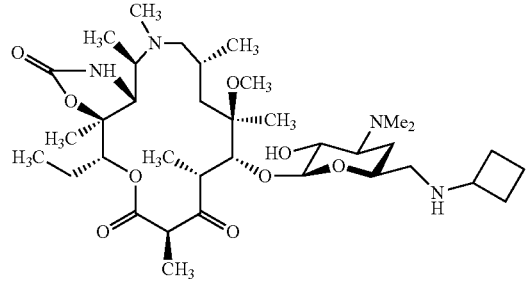 |
| 73 | 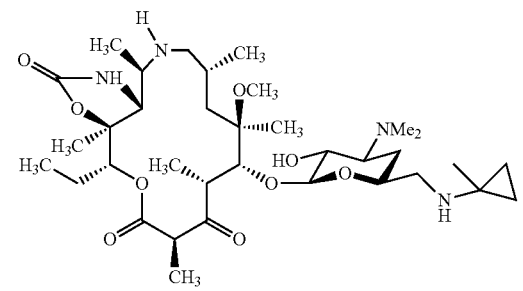 |
| 74 | 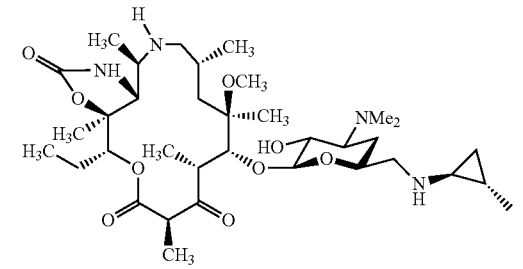 |
| 75 | 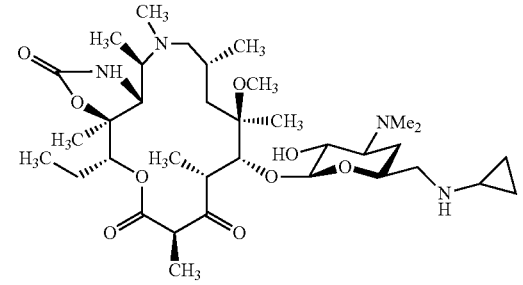 |
| 76 | 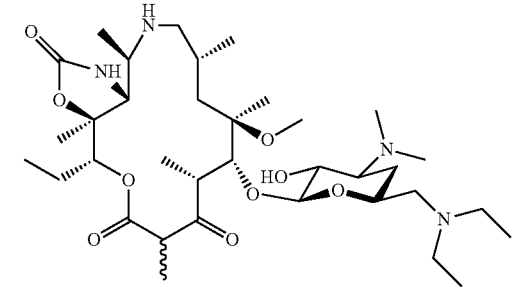 |

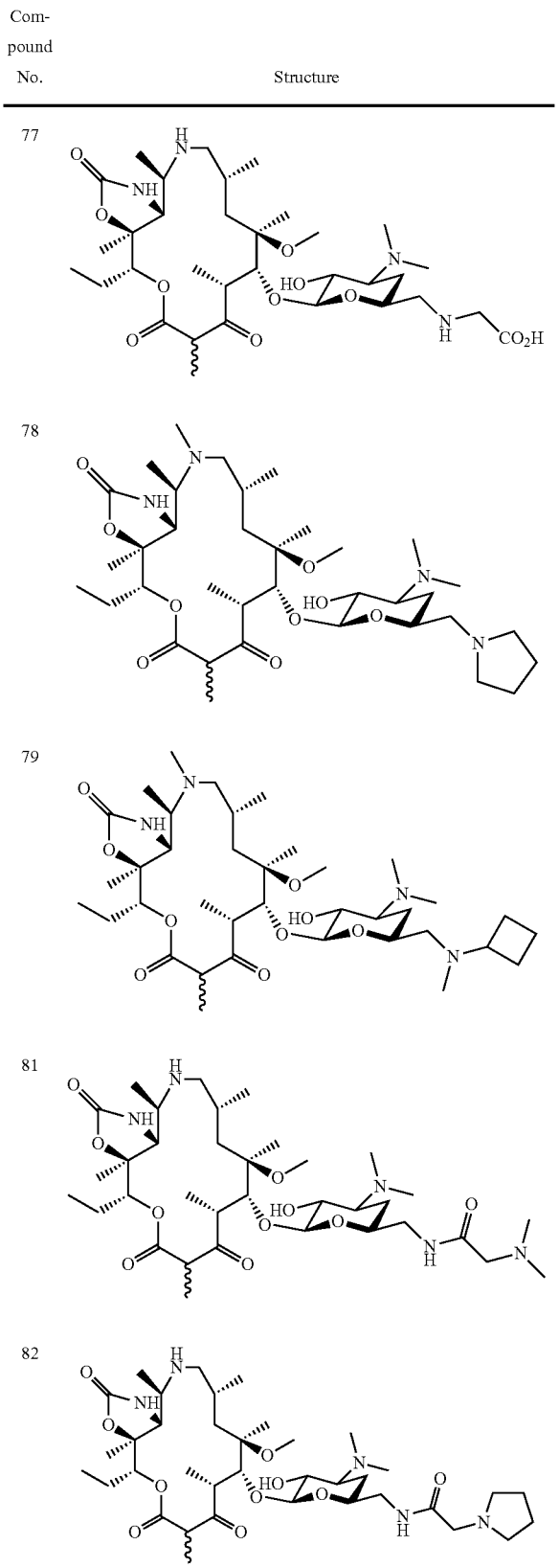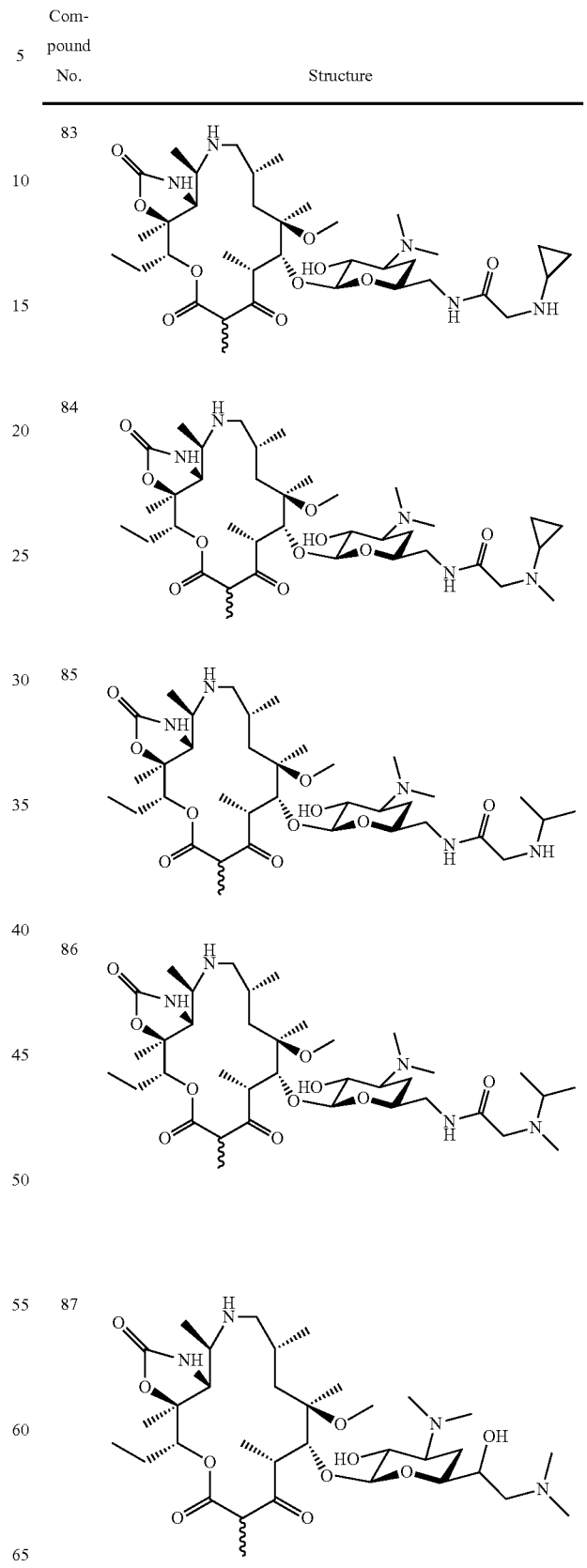

| Compound No. | Structure |
|---|---|
| 88 | 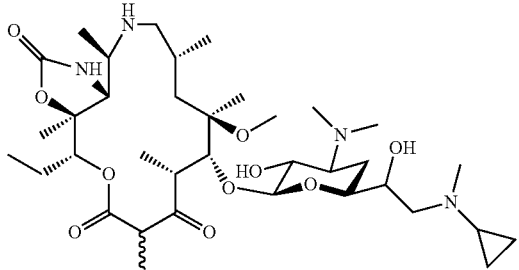 |
| 89 | 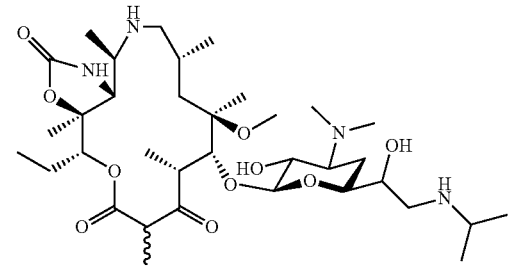 |
| 90 | 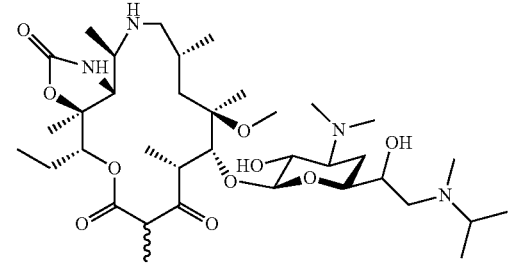 |
| 91 | 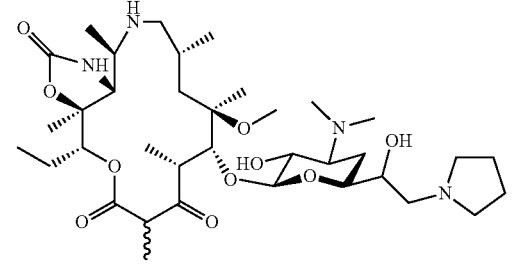 |
| Compound No. | Structure |
|---|---|
| 92 | 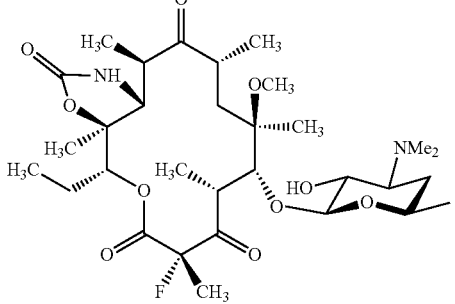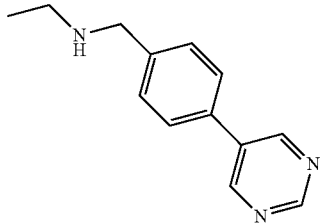 |
| 93 | 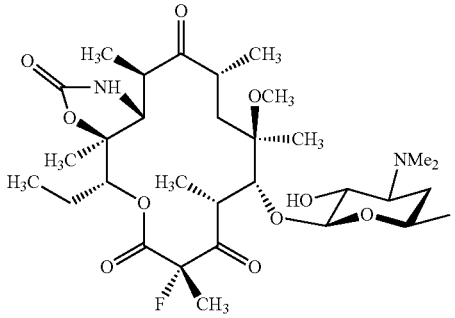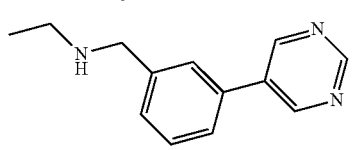 |
| 94 | 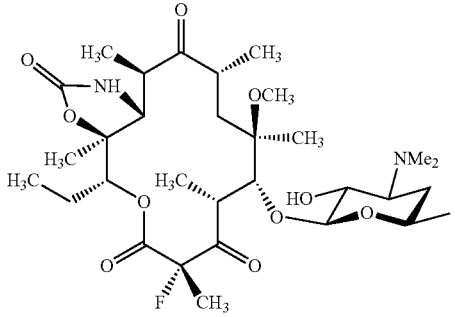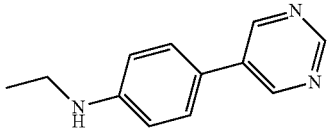 |

-continued
| Compound No. | Structure |
|---|---|
| 100 | 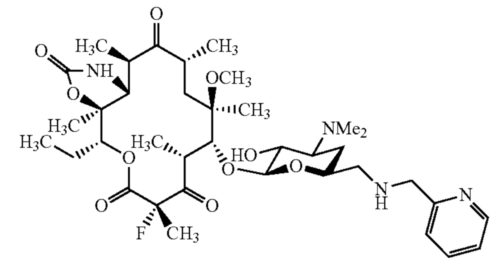 |
| 101 | 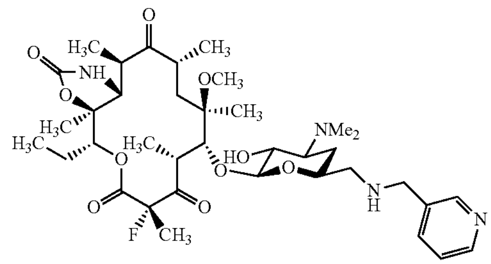 |
| 102 | 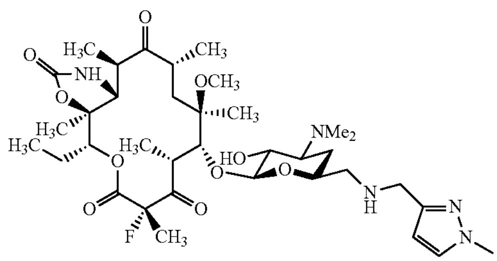 |
| 103 | 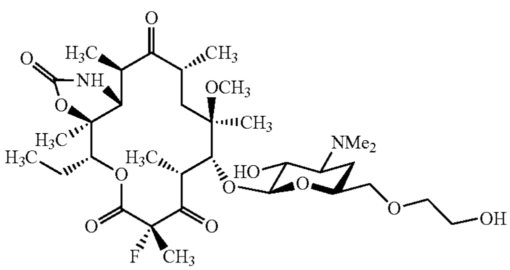 |
| 104 | 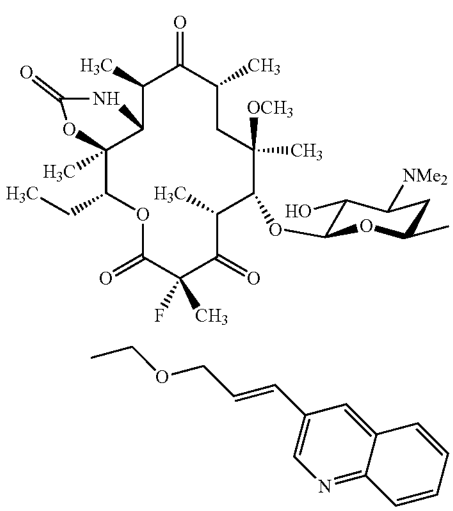 |
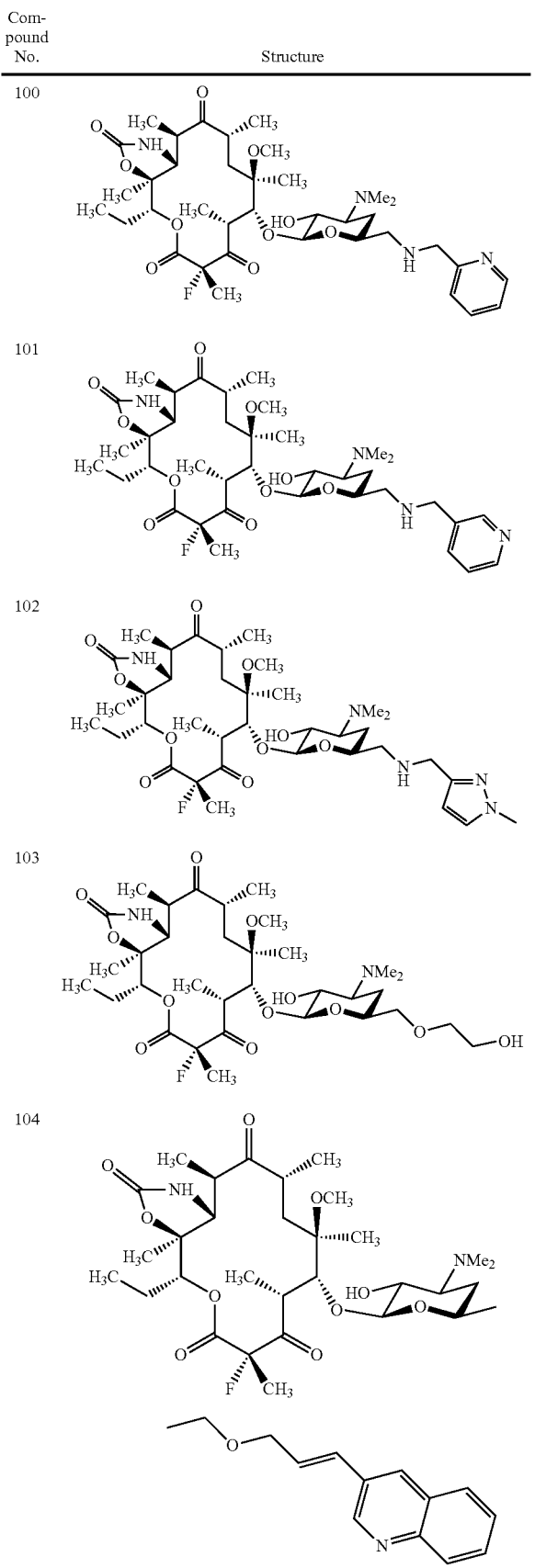
-continued
| Compound No. | Structure |
|---|---|
| 105 | 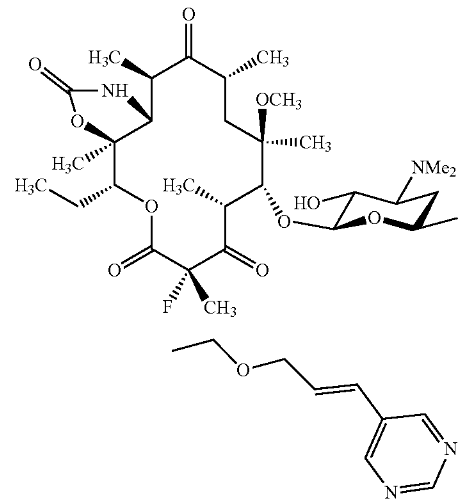 |
| 106 | 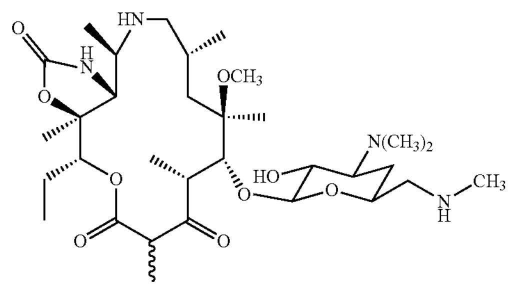 [SMILES: CC[C@H]1OC(=O)C(C)C(=O)[C@H](C)[C@@H](OC2OC(CNC)CC(N(C)C)C2O)[C@](C)(OC)C[C@@H](C)CN[C@H](C)[C@H]2NC(=O)O[C@@]21C] |
| 108 | 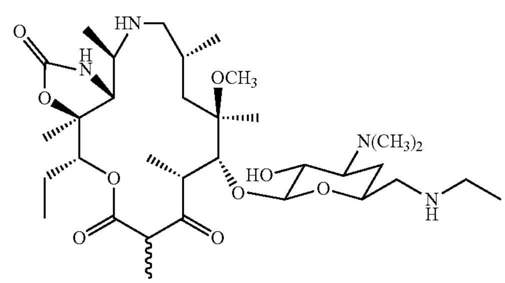 [SMILES: CCNCC1CC(N(C)C)C(O)C(O[C@@H]2[C@@H](C)C(=O)C(C)C(=O)O[C@H](CC)[C@@]3(C)OC(=O)N[C@@H]3[C@@H](C)NC[C@H](C)C[C@@]2(C)OC)O1] |
| 109 | 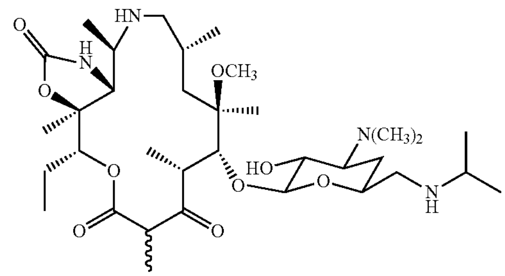 [SMILES: CC[C@H]1OC(=O)C(C)C(=O)[C@H](C)[C@@H](OC2OC(CNC(C)C)CC(N(C)C)C2O)[C@](C)(OC)C[C@@H](C)CN[C@H](C)[C@H]2NC(=O)O[C@@]21C] |
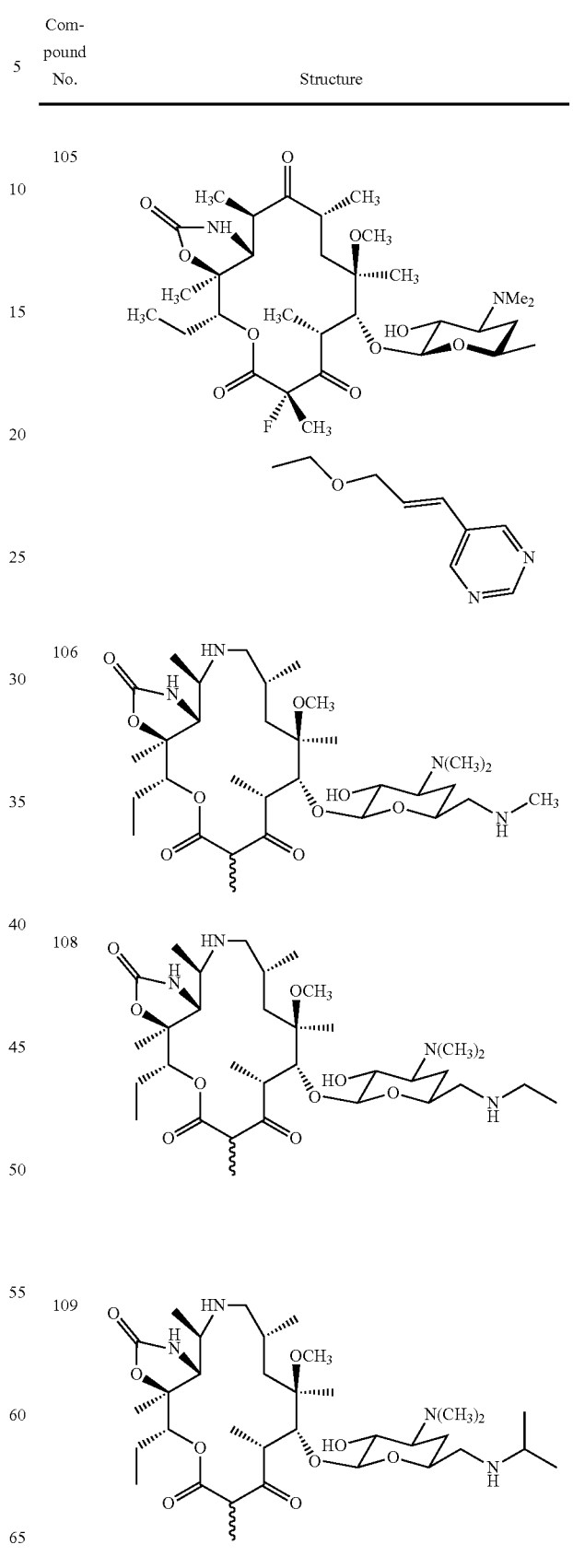

| Compound No. | Structure |
|---|---|
| 110 | 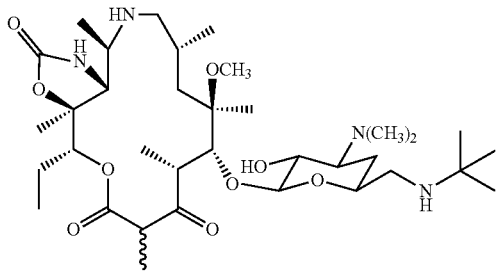 [SMILES: CC[C@H]1OC(=O)C(C)C(=O)[C@H](C)[C@@H](OC2OC(CNC(C)(C)C)CC(N(C)C)C2O)[C@](C)(OC)C[C@@H](C)CN[C@H](C)[C@H]2NC(=O)O[C@@]21C] |
| 111 | 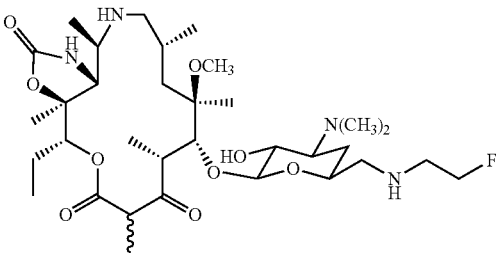 [SMILES: CC[C@H]1OC(=O)C(C)C(=O)[C@H](C)[C@@H](OC2OC(CNCCF)CC(N(C)C)C2O)[C@](C)(OC)C[C@@H](C)CN[C@H](C)[C@H]2NC(=O)O[C@@]21C] |
| 112 | 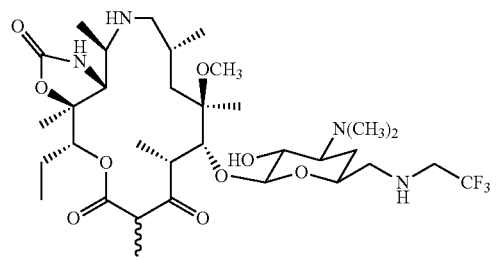 [SMILES: CC[C@H]1OC(=O)C(C)C(=O)[C@H](C)[C@@H](OC2OC(CNCC(F)(F)F)CC(N(C)C)C2O)[C@](C)(OC)C[C@@H](C)CN[C@H](C)[C@H]2NC(=O)O[C@@]21C] |
| 113 | 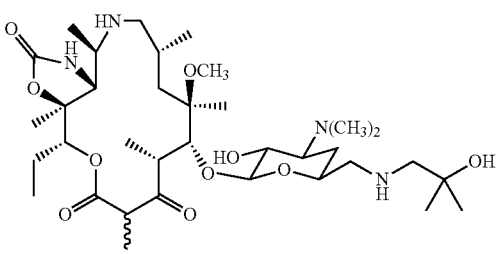 [SMILES: CC[C@H]1OC(=O)C(C)C(=O)[C@H](C)[C@@H](OC2OC(CNCC(C)(C)O)CC(N(C)C)C2O)[C@](C)(OC)C[C@@H](C)CN[C@H](C)[C@H]2NC(=O)O[C@@]21C] |
| 114 | 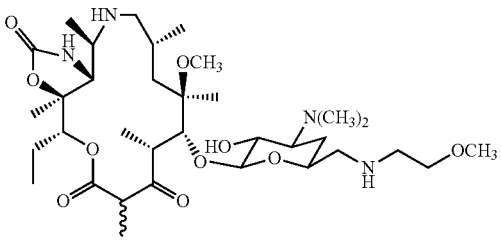 [SMILES: CC[C@H]1OC(=O)C(C)C(=O)[C@H](C)[C@@H](OC2OC(CNCCOC)CC(N(C)C)C2O)[C@](C)(OC)C[C@@H](C)CN[C@H](C)[C@H]2NC(=O)O[C@@]21C] |
| 115 | 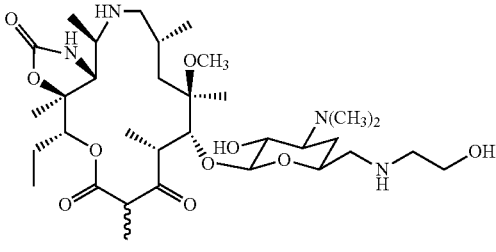 [SMILES: CC[C@H]1OC(=O)C(C)C(=O)[C@H](C)[C@@H](OC2OC(CNCCO)CC(N(C)C)C2O)[C@](C)(OC)C[C@@H](C)CN[C@H](C)[C@H]2NC(=O)O[C@@]21C] |
| Compound No. | Structure |
|---|---|
| 116 | 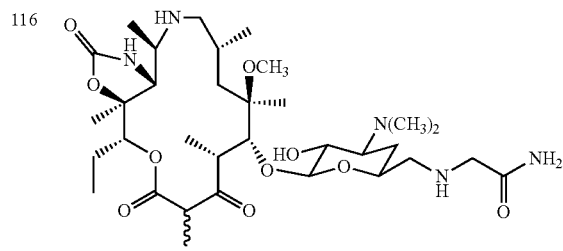 |
| 117 | 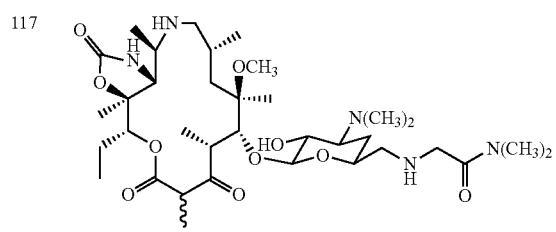 |
| 118 | 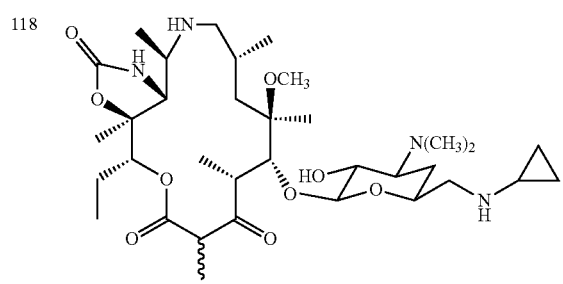 |
| 119 | 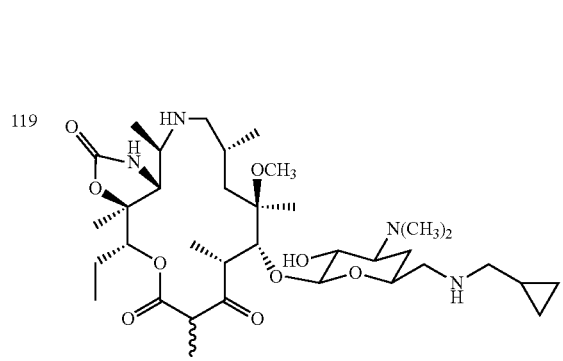 |
| 120 | |

409
-continued

| Compound No. | Structure |
|---|---|
| 121 | 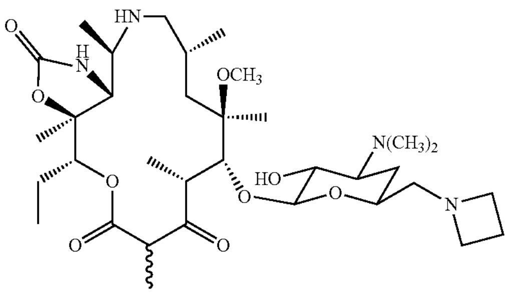 [SMILES: CC[C@H]1OC(=O)C(C)C(=O)[C@H](C)[C@@H](OC2OC(CN3CCC3)CC(N(C)C)C2O)[C@](C)(OC)C[C@@H](C)CN[C@H](C)[C@H]2NC(=O)O[C@@]21C] |
| 122 | 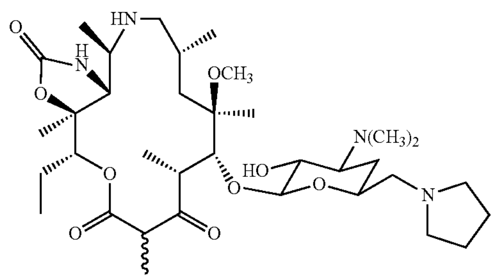 [SMILES: CC[C@H]1OC(=O)C(C)C(=O)[C@H](C)[C@@H](OC2OC(CN3CCCC3)CC(N(C)C)C2O)[C@](C)(OC)C[C@@H](C)CN[C@H](C)[C@H]2NC(=O)O[C@@]21C] |
| 123 | 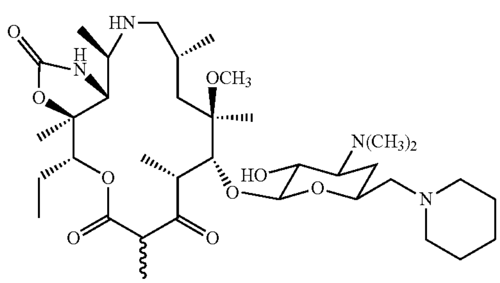 [SMILES: CC[C@H]1OC(=O)C(C)C(=O)[C@H](C)[C@@H](OC2OC(CN3CCCCC3)CC(N(C)C)C2O)[C@](C)(OC)C[C@@H](C)CN[C@H](C)[C@H]2NC(=O)O[C@@]21C] |
| 124 | 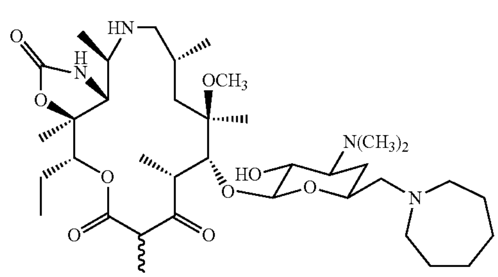 [SMILES: CC[C@H]1OC(=O)C(C)C(=O)[C@H](C)[C@@H](OC2OC(CN3CCCCCC3)CC(N(C)C)C2O)[C@](C)(OC)C[C@@H](C)CN[C@H](C)[C@H]2NC(=O)O[C@@]21C] |
| 125 | 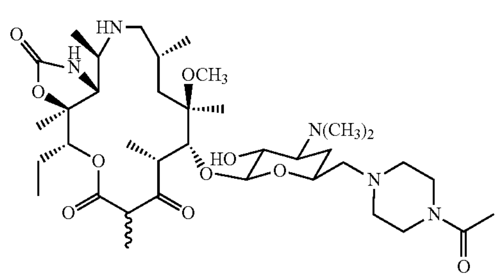 [SMILES: CC[C@H]1OC(=O)C(C)C(=O)[C@H](C)[C@@H](OC2OC(CN3CCN(C(C)=O)CC3)CC(N(C)C)C2O)[C@](C)(OC)C[C@@H](C)CN[C@H](C)[C@H]2NC(=O)O[C@@]21C] |

410
-continued

| Compound No. | Structure |
|---|---|
| 126 | 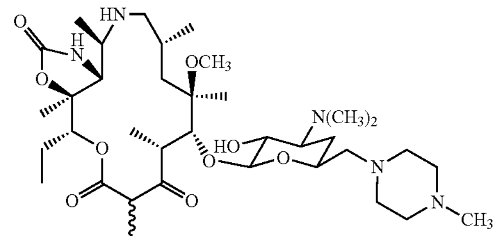 [SMILES: CC[C@H]1OC(=O)C(C)C(=O)[C@H](C)[C@@H](OC2OC(CN3CCN(C)CC3)CC(N(C)C)C2O)[C@](C)(OC)C[C@@H](C)CN[C@H](C)[C@H]2NC(=O)O[C@@]21C] |
| 127 | 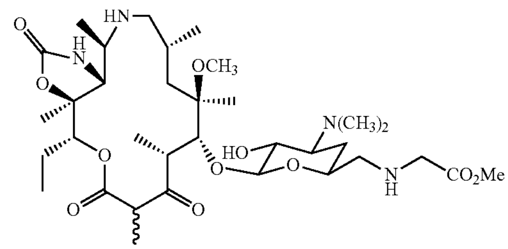 [SMILES: CC[C@H]1OC(=O)C(C)C(=O)[C@H](C)[C@@H](OC2OC(CNCC(=O)OC)CC(N(C)C)C2O)[C@](C)(OC)C[C@@H](C)CN[C@H](C)[C@H]2NC(=O)O[C@@]21C] |
| 128 | 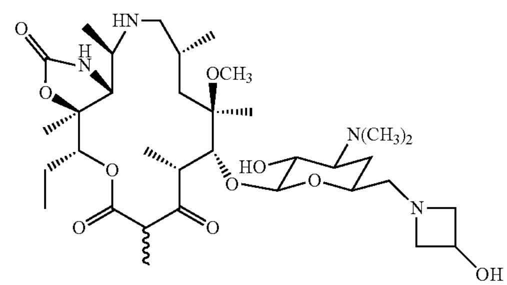 [SMILES: CC[C@H]1OC(=O)C(C)C(=O)[C@H](C)[C@@H](OC2OC(CN3CC(O)C3)CC(N(C)C)C2O)[C@](C)(OC)C[C@@H](C)CN[C@H](C)[C@H]2NC(=O)O[C@@]21C] |
| 129 | 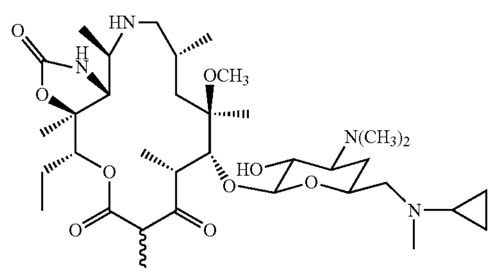 [SMILES: CC[C@H]1OC(=O)C(C)C(=O)[C@H](C)[C@@H](OC2OC(CN(C)C3CC3)CC(N(C)C)C2O)[C@](C)(OC)C[C@@H](C)CN[C@H](C)[C@H]2NC(=O)O[C@@]21C] |
| 130 | 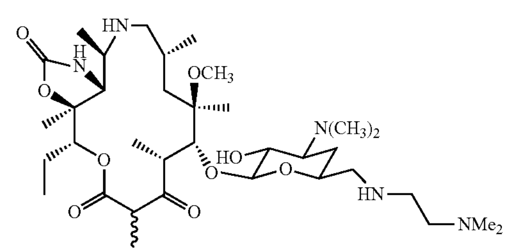 [SMILES: CC[C@H]1OC(=O)C(C)C(=O)[C@H](C)[C@@H](OC2OC(CNCCN(C)C)CC(N(C)C)C2O)[C@](C)(OC)C[C@@H](C)CN[C@H](C)[C@H]2NC(=O)O[C@@]21C] |
| 131 | 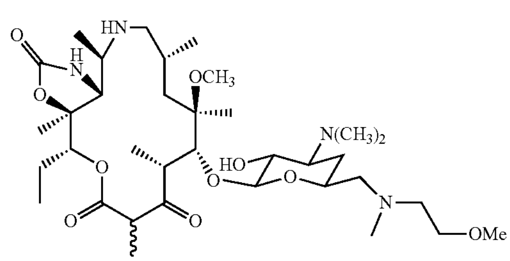 [SMILES: CC[C@H]1OC(=O)C(C)C(=O)[C@H](C)[C@@H](OC2OC(CN(C)CCOC)CC(N(C)C)C2O)[C@](C)(OC)C[C@@H](C)CN[C@H](C)[C@H]2NC(=O)O[C@@]21C] |

-continued

| Compound No. | Structure |
|---|---|
| 132 | (structure) |
| 133 | (structure) |
| 134 | (structure) |
| 135 | (structure) |
| 136 | (structure) |

-continued

| Compound No. | Structure |
|---|---|
| 137 | (structure) |
| 138 | (structure) |
| 139 | (structure) |
| 140 | (structure) |
| 141 | (structure) |

| Compound No. | Structure |
|---|---|
| 142 | 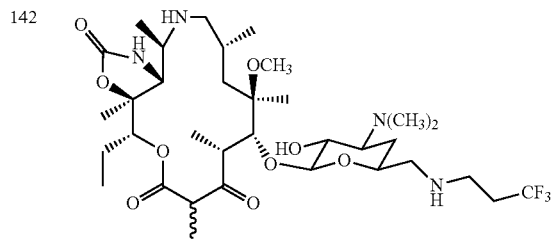 |
| 143 | 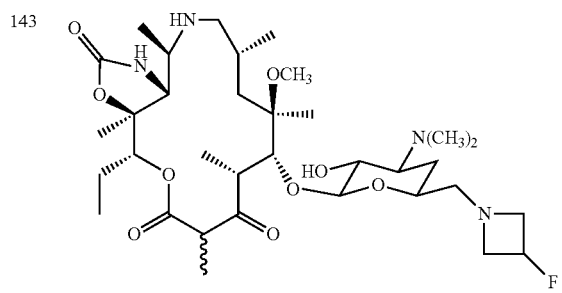 |
| 144 | 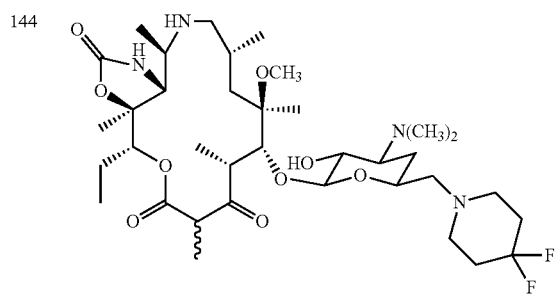 |
| 145 | 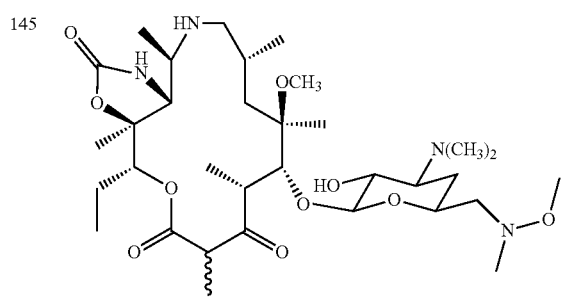 |
| 146 | 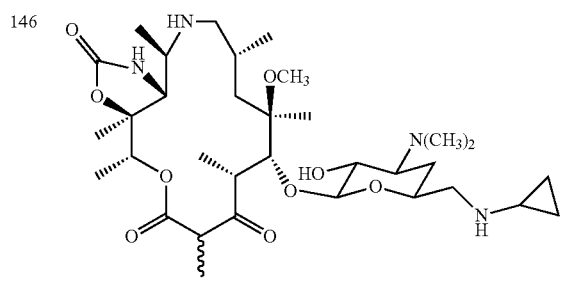 |
| Compound No. | Structure |
|---|---|
| 147 | 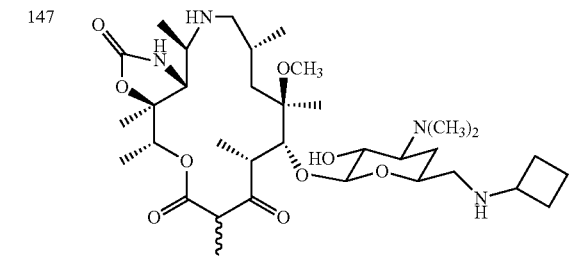 |
| 148 | 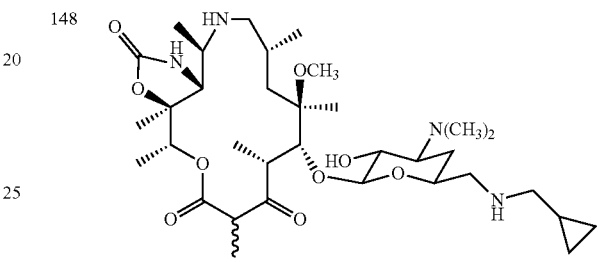 |
| 149 | 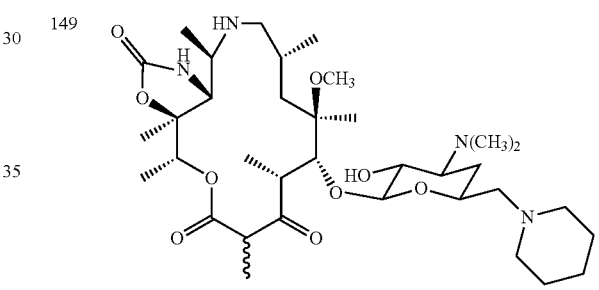 |
| 150 | 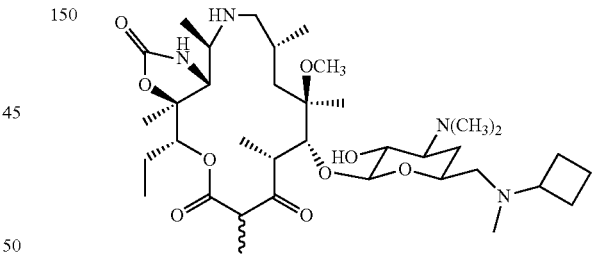 |
| 151 | 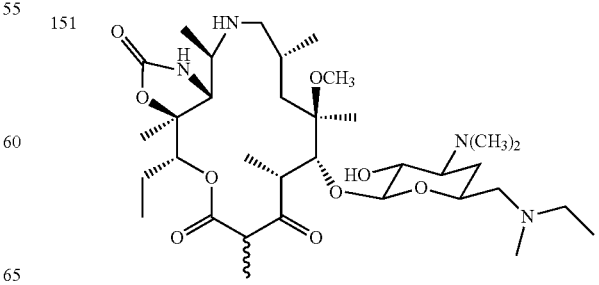 |

-continued
| Compound No. | Structure |
|---|---|
| 152 | 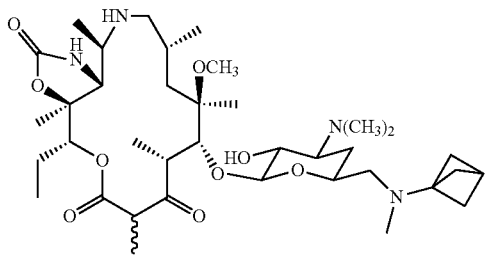 [SMILES: CC[C@H]1OC(=O)C(C)C(=O)[C@H](C)[C@@H](OC2OC(CN(C)C34CC(C3)C4)CC(N(C)C)C2O)[C@](C)(OC)C[C@@H](C)CN[C@H](C)[C@H]2NC(=O)O[C@@]21C] |
| 153 | 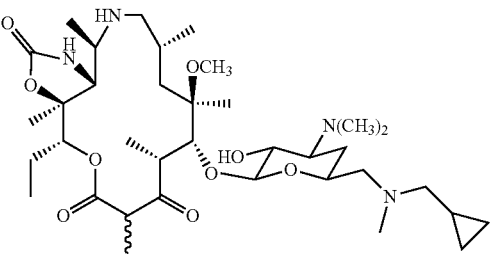 [SMILES: CC[C@H]1OC(=O)C(C)C(=O)[C@H](C)[C@@H](OC2OC(CN(C)CC3CC3)CC(N(C)C)C2O)[C@](C)(OC)C[C@@H](C)CN[C@H](C)[C@H]2NC(=O)O[C@@]21C] |
| 154 | 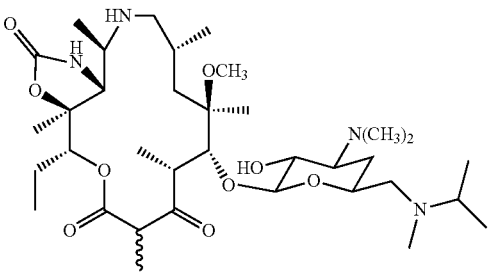 [SMILES: CC[C@H]1OC(=O)C(C)C(=O)[C@H](C)[C@@H](OC2OC(CN(C)C(C)C)CC(N(C)C)C2O)[C@](C)(OC)C[C@@H](C)CN[C@H](C)[C@H]2NC(=O)O[C@@]21C] |
| 155 | 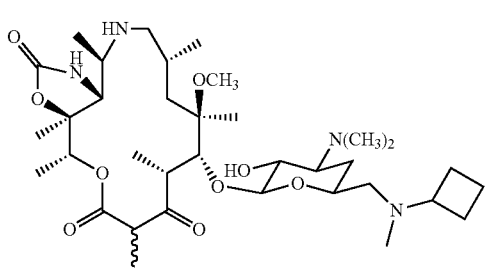 [SMILES: CO[C@]1(C)C[C@@H](C)CN[C@H](C)[C@H]2NC(=O)O[C@]2(C)[C@@H](C)OC(=O)C(C)C(=O)[C@H](C)[C@H]1OC1OC(CN(C)C2CCC2)CC(N(C)C)C1O] |
| 156 | 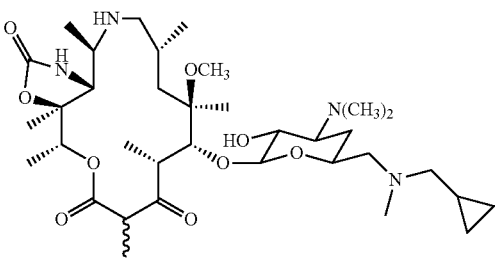 [SMILES: CO[C@]1(C)C[C@@H](C)CN[C@H](C)[C@H]2NC(=O)O[C@]2(C)[C@@H](C)OC(=O)C(C)C(=O)[C@H](C)[C@H]1OC1OC(CN(C)CC2CC2)CC(N(C)C)C1O] |
-continued
| Compound No. | Structure |
|---|---|
| 157 | 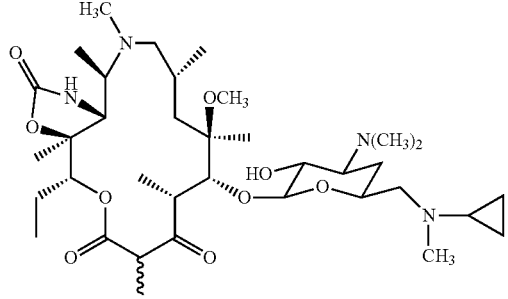 [SMILES: CC[C@H]1OC(=O)C(C)C(=O)[C@H](C)[C@@H](OC2OC(CN(C)C3CC3)CC(N(C)C)C2O)[C@](C)(OC)C[C@@H](C)CN(C)[C@H](C)[C@H]2NC(=O)O[C@@]21C] |
| 158 | 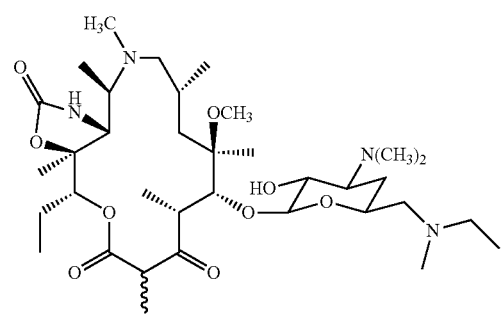 [SMILES: CC[C@H]1OC(=O)C(C)C(=O)[C@H](C)[C@@H](OC2OC(CN(C)CC)CC(N(C)C)C2O)[C@](C)(OC)C[C@@H](C)CN(C)[C@H](C)[C@H]2NC(=O)O[C@@]21C] |
| 159 | 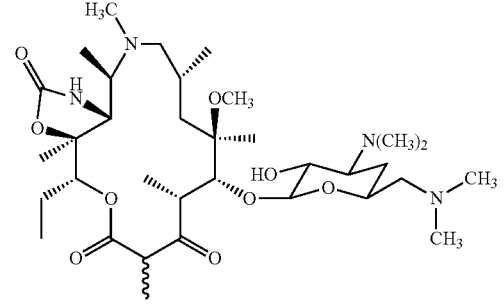 [SMILES: CC[C@H]1OC(=O)C(C)C(=O)[C@H](C)[C@@H](OC2OC(CN(C)C)CC(N(C)C)C2O)[C@](C)(OC)C[C@@H](C)CN(C)[C@H](C)[C@H]2NC(=O)O[C@@]21C] |
| 160 | 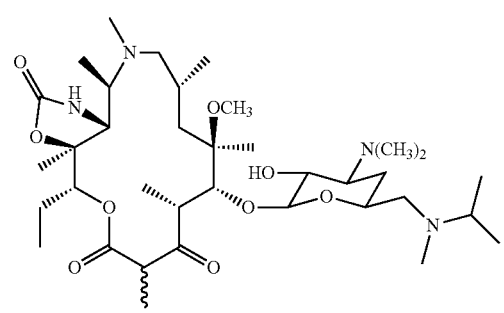 [SMILES: CC[C@H]1OC(=O)C(C)C(=O)[C@H](C)[C@@H](OC2OC(CN(C)C(C)C)CC(N(C)C)C2O)[C@](C)(OC)C[C@@H](C)CN(C)[C@H](C)[C@H]2NC(=O)O[C@@]21C] |

| Compound No. | Structure |
|---|---|
| 161 | 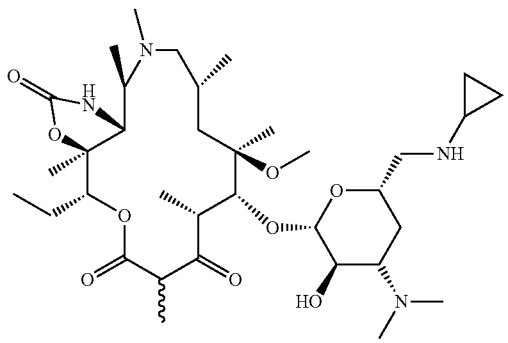 |
| 162 | 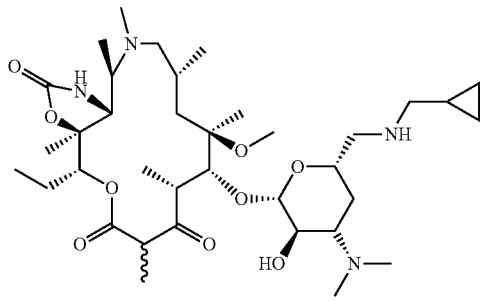 |
| 163 | 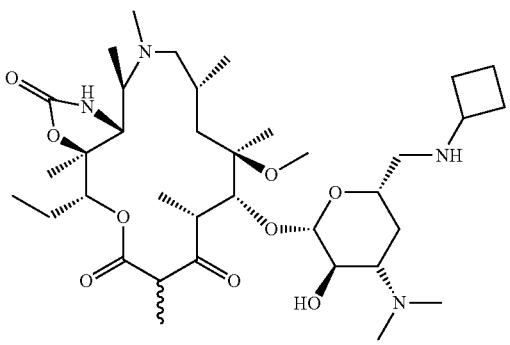 |
| 164 | 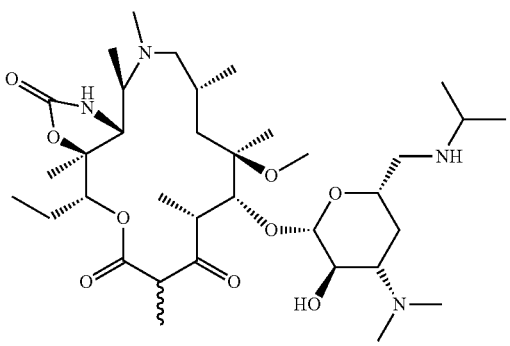 |
| Compound No. | Structure |
|---|---|
| 165 | 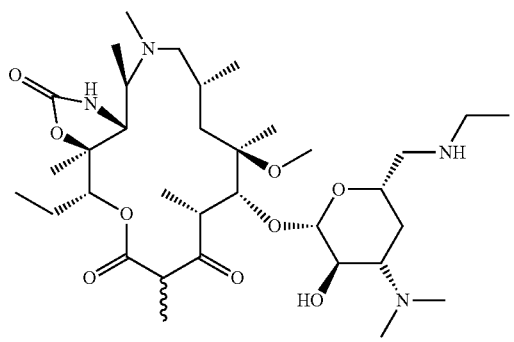 |
| 166 | 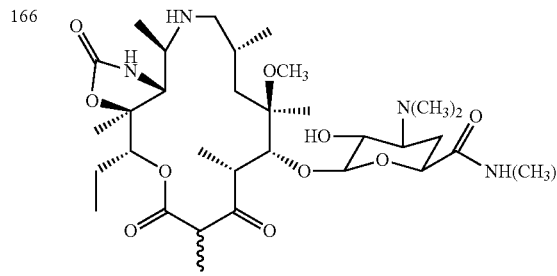 |
| 167 | 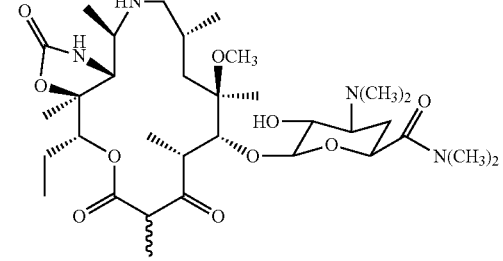 |
| 168 | 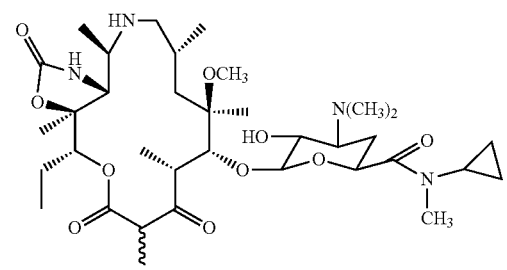 [SMILES: CC[C@H]1OC(=O)C(C)C(=O)[C@H](C)[C@@H](OC2OC(C(=O)N(C)C3CC3)CC(N(C)C)C2O)[C@](C)(OC)C[C@@H](C)CN[C@H](C)[C@H]2NC(=O)O[C@@]21C] |
| 169 | 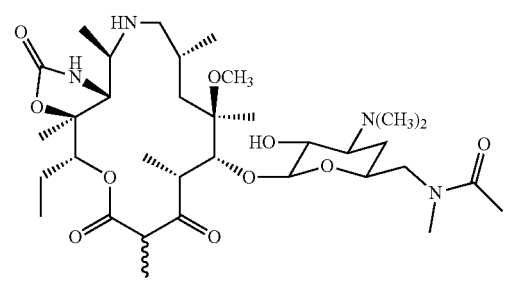 [SMILES: CC[C@H]1OC(=O)C(C)C(=O)[C@H](C)[C@@H](OC2OC(CN(C)C(C)=O)CC(N(C)C)C2O)[C@](C)(OC)C[C@@H](C)CN[C@H](C)[C@H]2NC(=O)O[C@@]21C] |

| Compound No. | Structure |
|---|---|
| 170 | 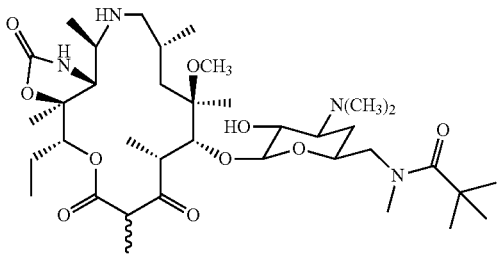 [SMILES: CC[C@H]1OC(=O)C(C)C(=O)[C@H](C)[C@@H](OC2OC(CN(C)C(=O)C(C)(C)C)CC(N(C)C)C2O)[C@](C)(OC)C[C@@H](C)CN[C@H](C)[C@H]2NC(=O)O[C@@]21C] |
| 171 | 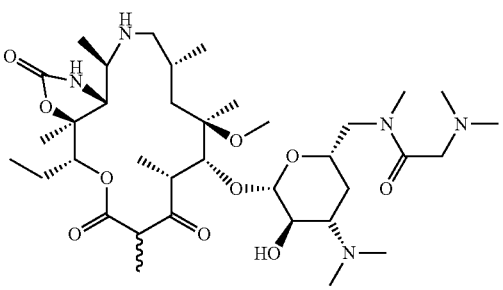 |
| 172 | 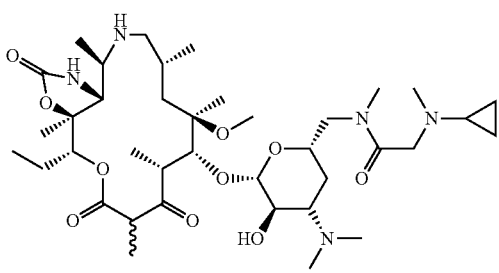 |
| 173 | 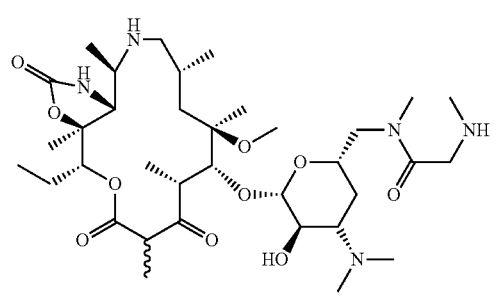 |
| 175 | 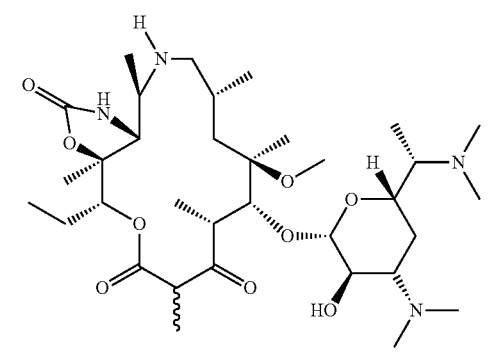 |
| Compound No. | Structure |
|---|---|
| 176 | 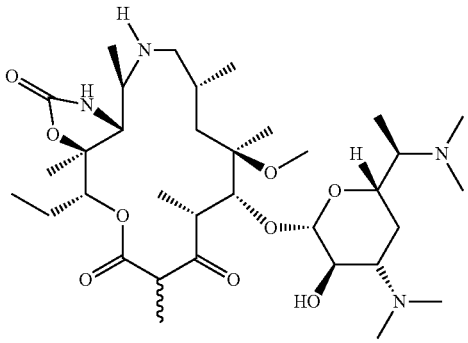 |
| 177 | 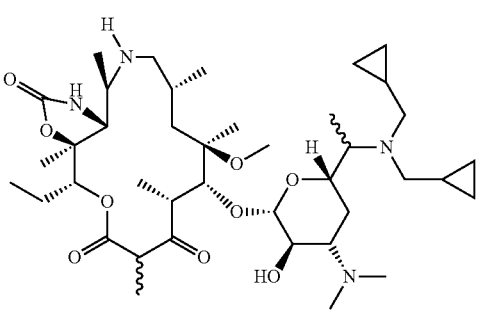 |
| 178 | 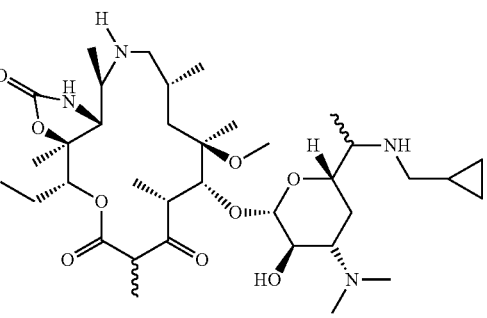 |
| 179 | 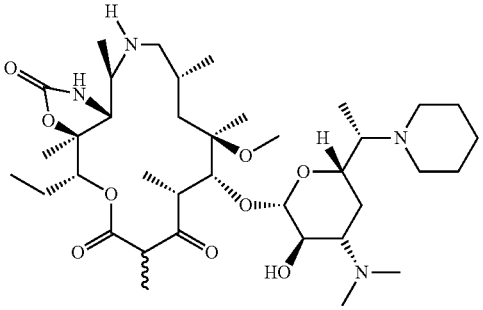 |

421
-continued
| Compound No. | Structure |
|---|---|
| 180 | 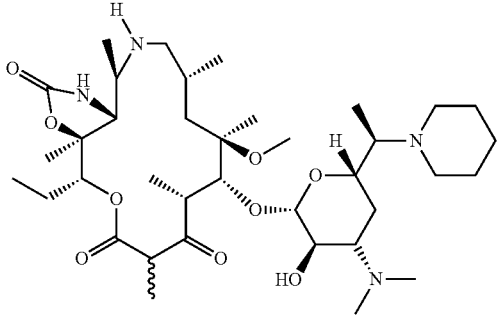 |
| 181 | 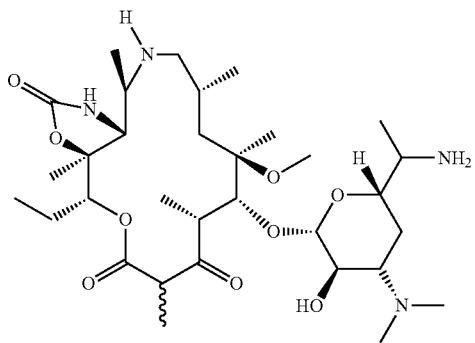 |
| 182 | 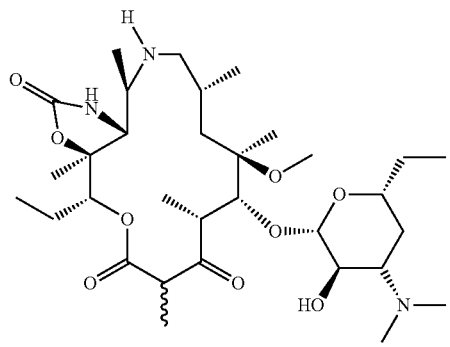 |
| 183 | 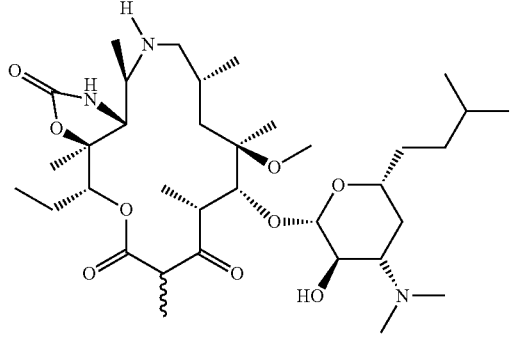 |
422
-continued
| Compound No. | Structure |
|---|---|
| 184 | 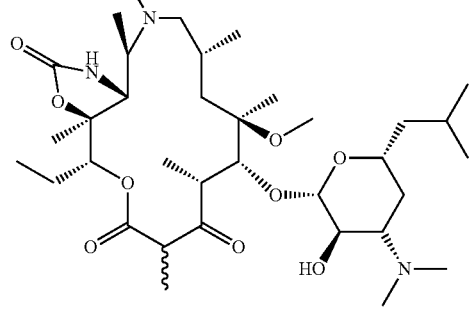 |
| 185 | 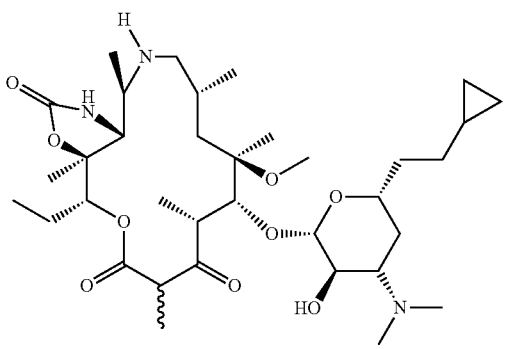 |
| 186 | 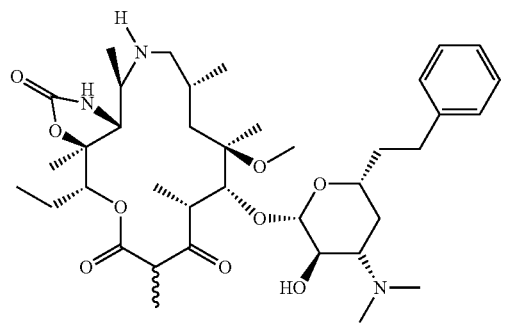 |
| 187 | 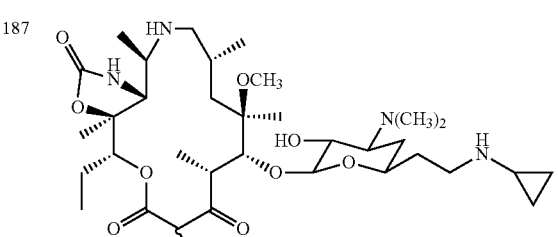 |
| 188 | 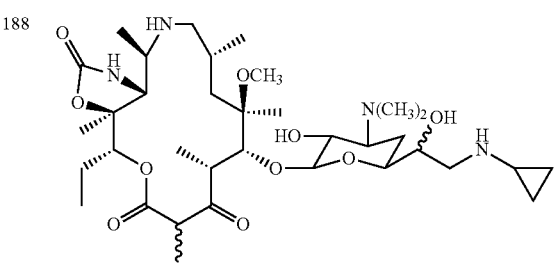 |

-continued

| Compound No. | Structure |
|---|---|
| 189 | 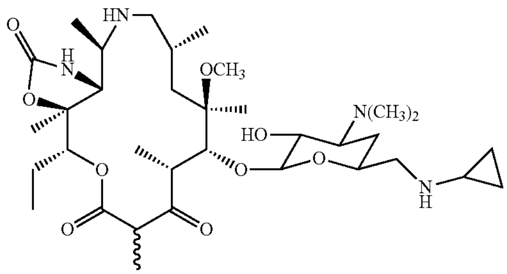 [SMILES: CC[C@H]1OC(=O)C(C)C(=O)[C@H](C)[C@@H](OC2OC(CNC3CC3)CC(N(C)C)C2O)[C@](C)(OC)C[C@@H](C)CN[C@H](C)[C@H]2NC(=O)O[C@@]21C] |
| 190 | 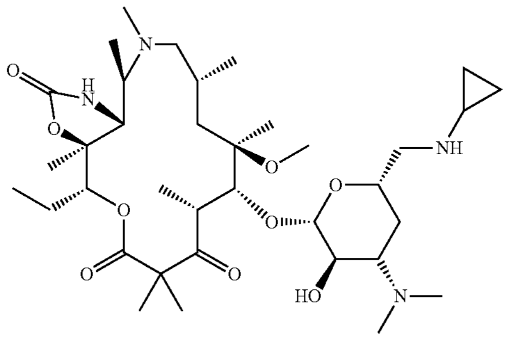 |
| 191 | 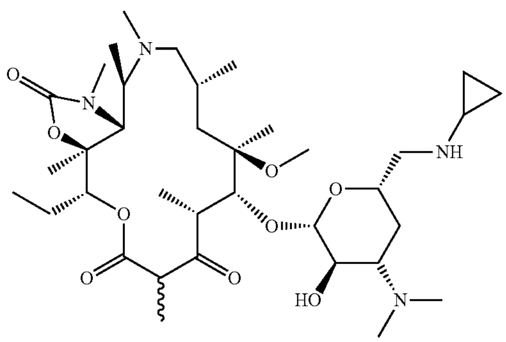 |

-continued

| Compound No. | Structure |
|---|---|
| 192 | , or |
| 193 | | or a pharmaceutically acceptable salt thereof.

2. A pharmaceutical composition comprising a compound of claim 1, or a pharmaceutically acceptable salt thereof, and a pharmaceutically acceptable excipient.

3. A method of treating an infectious disease comprising administering an effective amount of a compound of claim 1, or pharmaceutically acceptable salt thereof.

\* \* \* \* \*